United States Patent
Chen et al.

(10) Patent No.: US 7,253,180 B2
(45) Date of Patent: Aug. 7, 2007

(54) PRE-ORGANIZED TRICYCLIC INTEGRASE INHIBITOR COMPOUNDS

(75) Inventors: James M. Chen, San Ramon, CA (US); Xiaowu Chen, San Mateo, CA (US); Maria Fardis, San Carlos, CA (US); Haolun Jin, Foster City, CA (US); Choung U. Kim, San Carlos, CA (US); Laura N. Schacherer, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 10/687,373

(22) Filed: Oct. 16, 2003

(65) Prior Publication Data

US 2004/0167124 A1    Aug. 26, 2004

Related U.S. Application Data

(60) Provisional application No. 60/478,783, filed on Jun. 16, 2003, provisional application No. 60/418,963, filed on Oct. 16, 2002.

(51) Int. Cl.
*A01N 43/42* (2006.01)
*A61K 31/44* (2006.01)
*C07D 471/00* (2006.01)
*C07D 491/00* (2006.01)
*C07D 498/00* (2006.01)

(52) U.S. Cl. ................ 514/292; 546/23; 546/84
(58) Field of Classification Search .......... 546/23, 546/84; 544/3, 126, 361, 58.1, 58.6; 514/292, 514/232.8, 253.03, 222.2, 228.2
See application file for complete search history.

(56) References Cited

U.S. PATENT DOCUMENTS

| | | | |
|---|---|---|---|
| 3,113,135 A | 12/1963 | Hodel et al. | |
| 4,816,570 A | 3/1989 | Farquhar | |
| 4,968,788 A | 11/1990 | Farquhar | |
| 5,252,560 A | 10/1993 | Myers et al. | |
| 5,324,839 A | 6/1994 | Clemence et al. | |
| 5,538,988 A | 7/1996 | Martinez et al. | |
| 5,602,146 A | 2/1997 | Billhardt-Troughton et al. | |
| 5,663,159 A | 9/1997 | Starrett, Jr. et al. | |
| 5,792,756 A | 8/1998 | Starrett, Jr. et al. | |
| 5,798,340 A | 8/1998 | Bischofberger et al. | |
| 5,854,275 A | 12/1998 | Robinson | |
| 6,187,907 B1 | 2/2001 | Chen et al. | |
| 6,218,402 B1 * | 4/2001 | Chalmers et al. | 514/292 |
| 6,245,806 B1 | 6/2001 | Dombrowski et al. | |
| 6,271,402 B1 | 8/2001 | Singh et al. | |
| 6,310,211 B1 | 10/2001 | Vaillancourt et al. | |
| 6,312,662 B1 | 11/2001 | Erion et al. | |
| 6,395,743 B1 | 5/2002 | Heimbuch et al. | |
| 2006/0116356 A1 * | 6/2006 | Cai et al. | 514/79 |

FOREIGN PATENT DOCUMENTS

| | | |
|---|---|---|
| WO | WO 91/19721 A1 | 12/1991 |
| WO | WO 99/62513 A1 | 12/1999 |
| WO | WO 99/62520 A1 | 12/1999 |
| WO | WO 00/39086 A1 | 7/2000 |
| WO | WO 00/75122 A1 | 12/2000 |
| WO | WO 01/00578 A1 | 1/2001 |
| WO | WO 02/30426 A1 | 4/2002 |
| WO | WO 02/30930 A2 | 4/2002 |
| WO | WO 02/30931 A2 | 4/2002 |
| WO | WO 02/36734 A2 | 5/2002 |
| WO | WO 02/055079 | 7/2002 |

OTHER PUBLICATIONS

Murray et al. Synthesis 1996, 10:1180-1182.*
Design of Prodrugs Handbook, Hans Bundgaard.*
Arterburn et al., "Catalytic Amination of 2-Substituted Pyridines wth Hydrazine Derivatives", 3(9):1351-1354, Organic Letters, 2001.
Artico et al, "Geometrically and Conformationally Restrainse Cinnamoyl Compounds as Inhibitors of HIV-1 Integrase: Synthesis, Biological Evaluation, and Molecular Modeling", 41:3948-3960, J Med Chem, 1998.
Beauchamp et al., "Guanine, Pyrazolo[3,4-d]pyrimidine, and Triazolo[4,5-d]pyrimidine (8-Azaguanine) Phosphonate Acyclic Derivatives as Inhihibitors . . . ", 39(4):949-956, J. Med Chem, 1996.
Bhuta et al, "Analogs of Chloramphenicol: Circular Dichroism Spectra, Inhibition of Ribosomal Peptidyltransferase, and Possible Mechanism of Action", 23(12):1299-1305, J Med Chem, 1980.

(Continued)

*Primary Examiner*—Margaret D. Seaman
*Assistant Examiner*—Niloofar Rahmani
(74) *Attorney, Agent, or Firm*—Mark L. Bosse; John S. Ward

(57) ABSTRACT

Tricyclic compounds according to the structure below, protected intermediates thereof, and methods for inhibition of HIV-integrase are disclosed.

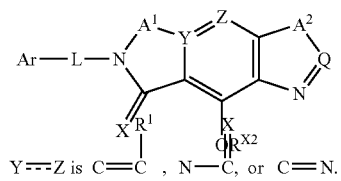

$A^1$ and $A^2$ are moieties forming a five, six, or seven membered ring. L is a bond or a linker connecting a ring atom of Ar to N. X is O, S, or substituted nitrogen. Ar is aryl or heteroaryl. Q is N, $^+$NR, or $CR^4$. The aryl carbons may be independently substituted with substituents other than hydrogen. The compounds may include prodrug moieties covalently attached at any site.

66 Claims, No Drawings

OTHER PUBLICATIONS

Benzaria et al, "Synthesis, in Vitro Antiviral Evaluation, and Stability Studies of Bis(S-acyl-2-thioethyl) Ester Derivatives of 9-[2-(Phosphonometyoxy)ethyl]adenine (PMEA) as Potential PMEA Prodrugs with Improved Oral Bioavailability", 39:4958-4965, J Med Chem, 1996.

Bigge et al., "Exploration of N-Phosphonoalkyl-, N-Phosphonoalkenyl-, and N-(Phosphonoalkyl)phenyl-Spaced . . . ", 35(8):1371, J Med Chem, 1992.

Buolamwini et al, "CoMFA and CoMSIA 3D QSAR and Docking Studies on Conformationally-Restrained Cinnamoyl HIV-1 Integrase Inhibitors: Exploration of a Binding Mode at the Active Site", 45:841-852, J Med Chem, 2002.

Campagne et al, "(1H-Benzotriazol-1-yloxy)tris(dimethylamino)phosphonium Hexafluorophosphate-and-Benzotriazol-1-yloxy)tripyrrolidinophosphonium Hexafluorophosphate-Mediated Activiation of Monophosphonate Esters: Synthesis of Mixed Phosphonate Diesters . . . ", 60(16):5214-5223, J Org Chem, 1995.

Cates et al., "Phosphorus Analogues of -Aminobutyric Acid, A New Class of Anticonvulsants", 27(5):654-659, J Med Chem, 1984.

Chen et al, "Design, Synthesis, and Biochemical Evaluation of Phosphonate and Phosphonamidate Analogs of Glutathionylspermidine as Inhibitors . . . ", 40(23):3842-3850, J Med Chem, 1997.

Corey et al, "Selective Cleavage of Allyl Ethers Under Mild Conditions By Transition Metal Reagents", 38(18):3224, J Org Chem, 1973.

Chen et al, "Structure-Based Design of a Novel, Potent, and Selective Inhibitor for MMP-13 Utilizing NMR Spectroscopy and Computer-Aided Molecular Design", 122:9648-9654, J Am Chem Soc, 2000.

Chen et al, "Anthranilate Sulfonamide Hydroxamate TACE Inhibitors, Part 1: Structure-Based Design of Novel Acetylenic P1' Groups", 12:1195-1198, Bioorg Med Chem Lett, 2002.

Chen et al, "Structure-Based Design of Potent Inhibitors of Scytalone Dehydratase; Displacement of a Water Molecule from the Active Site", 37:17735-17744, Biochem, 1998.

Chihab-Eddine et al, "Synthesis and reactivity of (1S)-N-(1-phenylethyl)maleimide towards nucleophiles: an application to preparation of chiral pyrroloisothiochroman and pyrrolobenzo[d]thiepine based . . . ", 42:573-576, Tet Lett, 2001.

Davies et al, "Dinucleotide Analogues as Inhibitors of Thymidine Kinase, Thyidylate Kinase, and Ribonucleotide Reductase", 31(7):1305-1308, J Med Chem, 1998.

DeLombaert et al, "N-Phosphonomehtyly Dipeptides and Their Phosphonate Prodrugs, a New Generation of Neutral Endopeptidase (NEP 3.4.24.11) Inhibitors", 37:498, J Med Chem, 1994.

Galeotti et al, "A Straightforward Synthesis of -Amino Phosphonate Monoesters Using BroP or TPyClU", 37(23):3997-3998, Tet Lett, 1996.

Gali et al, "Facile Ring-Opening Reactions of Phthalimides as a New Strategy to Synthesize Amid Functionalized Phosphonates, Primary Phosphines, and Bisphosphines", 65(3):676-680, J Org Chem, 2000.

Goldgur et al, "Structure of the HIV-1 integrase catalytic domain complexed with an inhibitor: A platform for antiviral drug design", 96:13040-13043, Proc Natl Acad Sci, 1999.

Jing et al, "Potassium-Dependent Folding: A Key to Intracellular Delivery of G-Quartet Olignonucleotides as HIV Inhibitors", 41:5397-5403, Biochem, 2002.

Khamnei et al, "Neighboring Group Catalysis in the Design of Nucleotide Prodrugs", 39:4109-4115, J Med Chem, 1996.

LaForge et al., "Rotenone. XXVI. Synthesis of the Parent Substances of Some Characteristic Rotenone Derivatives", 55(7):3040-3048, J Am Chem Soc, 1933.

Lam et al., "Cyclic HIV Protease Inhibitors: Synthesis, Conformational Analysis, P2/P2' Structure-Activity Relationship, and Molecular Recognition of Cyclic Ureas", 39:3514-3525, J Med Chem, 1996.

Morgan et al, "Structure-Based Design of an Inhibitor of the Zinc Peptidase Thermolysin", 116(8):3251-3260, J Med Chem Soc, 1994.

Morr et al, "Formation of Phostonic Acids During The Reduction of Azidonucleosidephosphonic Acids", 42:8841-8843, Tet Lett, 2001.

Musiol et al, "On the Synthesis of Phosphonamidate Peptides", 59(21):6144-6146, J Org Chem, 1994.

Matier et al, "Sulfamoyl Azides. Hydrolysis Rates and Hypotensive Activity", 15(5):538-541, J Med Chem, 1972.

Matsumura, "Friedel and Crafts Reaction with 8-Hydroxyquinoline"; 57:124-128, J Am Chem Soc, 1935.

Mattson et al., "An Improved Method for Reductive Alkylation of Amines Using Titanium (IV) Isopropoxide and Sodium Cyanoborohydride", 55(8):2552-2554, J Org Chem, 1990.

Mitchell et al, "Bioreversible Protection for the Phospho Group: Bioactivation of the Di(4-acyloxybenzyl) and Mono(4-acyloxybenzyl) Phosphoesters of Methylphosphonate and Phosphonoacetate", 2345, J Chem Soc Perkin Trans I, 1992.

Ornstein et al, "Synthesis and Pharmacology of a Series of 3- and 4-(Phosphonoalkyl)pyridine-and -piperidine-2-carboxylic Acids. Potent N-Methyl-D-aspartate Receptor Antagonists", 32:827-833, J Med Chem, 1989.

Pais et al, "Structure Activity of 3-Aryl-1,3-diketo-Containing Compounds as HIV-1 Integrase Inhibitors", 45:3184-3194, J. Med Chem, 2002.

Pallella et al., "Declining Morbidity and Mortality Among Patients with Advanced Human Immunodeficiency Virus Infection", 338:853-860, J Med Chem, 1998.

Pommier et al, "Retroviral integrase inhibitors year 2000: update and perspectives", 47:139-148, Antiviral Res, 2000.

Saddy et al, "Selective Monodeprotection of Phosphonate, Phosphite, Phosphonate, and Phosphoramide Benzyl Esters", 60(9):2946-2947, J Org Chem, 1995.

Sasaki et al., "Convenient Synthesis of Some Purine 8,5'-Imino Cyclonucleosides", 43(12):2320-2325, J Org Chem, 1978.

Serafinowska et al., "Synthesis and in Vivo Evaluation of Prodrugs of 9-[2-(Phosphonomethoxy)ethoxy]adenine", 38:1372-1379, J Med Chem, 1995.

Smith et al, "A novel MyD-1 (SIRP-1) signaling pathway that inhibits LPS-induced TNF production by monocytes", 102(7):2532-2540, BLOOD, 2003.

Van Der Laan et al, "An Approach Towards the Synthesis of Oligomers Containing a N-2-Hydroxyethyl-aminomethylphosphonate Backbone:A Novel PNA Analogue", 37(43):7857-7860, Tet Lett, 1996.

Yamauchi et al, "Synthesis of Peptides Analogs Containing(2-aminoethyl)phosphonic acid (ciliatine)", 49(7):1158-1163, J Org Chem, 1984.

* cited by examiner

PRE-ORGANIZED TRICYCLIC INTEGRASE INHIBITOR COMPOUNDS

This non-provisional application claims the benefit of Provisional Application No. 60/418,963, filed Oct. 16, 2002, and Provisional Application No. 60/478,783, filed Jun. 16, 2003, which are incorporated herein by reference.

FIELD OF THE INVENTION

The invention relates generally to compounds with antiviral activity and more specifically with HIV-integrase inhibitory properties.

BACKGROUND OF THE INVENTION

Human immunodeficiency virus (HIV) infection and related diseases are a major public health problem worldwide. A virally encoded integrase protein mediates specific incorporation and integration of viral DNA into the host genome. Integration is necessary for viral replication. Accordingly, inhibition of HIV integrase is an important therapeutic pursuit for treatment of HIV infection of the related diseases.

Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, etal *N. Engl. J. Med.* (1998) 338:853-860; Richman, D. D. *Nature* (2001) 410:995-1001). There is a need for new agents directed against alternate sites in the viral life cycle. Integrase has emerged as an attractive target, because it is necessary for stable infection and homologous enzymes are lacking in the human host (LaFemina, etal *J. Virol.* (1992) 66:7414-7419). The function of integrase is to catalyze integration of proviral DNA, resulting from the reverse transcription of viral RNA, into the host genome, by a stepwise fashion of endonucleolytic processing of proviral DNA within a cytoplasmic preintegration complex (termed 3'-processing or "3'-P") with specific DNA sequences at the end of the HIV-1 long terminal repeat (LTR) regions, followed by translocation of the complex into the nuclear compartment where integration of 3'-processed proviral DNA into host DNA occurs in a "strand transfer" (ST) reaction (Hazuda, etal *Science* (2000) 287:646-650; Katzman, etal *Adv. Virus Res.* (1999) 52:371-395; Asante-Applah, etal *Adv. Virus Res.* (1999) 52:351-369). Although numerous agents potently inhibit 3'-P and ST in extracellular assays that employ recombinant integrase and viral long-terminal-repeat oligonucleotide sequences, often such inhibitors lack inhibitory potency when assayed using fully assembled preintegration complexes or fail to show antiviral effects against HIV-infected cells (Pommier, etal *Adv. Virus Res.* (1999) 52:427-458; Farnet, etal *Proc. Natl. Acad. Sci. U.S.A.* (1996) 93:9742-9747; Pommier, etal *Antiviral Res.* (2000) 47:139-148.

Certain HIV integrase inhibitors have been disclosed which block integration in extracellular assays and exhibit good antiviral effects against HIV-infected cells (Anthony, etal WO 02/30426; Anthony, etal WO 02/30930; Anthony, etal WO 02/30931; WO 02/055079; Zhuang, etal WO 02/36734; U.S. Pat. No. 6,395,743; U.S. Pat. No. 6,245,806; U.S. Pat. No. 6,271,402; Fujishita, etal WO 00/039086; Uenaka etal WO 00/075122; Selnick, etal WO 99/62513; Young, etal WO 99/62520; Payne, etal WO 01/00578; Jing, etal *Biochemistry* (2002) 41:5397-5403; Pais, etal *Jour. Med. Chem.* (2002) 45:3184-94; Goldgur, etal *Proc. Natl. Acad. Sci. U.S.A.* (1999) 96:13040-13043; Espeseth, etal *Proc. Natl. Acad. Sci. U.S.A.* (2000) 97:11244-11249).

HIV integrase inhibitory compounds with improved antiviral and pharmacokinetic properties are desirable, including enhanced activity against development of HIV resistance, improved oral bioavailability, greater potency and extended effective half-life in vivo (Nair, V. "HIV integrase as a target for antiviral chemotherapy" *Reviews in Medical Virology* (2002) 12(3):179-193). Three-dimensional quantitative structure-activity relationship studies and docking simulations (Buolamwini, etal *Jour. Med Chem.* (2002) 45:841-852) of conformationally-restrained cinnamoyl-type integrase inhibitors (Artico, etal *Jour. Med. Chem.* (1998) 41:3948-3960) have correlated hydrogen-bonding interactions to the inhibitory activity differences among the compounds.

Improving the delivery of drugs and other agents to target cells and tissues has been the focus of considerable research for many years. Though many attempts have been made to develop effective methods for importing biologically active molecules into cells, both in vivo and in vitro, none has proved to be entirely satisfactory. Optimizing the association of the inhibitory drug with its intracellular target, while minimizing intercellular redistribution of the drug, e.g. to neighboring cells, is often difficult or inefficient.

Most agents currently administered parenterally to a patient are not targeted, resulting in systemic delivery of the agent to cells and tissues of the body where it is unnecessary, and often undesirable. This may result in adverse drug side effects, and often limits the dose of a drug (e.g., cytotoxic agents and other anti-cancer or anti-viral drugs) that can be administered. By comparison, although oral administration of drugs is generally recognized as a convenient and economical method of administration, oral administration can result in either (a) uptake of the drug through the cellular and tissue barriers, e.g. blood/brain, epithelial, cell membrane, resulting in undesirable systemic distribution, or (b) temporary residence of the drug within the gastrointestinal tract. Accordingly, a major goal has been to develop methods for specifically targeting agents to cells and tissues. Benefits of such treatment includes avoiding the general physiological effects of inappropriate delivery of such agents to other cells and tissues, such as uninfected cells. Intracellular targeting may be achieved by methods and compositions which allow accumulation or retention of biologically active agents inside cells.

SUMMARY OF THE INVENTION

The present invention provides compositions and methods for inhibition of HIV integrase.

In one aspect, the invention is a compound having the structure:

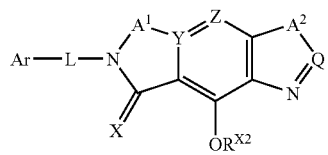

wherein:

$A^1$ is independently selected from $C(R^2)_2$, $CR^2OR$, $CR^2OC(=O)R$, $C(=O)$, $C(=S)$, $CR^2SR$, and $C(=NR)$, $A^2$ is independently selected from $C(R^2)_2$—$C(R^3)_2$, $C(R^2)=C(R^3)$, and $C(=O)C(R^3)_2$;

Q is $CR^4$;

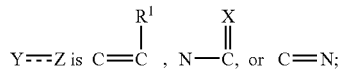

L is selected from a bond, O, S, S—S, $S(=O)$, $S(=O)_2$, $S(=O)_2NR$, NR, N—OR, $C_1$-$C_{12}$ alkylene, $C_1$-$C_{12}$ substituted alkylene, $C_2$-$C_{12}$ alkenylene, $C_2$-$C_{12}$ substituted alkenylene, $C_2$-$C_{12}$ alkynylene, $C_2$-$C_{12}$ substituted alkynylene, $C(=O)NH$, $OC(=O)NH$, $NHC(=O)NH$, $C(=O)$, $C(=O)NH(CH_2)_n$, or $(CH_2CH_2O)_n$, where n is optionally 1, 2, 3, 4, 5, or 6;

X is selected from O, S, NH, NR, N—OR, N—$NR_2$, N—$CR_2OR$ and N—$CR_2NR_2$;

Ar is selected from (a) a $C_3$-$C_{12}$ carbocycle, $C_3$-$C_{12}$ substituted carbocycle, $C_6$-$C_{20}$ aryl, $C_6$-$C_{20}$ substituted aryl, $C_2$-$C_{20}$ heteroaryl, and $C_2$-$C_{20}$ substituted heteroaryl;

or (b) a saturated, unsaturated or aromatic ring or ring system having a mono- or bicyclic carbocycle or heterocycle containing 3 to 12 ring atoms;

$R^2$, $R^3$ and $R^4$ are each independently selected from H, F, Cl, Br, I, OH, —$NH_2$, —$NH_3^+$, —NHR, —$NR_2$, —$NR_3^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —$SO_2R$, —$SO_2Ar$, —SOAr, —SAr, —$SO_2NR_2$, —SOR, —$CO_2R$, —$C(=O)NR_2$, 5-7 membered ring lactam, 5-7 membered ring lactone, —CN, —$N_3$, —$NO_2$, $C_1$-$C_8$ alkoxy, $C_1$-$C_8$ trifluoroalkyl, $C_1$-$C_8$ alkyl, $C_1$-$C_8$ substituted alkyl, $C_3$-$C_{12}$ carbocycle, $C_3$-$C_{12}$ substituted carbocycle, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, phosphate, and a prodrug moiety;

when taken together on a single carbon, two $R^2$ or two $R^3$ may form a spiro ring; $R^1$ is independently selected from $CR_3$, $NRSO_2R$, $OC(=O)NR_2$ $OC(=O)R$, SR, H, F, Cl, Br, I, OH, —$NH_2$, —$NH_3^+$, —NHR, —$NR_2$, —$NR_{3+}$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —$SO_2R$, —$SO_2Ar$, —SOAr, —SAr, —$SO_2NR_2$, —SOR, —$CO_2R$, —$C(=O)NR_2$, 5-7 membered ring lactam, 5-7 membered ring lactone, —CN, —$N_3$, —$NO_2$, $C_1$-$C_8$ alkoxy, $C_1$-$C_8$ trifluoroalkyl, $C_1$-$C_8$ alkyl, $C_1$-$C_8$ substituted alkyl, $C_3$-$C_{12}$ carbocycle, $C_3$-$C_{12}$ substituted carbocycle, $C_6$-$C_{20}$ aryl, $C_6C_{20}$ substituted aryl, $C_2$-$C_{20}$ heteroaryl, and $C_2$-$C_{20}$ substituted heteroaryl, polyethyleneoxy, phosphonate, phosphate, and a prodrug moiety;

R is independently selected from H, $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, polythenyleneoxy, phosphonate, phosphate, and prodrug moiety;

$R^{X2}$ is independently selected from H, $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, polythenyleneoxy, phosphonate, phosphate, a prodrug moiety, and a protecting group;

and the tautomers, salts, solvates, resolved enantiomers and purified diastereomers thereof;

with the provisio that when Y=Z is C=C(OH), X is O, $A^1$ is C(=O), $A^2$ is $C(R^2)=C(R^3)$, and Q is CH, then L is not a bond.

$A^1$ and $A^2$ are independently selected from O, S, NR, $C(R^2)_2$, $CR^2OR$, $CR^2OC(=O)R$, (C=O), C(=S), $CR^2SR$, C(=NR), $C(R^2)_2$—$C(R^3)_2$, $C(R^2)=C(R^3)$, $C(R^2)_2$—O, NR—$C(R^3)_2$, $N=C(R^3)$, N=N, $SO_2$—NR, $C(=O)(C(R^3)_2$, C(=O)NR, $C(R^2)_2$—$C(R^3)_2$—$C(R^3)_2$, $C(R^2)=C(R^3)$—C$(R^3)_2$, $C(R^2)C(=O)NR$, $C(R^2)C(=S)NR$, $C(R^2)=N$—$C(R^3)_2$,$C(R^2)=N$—NR, and $N=C(R^3)$—NR;

In one aspect, the invention includes tricyclic compounds represented by the following structure:

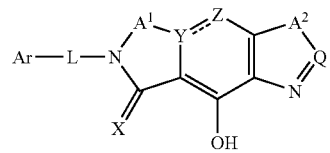

The compounds of the invention share a tricyclic scaffold and a potential active site or metal binding motif defined by the lower side of the Formula above including the amide-type functionality, i.e. N—C(=X), of the left ring, the aromatic hydroxyl of the middle ring, and the nitrogen of the right ring. The compounds of the invention have binding functionality, e.g. nitrogen, hydroxyl, and X-carbonyl, in a pre-organized configuration which may confer optimized inhibitory properties against HIV integrase.

$A^1$ and $A^2$ are each and independently a moiety forming a five, six, or seven membered ring. Q is N, substituted nitrogen (NR), CH, or substituted carbon. L is a bond or a linker connecting a ring atom of Ar to N. X is O, S, NH, or substituted nitrogen (NR). Ar is a carbocycle, aryl or heteroaryl group. R is a substituent including H, alkyl, aryl, heteroaryl and substituted forms thereof, as well as polyethyleneoxy, phosphonate, phosphate, or a prodrug moiety. The 5 and 6 positions are represented in the structure above by Y and Z respectively. The chemical bond between Y and Z may be a single bond, a double bond, or a bond with enolic, tautomeric character, depending on the substituent on Z, i.e. $R^1$ or X. The Y and Z substructure is represented wherein:

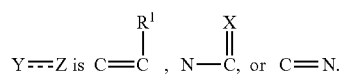

The compounds of the invention may include prodrug moieties covalently attached at any site. The prodrug moiety may be a phosphonate group.

The invention also includes a pharmaceutical composition comprising a therapeutically effective amount of a compound of the invention, or a pharmaceutically acceptable salt thereof, in combination with a pharmaceutically acceptable diluent or carrier.

The invention also includes a pharmaceutical composition comprising a therapeutically effective amount of a compound of the invention, or a pharmaceutically acceptable salt thereof, in combination with a therapeutically effective amount of an AIDS treatment agent selected from an HIV inhibitor agent, an anti-infective agent, and an immunomodulator. The HIV inhibitor agent may include an HIV-protease inhibitor, a nucleoside reverse transcriptase inhibitor, or a non-nucleoside reverse transcriptase inhibitor.

The invention also includes methods of preventing the proliferation of HIV virus, treating AIDS, delaying the onset of AIDS or ARC symptoms, and generally inhibiting HIV integrase. The methods comprise administering to a mammal infected with HIV (HIV positive) an amount of a compound of the invention, in a therapeutically effective dose or administration to inhibit the growth of HIV infected cells of the mammal.

In another aspect of the invention, the activity of HIV integrase is inhibited by a method comprising the step of treating a sample suspected of containing HIV virus with a compound or composition of the invention.

The invention also includes processes and novel intermediates disclosed herein which are useful for preparing compounds of the invention. Some of the compounds of the invention are useful to prepare other compounds of the invention.

This invention also includes methods of increasing cellular accumulation, bioavailability, or retention of drug compounds, thus improving their therapeutic and diagnostic value, by administering a phosphonate prodrug form of a compound of the invention.

Another aspect of the invention provides a method for inhibiting the activity of HIV integrase comprising the step of contacting a sample suspected of containing HIV virus with the composition embodiments of the invention.

In other aspects, novel methods for the synthesis, analysis, separation, isolation, crystallization, purification, characterization, resolution of isomers including enantiomers and diastereomers, and testing of the compounds of this invention are provided.

DETAILED DESCRIPTION OF EXEMPLARY EMBODIMENTS

Reference will now be made in detail to certain embodiments of the invention, examples of which are illustrated in the accompanying descriptions, structure and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

Definitions

Unless stated otherwise, the following terms and phrases as used herein are intended to have the following meanings:

The terms "phosphonate" and "phosphonate group" mean a functional group or moiety within a molecule that comprises at least one phosphorus-carbon bond, and at least one phosphorus-oxygen double bond. The phosphorus atom is further substituted with oxygen, sulfur, and nitrogen substituents. These substituents may be part of a prodrug moiety. As defined herein, "phosphonate" and "phosphonate group" include molecules with phosphonic acid, phosphonic monoester, phosphonic diester, phosphonamidate, phosphondiamidate, and phosphonthioate functional groups.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Pharmaceutically acceptable prodrug" refers to a compound that is metabolized in the host, for example hydrolyzed or oxidized, by either enzymatic action or by general acid or base solvolysis, to form an active ingredient. Typical examples of prodrugs of the compounds of the invention have biologically labile protecting groups on a functional moiety of the compound. Prodrugs include compounds that can be oxidized, reduced, aminated, deaminated, esterified, deesterified, alkylated, dealkylated, acylated, deacylated, phosphorylated, dephosphorylated, photolyzed, hydrolyzed, or other functional group change or conversion involving forming or breaking chemical bonds on the prodrug.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in Textbook of Drug Design and Development (1991), P. Krogsgaard-Larsen and H. Bundgaard, Eds. Harwood Academic Publishers, pp. 113-191). Enzymes which are capable of an enzymatic activation mechanism with the prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A "prodrug" is thus a covalently modified analog of a therapeutically-active compound.

Exemplary prodrug moieties include the hydrolytically sensitive or labile acyloxymethyl esters —$CH_2OC(=O)R^9$ and acyloxymethyl carbonates —$CH_2OC(=O)OR^9$ where $R^9$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar etal (1983) J. Pharm. Sci. 72: 324; also U.S. Pat. Nos. 4,816,570, 4,968,788, 5,663,159 and 5,792,756. In certain compounds of the invention, a prodrug moiety is part of a phosphonate group. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2OC(=O)C(CH_3)_3$. An exemplary acyloxymethyl carbonate prodrug moiety is pivaloyloxymethylcarbonate (POC) —$CH_2OC(=O)OC(CH_3)_3$.

The phosphonate group may be a phosphonate prodrug moiety. The prodrug moiety may be sensitive to hydrolysis, such as, but not limited to a pivaloyloxymethyl carbonate (POC) or POM group. Alternatively, the prodrug moiety may be sensitive to enzymatic potentiated cleavage, such as a lactate ester or a phosphonamidate-ester group. Exemplary phosphonate prodrug moieties include by way of example and not limitation groups of the structure $A^3$.

Aryl esters of phosphorus groups, especially phenyl esters, are reported to enhance oral bioavailability (DeLambert etal (1994) J. Med. Chem. 37: 498). Phenyl esters containing a carboxylic ester ortho to the phosphate have also been described (Khamnei and Torrence, (1996) J. Med. Chem. 39:4109-4115). Benzyl esters are reported to generate the parent phosphonic acid. In some cases, substituents at the ortho- or para-position may accelerate the hydrolysis. Benzyl analogs with an acylated phenol or an alkylated phenol may generate the phenolic compound through the action of enzymes, e.g. esterases, oxidases, etc., which in turn undergoes cleavage at the benzylic C—O bond to generate the phosphoric acid and the quinone methide intermediate. Examples of this class of prodrugs are described by Mitchell etal (1992) *J. Chem. Soc. Perkin Trans. I* 2345; Brook etal WO 91/19721. Still other benzylic prodrugs have been described containing a carboxylic ester-containing group attached to the benzylic methylene (Glazier etal WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech etal (1993) *Antiviral Res.*, 22: 155-174; Benzaria etal (1996) *J. Med. Chem.* 39: 4958). Cyclic phosphonate esters have also been described as prodrugs of phosphorus-containing compounds (Erion etal, U.S. Pat. No. 6,312,662).

"Protecting group" refers to a moiety of a compound that masks or alters the properties of a functional group or the properties of the compound as a whole. The chemical substructure of a protecting group varies widely. One function of a protecting group is to serve as intermediates in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991, which is incorporated herein by reference. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous. Exemplary protecting groups include by way of example and not limitation groups of the structure $R^X$ other than hydrogen.

Any reference to any of the compounds of the invention also includes a reference to a physiologically acceptable salt thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of an hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$).

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: ethylene or vinyl (—$CH=CH_2$), allyl (—$CH_2CH=CH_2$), cyclopentenyl (—$C_5H_7$), and 5-hexenyl (—$CH_2CH_2CH_2CH_2CH=CH_2$)

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—$CH_2C$≡CH), The terms "alkylene" and "alkyldiyl" each refer to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene, i.e. double carbon-carbon bond moiety. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne, i.e. triple carbon-carbon bond moiety. Typical alkynylene radicals include, but are not limited to: acetylene (—C≡C—), propargyl (—CH$_2$C≡C—), and 4-pentynyl (—CH$_2$CH$_2$CH$_2$C≡CH—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Heteroaryl" means a monovalent aromatic radical of one or more carbon atoms and one or more atoms selected from N, O, S, or P, derived by the removal of one hydrogen atom from a single atom of a parent aromatic ring system. Heteroaryl groups may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). Heteroaryl bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The heteroaryl group may be bonded to the drug scaffold through a carbon, nitrogen, sulfur, phosphorus or other atom by a stable covalent bond.

Heteroaryl groups include, for example: pyridyl, dihydropyridyl isomers, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

Substituted substituents such as "substituted alkyl", "substituted aryl", "substituted heteroaryl" and "substituted arylalkyl" mean alkyl, aryl, and arylalkyl respectively, in which one or more hydrogen atoms are each independently replaced with a substituent. Typical substituents include, but are not limited to, —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR —S(=O)$_2$O$^-$, —S(=O)$_2$OH, —S(=O)$_2$R, —OS(=O)$_2$OR, —S(=O)$_2$NR, —(=O)R, —OP(=O)O$_2$RR, —P(=O)O$_2$RR —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, protecting group or prodrug moiety. Alkylene, alkenylene, and alkynylene groups may also be similarly substituted.

"Heterocycle" means a saturated, unsaturated or aromatic ring system including at least one N, O, S, or P. Heterocycle thus include heteroaryl groups. Heterocycle as used herein includes by way of example and not limitation these heterocycles described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; Katritzky, Alan R., Rees, C. W. and Scriven, E. "Comprehensive Heterocyclic Chemistry" (Pergamon Press, 1996); and J. Am. Chem. Soc. (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

One embodiment of the bis-tetrahydrofuranyl group is:

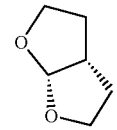

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" means a saturated, unsaturated or aromatic ring system having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. Carbocycle thus includes some aryl groups.

"Linker" or "link" means a chemical moiety comprising a covalent bond or a chain of atoms that covalently attaches a phosphonate group to a drug. Linkers include L interposed between Ar and the nitrogen of the tricyclic compounds of the invention. The structures herein may refer to linkers as "link" or "L". Linkers may also be interposed between a phosphorus-containing $A^3$ group and the $R^1$, $R^2$, $R^3$, or $R^4$ position of the compounds of the invention. Linkers include, but are not limited to moieties such as O, S, NR, N—OR, $C_1$-$C_{12}$ alkylene, $C_1$-$C_{12}$ substituted alkylene, $C_2$-$C_{12}$ alkenylene, $C_2$-$C_{12}$ substituted alkenylene, $C_2$-$C_{12}$ alkynylene, $C_2$-$C_{12}$ substituted alkynylene, C(=O)NH, C(=O), S(=O)$_2$, C(=O)NH(CH$_2$)$_n$, and (CH$_2$CH$_2$O)$_n$, where n may be 1, 2, 3, 4, 5, or 6. Linkers also include repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

HIV-Integrase Inhibitor Compounds

Novel tricyclic compounds with inhibitory activity against HIV integrase are described, including any pharmaceutically acceptable salts thereof.

In one aspect, the invention comprises a compound having the structure:

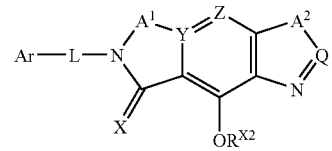

wherein:

$A^1$ and $A^2$ are independently selected from O, S, NR, C(R$^2$)$_2$, CR$^2$OR, CR$^2$OC(=O)R, C(=O), C(=S), CR$^2$SR, C(=NR), C(R$^2$)$_2$—C(R$^3$)$_2$, C(R$^2$)=C(R$^3$), C(R$^2$)$_2$—O, NR—C(R$^3$)$_2$, N=C(R$^3$), N=N, SO$_2$—NR, C(=O)C(R$^3$)$_2$, C(=O)NR, C(R$^2$)$_2$—C(R$^3$)$_2$—C(R$^3$)$_2$, C(R$^2$)=C(R$^3$)—C(R$^3$)$_2$, C(R$^2$)C(=O)NR, C(R$^2$)C(=S)NR, C(R$^2$)=N—C(R$^3$)$_2$, C(R$^2$)=N—NR, and N=C(R$^3$)—NR;

Q is N, $^+$NR, or CR$^4$;

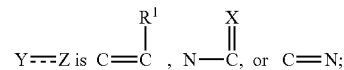

L is selected from a bond, O, S, S—S, S(=O), S(=O)$_2$, S(=O)$_2$NR, NR, N—OR, $C_1$-$C_{12}$ alkylene, $C_1$-$C_{12}$ substituted alkylene, $C_2$-$C_{12}$ alkenylene, $C_2$-$C_{12}$ substituted alkenylene, $C_2$-$C_{12}$ alkynylene, $C_2$-$C_{12}$ substituted alkynylene, C(=O)NH, OC(=O)NH, NHC(=O)NH, C(=O), C(=O)NH(CH$_2$)$_n$, or (CH$_2$CH$_2$O)$_n$, where n may be 1, 2, 3, 4, 5, or 6;

X is selected from O, S, NH, NR, N—OR, N—NR$_2$, N—CR$_2$OR and N—CR$_2$NR$_2$;

Ar is selected from $C_3$-$C_{12}$ carbocycle, $C_3$-$C_{12}$ substituted carbocycle, $C_6$-$C_{20}$ aryl, $C_6$-$C_{20}$ substituted aryl, $C_2$-$C_{20}$ heteroaryl, and $C_2$-$C_{20}$ substituted heteroaryl;

$R^1$, $R^2$, $R^3$ and $R^4$ are each independently selected from H, F, Cl, Br, I, OH, —NH$_2$, —NH$_3^+$, —NHR, —NR$_2$, —NR$_3^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —SO$_2$R, —SO$_2$Ar, —SOAr, —SAr, —SO$_2$NR$_2$, —SOR, —CO$_2$R, —C(=O)NR$_2$, 5-7 membered ring lactam, 5-7 membered ring lactone, —CN, —N$_3$, —NO$_2$, $C_1$-$C_8$ alkoxy, $C_1$-$C_8$ trifluoroalkyl, $C_1$-$C_8$ alkyl, $C_1$-$C_8$ substituted alkyl, $C_3$-$C_{12}$ carbocycle, $C_3$-$C_{12}$ substituted carbocycle, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, phosphate, and a prodrug moiety;

when taken together on a single carbon, two $R^2$ or two $R^3$ may form a spiro ring; and R is independently selected from H, $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, phosphate, and a prodrug moiety;

$R^{X2}$ is independently selected from H, $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, phosphate, a prodrug, a pharmaceutically acceptable prodrug, a prodrug moiety, a protecting group, and a phosphonate prodrug moiety;

and the salts, solvates, resolved enantiomers and purified diastereomers thereof;

with the proviso that when Y=Z is C=C(OH), X is O, $A^1$ is C(=O), $A^2$ is $C(R^2)$=$C(R^3)$, and Q is CH, then L is not a bond.

In one aspect, the invention is a compound having the structure:

or salt thereof;
wherein:

$A^1$ and $A^2$ are independently selected from O, S, NR, $C(R^2)_2$, $CR^2OR$, $CR^2OC(=O)R$, C(=O), C(=S), $CR^2SR$, C(=NR), $C(R^2)_2$—$C(R^3)_2$, $C(R^2)$=$C(R^3)$, NR—$C(R^3)_2$, N=$C(R^3)$, N=N, $SO_2$—NR, $C(=O)C(R^3)_2$, C(=O)NR, $C(R^2)_2$—$C(R^3)_2$—$C(R^3)_2$, $C(R^2)$≡$C(R^3)$—$C(R^3)_2$, $C(R^2)C$(=O)NR, $C(R^2)C$(=S)NR, $C(R^2)$=N—$C(R^3)_2$, $C(R^2)$=N—NR, and N=$C(R^3)$—NR;

Q is N, $^+$NR, or $CR^4$;

L is selected from a bond, O, S, S—S, S(=O), $S(=O)_2$, $S(=O)_2NR$, NR, N—OR, $C_1$-$C_{12}$ alkylene, $C_1$-$C_{12}$ substituted alkylene, $C_2$-$C_{12}$ alkenylene, $C_2$-$C_{12}$ substituted alkenylene, $C_2$-$C_{12}$ alkynylene, $C_2$-$C_{12}$ substituted alkynylene, C(=O)NH, OC(=O)NH, NCH(=O)NH, C(=O), C(=O)NH$(CH_2)_n$, or $(CH_2CH_2O)_n$, where n may be 1, 2, 3, 4, 5, or 6;

X is selected from O, S, NH, NR, N—OR, N—$NR_2$, N—$CR_2OR$ and N—$CR_2NR_2$;

Ar is selected from $C_3$-$C_{12}$ carbocycle, $C_3$-$C_{12}$ substituted carbocycle, $C_6$-$C_{20}$ aryl, $C_6$-$C_{20}$ subsituted aryl, $C_2$-$C_{20}$ heteroaryl, and $C_2$-$C_{20}$ substituted heteroaryl;

$R^1$, $R^2$, $R^3$ and $R^4$ are each independently selected from H, F, Cl, Br, I, OH, —$NH_2$, —$NH_3^+$, —NHR, —$NR_2$, —$NR_3^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$$C_8$ alkylhydroxyl, $C_1$-$C_8$ alkylthiol, —$SO_2R$, —$SO_2Ar$, —SOAr, —SAr, —$SO_2NR_2$, —SOR, —$CO_2R$, —C(=O)$NR_2$, 5-7 membered ring lactam, 5-7 membered ring lactone, —CN, —$N_3$, —$NO_2$, $C_1$-$C_8$ alkoxy, $C_1$-$C_8$ trifluoroalkyl, $C_1$-$C_8$ alkyl, $C_1$-$C_8$ substituted alkyl, $C_3$-$C_{12}$ carbocycle, $C_3$-$C_{12}$ substituted carbocycle, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, phosphate, and a prodrug moiety;

when taken together on a single carbon, two $R^2$ or two $R^3$ may form a spiro ring;

R is independently selected from H, $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, phosphate, and a prodrug; and P is a protecting group selected from benzyhydryl ($CHPh_2$), trialkylsyl ($R_3Si$), 2-trimethylsiloxyethyl, alkoxymethyl ($CH_2OR$), and ester (C(=O)R).

Substituted alkylene, substituted alkyenylene, substituted alkynylene, substituted aryl, and substituted heteroaryl are independently substituted with one or more substituents selected from F, Cl, Br, I, OH, amino (—$NH_2$), ammonium (—$NH_3^+$), alkylamino, dialkylamino, trialkylammonium, $C_1$-$C_8$ alkyl, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—$SO_2R$), arylsulfone (—$SO_2Ar$), arylsulfoxide (—SOAr), arylthio (—SAr), sulfonamide (—$SO_2NR_2$), alkylsulfoxide (—SOR), ester (—$CO_2R$), amido (—C(=O)$NR_2$), 5-7 membered ring lactam, 5-7 membered ring lactone, nitrile (—CN), azido (—$N_3$), nitro (—$NO_2$), $C_1$-$C_8$ alkoxy (—OR), $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, phosphonate, phosphate, polyethyleneoxy, and a prodrug moiety.

X may be O, S, NH, NR, N—OR, N—$NR_2$, N—$CR_2OR$ or N—$CR_2NR_2$.

Ar groups may be any saturated, unsaturated or aromatic ring or ring system comprising a mono- or bicyclic carbocycle or heterocycle, e.g. 3 to 12 ring atoms. The rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

For example, Ar may be $C_3$-$C_{12}$ carbocycle, $C_3$-$C_{12}$ substituted carbocycle, $C_6$-$C_{20}$ aryl, $C_6$-$C_{20}$ substituted aryl, $C_2$-$C_{20}$ heteroaryl, or $C_2$-$C_{20}$ substituted heteroaryl.

Exemplary embodiments of $C_6$-$C_{20}$ substituted aryl groups include halo-substituted phenyl such as 4-fluorophenyl, 4-chlorophenyl, 4-trifluoromethyl, 2-amide phenyl, 3,5-dichlorophenyl, and 3,5-difluorophenyl.

Ar groups include substituted phenyl groups such as, but not limited to:

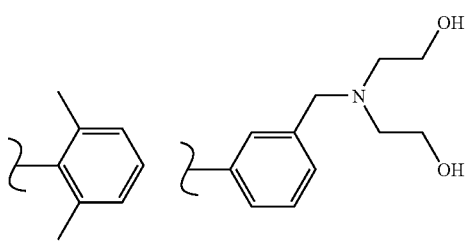

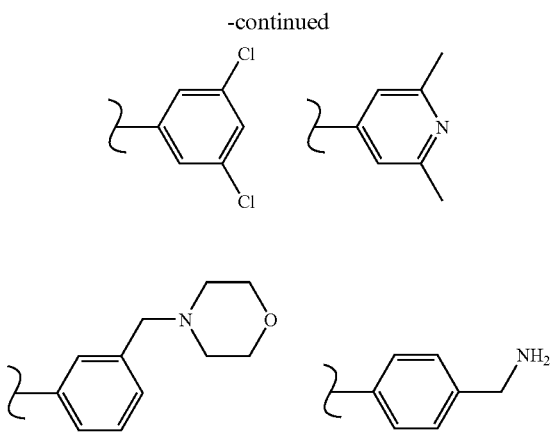

Other examples of substituted phenyl groups include:

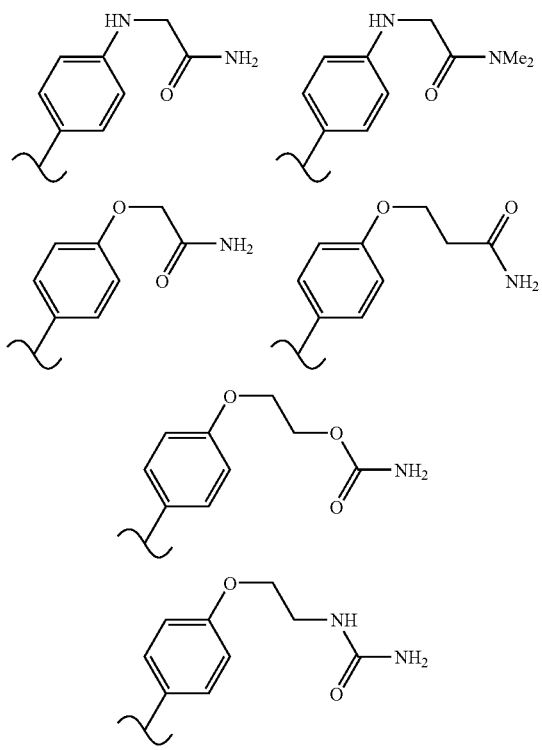

where a wavy line ⌇, in any orientation, indicates the covalent attachment site to L.

Ar groups also include disubstituted phenyl groups such as, but not limited to:

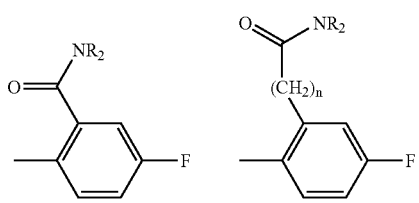

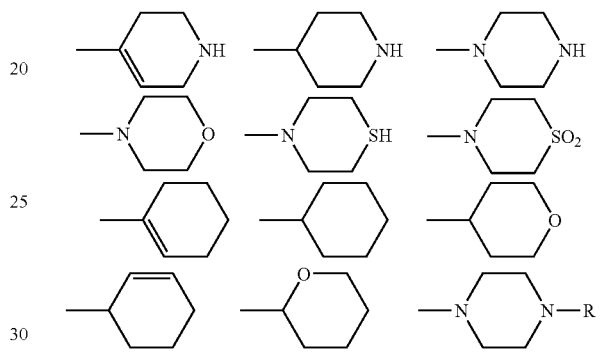

where n is 1 to 6.

Ar groups also include carbocycles such as, but not limited to:

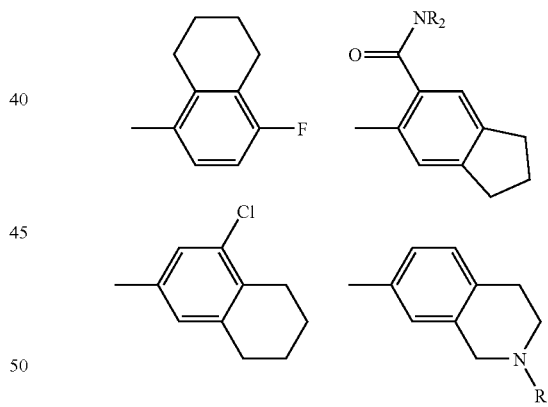

Ar groups also include phenyl and substituted phenyl fused to a carbocycle to form groups including:

$R^1$, $R^2$, $R^3$, and $R^4$, and substituents of Ar, may independently be H, F, Cl, Br, I, OH, amino (—$NH_2$), ammonium (—$NH_3^+$), alkylamino, dialkylamino, trialkylammonium, $C_1$-$C_8$ alkylhalide, carboxylate, sulfate, sulfainate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, alkylsulfone (—$SO_2R$), arylsulfone (—$SO_2Ar$), arylsulfoxide (—SOAr), arylthio (—SAr), sulfonamide (—$SO_2NR_2$), alkylsulfoxide (—SOR), ester (—$CO_2R$), amido (—C(=O)$NR_2$), 5-7 membered ring lactam, 5-7 membered ring lactone, nitrile (—CN), azido (—$N_3$), nitro (—$NO_2$), $C_1$-$C_8$ alkoxy (—OR), $C_1$-$C_8$ trifluoroalkyl, $C_1$-$C_8$ alkyl, $C_1$-$C_8$ substituted alkyl, $C_3$-$C_{12}$ carbocycle, $C_3$-$C_{12}$ substituted carbocycle, $C_6$-$C_{20}$ aryl, $C_6$-$C_{20}$ substituted aryl, $C_2$-$C_{20}$ heteroaryl, and $C_2$-$C_{20}$ substituted heteroaryl, phosphonate, phosphate, polyethyleneoxy, and a prodrug moiety.

$R^1$, $R^2$, $R^3$, and $R^4$ also include: —OC(=O)OR, —OC(=O)NR$_2$, —OC(=S)NR$_2$, —OC(=O)NRNR$_2$, —OC(=O)R, —C(=O)OR, —C(=O)NR$_2$, —C(=O)NRNR$_2$, —C(=O)R, —OSO$_2$NR$_2$ (sulfamate), —NR$_2$, —NRSO$_2$R, —NRC(=S)NR$_2$, —SR, —S(O)R, —SO$_2$R, —SO$_2$NR$_2$ (sulfonamide), —OSO$_2$R (sulfonate), —P(=O)(OR)$_2$, —P(=O)(OR)(NR$_2$), —P(=O)(NR$_2$)$_2$, —P(=S)(OR)$_2$, —P(=S)(OR)(NR$_2$), —P(=S)(NR$_2$)$_2$, and including prodrug substituted forms thereof.

Exemplary embodiments of $R^1$, $R^2$, $R^3$, and $R^4$ include the structures:

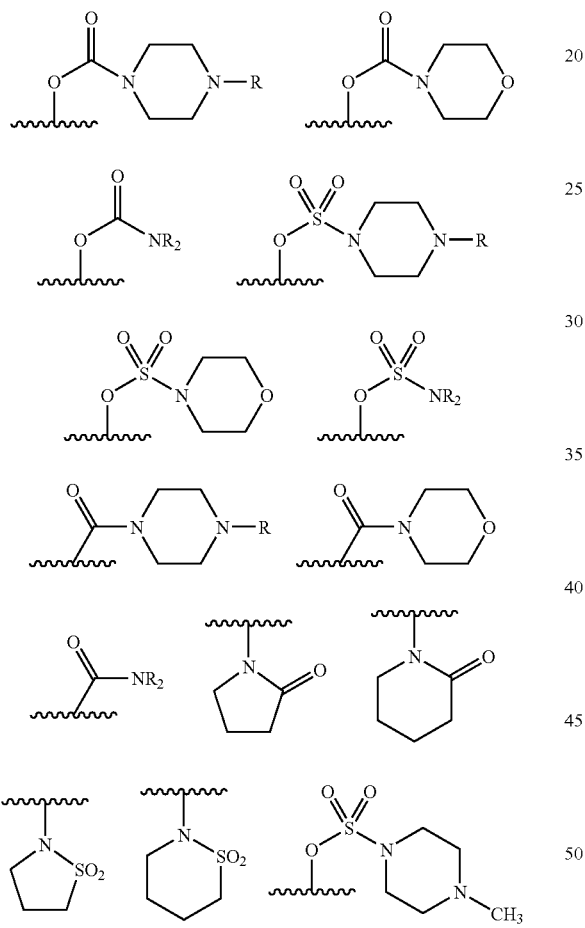

where the wavy line indicates the point of covalent attachment on the tricyclic structure.

R may be independently selected from H, $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, $C_2$-$C_{20}$ substituted heteroaryl, polyethyleneoxy, phosphonate, phosphate, and a prodrug moiety. Two R groups may form a ring, such as when the two R groups are bonded to a nitrogen atom and form a ring such as aziridinyl, azetidinyl, pyrrolidinyl, pyrazinyl, imidazolyl, piperidyl, piperazinyl, pyridinium, or morpholino.

The following embodiments of $A^1$ and $A^2$ in the compounds of the invention include but are not limited to the following structures. Various embodiments of $A^1$ form 5-membered rings in the exemplary structures:

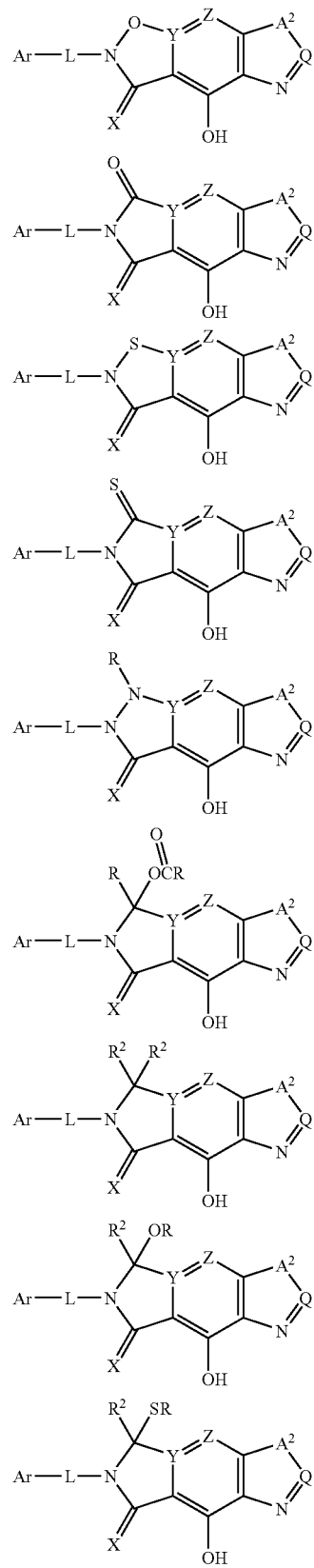

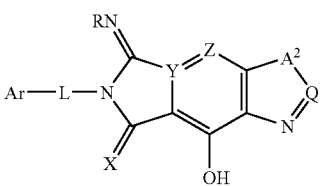
Various embodiments of A¹ form 6-membered rings in the exemplary structures:
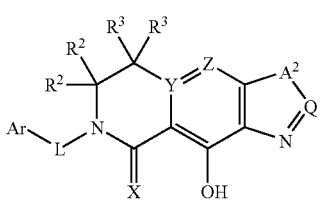
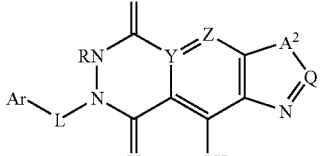
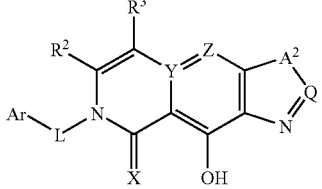
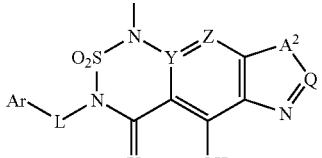
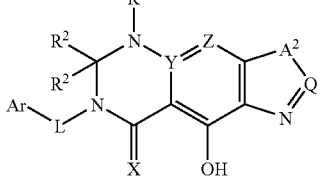
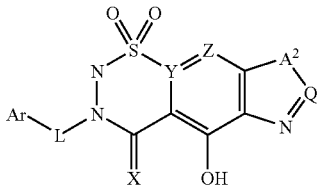
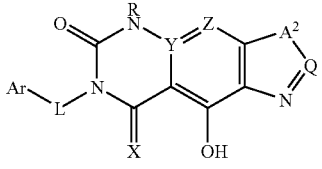
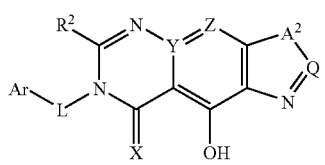
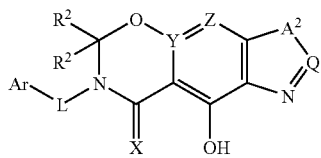
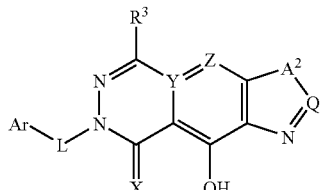
Various embodiments of A¹ form 7-membered rings in the exemplary structures:
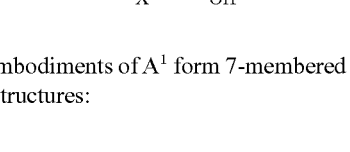
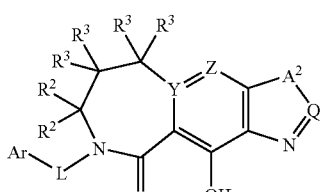
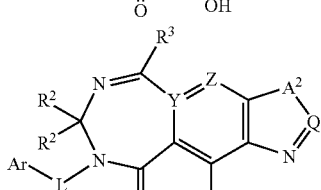
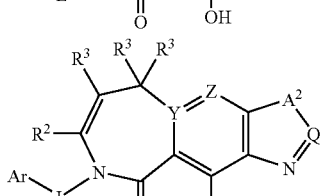
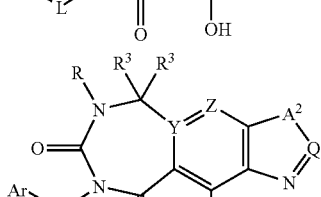
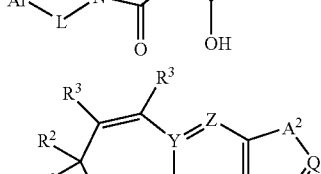
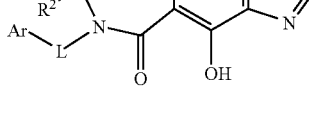

-continued
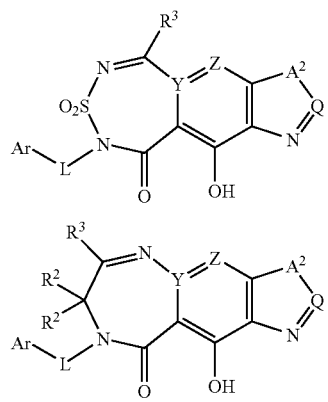
Various embodiments of $A^2$ form 5-membered rings in the exemplary structures:
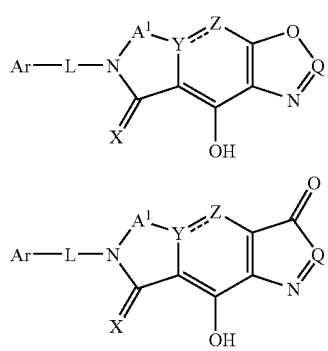
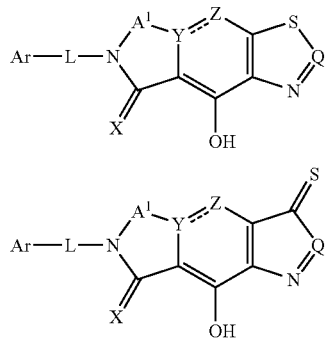
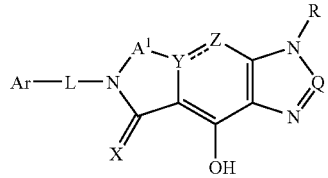
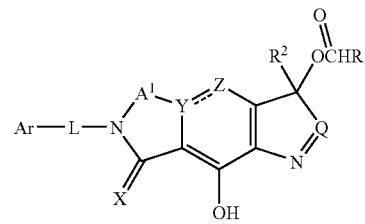
-continued
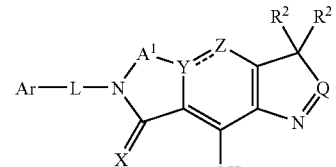
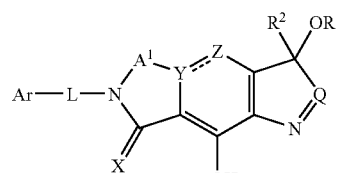
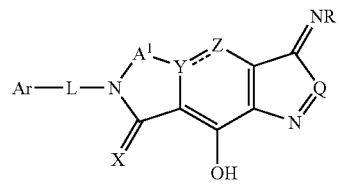
and
Other various embodiments of $A^2$ form 6-membered rings in the exemplary structures:
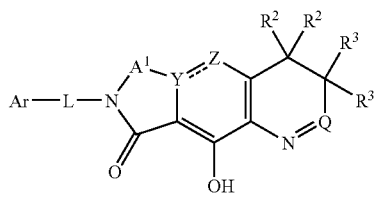
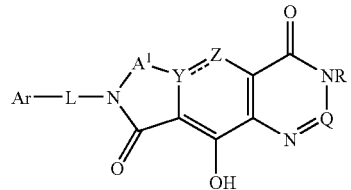
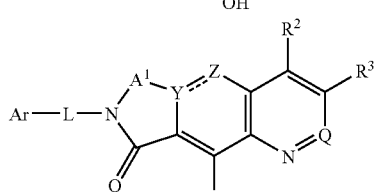
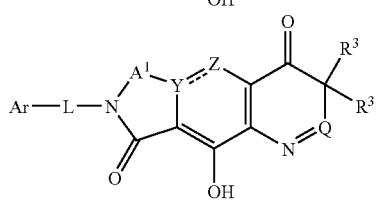

-continued
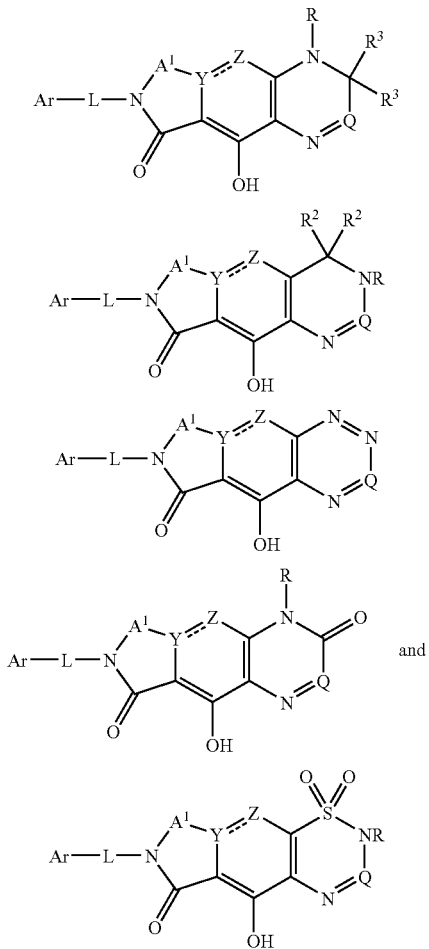
Other various embodiments of A² form 7-membered rings in the exemplary structures:
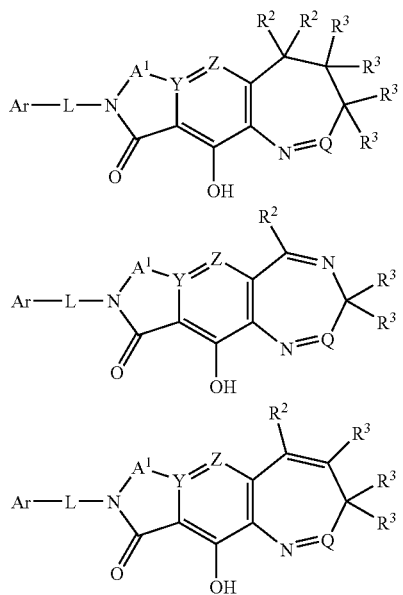
-continued
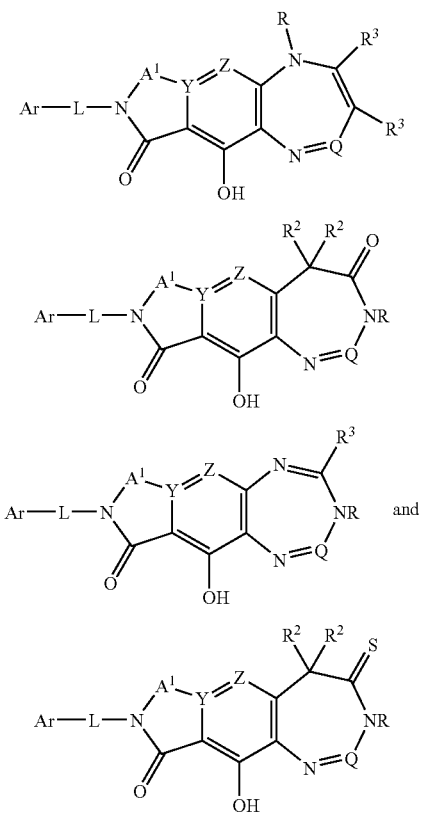
Compounds of the invention include Formulas I-IV, represented by the following structures:
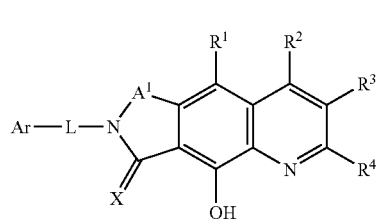
I
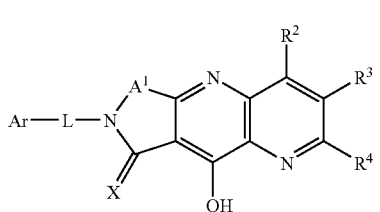
II
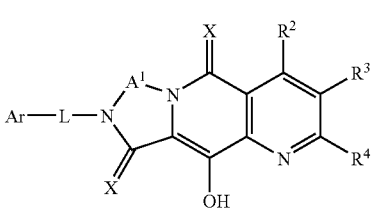
III -continued

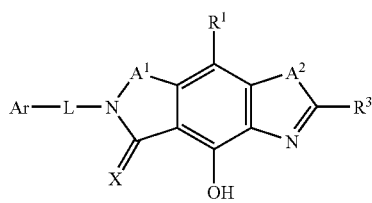

Formula I compounds thus include the following succinimide structure:

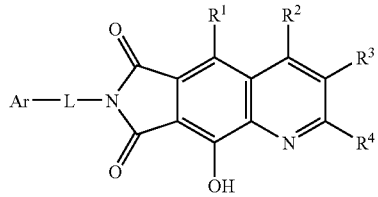

Embodiments of Formula I also include Ia-c where A is $CH_2$, $CH_2CH_2$, and $CH_2CH_2CH_2$, respectively:

Ia
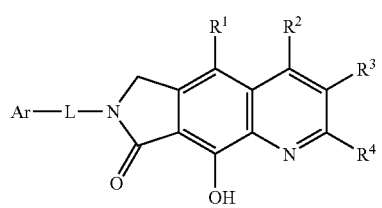

Ib
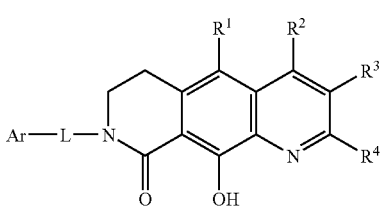

Ic
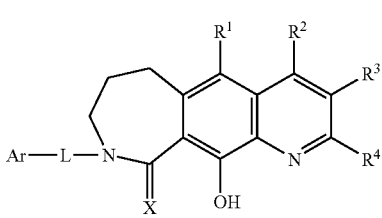

Where A forms a seven-membered ring, the 7 membered ring may be comprised of a second amide group, as shown by exemplary Formula Id:

Id
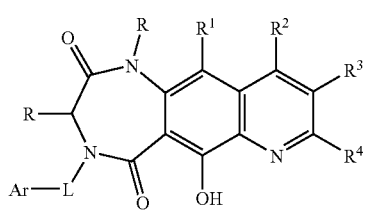

One aspect of the invention includes compounds with a cyclic imide group, e.g. 5,9-dihydroxy-pyrrolo[3,4-g]quinoline-6,8-dione (Myers, etal U.S. Pat. No. 5,252,560; Robinson, U.S. Pat. No. 5,854,275), where A is C(=O) and X is O, as in formula Ie:

Ie
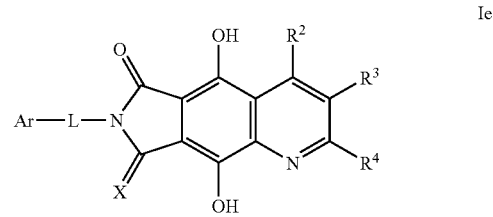

Along with other compounds of the invention, the cyclic imide group of Formula Ie provides functionality which may be in a pre-organized state for optimized HIV integrase inhibition relative to compounds without the cyclic imide group (Anthony, etal WO 02/30931; Zhuang, etal "Design and synthesis of 8-hydroxy-1,6-naphthyridines as novel HIV-1 integrase inhibitors" Interscience Conference on Antimicrobial Agents and Chemotherapy, San Diego, Calif., Sep. 27-30, 2002).

Formula Ia compounds include the following amide structure:

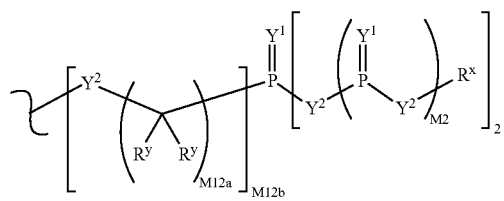

$R^1$, $R^2$, $R^3$, or $R^4$ may independently comprise a phosphonate group or phosphonate prodrug moiety. A tricyclic integrase inhibitor compound of the invention may include one or more phosphonate group or phosphonate prodrug moiety. For example, $R^1$, $R^2$, $R^3$, or $R^4$ may comprise the structure $A^3$, where $A^3$ is:

$$\left\{ \left[ Y^2 \left( \begin{matrix} R^y \\ R^y \end{matrix} \right)_{M12a} \right]_{M12b} \begin{pmatrix} Y^1 \\ \| \\ P \\ Y^2 \end{pmatrix} \left( Y^2 \begin{matrix} Y^1 \\ \| \\ P \\ Y^2 \end{matrix} R^x \right)_{M2} \right\}_2$$

$Y^1$ is independently O, S, $N(R^x)$, $N(O)(R^x)$, $N(OR^x)$, $N(O)(OR^x)$, or $N(N(R^x)_2)$.

$Y^2$ is independently a bond, O, $N(R^x)$, $N(O)(R^x)$, $N(OR^x)$, $N(O)(OR^x)$, $N(N(R^x)_2)$, —S(=O)— (sulfoxide), —S(=O)$_2$— (sulone), —S— (sulide), or —S—S— (disulfide).

M2 is 0, 1 or 2.

M12a is 1, 2, 3, 4, 5, 6, 7, 8, 9, 10, 11, or 12.

M12b is 0, 1, 2, 3, 4, 5, 6, 7, 8, 9, 10, 11, or 12.

$R^y$ is independently H, $C_1$-$C_6$ alkyl, $C_1$-$C_6$ substituted alkyl, aryl, substituted aryl, or a protecting group. Alternatively, taken together at a carbon atom, two vicinal $R^y$ groups form a ring, i.e. a spiro carbon. The ring may be all carbon atoms, for example, cyclopropyl, cyclobutyl, cyclopentyl, or cyclohexyl, or alternatively, the ring may contain one or more heteroatoms, for example, piperazinyl, piperidinyl, pyranyl, or tetrahydrofuryl.

$R^x$ is independently H, $C_1$-$C_6$ alkyl, $C_1$-$C_6$ substituted alkyl, $C_6$-$C_{20}$ aryl, $C_6$-$C_{20}$ substituted aryl, or a protecting group, or the formula:

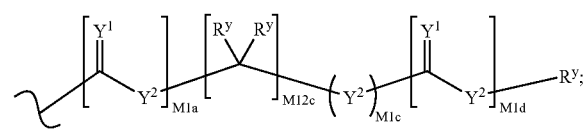

M1a, M1c, and M1d are independently 0 or 1.

M12c is 0, 1, 2, 3, 4, 5, 6, 7, 8, 9, 10, 11 or 12.

A linker may be interposed between positions $R^1$, $R^2$, $R^3$ or $R^4$ and substituent $A^3$. The linker may be O, S, NR, N—OR, $C_1$-$C_{12}$ alkylene, $C_1$-$C_{12}$ substituted alkylene, $C_2$-$C_{12}$ alkenylene, $C_2$-$C_{12}$ substituted alkenylene, $C_2$-$C_{12}$ alkynylene, $C_2$-$C_{12}$ substituted alkynylene, C(=O)NH, C(=O), S(=O)$_2$, C(=O)NH(CH$_2$)$_n$, and (CH$_2$CH$_2$O)$_n$, where n may be 1, 2, 3, 4, 5, or 6. Linkers may also be repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide. For example, the linker may comprise propargyl, urea, or alkoxy groups in the exemplary structures:

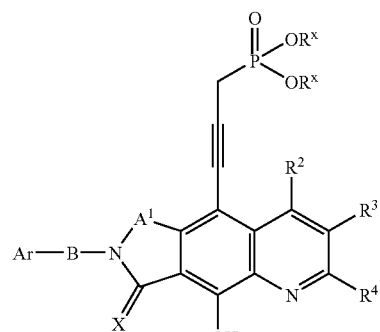

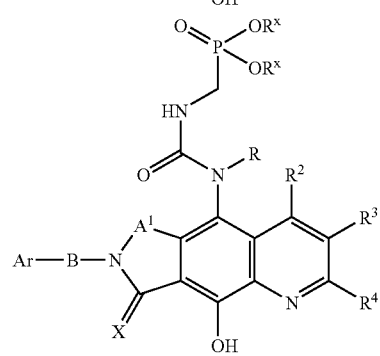

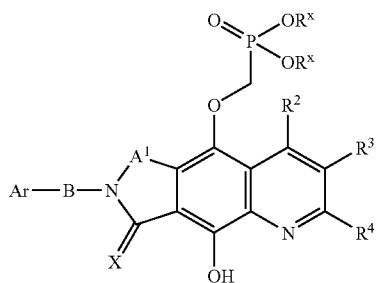

Embodiments of $A^3$ include where M2 is 0, such as:

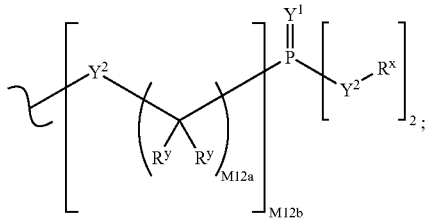

and where M12b is 1, $Y^1$ is oxygen, and $Y^{2b}$ is independently oxygen (O) or nitrogen (N($R^x$)) such as:

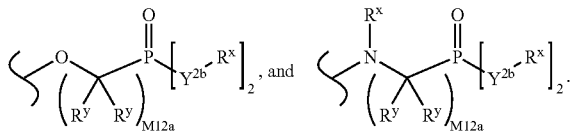

An embodiment of $A^3$ includes:

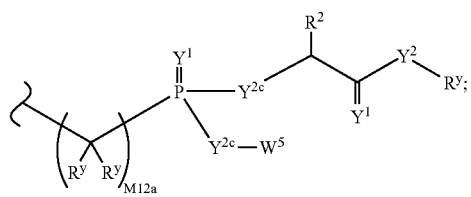

where $W^5$ is a carbocycle such as phenyl or substituted phenyl, and $Y^{2c}$ is independently O, N($R^y$) or S. For example, $R^1$ may be H and n may be 1.

$W^5$ also includes, but is not limited to, aryl and heteroaryl groups such as:

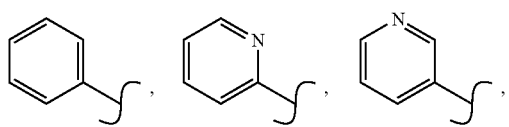

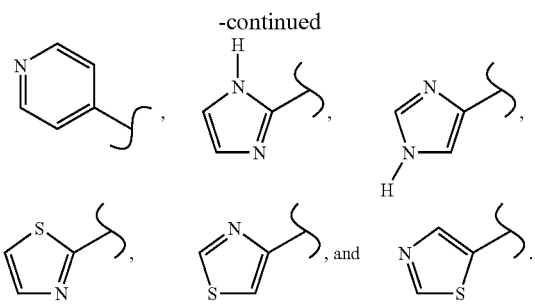

Another embodiment of $A^3$ includes:

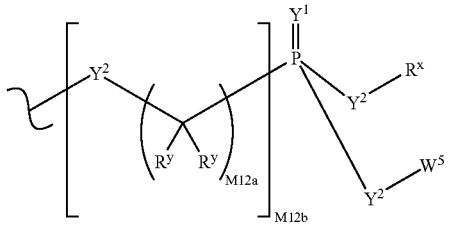

Such embodiments include:

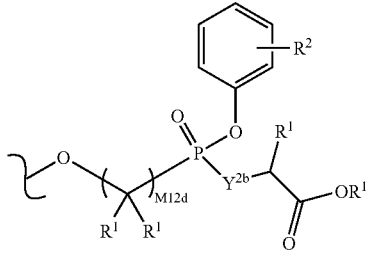

where $Y^{2b}$ is O or $N(R^x)$; M12d is 1, 2, 3, 4, 5, 6, 7 or 8; $R^1$ is H or $C_1$-$C_6$ alkyl; and phenyl carbocycle is substituted with 0 to 3 $R^2$ groups where $R^2$ is $C_1$-$C_6$ alkyl or substituted alkyl. Such embodiments of $A^3$ include phenyl phosphonamidate amino acid, e.g. alanate esters and phenyl phosphonate-lactate esters:

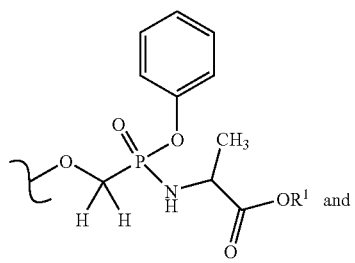

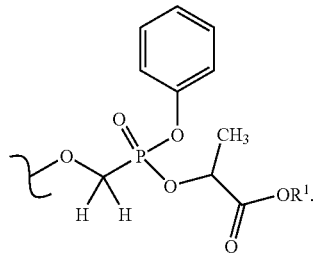

Embodiments of $R^x$ include esters, carbamates, carbonates, thioesters, amides, thioamides, and urea groups:

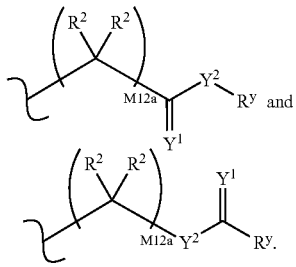

The compounds of the invention may also include one or more prodrug moieties located as a covalently-attached substituent at any location or site, e.g. Ar, L, X, A, $R^1$, $R^2$, $R^3$, $R^4$, or the 9-hydroxyl. One substituent which may be modified as a prodrug moiety is a phosphonate, phosphate, phosphinate or other phosphorus functionality (Oliyai etal *Pharmaceutical Res.* (1999) 16:1687-1693; Krise, J. and Stella, V. *Adv. Drug Del. Reviews* (1996) 19:287-310; Bischofberger etal, U.S. Pat. No. 5,798,340). Prodrug moieties of phosphorus functionality serve to mask anionic charges and decrease polarity. The phosphonate prodrug moiety may be an ester (Oliyai, etal *Intl. Jour. Pharmaceutics* (1999) 179:257-265), e.g. POC and POM (pivaloyloxymethyl, Yuan, etal *Pharmaceutical Res.* (2000) 17:1098-1103), or amidate which separates from the integrase inhibitor compound in vivo or by exposure in vitro to biological conditions, e.g. cells, tissue isolates. The separation may be mediated by general hydrolytic conditions, oxidation, enzymatic action or a combination of steps.

Compounds of the invention bearing one or more prodrug moieties may increase or optimize the bioavailability of the compounds as therapeutic agents. For example, bioavailability after oral administration may be preferred and depend on resistance to metabolic degradation in the gastrointestinal tract or circulatory system, and eventual uptake inside cells. Prodrug moieties are considered to confer said resistance by slowing certain hydrolytic or enzymatic metabolic processes. Lipophilic prodrug moieties may also increase active or passive transport of the compounds of the invention across cellular membranes (Darby, G. *Antiviral Chem. & Chemotherapy* (1995) Supp. 1, 6:54-63).

$R^{X2}$ is independently selected from H, $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, phosphate, a prodrug, a pharmaceutically acceptable prodrug, a prodrug moiety, a protecting group, and a phosphonate prodrug moiety; preferably H, a prodrug or a protecting group; more preferably, H or a prodrug; more preferably yet $R^{X2}$ is H.

Exemplary embodiments of the invention includes phosphonamidate and phosphoramidate (collectively "amidate") prodrug compounds. General formulas for phosphonamidate and phosphoramidate prodrug moieties include:

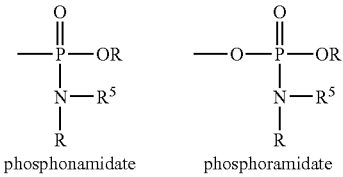

The phosphorus atom of the phosphonamidate group is bonded to a carbon atom. The nitrogen substituent $R^5$ may include an ester, an amide, or a carbamate functional group.

For example, $R^5$ may be $-CR_2C(=O)OR'$ where R' is H, $C_1$-$C_6$ alkyl, $C_1$-$C_6$ substituted alkyl, $C_6$-$C_{20}$ aryl, $C_6$-$C_{20}$ substituted aryl, $C_2$-$C_{20}$ heteroaryl, or $C_2$-$C_{20}$ substituted heteroaryl.

Exemplary embodiments of phosphonamidate and phosphoraridate prodrugs include:

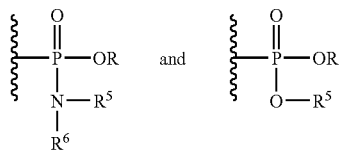

wherein $R^5$ is $-CR_2CO_2R^7$ where $R^6$ and $R^7$ are independently H or $C_1$-$C_8$ alkyl.

The nitrogen atom may comprise an amino acid residue within the prodrug moiety, such as a glycine, alanine, or valine ester (e.g. valacyclovir, see: Beauchamp, etal *Antiviral Chem. Chemotherapy* (1992) 3:157-164), such as the general structure:

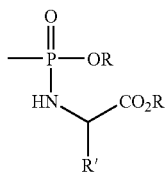

where R' is the amino acid side-chain, e.g. H, $CH_3$, CH$(CH_3)_2$, etc.

An exemplary embodiment of a phosphonamidate prodrug moiety is:

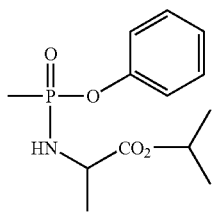

Another embodiment of the invention is directed toward an HIV integrase inhibitor tricyclic compound of the invention which is capable of accumulating in human PBMC (peripheral blood mononuclear cells). PBMC refer to blood cells having round lymphocytes and monocytes. Physiologically, PBMC are critical components of the mechanism against infection. PBMC may be isolated from heparinized whole blood of normal healthy donors or buffy coats, by standard density gradient centrifugation and harvested from the interface, washed (e.g. phosphate-buffered saline) and stored in freezing medium. PBMC may be cultured in multi-well plates. At various times of culture, supernatant may be either removed for assessment, or cells may be harvested and analyzed (Smith R. etal (2003) *Blood* 102(7): 2532-2540). The compounds of this embodiment may further comprise a phosphonate or phosphonate prodrug. Typically, the phosphonate or phosphonate prodrug has the structure $A^3$ as described herein.

Optionally, the compounds of this embodiment demonstrate improved intracellular half-life of the compounds or intracellular metabolites of the compounds in human PBMC when compared to analogs of the compounds not having the phosphonate or phosphonate prodrug. Typically, the half-life is improved by at least about 50%, more typically at least in the range 50-100%, still more typically at least about 100%, more typically yet greater than about 100%.

In another embodiment, the intracellular half-life of a metabolite of the compound in human PBMCs is improved when compared to an analog of the compound not having the phosphonate or phosphonate prodrug. In such embodiments, the metabolite may be generated intracellularly, or it is generated within human PBMC. The metabolite may be a product of the cleavage of a phosphonate prodrug within human PBMCs. The phosphonate prodrug may be cleaved to form a metabolite having at least one negative charge at physiological pH. The phosphonate prodrug may be enzymatically cleaved within human PBMC to form a phosphonate having at least one active hydrogen atom of the form P—OH.

The compounds of the invention may have pre-organized binding modes which optimize the binding affinity of other, known HIV integrase inhibitors. During binding between the inhibitor and the active site of the target HIV integrase enzyme, the inhibitor may attain a low energy conformation (also called bound conformation) in order to interact within an active site. Generally, ligands of molecules with multiple rotational bonds exist in many potential conformational states, most of which are not able to bind to the active site. The greater the number of possible ligand conformations typically results in a greater decrease in efficiency of the entropy contribution to the free energy of binding, and will result in less favorable binding affinities. One aspect of designing pre-organized binding features in an integrase inhibitor compound is incorporating conformational constraints that reduces the total number of conformational states and places the inhibitor into a correct binding conformation (Lam, P. Y. S. et al. *J. Med. Chem*, (1996) 39:3514-3525; Chen, J. M. et al. *Biochemistry* (1998) 37:17735-17744; Chen, J. M. et al. *Jour. Amer. Chem. Soc.* (2000) 122:9648-9654; Chen, J. M. et al U.S. Pat. No. 6,187,907; Chen, et al *Bio. Org. Med. Chem. Letters* (2002) 12:1195-1198). Knowledge of one or more preferred, i.e. low-energy, binding conformations is important for rational structure design and avoid inactive lead compounds.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The compounds of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exists in a variety of different forms, the invention is intended to encompass not only forms of the compounds that are in association with counter ions (e.g., dry salts), but also forms that are not in association with counter ions (e.g., aqueous or organic solutions).

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their unionized, as well as zwitterionic form, and combinations with stoichiometric amounts of water as in hydrates.

Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the invention can also exist as tautomeric, resonance isomers in certain cases. Typically, the structures shown herein exemplify only one tautomeric or resonance form of the compounds. For example, hydrazine, oxime, hydrazone groups may be shown in either the syn or anti configurations. The corresponding alternative configuration is contemplated as well. All possible tautomeric and resonance forms are within the scope of the invention.

One enantiomer of a compound of the invention can be separated substantially free of its opposing enantiomer by a method such as formation of diastereomers using optically active resolving agents (*Stereochemistry of Carbon Compounds* (1962) by E. L. Eliel, McGraw Hill; Lochmuller, C. H., (1975) *J. Chromatogr.*, 113:(3) 283-302). Separation of diastereomers formed from the racemic mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers. Alternatively, enantiomers can be separated directly under chiral conditions, method (3).

Under method (1), diastereomeric salts can be formed by reaction of enantiomerically pure chiral bases such as brucine, quinine, ephedrine, strychnine, (α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved may be reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111).

By method (3), a racemic mixture of two asymmetric enantiomers can be separated by chromatography using a chiral stationary phase (*Chiral Liquid Chromatography* (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", *J. of Chromatogr.* 513:375-378).

Enantiomers can be distinguished by methods used to distinguish other chiral molecules with asymmetric carbon atoms, such as optical rotation and circular dichroism.

Synthesis of HIV-Integrase Inhibitor Compounds

The compounds of the invention may be prepared by a variety of synthetic routes and methods known to those skilled in the art. The invention also relates to methods of making the compounds of the invention. The compounds are prepared by any of the applicable techniques of organic synthesis. Many such techniques are well known in the art. However, many of the known techniques are elaborated in: "Compendium of Organic Synthetic Methods", John Wiley & Sons, New York, Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., "Advanced Organic Chemistry", Third Edition, John Wiley & Sons, New York, 1985; "Comprehensive Organic Synthesis. Selectivity, Strategy & Efficiency in Modern Organic Chemistry" (9 Volume set) Barry M. Trost, Editor-in-Chief, Pergamon Press, New York, 1993.

A number of exemplary methods for the preparation of the compounds, Formulas I-IV, of the invention are provided herein. These methods are intended to illustrate the nature of such preparations are not intended to limit the scope of applicable methods.

Deliberate use may be made of protecting groups to mask reactive functionality and direct reactions regioselectively (Greene, etal (1991) "Protective Groups in Organic Synthesis", 2nd Ed., John Wiley & Sons). For example, useful protecting groups for the 8-hydroxyl group and other hydroxyl substituents include methyl, MOM (methoxymethyl), trialkylsilyl, benzyl, benzoyl, trityl, and tetrahydropyranyl. Certain aryl positions may be blocked from substitution, such as the 2-position as fluorine.

Formula I Compounds

Exemplary methods of synthesis of Formula I compounds are described below in Schemes 1-10 and 15-17. One method of synthesis of Formula I compounds of the invention is cyclization of a succinimide compound with a pyridine dicarboxylate compound to give tricyclic compounds (Murray and Semple, *Synthesis* (1996) 11:80-82; Jones and Jones, *Jour. Chem. Soc., Perkin Transactions I* (1973) 26-32), according to Scheme 1.

Scheme 1

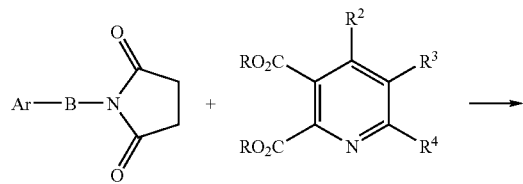

-continued

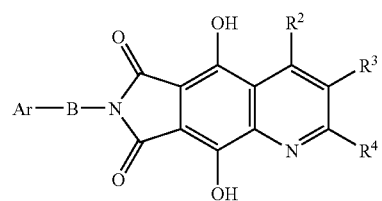

Alternatively, a succinimide with a labile protecting group (P) on the nitrogen may be reacted with a pyridine dicarboxylate compound. P may be an acid-labile protecting group, such as trialkylsilyl. Trialkylsilyl groups may also be removed with fluoride reagents. After P is removed, a variety of Ar-L groups may be covalently attached, according to Scheme 2.

Scheme 2

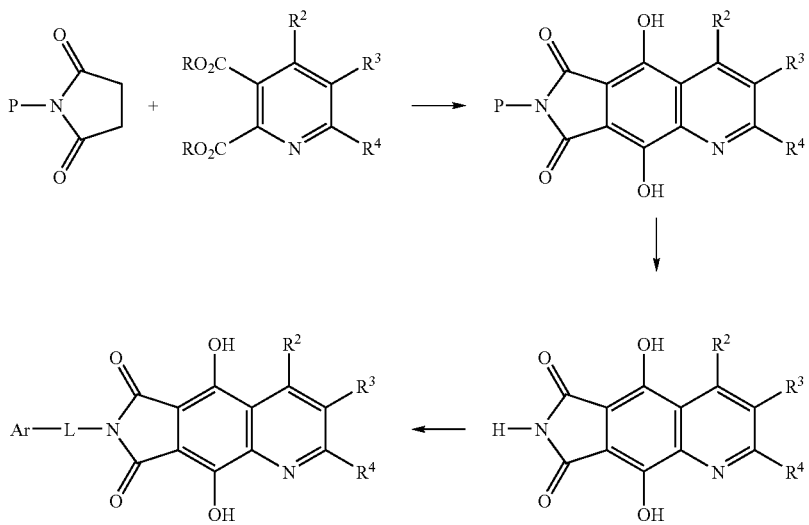

Imide compounds can be reduced with dissolving metal reducing agents, e.g. Zn, or hydride reagents, e.g. NaBH$_4$, to form a lactam. Exemplary regioselective conversions shown in Scheme 3 include:

Scheme 3

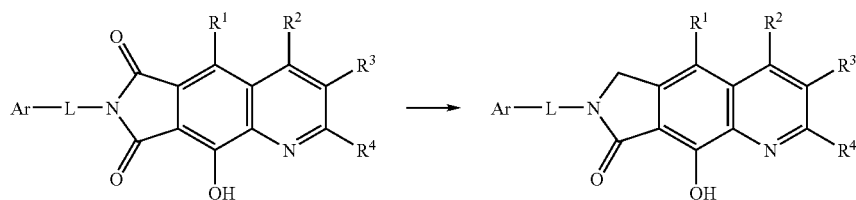

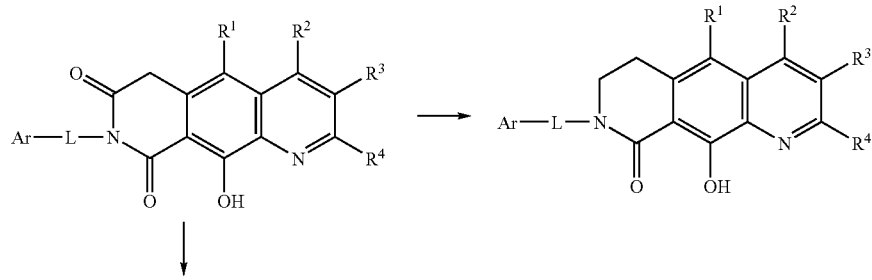

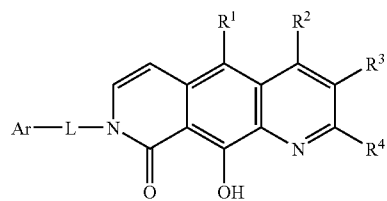

Imide compounds may also be reduced to the hydroxylactam under mild conditions. Reductions with sodium borohydride and cerium or samarium salts have been shown to proceed with regioselectivity on asymmetric imides (Mase, etal *J. Chem. Soc. Perkin Communication* 1 (2002) 707-709), as in Scheme 4, upper. Grignard reagents and acetylenic anions (Chihab-Eddine, etal *Tetrahedron Lett.* (2001) 42:573-576) may also add with regioselectivity to an imide carbonyl to form alkyl-hydroxylactam compounds, as in Scheme 4, lower). The phenolic oxygen groups may be protected and deprotected as necessary to furnish yield reactions.

Another synthetic route to the compounds of the invention proceeds through substituted quinoline intermediates (Clemence, etal U.S. Pat. No. 5,324,839; Billhardt-Troughton, etal U.S. Pat. No. 5,602,146; Matsumura, *J. Amer. Chem. Soc.* (1935) 57:124-128) having the general formula:

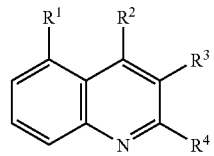

Scheme 4

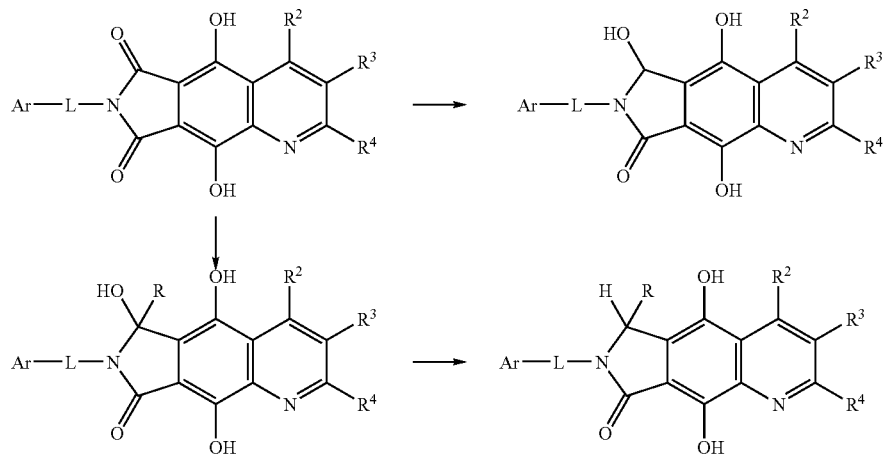

5,8-Dihydroxy quinoline compounds may be elaborated according to Scheme 5:

applied to the 5-membered lactam synthesis to control the regiochemistry as in Scheme 7:

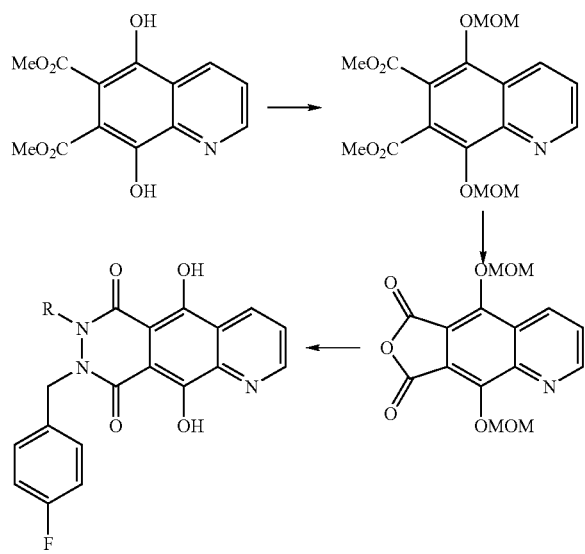

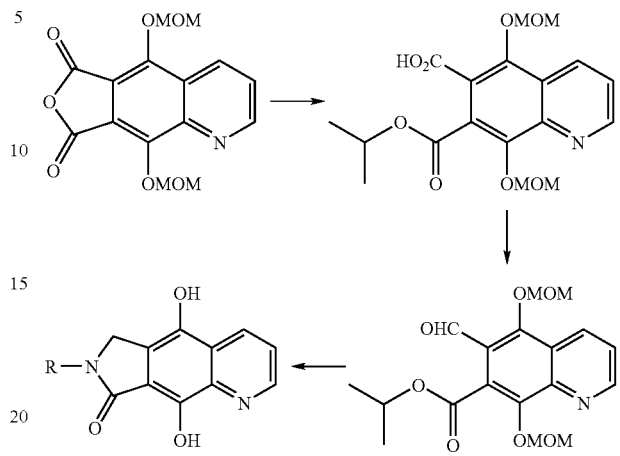

A cyclic imide may be conveniently alkylated, acylated, or otherwise reacted to form a broad array of compounds with Ar—L groups:

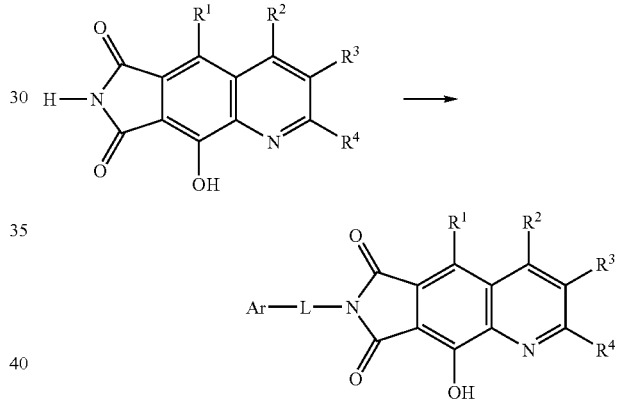

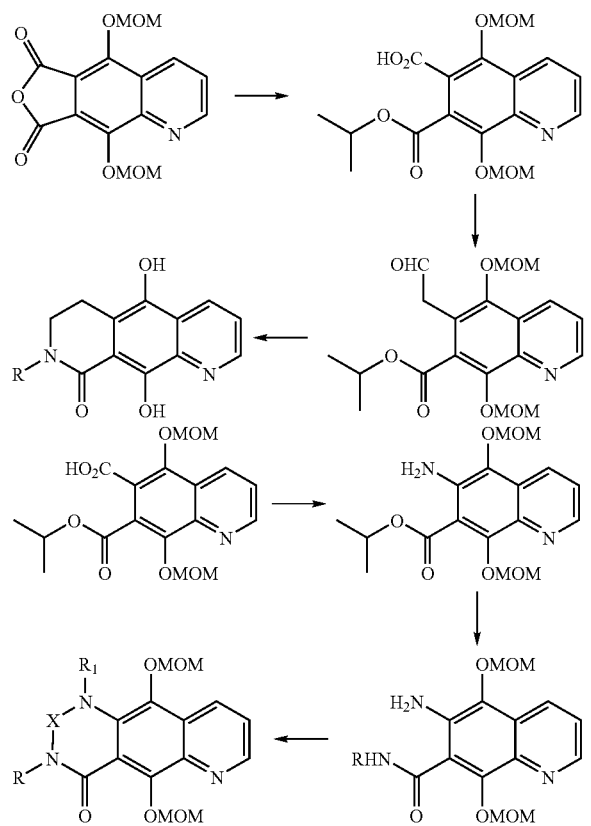

The cyclic anhydride below may be regioselectively esterified to give the compounds of the invention, for example via the route in Scheme 6 where MOM is methoxymethyl and X is, for example, C(═O), CRC(═O), C(═O)C(═O), and SO₂. See Ornstein, etal *Jour. Med. Chem.* (1989) 32:827-833. The same chemistry can be The Ar—L group may be attached as one reactant group, for example as an alkylating reagent like benzyl bromide (Ar=phenyl, L=CH₂) or a sulfonating reagent, like 4-methoxyphenyl sulfonyl chloride (Ar=4-methoxyphenyl, L=S(═O)₂. Alternatively, the Ar—L group may be attached by a multi step process. For example, the imide nitrogen may react with a sulfurizing reagent such as 2,2-dipyridyl disulfide to form an N-sulfide intermediate (Ar=2-pyridyl, L=S). Such an intermediate may be further elaborated to a variety of Ar—L groups where L is S, S(═O) or S(═O)₂.

Another synthetic route to the compounds of the invention proceeds through 7-substituted, 8-quinolinol intermediates (Zhuang, etal WO 02/36734; Vaillancourt, etal U.S. Pat. No. 6,310,211; Hodel, U.S. Pat. No. 3,113,135) having the general formulas, including aryl substituted compounds:

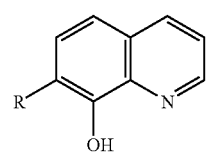

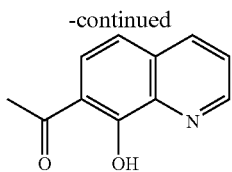

Annulation of the third, 5-7 membered ring can be conducted by appropriate selection of aryl substituents on the quinoline ring system, utilizing known synthetic transformations to give compounds of Formula I. For example, methods for coupling carboxylic acids and other activated acyl groups with amines to form carboxamides are well known in the art (March, J. *Advanced Organic Chemistry*, 3rd Edition, John Wiley & Sons, 1985, pp. 370-376). An exemplary cyclization includes the following:

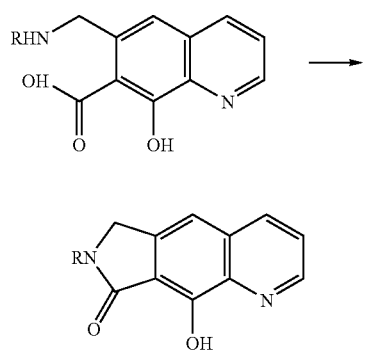

Scheme 8 below shows another synthetic route to compounds of the invention, i.e. Formula I. This route proceeds by cyclization of a 2-O-protected, 3 halo-aniline compound with an α,β-unsaturated carbonyl compound to give a functionalized quinoline. The α,β-unsaturated carbonyl compound may be, for example, an aldehyde (X=H), ketone (X=R), ester (X=OR), amide (X=NR2), acyl halide (X=Cl), or anhydride. Carbonylation via palladium catalysis can give an ester which may be elaborated to the amide functionality and cyclization to form a 5, 6, or 7 membered ring. The R group of phenolic oxygen may be a labile protecting group, e.g. trialkylsilyl or tetrahydropyranyl, which may be removed at a step in the synthetic route, or it may be a substituent which is retained in the putative integrase inhibitor compound.

Scheme 8

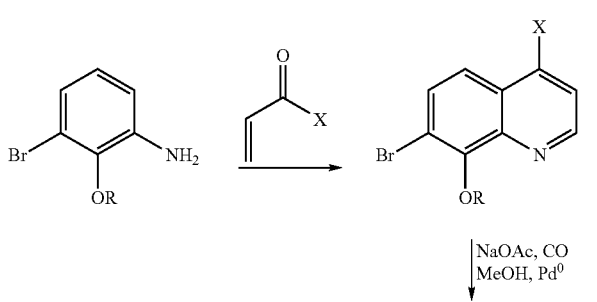

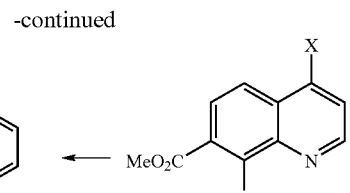

Halo quinoline intermediates may undergo a flexible array of nucleophilic aromatic substitutions and Suzuki-type reactions, as shown in Scheme 9 below. Suzuki coupling of aryl halide compounds with acetylenic and vinylic palladium complexes are carbon-carbon bond forming reactions under relatively mild conditions. In some instances it may be necessary to block the 2 position to direct reaction at the desired aryl position.

Scheme 9

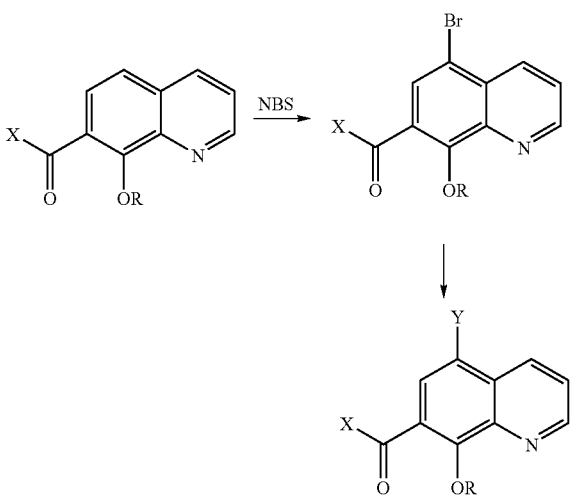

X = H, R, OR, NR$_2$
Y = OR, CN, NR$_2$, SR, SOR, SO$_2$R,
—C≡C—R

Formula I compounds with a 5,9-dihydroxy-pyrrolo[3,4-g]quinoline-6,8-dione were prepared by selective protection of the C9 phenol in 5,9-dihydroxy-pyrrolo[3,4-g]quinoline-6,8-dione. The C9 phenol was protected with a TIPS group and the C5 phenol could then be alkylated or acylated (Scheme 10).

Scheme 10
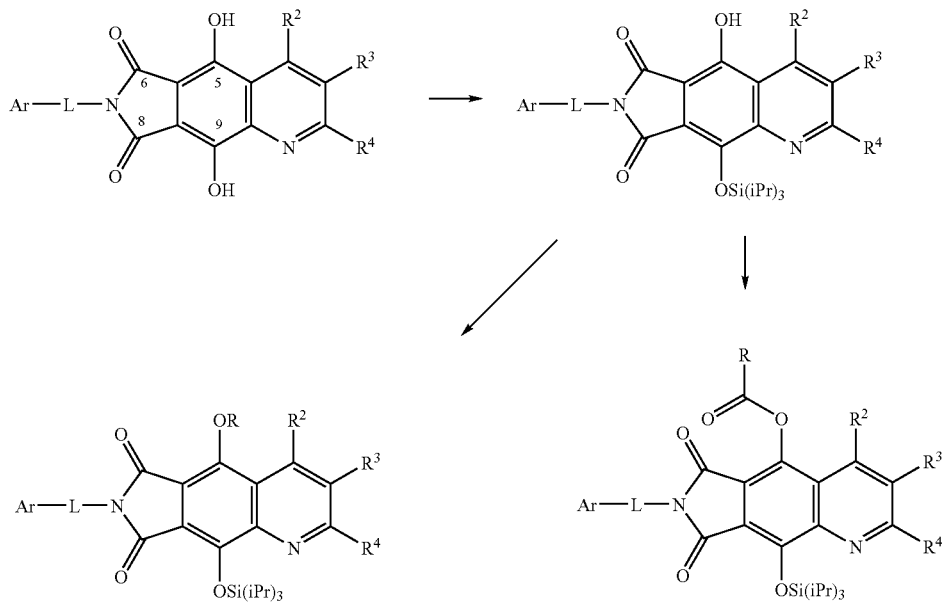
Formula III Compounds
Formula III compounds may be prepared by the following methods in Schemes 11-14:
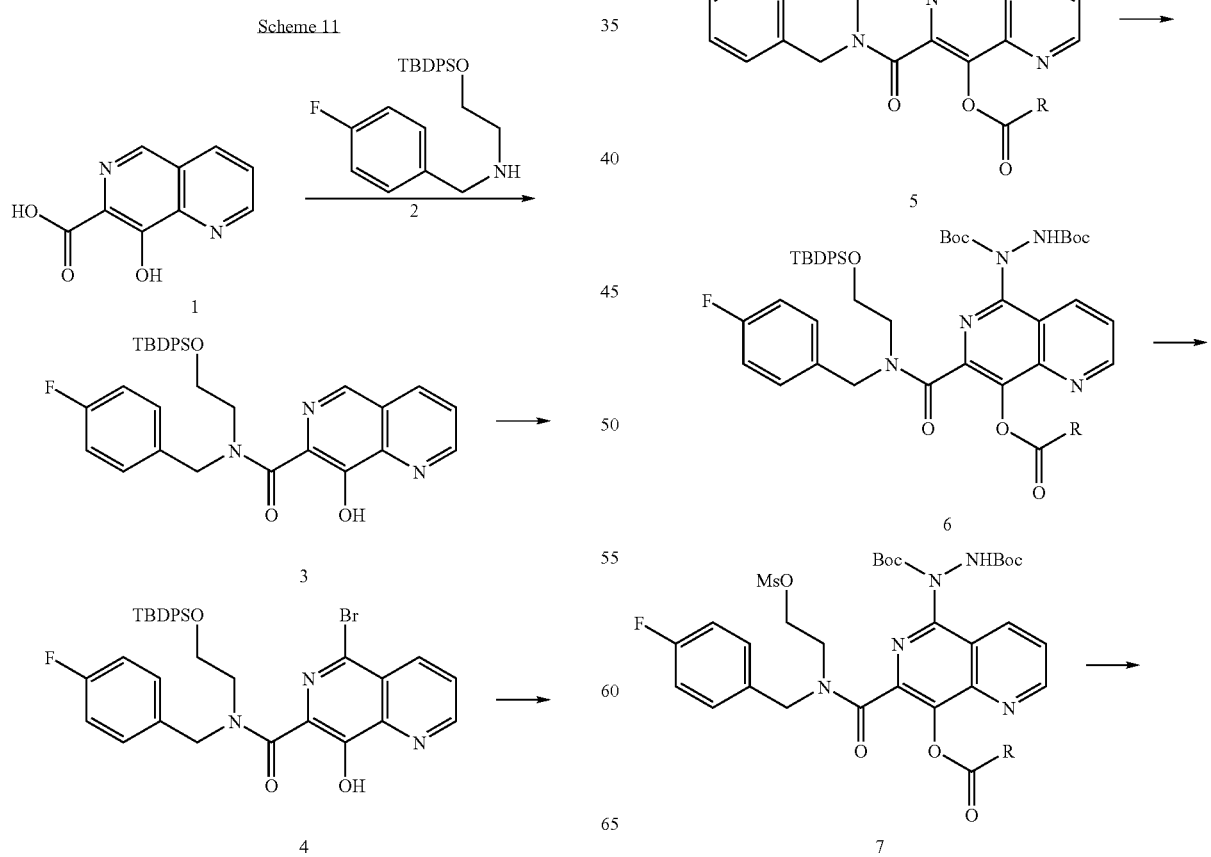

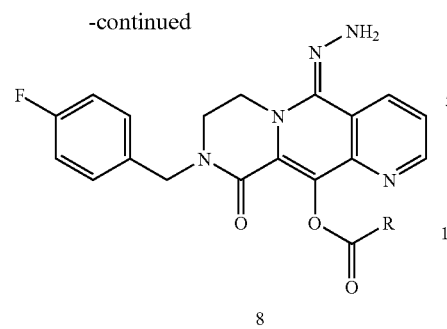

8

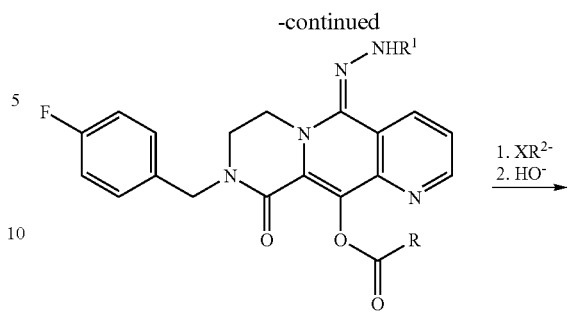

9

The acid 1 (WO02/30930, p.173) may be reacted with amine 2 (prepared according to the methods described by T. Morie, et al, Chem. Pharm. Bull., 42, 1994, 877-882; D. Wenninger, et al, Nucleosides Nucleotides, 16, 1997,977-982) by the method of peptide coupling such as described in WO02/30930, p. 173 to form amide 3. Bromination with NBS generates compound 4. The phenol is protected with a bulky acyl group such as pivaloyl. Displacement of bromine at C5 of naphthyridine by Bis-boc protected hydrazine is achieved using the method reported by J. B. Arteburn, et al, Org. Lett., 3, 2001, 1351-1354. The silyl protecting group is removed by TBAF (T. Green and P. Wuts, "Protective Groups in Organic Synthesis", p.142, Wiley Science, 1999) and mesylate 7 is formed by reacting the alcohol formed with methanesulfonyl chloride. Treatment of compound 7 with TFA followed by heating hydrazino mesylate in the basic condition affords hydrazono triaza anthracene 8.

Compound 8 is converted to many different derivatives, e.g. carbazones 9 ($R^1$=$COR^3$) are generated by reaction with acid chlorides or activated carboxylic acids. Carbamates 9 ($R^1$=$COOR^3$) are obtained upon reaction of 8 with chloro formates $ClCOOR^3$. Semicarbazones 9 ($R^1$=$CONR^2R^3$) are formed using isocyanates or N,N-dialkyl chloroformaides. Thiosemicarbazones 9 ($R^1$=$CSNR^3R^4$) are generated with thioisocyanates. Sulfonyl ureas 9 ($R^1$=$SO_2NR^3R^4$) are obtained by reaction of 8 with sulfamoyl chlorides using procedures reported by M. L. Matier, et al, J. Med. Chem., 15, 1972, 538-541. The simple sulfonamides are produced when 8 reacts with sulfonyl chlorides. The ester group in compounds 9 is removed upon saponification to give compound 10.

Alternatively, many of hydrazone derivatives 9 are subjected to alkylation followed by saponification to afford compounds 11.

Scheme 12

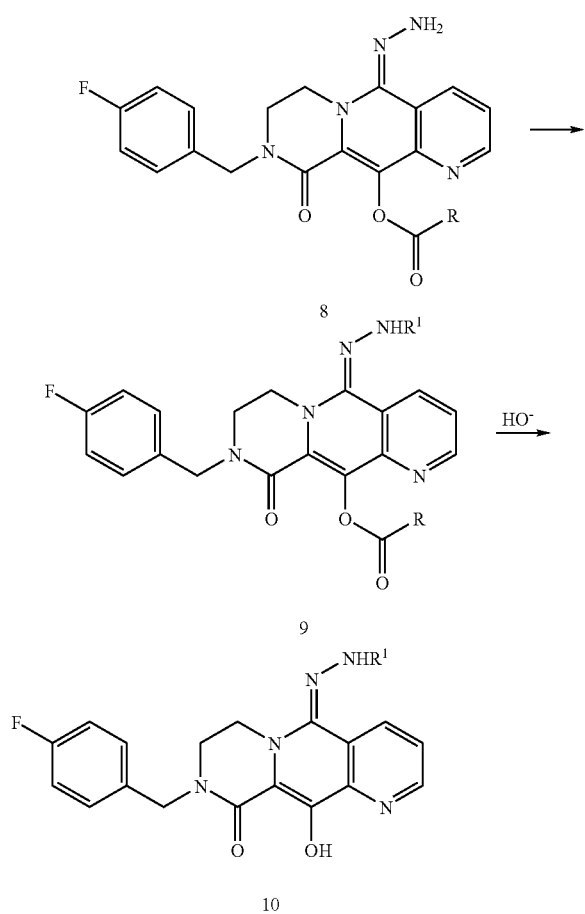

Scheme 13

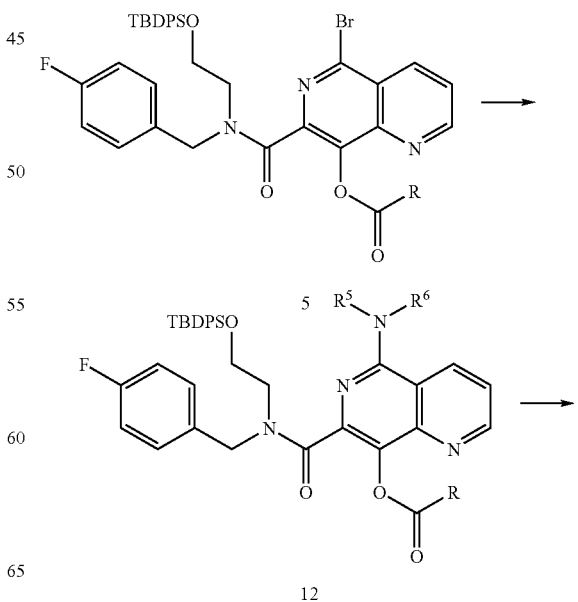

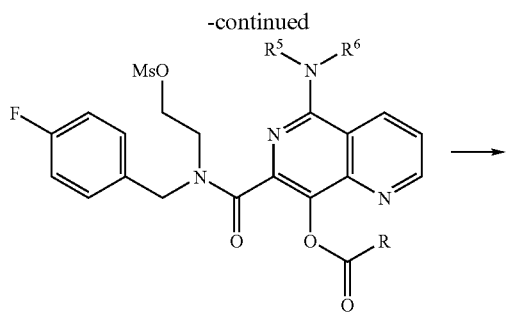

13

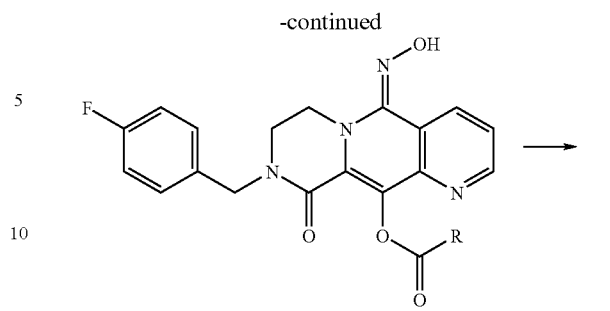

16

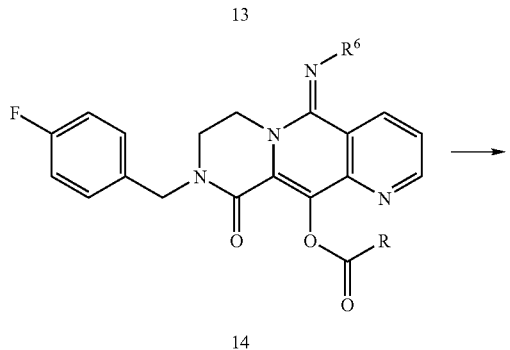

14

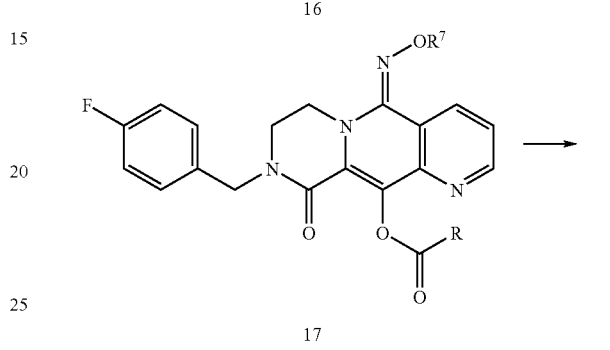

17

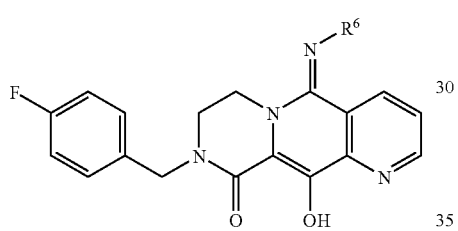

15

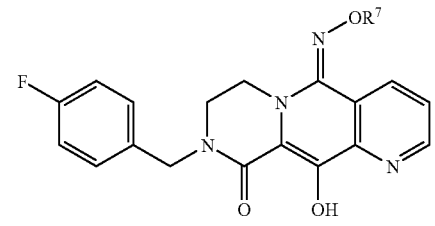

18

Compound 5 from Scheme 11 is reacted with a substituted hydroxyamine or amine ($R^5$=Boc; $R^6$=$OR^a$ or alkyl) in a manner similar to that described by L. A., Carpino et al, Org. Lett., 3, 2001, 2793-2795 to give derivative 12. After transforming the silyl protected hydroxyl in 12 to a leaving group such as the mesylate in 13, cyclization is accomplished in the heating condition and the presence of a base to afford compound 14. Final deprotection by hydrolysis of 14 gives compound 15.

When $R^6$ in 14 is $OR^a$, or where $R^a$ can be removed, oxime 16 is obtained and can be functionalized with many reagents to yield compound 17. Hydrolysis of ester group affords 18. For example, when 16 is treated with an alkyl halide ($R^7$—X) or an alcohol under Mitsunobu condition, an ether 18 is formed. When an isocyanate or thioisocyanate is applied, a carbamate or thiocarbamate 18 ($R^7$: C(=O)$NHR^8$ or C(=S)$NHR^8$) is generated. An N,N-disubstitued carbamate 18 ($R^7$: C(=O)$NR^2R^3$) is obtained when a chloroformate ClC(=O)$NR^2R^3$ is reacted with 16. Similarly, treating 16 with a sulfamoyl chlorides affords a sulfamate 18 ($R^7$: $SO_2NR^1R^2$).

Scheme 14

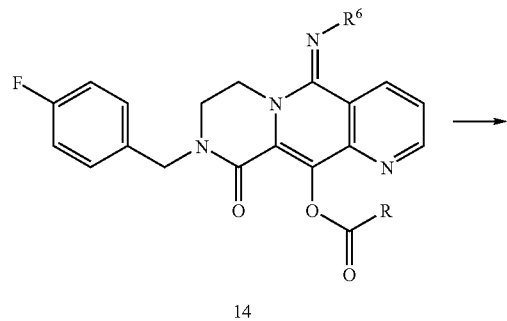

14

Scheme 15

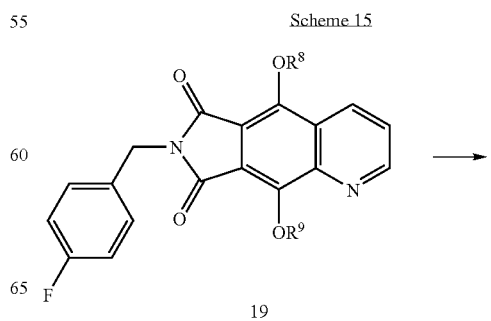

19

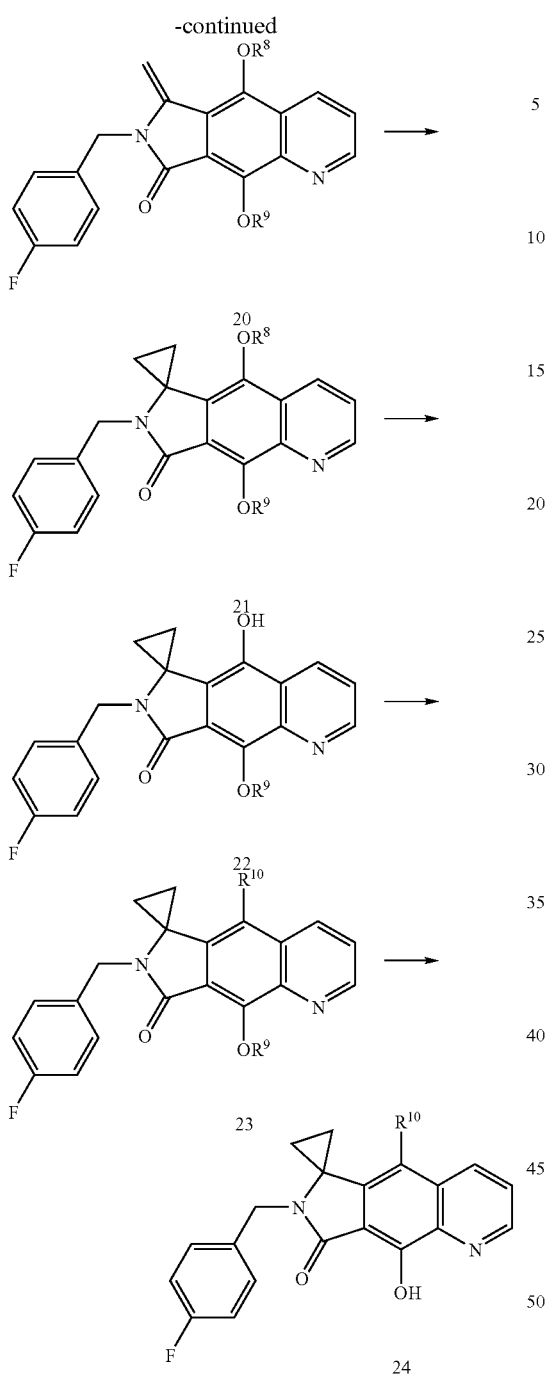

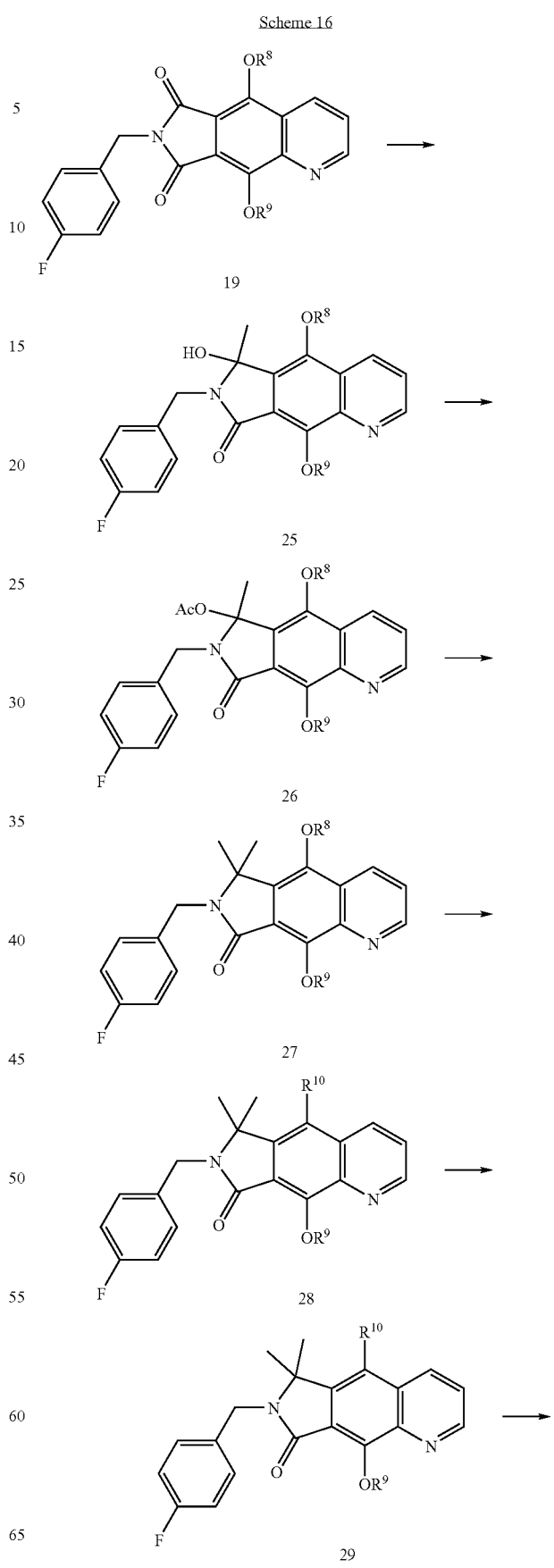

Scheme 15 depicts one of the methods to prepare a spiro-cyclopropane-containing lactam fused to quinoline, an embodiment of Formula I. A differentially protected phenol 19 is used where $R^8$ can be a removable ether group such as trimethylsilyethyl ether and $R^9$ can be a bulky group such as diphenylmethyl or t-butyl ether. The carbonyl of C6 is converted to an olefin regioselectively by treating 19 with methylmagnesium bromide followed by dehydration of aminal to give 20. Carbene insertion by Simmons-Smith reaction (for example, Y. Biggs et al, JOC, 57, 1992, 5568-5573) produces cyclopropane 21. Selective removal of $R^8$ by TBAF followed by fuctionalization using the methods described in many examples leads to compound 24.

Alternatively:

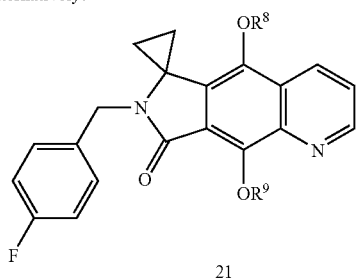
21

A dimethyl substituted lactam can be prepared by reacting 19 with a Grignard reagent followed by converting aminal 25 to acetate 26 and treating 26 with $Me_3Al/TMSOTf$, a method reported by C. U. Kim, et al, Tetrahedron Letters, 35, 1994, 3017-3020, to afford 27. An alternative method can be used by reducing cyclopropane 21 with $PtO_2/H_2$ as reported by C. K. Cheung et al, JOC, 54, 1989, 570-573, to give 27.

Scheme 17

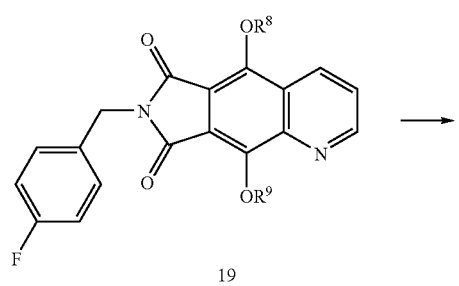
19

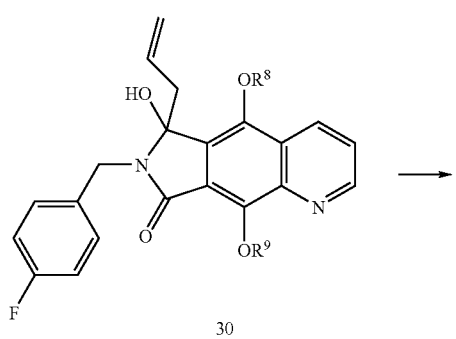
30

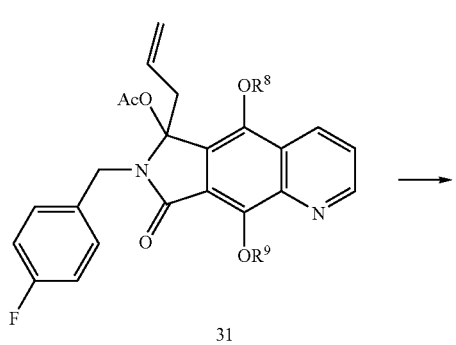
31

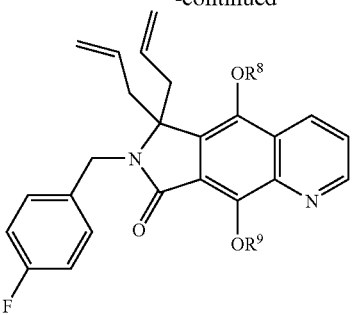
32

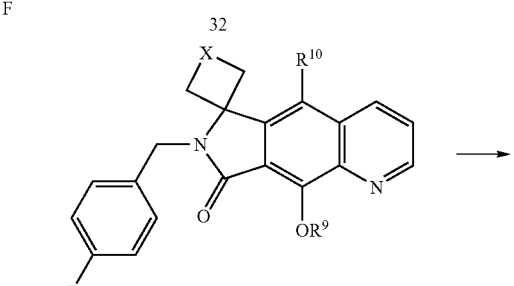
33

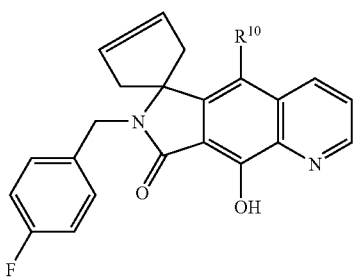
34 examples:

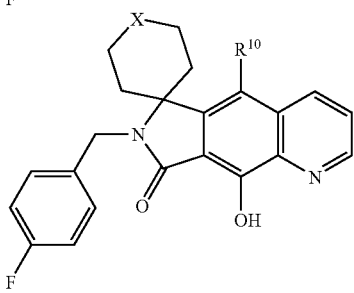

X = NR

Another version of modified lactam can be obtained according to Scheme 17. Treating 19 with an allyl Grignard reagent gives 30. Activating aminal 30 by forming acetate 31 followed by treating 31 with allyl trimethylsilane mediated by a Lewis acid such as TMSOTf affords 32. Cyclization can be achieved by using Grubb's RCM (ring closure metathesis) method (P. Schwab et al, Angew. Chem. Intl. 34, 1995, 2039). Alternatively, the terminal olefins in 32 can be converted to aldehydes and reductive amination leads to a spiro-piperidine.
Scheme 18
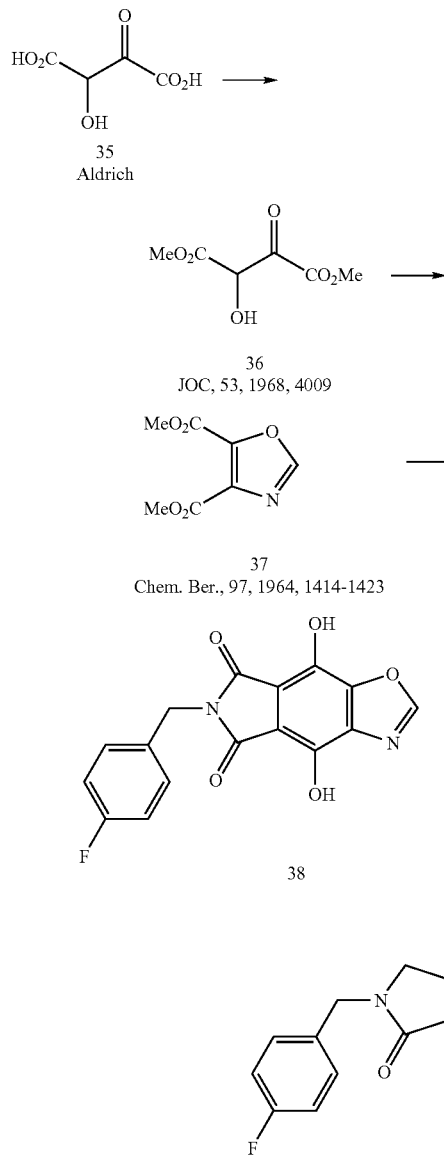
Scheme 19
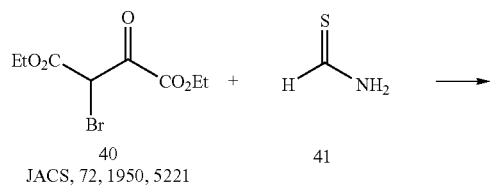
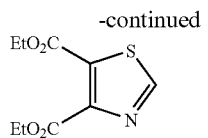
42
J. Heterocyclic Chem.,
1968, 331
Scheme 20
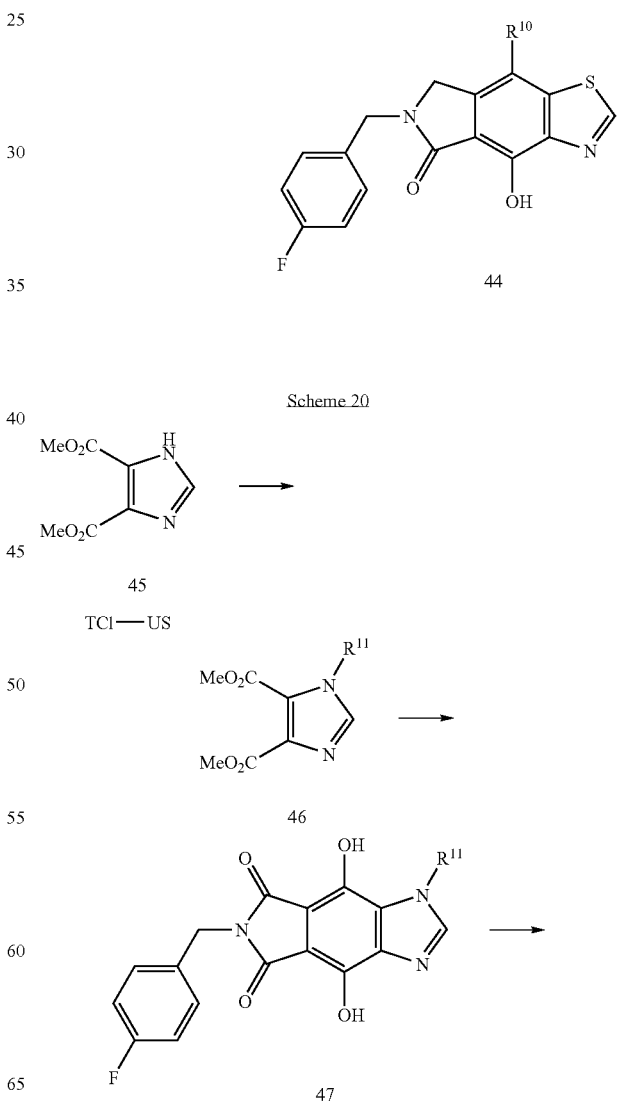

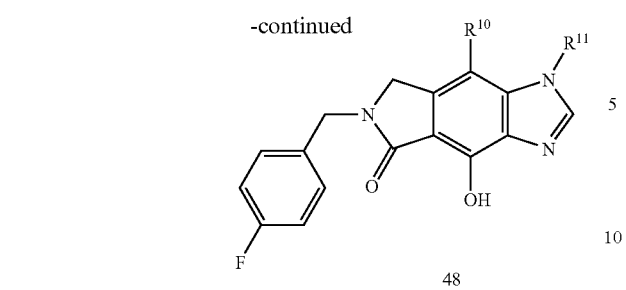
48
Scheme 21
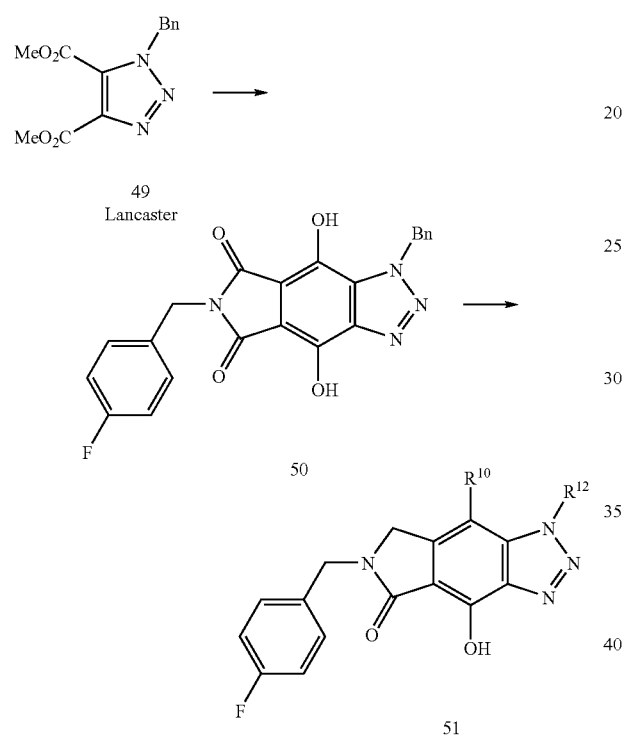
49
Lancaster
50
51
Scheme 22
53
Pfaltz-Bauer
54
JACS, 112, 1990, 8126
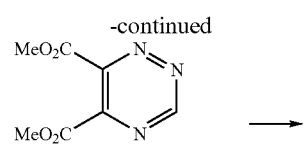
56
JOC, 23, 1958, 1931
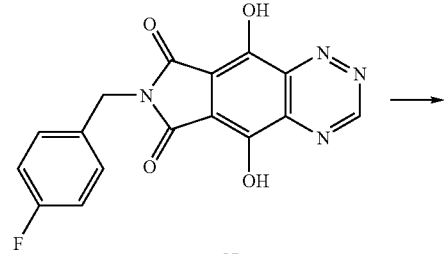
57
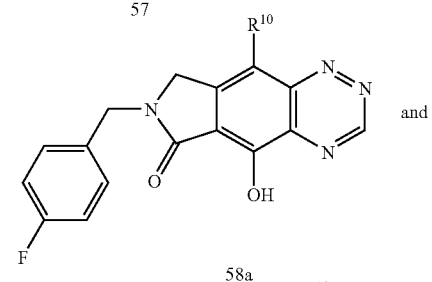
58a
58b
Scheme 23
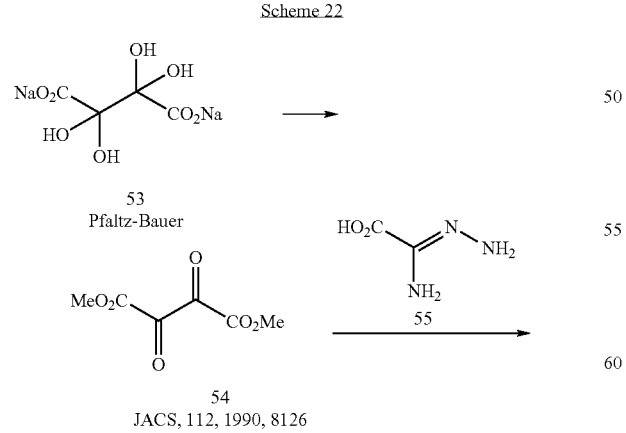
59
Aldrich
60
61
J. Het. Chem., 30, 1993, 1597

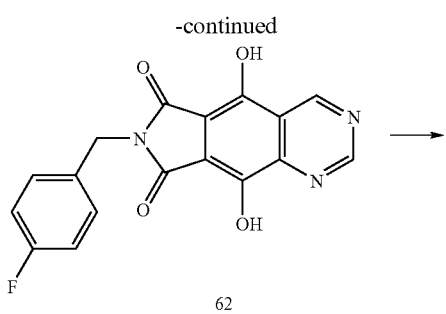

62

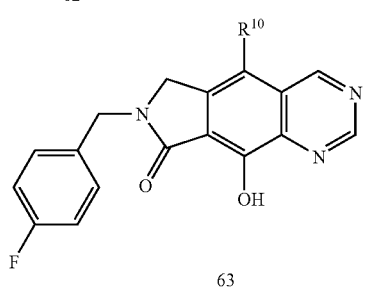

63

Scheme 24

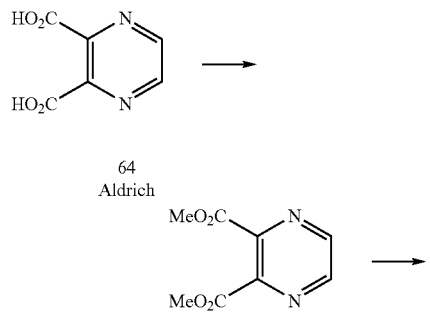

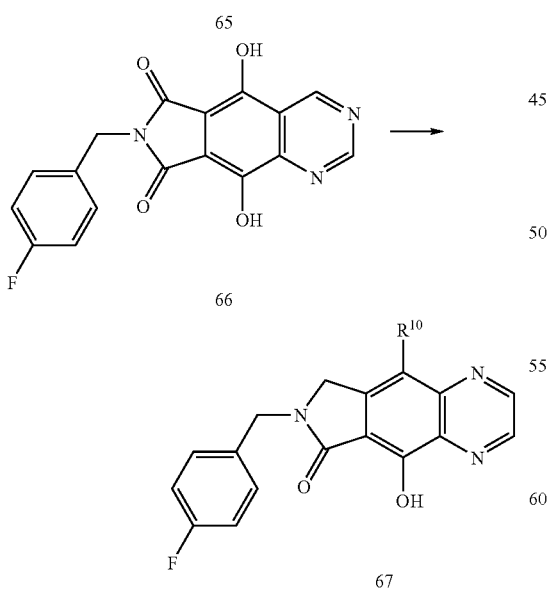

Many tricyclic compounds can bear a heterocycle different from 9-hydroxy-6,7-dihydro-pyrrolo[3,4-g]quinolin-8- one, i.e. Formula IV. Some examples and methods to prepare Formula IV compounds are depicted in Schemes 18-24 above.

Preparation of the Intermediate Phosphonate Esters Iaa-IVcc.

The structures of the intermediate phosphonate esters Iaa to IVcc are shown in Chart 1, in which the substituents $R^1$, $R^2$, $R^3$, $R^4$, $A^1$ and $A^2$ are as previously defined. The groups $A^{1a}$ and $A^{2a}$ are the same as the groups $A^1$ and $A^2$, except that a substituent link-$P(O)(OR^5)_2$ is appended. The substituent $R^5$ is hydrogen, alkyl, alkenyl, aralkyl, or aryl. Subsequent chemical modifications to the compounds Iaa to Vcc, as described herein, permit the synthesis of the final compounds of this invention.

The intermediate compounds Iaa to IVcc incorporate a phosphonate moiety $(R^5O)_2P(O)$ connected to the nucleus by means of a variable linking group, designated as "link" in the attached structures. Chart 2 illustrates examples of the linking groups present in the structures Iaa-IVcc.

Schemes A1-A33 illustrate the syntheses of the intermediate phosphonate compounds of this invention, Iaa-IVcc, and of the intermediate compounds necessary for their synthesis.

The methods described for the introduction of phosphonate substituents are, with modifications made by one skilled in the art, transferable within the substrates I-V. For example, reaction sequences which produce the phosphonates Iaa are, with appropriate modifications, applicable to the preparation of the phosphonates IIaa, IIIaa, or IVaa. Methods described below for the attachment of phosphonate groups to reactive substituents such as OH, $NH_2$, $CH_2Br$, COOH, CHO etc are applicable to each of the scaffolds I-V.

Scheme A34 illustrates methods for the interconversion of phosphonate diesters, monoesters and acids.

Chart 1. Structures of the Phosphonate Esters Iaa-IVcc.

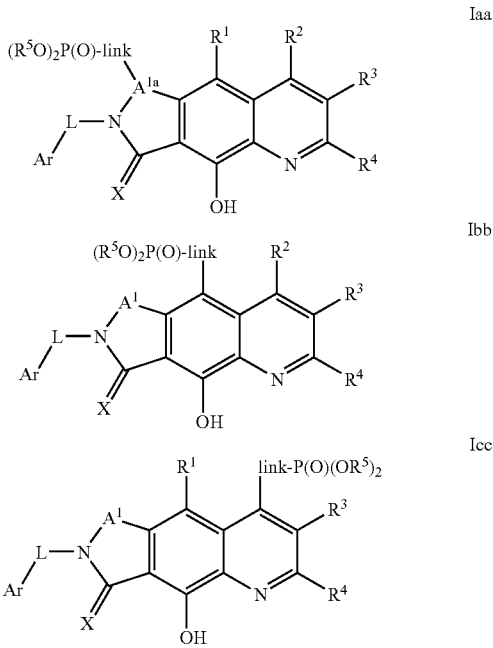

-continued
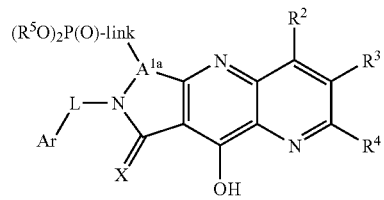
IIaa
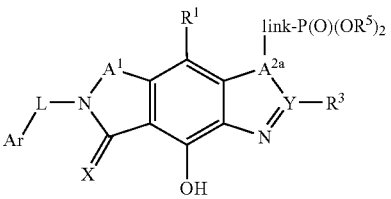
IVcc
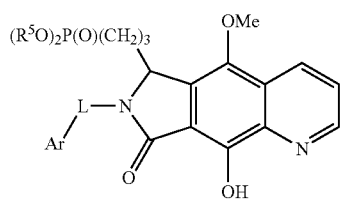
IIcc
Chart 2 Examples of Phosphonate Linkages
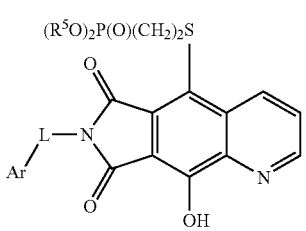
Iaa
IIIaa
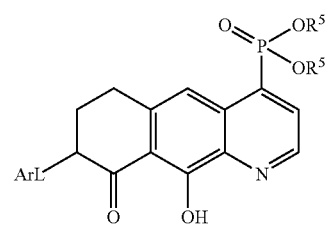
Ibb
IIIbb
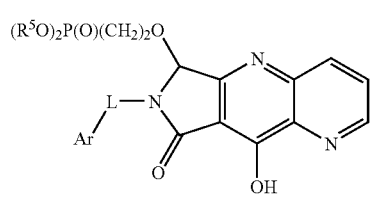
Icc
IIIcc
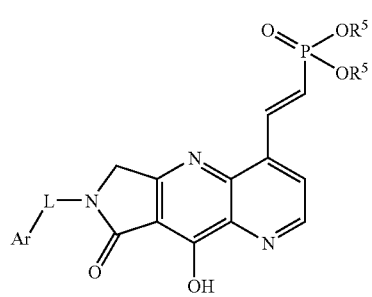
IIaa
IVaa
IIcc
IVbb

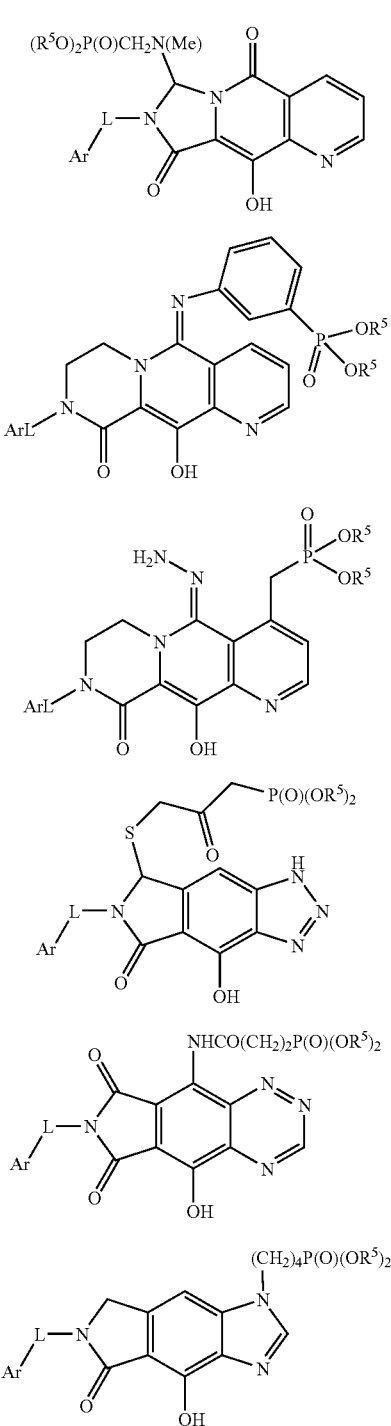

Protection of Reactive Substituents.

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M Wuts, Wiley, Second Edition 1990.

Reactive substituents which may be protected are shown in the accompanying schemes as, for example, [OH], [SH], etc.

Preparation of the Intermediate Phosphonate Esters 1aa.

Schemes A1-A5 illustrate methods for the preparation of the intermediate phosphonate esters Iaa.

As shown in Scheme A1, the phenolic hydroxyl substituent present in the tricyclic compound A1.1 is protected to afford the derivative A1.2. The protection of hydroxyl groups is described in Protective Groups in Organic Synthesis, by T. W. Greene and P. G. M Wuts, Wiley, Second Edition 1990, p. 10. For example, hydroxyl substituents are protected as trialkylsilyloxy, methoxymethyl, benzyl or tert-butyl ethers. Trialkylsilyl groups are introduced by the reaction of the phenol with a chlorotrialkylsilane and a base such as imidazole, for example as described in Protective Groups in Organic Synthesis, by T. W. Greene and P. G. M Wuts, Wiley, Second Edition 1990, p. 10ff. The protected product A1.2 is then reacted, in the presence of a strong base, with a bromoalkyl phosphonate A1.3, to give the alkylation product A1.4. The reaction is effected in a polar organic solvent such as dimethylformamide, dimethylacetamide, diglyme, tetrahydrofuran and the like, in the presence of a base such as sodium hydride, an alkali metal alkoxide, lithium hexamethyldisilazide, and the like, at from ambient temperature to about 100° C., to yield the alkylated product A1.4. The phenolic hydroxyl group is then deprotected to afford the phenol A1.5. Methods for the deprotection of hydroxyl groups are described in Protective Groups in Organic Synthesis, by T. W. Greene and P. G. M Wuts, Wiley, Second Edition 1990, p. 10ff.

For example, 7-(4-fluoro-benzyl)-9-hydroxy-5H-1,7-diaza-anthracene-6,8-dione A1.6 is reacted with one molar equivalent of chlorotriisopropylsilane and imidazole in dimethylformamide at ambient temperature, as described in Tet. Lett., 2865, 1974, to produce 7-(4-fluoro-benzyl)-9-triisopropylsilanyloxy-5H-1,7-diaza-anthracene-6,8-dione A1.7. The product is then reacted in dimethylformamide solution at about 60° C. with one molar equivalent of a dialkyl 2-bromoethyl phosphonate A1.8 (Aldrich) and lithium hexamethyldisilazide, to yield the alkylated product A1.9. The silyl protecting group is then removed by reaction with tetrabutylammonium fluoride in tetrahydrofuran, as described in J. Org. Chem., 51, 4941, 1986, to give the phenolic product A1.10.

Using the above procedures, but employing, in place of the 4-fluorobenzyl-substituted phenol A1.6, different phenols A1.1 and/or different phosphonates A1.3, the corresponding products A1.5 are obtained.

Scheme A2 illustrates the preparation of phosphonate esters of structure Iaa in which the phosphonate group is attached by means of an aryl of heteroaryl ring.

In this procedure, a hydroxy-substituted phthalimide derivative A2.1 (Formula I) is protected, as described above, to afford the product A2.2. This compound is then reacted with a bromoaryl magnesium bromide Grignard reagent A2.3, in which the group Ar¹ is an aromatic or heteroaromatic group such as, for example, benzene or thiophene, to afford the carbinol A2.4. The regioselective addition of organometallic derivatives to phthalimides is described in Scheme 4. The reaction is performed between approximately equimolar amounts of the reactants in an ethereal solvent such as diethyl ether, tetrahydrofuran and the like, at from −40° C. to ambient temperature, to give the carbinol product A2.4. This material is then reacted with a dialkyl phosphite A2.5 and a palladium catalyst, to give the phosphonate A2.6. The preparation of arylphosphonates by means of a coupling reaction between aryl bromides and dialkyl phosphites is described in J. Med. Chem., 35, 1371, 1992. The reaction is conducted in a hydrocarbon solvent such as benzene, toluene or xylene, at about 100° C., in the presence of a palladium (0) catalyst such as tetrakis(triphenylphosphine)palladium(0), and a tertiary base such as triethylamine or diisopropylethylamine. The hydroxyl group is then deprotected to yield the phenolic product A2.7. Optionally, the benzylic hydroxyl substituent in the product A2.7 is removed by means of a reductive procedure, as shown on Scheme 4. Benzylic hydroxyl groups are removed by catalytic hydrogenation, for example by the use of 10% palladium on carbon in the presence of hydrogen or a hydrogen donor, or by means of chemical reduction, for example employing triethylsilane and boron trifluoride etherate.

For example, 7-(3,5-dichloro-benzyl)-5,9-bis-triisopropylsilanyloxy-pyrrolo[3,4-g]quinoline-6,8-dione A2.9, prepared by silylation of the corresponding diol, which is reacted with one molar equivalent of 4-bromophenyl magnesium bromide A2.10 in ether at 0° C. to produce the carbinol A2.11. The latter compound is then reacted, in toluene solution at reflux, with a dialkyl phosphite A2.5, triethylamine and tetrakis(triphenylphosphine)palladium(0), as described in J. Med. Chem., 35, 1371, 1992, to afford the phosphonate product A2.12. Desilylation, for example by reaction with tetrabutyl ammonium fluoride, gives the diol product A2.13. Optionally, the product A2.12 is reduced, for example by reaction in dichloromethane solution at ambient temperature with ca. four molar equivalents of triethylsilane and boron trifluoride etherate, as described in Example 18 to yield after deprotection the reduced product A2.14.

Using the above procedures, but employing, in place of the 3,5-dichlorobenzyl-substituted phenol derivative A2.9, different phenol derivatives A2.1 and/or different bromoaryl Grignard reagents A2.3, the corresponding products A2.7 and A2.8 are obtained.

Scheme A3 illustrates the preparation of phosphonate esters of structure Iaa in which the phosphonate group is attached by means of an alkylene chain.

In this sequence, a 6-aminoquinoline ester A3.1, prepared, for example, from the corresponding carboxylic acid by means of a Curtius rearrangement, (Advanced Organic Chemistry, Part B, by F. A. Carey and R. J. Sundberg, Plenum, 2001, p.646) is reacted, under reductive amination conditions, with a dialkyl formylalkyl phosphonate A3.2. The preparation of amines by means of reductive amination procedures is described, for example, in Comprehensive Organic Transformations, by R. C. Larock, VCH, p 421, and in Advanced Organic Chemistry, Part B, by F. A. Carey and R. J. Sundberg, Plenum, 2001, p 269. In this procedure, the amine component and the aldehyde or ketone component are reacted together in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in J. Org. Chem., 55, 2552, 1990. The product A3.3 is then converted, by reaction with the amine ArBNH$_2$ A3.4, or a derivative thereof, into the amide A3.5. The conversion of esters into amides is described in Comprehensive Organic Transformations, by R. C. Larock, VCH, 1989, p. 987. The reactants are combined in the presence of a base such as sodium methoxide under azeotropic conditions, or of a dialkyl aluminum or trialkyl tin derivative of the amine. The use of trimethylaluminum in the conversion of esters to amides is described in J. Med. Chem. Chim. Ther., 34, 1999, 1995, and Syn. Comm., 25, 1401, 1995. The reaction is conducted in an inert solvent such as dichloromethane or toluene. The amide product A3.5 is then cyclized by reaction with a reagent such as phosgene or a functional equivalent thereof, such as triphosgene or a dialkyl carbonate, or a reagent such as diiodomethane, to give the cyclized product A3.6 in which D is CO or $CH_2$. The reaction is conducted in an aprotic solvent such as tetrahydrofuran, in the presence of an inorganic or organic base such as potassium carbonate or diisopropylethylamine.

For example, the amine A3.7, prepared by means of a Curtius rearrangement of the corresponding MOM-protected carboxylic acid, is reacted in isopropanol solution with a dialkyl formylmethyl phosphonate A3.8, prepared as described in Zh. Obschei. Khim., 1987, 57, 2793, sodium cyanoborohydride and acetic acid, to give the reductive amination product A3.9. The product is then reacted with an excess of 3,4-dichlorobenzylamine and sodium methoxide in toluene at reflux, to yield the amide A3.10. The latter compound is then reacted with one molar equivalent of triphosgene and N,N-dimethylaaminopyridine in dichloromethane, to afford the cyclized product A3.11. The MOM protecting groups are then removed, for example by reaction with a catalytic amount of methanolic hydrogen chloride, as described in J. Chem. Soc., Chem. Comm., 298, 1974, to give the dihydroxy product A3.12.

Using the above procedures, but employing, in place of the amine A3.7, different amines A3.1, and/or different aldehydes A3.2, and/or different amines A3.4, the corresponding products A3.6 are obtained.

Scheme A4 illustrates the preparation of phosphonate esters of structure Iaa in which the phosphonate group is attached by means of an alkylene chain or an aryl, heteroaryl or aralkyl group and a heteroatom O, S or N. In this sequence, a tricyclic aminal A4.1 is reacted in the presence of an acid catalyst with a hydroxy, mercapto or amino-substituted dialkyl phosphonate A4.2 in which X is O, S, NH or N-alkyl, and R is alkyl, alkenyl, aryl, heteroaryl or aralkyl. The reaction is effected at ambient temperature in an inert solvent such as dichloromethane, in the presence of an acid such as p-toluenesulfonic acid or trifluoroacetic acid and an excess of the reagent A4.2. The hydroxyl group is then deprotected to yield the phenolic product A4.4.

For example, 7-(4-fluoro-benzyl)-6-hydroxy-5-methoxy-9-triisopropylsilanyloxy-6,7-dihydro-pyrrolo[3,4-g]quinolin-8-one A4.5 (Example 20, Scheme 15) is reacted at ambient temperature in dichloromethane solution with a dialkyl 2-mercaptoethyl phosphonate A4.6 (Zh. Obschei. Khim., 1973, 43, 2364) and trifluoroacetic acid to give the thioether product A4.7, which upon deprotection with tetrabutylammonium fluoride yields the phenol A4.8.

As a further example, 6-hydroxy-5-methoxy-7-(4-trifluoromethyl-benzyl)-9-triisopropylsilanyloxy-6,7-dihydro-pyrrolo[3,4-g]quinolin-8-one A4.9, prepared analogously to the 4-fluoro analog A4.5, is reacted, under the same conditions, with a dialkyl 3-mercaptophenyl phosphonate A4.10 to give the thioether A4.11 which upon deprotection affords the phenol A4.12. The phosphonate reagent A4.10 is obtained by palladium (0) catalyzed coupling reaction, as described in Scheme A2, between a dialkyl phosphite and an S-protected derivative of 3-bromothiophenol, for example the S-trityl derivative, followed by removal of the sulfur protecting group. Protection and deprotection of thiols is described in Protective Groups in Organic Synthesis, by T. W. Greene and P. G. M Wuts, Wiley, Second Edition 1990, p. 277.

Using the above procedures, but employing, in place of the carbinols A4.5 and A4.9, different carbinols A4.1, and/or different alcohols, thiols or amines A4.2, the corresponding products A4.4 are obtained.

Scheme A5 illustrates the preparation of phosphonate esters of structure Iaa in which the phosphonate group is attached to a 7-membered ring by means of an alkylene or arylmethylene chain. In this sequence, a suitable protected quinoline acid ester A5.1 is subjected to a Curtius rearrangement, as described in Scheme A3 to yield the amine A5.2. The product is then reductively aminated, as described in Scheme A3, with a phosphonate aldehyde A5.3, in which the group R is an alkyl group or an aryl group, to give the amine product A5.4. This material is then coupled with the glycine derivative A5.5 to yield the amide A5.6. The preparation of amides from carboxylic acids and derivatives is described, for example, in Organic Functional Group Preparations, by S. R. Sandler and W. Karo, Academic Press, 1968, p. 274, and Comprehensive Organic Transformations, by R. C. Larock, VCH, 1989, p. 972ff. The carboxylic acid is reacted with the amine in the presence of an activating agent, such as, for example, dicyclohexylcarbodiimide or diisopropyl-carbodiimide, optionally in the presence of, for example, hydroxybenztriazole, N-hydroxysuccinimide or N-hydroxy-pyridone, in a non-protic solvent such as, for example, pyridine, DMF or dichloromethane, to afford the amide. Alternatively, the carboxylic acid may first be converted into an activated derivative such as the acid chloride, anhydride, mixed anhydride, imidazolide and the like, and then reacted with the amine, in the presence of an organic base such as, for example, pyridine, to afford the amide. The conversion of a carboxylic acid into the corresponding acid chloride can be effected by treatment of the carboxylic acid with a reagent such as, for example, thionyl chloride or oxalyl chloride in an inert organic solvent such as dichloromethane, optionally in the presence of a catalytic amount of dimethylformamide. The product A5.6 is then cyclized, for example by heating at reflux temperature in toluene in the presence of a basic catalyst such as sodium methoxide, or by reaction with trimethylaluminum, as described in Syn. Comm., 25, 1401, 1995, to afford after deprotection of the hydroxyl groups, the diazepindione derivative A5.7.

For example, the MOM-protected amine A3.7 is reductively aminated by reaction with a dialkyl phosphonoacetaldehyde A5.8 (Aurora) and sodium triacetoxyborohydride, to produce the amine A5.9. The product is then coupled in dimethylformamide solution, in the presence of dicyclohexyl carbodiimide, with (4-fluoro-benzylamino)-acetic acid A5.10, to give the amide A5.11. This material is converted, by reaction with trimethylaluminum in dichloromethane, as described above, into the diazepin derivative A5.12. Removal of the MOM protecting groups, as previously described, then affords the phenolic product A5.13.

Using the above procedures, but employing, in place of the amine A3.7, different amines A5.2, and/or different aldehydes A5.3, and/or different carboxylic acids A5.5, the corresponding products A5.7 are obtained.

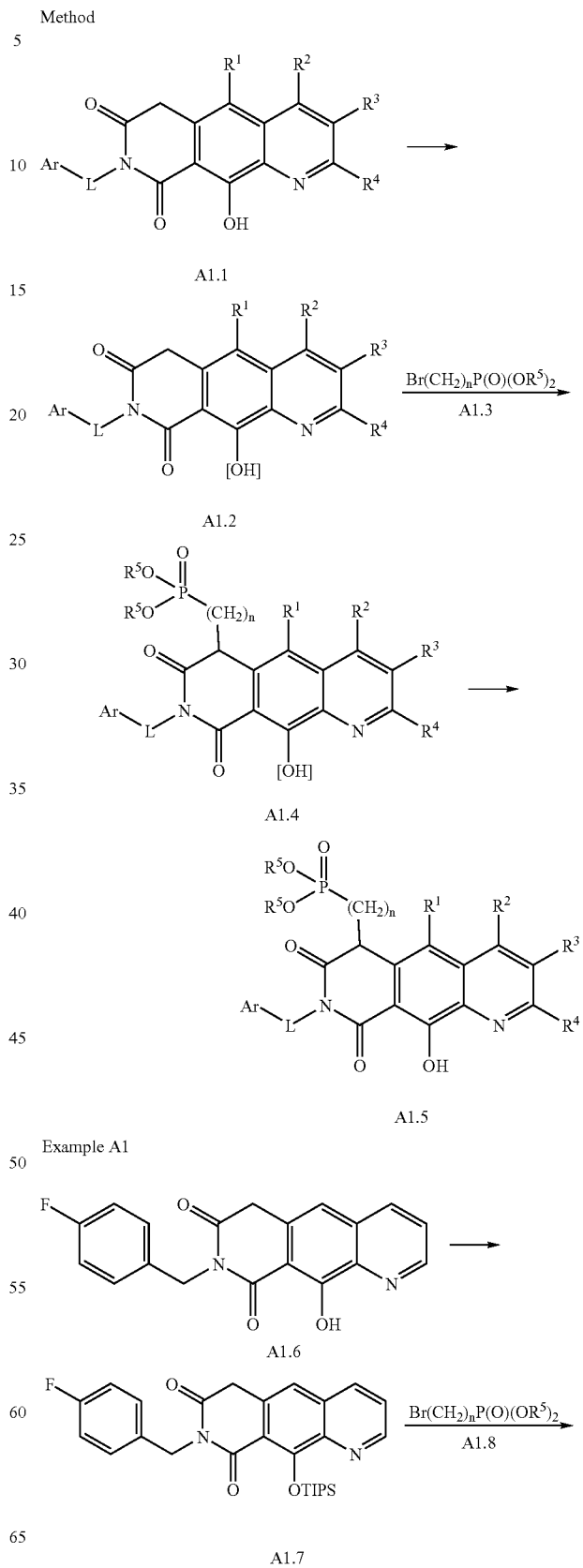

Scheme A1. Phosphonates Iaa.

Method

A1.1

A1.2

A1.4

A1.5

Example A1

A1.6

A1.7

-continued
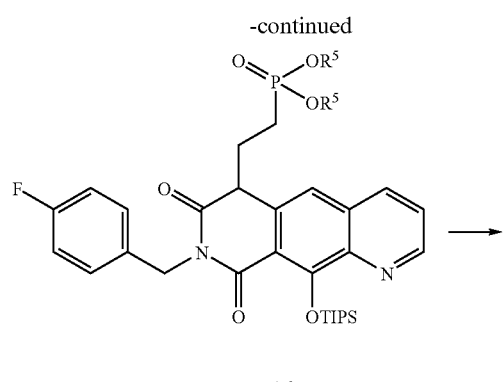
A1.9
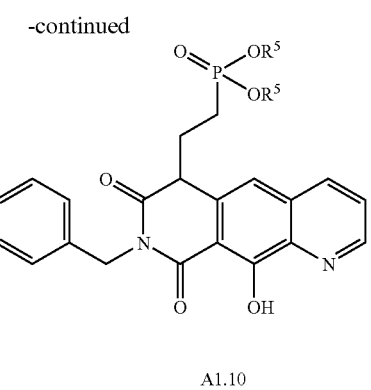
A1.10
Scheme A2. Phosphonates Iaa.
Method
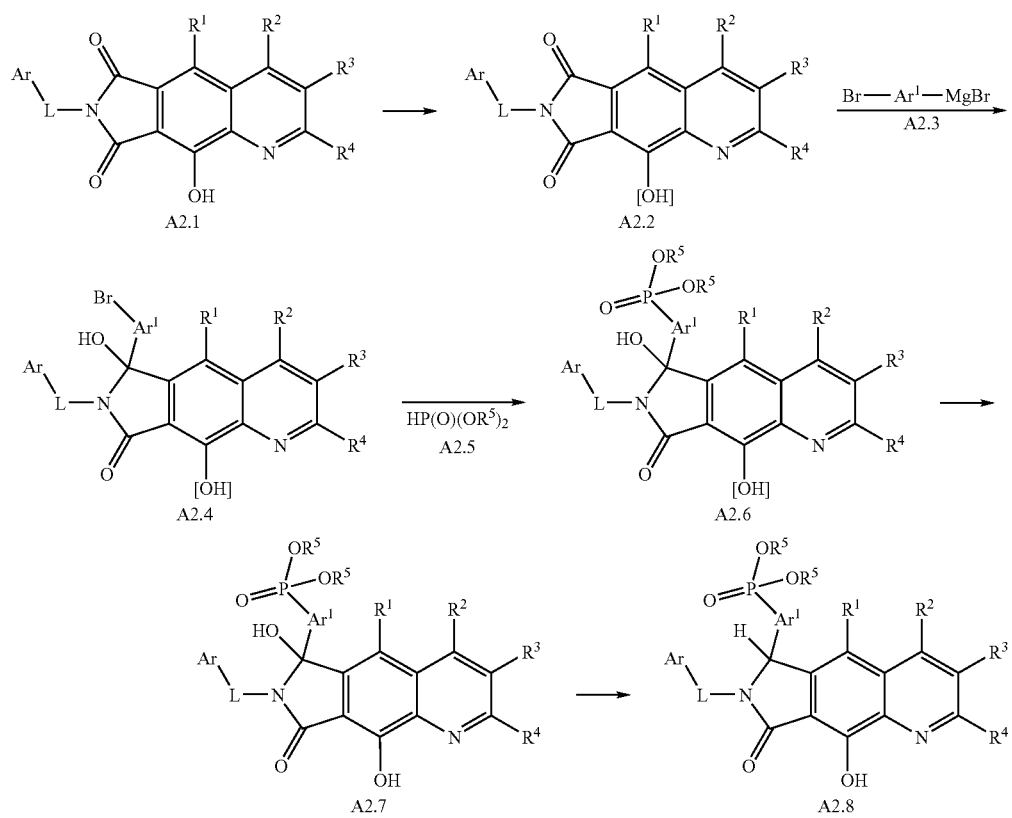
Example A2
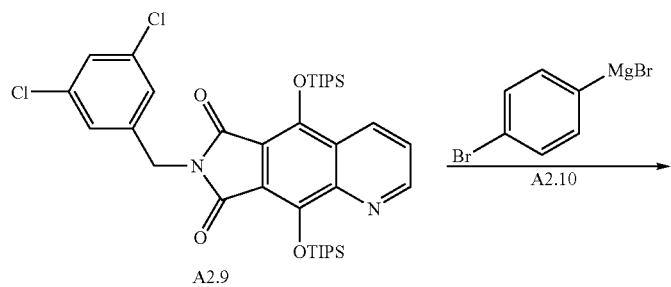
A2.9

-continued
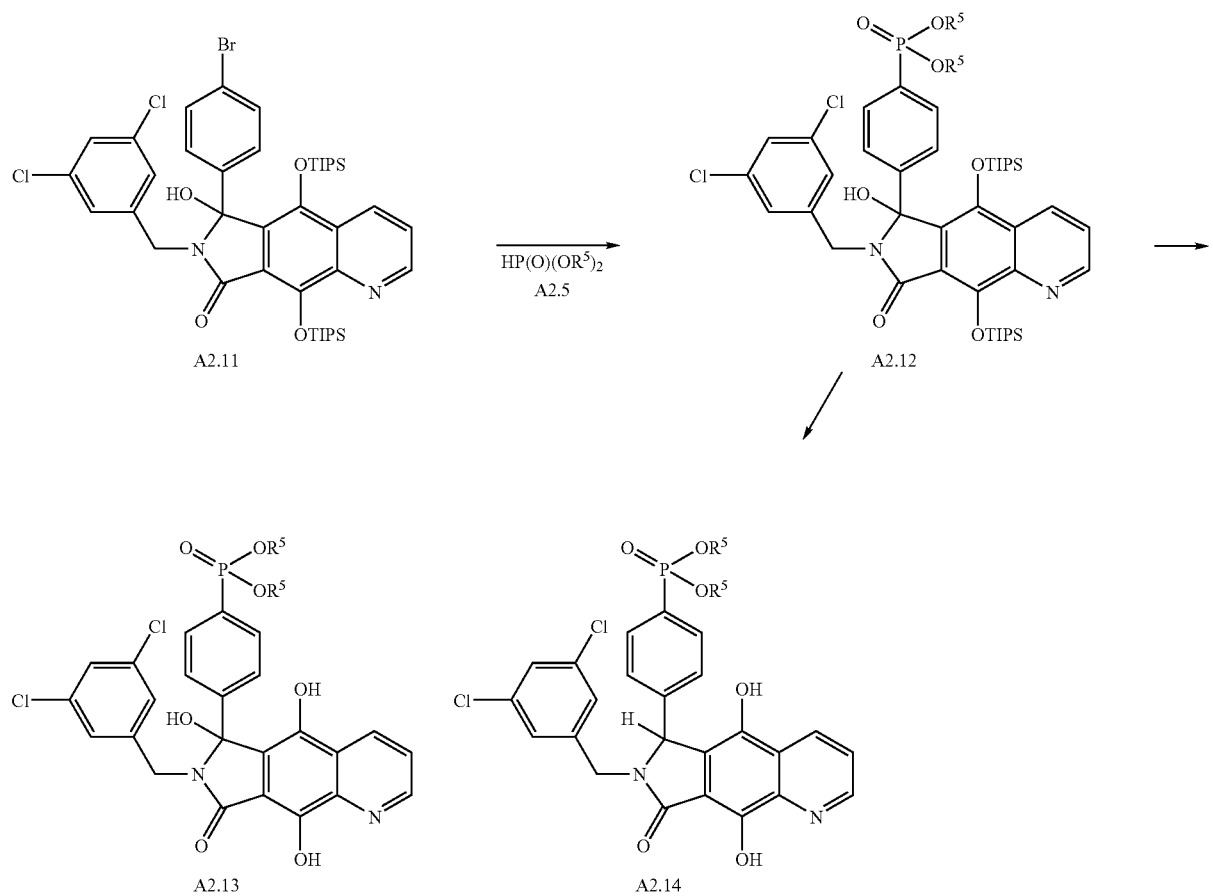
Scheme A3. Phosphonates Iaa.
Method
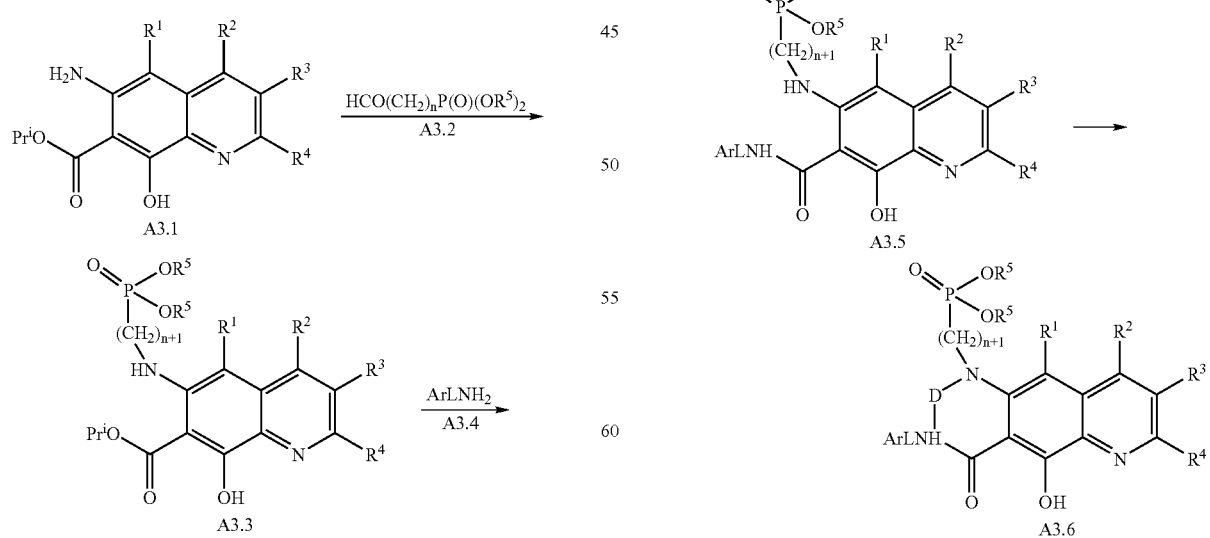

-continued
Example A3
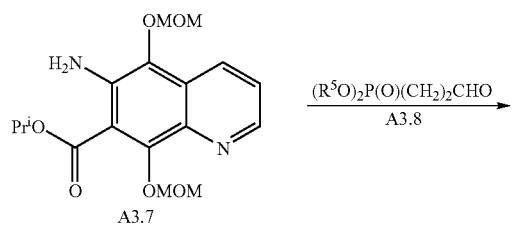
A3.7
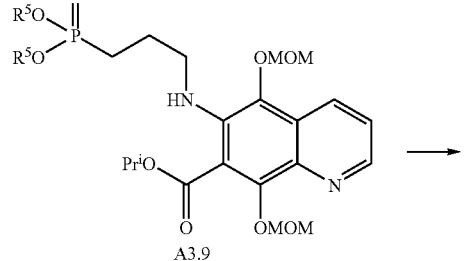
A3.9
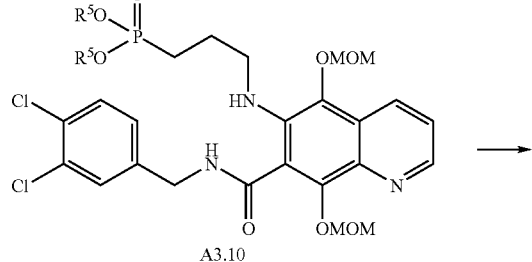
A3.10
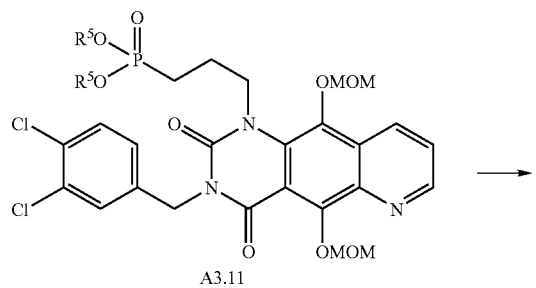
A3.11
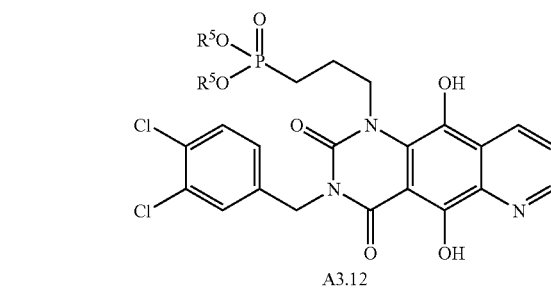
A3.12
Scheme A4. Phosphonates Iaa.
Method
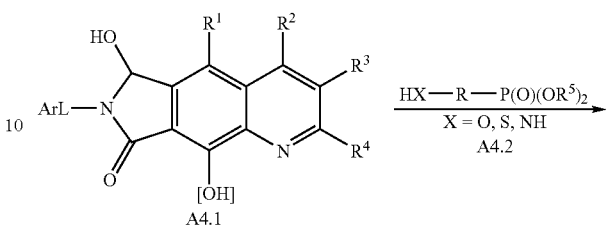
A4.1
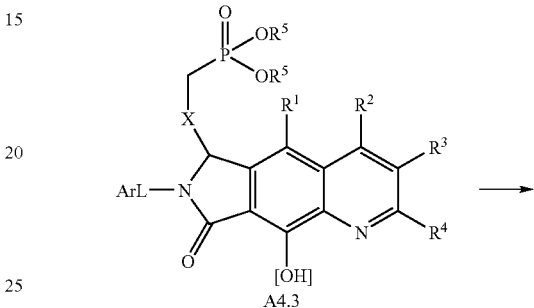
A4.3
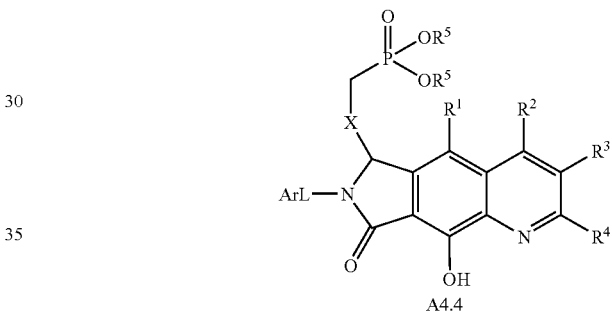
A4.4
Example A4-1
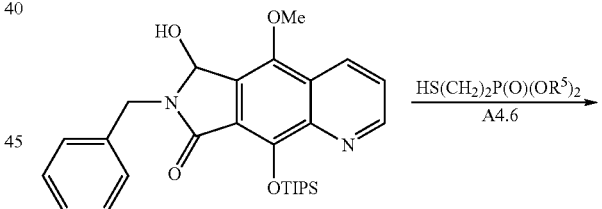
A4.5
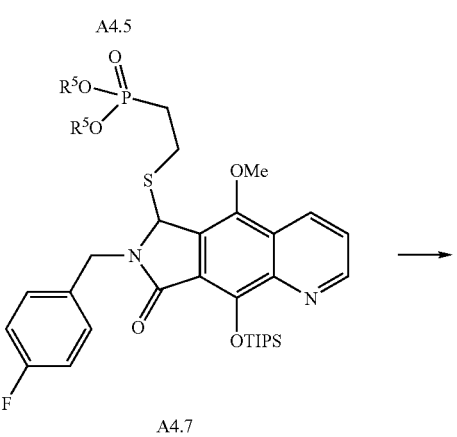
A4.7

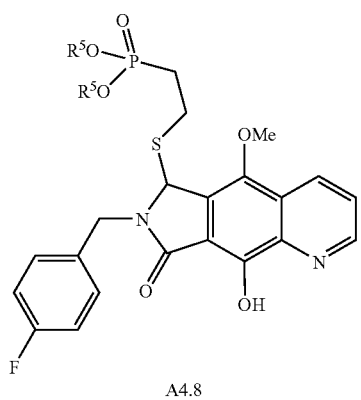
Example A4-2
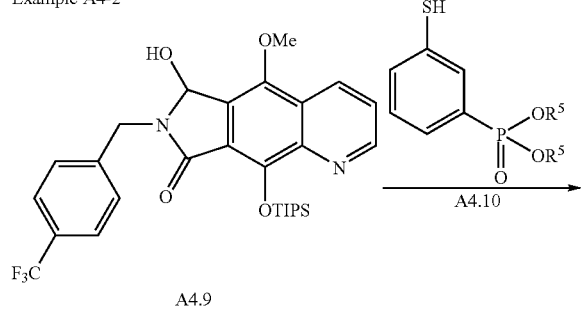
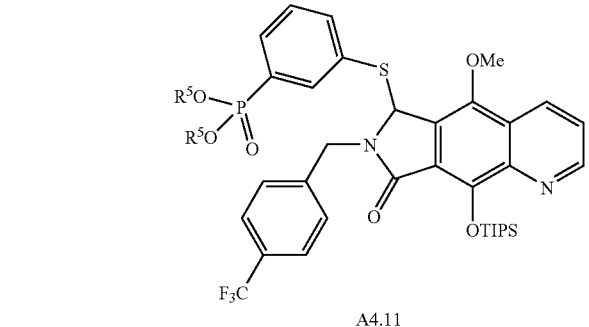
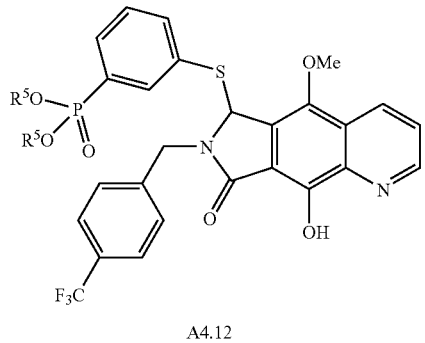
Scheme A5. Phosphonates Iaa.
Method
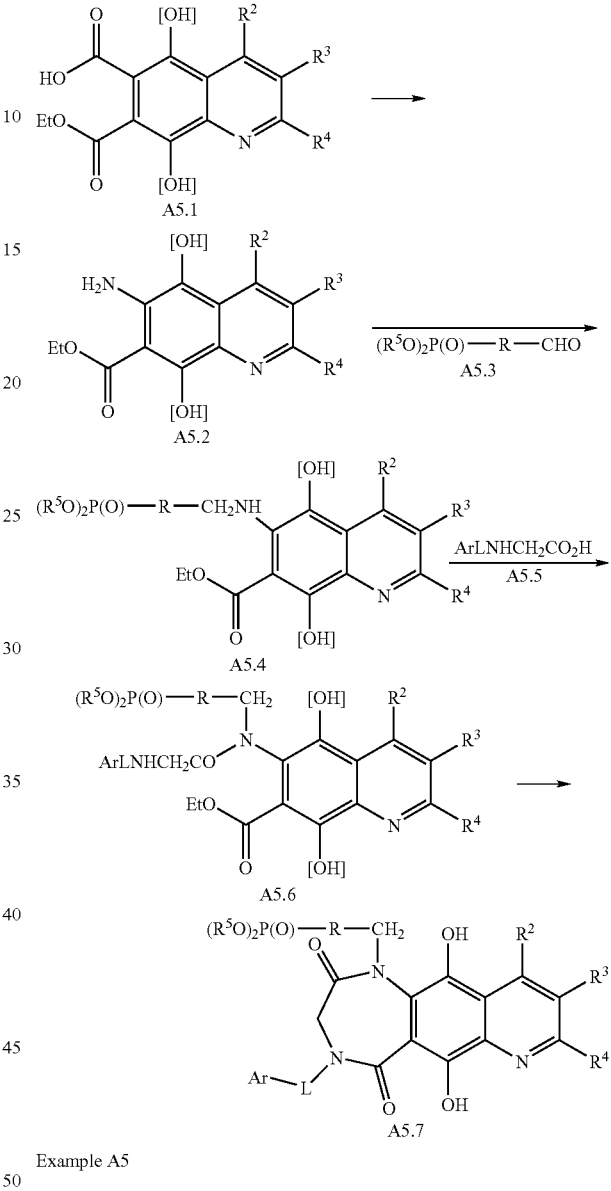
Example A5
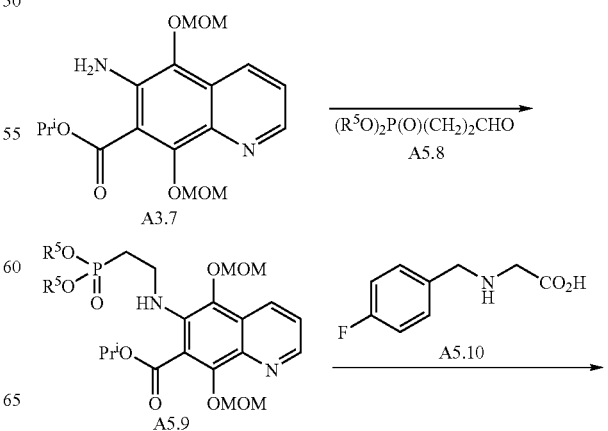

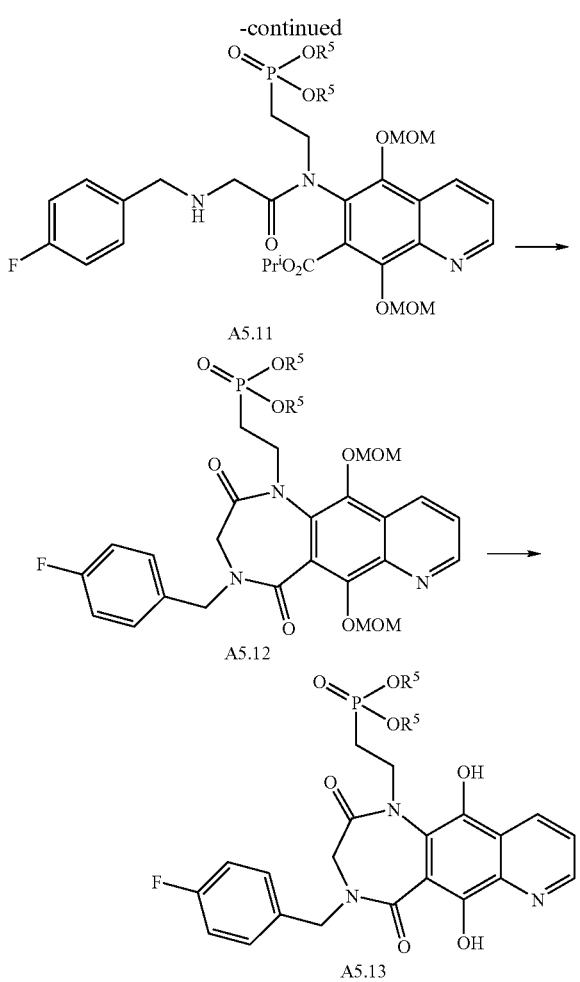

Preparation of the Intermediate Phosphonate Esters Ibb.

Schemes A6-A16 illustrate methods for the preparation of the phosphonate esters of general structure Ibb.

Scheme A6 depicts two methods for the preparation of phosphonate esters in which the phosphonate group is linked by means of a saturated or unsaturated alkylene chain, or alkylene chains incorporating carbocyclic, aryl or heteroaryl rings. In this procedure, a mono-protected phenol A6.1, for example, is reacted either with a bromo-substituted alkyl phosphonate A6.2, in which the group R is alkylene, cycloalkyl, alkenyl, aralkyl, heterarylalkyl and the like, or with an analogous hydroxyl-substituted dialkyl phosphonate A6.3. The reaction between the phenol and the bromo compound A6.2 is conducted in a polar organic solvent such as dimethylformamide, in the presence of a base such as potassium carbonate, and optionally in the presence of a catalytic amount of potassium iodide, to afford the ether product A6.4. Alternatively, the ether compounds A6.4 are obtained by means of a Mitsonobu reaction between the phenol A6.1 and the hydroxy compound A6.3. The preparation of aromatic ethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4 and in Org. React., 1992, 42, 335. The phenol and the alcohol component are reacted together in an aprotic solvent such as, for example, tetrahydrofuran, in the presence of a dialkyl azodicarboxylate and a triarylphosphine, to afford the ether or thioether products. The procedure is also described in Org. React., 1992, 42, 335-656. Deprotection of the phenolic hydroxyl group then affords the phenol A6.5.

For example, 7-(4-fluoro-benzyl)-5-hydroxy-9-triethylsilanyloxy-pyrrolo[3,4-g]quinoline-6,8-dione A6.6, (Example 12, Scheme 11) is reacted at ambient temperature in dimethoxyethane solution with one molar equivalent of a dialkyl 4-bromo-2-butenylphosphonate A6.7 (J. Med. Chem., 1992, 35, 1371) and potassium carbonate, to yield the ether product A6.8, which upon deprotection with tetrabutylammonium fluoride gives the phenol A6.9.

As a further example, 7-[2-(4-fluoro-phenyl)-ethyl]-5-hydroxy-9-triethylsilanyloxy-pyrrolo[3,4-g]quinoline-6,8-dione A6.10 prepared by analogous procedures to those shown is reacted in tetrahydrofuran solution with a dialkyl 3-hydroxypropyl phosphonate A6.11 (Acros), diethyl azodicarboxylate and triphenylphosphine, to afford the ether product A6.12 which upon deprotection gives the phenol A6.13.

Using the above procedures, but employing, in place of the phenols A6.6 and A6.10, the phenols A6.1, and/or different bromides A6.2, or alcohols A6.3, the corresponding products A6.5 are obtained.

Scheme A7 illustrates the preparation of phosphonate esters of structure Ibb in which the phosphonate is linked by means of an aryl or a heteroaryl group.

In this procedure, a mono-protected phenol A7.1 (Formula I) is converted into the triflate A7.2 by reaction, in an inert solvent such as dichloromethane, with trifluoromethanesulfonyl chloride or anhydride, or with trimethylsilyl triflate and triethylsilane, in each case in the presence of a tertiary base such as triethylamine. The triflate is then coupled with a bromo-substituted arylboronate A7.3, in which the group Ar$^1$ is an aromatic or heteroaromatic moiety, to afford the coupled product A7.4. The Suzuki coupling of aryl triflates and aryl boronic acids is described in Palladium Reagents and Catalysts by J. Tsuji, Wiley 1995, p 218. The reactants are combined in an inert solvent such as toluene or dioxan, in the presence of a palladium (0) catalyst such as tetrakis(triphenylphosphine)palladium and a base such as sodium bicarbonate. The coupled product A7.4 is then reacted, as described previously (Scheme A2) with a dialkyl phosphite A7.5, to give the phosphonate ester A7.6, which upon deprotection yields the phenol A7.7.

For example, trifluoro-methanesulfonic acid 9-benzhydryloxy-7-(4-fluoro-benzyl)-8-oxo-7,8-dihydro-6H-pyrrolo[3,4-g]quinolin-5-yl ester A7.8 (Example 46) is reacted in dioxan solution at 70° C. with one molar equivalent of 3-bromophenyl boronic acid A7.9 (Maybridge), sodium bicarbonate and a catalytic amount of tri-(o-tolyl)phosphine, to produce the coupled compound A7.10. This material is then reacted, as described in Scheme A2, with a dialkyl phosphite and a palladium (0) catalyst, to give the phosphonate product A7.10. Removal of the benzhydryl protecting group, for example by treatment with trifluoroacetic acid and anisole in dichloromethane, as described in Tet. Lett., 25, 3909, 1984, then affords the phenol A7.11.

Using the above procedures, but employing, in place of the phenol A7.8, the phenol A7.1, and/or different boronic acids A7.3, the corresponding products A7.7 are obtained.

Scheme A8 illustrates the preparation of phosphonate esters of structure Ibb in which the phosphonate group is linked by means of a oxygen, sulfur or nitrogen and an aliphatic or aromatic moiety.

In this method, a monoprotected phenol A8.1 (Formula I) is converted into the corresponding triflate A8.2, as described above (Scheme A7). The product is then subjected to a nucleophilic displacement reaction with various carbinols, thiols or amines A8.3, in which the group R is an acyclic or cyclic saturated or unsaturated alkylene, or aryl, aralkyl or heteroaryl moiety, to afford after deprotection the ether, thioether or amine products A8.4. The displacement reaction is performed in an inert solvent such as dichloroethane or dioxan, at from ambient temperature to about 80° C., in the presence of a tertiary organic base such as N-methyl morpholine and the like.

For example, trifluoro-methanesulfonic acid 9-benzhydryloxy-7-(4-fluoro-benzyl)-6,8-dioxo-7,8-dihydro-6H-pyrrolo[3,4-g]quinolin-5-yl ester A8.5 (Example 56) is reacted in dioxan at 50° C. with one molar equivalent of a dialkyl methylaminomethyl phosphonate A8.6 and diisopropylethylamine, to give the amine product A8.7. Deprotection then affords the phenol A8.8.

Using the above procedures, but employing, in place of the triflate A8.5, different triflates A8.2, and/or different carbinols, thiols or amines A8.3, the corresponding products A8.4 are obtained.

Scheme A9 depicts the preparation of phosphonate esters of structure Ibb in which the phosphonate group is attached by means of a methylamino group and a carbon link R, in which the group R is an acyclic or cyclic saturated or unsaturated alkylene, or aryl, aralkyl or heteroaryl moiety. The compounds are obtained by means of a reductive alkylation reaction, as described above (Scheme A3) between the aldehyde A9.1, prepared by the method shown in Example 49, and a dialkyl aminoalkyl or aryl phosphonate A9.2. The amination product A9.3 is then deprotected to give the phenol A9.3.

For example, 9-benzhydryloxy-7-(4-fluoro-benzyl)-8-oxo-7,8-dihydro-6H-pyrrolo[3,4-g]quinoline-5-carbaldehyde A9.5 (Example 49) is reacted with a dialkyl aminopropyl phosphonate A9.6 (Acros), sodium cyanoborohydride and acetic acid in isopropanol to yield the amination product A9.7, which is deprotected to produce the phenol A9.8.

Using the above procedures, but employing, in place of the aldehyde A9.5, different aldehydes A9.1, and/or different amines A9.2, the corresponding products A9.4 are obtained.

Scheme A10 depicts the preparation of phosphonate esters of structure Ibb in which the phosphonate group is attached by means of an amide linkage and a carbon link R, in which the group R is an acyclic or cyclic saturated or unsaturated alkylene, or aryl, aralkyl or heteroaryl moiety. In this sequence, the aldehyde A10.1, prepared, for example, as shown in Example 49 is oxidized to the corresponding carboxylic acid A10.2. The conversion of an aldehyde to the corresponding carboxylic acid is described in Comprehensive Organic Transformations, by R. C. Larock, VCH, 1989, p. 838. The reaction is effected by the use of various oxidizing agents such as, for example, potassium permanganate, ruthenium tetroxide, silver oxide or sodium chlorite. The carboxylic acid is then coupled, as described in Scheme A5, with an amine A10.3 to afford the amide, which upon deprotection gives the phenolic amide A10.4.

For example, 9-benzhydryloxy-7-(4-chloro-benzyl)-6,8-dioxo-7,8-dihydro-6H-pyrrolo[3,4-g]quinoline-5-carbaldehyde A10.5, prepared using the methods described in Example 49, is treated with silver oxide in acetonitrile, as described in Tet. Lett., 5685, 1968, to produce the corresponding carboxylic acid 9-benzhydryloxy-7-(4-chloro-benzyl)-6,8-dioxo-7,8-dihydro-6H-pyrrolo[3,4-g]quinoline-5-carboxylic acid A10.6. This material is then coupled, in dimethylformamide solution, with one molar equivalent of a dialkyl aminoethyl phosphonate A10.7 (Aurora) and dicyclohexyl carbodiimide, to afford the amide, which upon deprotection gives the phenolic product A10.8.

Using the above procedures, but employing, in place of the aldehyde A10.5, different aldehydes A10.1, and/or different amines A10.3, the corresponding products A10.4 are obtained.

Scheme A11 depicts the preparation of phosphonate esters of structure Ibb in which the phosphonate group is attached by means of a methylene group. In this procedure, a hydroxymethyl-substituted O-protected phenol A11.1, prepared by the method shown in Example 50, is converted into the corresponding bromomethyl derivative A11.2. The conversion of alcohols into the corresponding bromides is described, for example, in Comprehensive Organic Transformations, by R. C. Larock, VCH, 1989, p. 356ff. For example, benzyl alcohols can be transformed into the bromo compounds by reaction with bromine and triphenyl phosphite, or by reaction with trimethylsilyl chloride and lithium bromide, or with carbon tetrabromide and triphenylphosphine, as described in J. Am. Chem. Soc., 92, 2139, 1970. The resultant bromomethyl compound A11.2 is treated with a trialkyl phosphite A11.3 in an Arbuzov reaction. The preparation of phosphonates by means of the Arbuzov reaction is described in Handb. Organophosphorus Chem., 1992, 115-72. The bromo compound is heated with an excess of the phosphite at from about 80° C.-130° C. to produce the phosphonate product, which upon deprotection affords the phenolic phosphonate A11.4.

For example, 9-benzhydryloxy-5-hydroxymethyl-7-(4-methoxy-benzyl)-6,7-dihydro-pyrrolo[3,4-g]quinolin-8-one A11.5 prepared by the method shown in Example 50, is reacted in dichloromethane with one molar equivalent of carbon tetrabromide and triphenylphosphine to produce 9-benzhydryloxy-5-bromomethyl-7-(4-methoxy-benzyl)-6,7-dihydro-pyrrolo[3,4-g]quinolin-8-one A11.6. The product is then heated at 120° C. with an excess of a trialkyl phosphite A11.3. The resulting phosphonate is then deprotected to afford the phenolic product A11.7.

Using the above procedures, but employing, in place of the carbinol A11.5, different carbinols A11.1, and/or different phosphites A11.3, the corresponding products A11.4 are obtained.

Scheme A12 depicts the preparation of phosphonate esters of structure Ibb in which the phosphonate group is attached by means of a methyleneoxy and a variable alkyl moiety. In this procedure, a protected hydroxymethyl-substituted tricyclic phenol A12.1 prepared according to the procedure of Example 50, is alkylated with a dialkyl bromo-substituted phosphonate A12.2, in which the group R is an acyclic or cyclic saturated or unsaturated alkylene, or aryl, aralkyl or heteroaryl moiety. The carbinol is reacted with one molar equivalent of the bromo compound in a polar aprotic organic solvent such as dimethylacetamide, dioxan and the like, in the presence of a strong base such as sodium hydride, lithium hexamethyldisilazide, or potassium tert. butoxide. The thus-obtained ether A12.3 is then deprotected to give the phenol A12.4.

For example, 9-benzhydryloxy-7-(4-fluoro-benzyl)-5-hydroxymethyl-6,7-dihydro-pyrrolo[3,4-g]quinolin-8-one A12.5 (Example 50) is treated in dimethylformamide solution at ambient temperature with one molar equivalent of lithium hexamethyldisilazide, followed by one molar equivalent of a dialkyl 4-(bromomethyl)benzyl phosphonate A12.6 (Tet., 1998, 54, 9341) to yield the alkylated product A12.7. Deprotection then gives the phenol A12.8.

Using the above procedures, but employing, in place of the carbinol A12.5, different carbinols A12.1, and/or different bromo compounds A12.2, the corresponding products A12.4 are obtained.

Scheme A13 depicts the preparation of phosphonate esters of structure Ibb in which the phosphonate group is attached by means of an aryl or heteroaryl ethenyl or ethyl linkage. In this procedure, a vinyl-substituted OH-protected phenol A13.1, prepared by the method shown in Example 59, is coupled in a palladium-catalyzed Heck reaction with a dibromo-substituted aromatic or heteroaromatic reagent A13.2, in which the group $Ar^1$ is an aromatic or heteroaromatic ring. The coupling of aryl halides with olefins by means of the Heck reaction is described, for example, in Advanced Organic Chemistry, by F. A. Carey and R. J. Sundberg, Plenum, 2001, p. 503ff and in Acc. Chem. Res., 12, 146, 1979. The aryl bromide and the olefin are coupled in a polar solvent such as dimethylformamide or dioxan, in the presence of a palladium(0) catalyst such as tetrakis (triphenylphosphine)palladium(0) or a palladium(II) catalyst such as palladium(II) acetate, and optionally in the presence of a base such as triethylamine or potassium carbonate. The coupled product A13.3 is then reacted, as described in Scheme A7, with a dialkyl phosphite A13.4 and a palladium catalyst, to afford, after deprotection of the phenolic hydroxyl, the ethenyl phosphonate ester A13.5. Catalytic or chemical reduction of the product then yields the saturated analog A13.6. The reduction reaction is effected chemically, for example by the use of dimide or diborane, as described in Comprehensive Organic Transformations, by R. C. Larock, VCH, 1989, p. 5, or catalytically, for example by the use of a palladium on carbon catalyst in the presence of hydrogen or a hydrogen donor.

For example, 9-benzhydryloxy-7-(4-fluoro-benzyl)-5-vinyl-6,7-dihydro-pyrrolo[3,4-g]quinolin-8-one A13.7 (Example 59) is reacted in dimethylformamide with 2,5-dibromothiophene A13.8 and a catalytic amount of palladium (II) acetate and triethylamine, to give the coupled product A13.9. This material is then coupled with a dialkyl phosphite, as described above, to afford after deprotection of the phenol, the ethenylthienyl phosphonate A13.10. The latter compound is reacted with diimide, prepared by basic hydrolysis of diethyl azodicarboxylate, as described in Angew. Chem. Int. Ed., 4, 271, 1965, to yield the saturated product A13.11.

Using the above procedures, but employing, in place of the vinyl-substituted compound A13.7, different analogs A13.1, and/or different dibromo compounds A13.2, the corresponding products A13.5 are obtained.

Scheme A14 depicts the preparation of phosphonate esters of structure Ibb in which the phosphonate group is attached by means of an alkoxy chain incorporating an amide linkage. In this procedure, a mono-protected phenol A14.1 (Example 6) is alkylated with a methyl bromoalkyl carboxylate A14.2. The alkylation reaction is conducted under similar conditions to those described in Scheme A6, to afford the ester ether A14.3. Hydrolysis of the ester group then gives the carboxylic acid A14.4. Hydrolysis methods for converting esters into carboxylic acids are described, for example, in Comprehensive Organic Transformations, by R. C. Larock, VCH, 1989, p 981. The methods include the use of enzymes such as pig liver esterase, and chemical methods such as the use of alkali metal hydroxides in aqueous organic solvent mixtures, for example lithium hydroxide in an aqueous organic solvent.

The resultant carboxylic acid is then coupled, as described in Scheme A10, with a dialkyl amino-substituted phosphonate A14.5, in which the group R is an acyclic or cyclic saturated or unsaturated alkylene, or aryl, aralkyl or heteroaryl moiety, to produce the amide A14.6. Deprotection then yields the phenol A14.7.

For example, 5-hydroxy-9-methoxymethoxy-7-(4-methyl-benzyl)-pyrrolo [3,4-g]quinoline-6,8-dione A14.8, prepared, for example, by the method shown in Example 6 is reacted in dimethylformamide solution with methyl bromoacetate A14.9 and cesium carbonate, to give the ether A14.10. The ester group is then hydrolyzed by reaction with one molar equivalent of lithium hydroxide in aqueous glyme, to produce the carboxylic acid A14.11. The carboxylic acid is then coupled in dimethylformamide solution in the presence of diisopropyl carbodiimide with a dialkyl 2-aminoethyl phosphonate A14.12, (J. Org. Chem., 2000, 65, 676) to form the amide A14.13. Deprotection, for example by the use of 50% aqueous acetic acid containing a catalytic amount of sulfuric acid, as described in J. Am. Chem. Soc., 55, 3040, 1933, then affords the phenol A14.14.

Using the above procedures, but employing, in place of the phenol A14.8, different phenols A14.1, and/or different bromoesters A14.2, and/or different amines A14.5, the corresponding products A14.7 are obtained.

Scheme A15 depicts the preparation of phosphonate esters of structure Ibb in which the phosphonate group is attached by means of an alkylene chain incorporating an amide linkage. In this procedure, the malonic ester derivative of a protected phenol A15.1, prepared, for example, by the methods shown in Example 86, is hydrolyzed and decarboxylated to give the corresponding acetic acid derivative A15.2. Hydrolysis and decarboxylation of malonic esters is described, for example, in Advanced Organic Chemistry, Part B, by F. A. Carey and R. J. Sundberg, Plenum, 2001, p. 15. The ester hydrolysis is effected under conventional basic conditions, and decarboxylation occurs after acidification either spontaneously or under mild heating. The resultant acetic acid derivative is then coupled, as described previously, with a dialkyl amino-substituted phosphonate A15.3, to give the amide product which upon deprotection affords the phenol A15.4.

For example, 2-[9-benzhydryloxy-7-(4-fluoro-benzyl)-8-oxo-7,8-dihydro-6H-pyrrolo[3,4-g]quinolin-5-yl]-malonic acid dimethyl ester A15.5 (Example 86) is reacted at ambient temperature with two molar equivalents of lithium hydroxide in aqueous dimethoxyethane, and the reaction mixture is then acidified to pH 4.0 and heated at reflux to effect decarboxylation and production of the acetic acid derivative A15.6. The carboxylic acid is then coupled in acetonitrile solution in the presence of a water-soluble carbodiimide with a dialkyl 4-aminophenyl phosphonate A15.7 (Epsilon) to yield after deprotection the phenolic amide A15.8.

Using the above procedures, but employing, in place of the malonic ester A15.5, different malonic esters A15.1, and/or different amines A15.3, the corresponding products A15.4 are obtained.

Scheme A16 depicts the preparation of phosphonate esters of structure Ibb in which the phosphonate group is attached by means of an alkoxy chain and the nucleus incorporates a benzazepin moiety. In this procedure, a quinoline monoester A16.1 is decarboxylated to afford the ester A16.2. Decarboxylation of carboxylic acids is described in Advanced Organic Chemistry, Part B, by F. A. Carey and R. J. Sundberg, Plenum, 2001, p. 676 and in Advanced Organic Chemistry, By J. Marsh, McGraw Hill, 1968, p. 435. The carboxylic acid is decarboxylated thermally in the presence of copper powder and quinoline, or by conversion to an ester with N-hydroxyphthalimide or N-hydroxythiopyridine, followed by photolysis in the presence of a hydrogen donor. The decarboxylated product A16.2 is then converted into the allyl ether A16.3 by reaction with allyl bromide in a polar solvent such as dimethylformamide in the presence of a base such h as triethylamine or potassium carbonate. The allyl ester is then subjected to a thermal Claisen rearrangement to afford the allyl-substituted phenol A16.4. The Claisen rearrangement of allyl aryl ethers is described in Advanced Organic Chemistry, By J. Marsh, McGraw Hill, 1968, p. 830 and in Advanced Organic Chemistry, Part B, by F. A. Carey and R. J. Sundberg, Plenum, 2001, p. 394. The reaction is conducted in a high-boiling solvent or without solvent at ca. 200° C. The free phenolic hydroxyl group is then protected to yield the doubly protected product A16.5. The latter compound is then subjected to a hydroboration procedure to afford the carbinol A16.6. Hydroboration of alkenes is described, for example, in Advanced Organic Chemistry, Part B, by F. A. Carey and R. J. Sundberg, Plenum, 2001, p. 226. The olefin is reacted with diborane or a substituted borane such as 9-BBN or catechyl borane, and the resulting borane is oxidized, for example with hydrogen peroxide, oxygen, sodium peroxycarbonate or a tertiary amine oxide. The resultant carbinol A16.6 is then converted into the substituted amine A16.7. The conversion is effected in two stages. In the first step, the carbinol is converted into a leaving group such as mesylate, tosylate or bromide by reaction with, for example, methanesulfonyl chloride, p-toluenesulfonyl chloride or triphenylphosphine/carbon tetrabromide. In the second step, the activated intermediate is reacted in a polar solvent such as N-methylpyrrolidinone or acetonitrile with the amine ArBNH$_2$ to give the product A16.7. The aminoester is then cyclized to yield the azepin derivative A16.8. The cyclization reaction is performed under similar conditions to those described above (Scheme A5). For example, the aminoester is heated in xylene at reflux temperature in the presence of a catalytic amount of sodium isopropoxide. The doubly protected azepin derivative A16.8 is then selectively deprotected to give the phenol A16.9. The procedure for the selective deprotection is dependent on the nature of the protecting groups. For example, if the phenol A16.1 is protected as the benzhydryl derivative, the phenol A16.4 is protected as, for example, the TIPS derivative. Deprotection of the azepin A16.8 is then effected by treatment with tetrabutylammonium fluoride in tetrahydrofuran. The phenol A16.9 is then reacted with a dialkyl hydroxy-substituted phosphonate A16.10, in which the group R is an alkylene or alkenyl chain, optionally incorporating an aryl or heteroaryl group. The reaction is performed under the conditions of the Mitsonobu reaction, as described in Scheme A6. The resultant ether is then deprotected to afford the phenol A16.11.

For example, 8-benzhydryloxy-7-methyl-quinolin-5-ol A16.12 prepared as described above from the corresponding carboxyester is converted, via allylation, rearrangement and hydroboration/oxidation, as described above, into 3-(8-benzhydryloxy-7-methyl-5-triisopropylsilanyloxy-quinolin-6-yl)-propan-1-ol A16.13. The latter compound is then converted into an activated derivative which is reacted, as described above, with 3-chloro-4-fluorobenzylaamine A16.14 to yield [3-(8-benzhydryloxy-7-methyl-5-triisopropylsilanyloxy-quinolin-6-yl)-propyl]-(3-chloro-4-fluoro-benzyl)-amine A16.15. Cyclization of the product, for example by reaction with trimethylaluminum, employing the conditions described above, affords 11-benzhydryloxy-9-(3-chloro-4-fluoro-benzyl)-5-triisopropylsilanyloxy-6,7,8,9-tetrahydro-1,9-diaza-cyclohepta[b]naphthalen-10-one A16.16. The compound is deprotected by reaction with tetrabutylammonium fluoride, to produce 11-benzhydryloxy-9-(3-chloro-4-fluoro-benzyl)-5-hydroxy-6,7,8,9-tetrahydro-1,9-diaza-cyclohepta[b]naphthalen-10-one A16.17. The product is then reacted with a dialkyl hydroxyethyl phosphonate A16.18, diethyl azodicarboxylate and triphenylphosphine in tetrahydrofuran to give after deprotection the phenolic ether A16.19.

Using the above procedures, but employing, in place of the phenol A16.12, different phenols A16.2, and/or different hydroxyesters A16.10, and/or different amines ArBNH$_2$, the corresponding products A16.11 are obtained.

Scheme A6. Phosphonates Ibb.

Method

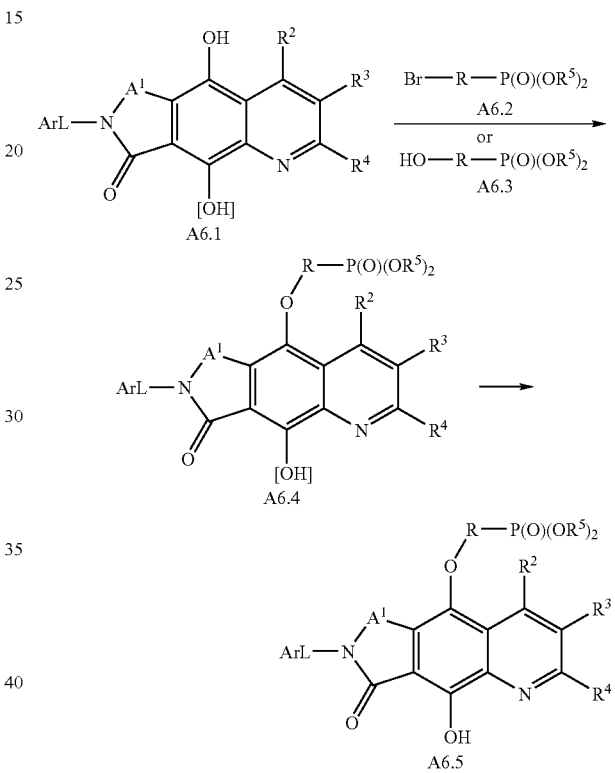

Example A6-1

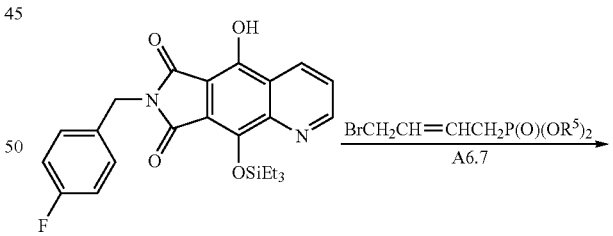

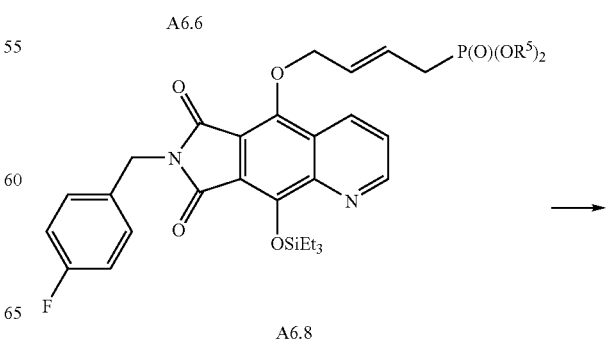

-continued
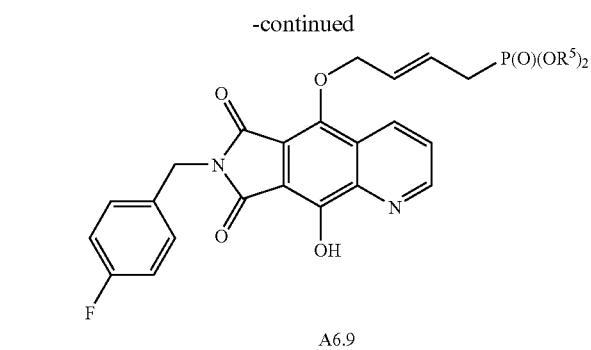
A6.9
Example A6-2
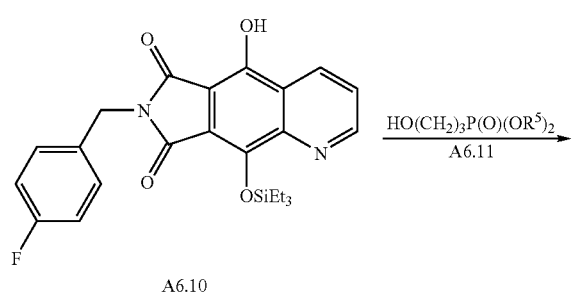
A6.10
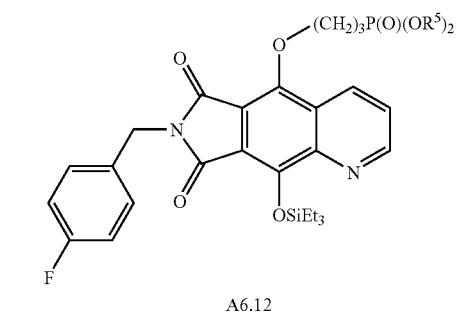
A6.12
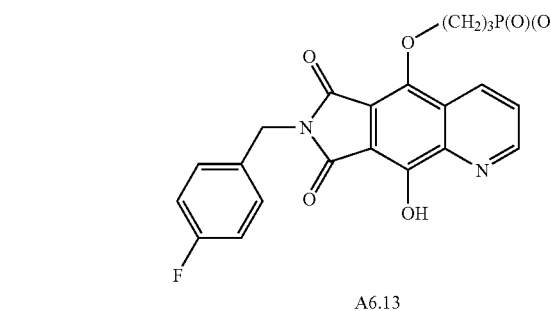
A6.13
Scheme A7. Phosphonates Ibb.
Method
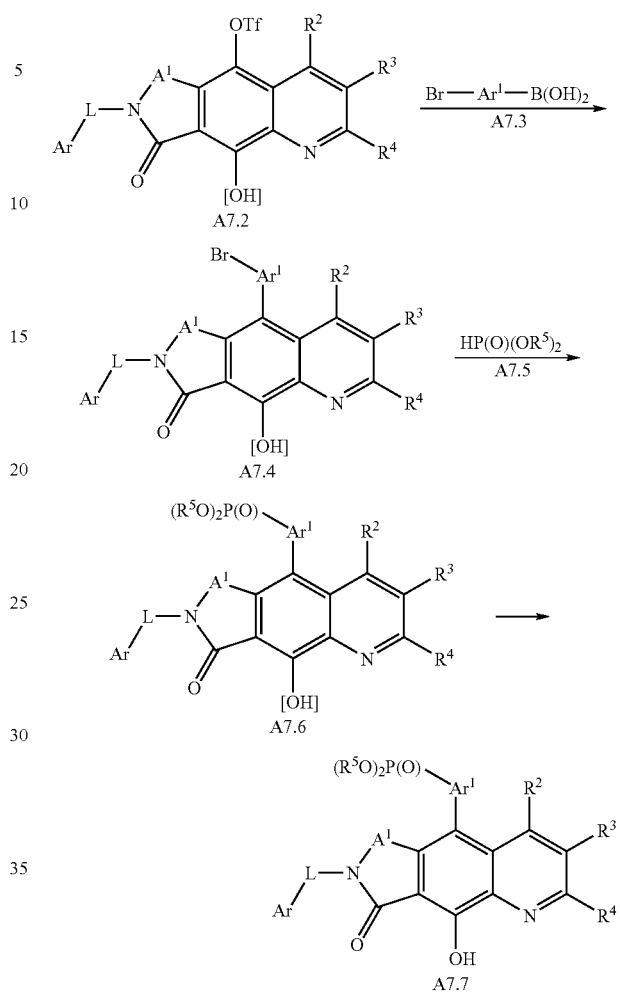
Example A7
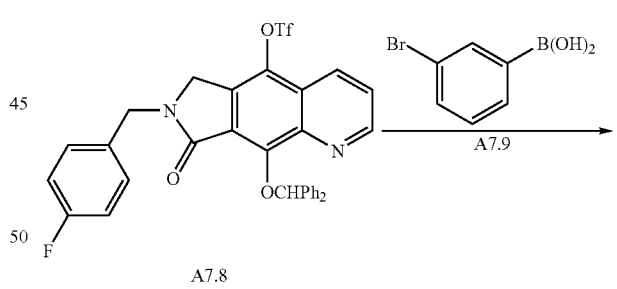
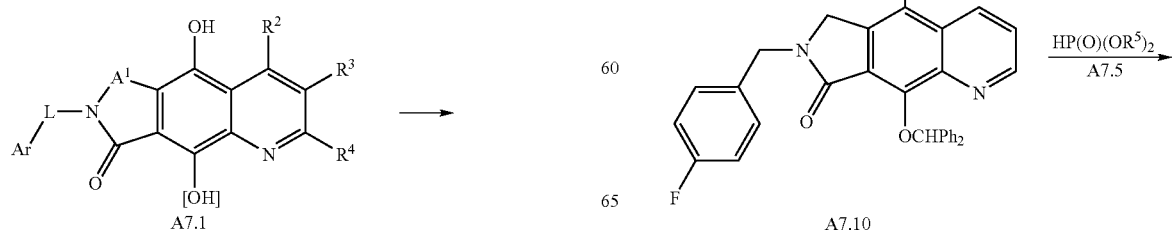

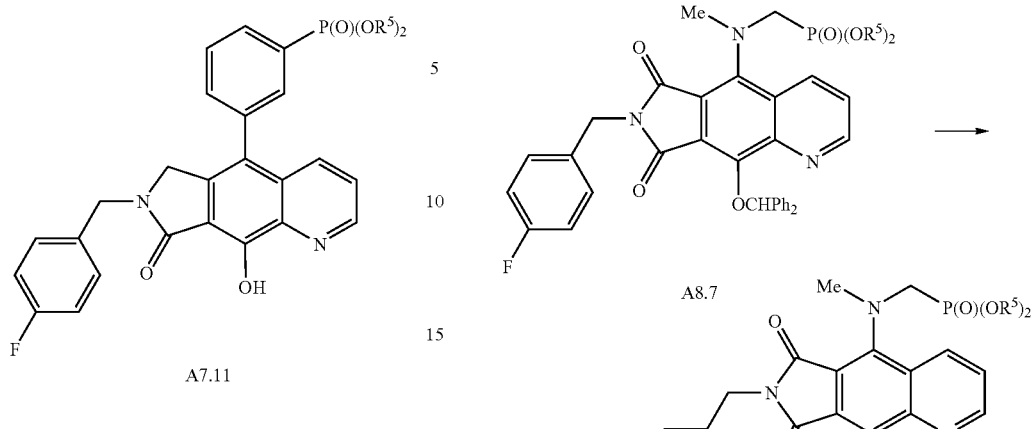
A7.11
Scheme A8. Phosphonates Ibb.
Method
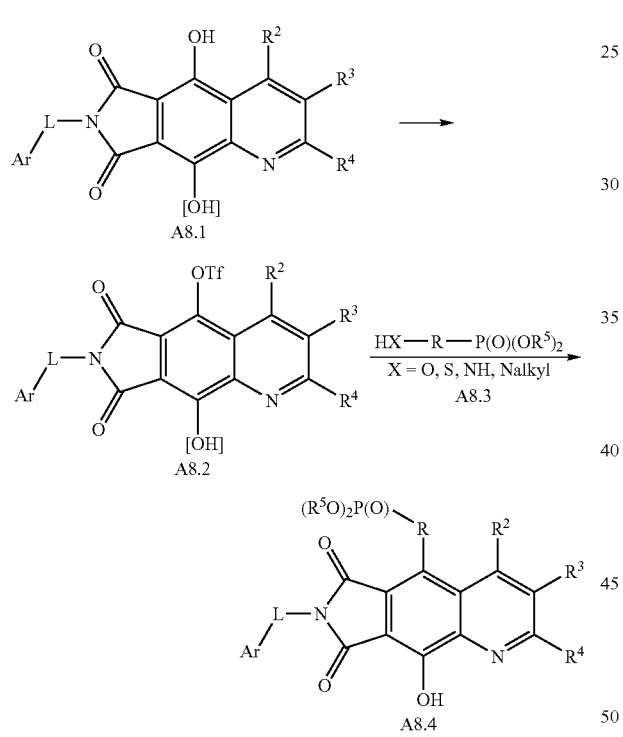
Example A8
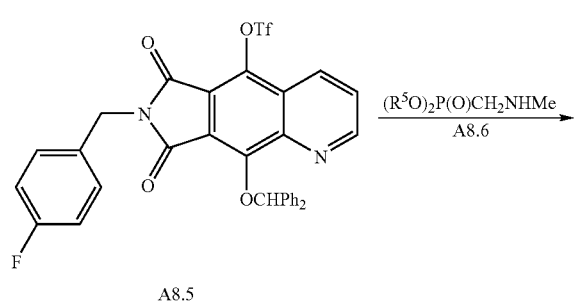
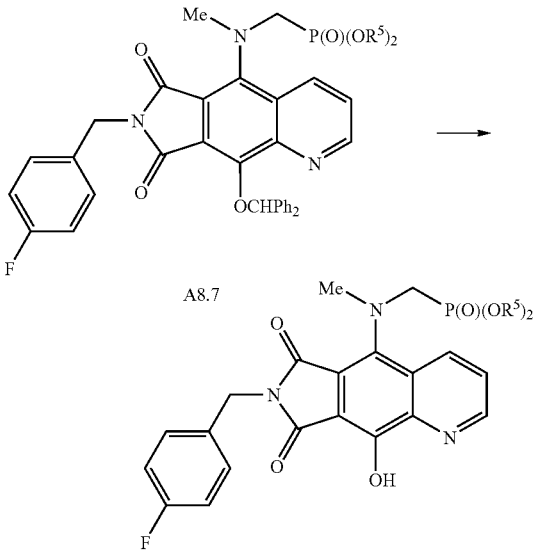
A8.7
A8.8
Scheme A9. Phosphonates Ibb.
Method
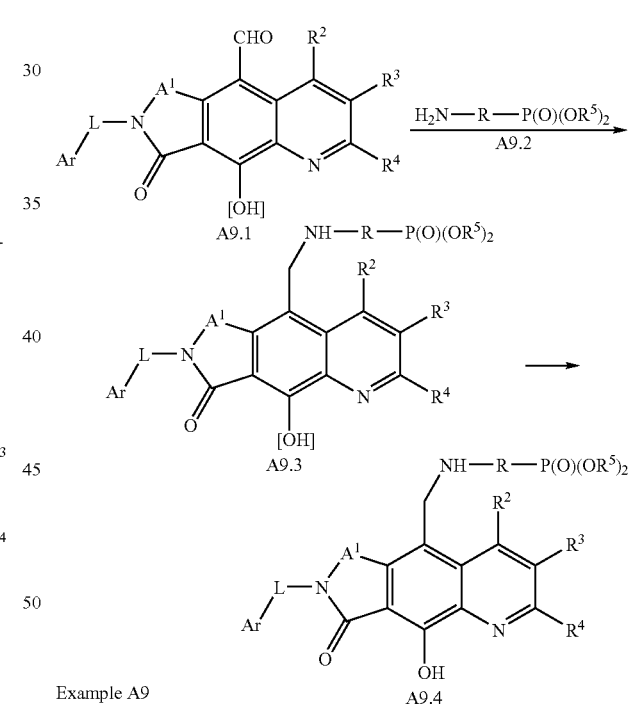
Example A9
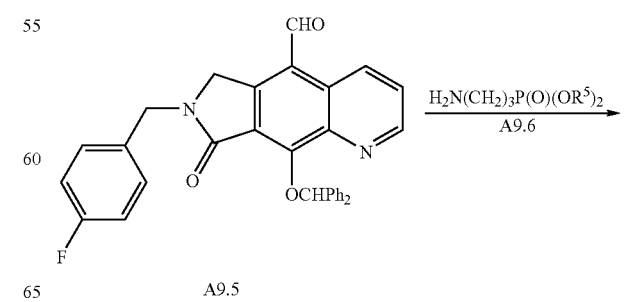
A9.5

-continued
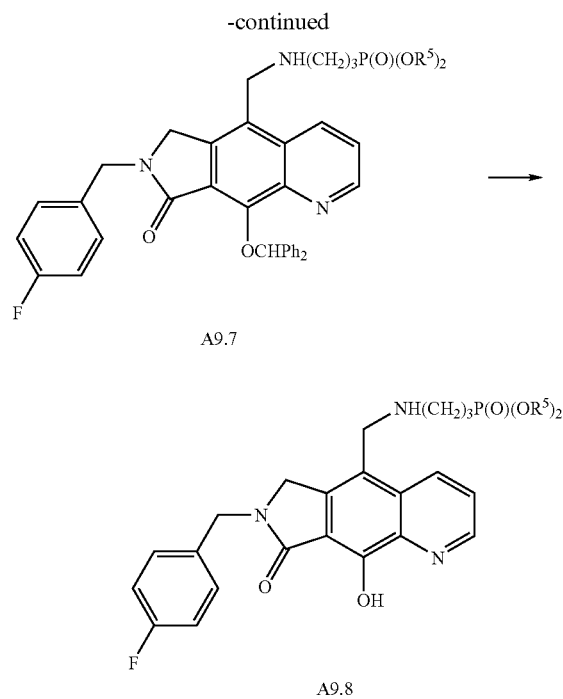
A9.7
A9.8
Scheme A10. Phosphonates Ibb.
Method
A10.1
A10.2
A10.4
Example A10
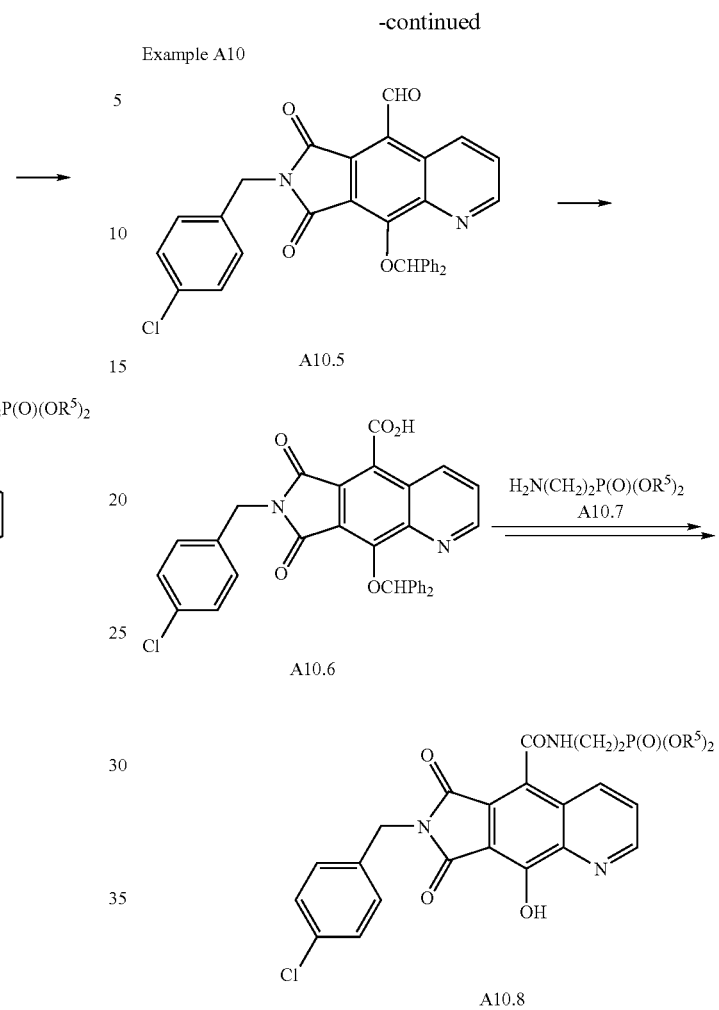
A10.5
A10.6
A10.8
Scheme A11. Phosphonates Ibb.
Method
A11.1
A11.2

-continued
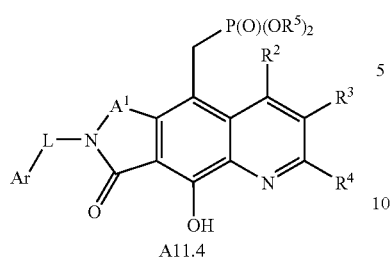
A11.4
Example A11
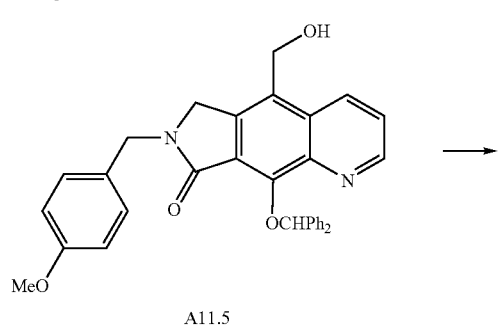
A11.5
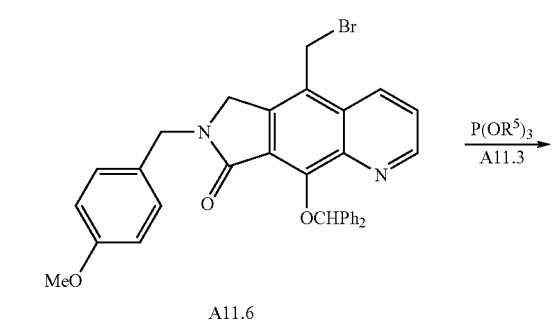
A11.6
$\xrightarrow{\text{P(OR}^5)_3}{\text{A11.3}}$
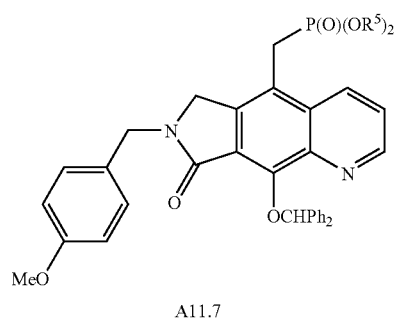
A11.7
Scheme A12. Phosphonates Ibb.
Method
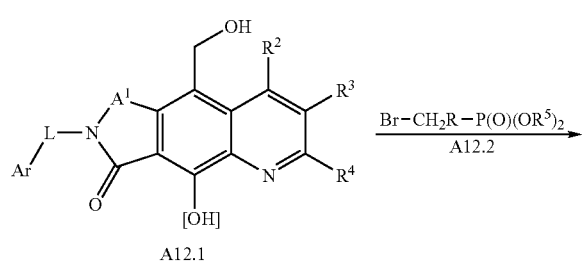
A12.1
$\xrightarrow{\text{Br—CH}_2\text{R—P(O)(OR}^5)_2}{\text{A12.2}}$
-continued
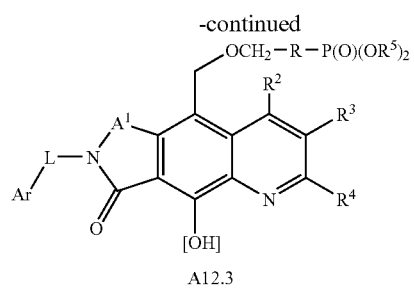
A12.3
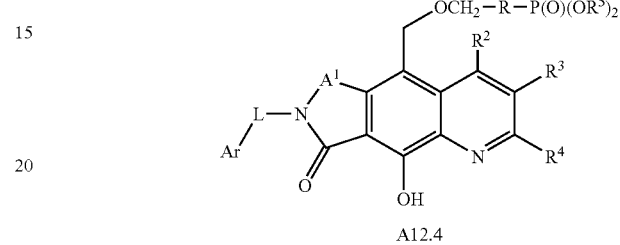
A12.4
Example A12
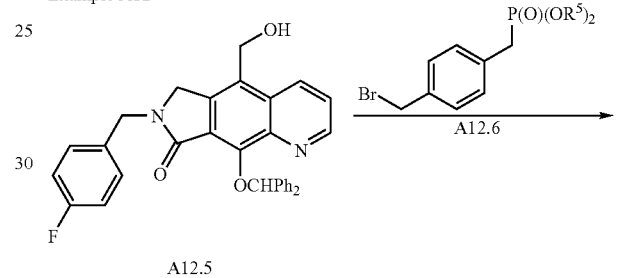
A12.5
$\xrightarrow[\text{A12.6}]{}$
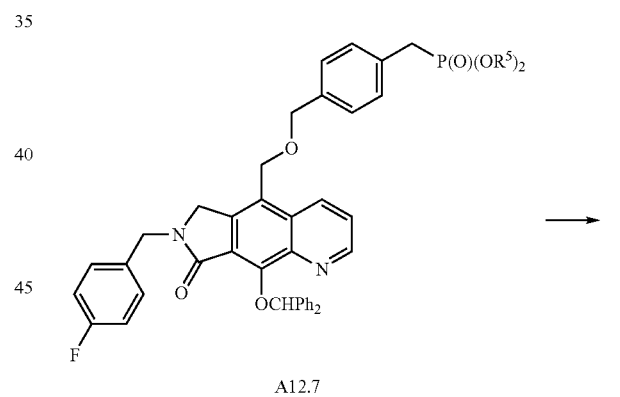
A12.7
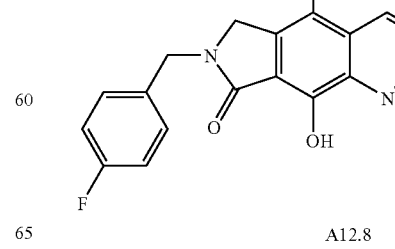
A12.8

Scheme A13. Phosphonates Ibb.
Method
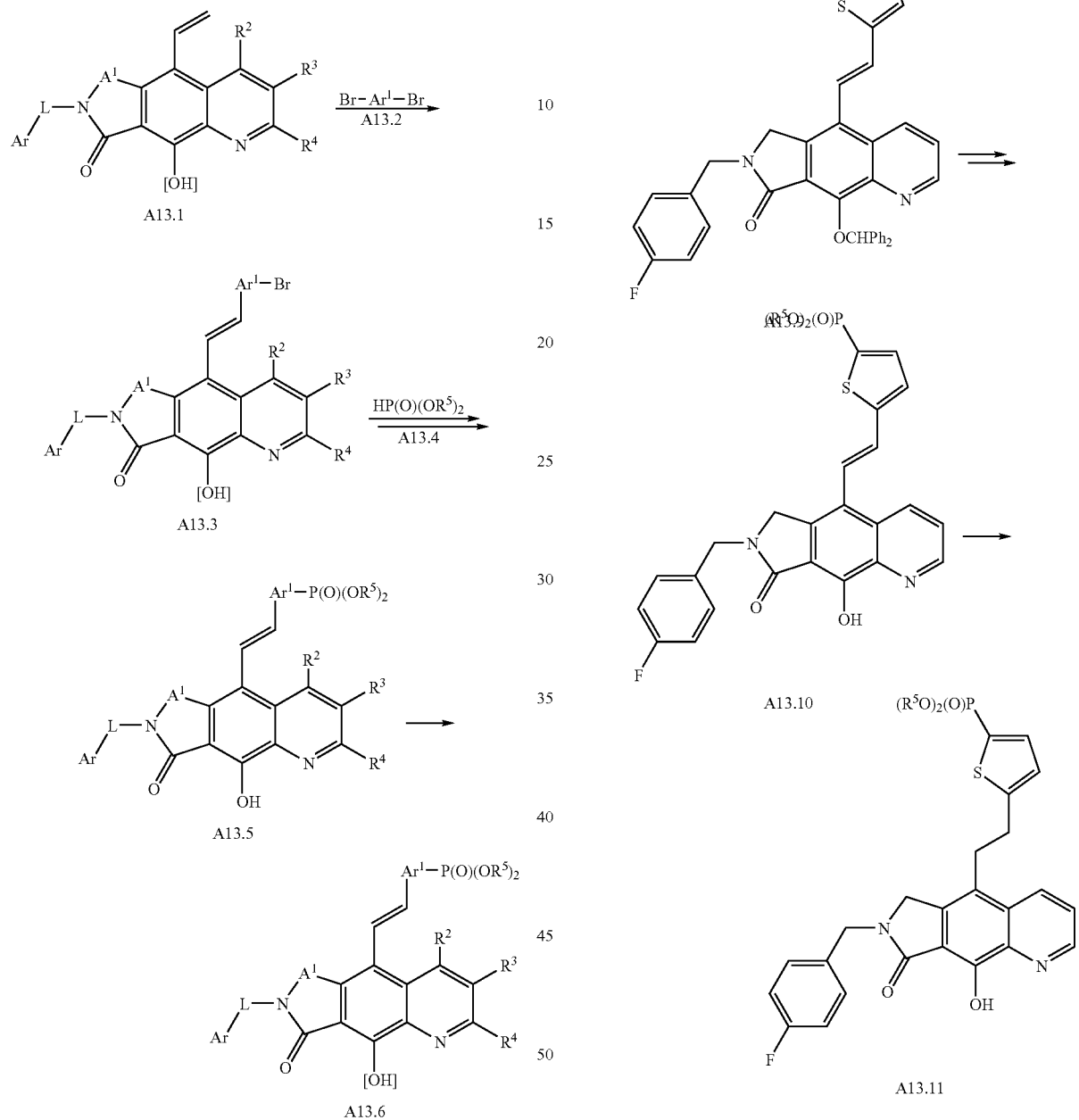
Example A13
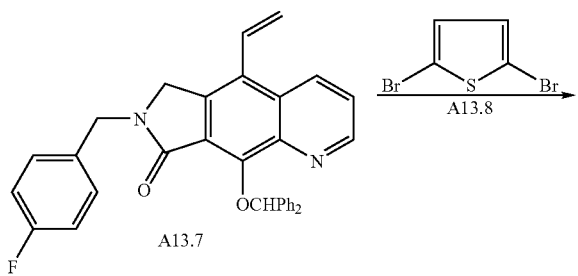
Scheme A14. Phosphonates Ibb.
Method
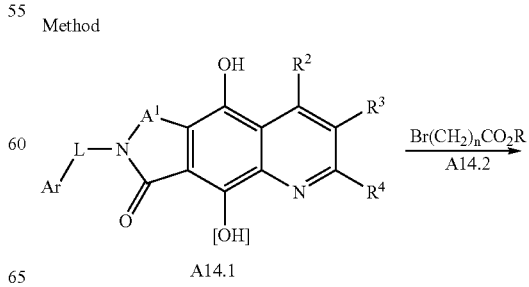

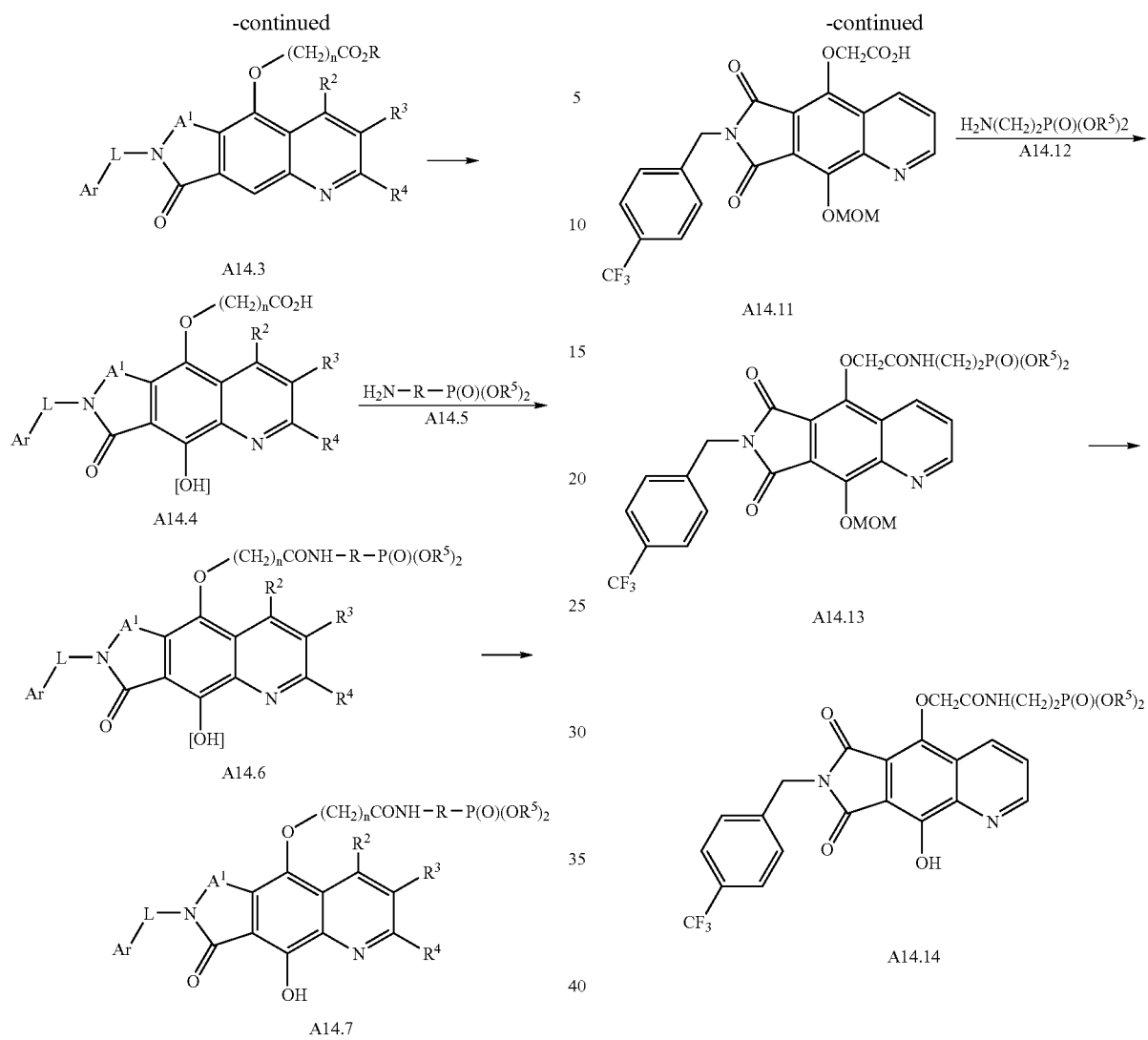
Example A14
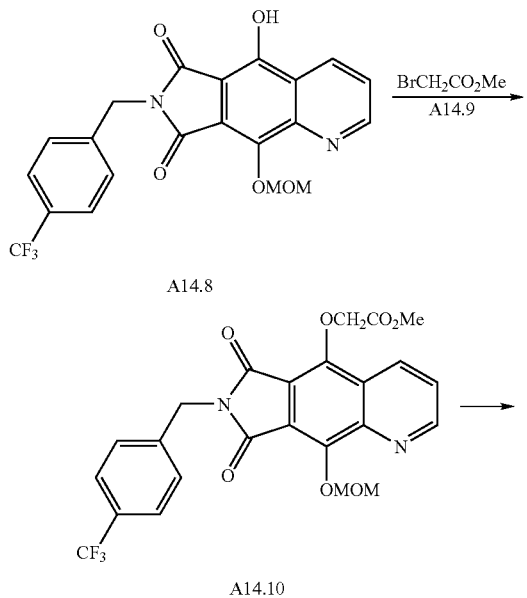
Scheme A15. Phosphonates Ibb.
Method
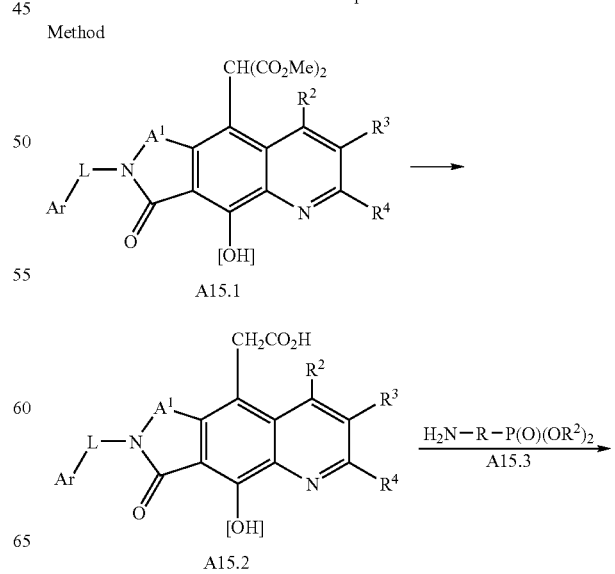

-continued
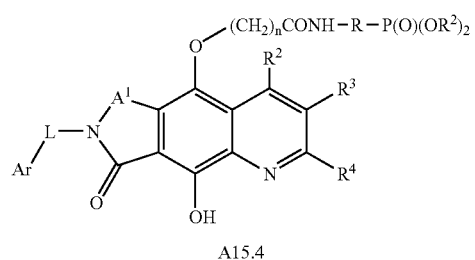
A15.4
Example A15
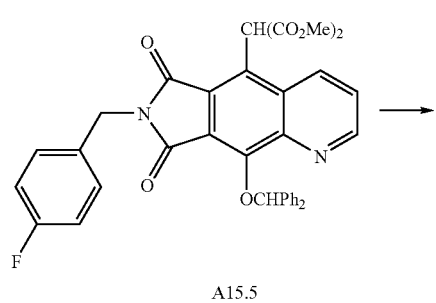
A15.5
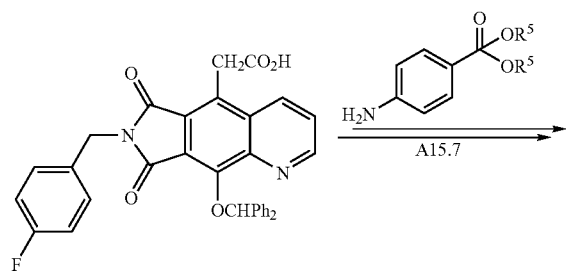
A15.6
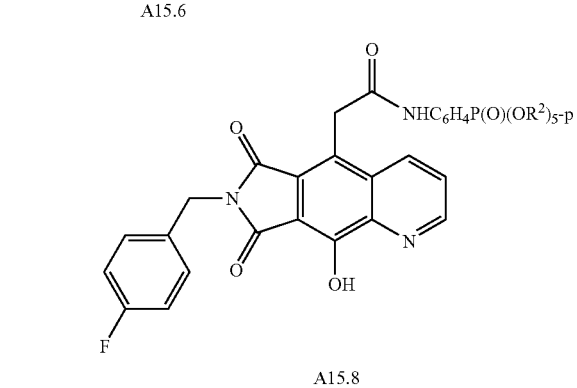
A15.8
Scheme A16. Phosphonates Ibb.
Method
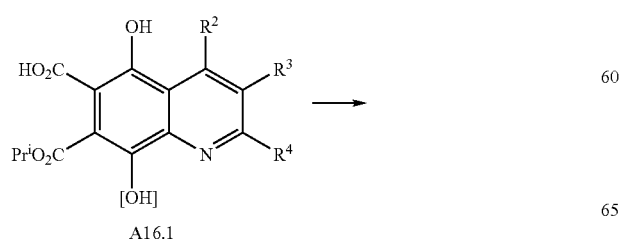
A16.1
-continued
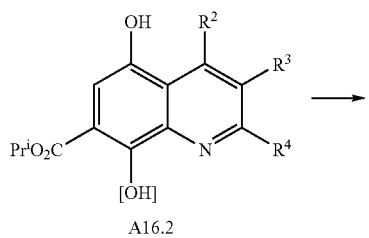
A16.2
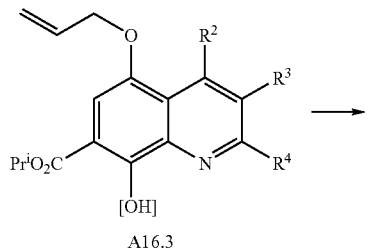
A16.3
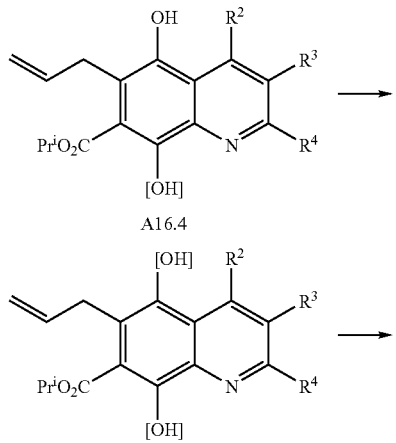
A16.4
A16.5
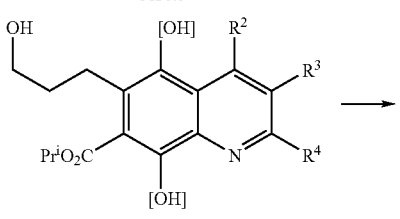
A16.6
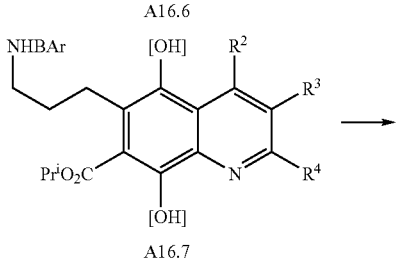
A16.7
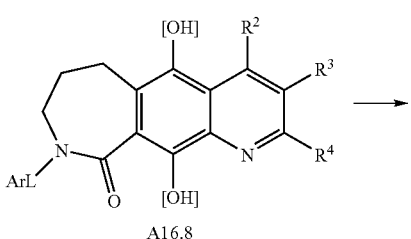
A16.8

-continued

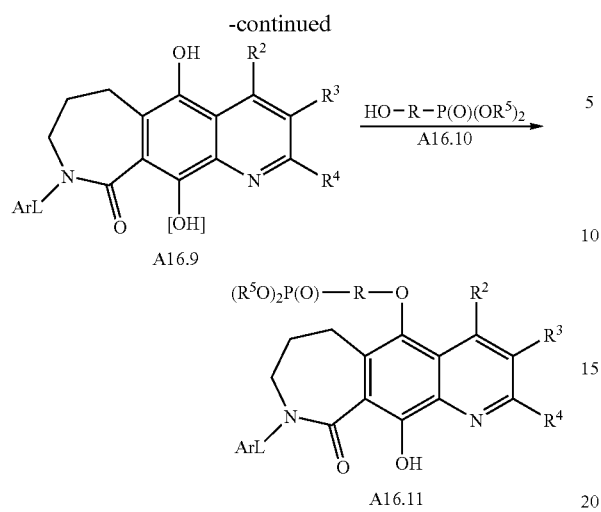

Example A16

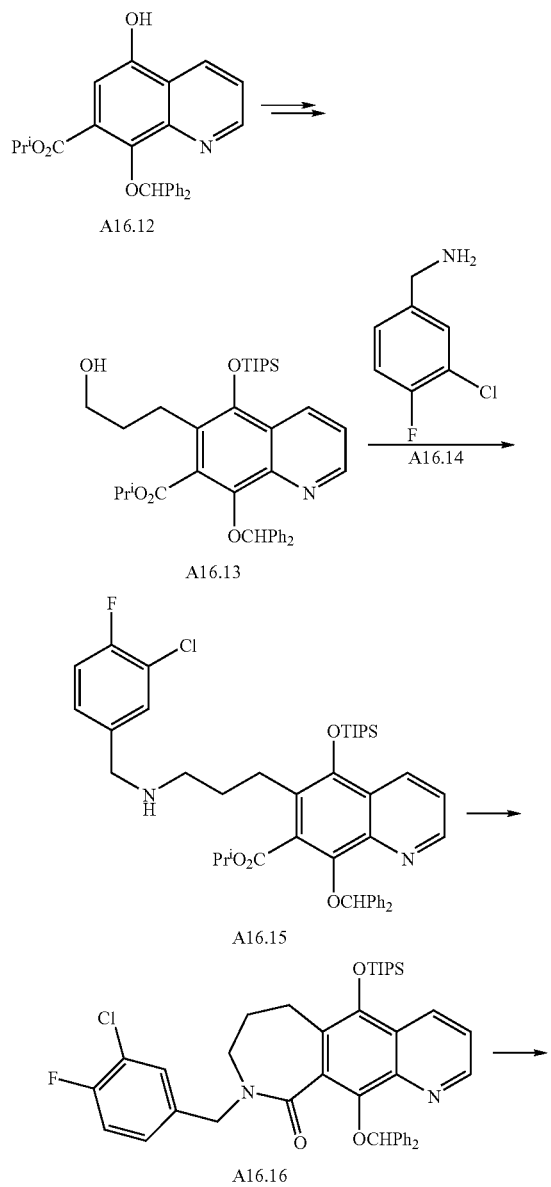

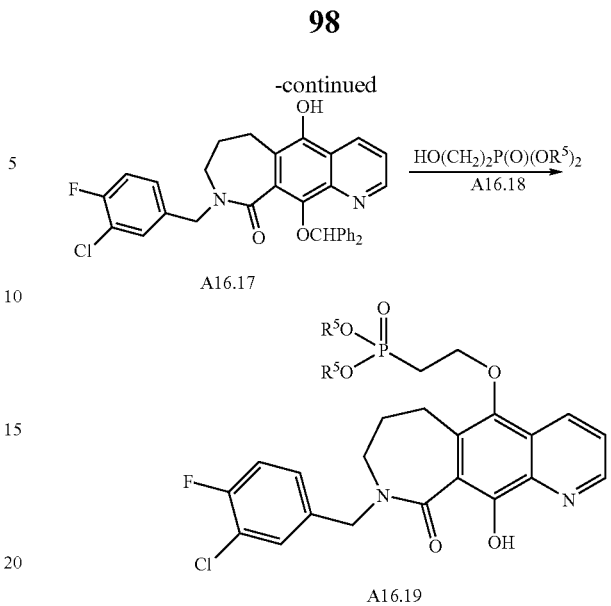

Preparation of the Intermediate Phosphonate Esters Icc.

Scheme A17 illustrates methods for the preparation of phosphonate esters of structure Icc in which the phosphonate group is attached by means of a one-carbon link, or by saturated or unsaturated multicarbon chains optionally incorporating a heteroatom. In this procedure, a 4-methyl-substituted quinoline A17.3 is prepared by means of a Doebner-von Miller condensation between an enone A17.2 and a substituted aniline A17.1. The preparation of quinolines by means of the Doebner-von Miller reaction is described in Heterocyclic Chemistry, by T. L. Gilchrist, Longman, 1992, p. 158. The reaction is performed by heating equimolar amounts of the reactants in an inert solvent such as dimethylacetamide. The bromohydroxyquinoline A17.3 is then transformed, by means of reaction sequence such as that illustrated in Scheme 8 into the protected tricyclic compound A17.4. Benzylic bromination of the latter compound, for example by reaction with N-bromosuccinimide or N-bromoacetamide in an inert solvent such as ethyl acetate at ca. 60° C., then yields the bromomethyl derivative A17.5. This compound is then reacted in an Arbuzov reaction, as described above (Scheme A11), with a trialkyl phosphite to produce after deprotection the phosphonate ester A17.8.

Alternatively, the bromomethyl derivative A17.5 is reacted, using the conditions described in Scheme A12, with a dialkyl hydroxy, mercapto or amino-substituted phosphonate A17.6, in which the group R is an acyclic or cyclic saturated or unsaturated alkylene, or aryl, aralkyl or heteroaryl moiety, to give after deprotection the ether, thioether or amino product A17.7.

Alternatively, the methyl-substituted tricyclic compound A17.4 is condensed, under basic conditions, with a dialkyl formyl-substituted phosphonate A17.9. The reaction is conducted between equimolar amounts of the reactants in a polar solvent such as dioxan or dimethylformamide, in the presence of a strong base such as sodium hydride or lithium tetramethyl piperidide. The procedure affords after deprotection the unsaturated phenol A17.10. Reduction of the double bond, as described above (Scheme A13) then produces the saturated analog A17.11.

For example, benzoic acid 7-cyclopent-3-enylmethyl-4-methyl-8-oxo-7,8-dihydro-6H-pyrrolo[3,4-g]quinolin-9-yl ester A17.12 is reacted with N-bromosuccinimide in refluxing ethyl acetate to afford benzoic acid 4-bromomethyl-7-cyclopent-3-enylmethyl-8-oxo-7,8-dihydro-6H-pyrrolo[3,4-g]quinolin-9-yl ester A17.13. This compound is heated to 120° C. with an excess of a trialkyl phosphite to give after deprotection the phenolic phosphonate ester A17.14.

As a further example, 4-bromomethyl-7-(4-fluoro-benzyl)-9-triisopropylsilanyloxy-6,7-dihydro-pyrrolo[3,4-g]quinolin-8-one A17.15, prepared by bromination of the corresponding methyl compound is reacted with a dialkyl 2-mercaptoethyl phosphonate A17.16 (Zh. Obschei. Khim., 1973, 43, 2793) and cesium carbonate in acetonitrile, to give the thioether product A17.17. Deprotection yields the corresponding phenol A17.18.

As a further example, 7-(3-chloro-4-fluoro-benzyl)-9-methoxymethoxy-4-methyl-6,7-dihydro-pyrrolo[3,4-g]quinolin-8-one A17.19 is condensed in dioxan solution with a dialkyl formylmethyl phosphonate A17.20 (Aurora) in the presence of lithium tetramethylpiperidide to form the unsaturated product A17.21. Deprotection then yields the phenol A17.22; reduction of the double bond then gives the saturated analog A17.23.

Using the above procedures, but employing, in place of the starting materials A17.12, A17.15 and A17.19, different starting materials A17.4 or A17.5, and/or different carbinols, thiols or amines A17.6 or aldehydes A17.9, the corresponding products A17.7, A17.8, A17.10 and A17.11 are obtained.

Scheme A17. Phosphonates Icc.

Method

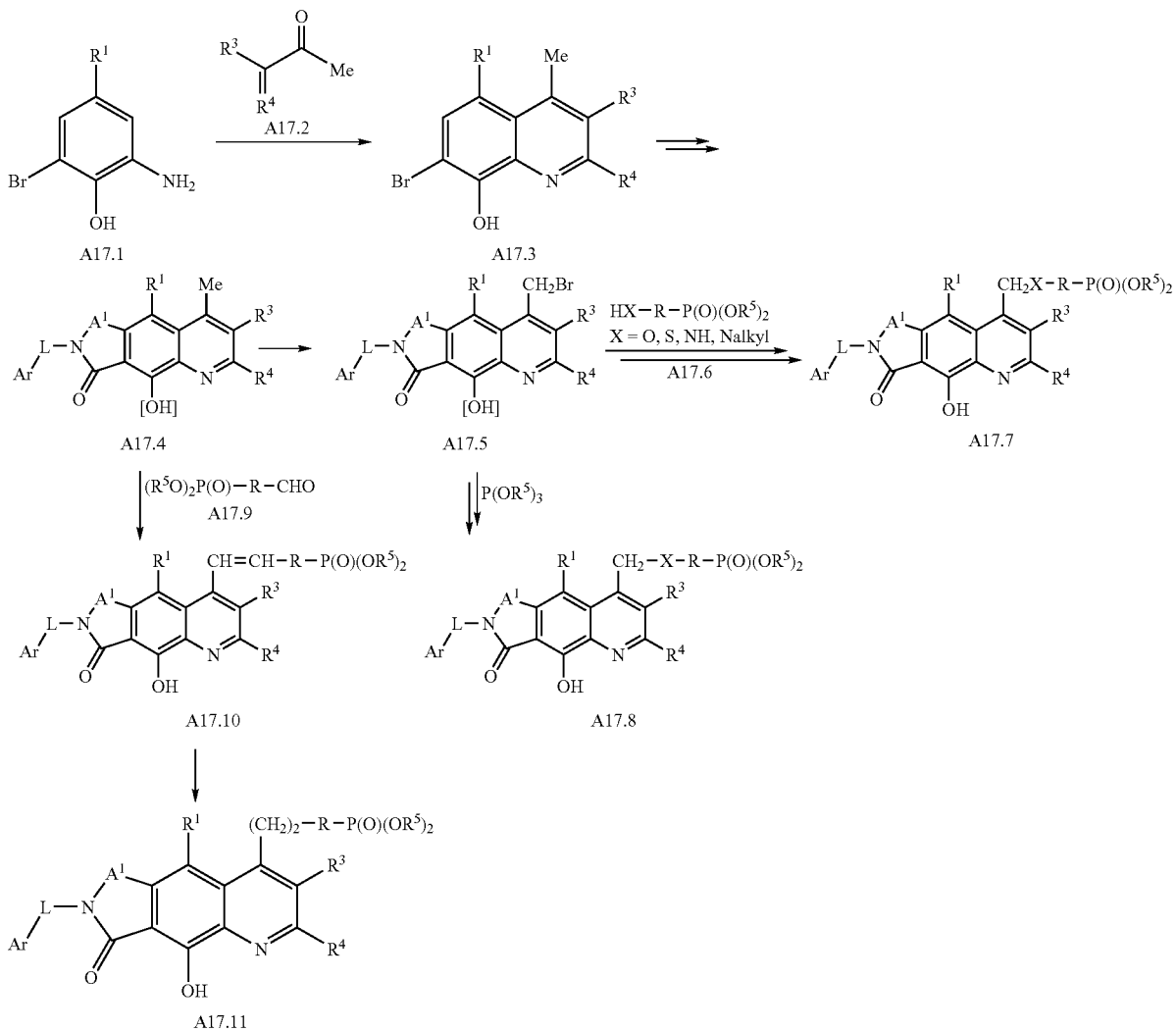

Preparation of the Intermediate Phosphonate Esters IIaa.

Schemes A18 and A19 illustrate the preparation of phosphonate esters of structure IIaa. Scheme A18 depicts the preparation of phosphonate esters of structure IIaa in which the phosphonate group is attached by means of an alkoxy, alkylthio or alkylamino group. In this procedure, an alkoxyethene triester A18.1 (JP 61289089) and a 3-aminopyridine A18.2 are reacted together, as described in JP 61289089 and GB 1509695, to produce the pyridylamino triester A18.3. The reaction is performed using equimolar amounts of the reactants at a temperature of about 150° C. The product is then cyclized to afford the 1,5-naphthyridine derivative A18.4. The reaction is performed in a high-boiling solvent such as diphenyl ether at a temperature of about 250° C. The diester is then converted to the anhydride, and the latter compound is transformed by reaction with the amine ArBNH₂, and protection of the phenolic hydroxyl group, into the cyclic imide A18.5. This material is then reduced, as described in Example 20, for example by the use of sodium borohydride, to afford the hydroxylactam A18.6. The latter compound is then reacted, in the presence of an acid catalyst, as described in Scheme A4, with a dialkyl hydroxy, mercapto or amino-substituted phosphonate A18.7, in which the group R is an acyclic or cyclic saturated or unsaturated alkylene, or aryl, aralkyl or heteroaryl moiety, to yield after deprotection of the phenolic hydroxy group, the ether, thioether or amino product A18.8.

For example, the triester A18.1 is reacted with 3-aminopyridine A18.9 to afford the pyridylamino triester A18.10. The product is heated in diphenyl ether at 250° C. to form the 1,5-naphthyridine A18.11. The latter compound is then transformed, as described above, into 7-(4-fluoro-benzyl)-6-hydroxy-9-triisopropylsilanyloxy-6,7-dihydro-pyrrolo[3,4-b][1,5]naphthyridin-8-one A18.12. The hydroxylactam is then reacted in dichloromethane solution with a dialkyl 4-hydroxybutyl phosphonate A18.13 (J. Med. Chem., 1996, 39, 949) and trifluoroacetic acid, by a similar reaction as Example 23, to generate the phosphonate product A18.14.

Using the above procedures, but employing, in place of the pyridine A18.9, different pyridines A18.2, and/or different phosphonates A18.7, the corresponding products A18.8 are obtained.

Scheme A19 depicts the preparation of phosphonate esters of structure IIaa in which the phosphonate group is attached by means of variable carbon linkage, and the nucleus is a 1,3,5,9-tetraazaanthracene. In this procedure, the 1,5-naphthyridine A18.4 is converted into the phenol-protected analog A19.1. The product is then subjected to a selective partial hydrolysis, for example by reaction with one molar equivalent of a base such as lithium hydroxide in an aqueous organic solvent mixture, to produce the carboxy ester A19.2. The product is then subjected to a Curtius rearrangement, as described in Scheme A3, to afford the amine A19.3. The product is then reductively aminated, as described in Scheme A3, by reaction with a dialkyl formyl-substituted phosphonate A19.4, in which the group R is an acyclic or cyclic saturated or unsaturated alkylene, or aryl, aralkyl or heteroaryl moiety, to give the amine A19.5. The ester group is then transformed, as described previously (Scheme A3), into the amide A19.6, by reaction with the amine ArBNH₂. The product is then cyclized to afford, after deprotection of the phenolic hydroxyl, the tricyclic product, A19.7, in which A is, for example, CO or CH₂, by reaction respectively with phosgene or an equivalent thereof, or with diiodomethane or a similar reagent.

For example, 2-amino-4-hydroxy-[1,5]naphthyridine-3-carboxylic acid methyl ester A19.8, prepared as described in Scheme A18 by the reaction between 3-aminopyridine and 1,2,2-tris-(carbomethoxy)-1-ethoxyethene, is converted, as described above, into 2-amino-4-benzyloxy-[1,5]naphthyridine-3-carboxylic acid methyl ester A19.9. The amine is then reacted in isopropanol solution with a dialkyl 3-formylphenyl phosphonate A19.10 (J. Med. Chem., 1984, 27, 654) and sodium triacetoxyborohydride, to yield the amine A19.11. The ester group of the latter compound is then transformed into the amide by reaction with 3,5-dichlorophenethylamine-trimethyl aluminum, as described previously, to afford the amide A19.12. The product is then reacted with triphosgene in pyridine solution at 80° C. to give the cyclized product A19.13. Deprotection then yields the phenol A19.14.

Using the above procedures, but employing, in place of the amine A19.9, different amines A19.3, and/or different formyl phosphonates A19.4, the corresponding products A19.7 are obtained.

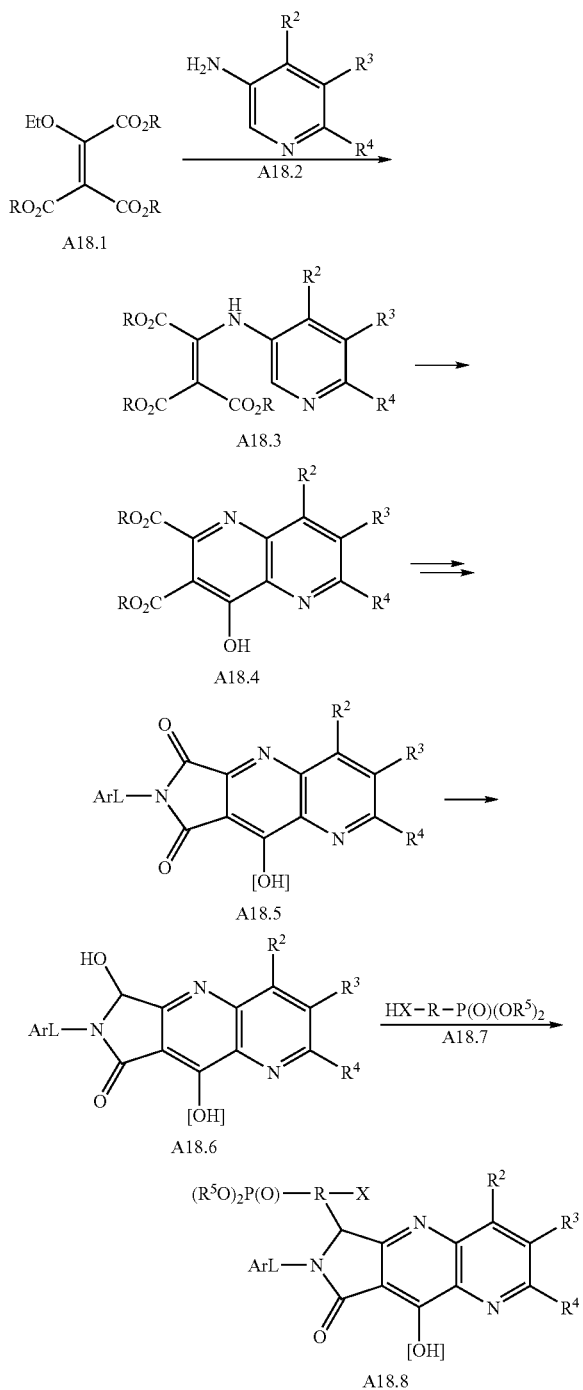

Scheme A18. Phosphonates IIaa.

Method

Example A18
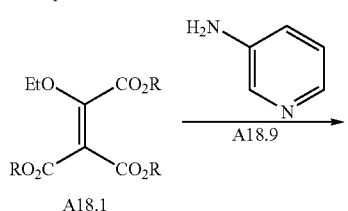
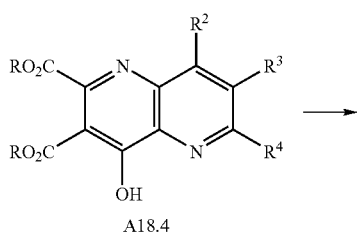
Scheme A19. Phosphonates IIaa.
Method
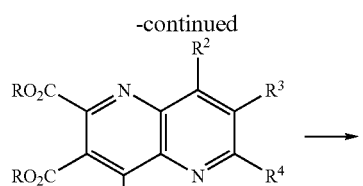
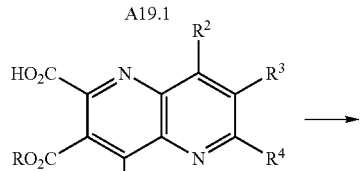
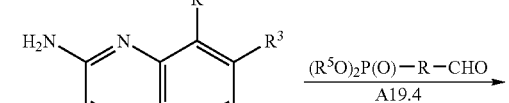
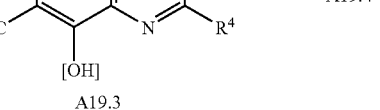
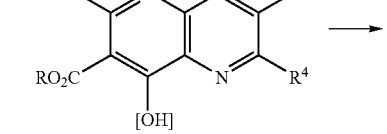
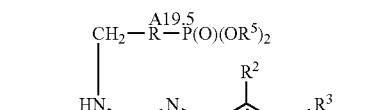
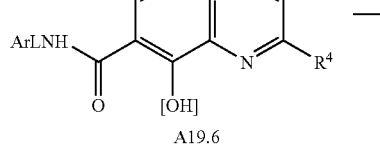
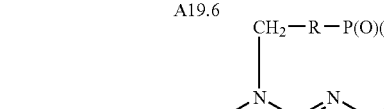
Example A19

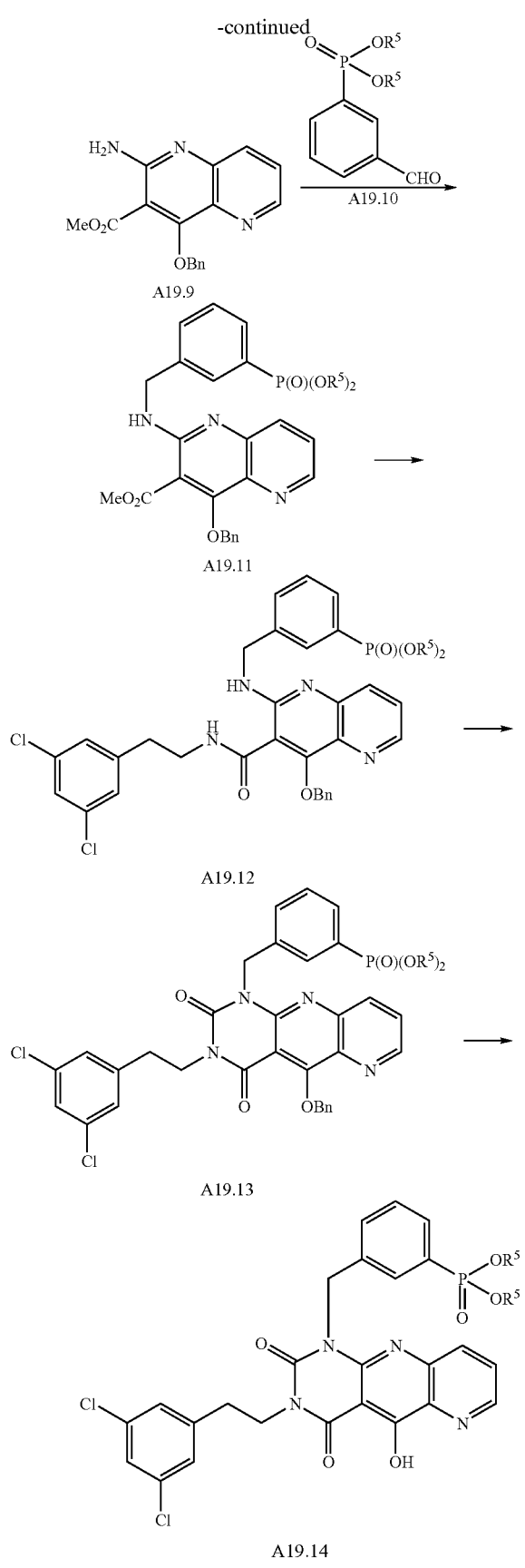

Preparation of the Intermediate Phosphonate Esters IIcc.

Scheme A20 illustrates the preparation of phosphonate esters of structure IIcc, in which the phosphonate group is attached by means of a one-carbon or multicarbon link, or by means of a heteroatom and a variable carbon linkage. In this procedure, the triester A18.1 is reacted, as described in Scheme A18, with a 3-amino-4-methylpyridine A20.1 to give the substituted pyridine product A20.2. The latter compound is then transformed, as described previously, into the methyl-substituted tricyclic compound A20.3. This compound is then subjected to benzylic bromination, for example by reaction with N-bromosuccinimide, to form the bromomethyl product A20.4. This compound is subjected to an Arbuzov reaction with a trialkyl phosphite, as described in Scheme A11, to afford after deprotection the phosphonate A20.5.

Alternatively, the bromomethyl compound A20.4 is reacted with a dialkyl phosphonate A20.6 in which X is O, S, NH or N-alkyl, and R is an acyclic or cyclic saturated or unsaturated alkylene, or aryl, aralkyl or heteroaryl moiety, using the procedures described in Scheme A17, to give, after deprotection of the phenolic hydroxyl, the ether, thioether or amine products A20.7.

Alternatively, the methyl compound A20.3 is subjected, as described in Scheme A17, to a base-catalyzed condensation reaction with a dialkyl formyl-substituted phosphonate A20.8, in which R is an acyclic or cyclic saturated or unsaturated alkylene, or aryl, aralkyl or heteroaryl moiety, to generate after deprotection of the phenolic hydroxyl, the unsaturated product A20.9. The double bond is then reduced, as described in Scheme A17, to afford the saturated analog A20.10.

For example, condensation between the triester A18.1 and 3-amino4-methylpyridine A20.11 gives the pyridine product A20.12. The compound is then transformed, as described above, into 7-[1-(4-fluoro-phenyl)-1-methyl-ethyl]-4-methyl-9-triisopropylsilanyloxy-pyrrolo[3,4-b][1,5]naphthyridine-6,8-dione A20.13. The latter compound is then reacted with a dialkyl formylethyl phosphonate A20.14 (Zh. Obschei. Khim., 1987, 57, 2793) and lithium tetramethylpiperidine in tetrahydrofuran to afford after deprotection the unsaturated product A20.15. The product is then reduced with diimide, as described above, (Scheme A13) to yield the saturated analog A20.16.

As a further example, 7-[1-(4-fluoro-phenyl)-cyclopropyl]-4-methyl-9-triisopropylsilanyloxy-pyrrolo[3,4-b][1,5]naphthyridine-6,8-dione A20.17, prepared according to the procedures described above, is reacted with N-bromosuccinimide in refluxing ethyl acetate to give 4-bromomethyl-7-[1-(4-fluoro-phenyl)-cyclopropyl]-9-triisopropylsilanyloxy-pyrrolo[3,4-b][1,5]naphthyridine-6,8-dione A20.18. The product is then heated at 120° C. with excess of a trialkyl phosphite to give after deprotection the phosphonate A20.19.

As a further example, 4-bromomethyl-7-(3-chloro-4-fluoro-benzyl)-9-triisopropylsilanyloxy-pyrrolo[3,4-b][1,5]naphthyridine-6,8-dione A20.20, prepared according to the procedures described above, is reacted in dimethylformamide solution with a dialkyl methylaminomethyl phosphonate A20.21(AsInEx) and potassium carbonate, to afford after deprotection the displacement product A20.22.

Using the above procedures, but employing, in place of the starting materials A20.13, A20.17 and A20.20, different starting materials A20.3 or A20.4, and/or different carbinols, thiols or amines A20.6 or aldehydes A20.8, the corresponding products A20.5, A20.7, A20.9 and A20.10 are obtained.

Scheme A20. Phosphonates IIcc.
Method
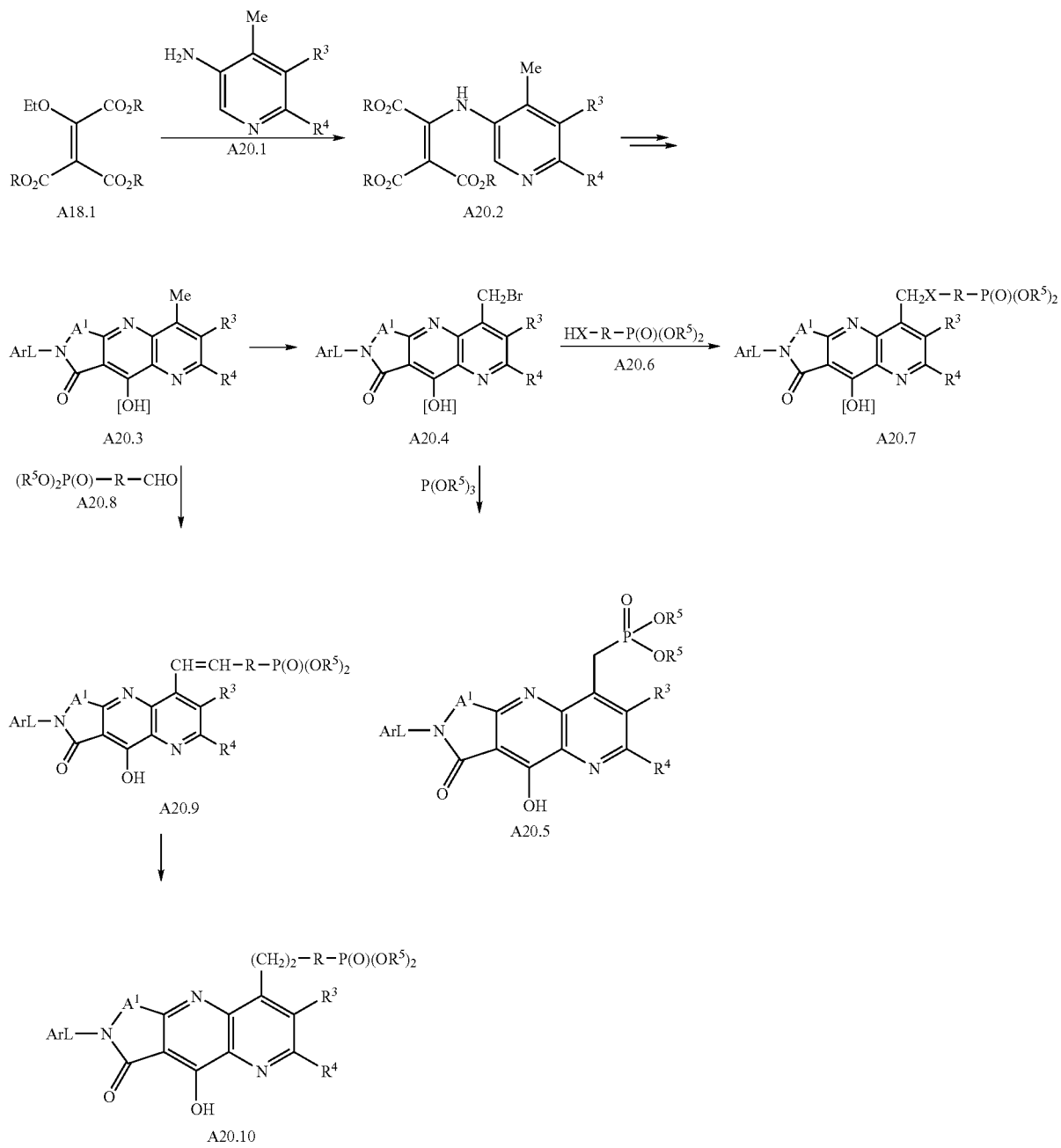
Example A20-1
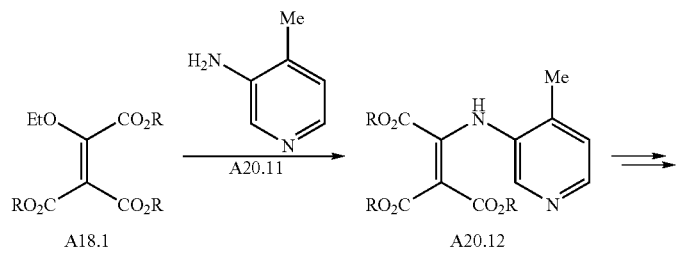

-continued
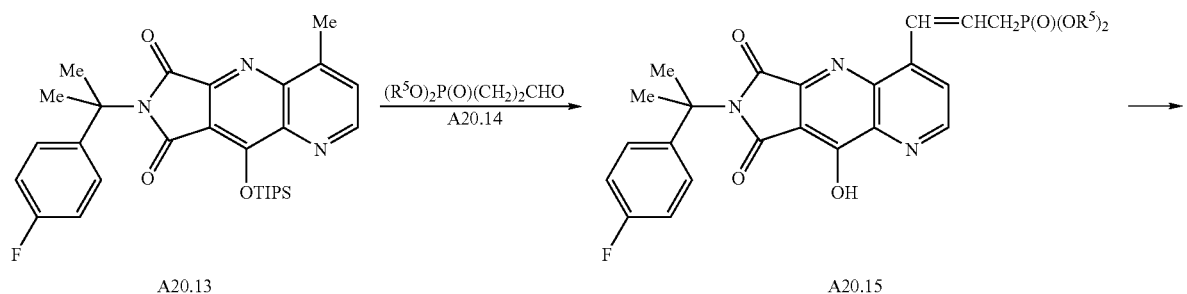
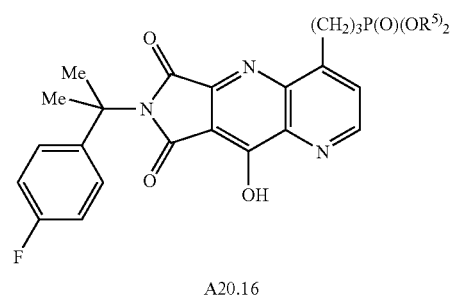
Example A20-2
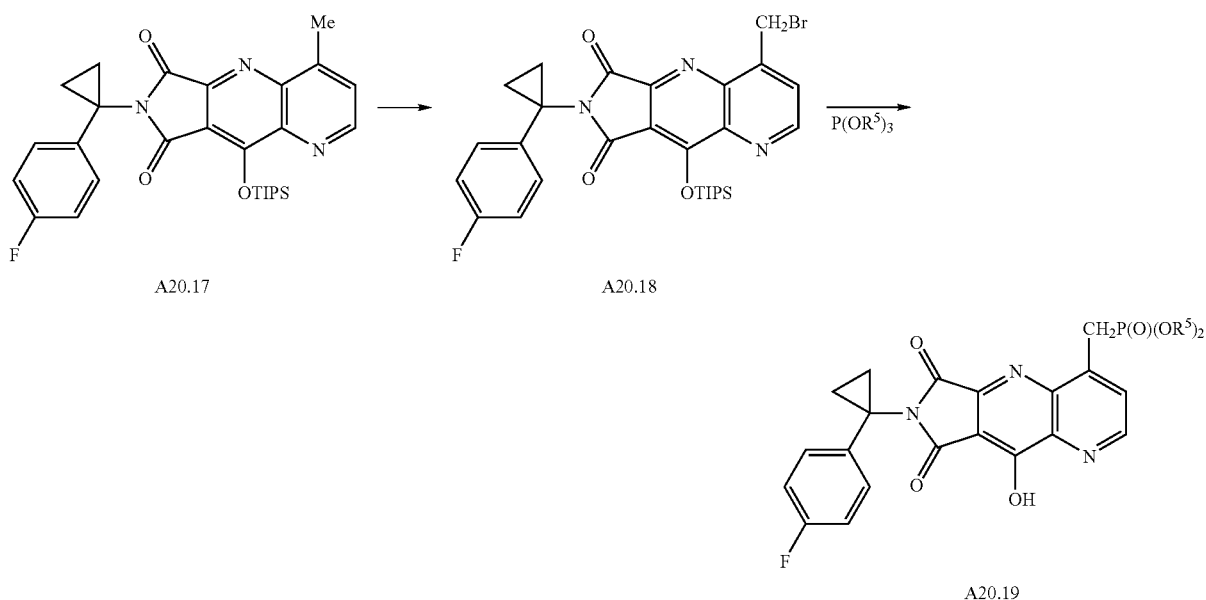
Example A20-3
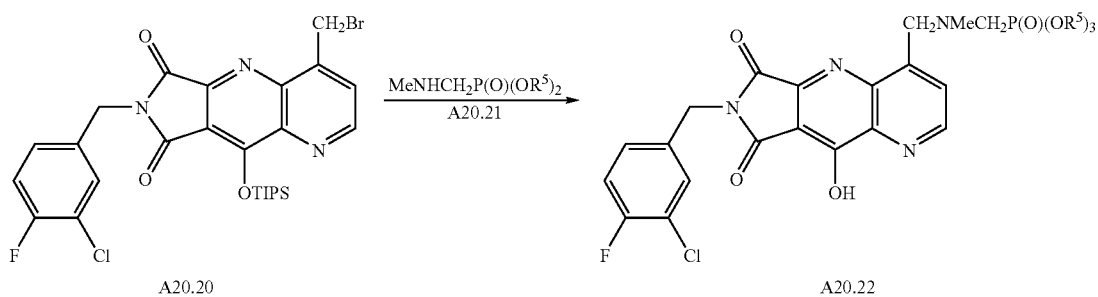

Preparation of the Intermediate Phosphonate Esters IIIaa.

Scheme A21 illustrates methods for the preparation of phosphonates of structure IIIaa in which the phosphonate group is attached by means of a heteroatom and a variable carbon link. In this sequence, a carbomethoxymethyl derivative of the amine $ArBNH_2$, A21.1 is coupled with the 1,6-naphthyridine carboxylic acid A21.2, prepared as described in WO 0230930, using the methods described previously, to prepare the amide A21.3. Bromination, for example using N-bromosuccinimide, yields the 5-bromo derivative A21.4. Protection of the phenolic hydroxyl group, followed by displacement of the bromine with a hydrazine or hydroxylamine nucleophile, as described for example in Example 69, affords the 5-imino derivative A21.5 in which X is $NH_2$ or OH. Lactam formation, for example by the use of potassium tert. butoxide in refluxing xylene, or by the use of trimethylaluminum, then gives the tricyclic product A21.6, which upon protection of the X substituent gives the product A21.7. Reduction of this material, for example by treatment with sodium borohydride, for example as in Example 20, then gives the aminol A21.8. The latter compound is reacted with a dialkyl hydroxy, mercapto, or amino-substituted phosphonate A21.9, in which the group R is an acyclic or cyclic saturated or unsaturated alkylene, or aryl, aralkyl or heteroaryl moiety, in the presence of an acid such as trifluoroacetic acid, as described in Scheme A4, to yield the ether, thioether or amine product A21.10. Deprotection then gives the phenol A21.11.

For example, (4-fluoro-benzylamino)-acetic acid methyl ester A21.12 is coupled in tetrahydrofuran solution with one molar equivalent of 8-hydroxy-[1,6]naphthyridine-7-carboxylic acid A21.13, (WO 0230930) in the presence of diisopropyl carbodiimide, to form [(4-fluoro-benzyl)-(8-hydroxy-[1,6]naphthyiidine-7-carbonyl)-amino]-acetic acid methyl ester A21.14. The latter compound is then transformed, by bromination, displacement and cyclization, as described above into the tricyclic product, 9-benzyloxy-7-(4-fluoro-benzyl)-1-hydrazono-6,7-dihydro-10H-1,7,10a-triaza-anthracene-5,8-dione A21.15. The hydrazono compound is then converted into the N, N-dibenzyl derivative A21.16. The conversion of amines into dibenzylamines, for example by treatment with benzyl bromide in a polar solvent such as acetonitrile or aqueous ethanol, in the presence of a base such as triethylamine or sodium carbonate, is described in Protective Groups in Organic Synthesis, by T. W. Greene and P. G. M Wuts, Wiley, Second Edition 1990, p. 364. The tribenzylated compound is then reduced with a limited amount of sodium borohydride in isopropanol to afford the aminal A21.17. This compound is reacted with a dialkyl 2-mercaptoethyl phosphonate A21.18 (Zh. Obschei. Khim., 1973, 43, 2364), and trifluoroacetic acid in dichloromethane, to give the thioether A21.19. Debenzylation, for example by the use of 5% palladium on carbon in the presence of ammonium formate, as described in Tet. Lett., 28, 515, 1987, then affords the hydrazono phenol A21.20.

Using the above procedures, but employing, in place of the amide A21.14, different amides A21.3, and/or different phosphonates A21.9, the corresponding products A21.11 are obtained.

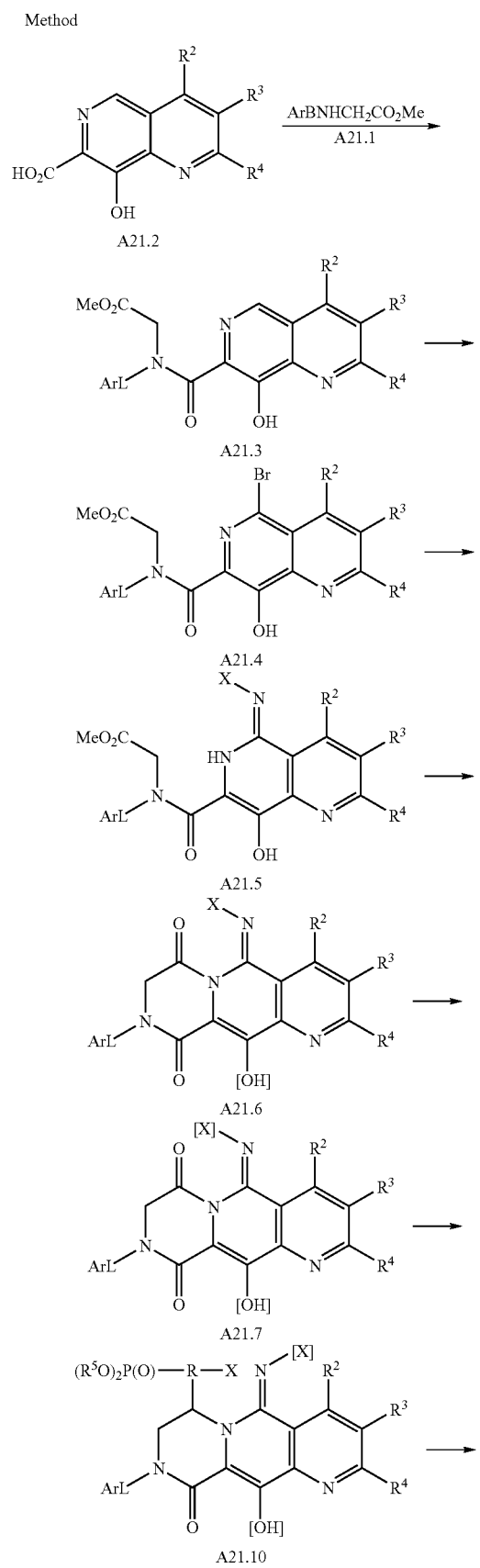

Scheme A21. Phosphonates IIIaa.

-continued

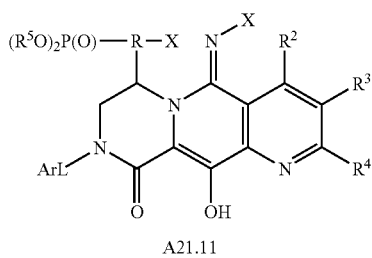

A21.11

Example A21

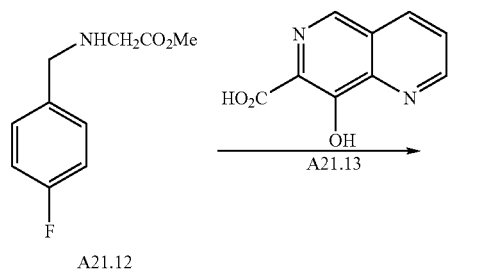

A21.12   A21.13

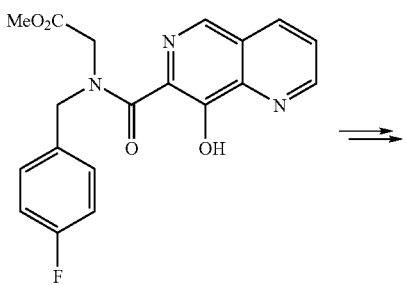

A21.14

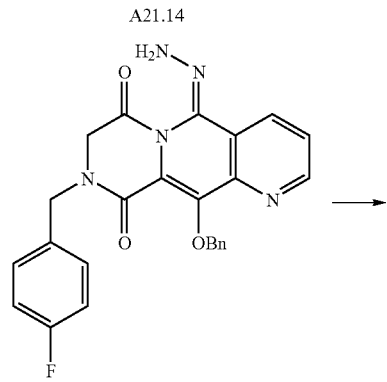

A21.15

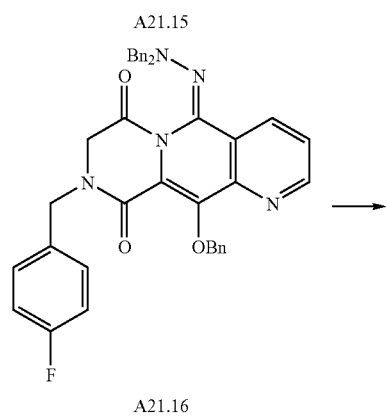

A21.16

-continued

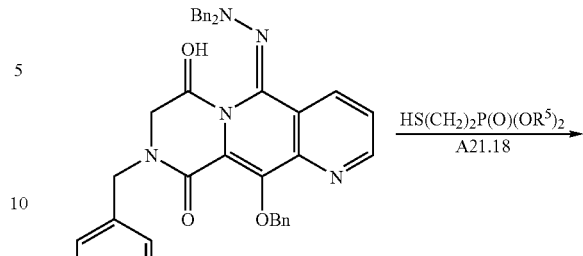

A21.17

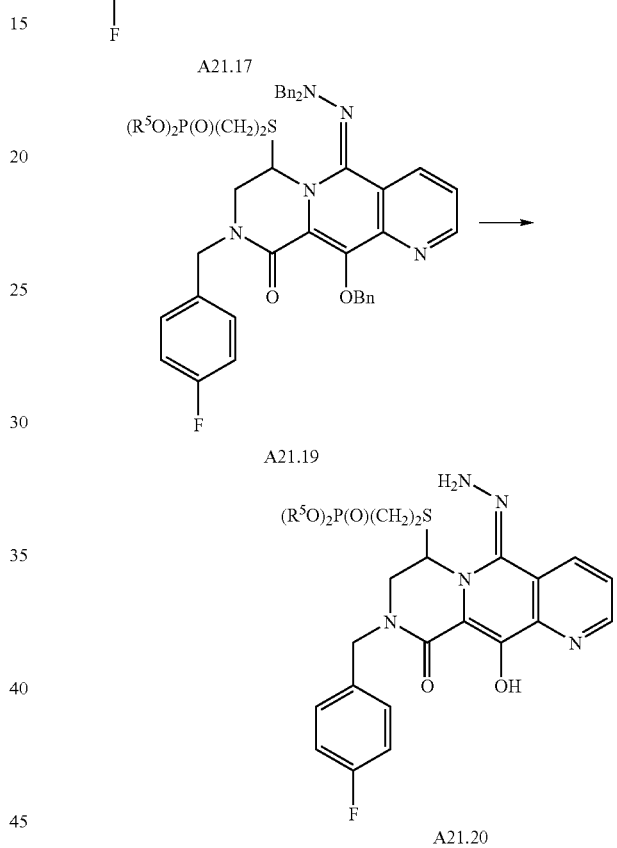

A21.19

A21.20

Preparation of the Intermediate Phosphonate Esters IIIbb.

Schemes A22-A24 illustrate methods for the preparation of phosphonate esters of structure IIIbb.

Scheme A22 illustrates methods for the preparation of phosphonates of structure IIIbb in which the phosphonate group is attached by means of a variable carbon linkage. In this sequence, the naphthyridine carboxylic acid A21.2 is coupled, as described previously, with the amine derivative A22.1, following a procedure similar to Example 28, to form the amide A22.2. Bromination, as described above, yields the 5-bromo derivative A22.3, which upon protection of the phenolic hydroxyl yields the compound A22.4. Displacement of the bromine, by reaction with a dialkyl aminosubstituted phosphonate A22.5, in which the group R is an acyclic or cyclic saturated or unsaturated alkylene, or aryl, aralkyl or heteroaryl moiety, affords the amine A22.6. The reaction is performed in a polar organic solvent such as dimethylformamide in the presence of a base such as potassium carbonate. Deprotection of the alcoholic hydroxyl group affords the carbinol A22.7, which upon activation and cyclization, for example as described in Scheme 11 then gives the tricyclic product A22.8, which upon deprotection affords the phenol A22.9.

For example, acetic acid 5-bromo-7-[(4-fluoro-benzyl)-propyl-carbamoyl]-[1,6]naphthyridin-8-yl ester A22.10, is reacted with one molar equivalent of a dialkyl aminopropyl phosphonate A22.11, (Acros) to yield the amine A22.12. Deprotection and activation of the alcoholic hydroxyl group, for example by conversion to the mesylate, followed by cyclization under basic conditions, and deprotection of the phenolic hydroxyl group, then affords the enol A22.13.

Using the above procedures, but employing, in place of the bromide A22.10, different bromides A22.4, and/or different aminophosphonates A22.5, the corresponding products A22.9 are obtained.

Scheme A23 illustrates methods for the preparation of phosphonates of structure IIIbb in which the phosphonate group is attached by means of a nitrogen and a variable carbon linkage. In this sequence, a tricyclic imine A23.1 (Scheme 12) is reacted with a dialkyl bromoalkyl phosphonate A23.2 to give the alkylated product A23.3. The reaction is performed in a polar organic solvent such as acetonitrile or dimethylsulfoxide, in the presence of a base such as diisopropylethylamine or 2,6-lutidine.

Alternatively, the imine A23.1 is converted into a hydrazone A23.5 by reaction with a dialkyl formyl-substituted phosphonate A23.4 in which the group R is an acyclic or cyclic saturated or unsaturated alkylene, or aryl, aralkyl or heteroaryl moiety. The hydrazone is prepared by the reaction of equimolar amounts of the reactants in a polar organic solvent such as ethanol, optionally in the presence of a catalytic amount of an acid such as acetic acid. Optionally, the hydrazone product A23.5 is reduced, for example by treatment with sodium borohydride, to give the dihydro derivative A23.6.

For example, acetic acid 7-(4-fluoro-benzyl)-10-hydrazono-8-oxo-6,7,8,10-tetrahydro-5H-1,7,10a-triaza-anthracen-9-yl ester A23.7 (Scheme 12) is reacted at 60° C. in dimethylformamide solution containing potassium carbonate with one molar equivalent of a dialkyl 2-bromoethyl phosphonate A23.8 (Aldrich), to prepare the alkylated product which upon deprotection yields the enol A23.9.

As a further example, the hydrazone A23.7 is reacted in ethanol solution at ambient temperature with one molar equivalent of a dialkyl 2-formylphenyl phosphonate A23.10 (Epsilon) to give the hydrazone product A23.11. Reduction of the double bond, by treatment with sodium cyanoborohydride in isopropanol, followed by deprotection, affords the enol product A23.12.

Using the above procedures, but employing, in place of the hydrazone A23.7, different hydrazones A23.1, and/or different bromophosphonates A23.2, or formyl phosphonates A23.4 the corresponding products A23.3, A23.5 and A23.6 are obtained.

Scheme A24 illustrates methods for the preparation of phosphonates of structure IIIbb in which the phosphonate group is attached by means of a hydroxyimino linkage. In this sequence, a tricyclic oxime A24.1 (Scheme 14) is reacted with a dialkyl bromo-substituted phosphonate A24.2 in which the group R is an acyclic or cyclic saturated or unsaturated alkylene, or aryl, aralkyl or heteroaryl moiety.

The reaction is performed in a polar organic solvent in the presence of a base such as sodium hydride or lithium hexamethyldisilazide. Deprotection then yields the enol A24.4.

For example, acetic acid 7-(4-fluoro-benzyl)-10-hydroxyimino-8-oxo-6,7,8,10-tetrahydro-5H-1,7,10a-triaza-anthracen-9-yl ester A24.5 (Scheme 14) is reacted in dimethylformamide solution with one molar equivalent of sodium hydride, followed by the addition of one molar equivalent of a dialkyl 4-(bromomethyl)phenyl phosphonate A24.6 (Tet., 1998, 54, 9341) to afford after deprotection the iminoether A24.7.

Using the above procedures, but employing, in place of the oxime A24.5, different oximes A24.1, and/or different phosphonates A24.2, the corresponding products A24.4 are obtained.

Scheme A22. Phosphonates IIIbb.

Method

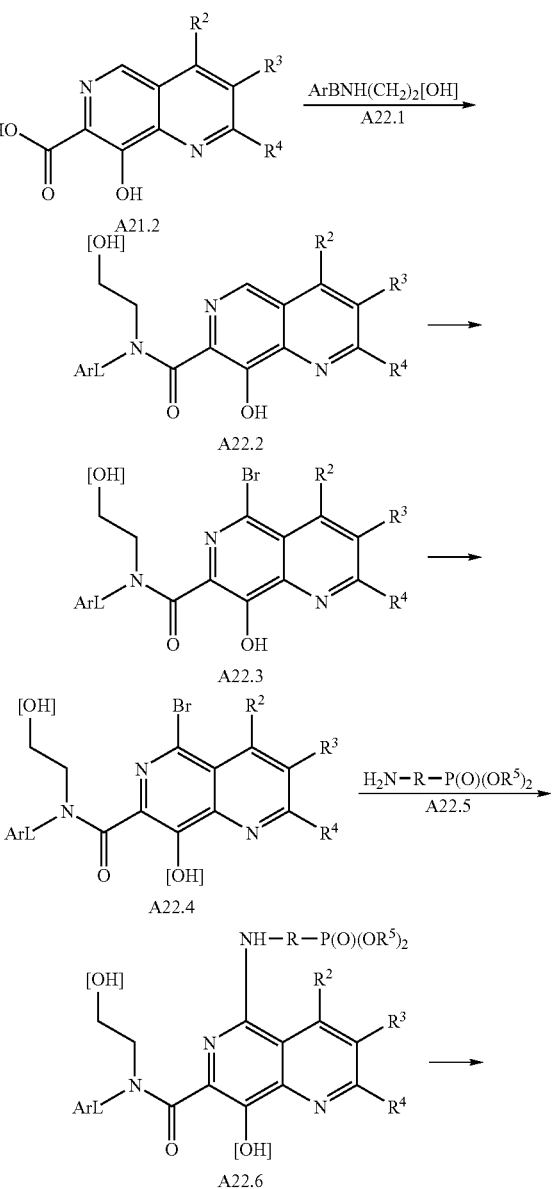

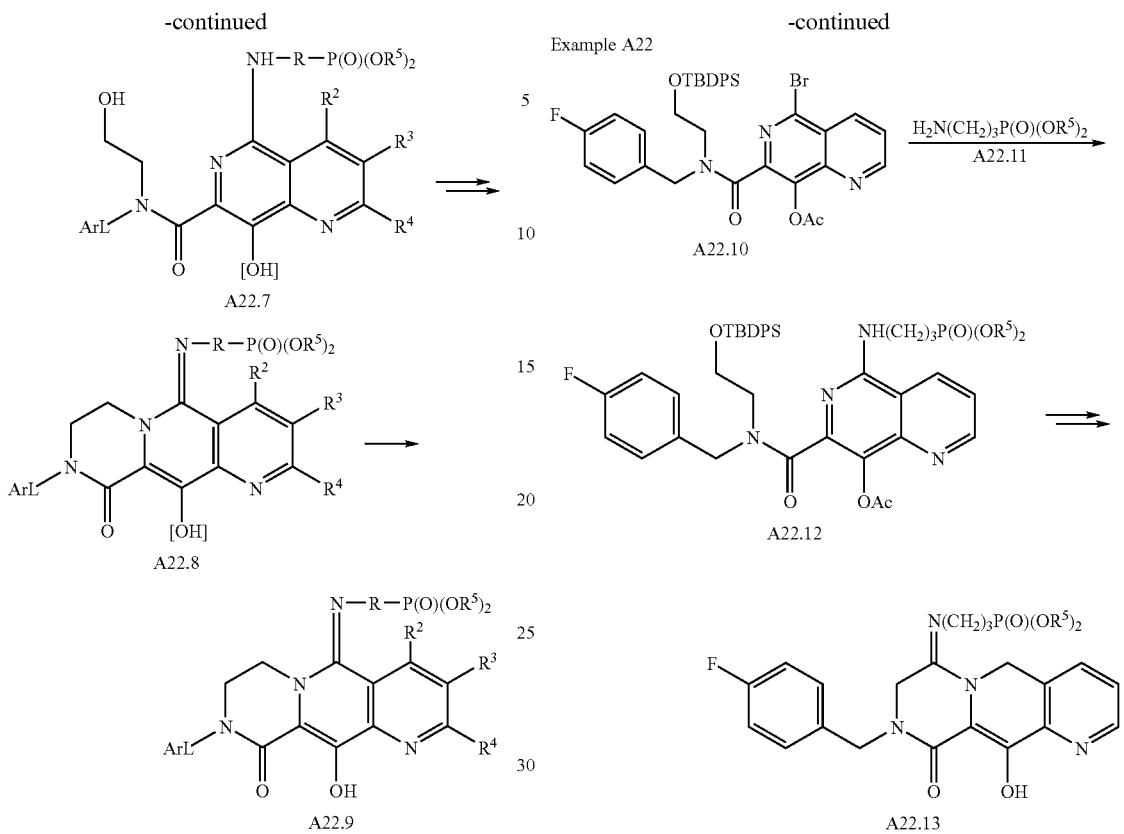
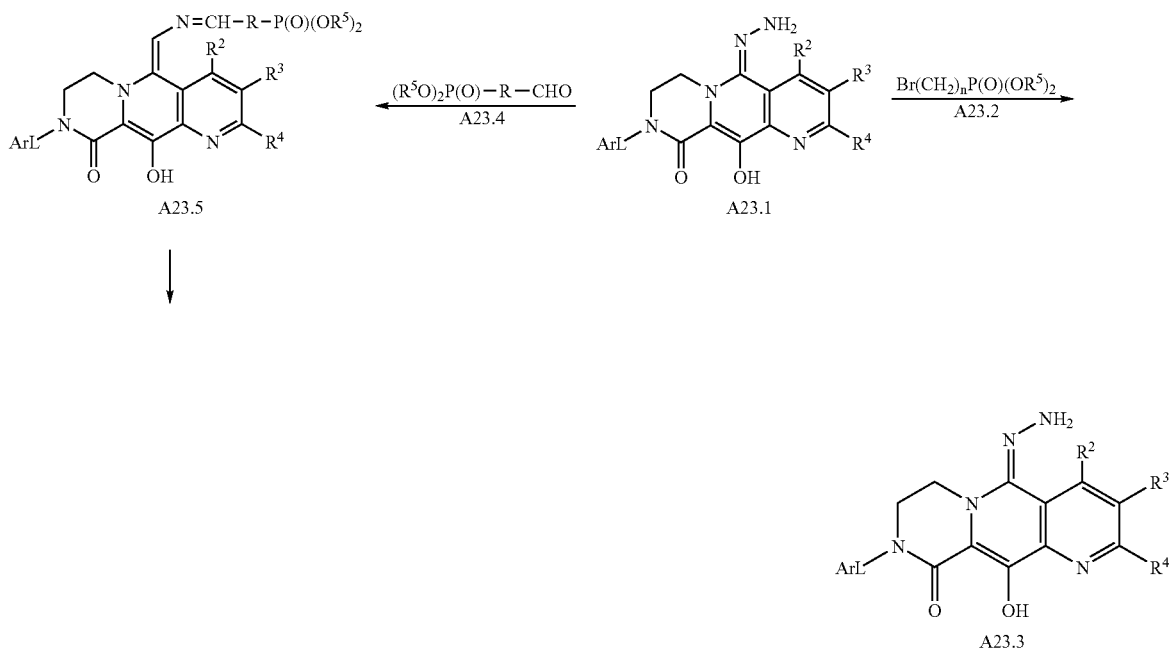
Scheme A23. Phosphonates IIIbb.

-continued
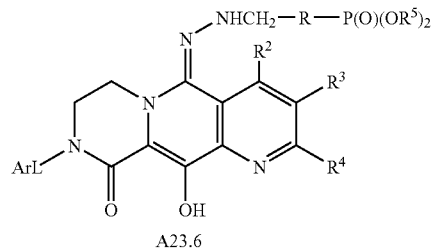
Example A23-1
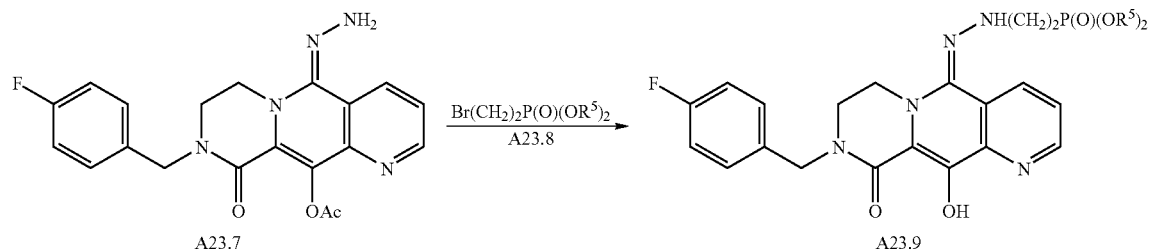
Example A23-2
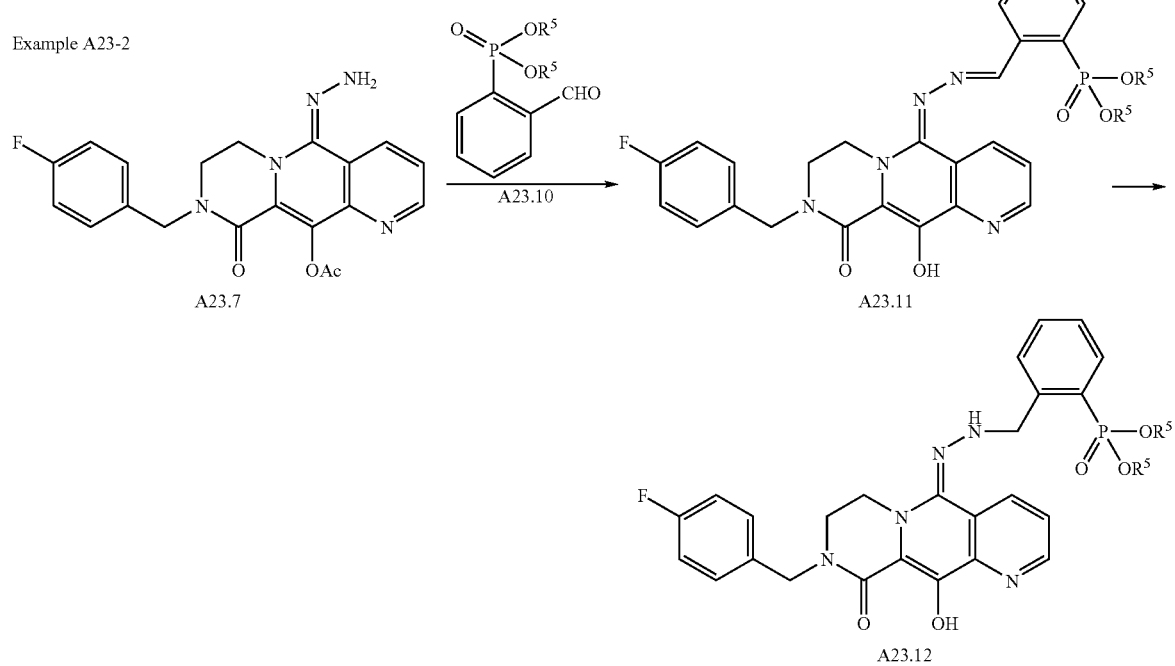
-continued
Scheme A24. Phosphonates IIIbb.
Method
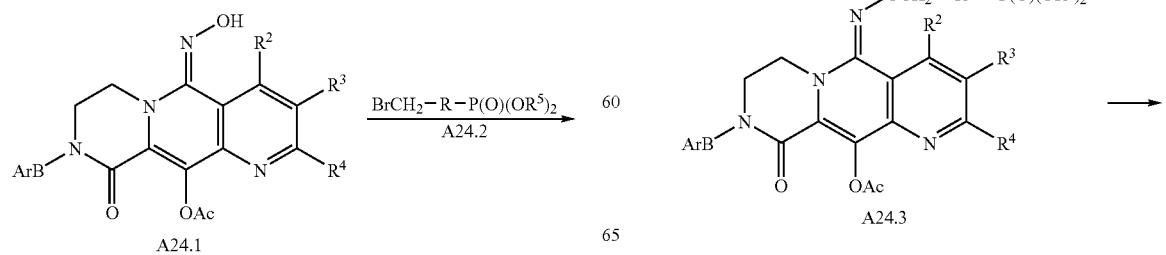

-continued

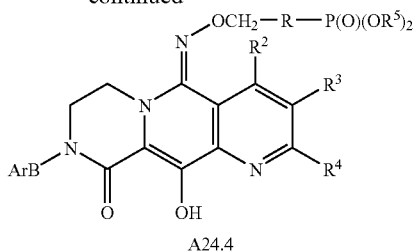

A24.4

Example A24

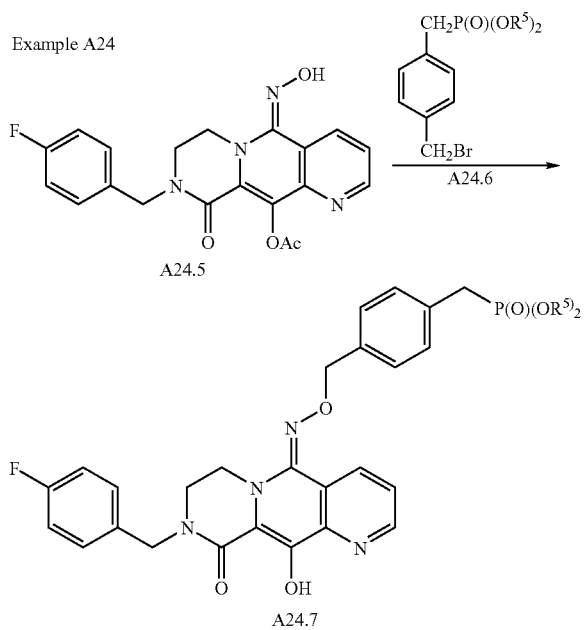

Preparation of the Intermediate Phosphonate Esters IIIcc.

Scheme A25 illustrates methods for the preparation of phosphonates of structure IIIcc. The conversion of pyridine-2,3-dicarboxylic anhydride (A25.1, R=H) into the naphthyridine A25.2, R=H, is described in WO 0255079. Using the same procedure, 4-methylpyridine-2,3-dicarboxylic anhydride A25.1, R=Me, (J. Org. Chem., 1961, 26, 808) is converted into the naphthyridine A25.2, R=Me. This compound is then transformed, as described in Scheme 12, into the imine A25.3. Protection of the hydroxyl and amino groups then furnishes the derivative A25.4. The product is then condensed under basic conditions, as described in Scheme A20, with a dialkyl formyl-substituted phosphonate A25.5, in which the group R is an acyclic or cyclic saturated or unsaturated alkylene, or aryl, aralkyl or heteroaryl moiety. After deprotection, the product A25.6 is optionally reduced, as described in Scheme A20, to give the saturated analog A25.17.

Alternatively, the methyl-substituted tricycle A25.4 is brominated, for example by reaction with N-bromosuccinimide, to give the bromomethyl product A25.7. The compound is then subjected to a Arbuzov reaction with a trialkyl phosphite, to yield after deprotection the phosphonate A25.8.

Alternatively, the bromomethyl compound A25.7 is reacted, as described previously (Scheme A20) with a dialkyl hydroxy, mercapto or amino-substituted phosphonate A25.18, in which the group R is an acyclic or cyclic saturated or unsaturated alkylene, or aryl, aralkyl or heteroaryl moiety, to give after deprotection the ether, thioether or amine product A25.9.

For example, acetic acid 7-[2-(4-fluoro-phenyl)-ethyl]-10-hydrazono-4-methyl-8-oxo-6,7,8,10-tetrahydro-5H-1,7,10a-triaza-anthracen-9-yl ester A25.10, prepared according to the procedures described above, is converted into the phthalimido derivative by reaction with one molar equivalent of phthalic anhydride, as described in J. Org. Chem., 43, 2320, 1978. The protected product is then reacted with N-bromosuccinimide in hexachloroethane to give the bromomethyl derivative A25.12. This compound is heated to 120° C. with an excess of a trialkyl phosphite to produce the phosphonate A25.13. Deprotection, for example by reaction with ethanolic hydrazine, as described in J. Org. Chem., 43, 2320, 1978, then affords the phosphonate A25.14.

As a further example, the phthalimido-protected methyl-substituted tricycle A25.11 is reacted in dioxan solution with a dialkyl formylphosphonate A25.12 (Tet., 1994, 50, 10277) and lithium tetramethyl piperidide, to yield, after removal of the protecting groups, the unsaturated phosphonate A25.13. Reduction of the double bond then gives the saturated analog A25.14.

As a further example, the bromomethyl derivative A25.12 is reacted in acetonitrile solution with one molar equivalent of a dialkyl 2-mercaptopropyl phosphonate A25.15(WO 007101) and diisopropylethylamine, to produce after deprotection the phosphonate A25.16.

Using the above procedures, but employing, in place of the starting materials A25.10, A25.11 or A25.12, different starting materials A25.4 and A25.7, and/or different aldehydes A25.5 or alcohols, thiols or amines A25.18, the corresponding products A25.6, A25.8, A25.9 and A25.17 are obtained.

Scheme A25. Phosphonates IIIcc.

Method

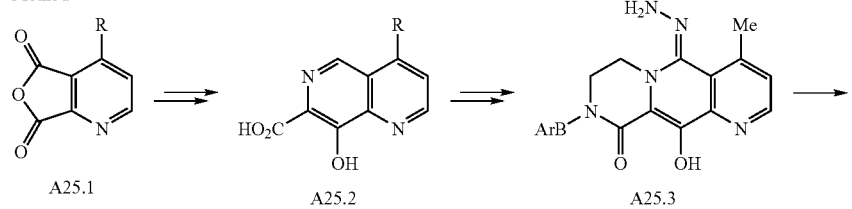

-continued
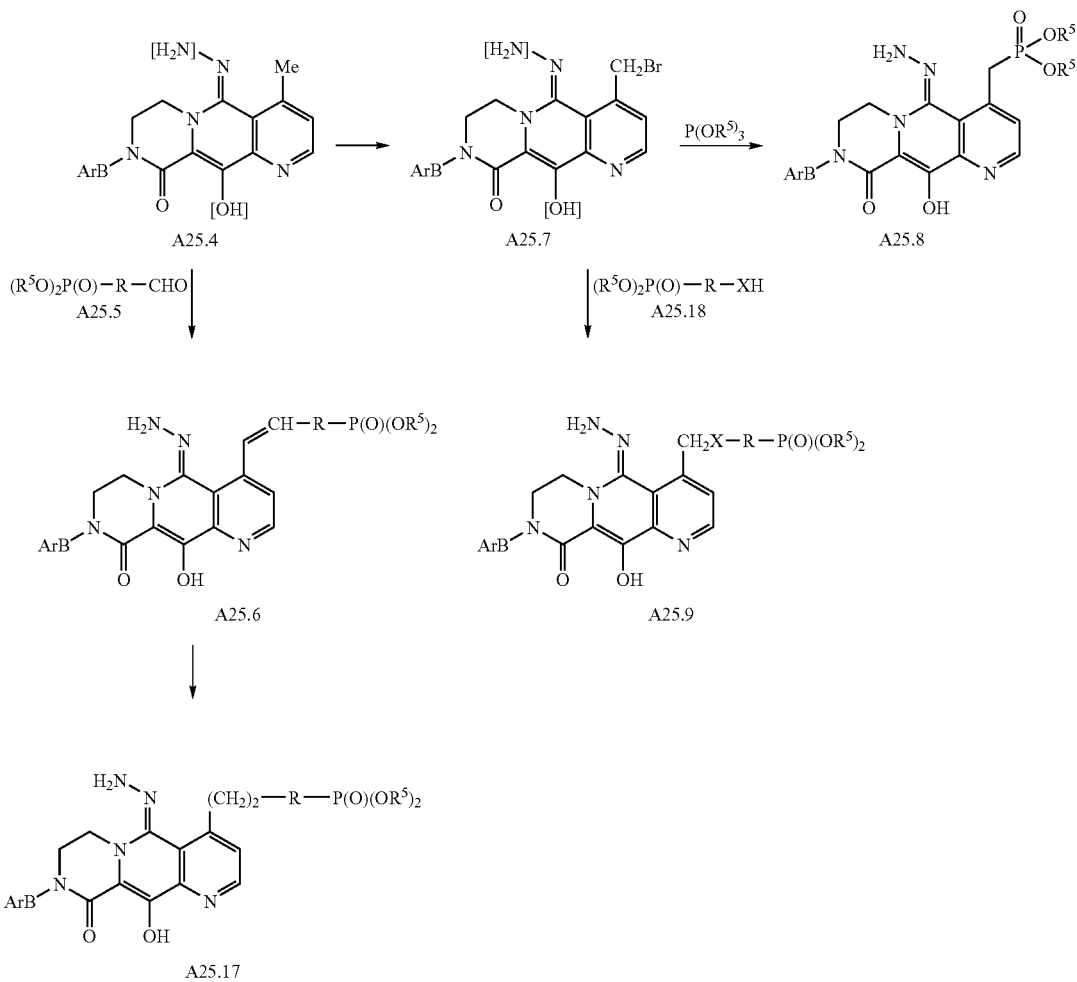
Example A25-1
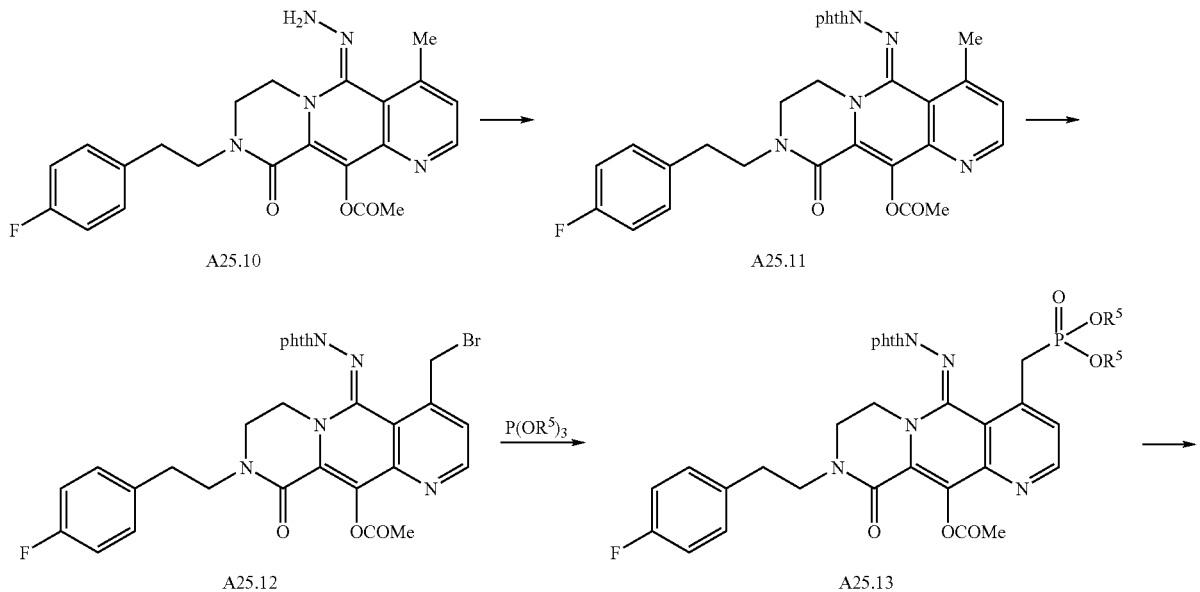

-continued

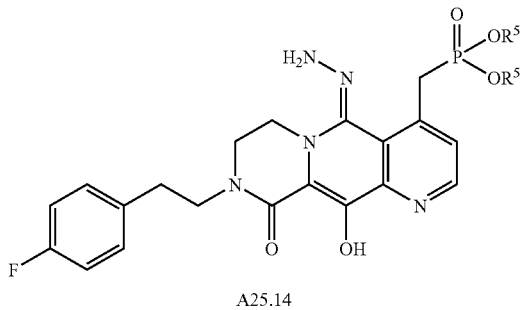

A25.14

Example A25-2

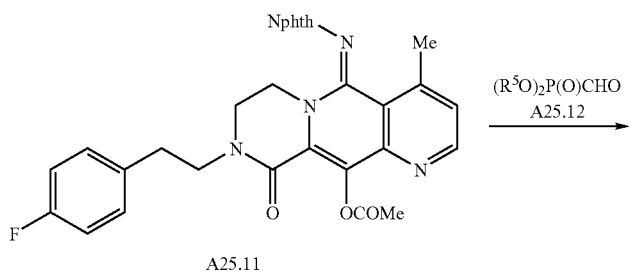

A25.11

$(R^5O)_2P(O)CHO$
A25.12
→

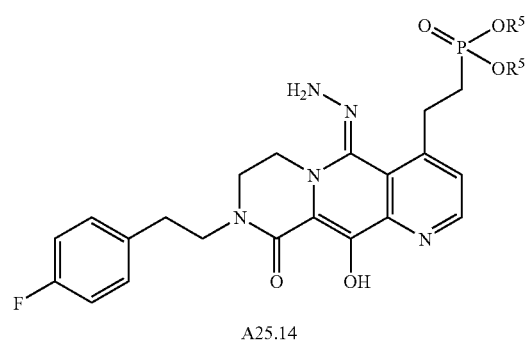

A25.13      A25.14

Example A25-3

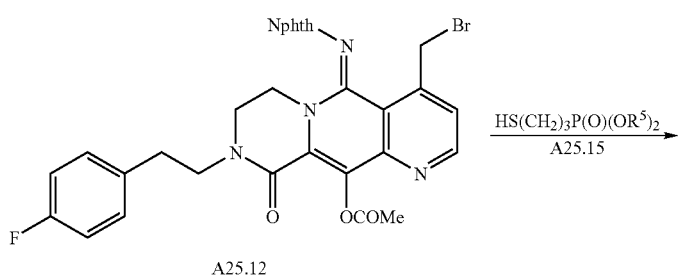

A25.12

$\underrightarrow{HS(CH_2)_3P(O)(OR^5)_2}$
A25.15

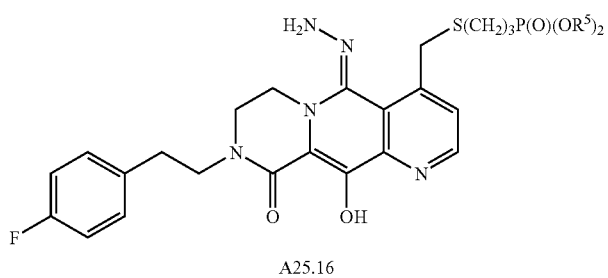

A25.16

Preparation of the Intermediate Phosphonate Esters IVaa.

Schemes A29 and A30 illustrates the preparation of phosphonate esters of structure IVaa.

Scheme A29 illustrates the preparation of compounds in which phosphonate is attached by means of an ether, thio-ether of amine linkage. In this procedure, a substituted succinimide A29.1 is condensed, as described in Scheme 1 and Example 2, with a heterocyclic diester A29.2 to afford after protection the tricyclic product A29.3. Reduction with sodium borohydride then yields the aminal A29.4, which upon acid-catalyzed reaction with a dialkyl hydroxy, mercapto or amino-substituted phosphonate A29.5, in which the group R is an acyclic or cyclic saturated or unsaturated alkylene, or aryl, aralkyl or heteroaryl moiety, to give after deprotection the ether, thioether or amine products A29.6.

For example, 1-[2-(4-fluoro-phenyl)-cyclopropyl]-pyrrolidine-2,5-dione A29.7, prepared from 4-fluorophenylcyclopropylamine (J. Med. Chem., 1996, 39, 1485) and succinic anhydride, is reacted with 4,5-dicarbomethoxyisoxazole A29.8 (Chem. Ber., 97, 1414, 1964) to afford after protection 6-[2-(4-fluoro-phenyl)-cyclopropyl]-4,8-bis-methoxymethoxy-oxazolo[4,5-f]isoindole-5,7-dione A29.9. Reduction with sodium borohydride then gives the aminal A29.10, which upon reaction with a dialkyl 3-mercaptopropyl phosphonate A29.11 (WO 0077101) and trifluoroacetic acid in dichloromethane yields the phosphonate thioether A29.12.

Using the above procedures, but employing, in place of the starting materials A29.7 and A29.8, different starting materials A29.1 and A29.2, and/or different phosphonates A29.5, the corresponding products A29.6 are obtained.

Preparation of the Intermediate Phosphonate Esters IVaa.

Scheme A30 illustrates the preparation of phosphonate esters of structure IVaa in which the phosphonate is attached by means of a variable carbon linkage. In this procedure, dimethyl succinate A30.1 is condensed, under base catalysis, for example using the procedure described on Scheme 1 and Example 2 with a heterocyclic diester A30.2, to yield after protection of the phenolic hydroxyl groups, the diester A30.3. Partial basic hydrolysis, for example by reaction with one molar equivalent of lithium hydroxide in aqueous dimethoxyethane, then affords the monoacid A30.4. The carboxylic acid is homologated to produce the corresponding acetic acid A30.5. The transformation is effected by means of the Arndt Eistert reaction. In this procedure, which is described in Advanced Organic Chemistry, Part B, by F. A. Carey and R. J. Sundberg, Plenum, 2001, p. 641, and in Advanced Organic Chemistry, By J. Marsh, McGraw Hill, 1968, p. 809, the carboxylic acid is converted into the acid chloride, which is reacted with diazomethane to give the corresponding diazoketone. Silver-catalyzed Wolff rearrangement of the diazoketone in an alcoholic solvent then yields the acetic acid ester, which upon hydrolyis yields the acetic acid A30.5. This material is coupled with the amine A30.6 to give the amide A30.7. Base-catalyzed thermal cyclization of the latter compound, for example by refluxing in xylene with sodium methoxide, then gives the cyclized product A30.8. The latter compound is then alkylated, as described above, (Scheme A10) with a dialkyl bromo-substituted phosphonate A30.9, in which the group R is an acyclic or cyclic saturated or unsaturated alkylene, or aryl, aralkyl or heteroaryl moiety, to afford after deprotection the phosphonate A30.10.

For example, condensation between dimethyl succinate and methyl 1-methylimidazole-4,5-dicarboxylate A30.11 (Eqypt. J. Chem., 1985, 28, 139) yields, after protection of the phenolic hydroxyl groups, 4,7-bis-methoxymethoxy-1-methyl-1H-benzoimidazole-5,6-dicarboxylic acid dimethyl ester A30.12. Partial hydrolysis then gives the monocarboxylic acid A30.13, and this compound is subjected to Arndt Eistert homologation to give the corresponding acetic acid A30.14. The carboxylic acid is coupled, in the presence of dicyclohexyl carbodiimide, with cyclohexylmethylamine A30.15 to give the amide A30.16. Cyclization is effected as described above to prepare 6-cyclohexylmethyl-4,9-bis-methoxymethoxy-1-methyl-1,5,6,8-tetrahydro-1,3,6-triaza-cyclopenta[b]naphthalen-7-one A30.17. The product is then reacted in dioxan solution with a dialkyl bromoethyl phosphonate A30.18 (Aldrich) and lithium hexamethyldisilazide, to give after deprotection the phosphonate A30.19.

Using the above procedures, but employing, in place of the starting materials A30.1 and A30.11, different starting materials A30.1 and A30.2, and/or different phosphonates A30.9, the corresponding products A30.10 are obtained.

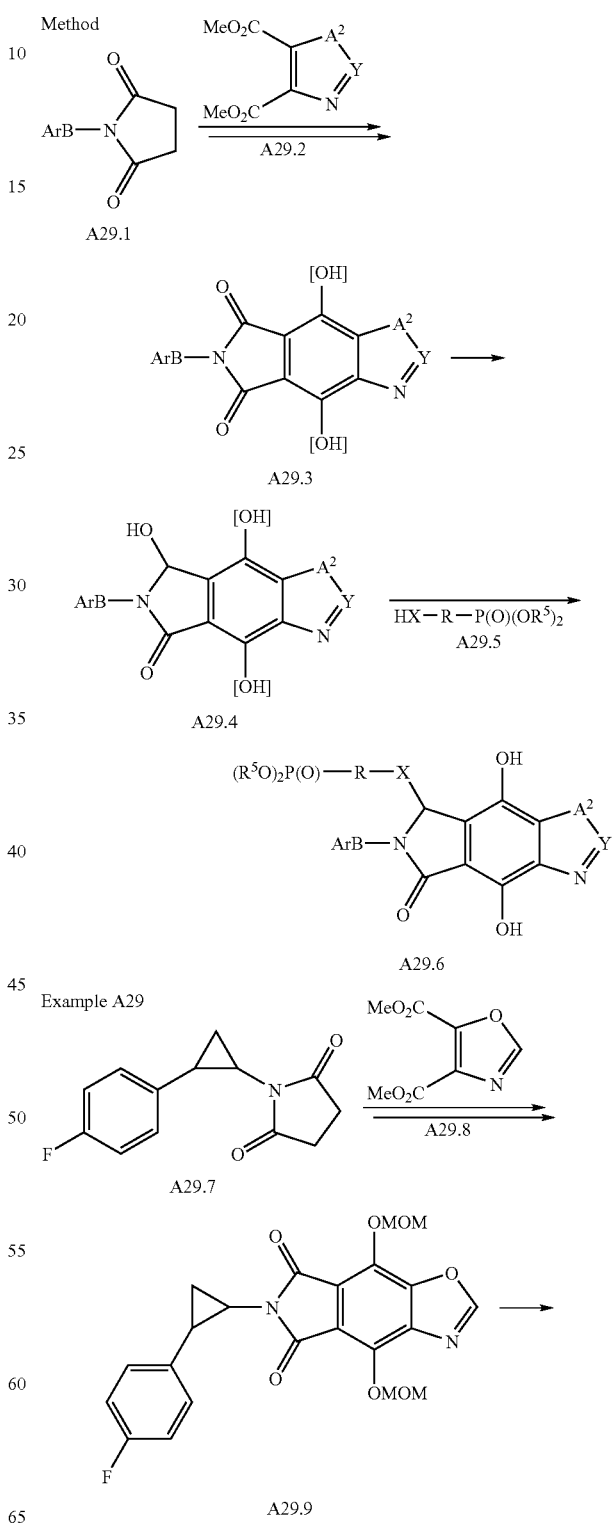

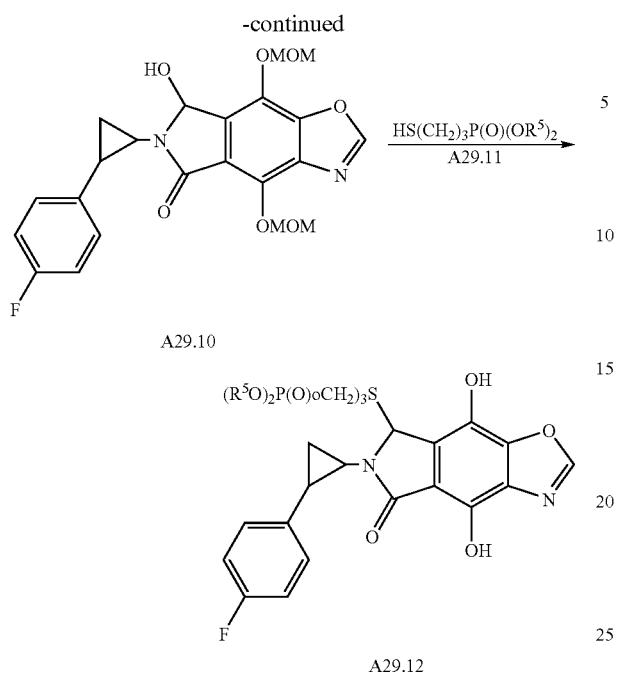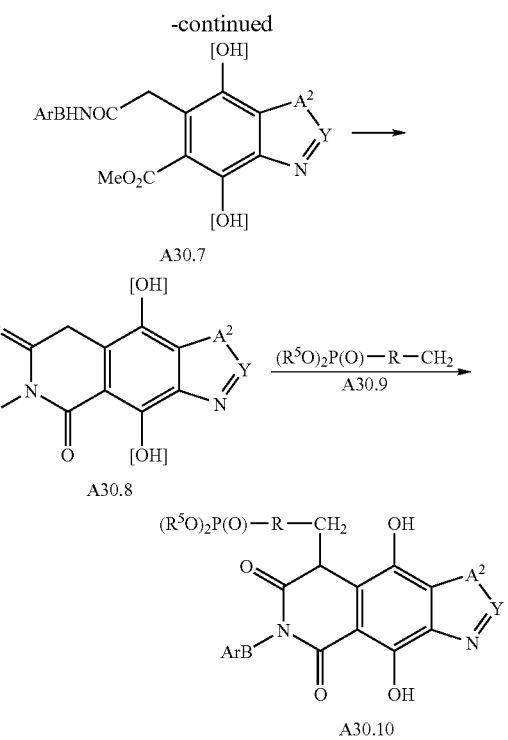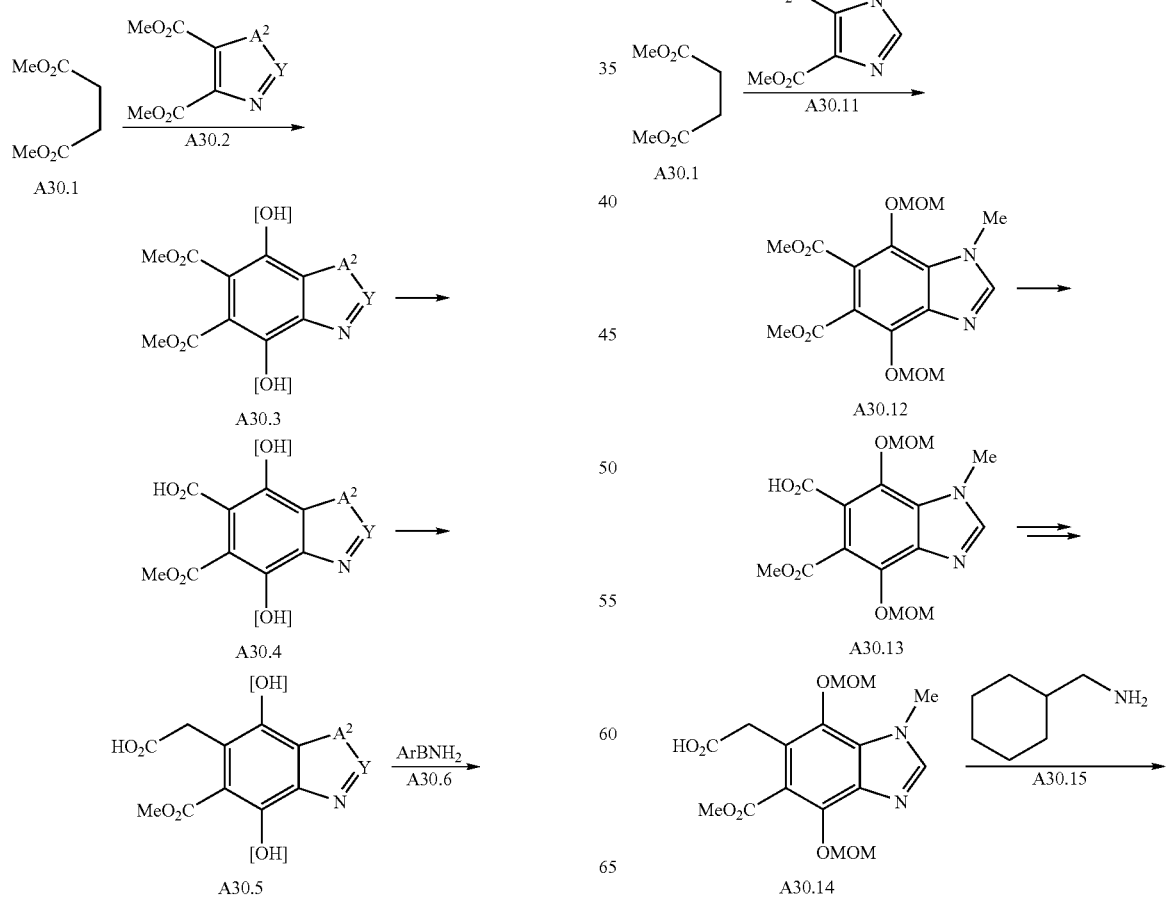

-continued

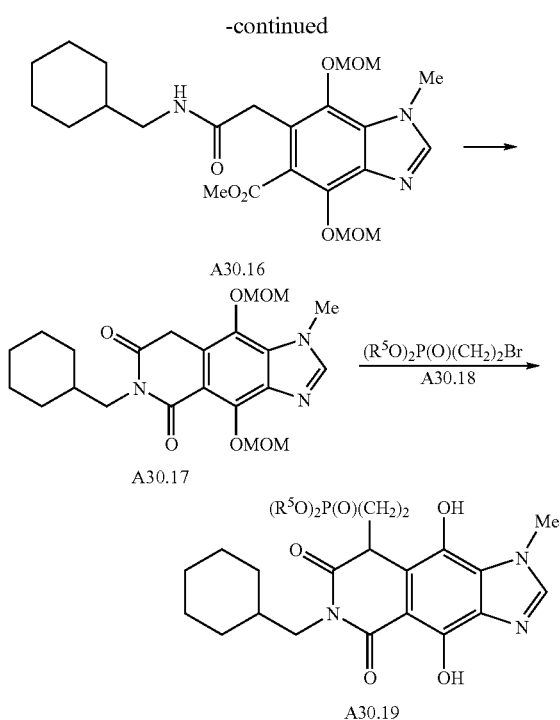

Preparation of the Intermediate Phosphonate Esters IVbb.

Schemes A31 and A32 illustrates the preparation of phosphonate esters of structure IVbb. Scheme A31 illustrates the preparation of phosphonate esters in which the phosphonate is attached by means of a variable carbon linkage linkage. In this procedure, the doubly protected phenol A29.3 is selectively deprotected to give the phenol A31.1. The product is converted into the triflate A31.2 and this material is reacted with a dialkyl hydroxy, mercapto or amino-substituted phosphonate A31.3, in which the group R is an acyclic or cyclic saturated or unsaturated alkylene, or aryl, aralkyl or heteroaryl moiety, in the presence of a base, as described in Scheme A8, to afford the displacement product A31.4, which upon deprotection gives the phenol A31.5.

For example, 2-naphthylmethylsuccinimide A31.6 is reacted with dimethyl pyrimidine 4,5-dicarboxylate A31.7 (Chem. Ber., 1975, 108, 3877) to afford after differential protection, as describe in Scheme 1 and Example 2 and triflate formation, trifluoro-methanesulfonic acid 7-naphthalen-2-ylmethyl-6,8-dioxo-9-triisopropylsilanyloxy-7,8-dihydro-6H-pyrrolo[3,4-g]quinazolin-5-yl ester A31.8. The compound is then reacted with a dialkyl 3-hydroxyphenyl phosphonate A31.9 (Aurora) and triethylamine in dichloromethane to give the phosphonate A31.10.

Using the above procedures, but employing, in place of the starting materials A31.6 and A31.7, different starting materials A29.3 and/or different phosphonates A31.3, the corresponding products A31.5 are obtained.

Scheme A32 depicts the preparation of phosphonate esters of structure Vbb in which the phosphonate is attached by means of an ether linkage. In this procedure, dimethyl succinate A32.1 is condensed under basic conditions, with a heterocyclic dicarboxylic ester A32.2 to afford the bicyclic product A32.3. Hydrolysis of the ester groups, followed by anhydride formation and selective protection of the phenolic hydroxyl groups, then gives the product A32.4. The anhydride is then reacted, as described with the substituted hydrazine A32.5, to yield the tricyclic product A32.6. Selective deprotection then affords the phenol A32.7, and this compound is then reacted with a dialkyl hydroxy-substituted phosphonate A32.8, in which the group R is an acyclic or cyclic saturated or unsaturated alkylene, or aryl, aralkyl or heteroaryl moiety, under the conditions of the Mitsonobu reaction, as described in Scheme A6, to form after deprotection the phenol A32.9.

For example, condensation between dimethyl succinate and dimethyl 1,3,4-triazine-5,6-dicarboxylate A32.10 (J. Org. Chem., 23, 1931, 1958) affords after selective silylation, following a procedure similar to Example 12, 6-(4-fluoro-benzyl)-9-hydroxy-10-triisopropylsilanyloxy-6,7-dihydro-1,2,4,6,7-pentaaza-anthracene-5,8-dione A32.11. The product is then reacted in tetrahydrofuran with a dialkyl hydroxyethyl phosphonate A32.12, (Epsilon) diethyl azodicarboxylate and triphenyl phosphine to yield after deprotection the phenolic phosphonate A32.13.

Using the above procedures, but employing, in place of the starting material A32.10 different starting materials A32.2 and/or different phosphonates A32.8, the corresponding products A32.9 are obtained.

Scheme A31. Phosphonates IVbb.

Method

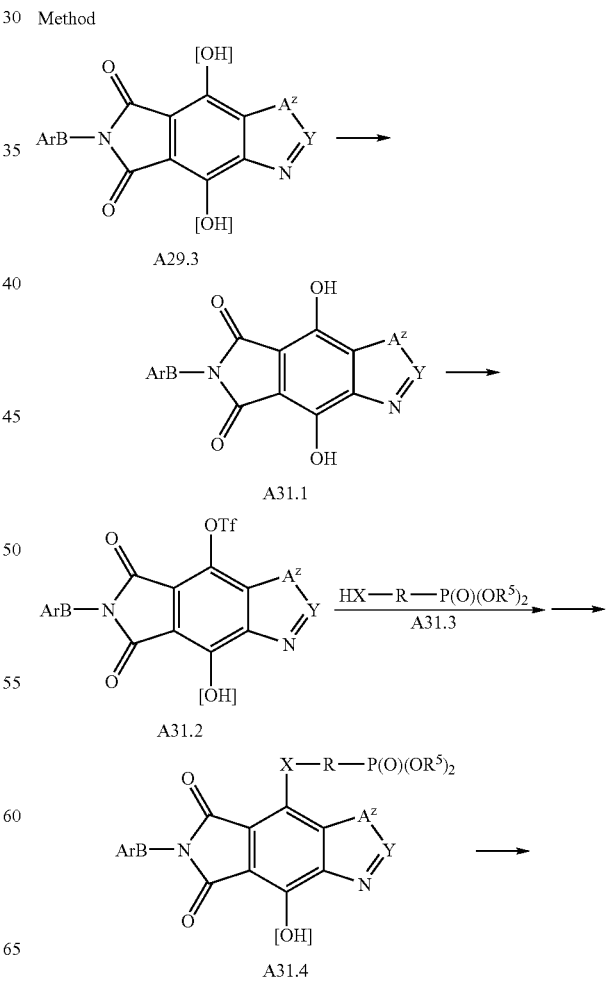

-continued
Example A31
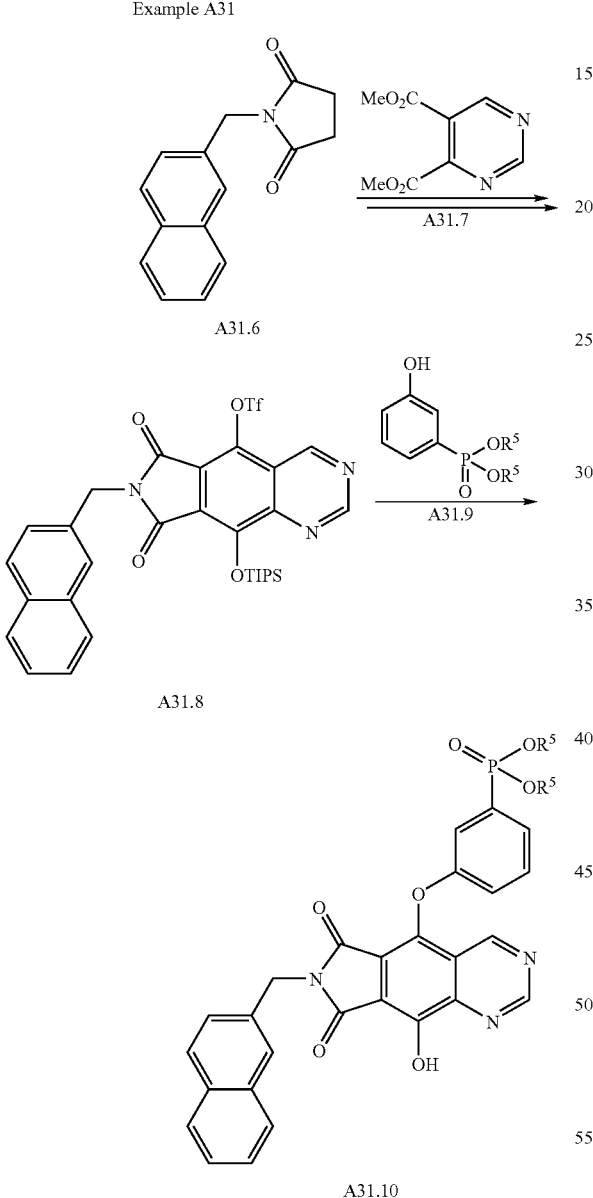
Scheme A32. Phosphonates IVbb.
Method
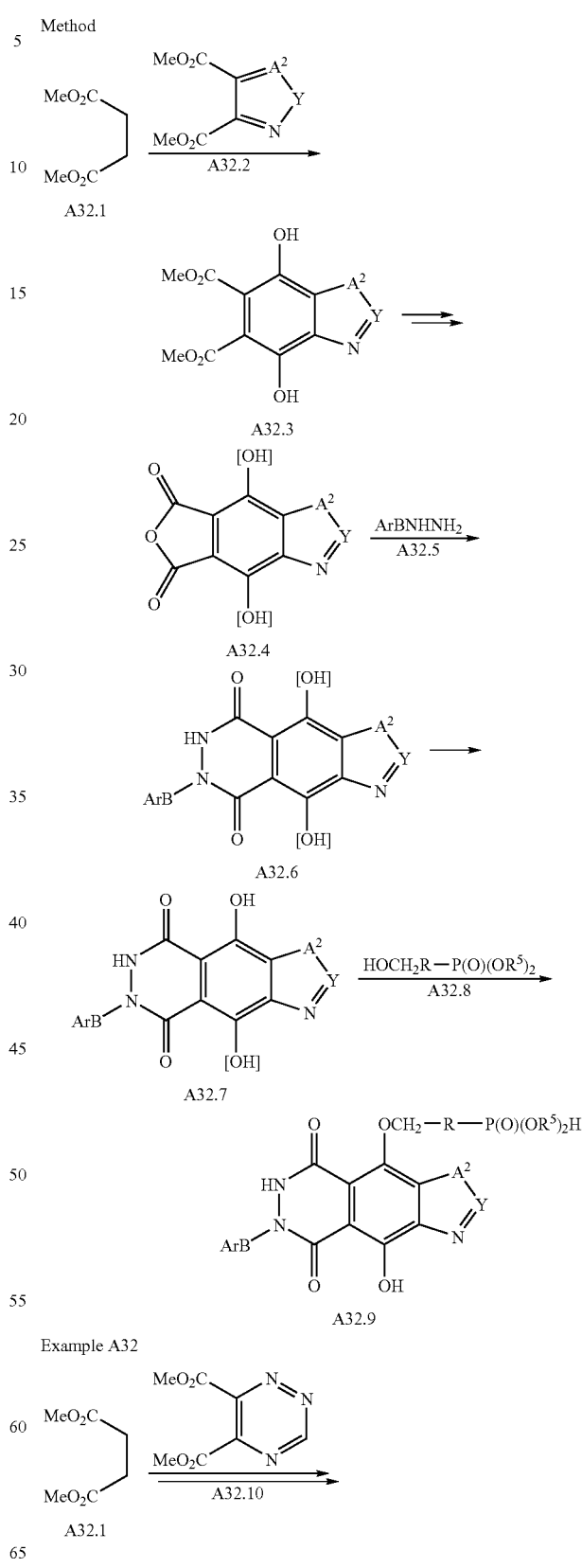
Example A32

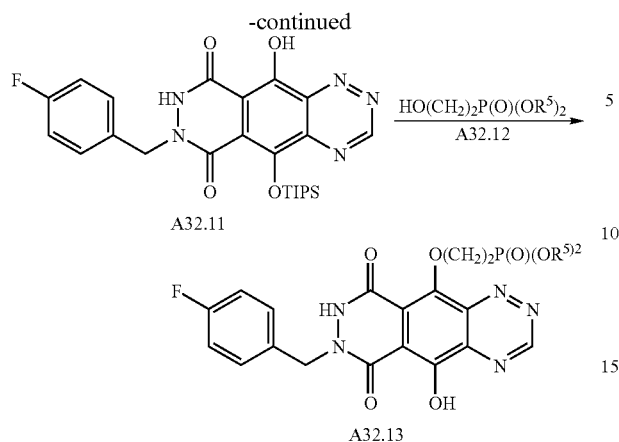

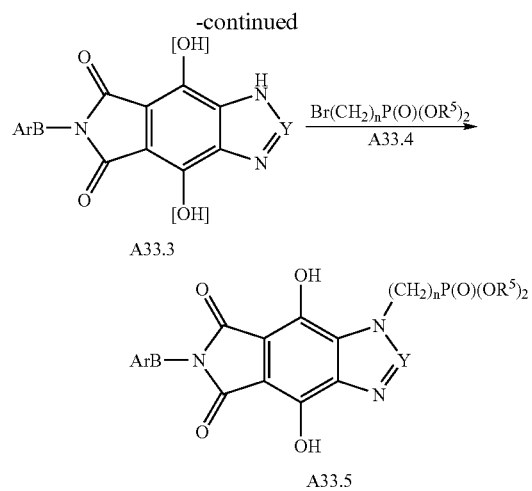

Preparation of the Intermediate Phosphonate Esters IVcc.

Scheme A33 illustrates the preparation of phosphonate esters of structure IVcc in which the phosphonate is attached by means of a carbon linkage. In this procedure, a substituted succinimide A33.1 is reacted with a heterocyclic diester A33.2 to afford after protection the bicyclic product A33.3. The amino group of the product is then alkylated by reaction with a dialkyl bromo-substituted phosphonate A33.4 to yield after deprotection the phenolic phosphonate A33.5.

For example, 1-(6-fluoro-1,2,3,4-tetrahydro-naphthalen-1-yl)-pyrrolidine-2,5-dione A33.6, prepared by the reaction of 2-amino-7-fluoro-1,2,3,4-tetrahydronaphthalene (U.S. Pat. No. 5,538,988) and succinic anhydride, is reacted with dimethyl 1,2,3-triazole-4,5-dicarboxylate A33.7 (Interchim) to afford after silylation of the phenolic hydroxyl groups 6-(6-fluoro-1,2,3,4-tetrahydro-naphthalen-1-yl)-4,8-bis-triisopropylsilanyloxy-1H-pyrrolo [3',4':4,5]benzo[1,2-d][1,2,3]triazole-5,7-dione A33.8. The product is then reacted, in dimethylformamide solution with one molar equivalent of sodium hydride and a dialkyl 4-bromobutyl phosphonate A33.9 (Syn., 1994, 9, 909) to afford after deprotection the phosphonate A33.10.

Using the above procedures, but employing, in place of the starting materials A33.6 and A33.7 different starting materials A33.1 and A33.2 and/or different phosphonates A33.4, the corresponding products A33.5 are obtained.

Scheme A33. Phisphonates IVcc.

Method

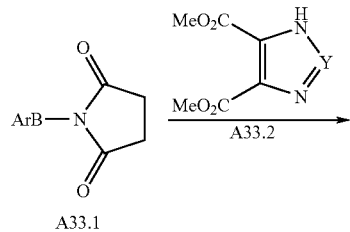

Interconversions of the Phosphonates R-link-P(O)(OR$^5$)$_2$, R-link-P(O)(OR$^5$)(OH) and R-link-P(O)(OH)$_2$.

Schemes A1-A33 described the preparations of phosphonate esters of the general structure R-link-P(O)(OR$^5$)$_2$, in which the groups R$^5$ may be the same or different. The R$^5$ groups attached to a phosphonate esters Iaa-IVcc, or to precursors thereto, may be changed using established chemical transformations. The interconversions reactions of phosphonates are illustrated in Scheme A34. The group R in Scheme A34 represents the substructure to which the substituent link-P(O)(OR$^5$)$_2$ is attached, either in the compounds Iaa-IVcc or in precursors thereto. The R$^5$ group may be changed, using the procedures described below, either in the precursor compounds, or in the esters Iaa-IVcc. The methods employed for a given phosphonate transformation depend on the nature of the substituent $R^5$. The preparation and hydrolysis of phosphonate esters is described in Organic Phosphorus Compounds, G. M. Kosolapoff, L. Maeir, eds, Wiley, 1976, p. 9ff.

The conversion of a phosphonate diester A34.1 into the corresponding phosphonate monoester A34.2 (Scheme A34, Reaction 1) can be accomplished by a number of methods. For example, the ester A34.1 in which $R^5$ is an aralkyl group such as benzyl, can be converted into the monoester compound A34.2 by reaction with a tertiary organic base such as diazabicyclooctane (DABCO) or quinuclidine, as described in J. Org. Chem., 1995, 60, 2946. The reaction is performed in an inert hydrocarbon solvent such as toluene or xylene, at about 110° C. The conversion of the diester A34.1 in which $R^5$ is an aryl group such as phenyl, or an alkenyl group such as allyl, into the monoester A34.2 can be effected by treatment of the ester A34.1 with a base such as aqueous sodium hydroxide in acetonitrile or lithium hydroxide in aqueous tetrahydrofuran. Phosphonate diesters A34.1 in which one of the groups $R^5$ is aralkyl, such as benzyl, and the other is alkyl, can be converted into the monoesters A34.2 in which $R^5$ is alkyl by hydrogenation, for example using a palladium on carbon catalyst. Phosphonate diesters in which both of the groups $R^5$ are alkenyl, such as allyl, can be converted into the monoester A34.2 in which $R^5$ is alkenyl, by treatment with chlorotris(triphenylphosphine)rhodium (Wilkinson's catalyst) in aqueous ethanol at reflux, optionally in the presence of diazabicyclooctane, for example by using the procedure described in J. Org. Chem., 38, 3224, 1973 for the cleavage of allyl carboxylates.

The conversion of a phosphonate diester A34.1 or a phosphonate monoester A34.2 into the corresponding phosphonic acid A34.3 (Scheme A34, Reactions 2 and 3) can effected by reaction of the diester or the monoester with trimethylsilyl bromide, as described in J. Chem. Soc., Chem. Comm., 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester A34.2 in which $R^5$ is aralkyl such as benzyl, can be converted into the corresponding phosphonic acid A34.3 by hydrogenation over a palladium catalyst, or by treatment with hydrogen chloride in an ethereal solvent such as dioxan. A phosphonate monoester A34.2 in which $R^5$ is alkenyl such as, for example, allyl, can be converted into the phosphonic acid A34.3 by reaction with Wilkinson's catalyst in an aqueous organic solvent, for example in 15% aqueous acetonitrile, or in aqueous ethanol, for example using the procedure described in Helv. Chim. Acta., 68, 618, 1985. Palladium catalyzed hydrogenolysis of phosphonate esters A34.1 in which $R^5$ is benzyl is described in J. Org. Chem., 24, 434, 1959. Platinum-catalyzed hydrogenolysis of phosphonate esters A34.1 in which $R^5$ is phenyl is described in J. Am. Chem. Soc., 78, 2336, 1956.

The conversion of a phosphonate monoester A34.2 into a phosphonate diester A34.1 (Scheme A34, Reaction 4) in which the newly introduced $R^5$ group is alkyl, aralkyl, haloalkyl such as chloroethyl, or aralkyl can be effected by a number of reactions in which the substrate A34.2 is reacted with a hydroxy compound $R^5OH$, in the presence of a coupling agent. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester A34.2 to the diester A34.1 can be effected by the use of the Mitsonobu reaction, as described above (Scheme A6). The substrate is reacted with the hydroxy compound $R^5OH$, in the presence of diethyl azodicarboxylate and a triarylphosphine such as triphenyl phosphine. Alternatively, the phosphonate monoester A34.2 can be transformed into the phosphonate diester A34.1, in which the introduced $R^5$ group is alkenyl or aralkyl, by reaction of the monoester with the halide $R^5Br$, in which $R^5$ is as alkenyl or aralkyl. The alkylation reaction is conducted in a polar organic solvent such as dimethylformamide or acetonitrile, in the presence of a base such as cesium carbonate. Alternatively, the phosphonate monoester can be transformed into the phosphonate diester in a two step procedure. In the first step, the phosphonate monoester A34.2 is transformed into the chloro analog $RP(O)(OR^5)Cl$ by reaction with thionyl chloride or oxalyl chloride and the like, as described in Organic Phosphorus Compounds, G. M. Kosolapoff, L. Maeir, eds, Wiley, 1976, p. 17, and the thus-obtained product $RP(O)(OR^5)Cl$ is then reacted with the hydroxy compound $R^5OH$, in the presence of a base such as triethylamine, to afford the phosphonate diester A34.1.

A phosphonic acid $R$-link-$P(O)(OH)_2$ can be transformed into a phosphonate monoester $RP(O)(OR^5)(OH)$ (Scheme A34, Reaction 5) by means of the methods described above of for the preparation of the phosphonate diester R-link-$P(O)(OR^5)_2$ A34.1, except that only one molar proportion of the component $R^5OH$ or $R^5Br$ is employed.

A phosphonic acid R-link-$P(O)(OH)_2$ A34.3 can be transformed into a phosphonate diester R-link-$P(O)(OR^5)_2$ A34.1 (Scheme A34, Reaction 6) by a coupling reaction with the hydroxy compound $R^5OH$, in the presence of a coupling agent such as Aldrithiol-2 (Aldrich) and triphenylphosphine. The reaction is conducted in a basic solvent such as pyridine. Alternatively, phosphonic acids A34.3 can be transformed into phosphonic esters A34.1 in which $R^5$ is aryl, by means of a coupling reaction employing, for example, dicyclohexylcarbodiimide in pyridine at ca 70° C. Alternatively, phosphonic acids A34.3 can be transformed into phosphonic esters A34.1 in which $R^5$ is alkenyl, by means of an alkylation reaction. The phosphonic acid is reacted with the alkenyl bromide $R^5Br$ in a polar organic solvent such as acetonitrile solution at reflux temperature, the presence of a base such as cesium carbonate, to afford the phosphonic ester A34.1.

Scheme A34

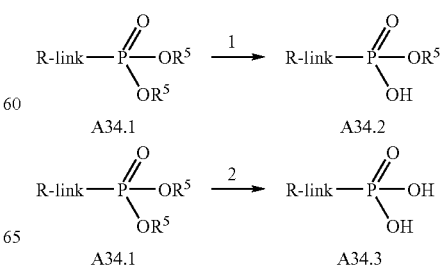

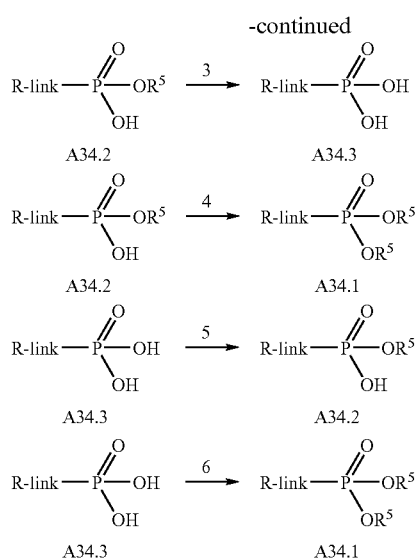

Preparation of Carboalkoxy-Substituted Phosphonate Bisamidates, Monoamidates, Diesters and Monoesters.

A number of methods are available for the conversion of phosphonic acids into arnidates and esters. In one group of methods, the phosphonic acid is either converted into an isolated activated intermediate such as a phosphoryl chloride, or the phosphonic acid is activated in situ for reaction with an amine or a hydroxy compound.

The conversion of phosphonic acids into phosphoryl chlorides is accomplished by reaction with thionyl chloride, for example as described in J. Gen. Chem. USSR, 1983, 53, 480, Zh. Obschei Khim., 1958, 28, 1063, or J. Org. Chem., 1994, 59, 6144, or by reaction with oxalyl chloride, as described in J. Am. Chem. Soc., 1994, 116,3251, or J. Org. Chem., 1994, 59, 6144, or by reaction with phosphorus pentachloride, as described in J. Org. Chem., 2001, 66, 329, or in J. Med. Chem., 1995, 38, 1372. The resultant phosphoryl chlorides are then reacted with amines or hydroxy compounds in the presence of a base to afford the amidate or ester products.

Phosphonic acids are converted into activated imidazolyl derivatives by reaction with carbonyl diimidazole, as described in J. Chem. Soc., Chem. Comm., 1991, 312, or Nucleosides Nucleotides 2000, 19, 1885. Activated sulfonyloxy derivatives are obtained by the reaction of phosphonic acids with trichloromethylsulfonyl chloride, as described in J. Med. Chem. 1995, 38, 4958, or with triisopropylbenzenesulfonyl chloride, as described in Tet. Lett., 1996, 7857, or Bioorg. Med. Chem. Lett., 1998, 8, 663. The activated sulfonyloxy derivatives are then reacted with amines or hydroxy compounds to afford amidates or esters.

Alternatively, the phosphonic acid and the amine or hydroxy reactant are combined in the presence of a diimide coupling agent. The preparation of phosphonic amidates and esters by means of coupling reactions in the presence of dicyclohexyl carbodiimide is described, for example, in J. Chem. Soc., Chem. Comm., 1991, 312, or J. Med. Chem., 1980,23, 1299 or Coll. Czech. Chem. Comm., 1987, 52, 2792. The use of ethyl dimethylaminopropyl carbodiimide for activation and coupling of phosphonic acids is described in Tet. Lett., 2001, 42, 8841, or Nucleosides Nucleotides, 2000, 19, 1885.

A number of additional coupling reagents have been described for the preparation of amidates and esters from phosphonic acids. The agents include Aldrithiol-2, and PYBOP and BOP, as described in J. Org. Chem., 1995, 60, 5214, and J. Med. Chem., 1997, 40, 3842, mesitylene-2-sulfonyl-3-nitro-1,2,4-triazole (MSNT), as described in J. Med. Chem., 1996, 39, 4958, diphenylphosphoryl azide, as described in J. Org. Chem., 1984, 49, 1158, 1-(2,4,6-triisopropylbenzenesulfonyl-3-nitro-1,2,4-triazole (TPSNT) as described in Bioorg. Med. Chem. Lett., 1998, 8, 1013, bromotris(dimethylamino)phosphonium hexafluorophosphate (BroP), as described in Tet. Lett., 1996, 37, 3997, 2-chloro-5,5-dimethyl-2-oxo-1,3,2-dioxaphosphinane, as described in Nucleosides Nucleotides 1995, 14, 871, and diphenyl chlorophosphate, as described in J. Med. Chem., 1988, 31, 1305.

Phosphonic acids are converted into amidates and esters by means of the Mitsonobu reaction, in which the phosphonic acid and the amine or hydroxy reactant are combined in the presence of a triaryl phosphine and a dialkyl azodicarboxylate. The procedure is described in Org. Lett., 2001, 3, 643, or J. Med. Chem., 1997, 40, 3842.

Phosphonic esters are also obtained by the reaction between phosphonic acids and halo compounds, in the presence of a suitable base. The method is described, for example, in Anal. Chem., 1987, 59, 1056, or J. Chem. Soc. Perkin Trans., I, 1993, 19, 2303, or J. Med. Chem., 1995, 38, 1372, or Tet. Lett., 2002,43, 1161.

Schemes 1-5 illustrate the conversion of phosphonate esters and phosphonic acids into carboalkoxy-substituted phosphorobisamidates (Scheme 1), phosphoroamidates (Scheme 2), phosphonate monoesters (Scheme 3) and phosphonate diesters, (Scheme 4)

Scheme 1 illustrates various methods for the conversion of phosphonate diesters 1.1 into phosphorobisamidates 1.5. The diester 1.1, prepared as described previously, is hydrolyzed, either to the monoester 1.2 or to the phosphonic acid 1.6. The methods employed for these transformations are described above. The monoester 1.2 is converted into the monoamidate 1.3 by reaction with an arninoester 1.9, in which the group $R^2$ is H or alkyl, the group $R^4$ is an alkylene moiety such as, for example, $CHCH_3$, $CHPr^1$, $CH(CH_2Ph)$, $CH_2CH(CH_3)$ and the like, or a group present in natural or modified aminoacids, and the group $R^5$ is alkyl. The reactants are combined in the presence of a coupling agent such as a carbodiimide, for example dicyclohexyl carbodiimide, as described in J. Am. Chem. Soc., 1957, 79, 3575, optionally in the presence of an activating agent such as hydroxybenztriazole, to yield the amidate product 1.3. The amidate-forming reaction is also effected in the presence of coupling agents such as BOP, as described in J. Org. Chem., 1995, 60, 5214, Aldrithiol, PYBOP and similar coupling agents used for the preparation of amides and esters. Alternatively, the reactants 1.2 and 1.9 are transformed into the monoamidate 1.3 by means of a Mitsonobu reaction. The preparation of amidates by means of the Mitsonobu reaction is described in J. Med. Chem., 1995, 38, 2742. Equimolar amounts of the reactants are combined in an inert solvent such as tetrahydrofuran in the presence of a triaryl phosphine and a dialkyl azodicarboxylate. The thus-obtained monoamidate ester 1.3 is then transformed into amidate phosphonic acid 1.4. The conditions used for the hydrolysis reaction depend on the nature of the $R^1$ group, as described previously. The phosphonic acid amidate 1.4 is then reacted with an aminoester 1.9, as described above, to yield the bisamidate product 1.5, in which the amino substituents are the same or different.

An example of this procedure is shown in Scheme 1, Example 1. In this procedure, a dibenzyl phosphonate 1.14 is reacted with diazabicyclooctane (DABCO) in toluene at reflux, as described in J. Org. Chem., 1995, 60, 2946, to afford the monobenzyl phosphonate 1.15. The product is then reacted with equimolar amounts of ethyl alaninate 1.16 and dicyclohexyl carbodiimide in pyridine, to yield the amidate product 1.17. The benzyl group is then removed, for example by hydrogenolysis over a palladium catalyst, to give the monoacid product 1.18. This compound is then reacted in a Mitsonobu reaction with ethyl leucinate 1.19, triphenyl phosphine and diethylazodicarboxylate, as described in J. Med. Chem., 1995, 38, 2742, to produce the bisamidate product 1.20.

Using the above procedures, but employing, in place of ethyl leucinate 1.19 or ethyl alaninate 1.16, different aminoesters 1.9, the corresponding products 1.5 are obtained.

Alternatively, the phosphonic acid 1.6 is converted into the bisamidate 1.5 by use of the coupling reactions described above. The reaction is performed in one step, in which case the nitrogen-related substituents present in the product 1.5 are the same, or in two steps, in which case the nitrogen-related substituents can be different.

An example of the method is shown in Scheme 1, Example 2. In this procedure, a phosphonic acid 1.6 is reacted in pyridine solution with excess ethyl phenylalaninate 1.21 and dicyclohexylcarbodiimide, for example as described in J. Chem. Soc., Chem. Comm., 1991, 1063, to give the bisamidate product 1.22.

Using the above procedures, but employing, in place of ethyl phenylalaninate, different aminoesters 1.9, the corresponding products 1.5 are obtained.

As a further alternative, the phosphonic acid 1.6 is converted into the mono or bis-activated derivative 1.7, in which Lv is a leaving group such as chloro, imidazolyl, triisopropylbenzenesulfonyloxy etc. The conversion of phosphonic acids into chlorides 1.7 (Lv=Cl) is effected by reaction with thionyl chloride or oxalyl chloride and the like, as described in Organic Phosphorus Compounds, G. M. Kosolapoff, L. Maeir, eds, Wiley, 1976, p. 17. The conversion of phosphonic acids into monoimidazolides 1.7 (Lv=imidazolyl) is described in J. Med. Chem., 2002, 45, 1284 and in J. Chem. Soc. Chem. Comm., 1991, 312. Alternatively, the phosphonic acid is activated by reaction with triisopropylbenzenesulfonyl chloride, as described in Nucleosides and Nucleotides, 2000, 10, 1885. The activated product is then reacted with the aminoester 1.9, in the presence of a base, to give the bisamidate 1.5. The reaction is performed in one step, in which case the nitrogen substituents present in the product 1.5 are the same, or in two steps, via the intermediate 1.11, in which case the nitrogen substituents can be different.

Examples of these methods are shown in Scheme 1, Examples 3 and 5. In the procedure illustrated in Scheme 1, Example 3, a phosphonic acid 1.6 is reacted with ten molar equivalents of thionyl chloride, as described in Zh. Obschei Khim., 1958, 28, 1063, to give the dichloro compound 1.23. The product is then reacted at reflux temperature in a polar aprotic solvent such as acetonitrile, and in the presence of a base such as triethylamine, with butyl serinate 1.24 to afford the bisamidate product 1.25.

Using the above procedures, but employing, in place of butyl serinate 1.24, different aminoesters 1.9, the corresponding products 1.5 are obtained.

In the procedure illustrated in Scheme 1, Example 5, the phosphonic acid 1.6 is reacted, as described in J. Chem. Soc. Chem. Comm., 1991, 312, with carbonyl diimidazole to give the imidazolide 1.32. The product is then reacted in acetonitrile solution at ambient temperature, with one molar equivalent of ethyl alaninate 1.33 to yield the monodisplacement product 1.34. The latter compound is then reacted with carbonyl diimidazole to produce the activated intermediate 1.35, and the product is then reacted, under the same conditions, with ethyl N-methylalaninate 1.33a to give the bisarnidate product 1.36.

Using the above procedures, but employing, in place of ethyl alaninate 1.33 or ethyl N-methylalaninate 1.33a, different aminoesters 1.9, the corresponding products 1.5 are obtained.

The intermediate monoamidate 1.3 is also prepared from the monoester 1.2 by first converting the monoester into the activated derivative 1.8 in which Lv is a leaving group such as halo, imidazolyl etc, using the procedures described above. The product 1.8 is then reacted with an arninoester 1.9 in the presence of a base such as pyridine, to give an intermediate monoamidate product 1.3. The latter compound is then converted, by removal of the $R^1$ group and coupling of the product with the aminoester 1.9, as described above, into the bisamidate 1.5.

An example of this procedure, in which the phosphonic acid is activated by conversion to the chloro derivative 1.26, is shown in Scheme 1, Example 4. In this procedure, the phosphonic monobenzyl ester 1.15 is reacted, in dichloromethane, with thionyl chloride, as described in Tet. Let., 1994, 35, 4097, to afford the phosphoryl chloride 1.26. The product is then reacted in acetonitrile solution at ambient temperature with one molar equivalent of ethyl 3-amino-2-methylpropionate 1.27 to yield the monoamidate product 1.28. The latter compound is hydrogenated in ethylacetate over a 5% palladium on carbon catalyst to produce the monoacid product 1.29. The product is subjected to a Mitsonobu coupling procedure, with equimolar amounts of butyl alaninate 1.30, triphenyl phosphine, diethylazodicarboxylate and triethylamine in tetrahydrofuran, to give the bisamidate product 1.31.

Using the above procedures, but employing, in place of ethyl 3-amino-2-methylpropionate 1.27 or butyl alaninate 1.30, different aminoesters 1.9, the corresponding products 1.5 are obtained.

The activated phosphonic acid derivative 1.7 is also converted into the bisamidate 1.5 via the diamino compound 1.10. The conversion of activated phosphonic acid derivatives such as phosphoryl chlorides into the corresponding amino analogs 1.10, by reaction with ammonia, is described in Organic Phosphorus Compounds, G. M. Kosolapoff, L. Maeir, eds, Wiley, 1976. The diamino compound 1.10 is then reacted at elevated temperature with a haloester 1.12, in a polar organic solvent such as dimethylformamide, in the presence of a base such as dimethylaminopyridine or potassium carbonate, to yield the bisamidate 1.5.

An example of this procedure is shown in Scheme 1, Example 6. In this method, a dichlorophosphonate 1.23 is reacted with ammonia to afford the diamide 1.37. The reaction is performed in aqueous, aqueous alcoholic or alcoholic solution, at reflux temperature. The resulting diamino compound is then reacted with two molar equivalents of ethyl 2-bromo-3-methylbutyrate 1.38, in a polar organic solvent such as N-methylpyrrolidinone at ca. 150° C., in the presence of a base such as potassium carbonate, and optionally in the presence of a catalytic amount of potassium iodide, to afford the bisamidate product 1.39.

Using the above procedures, but employing, in place of ethyl 2-bromo-3-methylbutyrate 1.38, different haloesters 1.12 the corresponding products 1.5 are obtained.

The procedures shown in Scheme 1 are also applicable to the preparation of bisamidates in which the aminoester moiety incorporates different functional groups. Scheme 1, Example 7 illustrates the preparation of bisamidates derived from tyrosine. In this procedure, the monoimidazolide 1.32 is reacted with propyl tyrosinate 1.40, as described in Example 5, to yield the monoamidate 1.41. The product is reacted with carbonyl diimidazole to give the imidazolide 1.42, and this material is reacted with a further molar equivalent of propyl tyrosinate to produce the bisamidate product 1.43.

Using the above procedures, but employing, in place of propyl tyrosinate 1.40, different aminoesters 1.9, the corresponding products 1.5 are obtained. The aminoesters employed in the two stages of the above procedure can be the same or different, so that bisamidates with the same or different amino substituents are prepared.

Scheme 2 illustrates methods for the preparation of phosphonate monoamidates.

In one procedure, a phosphonate monoester 1.1 is converted, as described in Scheme 1, into the activated derivative 1.8. This compound is then reacted, as described above, with an aminoester 1.9, in the presence of a base, to afford the monoamidate product 2.1.

The procedure is illustrated in Scheme 2, Example 1. In this method, a monophenyl phosphonate 2.7 is reacted with, for example, thionyl chloride, as described in J. Gen. Chem. USSR., 1983, 32, 367, to give the chloro product 2.8. The product is then reacted, as described in Scheme 1, with ethyl alaninate 2.9, to yield the amidate 2.10.

Using the above procedures, but employing, in place of ethyl alaninate 2.9, different aminoesters 1.9, the corresponding products 2.1 are obtained.

Alternatively, the phosphonate monoester 1.1 is coupled, as described in Scheme 1, with an aminoester 1.9 to produce the amidate 2.1. If necessary, the $R^1$ substituent is then altered, by initial cleavage to afford the phosphonic acid 2.2. The procedures for this transformation depend on the nature of the $R^1$ group, and are described above. The phosphonic acid is then transformed into the ester amidate product 2.3, by reaction with the hydroxy compound $R^3OH$, in which the group $R^3$ is aryl, heteroaryl, alkyl, cycloalkyl, haloalkyl etc, using the same coupling procedures (carbodiimide, Aldrithiol-2, PYBOP, Mitsonobu reaction etc) described in Scheme 1 for the coupling of amines and phosphonic acids.

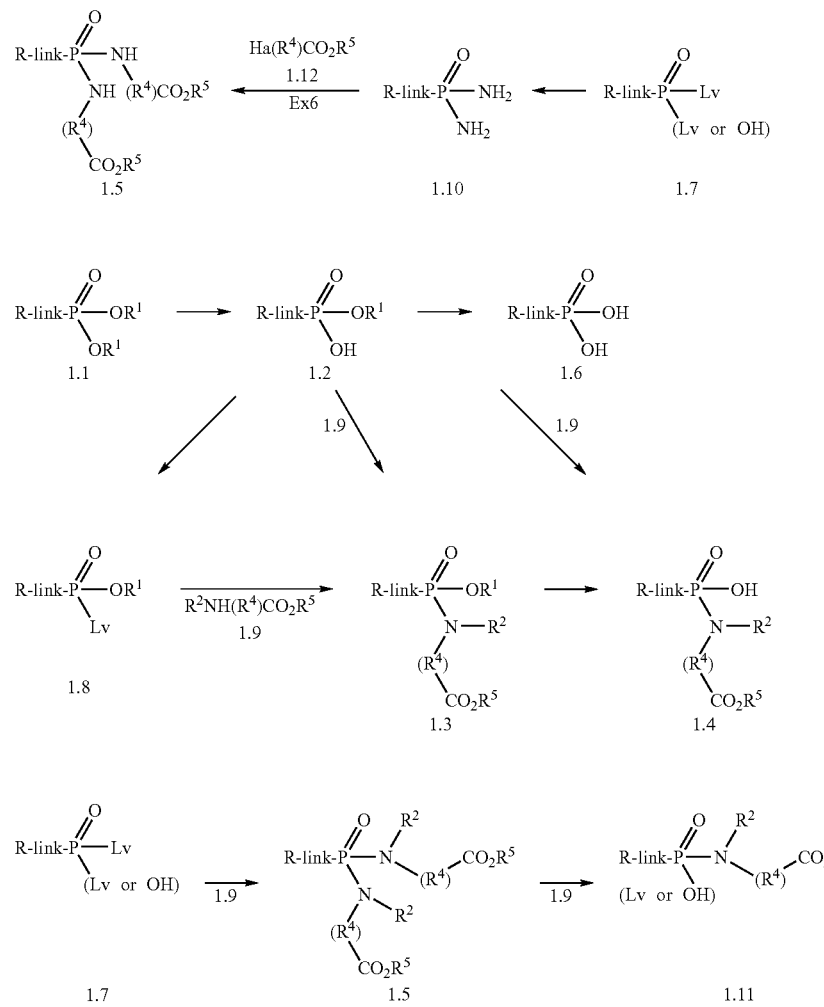

Scheme 1

-continued
Scheme 1 Example 1
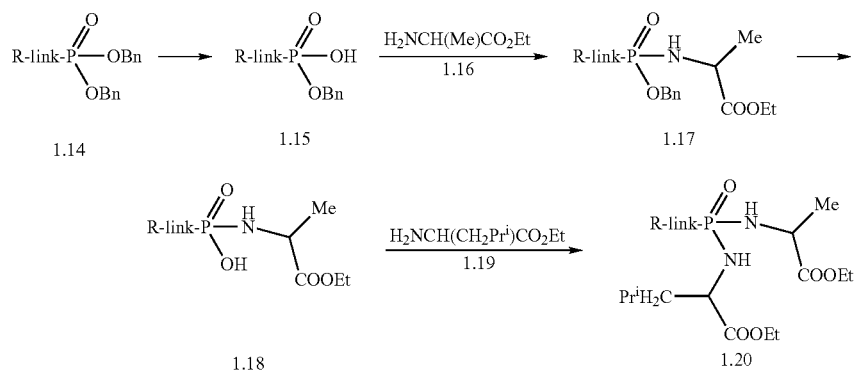
Scheme 1 Example 2
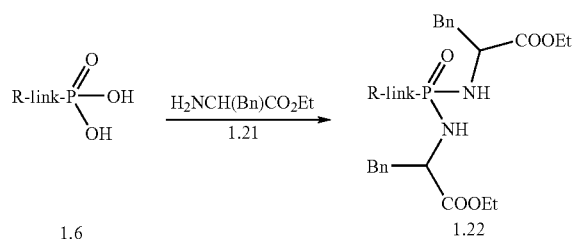
Scheme 1 Example 3
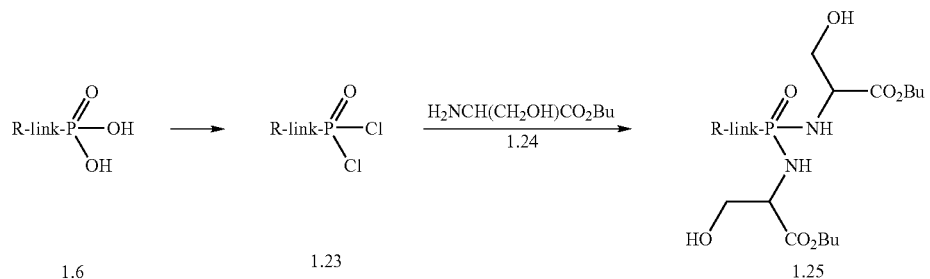
Scheme 1 Example 4
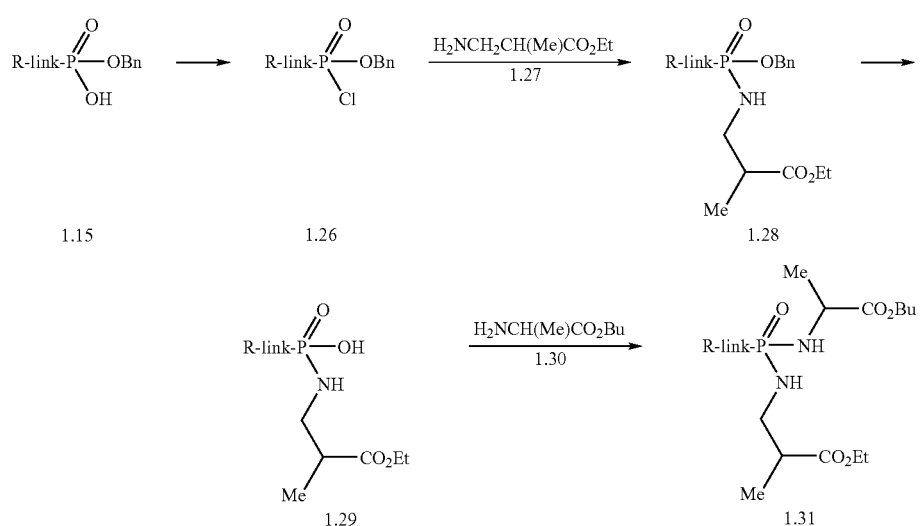

-continued
Scheme 1 Example 5

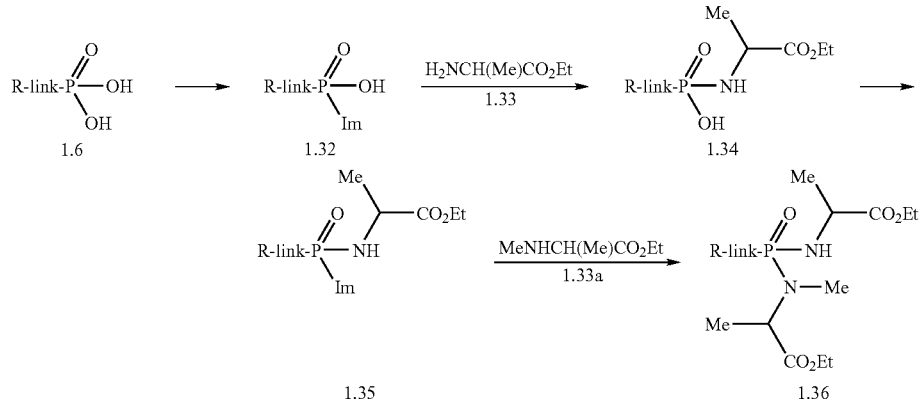

Scheme 1 Example 6

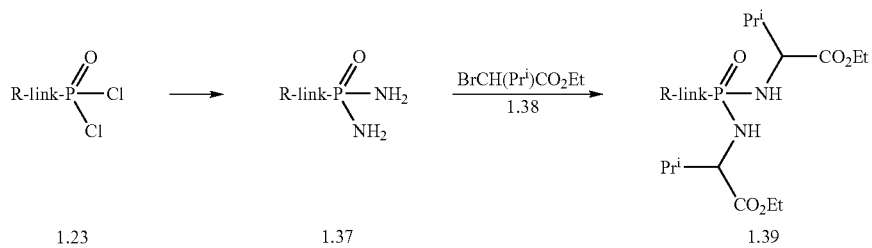

Scheme 1 Example 7

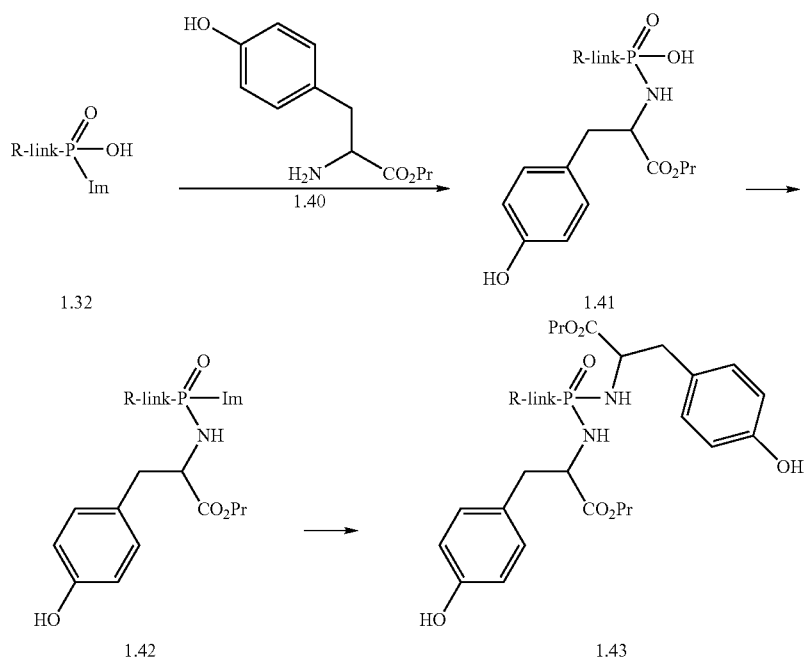

Examples of this method are shown in Scheme 2, Examples and 2 and 3. In the sequence shown in Example 2, a monobenzyl phosphonate 2.11 is transformed by reaction with ethyl alaninate, using one of the methods described above, into the monoamidate 2.12. The benzyl group is then removed by catalytic hydrogenation in ethylacetate solution over a 5% palladium on carbon catalyst, to afford the phosphonic acid amidate 2.13. The product is then reacted in dichloromethane solution at ambient temperature with equimolar amounts of 1-(dimethylaminopropyl)-3-ethylcarbodiimide and trifluoroethanol 2.14, for example as described in Tet. Lett., 2001, 42, 8841, to yield the amidate ester 2.15.

In the sequence shown in Scheme 2, Example 3, the monoamidate 2.13 is coupled, in tetrahydrofuran solution at ambient temperature, with equimolar amounts of dicyclohexyl carbodiimide and 4-hydroxy-N-methylpiperidine 2.16, to produce the amidate ester product 2.17.

Using the above procedures, but employing, in place of the ethyl alaninate product 2.12 different monoacids 2.2, and in place of trifluoroethanol 2.14 or 4-hydroxy-N-methylpiperidine 2.16, different hydroxy compounds R³OH, the corresponding products 2.3 are obtained.

Alternatively, the activated phosphonate ester 1.8 is reacted with ammonia to yield the amidate 2.4. The product is then reacted, as described in Scheme 1, with a haloester 2.5, in the presence of a base, to produce the amidate product 2.6. If appropriate, the nature of the R¹ group is changed, using the procedures described above, to give the product 2.3. The method is illustrated in Scheme 2, Example 4. In this sequence, the monophenyl phosphoryl chloride 2.18 is reacted, as described in Scheme 1, with ammonia, to yield the amino product 2.19. This material is then reacted in N-methylpyrrolidinone solution at 170° C. with butyl 2-bromo-3-phenylpropionate 2.20 and potassium carbonate, to afford the amidate product 2.21.

Using these procedures, but employing, in place of butyl 2-bromo-3-phenylpropionate 2.20, different haloesters 2.5, the corresponding products 2.6 are obtained.

The monoamidate products 2.3 are also prepared from the doubly activated phosphonate derivatives 1.7. In this procedure, examples of which are described in Synlett., 1998, 1, 73, the intermediate 1.7 is reacted with a limited amount of the aminoester 1.9 to give the mono-displacement product 1.11. The latter compound is then reacted with the hydroxy compound R³OH in a polar organic solvent such as dimethylformamide, in the presence of a base such as diisopropylethylamine, to yield the monoamidate ester 2.3.

The method is illustrated in Scheme 2, Example 5. In this method, the phosphoryl dichloride 2.22 is reacted in dichloromethane solution with one molar equivalent of ethyl N-methyl tyrosinate 2.23 and dimethylaminopyridine, to generate the monoamidate 2.24. The product is then reacted with phenol 2.25 in dimethylformamide containing potassium carbonate, to yield the ester amidate product 2.26.

Using these procedures, but employing, in place of ethyl N-methyl tyrosinate 2.23 or phenol 2.25, the aminoesters 1.9 and/or the hydroxy compounds R³OH, the corresponding products 2.3 are obtained.

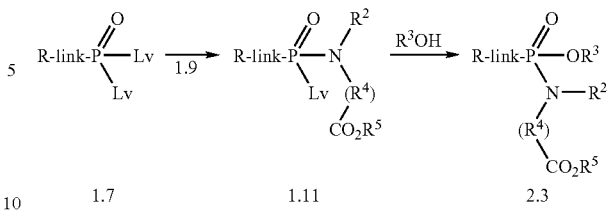

Scheme 2 Example 1

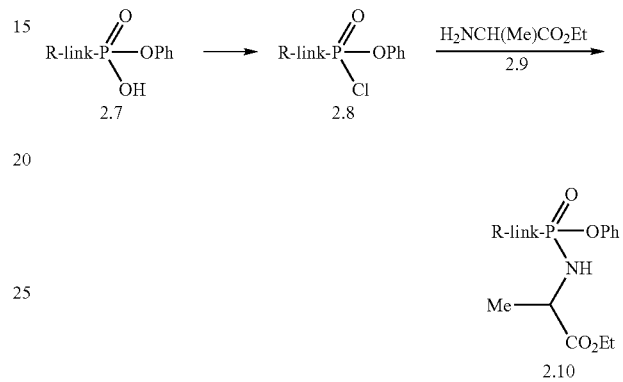

Scheme 2 Example 2

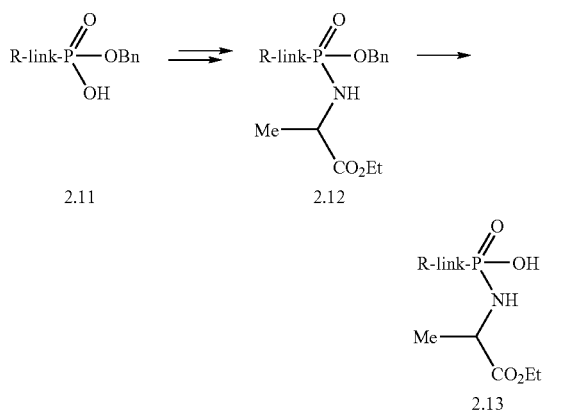

Scheme 2 Example 3

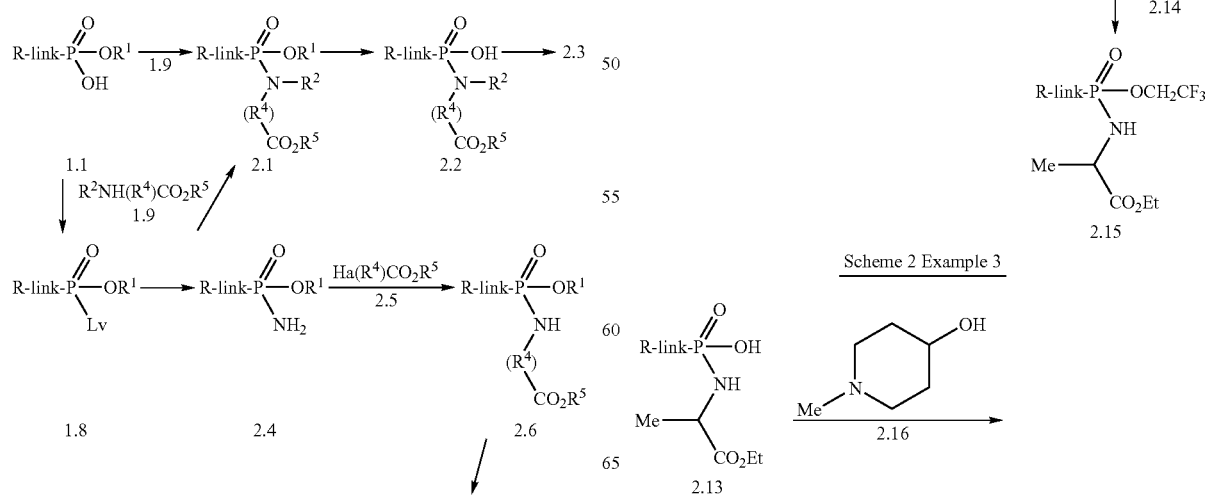

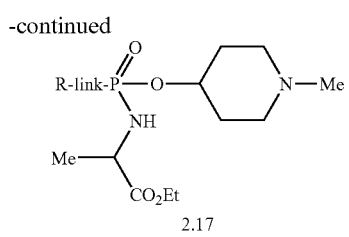

Scheme 2 Example 4

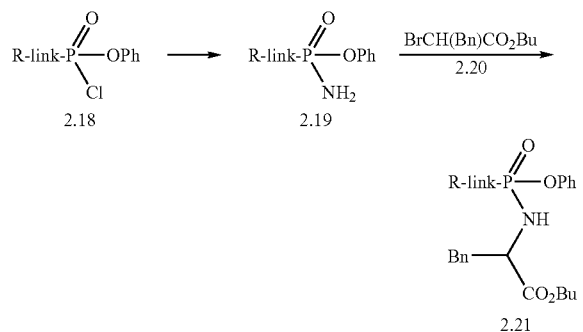

Scheme 2 Example 5

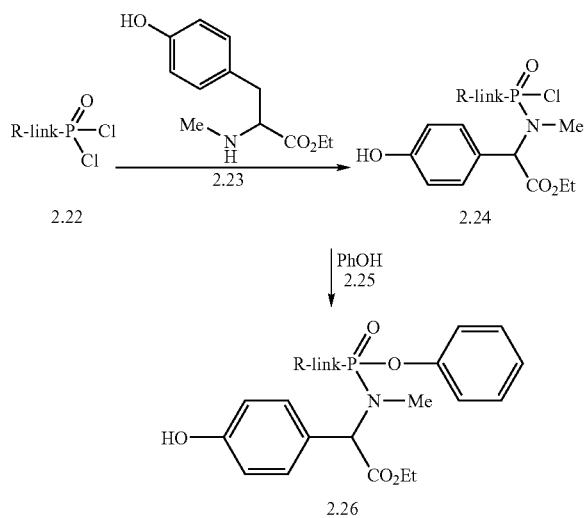

Scheme 3 illustrates methods for the preparation of carboalkoxy-substituted phosphonate diesters in which one of the ester groups incorporates a carboalkoxy substituent.

In one procedure, a phosphonate monoester 1.1, prepared as described above, is coupled, using one of the methods described above, with a hydroxyester 3.1, in which the groups $R^4$ and $R^5$ are as described in Scheme 1. For example, equimolar amounts of the reactants are coupled in the presence of a carbodiimide such as dicyclohexyl carbodiimide, as described in Aust. J. Chem., 1963, 609, optionally in the presence of dimethylaminopyridine, as described in Tet., 1999, 55, 12997. The reaction is conducted in an inert solvent at ambient temperature.

The procedure is illustrated in Scheme 3, Example 1. In this method, a monophenyl phosphonate 3.9 is coupled, in dichloromethane solution in the presence of dicyclohexyl carbodiimide, with ethyl 3-hydroxy-2-methylpropionate 3.10 to yield the phosphonate mixed diester 3.11.

Using this procedure, but employing, in place of ethyl 3-hydroxy-2-methylpropionate 3.10, different hydroxyesters 3.1, the corresponding products 3.2 are obtained.

The conversion of a phosphonate monoester 1.1 into a mixed diester 3.2 is also accomplished by means of a Mitsonobu coupling reaction with the hydroxyester 3.1, as described in Org. Lett., 2001, 643. In this method, the reactants 1.1 and 3.1 are combined in a polar solvent such as tetrahydrofuran, in the presence of a triarylphosphine and a dialkyl azodicarboxylate, to give the mixed diester 3.2. The $R^1$ substituent is varied by cleavage, using the methods described previously, to afford the monoacid product 3.3. The product is then coupled, for example using methods described above, with the hydroxy compound $R^3OH$, to give the diester product 3.4.

The procedure is illustrated in Scheme 3, Example 2. In this method, a monoallyl phosphonate 3.12 is coupled in tetrahydrofuran solution, in the presence of triphenylphosphine and diethylazodicarboxylate, with ethyl lactate 3.13 to give the mixed diester 3.14. The product is reacted with tris(triphenylphosphine) rhodium chloride (Wilkinson catalyst) in acetonitrile, as described previously, to remove the allyl group and produce the monoacid product 3.15. The latter compound is then coupled, in pyridine solution at ambient temperature, in the presence of dicyclohexyl carbodiimide, with one molar equivalent of 3-hydroxypyridine 3.16 to yield the mixed diester 3.17.

Using the above procedures, but employing, in place of the ethyl lactate 3.13 or 3-hydroxypyridine, a different hydroxyester 3.1 and/or a different hydroxy compound $R^3OH$, the corresponding products 3.4 are obtained.

The mixed diesters 3.2 are also obtained from the monoesters 1.1 via the intermediacy of the activated monoesters 3.5. In this procedure, the monoester 1.1 is converted into the activated compound 3.5 by reaction with, for example, phosphorus pentachloride, as described in J. Org. Chem., 2001, 66, 329, or with thionyl chloride or oxalyl chloride (Lv=Cl), or with triisopropylbenzenesulfonyl chloride in pyridine, as described in Nucleosides and Nucleotides, 2000, 19, 1885, or with carbonyl diimidazole, as described in J. Med. Chem., 2002, 45, 1284. The resultant activated monoester is then reacted with the hydroxyester 3.1, as described above, to yield the mixed diester 3.2.

The procedure is illustrated in Scheme 3, Example 3. In this sequence, a monophenyl phosphonate 3.9 is reacted, in acetonitrile solution at 70° C., with ten equivalents of thionyl chloride, so as to produce the phosphoryl chloride 3.19. The product is then reacted with ethyl 4-carbamoyl-2-hydroxybutyrate 3.20 in dichloromethane containing triethylamine, to give the mixed diester 3.21.

Using the above procedures, but employing, in place of ethyl 4-carbamoyl-2-hydroxybutyrate 3.20, different hydroxyesters 3.1, the corresponding products 3.2 are obtained.

The mixed phosphonate diesters are also obtained by an alternative route for incorporation of the $R^3O$ group into intermediates 3.3 in which the hydroxyester moiety is already incorporated. In this procedure, the monoacid intermediate 3.3 is converted into the activated derivative 3.6 in which Lv is a leaving group such as chloro, imidazole, and the like, as previously described. The activated intermediate is then reacted with the hydroxy compound $R^3OH$, in the presence of a base, to yield the mixed diester product 3.4.

The method is illustrated in Scheme 3, Example 4. In this sequence, the phosphonate monoacid 3.22 is reacted with trichloromethanesulfonyl chloride in tetrahydrofuran containing collidine, as described in J. Med. Chem., 1995, 38, 4648, to produce the trichloromethanesulfonyloxy product 3.23. This compound is reacted with 3-(morpholinomethyl)phenol 3.24 in dichloromethane containing triethylamine, to yield the mixed diester product 3.25.

Using the above procedures, but employing, in place of with 3-(morpholinomethyl)phenol 3.24, different carbinols $R^3OH$, the corresponding products 3.4 are obtained.

The phosphonate esters 3.4 are also obtained by means of alkylation reactions performed on the monoesters 1.1. The reaction between the monoacid 1.1 and the haloester 3.7 is performed in a polar solvent in the presence of a base such as diisopropylethylamine, as described in Anal. Chem., 1987, 59, 1056, or triethylamine, as described in J. Med. Chem., 1995, 38, 1372, or in a non-polar solvent such as benzene, in the presence of 18-crown-6, as described in Syn. Comm., 1995, 25, 3565.

The method is illustrated in Scheme 3, Example 5. In this procedure, the monoacid 3.26 is reacted with ethyl 2-bromo-3-phenylpropionate 3.27 and diisopropylethylamine in dimethylformamide at 80° C. to afford the mixed diester product 3.28.

Using the above procedure, but employing, in place of ethyl 2-bromo-3-phenylpropionate 3.27, different haloesters 3.7, the corresponding products 3.4 are obtained.

Scheme 3

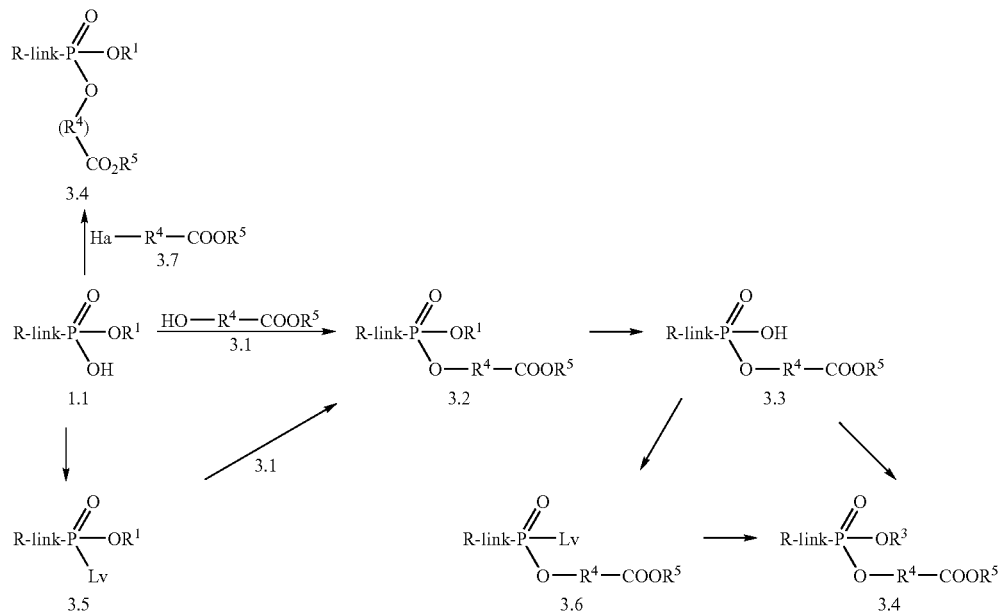

Scheme 3 Example 1

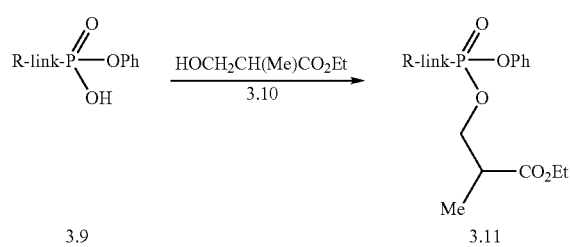

Scheme 3 Example 2

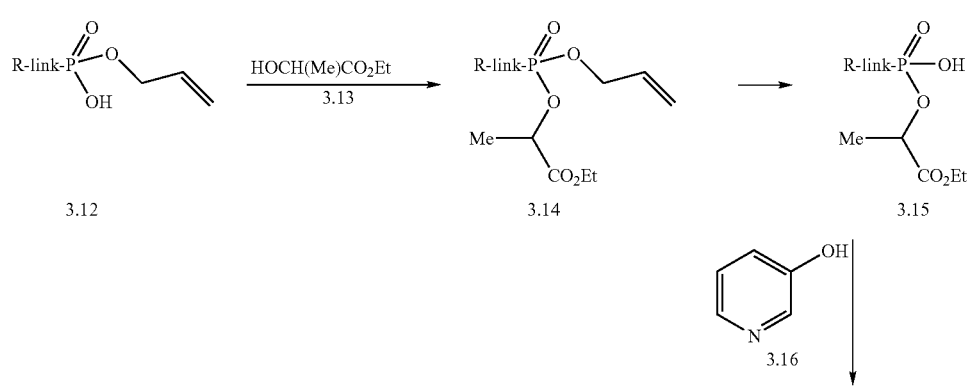

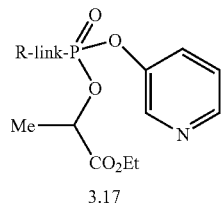

Scheme 3 Example 3

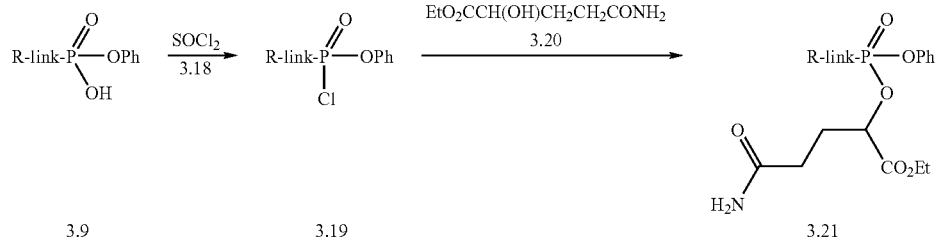

Scheme 3 Example 4

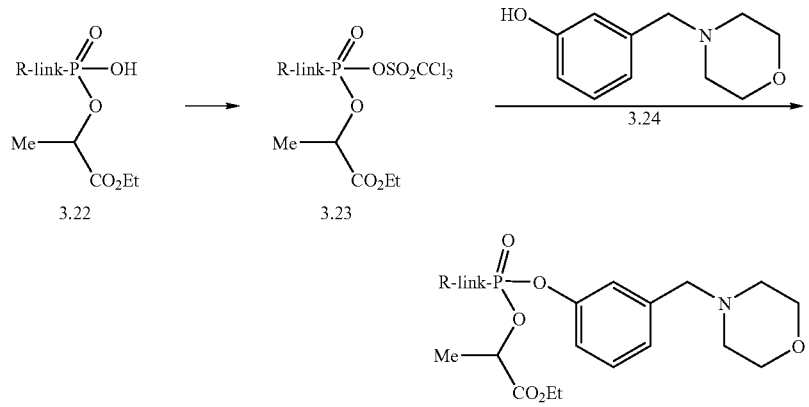

Scheme 3 Example 5

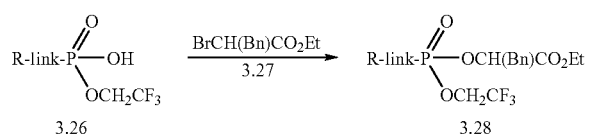

Scheme 4 illustrates methods for the preparation of phosphonate diesters in which both the ester substituents incorporate carboalkoxy groups.

The compounds are prepared directly or indirectly from the phosphonic acids 1.6. In one alternative, the phosphonic acid is coupled with the hydroxyester 4.2, using the conditions described previously in Schemes 1-3, such as coupling reactions using dicyclohexyl carbodiimide or similar reagents, or under the conditions of the Mitsonobu reaction, to afford the diester product 4.3 in which the ester substituents are identical.

This method is illustrated in Scheme 4, Example 1. In this procedure, the phosphonic acid 1.6 is reacted with three molar equivalents of butyl lactate 4.5 in the presence of Aldrithiol-2 and triphenyl phosphine in pyridine at ca. 70° C., to afford the diester 4.6.

Using the above procedure, but employing, in place of butyl lactate 4.5, different hydroxyesters 4.2, the corresponding products 4.3 are obtained.

Alternatively, the diesters 4.3 are obtained by alkylation of the phosphonic acid 1.6 with a haloester 4.1. The alkylation reaction is performed as described in Scheme 3 for the preparation of the esters 3.4.

This method is illustrated in Scheme 4, Example 2. In this procedure, the phosphonic acid 1.6 is reacted with excess ethyl 3-bromo-2-methylpropionate 4.7 and diisopropylethylamine in dimethylformamide at ca. 80° C., as described in Anal. Chem., 1987, 59, 1056, to produce the diester 4.8.

Using the above procedure, but employing, in place of ethyl 3-bromo-2-methylpropionate 4.7, different haloesters 4.1, the corresponding products 4.3 are obtained.

The diesters 4.3 are also obtained by displacement reactions of activated derivatives 1.7 of the phosphonic acid with the hydroxyesters 4.2. The displacement reaction is performed in a polar solvent in the presence of a suitable base, as described in Scheme 3. The displacement reaction is performed in the presence of an excess of the hydroxyester, to afford the diester product 4.3 in which the ester substituents are identical, or sequentially with limited amounts of different hydroxyesters, to prepare diesters 4.3 in which the ester substituents are different.

The methods are illustrated in Scheme 4, Examples 3 and 4. As shown in Example 3, the phosphoryl dichloride 2.22 is reacted with three molar equivalents of ethyl 3-hydroxy-2-(hydroxymethyl)propionate 4.9 in tetrahydrofuran containing potassium carbonate, to obtain the diester product 4.10.

Using the above procedure, but employing, in place of ethyl 3-hydroxy-2-(hydroxymethyl)propionate 4.9, different hydroxyesters 4.2, the corresponding products 4.3 are obtained.

Scheme 4, Example 4 depicts the displacement reaction between equimolar amounts of the phosphoryl dichloride 2.22 and ethyl 2-methyl-3-hydroxypropionate 4.11, to yield the monoester product 4.12. The reaction is conducted in acetonitrile at 70° C. in the presence of diisopropylethylamine. The product 4.12 is then reacted, under the same conditions, with one molar equivalent of ethyl lactate 4.13, to give the diester product 4.14.

Using the above procedures, but employing, in place of ethyl 2-methyl-3-hydroxypropionate 4.11 and ethyl lactate 4.13, sequential reactions with different hydroxyesters 4.2, the corresponding products 4.3 are obtained.

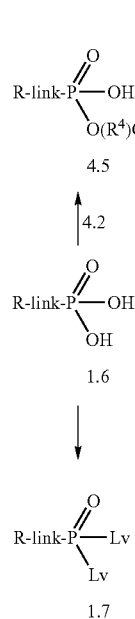

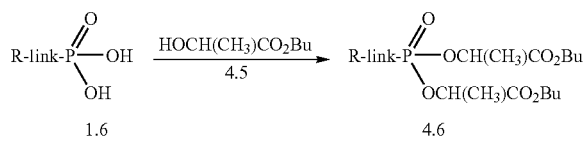

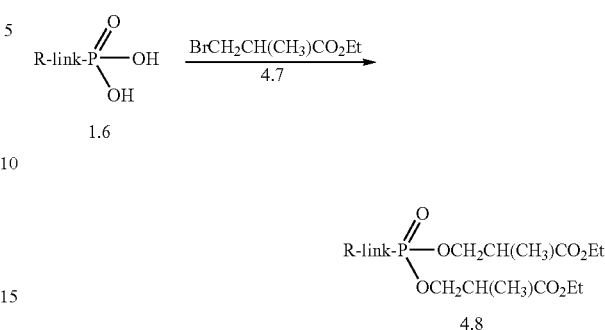

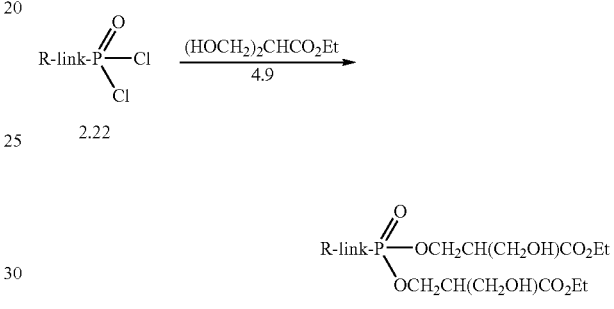

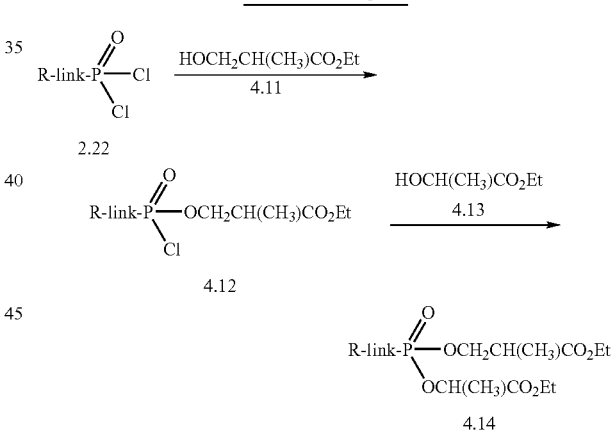

2,2-Dimethyl-2-arinoethylphosphonic acid intermediates can be prepared by the route in Scheme 5. Condensation of 2-methyl-2-propanesulfinamide with acetone give sulfinyl imine 11 (*J. Org. Chem.* 1999, 64, 12). Addition of dimethyl methylphosphonate lithium to 11 afford 12. Acidic methanolysis of 12 provide amine 13. Protection of amine with Cbz group and removal of methyl groups yield phosphonic acid 14, which can be converted to desired 15 (Scheme 5a) using methods reported earlier on. An alternative synthesis of compound 14 is also shown in Scheme 5b. Commercially available 2-amino-2-methyl-1-propanol is converted to aziridines 16 according to literature methods (*J. Org. Chem.* 1992, 57, 5813; *Syn. Lett.* 1997, 8, 893). Aziridine opening with phosphite give 17 (*Tetrahedron Lett.* 1980, 21, 1623). Reprotection) of 17 affords 14.

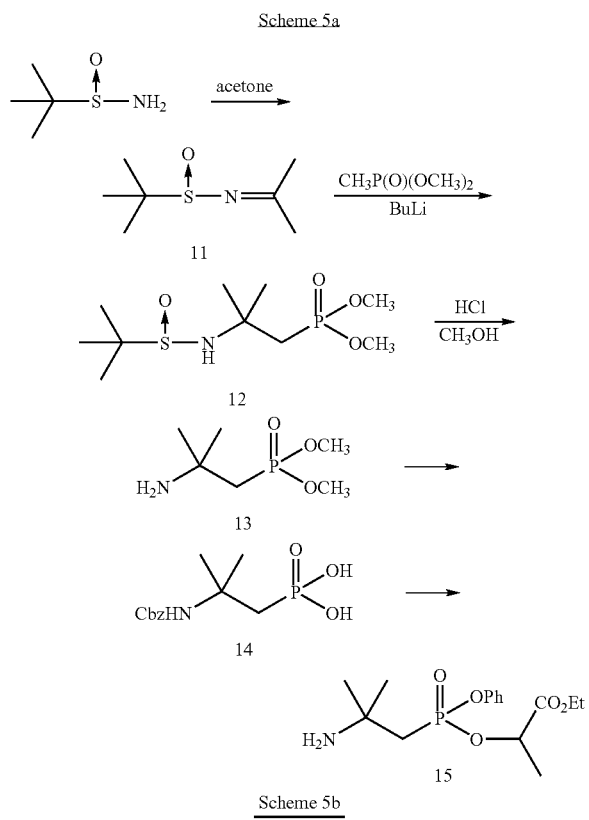

Biological Activity of HIV-Integrase Inhibitor Compounds

Representative compounds of the invention were tested for biological activity by methods including anti-HIV assay, measuring inhibition of FIW-integrase strand transfer catalysis, and cytotoxicity. See: Wolfe, etal *J. Virol.* (1996) 70:1424-1432; Hazuda, etal *Nucleic Acids Res.* (1994) 22:1121-22; Hazuda, etal *J. Virol.* (1997) 71:7005-7011; Hazuda, etal *Drug Design and Discovery* (1997) 15:17-24; and Hazuda, etal *Science* (2000) 287:646-650. The antiviral activity of a compound of the invention can be determined using pharmacological models which are well known in the art. While many of the compounds of the present invention demonstrate inhibition of integration of HIV reverse-transcribed DNA, there may be other mechanisms of action whereby HIV replication or proliferation is affected. The compounds of the invention may be active via inhibition of HIV-integrase or other enzymes associated with HIV infection, AIDS, or ARC. Furthermore, the compounds of the invention may have significant activity against other viral diseases. Thus, the specific assays embodied in Examples x-y are not meant to limit the present invention to a specific mechanism of action.

Pharmaceutical Formulations and Routes of Administration

The compounds of the invention may be formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferably to present them as pharmaceutical formulations. The formulations, both for veterinary and for human use, of the present invention comprise at least one active ingredient, as above defined, together with one or more pharmaceutically acceptable carriers therefor and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the present invention include Tween™ 60, Span™ 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents such as pentamidine for treatment of pneumocystis pneumonia.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

The present invention further provides veterinary compositions comprising at least one active ingredient as above defined together with a veterinary carrier therefor. Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods. Controlled release formulations may be employed for the treatment or prophylaxis of various microbial infections particularly human bacterial, human parasitic protozoan or human viral infections caused by microbial species including Plasmodium, Pneumocystis, herpes viruses (CMV, HSV 1, HSV 2, VZV, and the like), retroviruses, adenoviruses and the like. The controlled release formulations can be used to treat HIV infections and related conditions such as tuberculosis, malaria, pneumocystis pneumonia, CMV retinitis, AIDS, AIDS-related complex (ARC) and progressive generalized lymphadeopathy (PGL), and AIDS-related neurological conditions such as multiple sclerosis, and tropical spastic paraparesis. Other human retroviral infections that may be treated with the controlled release formulations according to the invention include Human T-cell Lymphotropic virus (HTLV)-I and IV and HIV-2 infections. The invention accordingly provides pharmaceutical formulations for use in the treatment or prophylaxis of the above-mentioned human or veterinary conditions and microbial infections.

Combination Therapy

The compounds of the invention may be employed in combination with other therapeutic agents for the treatment or prophylaxis of the infections or conditions indicated above. Examples of such further therapeutic agents include agents that are effective for the treatment or prophylaxis of viral, parasitic or bacterial infections or associated conditions or for treatment of tumors or related conditions include 3'-azido-3'-deoxythymidine (zidovudine, AZT), 2'-deoxy-3'-thiacytidine (3TC), 2',3'-dideoxy-2',3'-didehydroadenosine (D4A), 2',3'-dideoxy-2',3'-didehydrothymidine (D4T), carbovir (carbocyclic 2',3'-dideoxy-2',3'-didehydroguanosine), 3'-azido-2',3'-dideoxyuridine, 5-fluorothymidine, (E)-5-(2-bromovinyl)-2'-deoxyuridine (BVDU), 2-chlorodeoxyadenosine, 2-deoxycoformycin, 5-fluorouracil, 5-fluorouridine, 5-fluoro-2'-deoxyuridine, 5-trifluoromethyl-2'-deoxyuridine, 6-azauridine, 5-fluoroorotic acid, methotrexate, triacetyluridine, 1-(2'-deoxy-2'-fluoro-1-β-arabinosyl)-5-iodocytidine (FIAC), tetrahydro-imidazo(4,5,1-jk)-(1,4)-benzodiazepin-2(1H)-thione (TIBO), 2'-nor-cyclicGMP, 6-methoxypurine arabinoside (ara-M), 6-methoxypurine arabinoside 2'-O-valerate, cytosine arabinoside (ara-C), 2',3'-dideoxynucleosides such as 2',3'-dideoxycytidine (ddC), 2',3'-dideoxyadenosine (ddA) and 2',3'-dideoxyinosine (ddI), acyclic nucleosides such as acyclovir, penciclovir, famciclovir, ganciclovir, HPMPC, PMEA, PMEG, PMPA, PMPDAP, FPMPA, HPMPA, HPMPDAP, (2R, 5R)-9->tetrahydro-5-(phosphonomethoxy)-2-furanyladenine, (2R, 5R)-1->tetrahydro-5-(phosphonomethoxy)-2-furanylthymine, other antivirals including ribavirin (adenine arabinoside), 2-thio-6-azauridine, tubercidin, aurintricarboxylic acid, 3-deazaneoplanocin, neoplanocin, rimantidine, adamantine, and foscarnet (trisodium phosphonoformate), antibacterial agents including bactericidal fluoroquinolones (ciprofloxacin, pefloxacin and the like), aminoglycoside bactericidal antibiotics (streptomycin, gentamicin, arnicacin and the like) β-lactamase inhibitors (cephalosporins, penicillins and the like), other antibacterials including tetracycline, isoniazid, rifampin, cefoperazone, claithromycin and azithromycin, antiparasite or antifungal agents including pentamidine (1,5-bis(4'-aminophenoxy)pentane), 9-deazainosine, sulfamethoxazole, sulfadiazine, quinapyrarnine, quinine, fluconazole, ketoconazole, itraconazole, Amphotericin B, 5-fluorocytosine, clotrimazole, hexadecylphosphocholine and nystatin, renal excretion inhibitors such as probenicid, nucleoside transport inhibitors such as dipyridamole, dilazep and nitrobenzylthioinosine, immunomodulators such as FK506, cyclosporin A, thymosin α-1, cytokines including TNF and TGF-β, interferons including IFN-α, IFN-β, and IFN-γ, interleukins including various interleukins, macrophage/granulocyte colony stimulating factors including GM-CSF, G-CSF, M-CSF, cytokine antagonists including anti-TNF antibodies, anti-interleukin antibodies, soluble interleukin receptors, protein kinase C inhibitors and the like.

EXAMPLES

Example 1

N-4-fluorobenzyl-succinimide 1

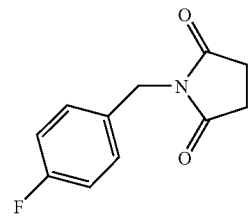

Freshly ground potassium carbonate, $K_2CO_3$ (31 g, 225 mmol) was added to dry acetone (200 ml) in a 3-necked flask equipped with drying tube, condenser, and mechanical stirrer. Succinimide (7.43 g, 75 mmol) and 4-fluorobenzylbromide (11.21 mL, 90 mmol) were added. The mixture was refluxed for 19 hours and filtered through Celite. Acetone was removed under vacuum, diluted with EtOAc, washed with saturated aqueous sodium bicarbonate and also with brine, dried ($MgSO_4$), filtered and concentrated to give crude. Crude product was chromatographed (EtOAc/Hexane) on silica gel to give N-4-fluorobenzyl-succinimide 1 as white solid (13.22 g, 85%). $^1$H NMR ($CDCl_3$) δ 7.4 (dd, 2H), 7.0 (t, 2H), 4.6 (s, 1H), 2.7 (s, 4 H).

Example 2

5,8-Dihydroxy-[6,7]-N-(4-fluorobenzyl)-succinimido-quinoline 2

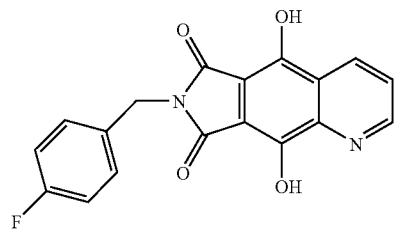

N-4-fluorobenzyl-succinimide 1 (8 g, 38.6 mmol) and 2,3-pyridine carboxylic acid dimethyl ester (7.9 g, 40.6 mmol) were dissolved in dry tetrahydrofuran (THF, 78 mL) and dry methanol (MeOH, 1.17 mL) in a 3-necked flask with mechanical stirrer and condenser. Sodium hydride (NaH, 60% in mineral oil, 3.4 g, 85 mmol) was added slowly in four portions. The mixture was stirred until bubbling ceased, then refluxed for 24 hours. HCl (30 mL 6 M) was then added to the mixture while in an ice bath, with stirring for 15 minutes. Diethylether (100 mL) was added. The precipitate was filtered, washed with diethylether and $H_2O$, and dried under vacuum at 100° C. Crude product was then recrystallized from 1 L refluxing dioxane and dried under vacuum at 100° C. to give solid 5,8-Dihydroxy-[6,7]-N-(4-fluorobenzyl)-succinimido-quinoline 2 (8.6 g, 66%). $^1$H NMR (CD$_3$SOCD$_3$) δ 9.05 (d, 1H), 8.75 (d, 1H), 7.79 (dd, 1H), 7.37 (dd, 2 H), 7.7 (t, 2H), 4.73 (s, 2 H). mp: 281.9-284.0.

Example 3

5-O-Propanoate, 8-hydroxy-[6,7]-N-(4-fluorobenzyl)-succinimido-quinoline 3

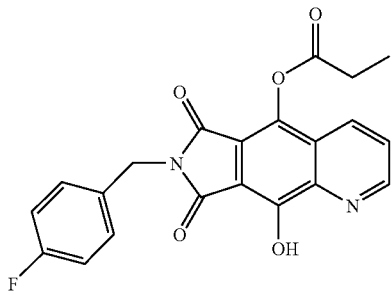

5,8-Dihydroxy-[6,7]-N-(4-fluorobenzyl)-succinimido-quinoline 2 is acylated with propanoyl chloride to give 5-O-propanoate, 8-hydroxy-[6,7]-N-(4-fluorobenzyl)-succinimido-quinoline 3.

Example 4

Carbonic acid ethyl ester 7-(4-fluoro-benzyl)-9-hydroxy-6,8-dioxo-7,8-dihydro-6H-pyrrolo[3,4-g]quinolin-5-yl ester 4

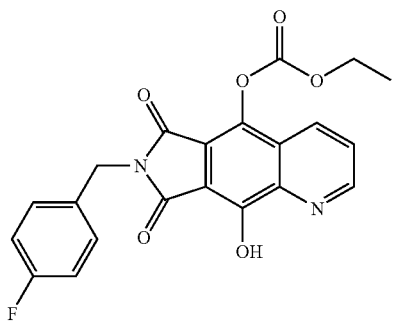

5,8-Dihydroxy-[6,7]-N-(4-fluorobenzyl)-succinimido-quinoline (300 mg, 0.887 mmol) 2 was suspended in 1,4 dioxane (5 mL) and water (20 mL). An aqueous solution of NaOH (0.567 M, 3.1 mL) was added slowly to form red solution which was then cooled in an ice-water bath. Ethyl chloroformate (0.093 mL, 0.975 mmol) was added and the mixture was stirred at room temperature for 30 minutes. Dichloromethane and 1N aqueous HCl were added to the mixture in a separate. The aqueous layer was extracted with dichloromethane two more times. The combined organic solution was washed with brine, dried (MgSO$_4$) and concentrated. The crude product was crystallized from EtOAc to give carbonic acid ethyl ester 7-(4-fluoro-benzyl)-9-hydroxy-6,8-dioxo-7,8-dihydro-6H-pyrrolo[3,4-g]quinolin-5-yl ester 4 (136 mg, 37%) as a yellow solid. $^1$H NMR (CDCl$_3$) δ 9.0 (d, 1H), 8.5 (d, 1H), 7.7 (dd, 1H), 7.5 (t, 2H), 7.4 (t, 2 H), 7.0 (t, 2 H), (s,2H), 4.5 (q, 2H), 1.5 (t, 3H); MS: 409 (M−1)

Example 5

Carbonic acid ethyl ester 7-(4-fluoro-benzyl)-9-methoxymethoxy-6,8-dioxo-7,8-dihydro-6H-pyrrolo[3,4-g]quinolin-5-yl ester 5

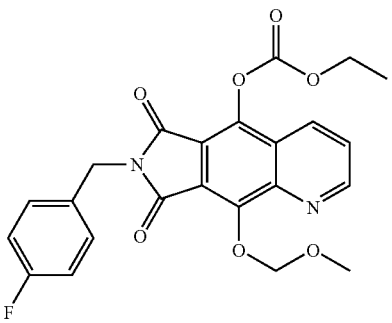

Carbonate (23.6 mg, 0.08 mmol) 4 was dissolved in acetonitrile (2 mL). Chloromethyl methyl ether (0.013 mL, 0.17 mmol) and Cs$_2$CO$_3$ (74 mg, 0.23 mmol) were added consecutively. The mixture was stirred at room temperature for 30 minutes when most of the starting material was consumed as indicated by TLC. Dichloromethane was added and the solution was washed with 1N HCl and brine, dried (MgSO$_4$) and concentrated. The crude product was chromatographed on silica gel column, eluting with EtOAc/hexanes to give the product, carbonic acid ethyl ester 7-(4-fluoro-benzyl)-9-methoxymethoxy-6,8-dioxo-7,8-dihydro-6H-pyrrolo[3,4-g]quinolin-5-yl ester 5 as a white solid (18 mg, 70%). $^1$H NMR (CDCl$_3$) δ 9.1 (dd, 1H), 8.5 (dd, 1H), 7.7 (dd, 1H), 7.4 (dd, 2H), 7.0 (t, 2H), 5.9 (s, 2H), 4.8 (s, 2H), 4.5 (q, 2H), 3.7 (s, 1H), 1.5 (t, 3H).

Example 6

7-(4-Fluoro-benzyl)-5-hydroxy-9-methoxymethoxy-pyrrolo[3,4-g]quinoline-6,8-dione 6

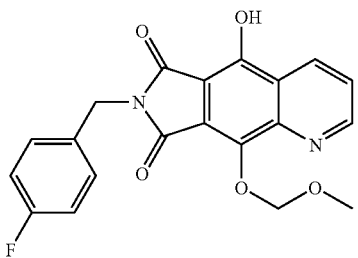

To the ethyl carbonate methoxymethyl ether 5 (70.9 mg, 0.156 mmol) in THF (7.6 mL) at room temperature was added a solution (5 mL) of K$_2$CO$_3$ (215 mg, 1.56 mmol) in water and 4-dimethylaminopyridine (3.8 mg, 0.03 mmol). The yellow solution was stirred at room temperature under nitrogen atmosphere overnight. Most of THF was removed under reduced pressure at 30-40° C. and the remaining solution was diluted with dichloromethane, washed with 1N HCl and brine, dried (MgSO$_4$) and concentrated to give solid crude product (51 mg, 85%), which is triturated in diethyl-ether/hexane to afford the product, 7-(4-fluoro-benzyl)-5-hydroxy-9-methoxymethoxy-pyrrolo [3,4-g]quinoline-6,8-dione 6 as a yellow solid (34 mg). $^1$H NMR (CDCl$_3$) δ 9.1 (dd, 1H), 8.7 (dd, 1H), 7.6 (dd, 1H), 7.4 (dd, 2H), 7.0 (t, 2H), 5.8 (s, 2H), 4.8 (s, 2H), 3.7 (s, 1H). MS: 383 (M+1); 381 (M-1).

Example 7

Trifluoro-methanesulfonic acid 7-(4-fluoro-benzyl)-9-methoxymethoxy-6,8-dioxo-7,8-dihydro-6H-pyrrolo[3,4-g]quinolin-5-yl ester 7

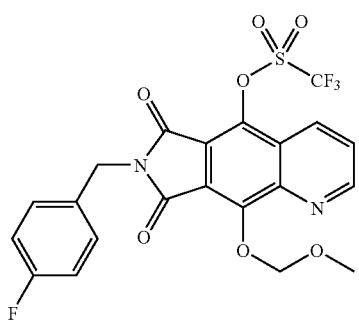

7

To the methoxymethyl ether 6 (13.7 mg, 0.036 mmol) in dichloromethane (1 mL) at −78° C. were added N,N-diisopropylethylamine (0.019 mL, 0.1 mmol) and trifluoromethanesulfonic anhydride (0.012 mL, 0.054 mmol) successively. The solution was stirred at the same temperature for 30 minutes and diluted with dichloromethane, washed with water and brine, dried (MgSO$_4$) and concentrated. The mixture was chromatographed on a silica gel column, eluting with EtOAc/hexanes to afford the product, trifluoro-methanesulfonic acid 7-(4-fluoro-benzyl)-9-methoxymethoxy-6,8-dioxo-7,8-dihydro-6H-pyrrolo[3,4-g]quinolin-5-yl ester 7 (6 mg, 33%). $^1$H NMR (CDCl$_3$) δ 9.1 (dd, 1H), 8.5 (dd, 1H), 7.8 (dd, 1H), 7.5 (dd, 2H), 7.0 (t, 2H), 5.9 (s, 2H), 4.9 (s, 2H), 3.7 (s, 1H). $^{19}$F NMR (CDCl$_3$) δ −72.8.

The reaction was repeated, where monophenol 6 (0.0444 g, 0.116 mmol) was dissolved in 2 mL dry dichloromethane. To this was added diisopropylethylamine (0.06 mL, 0.348 mmol.) After cooling to −78° C., triflic anhydride was added (0.029 mL, 0.342 mmol) and was stirred at this temperature for thirty minutes. Reaction was then complete by TLC, diluted with dichloromethane, washed with 1M HCl, saturated NaHCO$_3$ solution, dried (MgSO$_4$) and organics concentrated to give product, trifluoro-methanesulfonic acid 7-(4-fluoro-benzyl)-9-methoxymethoxy-6,8-dioxo-7,8-dihydro-6H-pyrrolo[3,4-g]quinolin-5-yl ester 7 (0.06 g, 0.116 mmol, 100%) which was used as crude for the next reaction. $^1$H NMR (CDCl$_3$) δ 9.15 (dd, 1H), 8.46 (d, 1H), 7.47 (dd, 1H), 7.01 (t, 2H), 5.92 (s, 2H), 4.87 (s, 2H.), 3.67 (s, 3H); MS: 537 (M+Na).

Example 8

7-(4-Fluoro-benzyl)-5-methoxy-9-methoxymethoxy-pyrrolo[3,4-g]quinoline-6,8-dione 8

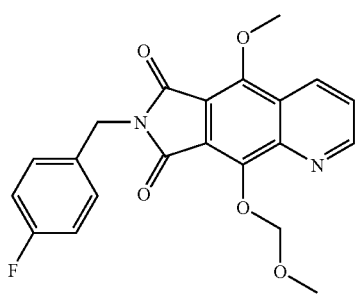

8

Methoxymethyl ether 6 (0.02 g, 0.052 mmol) was dissolved in 2 mL dry dichloromethane at 0° C. An excess of a diazomethane solution in diethylether was added. After about 20 minutes, all starting 6 was consumed. The mixture was concentrated in vacuo to give crude 7-(4-fluoro-benzyl)-5-methoxy-9-methoxymethoxy-pyrrolo[3,4-g]quinoline-6,8-dione 8 (0.0223 g, 0.0527 mmol). $^1$H NMR (CDCl$_3$) δ 9.1 (dd, 1H), 8.7 (dd, 1H), 7.6 (dd, 1H), 7.5 (t, 2H), 7.0 (t, 2H), 5.8 (s, 2H), 4.8 (s, 2H), 4.4 (s, 3H), 3.7 (s, (s, 3H), MS: 397 (M+1); 419 (M+23).

Example 9

7-(4-Fluoro-benzyl)-9-hydroxy-5-methoxy-pyrrolo[3,4-g]quinoline-6,8-dione 9

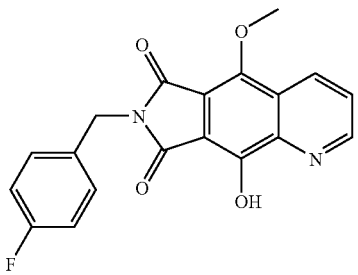

9

Crude diether 8 (0.0223 g, 0.0527 mmol) was dissolved in 1 mL dichloromethane. Ten equivalents of trifluoroacetic acid was added. The mixture was stirred at room temperature for 45 minutes. The reaction mixture was concentrated and azeotroped with toluene (2×) to give crude 7-(4-fluoro-benzyl)-9-hydroxy-5-methoxy-pyrrolo[3,4-g]quinoline-6,8-dione 9 which was triturated with 8 mL of 1:1 diethylether/hexane and filtered to give 9 (0.0161 g, 0.0456 mmol, 83% for two steps). $^1$H NMR (CDCl$_3$) δ 9.0 (br s, 1 H), 8.7 (d, 1 H), 7.7 (d, 1H), 7.5 (m, 2 H), 7.0 (t, 2 H), 4.8 (s, 2H), 4.4 (s, 3H). (M+1).

Example 10

5-Allyloxy-7-(4-fluoro-benzyl)-9-methoxymethoxy-pyrrolo[3,4-g]quinoline-6,8-dione 10

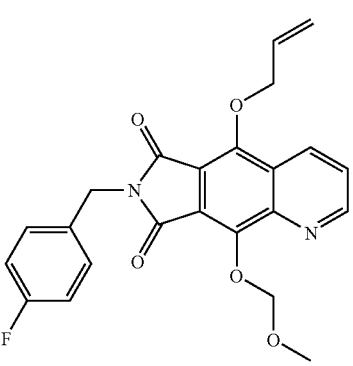

10

Methoxymethyl ether 6 (0.0172 g, 0.045 mmol) was dissolved in 1.5 mL dry dimethylformamide (DMF). Ground K$_2$CO$_3$ (0.0186 g, 0.135 mmol) was added, followed by allyl bromide (0.0077 mL, 0.09 mmol). The mixture was stirred at room temperature overnight, then diluted with 100 mL of ethylacetate, washed with saturated NH$_4$Cl solution, dried (MgSO$_4$), and concentrated to give crude 10. The crude product 10 was chromatographed on silica gel, eluting with ethylacetate and hexanes to give white solid allyl, methoxymethyl diether 10: (0.0063 g, 33%). $^1$H NMR (CDCl$_3$) δ 9.1 (dd, 1H), 8.8 (dd, 1H), 7.6 (dd, 1H), 7.5 (dd, 2H), 7.0 (t, 2H), 6.1 (m, 1H), 5.8 (s, 2H), 5.5 (d, 1H), 5.3 (d, 1H), 5.1 (d, 2H), 4.8 (s, 2H). MS: 423 (M+1); 445 (M+23).

Example 11

5-Allyloxy-7-(4-fluoro-benzyl)-9-hydroxy-pyrrolo[3,4-g]quinoline-6,8-dione 11

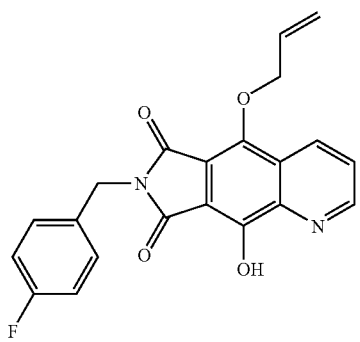

11

5-Allyloxy-7-(4-fluoro-benzyl)-9-methoxymethoxy-pyrrolo[3,4-g]quinoline-6,8-dione 10 was dissolved in 1 mL dichloromethane. Ten equivalents of trifluoroacetic acid was added and the mixture was stirred at room temperature. After one hour another 10 equivalents of trifluoroacetic acid was added. The mixture was then stirred overnight, concentrated in vacuo, and azeotroped with toluene (2×), to give crude 11 which was triturated with 2 mL of 1:1 diethylether/hexane two times to give allyl ether 11 (0.0025 g, 0.0066 mmol, 44%). $^1$H NMR (CDCl$_3$) δ 9.0 (s, 1H), 8.7 (d, 1H), 7.7 (m, 1H), 7.5 (m, 2H), 7.0 (t, 2H), 6.1 (m, 1H), 5.4 (d, 1H), 5.3 (d, 1H), 5.1 (d, 2H), 4.8 (s, 2H). MS: 379 (M+1).

Example 12

7-(4-Fluoro-benzyl)-5-hydroxy-9-triisopropylsilanyloxy-pyrrolo[3,4-g]quinoline-6,8-dione 12

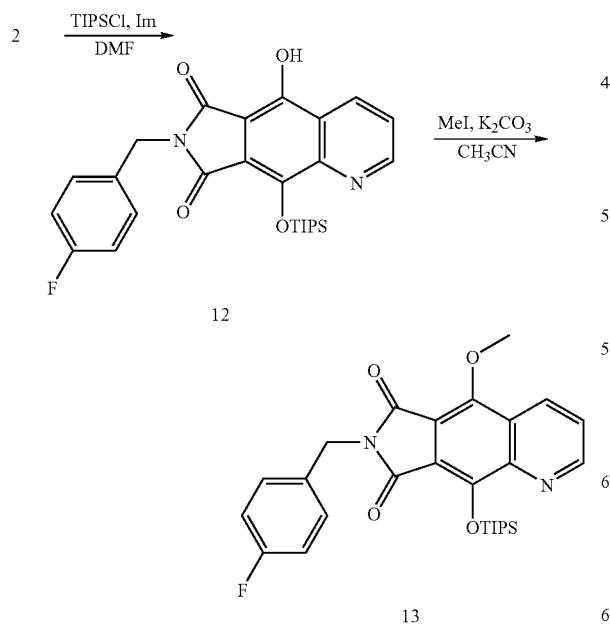

A solution of 7-(4-fluoro-benzyl)-5,9-dihydroxy-pyrrolo[3,4-g]quinoline-6,8-dione 2 (1.039 g, 3.07 mmol) in 31 mL of DMF was stirred with imidazole (314 mg, 4.62 mmol) and triisopropylsilylchloride (TIPSCl, 0.723 mL, 3.38 mmol) under a N$_2$ atmosphere for 1.5 days when most of the starting materials was converted to the regiospecific mono TIPS (triisopropylsilyl) protected compound. The solid bisphenol left in the reaction was filtered and recycled. The mother liquor was dried and the residue was suspended in EtOAc. The organic layer was washed with water and dried. The resulted solid 12 was carried to the next step. EI MS (m/z) 495.6 [MH$^+$], 517.4 [M+Na].

Example 13

7-(4-Fluoro-benzyl)-5-methoxy-9-triisopropylsilanyloxy-pyrrolo[3,4-g]quinoline-6,8-dione 13

A mixture of 12 from the monosilylation reaction was heated at 40° C. in anhydrous acetonitrile with K$_2$CO$_3$ (1.64 g, 11.8 mmol) and methyl iodide (4.2 g, 29.6 mmol) for 5 hours. The reaction mixture was worked up by addition of H$_2$O and EtOAc. The organic layer was washed with H$_2$O and the solvent was removed in vacuo. The residue was purified by column chromatography using a gradient of 10% EtOAc-Hex to elute the product 13 as a yellow solid (72% for two steps). $^1$H NMR (300 MHz, CDCl$_3$) δ 1.13 (d, 18H, J=8 Hz), 1.53 (septet, 3H, J=7 Hz), 4.29 (s, 3H), 4.84 (s, 2H), 7.00 (t, 2H, J=8 Hz), 7.48 (dd, 2H, J=5, 8 Hz), 7.58 (dd, 1H, J=4, 8 Hz), 8.65 (dd, 1H, J=2, 8 Hz), 8.93 (dd, 1H, J=2, 4 Hz); EI MS (m/z) 509.7 [MH$^+$], 531.4 [M+Na].

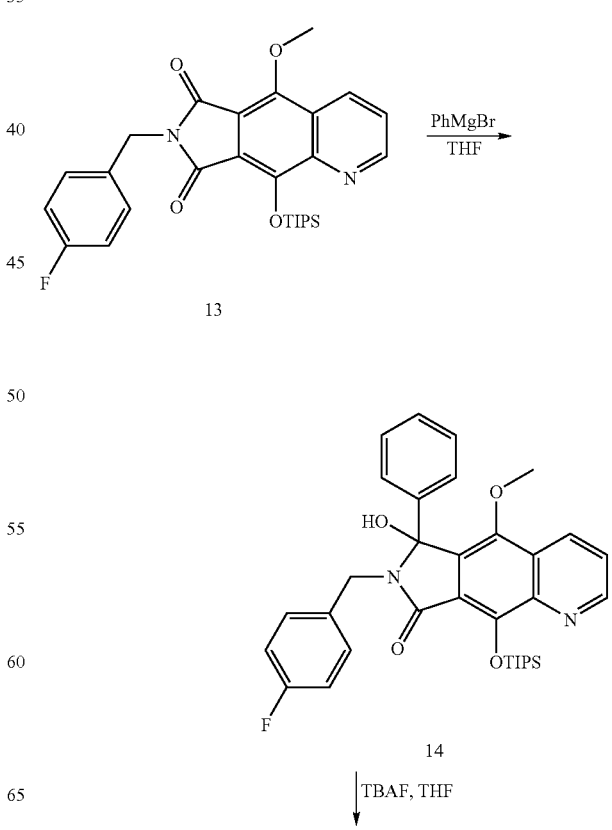

-continued

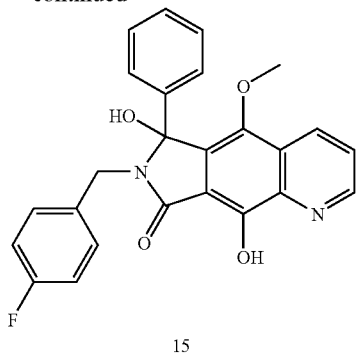

15

Example 14

7-(4-Fluoro-benzyl)-6-hydroxy-5-methoxy-6-phenyl-9-triisopropylsilanyloxy-6,7-dihydro-pyrrolo[3,4-g]quinolin-8-one 14

A mixture of 13 (36 mg, 0.071 mmol) in 0.35 mL of dry THF was cooled to 0° C. A 26 μL aliquot of a 3 M solution of phenyl magnesium bromide in ether (0.078 mmol) was added to the mixture and the reaction was allowed to warm up to room temperature. The reaction was worked up in 30 minutes when the reaction was complete as indicated by TLC. The mixture was diluted with EtOAc and washed with water. The product 14 was purified by column chromatography using 20% EtOAc-Hex solvent system to provide 33 mg (80%) of the product as a solid. $^1$H NMR (300 MHz, CDCl$_3$) δ 1.20 (s, 18H), 1.52-1.68 (m, 3H), 2.95 (s, 1H), 3.93 (s, 3H), 4.08 (d, 1H, J=15 Hz), 4.77 (d, 1H, J=15 Hz), 6.85 (t, 2H, J=9Hz), 7.19-7.25 (m, 2H), 7.25-7.35 (m, 3H), 7.39-7.49 (m, 3H), 8.26 (d, 1H, J=8 Hz), 8.84 (br d, 1H, J=4 Hz); $^{19}$F NMR (282.6 MHz, CDCl$_3$) δ −76.2, 60.7; EI MS (m/z) 587.5 [MH$^+$], 609.4 [M+Na].

Example 15

7-(4-Fluoro-benzyl)-6,9-dihydroxy-5-methoxy-6-phenyl-6,7-dihydro-pyrrolo[3,4-g]quinolin-8-one 15

A mixture of 14 (27 mg, 0.046 mmol) in THF (0.46 mL) and tetrabutyl ammonium fluoride (50 μL, 0.050 mmol) was stirred at room temperature under a N$_2$ atmosphere for 2 hours when reaction was complete as demonstrated by LCMS analysis. The organic solvent was removed in vacuo and the residue was suspended in EtOAc. The organic layer was washed with water and dried. The solid was washed with hexane and dried to provide 15 mg (76%) of the product 15 as a light orange solid. $^1$H NMR (300 MHz, CD$_3$OD) δ 3.54 (s, 3H), 4.36 (d, 1H, J=15 Hz), 4.48 (d, 1H, J=15 Hz), 6.84 (t, 2H, J=9 Hz), 7.17-7.23 (m, 2H), 7.24-7.26 (m, 3H), 7.35-7.46 (m, 2H), 7.62 (dd, 1H, J=4, 9 Hz), 8.44 (d, 1H, J=9 Hz), 8.89 (d, 1H, J=3 Hz); $^{19}$F NMR (282.6 MHz, CDCl$_3$) δ 58.5; EI MS (m/z) 431.2 [MH$^+$], 453.2 [M+Na].

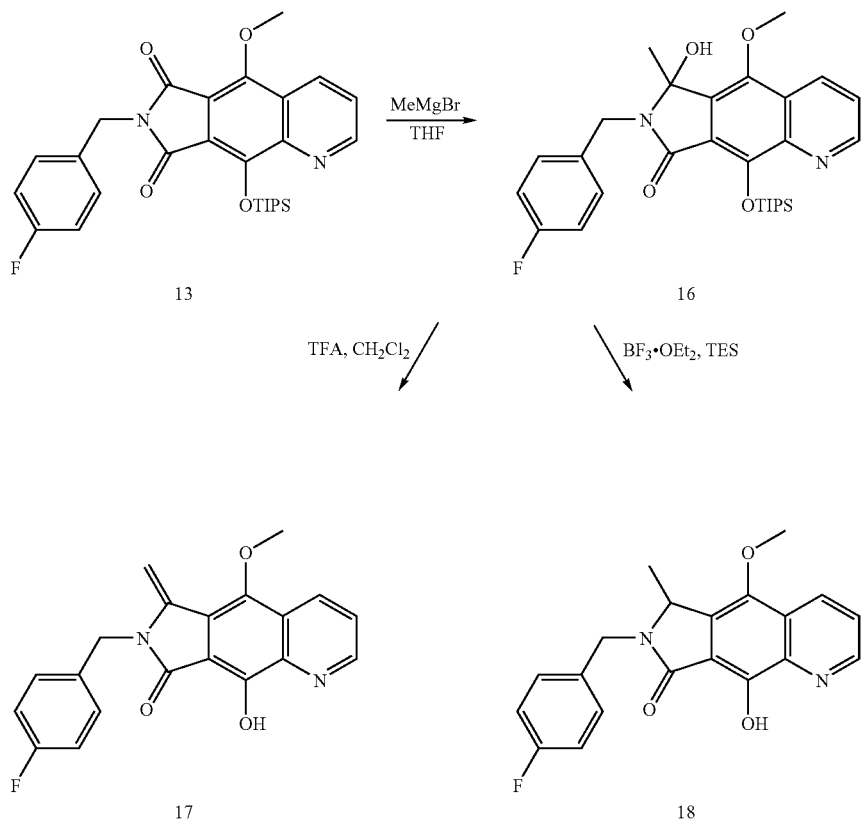

Example 16

7-(4-Fluoro-benzyl)-6-hydroxy-5-methoxy-6-methyl-9-triisopropylsilanyloxy-6,7-dihydro-pyrrolo[3,4-g]quinolin-8-one 16

Under a nitrogen atmosphere, a solution of 13 (90 mg, 0.18 mmol) was dissolved in 0.885 mL of dry THF. A solution of 3 M of methylmagnesium bromide in ether (71 µL, 0.213 mmol) was added. The solution was allowed to stir at ambient temperature for 2 hours when TLC indicated complete consumption of starting materials. The reaction mixture was diluted with EtOAc and washed with water and saturated aqueous NH$_4$Cl. The organic layer was reduced in vacuo to 1 mL and cooled to get the product 16 to crystallize from the solvent (92 mg, 99%). $^1$H NMR (300 MHz, CDCl$_3$) δ 1.16 (d, 18H, J=8 Hz), 1.55 (septet, 3H, J=8 Hz), 1.78 (s, 3H), 2.29 (s, 1H), 4.04 (s, 3H), 4.72 (ABqt, 2H, J=13 Hz), 6.99 (t, 2H, J=9 Hz), 7.38 (dd, 2H, J=6,9 Hz), 7.52 (dd, 1H, J=4, 9 Hz), 8.42 (dd, 1H, J=2, 8 Hz), 8.87 (dd, 1H, J=2, 4 Hz); $^{19}$F NMR (282.6 MHz, CDCl$_3$) δ 60.8.

Example 17

7-(4-Fluoro-benzyl)-9-hydroxy-5-methoxy-6-methylene-6,7-dihydro-pyrrolo[3,4-g]quinolin-8-one 17

A solution of 16 (10 mg, 0.019 mmol) in 3 mL of CH$_2$Cl$_2$ and TFA (30 µL, 0.389 mmol) was aged for 18 hours. Analysis of the reaction demonstrated complete conversion of starting materials to the product. The solvents were removed under reduced pressure. The residue was dissolved in EtOAc and precipitated with hexanes. The mother liquor was removed and the solid residue was washed with hexanes and subsequently with Et$_2$O to yield the product 17 as a solid. $^1$H NMR (300 MHz, CDCl$_3$) δ 3.97 (s, 3H), 4.99 (s, 2H), 5.04 (d, 1H, J=2 Hz), 5.63 (d, 1H, J=2 Hz), 6.90 (br s, 1H), 7.04 (t, 2H, J=8 Hz), 7.31 (dd, 2H, J=5, 8 Hz), 7.71 (dd, 1H, J=4, 8 Hz), 8.64 (dd, 1H, J=2, 9 Hz), 9.11 (d, 1H J=3Hz); $^{19}$F NMR (282.6 MHz, CDCl$_3$) δ 62.1; EI MS (m/z) 351.5 [MH$^+$], 383.3 [M+Na].

Example 18

7-(4-Fluoro-benzyl)-9-hydroxy-5-methoxy-6-methyl-6,7-dihydro-pyrrolo[3,4-g]quinolin-8-one 18

To a solution of 16 (52 mg, 0.099 mmol) in 1.4 mL of dry CH$_2$Cl$_2$ under a N$_2$ atmosphere, was added BF$_3$.OEt$_2$ (49 µL, 0.397 mmol) followed by triethylsilane (63 µL, 0.397 mmol). The solution was allowed to stir at ambient temperature for 1 day when LCMS indicated a clean conversion of starting materials to the desired product. The reaction was worked up by removing the solvent and dissolving the residue in EtOAc. The organic layer was washed with water and the solvent removed under reduced pressure. The residue was dissolved in 1 mL of EtOAc and triturated by addition of hexanes to provide the product 18. $^1$H NMR (300 MHz, CDCl$_3$) δ 1.60 (d, 3H, J=7 Hz), 3.93 (s, 3H), 4.28 (d, 1H), J=15 Hz), 4.65 (q, 1H, J=7 Hz), 5.25 (d, 1H, J=15 Hz), 7.06 (t, 2H, J=8 Hz), 7.32 (dd, 2H, J=6, 8 Hz), 7.67 (dd, 1H, J=4, 8 Hz), 8.59 (br s, 1H), 8.61 (d, 1H, J=8 Hz), 9.11 (br s, 1H); $^{13}$C NMR (75 MHz, CDCl$_3$) δ 16.9,42.8, 54.5, 61.9, 113.9, 115.7, 116.0, 122.7, 126.6, 129.8, 129.9, 130.8, 132.1, 133.1, 136.7, 142.4, 147.8, 148.3, 162.3 (d, J=245 Hz), 168.1; $^{19}$F NMR (282.6 MHz, CDCl$_3$) δ 62.5; EI MS (m/z) 353.5 [MH$^+$], 385.4 [M+Na].

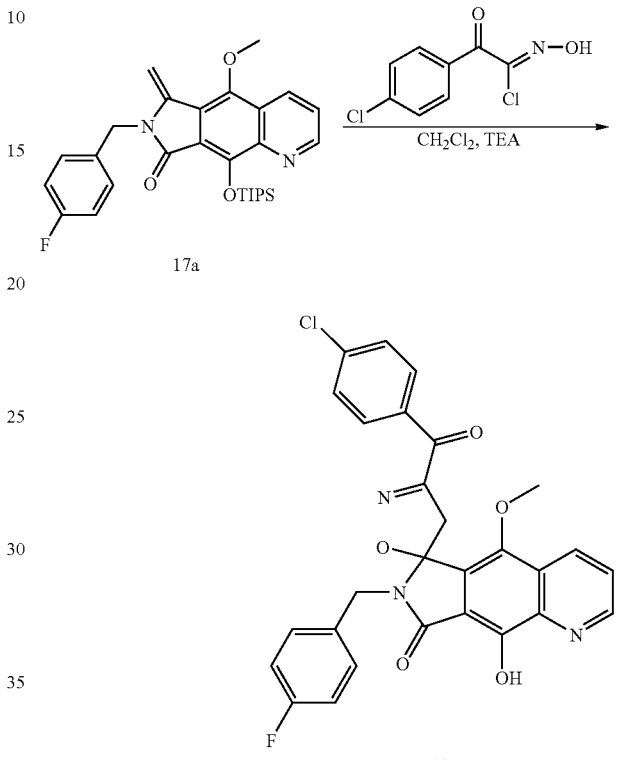

Example 19

Isoxazole 19

The exocyclic olefin in 17 can be utilized toward a cycloaddition reaction. Under a nitrogen atmosphere, a TIPS protected analog 17a (17 mg, 0.033 mmol) was suspended in 0.17 mL of dry CH$_2$Cl$_2$. To this solution was added 4-chlorophenylglyoxyl-O-hydroxamyl chloride (7.3 mg, 0.034 mmol) and TEA (4.7 µL, 0.034 mmol). The solution was stirred at room temperature for 12 hours. The reaction was worked up by diluting the solution with EtOAc and washing the organic layer with water. The organic layer was removed under reduced pressure. The residue was dissolved in EtOAc and diluted with hexanes. The solution was filtered and the mother liquor was dried to provide 18 mg (100%) of the product 19 as a white solid. $^1$H NMR (300 MHz, CDCl$_3$) δ 3.31 (d, 1H, J=19 Hz), 3.94 (s, 3H), 4.01 (d, 1H, J=19 Hz), 4.36 (d, 1H, J=16 Hz), 4.96 (d, 1H, J=15 Hz), 6.95 (t, 2H, J=9 Hz), 7.29 (dd, 2H, J=5, 9 Hz), 7.55 (d, 2H, J=9 Hz), 7.65 (dd, 1H, J=4, 8 Hz), 8.29 (d, 2H, J=9 Hz), 8.45 (dd, 1H, J=2, 9 Hz), 8.99 (dd, 1H, J=2, 4 Hz); $^{19}$F NMR (282.6 MHz, CDCl$_3$) δ 62.8; EI MS (m/z) 532.6 [MH$^+$].

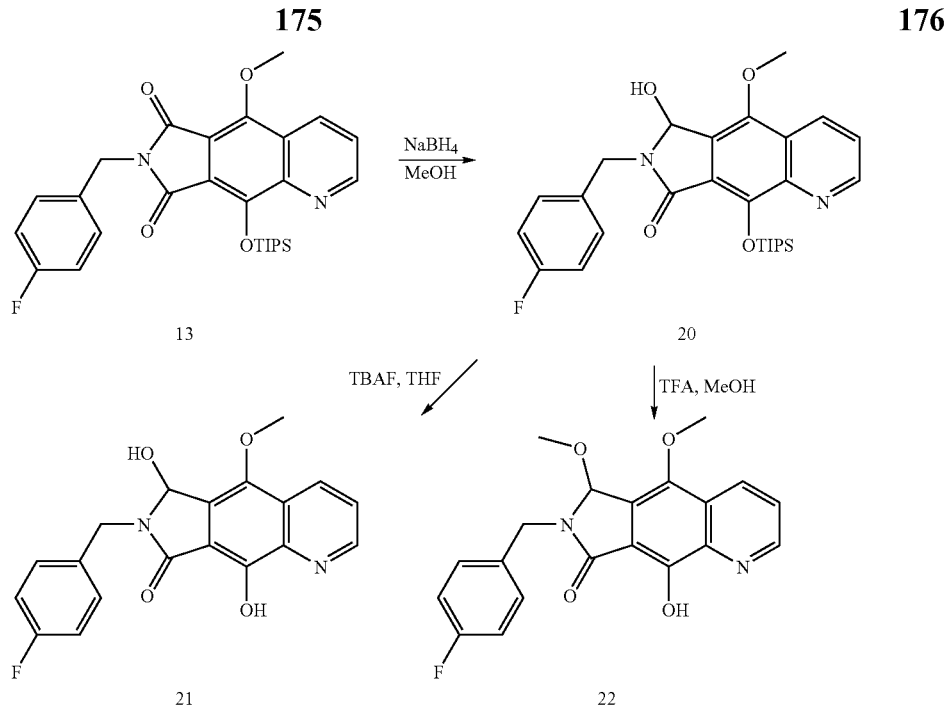

Example 20

7-(4-Fluoro-benzyl)-6,9-dihydroxy-5-methoxy-6,7-dihydro-pyrrolo[3,4-g]quinolin-8-one 20

To a solution of 13 (0.699 g, 1.38 mmol) in 14 mL of a 1:1 solution of dry MeOH: $CH_2Cl_2$ under a $N_2$ atmosphere was added sodium borohydride ($NaBH_4$, 156 mg, 4.13 mmol). The reaction mixture was dried after 5 hours and the residue was loaded onto a silica column. The product was eluted with a 10% EtOAc-Hex to provide the product 20. $^1$H NMR (300 MHz, $CDCl_3$) δ 1.10 (d, 9H, J=8 Hz), 1.16 (d, 9H, J=7 Hz), 1.52 (septet, 3H, J=8 Hz), 3.72 (d, 1H, J=11 Hz), 4.11 (s, 3H), 4.23 (d, 1H, J=15 Hz), 4.85 (d, 1H, J=15 Hz), 5.79 (d, 11H, J=11 Hz), 6.97 (t, 2H, J=9 Hz), 7.27 (dd, 2H, J=6, 9 Hz), 7.43 (dd, 1H, J=4, 8 Hz), 8.43 (dd, 1H, J=2, 8 Hz), 8.81 (dd, 1H, J=2,4 Hz); $^{13}$C NMR (75 MHz, $CDCl_3$) δ 14.8. 18.2,41.3, 61.6, 78.6, 115.3, 115.6, 116.6, 122.3, 126.0, 126.8, 130.1, 130.2, 131.1, 132.8, 143.1, 143.8, 148.3, 162.1 (d, J=244 Hz), 165.2; EI MS (m/z) 511.5 [MH$^+$], 533.4 [M+Na].

Example 21

7-(4-Fluoro-benzyl)-6,9-dihydroxy-5-methoxy-6,7-dihydro-pyrrolo[3,4-g]quinolin-8-one 21

A solution of 20 (35 mg, 0.069 mmol) was stirred in 0.69 mL of dry THF and 75 μL of a 1 M solution of tetra-butylammonium fluoride (TBAF, 0.075 mmol) under a $N_2$ atmosphere for 2 hours at ambient temperature. The solution was diluted with EtOAc and the organic layer was washed with water. The organic layer was removed in vacuo to leave a yellow residue. The solid was washed with hexanes and dried to give 27 mg (100%) of the product 21. $^1$H NMR (300 MHz, $CD_3OD$) δ 4.13 (s, 3H), 4.46 (d, 1H, J=15 Hz), 5.04 (d, 1H, J=15 Hz), 6.01 (s, 1H), 7.09 (t, 2H, J=9 Hz), 7.42-7.47 (m, 2H), 7.65 (dd, 1H, J=4, 9 Hz), 8.61 (d, 1H, J=8 Hz), 8.89 (d, 1H, J=3 Hz); $^{13}$C NMR (75 MHz, $CD_3OD$) δ41.1, 79.3, 60.0, 111.6, 115.0, 115.4, 122.4, 125.1, 125.9, 129.6, 130.0, 131.5, 132.9, 139.5, 142.8, 148.8, 161.8 (d, J=245 Hz), 166.7; $^{19}$F NMR (282.6 MHz, $CDCl_3$) δ 59.4; EI MS (m/z) 355.4 [MH$^+$].

Example 22

7-(4-Fluoro-benzyl)-9-hydroxy-5,6-dimethoxy-6,7-dihydro-pyrrolo[3,4-g]quinolin-8-one 22

A solution of 21 (6.7 mg, 0.019 mmol) in a 1:1 solution of $CH_2Cl_2$:MeOH was stirred with TFA (3 μL, 0.038 mmol) at room temperature for 2 hours when complete conversion was observed by LCMS. The solution was dried in vacuo and the residue was washed with hexanes to yield 7 mg of the product 22. EI MS (m/z) 355.4 [MH$^+$].

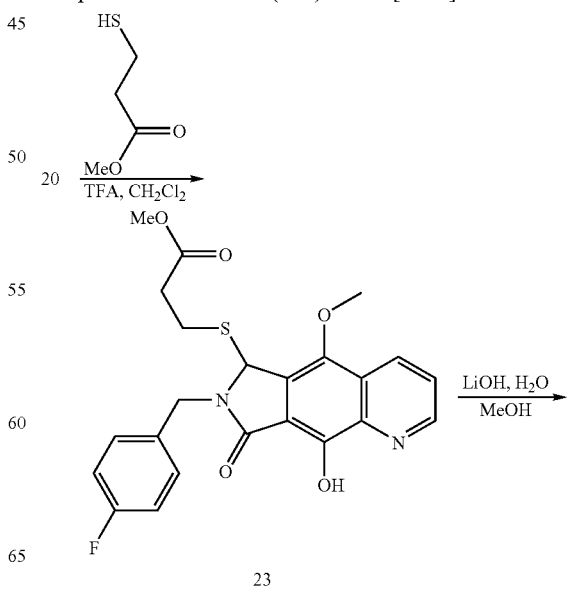

-continued

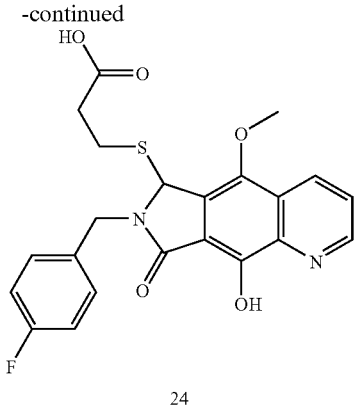

24

Example 23

3-[7-(4-Fluoro-benzyl)-9-hydroxy-5-methoxy-8-oxo-7,8-dihydro-6H-pyrrolo[3,4-g]quinolin-6-ylsulfanyl]-propionic acid methyl ester 23

To a solution of 20 (215 mg, 0.422 mmol) in $CH_2Cl_2$ (4.2 mL) and TFA (98 μL, 1.26 mmol) was added methyl-3-mercaptopropionate (56 μL, 0.506 mmol). The solution was stirred at ambient temperature for 5 hours when LCMS analysis indicated complete conversion of the starting materials to the products. The solution was dried under reduced pressure and azeotroped with $CH_2Cl_2$ three times to provide the product 23 as a yellow solid. $^1$H NMR (300 MHz, $CDCl_3$) δ 2.30-2.38 (m, 4H), 3.63 (s, 3H), 4.04 (s, 3H), 4.42 (d, 1H, J=15 Hz), 5.33 (d, 1H, J=15 Hz), 5.49 (s, 1H), 7.05 (t, 2H, J=9 Hz), 7.38 (dd, 2H, J=5, 8 Hz), 7.59 (dd, 1H, J=4,9 Hz), 8.53 (d, 1H, J=8 Hz), 8.91-9.01 (m, 1H); $^{19}$F NMR (282.6 MHz, $CDCl_3$) δ 62.6; EI MS (m/z) 457.3 [MH$^+$], 479.2 [M+Na].

Example 24

3-[7-(4-Fluoro-benzyl)-9-hydroxy-5-methoxy-8-oxo-7,8-dihydro-6H-pyrrolo[3,4-g]quinolin-6-ylsulfanyl]-propionic acid 24

A solution of 23 (150 mg, 0.329 mmol) in 3.29 mL of a 1:2:3 solution of $H_2O$:MeOH:THF was stirred with LiOH.$H_2O$ (69 mg, 1.65 mmol) for 1 hour when LCMS demonstrated complete conversion of starting materials to product. The reaction mixture was dried under reduced pressure and the residue was suspended in water and the pH was adjusted to 11 with aqueous 1N NaOH solution. The aqueous layer was washed with EtOAc twice. The pH of the aqueous layer was then adjusted to 5 using 1N HCl and the product was extracted with $CH_2Cl_2$ under continuous extraction conditions. The organic layer was dried in vacuo to yield the product 24 as an orange solid. $^1$H NMR (300 MHz, $CDCl_3$) δ 2.1 (s, 1H), 2.25-2.45 (m, 4H), 4.04 (s, 3H), 4.43 (d, 1H, J=15 Hz), 5.32 (dd, 1H, J=3, 14 Hz), 5.49 (s, 1H), 7.03 (t, 2H, J=9 Hz), 7.35 (dd, 2H, J=5, 8 Hz), 7.57 (dd, 1H, J=4, 8 Hz), 8.52 (dd, 1H, J=2, 8 Hz), 8.98 (dd, 1H, J=2, 5 H); $^{13}$C NMR (75 MHz, $CD_3OD$) δ 21.4, 33.6, 41.9, 61.8, 61.9, 112.3, 115.7, 116.0, 123.1, 125.0, 126.5, 130.4, 130.5, 131.8, 131.8, 139.3, 142.6, 148.3, 149.6, 162.4 (d, J=245 Hz), 167.2, 175.3; $^{19}$F NMR (282.6 MHz, $CDCl_3$) δ 62.6; EI MS (m/z) 441.4 [M−H]$^-$, 883.1 [2M−2H]$^-$.

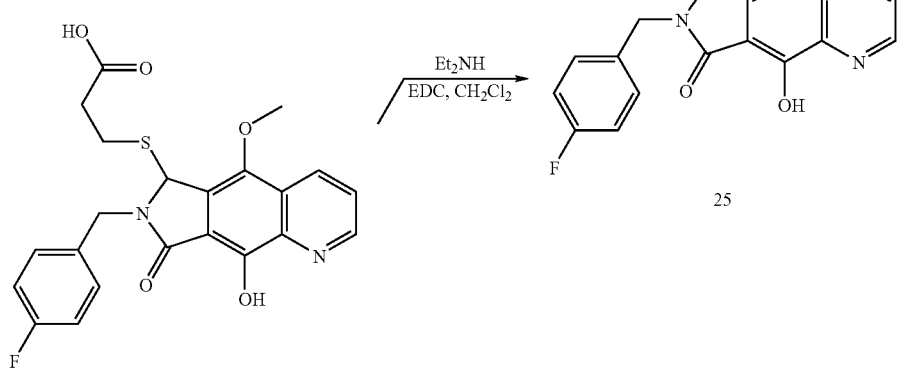

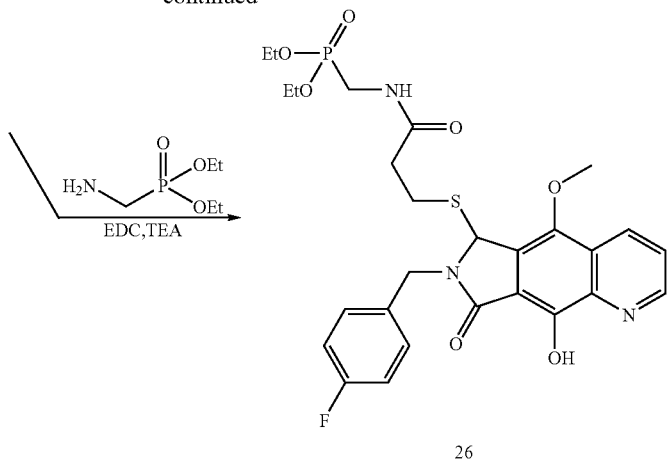

Example 25

N,N-Diethyl-3-[7-(4-fluoro-benzyl)-9-hydroxy-5-methoxy-8-oxo-7,8-dihydro-6H-pyrrolo[3,4-g]quinolin-6-ylsulfanyl]-propionamide 25

A solution of 24 (10.7 mg, 0.024 mmol) in $CH_2Cl_2$ (0.24 mL) was stirred with EDC (14 mg, 0.73 mmol) and diethyl amine (10 μL, 0.097 mmol) for 1 day at ambient temperature. The product 25 was purified by reverse phase HPLC using 5-95% A. Buffer A contained $CH_3CN$—1% HOAc and B contained $H_2O$—1% HOAc. $^1H$ NMR (300 MHz, $CDCl_3$) δ 0.984 (t, 3H, J=6 Hz), 1.05 (t, 3H, J=7 Hz), 2.23-2.45 (m, 4H) 3.04 (q, 2H, J=7 Hz), 3.29 (q, 2H, J=8 Hz), 4.06 (s, 3H), 4.47 (d, 1H, J=14 Hz), 5.31 (d, 1H, J=15 Hz), 5.50 (s, 1H), 7.05 (t, 2H, J=9 Hz), 7.36-7.44 (m, 2H), 7.55-7.62 (m, 1H), J=9 Hz), 8.95-9.00 (m, 1H); EI MS (m/z) 520.2 [$MH^+$], 1016.9 [2M+Na].

Example 26

({3-[7-(4-Fluoro-benzyl)-9-hydroxy-5-methoxy-8-oxo-7,8-dihydro-6H-pyrrolo[3,4-g]quinolin-6-ylsulfanyl]-propionylamino}-methyl)-phosphonic acid diethyl ester 26

To a solution of 24 (15 mg, 0.035 mmol) in 0.35 mL of $CH_2Cl_2$ (0.35 mL) was added diethyl(aminomethyl)phosphonate oxalate (27 mg, 0.105 mmol), EDC (20 mg, 0.105 mmol) and TEA (15 μL, 0.105 mmol). The solution was stirred at room temperature for 1 day when the same amount of the aminomethyl phosphonate, EDC and TEA were added. The reaction was stirred for another day when complete conversion of starting materials to the desired product was observed by LCMS. The product 26 was purified by reverse phase HPLC using 5-95% A. Buffer A contained $CH_3CN$-1% HOAc and buffer B was $H_2O$-1% HOAc. $^1H$ NMR (300 MHz, $CDCl_3$) δ 1.33-1.40 (m, 6H), 2.37-2.45 (m, 4H), 3.60-3.72 (m, 2H), 4.05 (s, 3H), 4.06-4.18 (m, 4H), 4.44 (d, 1H, J=15 Hz), 5.33 (d, 1H, J=14 Hz), 5.49 (s, 1H), 6.17 (br s, 1H), 6.98-7.08 (m, 2H), 7.33-7.43 (m, 2H), 7.55-7.63 (m, 1H), 8.50-8.57 (br d, 1H), 8.97 (br s, 1H); $^{31}P$ (121.4 MHz, $CDCl_3$) δ 22.7; $^{19}F$ NMR (282.6 MHz, $CDCl_3$) δ 62.6; EI MS (m/z) 590.4 [$M-H$]$^-$, 614.2 [M+Na].

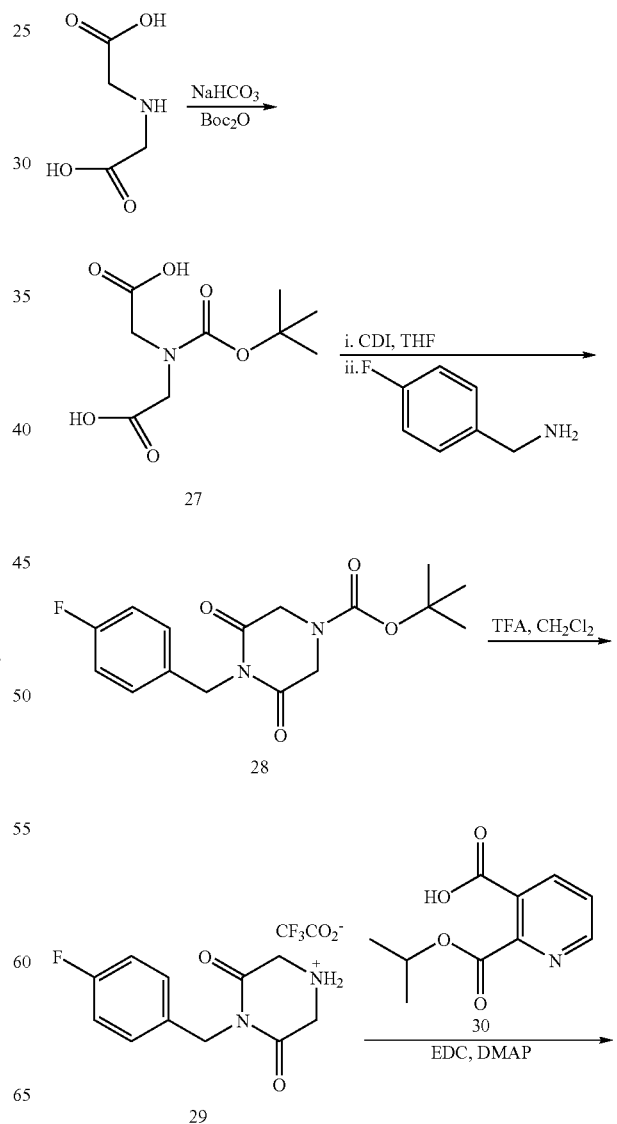

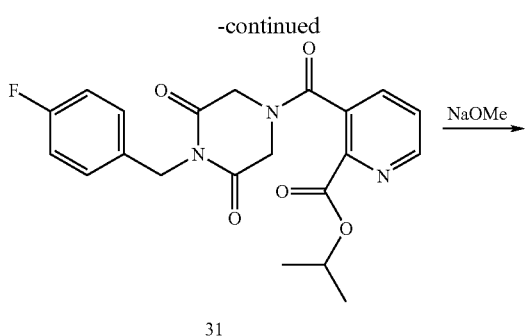

Example 27

(tert-Butoxycarbonyl-carboxymethyl-amino)-acetic acid 27

A mixture of iminodiacetic acid (5.1 g, 38.3 mmol) and sodium hydrogen carbonate (NaHCO$_3$, 12.9 g, 153 mmol) were dissolved in 50 mL of water. Once the bubbling subsided, 50 mL of THF was added followed by 10.0 g (46.0 mmol) of BOC$_2$O. The mixture was stirred at ambient temperature for 2 days when starting materials were completely consumed as detected by ESI. The reaction was worked up by removing THF and washing the aqueous layer with Et$_2$O twice. The pH of the aqueous layer was then adjusted to 1 using conc. HCl. The product was extracted with EtOAc and solvent removed in vacuo to provide the product as a white solid. The product was purified by crystallization from EtOAc to give 8.04 g (90%) of clear crystals of 27. ES MS [M–H]$^-$232.1.

Example 28

4-(4-Fluoro-benzyl)-3,5-dioxo-piperazine-1-carboxylic acid tert-butyl ester 28

A solution of 27 (547 mg, 2.35 mmol) and carbonyl diimidazole (837 mg, 5.16 mmol) in 4.7 mL of dry THF under a N$_2$ atmosphere was refluxed for 5 minutes. Once the reaction cooled down to room temperature 4-fluorobenzyl amine (0.295 mL, 2.58 mmol) was added and the mixture was heated to reflux overnight. The reaction mixture was then concentrated and re-dissolved in EtOAc. The organic layer was washed with an aqueous 0.5 N HCl solution and the solvent was removed in vacuo. The product was purified by column chromatography eluting with CH$_2$Cl$_2$ to provide clean product 28 as a clear oil. $^1$H NMR (300 MHz, CDCl$_3$) δ 1.47 (s, 9H), 4.39 (s, 4H), 4.92 (s, 2H), 6.99 (t, 2H, J=9 Hz), 7.40 (dd, 2H, J=5, 9 Hz); $^{13}$C NMR (75 MHz, CDCl$_3$) δ 28.1, 42.0, 47.1, 82.3, 115.2, 115.5, 131.1, 131.2, 132.0, 153.0, 162.7 (d, J=245 Hz), 168.0; $^{19}$F NMR (282.6 MHz, CDCl$_3$) δ 62.5; EI MS (m/z) 340.5 [M+Na].

Example 29

4-(4-Fluoro-benzyl)-3,5-dioxo-piperazin-1-ium; trifluoro-acetate 29

A solution of 28 (26 mg, 0.080 mmol) in 2 mL of CH$_2$Cl$_2$ was stirred with 1 mL of TFA for 1.5 hours when TLC indicated complete conversion to the product. The solution was dried in vacuo to yield a white solid. The product was purified by crystallization using CH$_2$Cl$_2$. $^1$H NMR (300 MHz, CD$_3$OD) δ 4.18 (s, 4H), 4.95 (s, 2H), 5.01 (s, 2H), 7.01 (dt, 2H, J=2, 9 Hz), 7.41 (ddd, 2H, J=2, 5, 9 Hz); $^{19}$F NMR (282.6 MHz, CDCl$_3$) δ –60.0.

Example 30

Pyridine-2,3-dicarboxylic acid 2-isopropyl ester 30

A mixture of 2,3-pyridine carboxylic anhydride (100 g, 0.67 mol) in 500 mL of i-PrOH was heated at reflux for 1 day according to the procedure of Ornstein, P. et. al. *J. Med. Chem.* (1989) 32, 4, 827. The reaction mixture was then dried in vacuo to provide the product 30 as a white solid. $^1$H NMR (300 MHz, CD$_3$OD) δ 1.37 (d, 6H, J=7 Hz), 5.27 (septet, 1H, J=6 Hz), 7.63 (dd, 1H, J=5, 8 Hz), 8.34 (dd, 1H, J=1, 8 Hz), 8.71 (d, 1H, J=5 Hz); EI MS (m/z) 210.0 [MH$^+$].

Example 31

3-[4-(4-Fluoro-benzyl)-3,5-dioxo-piperazine-1-carbonyl]-pyridine-2-carboxylic acid isopropyl ester 31

A solution of 29 (54 mg, 0.16 mmol), 30 (34 mg, 0.16 mmol), EDC (92 mg, 0.48 mmol), dimethylaminopyridine (20 mg, 0.16 mmol), triethylamine (67 μL, 0.48 mmol) in 1.6 mL of a 1:1 mixture of CH$_2$Cl$_2$:DMF was stirred for 1 day at ambient temperature. The reaction mixture was directly loaded onto a silica column and the product was eluted with a gradient of 1:1 Hex-EtOAc to EtOAc followed by 10% MeOH-EtOAc. The product 31 was obtained as a clear oil. EI MS (m/z) 414.7 [MH$^+$], 436.4 [M+Na].

Example 32

7-(4-Fluoro-benzyl)-9-hydroxy-1,7,10a-triaza-anthracene-6,8,10-trione 32

A solution of 31 (5 mg, 0.01 mmol) in 0.3 mL of dry 0.5 M NaOMe was stirred at ambient temperature for 15 minutes when a yellow precipitate formed. The solvent was removed in vacuo and the solid was dissolved in a mixture of CH$_2$Cl$_2$— 1N HCl. The layers were separated and the aqueous layer was washed with CH$_2$Cl$_2$. The organic solvent was removed to provide an off-white solid. The product 32 was purified by trituration using CH$_2$Cl$_2$ and hexane. $^1$H NMR (300 MHz, CDCl$_3$) δ 5.01 (s, 2H), 5.16 (s, 2H), 7.02 (dt, 2H, J=2, 9 Hz), 7.51 (ddd, 2H, J=2, 5, 9 Hz), 7.79 (dd, 1H, J=8, 5 Hz), 8.61 (dd, 1H, J=8, 2 Hz), 9.13 (dd, 1H, J=4, 2 Hz), 12.35 (s, 1H); $^{13}$C NMR (75 MHz, CDCl$_3$) δ 42.4, 46.1 107.0, 115.5, 115.8, 126.7, 127.1, 130.8, 131.4, 131.5, 132.5, 143.2, 148.4, 153.7, 156.0, 162.2 (d, J=249 Hz), 163.9, 164.0; EI MS (m/z) 354.6 [MH$^+$].

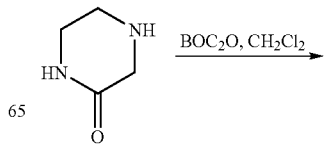

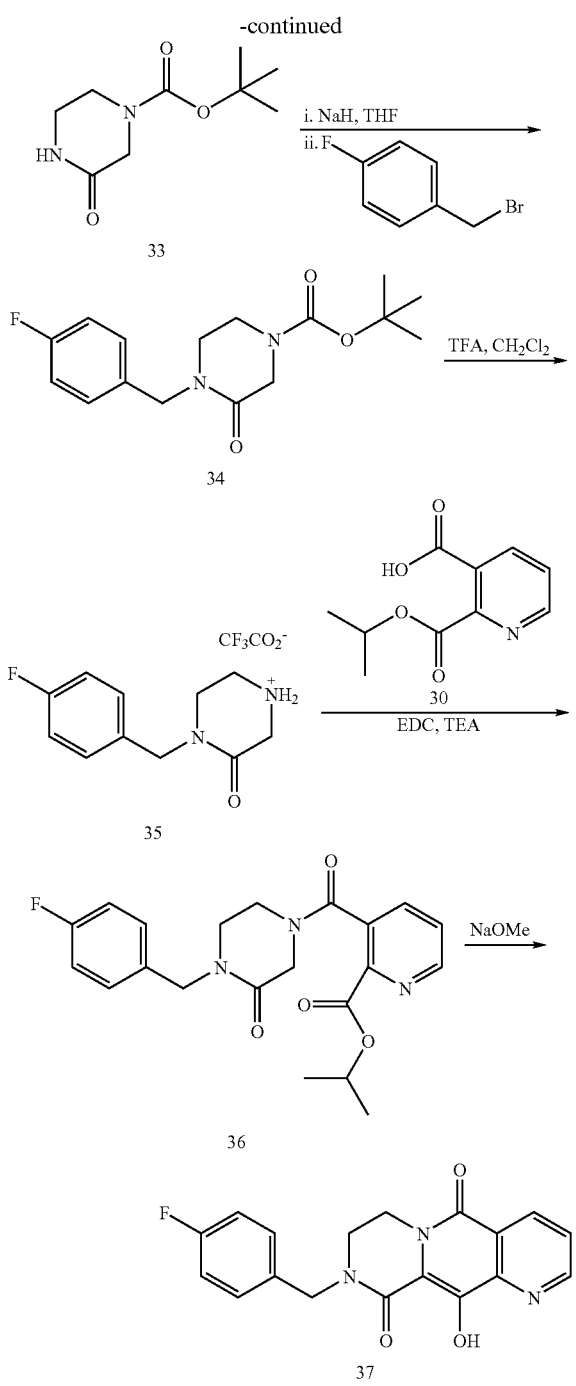

Example 33

3-Oxo-piperazine-1-carboxylic acid tert-butyl ester 33

To a mixture of piperazine-2-one (1.037 g, 10.4 mmol) in 52 mL of CH$_2$Cl$_2$, was added BOC$_2$O (2.5 g, 11.4 mmol). The reaction became homogeneous after 3 hours when the starting material was completely consumed. The reaction was diluted with CH$_2$Cl$_2$ and the organic layer was washed with water. The solvent was removed in vacuo to yield quantitative amount of product 33 as a white solid. $^1$H NMR (300 MHz, CDCl$_3$) δ 1.48 (s, 9H), 3.35-3.44 (m, 2H), 3.64 (t, 2H, J=5 Hz), 4.10 (s, 2H), 6.41 (br s, 1H).

Example 34

4-(4-Fluoro-benzyl)-3-oxo-piperazine-1-carboxylic acid tert-butyl ester 34

To a heterogeneous solution of 33 (1.6 g, 8.1 mmol) in 16.2 mL of dry THF under a N$_2$ atmosphere was added 0.211 g (8.80 mmol) of 95% NaH. Once the bubbling subsided, 4-fluorobenzylbromide (1.2 mL, 9.7 mmol) was added dropwise to the solution. After 1 hour, when the reaction was complete as judged by TLC, the reaction was quenched by addition of water and the organic layer was diluted with EtOAc. The organic layer was washed with water and the solvent removed in vacuo. The product was purified by column chromatography using 1:1 EtOAc-Hex solvent system to provide 2.3 g (93%) of the product 34 as a white solid. $^1$H NMR (300 MHz, CDCl$_3$) δ 1.47 (s, 9H), 3.24 (t, 2H, J=5 Hz), 3.60 (t, 2H, J=5 Hz), 4.16 (s, 2H), 4.59 (s, 2H), 7.03 (t, 2H, J=9 Hz), 7.26 (dd, 2H, J=5.8 Hz); $^{19}$F NMR (282.6 MHz, CDCl$_3$) δ 62.2.

Example 35

4-(4-Fluoro-benzyl)-3-oxo-piperazin-1-ium trifluoroacetate salt 35

A solution of 34 (1.4 g, 4.5 mmol) in 6 mL of a 1:1 solution of CH$_2$Cl$_2$:TFA was stirred at ambient temperature for 2 hours when all of the starting materials were consumed as judged by TLC. The reaction mixtures were dried in vacuo to yield 1.5 g of 35 as a thick oil which was used in the next reaction without purification.

Example 36

3-[4-(4-Fluoro-benzyl)-3-oxo-piperazine-1-carbonyl]-pyridine-2-carboxylic acid isopropyl ester 36

A solution of 35 (1.46 g, 4.55 mmol) was dissolved in 20 mL of a 1:1 solution of CH$_2$Cl$_2$:DMF. To this solution was added 0.95 g (4.55 mmol) of 30, EDC (1.74 g, 9.10 mmol) and triethylamine (1.90 mL, 13.7 mmol). The solution was stirred at room temperature for 4 hours when the reaction was complete. The solution was diluted with CH$_2$Cl$_2$ and washed with water. The organic layer was subsequently washed with aq. saturated solution of NH$_4$Cl and the solvent was removed. The yellow residue was purified by column chromatography using EtOAc-10% MeOH gradient to yield 1.8 g (100%) of the product 36 as a clear oil. EI MS (m/z) 400.5 [MH$^+$], 422.3 [M+Na].

Example 37

7-(4-Fluoro-benzyl)-9-hydroxy-6,7-dihydro-5H-1,7,10a-triaza-anthracene-8,10-dione 37

To a solution of 36 (0.900 g, 2.26 mmol) in 12 mL of dry MeOH under a N$_2$ atmosphere was added 12.5 mL of a 0.5 M sodium methoxide (NaOMe). The solution was stirred at ambient temperature for 2.5 hours. The reaction was worked up by removing the solvent and dissolving the residue in CH$_2$Cl$_2$. The organic layer was washed with a saturated aqueous solution of NH$_4$Cl and dried to provide 610 mg of the product 37 as a yellow solid. $^1$H NMR (300 MHz, CDCl$_3$) δ 3.58 (t, 2H, J=6 Hz), 4.308 (t, 2H, J=5 Hz), 4.77 (s, 2H), 7.09 (t, 2H, J=8 Hz), 7.34 (t, 2H, J=8 Hz), 7.61 (dd, 1H, J=5.8 Hz), 8.73 (d, 1H, J=8 Hz), 9.12 (d, 1H, J=3 Hz), 13.00 (s, 1H); $^{13}$C NMR (75 M, CDCl$_3$) δ 38.8, 43.9, 49.5, 111.9, 115.9, 116.2, 124.7, 130.0, 130.1, 131.0, 136.4, 146.8, 147.2, 154.7, 157.3, 163.0 (d, J=245 Hz), 163.7; $^{19}$F NMR (282.6 MHz, CDCl$_3$) δ 63.2; EI MS (m/z) 340.5 [MH$^+$], 362.3 [M+Na].

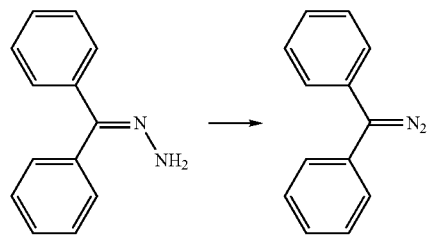

Example 38

Diphenyldiazomethane 38

Benzophenone hydrazone (25 g, 122.3 mmol) and sodium sulfate (anhydrous) (26 g, 183.5 mmol) were suspended in ether (anhydrous, 400 mL). To this mixture, a potassium hydroxy (powder) saturated ethanol solution (10 mL) was added, followed by mercury oxide (66.2 g, 305.8 mmol) to form a red solution. This solution was shaken at room temperature for 1.5 hours. The solid was filtered off. The filtrate was concentrated to a residue, which was redissolved in 200 mL of hexane and placed in a cold room overnight. The solidified solution was evaporated to dryness, which gave diphenyldiazomethane 38 as a red solid (24.7 g, 99.7%).

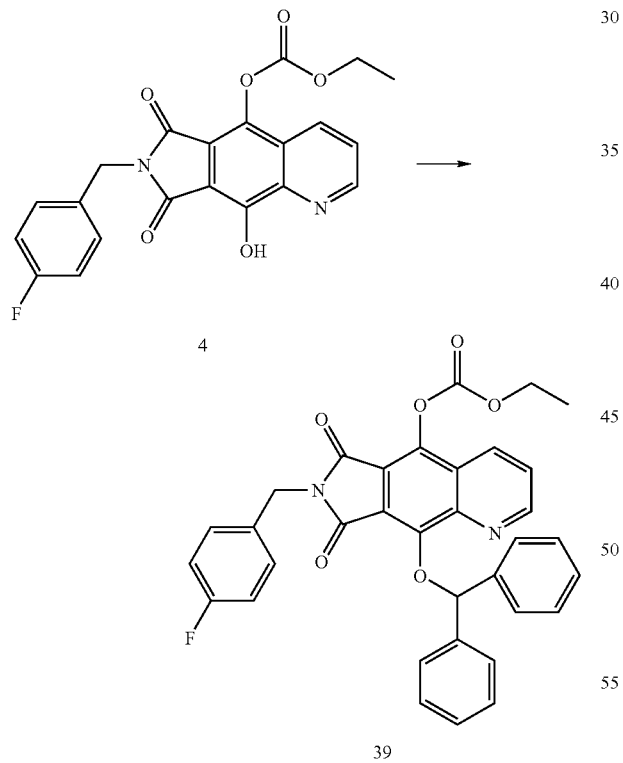

Example 39

Mono carbonate 4 (8.9 g, 21.7 mmol) was dissolved in 1,2-dichloroethane (400 mL). Diphenyldiazomethane 38 (8.4 g, 43.4 mmol) was added in one portion. The mixture was stirred at 70° C. for 3 hours. The reaction was monitored by TLC (EtOAc/Hexane=3/7). After completion of the reaction, the solution was cooled down to room temperature. The solvent was evaporated. The crude product is chromatographed on a silica gel column, eluting with EtOAc/hexane to give the product 39 as a white solid (10.1 g, 80%). $^1$H NMR (CDCl$_3$): δ 9.1 (d, 1H), 8.4 (d, 1H), 8.0 (s, 1H), 7.6 (dd, 1H), 7.6 (d, 4H), 7.4 (dd, 2H), 7.2-7.3 (m, 6H), 7.0 (t, 2H), 4.8 (s, 2H), 4.4 (q, 2H), 1.4 (t, 3H). MS: 577 (M+1) 599 (M+23).

The reaction was repeated, where mono-carbonate 4 (2 g, 0.4878 mmol) was dissolved in 9 mL of dichloroethane. To this was added diphenyldiazomethane (0.189 g, 0.9756 mmol) and stirred at 70° C. for two hours. After starting material consumed, concentrated off some solvent, and chromatographed (25% ethylacetate/hexanes) to give product 39 (0.2653 g, 0.4598 mmol, 94%.) $^1$H NMR (CDCl$_3$) δ 9.14 (d, 1H), 8.47 (d, 1H), 7.99 (s, 1H), 7.61 (m, 5H), 7.43 (dd, 2H), 7.27 (m, 6H), 7.02 (dd, 2H), 4.82 (s, 2H), 4.45 (q, 2H), 1.47 (t, 3H.) MS: 577 (M+1)

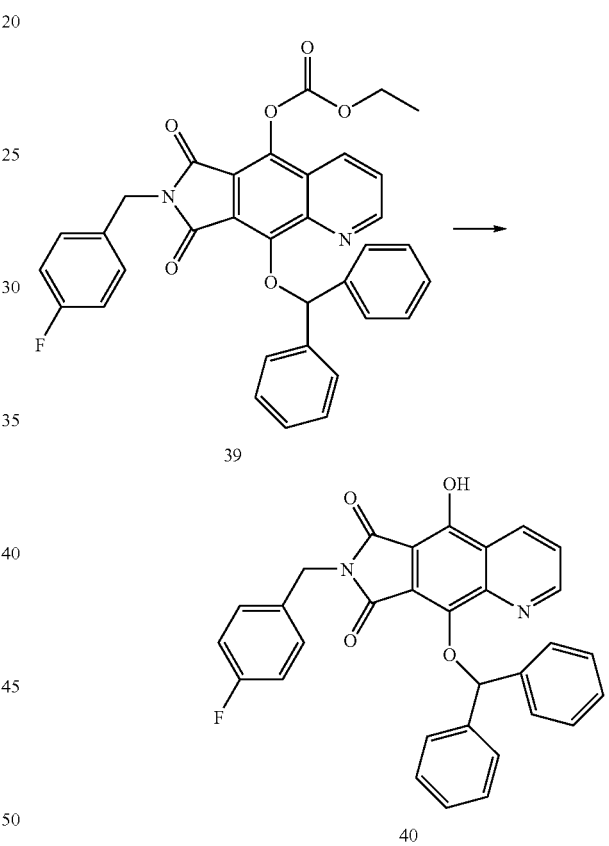

Example 40

A solution of K$_2$CO$_3$ (24.2 g, 175.2 mmol) in water (120 mL) and 4-dimethylaminopyridine (4.24 g, 35.0 mmol) was added to the ethyl carbonate 39 (10.1 g, 17.5 mmol) in THF (180 mL). The mixture is stirred at room temperature under nitrogen atmosphere overnight. Most of THF is removed under reduced pressure at 30-40° C. and the remaining solution is diluted with dichloromethane. To this, it is acidified with 1N HCl to pH about 4. The organic phase was separated and washed with brine, dried (MgSO$_4$) and concentrated to give a yellow solid crude product 40 (9.9 g, 100%). $^1$H NMR (CDCl$_3$): δ 9.1 (d, 1H), 8.6 (d, 1H), 8.4 (s, 1H, (OH)), 7.8 (s, 1H), 7.6 (dd, 1H), 7.6 (dd, 4H), 7.4 (d, 2H), 7.2-7.3 (m, 6H), 7.0 (t, 2H), 4.8 (s, 2H). LC/MS: 527 (M+23).

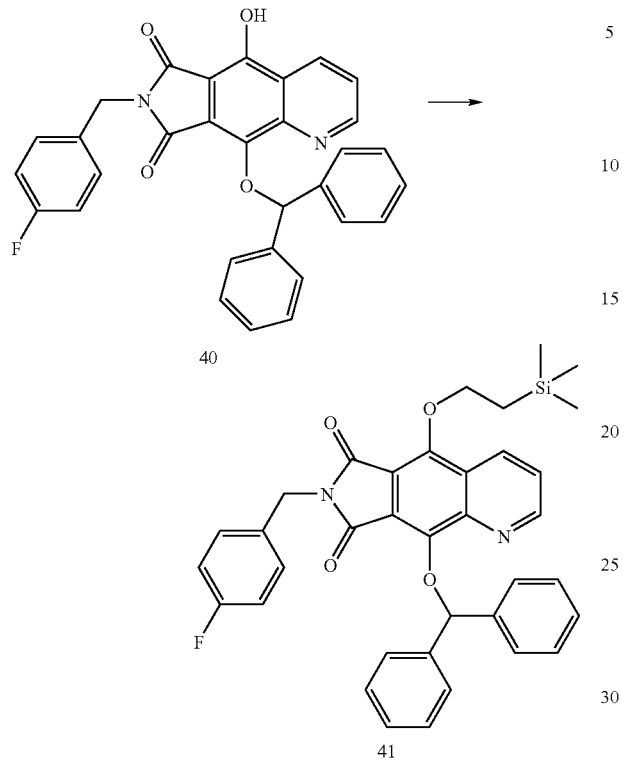

40

Example 41

2-(Trimethylsilyl) ethanol (2.4 mL, 16.7 mmol), triphenylphosphine (3.5 g, 13.4 mmol) and diethyl azodicarboxylate (92.1 mL, 13.4 mmol) was added to the phenol 40 (3.37 g, 6.7 mmol) in anhydrous THF (70 mL). The solution was stirred at room temperature for 3 hours under nitrogen. TLC indicated the completion of the reaction. The solvent was evaporated and the residue oil was purified by silica gel chromatography, eluting with EtOAc/hexane to afford the product 41 (3.3 g, 82%). $^1$H NMR (CDCl$_3$): δ 9.1 (d, 1H), 8.6 (d, 1H), 7.9 (s, 1H), 7.6 (dd, 1H), 7.6 (d, 4H), 7.4 (d, 2H), 7.2-7.3 (m, 6H), 7.0 (t, 2H), 4.8 (s, 2H), 4.6 (t, 2H), 1.2 (t, 2H). MS: 605 (M+1), 627 (M+23).

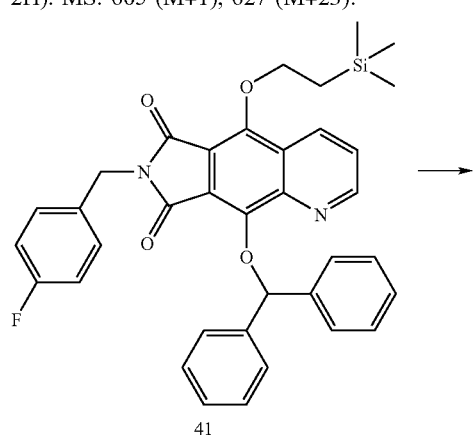

41

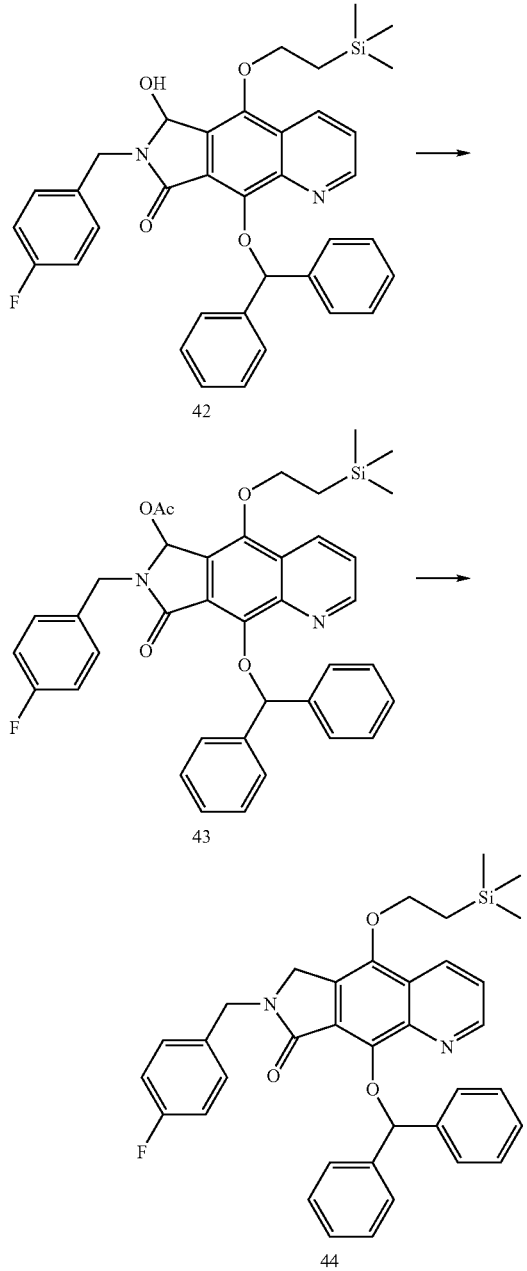

Example 42

Compound 41 (3.3 g, 5.46 mmol) was dissolved in the mixture of THF (40 mL), isopropanol (20 mL) and water (10 mL) and chilled to 0° C. in an ice-bath. To this was added lithium borohydride (373.0 mg, 16.4 mmol) slowly. The mixture was stirred at 0° C. for 1 hour and at room temperature for 1 hour under nitrogen. TLC indicated the completion of the reaction. A solution of 1N HCl (30 mL) was added and the mixture was extracted twice with CH$_2$Cl$_2$ (2×50 mL). The organic layer was washed with saturated NaHCO$_3$ and dried over Mg$_2$SO$_4$ and evaporated to dryness to give 42 as an oil (3.3 g).

Example 43

Crude product 42 was dissolved in anhydrous dichloromethane (50 mL). N-dimethylaminopyridine (66.7 mg, 0.546 mmol), N, N-diisopropylethylamine (2.85 mL, 16.4 mmol) and acetic anhydride (1.03 mL, 109 mmol) were added. The mixture was stirred at room temperature under nitrogen overnight. TLC indicated the completion of the reaction. The reaction was quenched with 1N HCl (30 mL) and extracted with $CH_2Cl_2$ twice (2×50 mL). The organic layer was washed with saturated $NaHCO_3$, dried ($Mg_2SO_4$) and concentrated to give crude product 43 (3.5 g).

Example 44

Crude product 43 was dissolved in anhydrous dichloromethane (60 mL) under nitrogen. To this solution was added 2,6-lutidine (3.2 mL, 23.7 mmol), triethylsiliane (10 mL), then trimethylsilyl triflate (1.5 mL, 8.2 mmol) slowly. The mixture was stirred at room temperature for 3 hours. TLC indicated the completion of the reaction. It was quenched with 1N HCl (30 mL) and extracted with $CH_2Cl_2$ twice (2×50 mL). The organic layer was washed with saturatedNaHCO$_3$, dried ($Mg_2SO_4$) and concentrated. The residue was chromatographed on a silica gel column, eluting with EtOAc/Hexane to afford 44 (1.4 g, 43.4% in 3 steps from 41). $^1H$ NMR (CDCl$_3$): δ 9.0 (d, 1H), 8.4 (d, 1H), 8.0 (s, 1H), 7.7 (d, 4H), 7.4 (dd, 1H), 7.1-7.3 (m, 8H), 7.0 (t, 2H), 4.8 (s, 2H), 4.2 (s, 2H), 4.1 (t, 2H), 1.1 (t, 2H), 0.1 (s, 9H). MS: 591 (M+1).

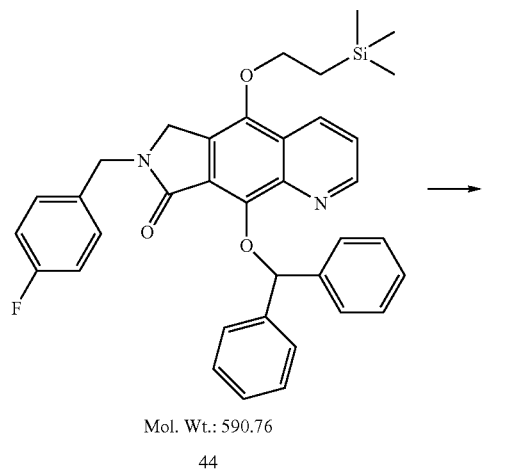

Mol. Wt.: 590.76

44

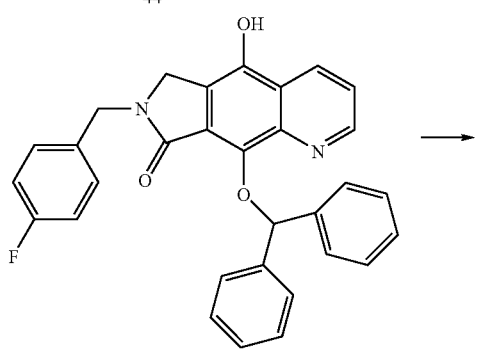

Mol. Wt.: 490.52

45

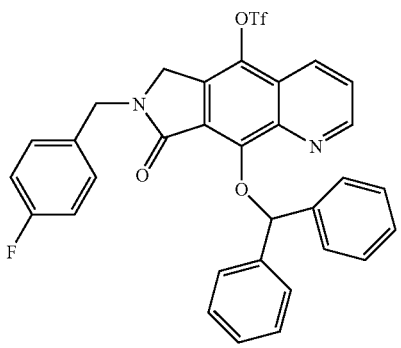

Mol. Wt.: 622.59

46

Example 45

To 9-benzhydryloxy-7-(4-fluoro-benzyl)-5-(2-tiimethyl-silanyi-ethoxy)-6,7-dihydro-pyrrolo[3,4-g]quinolin-8-one 44 (300.8 mg, 0.509 mmol) in anhydrous THF (20 mL), was added tetrabutylammonium fluoride hydrate (500 mg, 1.02 mmol). The reaction mixture turned to red and was stirred at room temperature under nitrogen for 1 hour. The reaction was monitored by TLC (EtOAc/Hexane=3/7). After completion of the reaction, it was diluted with EtOAc (50 mL) and washed with 1N HCl, saturated NaHCO$_3$ and brine. The organic layer was dried (MgSO$_4$) and concentrated to give a crude product 45 (280 mg).

The reaction was repeated whereby, to a solution of lactam 44 (0.026 g, 0.044 mmol) in THF (0.441 mL) was added triethylamine (0.025 mL, 0.176 mmol) and tetrabutylammonium fluoride in 1M THF (0.066 mL). The reaction mixture was stirred at room temperature under an inert atmosphere for 30 minutes, monitored to completion by MS. The mixture was diluted with dichloromethane, washed with saturated NH$_4$Cl, dried (MgSO$_4$), and concentrated in vacuo. The crude material 45 was taken forward immediately with no further purification or characterization: MS: 491 (M+1).

Alternatively, to a solution of 9-benzhydryloxy-7-(4-fluoro-benzyl)-5-(2-trimethylsilanyl-ethoxy)-6,7-dihydro-pyrrolo[3,4-g]quinolin-8-one 44 (30 mg, 0.051 mmol) dissolved in THF (1 mL) was added tetrabutylammonium fluoride hydrate (1M in THF, 150 μL). The reaction mixture turned to red and was stirred at room temperature for ½ hours under an inert atmosphere, which generated 9-benzhydryloxy-7-(4-fluoro-benzyl)-5-hydroxy-6,7-dihydro-pyrrolo[3,4-g]quinolin-8-one 45. TLC was used to monitor the reaction.

Example 46

Crude compound 45 was dissolved in dichloromethane (20 mL). To this was added cesium carbonate (200 mg, 0.611 mmol) and N-phenyltrifluoromethane sulfonimide (220 mg, 0.611 mmol). The mixture was stirred at room temperature under nitrogen for 16 hours. The reaction was monitored by TLC (EtOAc/Hexane=3/7). After completion of the reaction, it was diluted with EtOAc (50 mL) and washed with 1N HCl, saturated NaHCO₃ and brine. The organic layer was dried (MgSO₄) and concentrated. The residue was chromatographed on a silica gel column, eluting with EtOAc/Hexane to afford the clean product 46 (135 mg, 42.6% in 2 steps). ¹H NMR (CDCl₃): δ 9.1 (d, 1H), 8.3 (d, 1H), 8.0 (s, 1H), 7.7 (d, 4H), 7.6 (dd, 1H), 7.2-7.4 (m, 8H), 7.1 (t, 2H), 4.8 (s, 2H), 4.4 (s, 2H). MS: 623 (M+1), 645(M+23).

room temperature, diluted with EtOAc and washed with 1N HCl, saturated NaHCO₃ and brine. The organic phase was dried (MgSO₄) and concentrated. The residue was chromatographed on a silica gel column, eluting with EtOAc/Hexane to afford the product 47 (51.4 mg, 83%). ¹H NMR (CDCl₃): δ 9.0 (d, 1H), 8.4 (d, 1H), 8.1 (s, 1H), 7.7 (d, 4H), 7.2-7.5 (m, 14H), 7.1 (d, 1H), 7.0 (dd, 2H), 6.8 (d, 1H), 4.8 (s, 2H), 4.4(s, 2H). MS: 577 (M+1), 599(M+23).

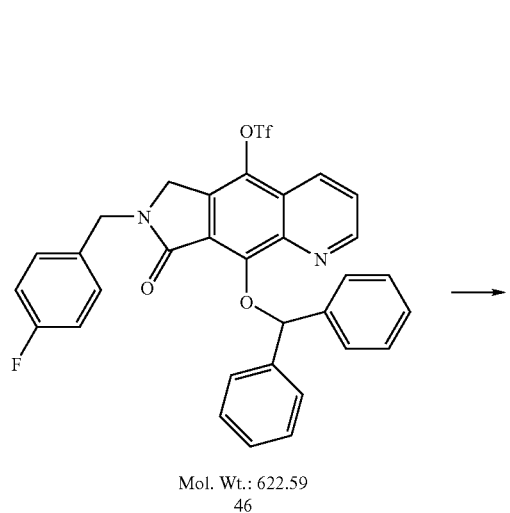

Mol. Wt.: 622.59
46

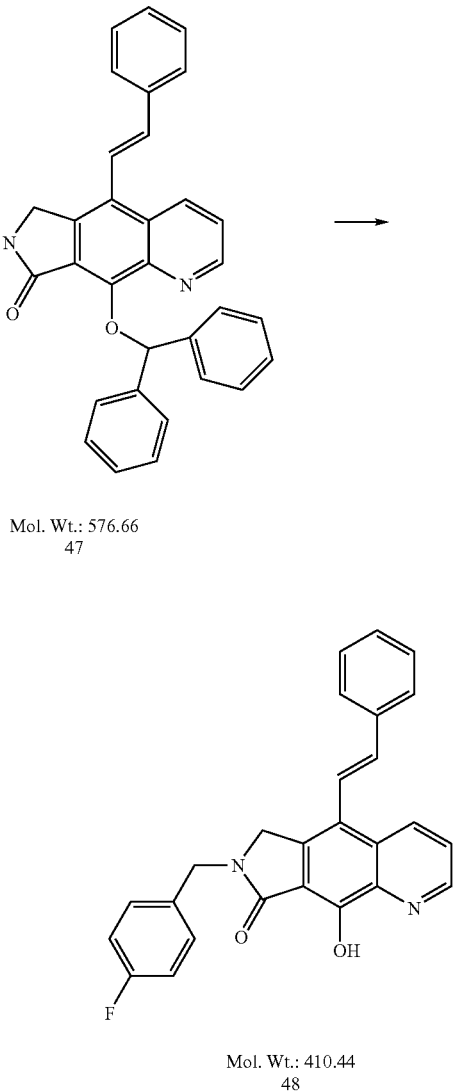

Mol. Wt.: 576.66
47

Mol. Wt.: 576.66
47

Mol. Wt.: 410.44
48

Example 47

To the triflate 46 (66.6 mg, 0.107 mmol) in toluene (2.8 mL)/ethanol (1.2 mL)/water (0.8 mL) was added potassium carbonate (37 mg, 0.268 mmol), trans-phenylvinylboronic acid (24.5 mg, 0.160 mmol) and tetrakis(triphenylphosphine)-palladium (0) (18.5 mg, 0.016 mmol). The mixture in the flask was flushed with argon three times and heated to 120° C. under argon for 3 hours. The mixture was cooled to

Example 48

The compound 47 (12 mg, 0.02 mmol) was dissolved in dichloromethane (1 mL) at room temperature under nitrogen. Triethylsilane (200 μL) was added followed by TFA (100 μL) slowly. The mixture became smoke and dark. It was stirred at room temperature for 30 min. The solvent was removed under reduced pressure. The crude product was triturated in diethylether/hexane to afford a yellow solid 48 (9 mg, 90%). ¹H NMR (CDCl₃): δ 9.0 (d, 1H), 8.6 (d, 1H), 7.5 (m, 3H), 7.2-7.4 (m, 6H), 7.1 (m, 2H), 6.8 (d, 1H), 4.8 (s, 2H), 4.5(s, 2H). MS: 411 (M+1).

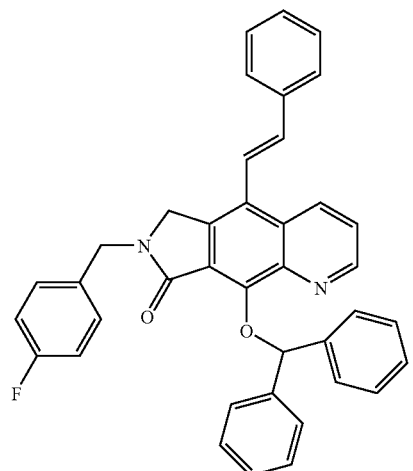

Mol. Wt.: 576.66
47

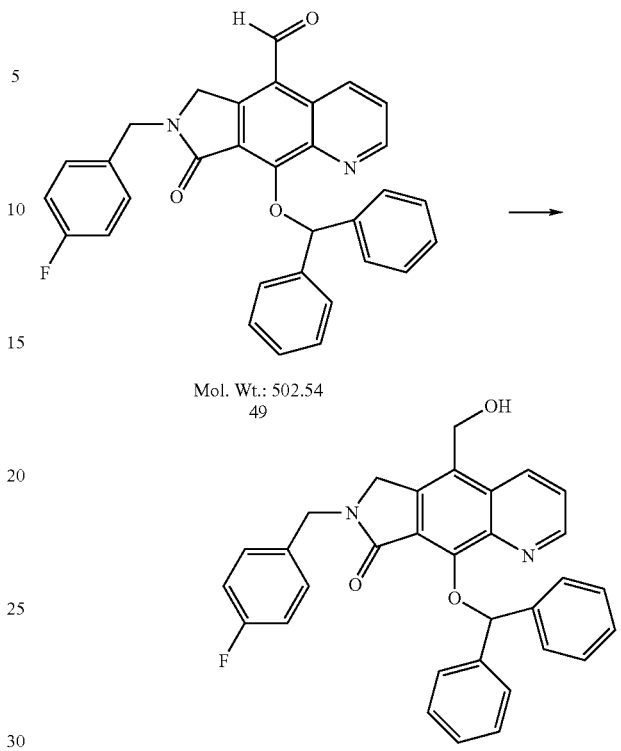

Mol. Wt.: 502.54
49

Mol. Wt.: 504.55
50

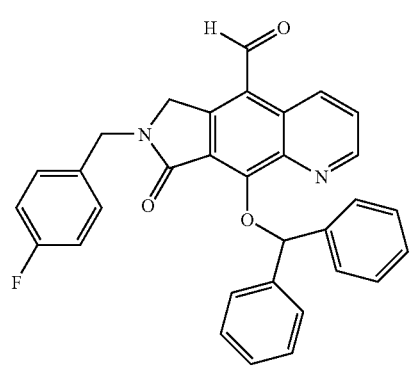

Mol. Wt.: 502.54
49

Example 49

Compound 47 (405 mg, 0.7 mmol) in dichloromethane (150 mL) was chilled to −78° C. Ozone (O₃) was passed slowly into the solution over 30 min. TLC indicated the completion of the reaction. Nitrogen was bubbled into the mixture for 10 min to expel excess O₃. Dimethyl sulfate (10 mL) was then added the mixture at −78° C. and the mixture was warmed to room temperature slowly with stirring. After 16 hours, the mixture was evaporated to dryness and the residue was purified by chromatography on a silica gel column, eluting with methanol/dichloromethane to give product of 49 (166.5 mg) and its hydrate form (122 mg), total yield of 80.8%. $^1$H NMR (CDCl$_3$): δ 10.7 (s, 1H, CHO), 9.1 (m, 2H), 8.4 (s, 1H), 7.7 (d, 4H), 7.6 (dd, 2H), 7.2-7.4 (m, 8H), 7.0 (t, 2H), 4.8 (s, 2H),4.6 (s, 2H). MS: 503 (M+1), 525(M+23).

Example 50

The aldehyde 49 (23 g, 0.046 mmol) was dissolved in anhydrous THF (1 mL) and MeOH (0.1 mL) at room temperature. To this was added sodium borohydride (5.2 mg, 0.14 mmol) slowly. The mixture was stirred at room temperature for 30 min under nitrogen. TLC indicated the completion of the reaction. The mixture was diluted with water (5 mL). The insoluble material was collected by filtration and washed with hexane and air-dried to give product 50 (13.5 mg, 59%). $^1$H NMR (CD$_3$OD): δ 9.3 (d, 1H), 9.1 (d, 1H), 8.1 (dd, 1H), 8.0 (s, 1H), 7.5 (d, 4H), 7.4 (dd, 2H), 7.3 (m, 6H), 7.1 (t, 2H), 5.0 (s, 2H), 4.9 (s, 2H), 4.7 (s, 2H). MS: 505 (M+1), 527(M+23).

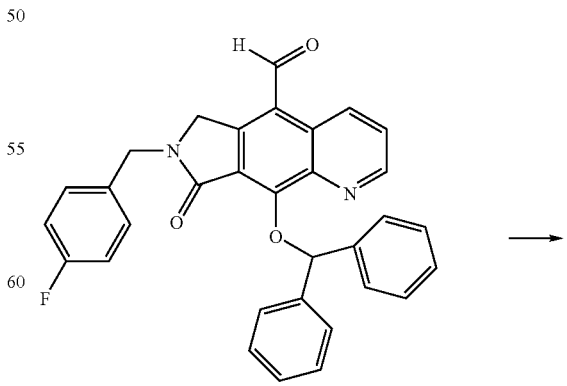

Mol. Wt.: 502.54
49

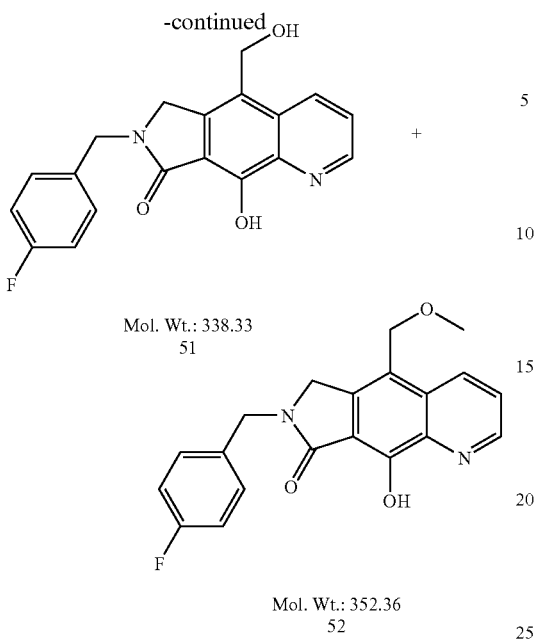
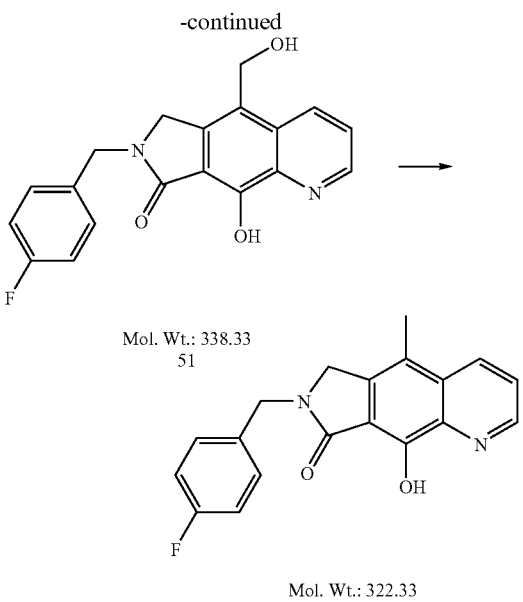

Example 51

The aldehyde 49 (121 mg, 0.24 mmol) was dissolved in anhydrous THF (5 mL) and MeOH (0.5 mL) at room temperature. To this was added sodium borohydride (27 mg, 0.72 mmol) slowly. The mixture was stirred at room temperature for 30 min under nitrogen. It was diluted with 1N HCl (10 mL), and stirred for 10 min. The phases were separated and the aqueous phase was lyophilized to give a yellow solid, which was washed with water and ether. The solid was dried to give 50 mg of product 51. $^1$H NMR (DMSO-$d_6$): δ 9.0 (d, 1H), 8.8 (d, 1H), 7.5 (m, 1H), 7.4 (m, 2H), 7.2 (m, 2H), 5.0 (s, 1H, PhOH), 4.8 (s, 2H), 4.7 (s, 2H), 4.5 (s, 2H). MS: 339 (M+1).

The organic phase was concentrated. The residue was dissolved in DMF (2 mL) land purified by Prep-HPLC to give 10 mg of product 52. HPLC condition: mobile phase A (1% AcOH in water), mobile phase B (1% AcOH in AcCN); gradient: 20% to 50% B in 30 min; flow rate: 20 mL/min; column: Phenomenex, Luna 5µ, C18 (2), 150 mm×21.2 mm. $^1$H NMR (DMSO-$d_6$): δ 9.5 (d, 1H), 89.0 (d, 1H), 7.7 (m, 1H), 7.3 (m, 2H), 7.2 (m, 2H), 4,7 (s, 2H), 4.6 (s, 2H), 4.5 (s, 2H), 3.5 (s, 3H, under water peak). MS: 353 (M+1).

Example 52

The aldehyde 49 (118 mg, 0.23 mmol) was dissolved in anhydrous THF (5 mL) and MeOH (0.5 mL) at room temperature. To this was added sodium borohydride (27 mg, 0.72 mmol) slowly. The mixture was stirred at room temperature for 30 min under nitrogen. It was diluted with 1N HCl (10 mL), and stirred for 10 min. The phases were separated and the aqueous phase was lyophilized to give a yellow solid as product 51.

The alcohol 51 (crude from reduction) was suspended in dichloromethane (10 mL) at room temperature under nitrogen. Triethylsilane (3 mL) was added followed by TFA (1 mL) slowly. The mixture became homogeneous and was stirred at room temperature overnight under nitrogen. The solvent was removed under reduced pressure. The crude product was dissolved in 2 mL of DMF then purified by prep-HPLC to gave a clean product of 53 (22.4 mg, 30%). HPLC condition: mobile phase A (1% TFA in water), mobile phase B (1% TFA in AcCN); gradient: 5% to 100% B in 20 min; flow rate: 20 mL/min; column: Phenomenex, Luna 5µ, C18 (2), 150 mm×21.2 mm. $^1$H NMR (CD$_3$OD): δ 9.0 (d, 1H), 8.9 (d, 1H), 7.9 (dd, 1H), 7.4 (d, 4H), 7.1 (t, 2H), 4.8 (s, 2H), 4.9 (s, 2H), 4.5 (s, 2H), 2.5 (s, 3H). MS: 323 (M+1).

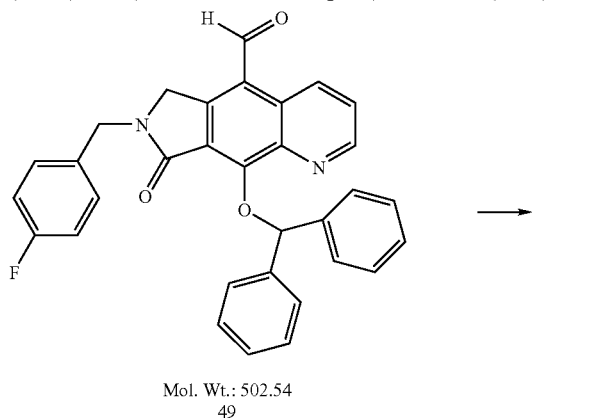
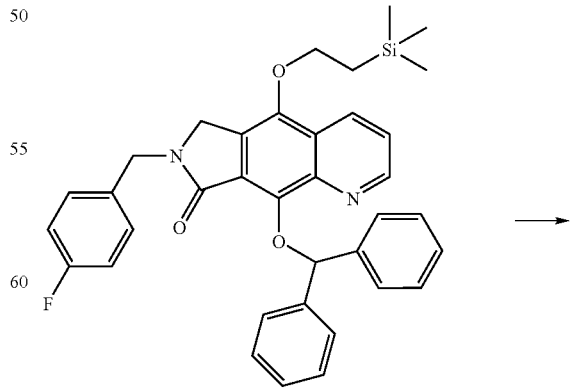

-continued

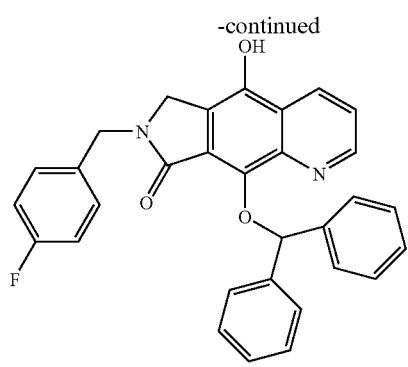

Mol. Wt.: 490.52
45

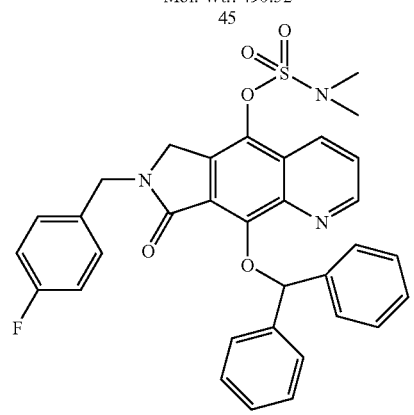

Mol. Wt.: 597.66
54

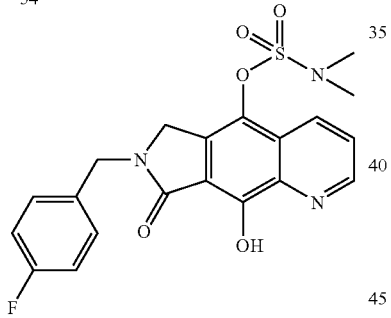

Mol. Wt.: 431.44
55

Example 53

To the compound 44 (350.0 mg, 0.592 mmol) in anhydrous THF (20 mL), was added tetrabutylammonium fluoride (1M in THF, 651 µl, 0.651 mmol) and triethylamine (330 µl, 2.37 mmol). The reaction mixture turned to red and was stirred at room temperature under nitrogen for 1 hour. The reaction forming 45 was monitored by TLC (EtOAc/Hexane=3/7).

Example 54

Triethylamine (330 µL, 2.37 mmol) was added to the reaction mixture followed by a catalytic amount of DMAP, and N, N-dimethylsulfamoyl chloride (160 µL, 1.5 mmol). The mixture was stirred at room temperature under nitrogen for 16 hours. After completion of the reaction, it was diluted with dichloromethane (50 mL) and washed with 1N HCl, saturated $NaHCO_3$ and brine. The organic layer was dried ($MgSO_4$) and concentrated. The residue was chromatographed on a silica gel column, eluting with EtOAc/Hexane to afford the product 54 (205.4 mg, 58% in 2 steps). $^1$H NMR ($CDCl_3$): δ 9.0 (d, 1H), 8.4 (d, 1H), 8.0 (s, 1H), 7.7 (d, 4H), 7.5 (dd, 1H), 7.1-7.3 (m, 8H), 7.0 (t, 2H), 4.8 (s, 2H), 4.4 (s, 2H), 3.0 (s, 3H). MS: 598 (M+1).

Example 55

The compound 54 ((205.4 mg, 0.344 mmol) was dissolved in dichloromethane (6 mL) at room temperature under nitrogen. Triethylsilane (2 mL) was added followed by TFA (1 mL) slowly. The mixture became smoky and dark and was stirred at room temperature for 30 min. The solvent was removed under reduced pressure. The crude product was triturated in diethyletherihexane to afford a yellow solid 55, 169 mg, 93%. $^1$H NMR ($CD_3OD$): δ 9.0 (d, 1H), 8.6 (d, 11H), 7.8 (dd, 1H), 7.4 (m, 2H), 7.1 (m, 2H), 4.8 (s, 2H), 4.6 (s, 2H), 3.1 (s, 6H). MS: 432 (M+1).

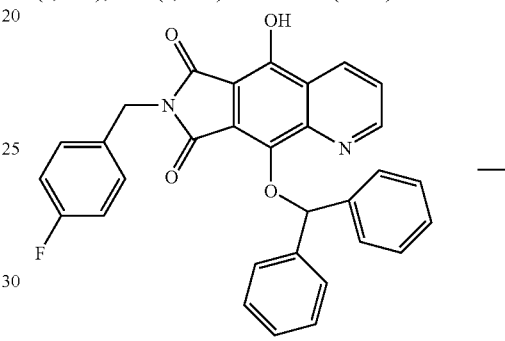

Mol. Wt.: 504.51
40

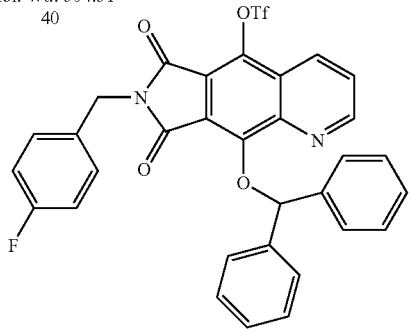

Mol. Wt.: 636.57
56

Example 56

The phenol 40 (1.0 g, 1.984 mmol) and DIEA (1.04 mL, 6.0 mmol) in dichloromethane (20 mL) was chilled to −78° C. To this was added trifluoromethanesulfonic anhydride (0.78 mL, 3.0 mmol) slowly under the nitrogen. The reaction was completed in 1 hour. It was quenched with 1.5 mL of methanol and stirred for 5 min more. Warmed to room temperature, it was washed with 1N HCl, saturated $NaHCO_3$ and brine. The organic phase was dried ($MgSO_4$) and concentrated to afford the forming product 56 (1.2 g, 95%).

The reaction was repeated, where monophenol 40 (0.1807 g, 0.358 mmol) was dissolved in 4 mL dry dichloromethane. To this was added diisopropylethylamine (0.182 mL, 1.074 mmol.) After cooling to −78° C., triflic anhydride was added (0.14 mL, 0.537 mmol) and was stirred at this temperature for twenty minutes. Reaction was then complete by TLC, diluted with dichloromethane, washed with 1M HCl, saturated NaHCO₃ solution, dried (MgSO₄) and organics concentrated to give product (0.2518 g, 0.396 mmol, 100%) which was stored crude as a solution in 10 mL dry benzene. ¹H NMR (CDCl₃) δ 9.2 (dd, 1H), 8.46 (d, 1H), 8.068 (s, 1H), 7.75 (dd, 1H), 7.6 (d, 4H), 7.47 (dd, 1H), 7.27 (m, 7H), 7.19, dd, 2H), 4.87 (s, 2H.) MS: 637 (M+1)

Example 57

To the triflate 56 (78.0 mg, 0.122 mmol) in toluene (2.8 mL)/ethanol (1.2 mL)/water (0.8 mL) was added potassium carbonate (42 mg, 0.306 mmol), 1-octeneboronic acid (29.0 mg, 0.184 mmol) and tetrakis (triphenylphosphine)-palladium (0) (21.0 mg, 0.018 mmol). The mixture in the flask was flushed with argon three times. It was heated to 120° C. under argon for 3 hours. Cooling to room temperature, it was diluted with EtOAc and washed with 1N HCl, saturated NaHCO₃ and brine. The organic phase was dried (MgSO₄) and concentrated. The residue was chromatographed on a silica gel column, eluting with EtOAc/Hexane to afford the product 57 (11.4 mg, 15.6%).

Example 58

The compound 57 (6 mg, 0.01 mmol) was dissolved in dichloromethane (1 mL) at room temperature under nitrogen. Triethylsilane (200 µL) was added followed by TFA (100 µL) slowly. The mixture became smoky and dark and was stirred at room temperature for 30 min. The solvent was removed under reduced pressure. The crude product was triturated in diethylether/hexane to afford a yellow solid TFA salt of 58, 3 mg, 57%. ¹H NMR (CD₃OD): δ 9.0 (d, 1H), 8.8 (d, 1H), 7.8 (dd, 1H), 7.4 (dd, 2H), 7.1 (d, 1H), 7.0 (dd, 2H), 6.2 (m, 1H), 4.8 (s, 2H), 2.4 (m, 2H), 1.6 (m, 2H), 1.3-1.5 (m, 6H), 0.9 (t, 3H). MS: 433 (M+1).

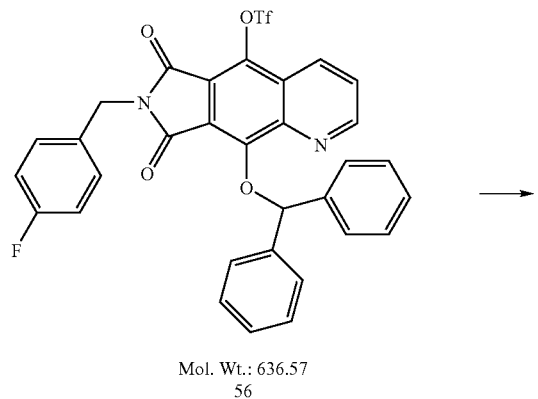
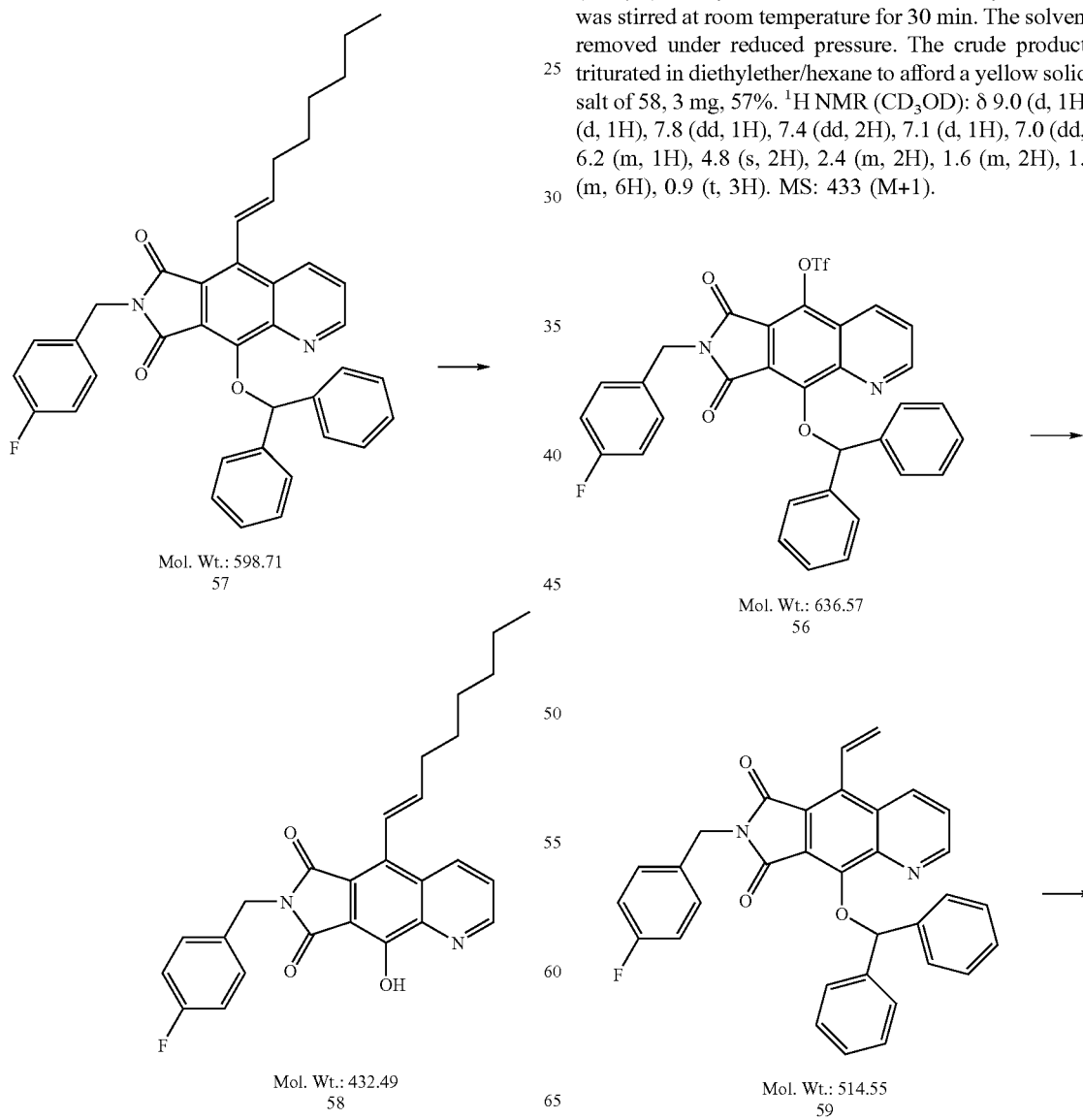

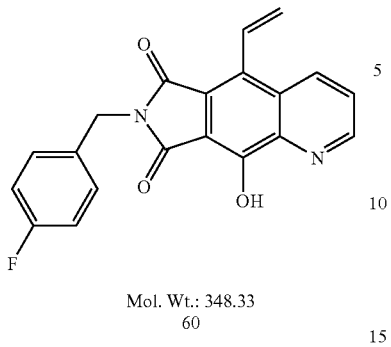

Mol. Wt.: 348.33
60

Example 59

To the triflate 56 (100 mg, 0.157 mrol) in toluene (2.8 mL)/ethanol (1.2 mL)/water (0.8 mL) was added potassium carbonate (54 mg, 0.392 mmol), vinylboronic acid (17 mg, 0.235 mmol) and tetrakis (triphenylphosphine)-palladium (0) (27.0 mg, 0.023 mmol). The mixture in the flask was flushed with argon three times. It was heated to 120° C. under argon for 3 hours. Cooling to room temperature, it was diluted with EtOAc and washed with 1N HCl, saturated NaHCO$_3$ and brine. The organic phase was dried (MgSO$_4$) and concentrated. The residue was chromatographed on a silica gel column, eluting with EtOAc/Hexane to afford the product 59 (32.3 mg, 40%).

Example 60

The compound 59 (11 mg, 0.01 mmol) was dissolved in dichloromethane (1 mL) at room temperature under nitrogen. Triethylsilane (200 µL) was added followed by TFA (100 µL) slowly. The mixture became smoky and dark and was stirred at room temperature for 30 min. The solvent was removed under reduced pressure. The crude product was triturated in diethylether/hexane to afford a yellow solid TFA salt of 60, 2.3 mg, 31.4%. $^1$H NMR (CDCl$_3$): δ 9.0 (d, 1H), 8.8 (d, 1H), 7.7 (dd, 1H), 7.5 (m, 2H), 7.0 (m, 2H), 6.0 (d, 1H), 5.6 (d, 1H), 5.3 (s, 1H, OH), 4.8 (s, 2H). MS: 349 (M+1).

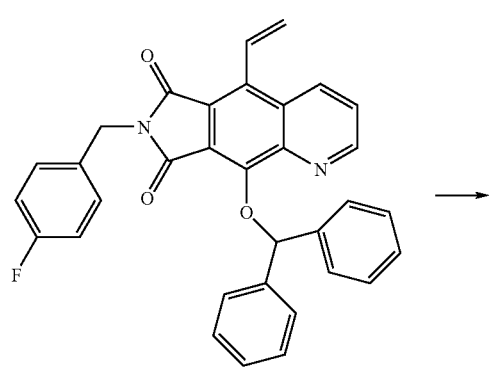

Mol. Wt.: 514.55
59

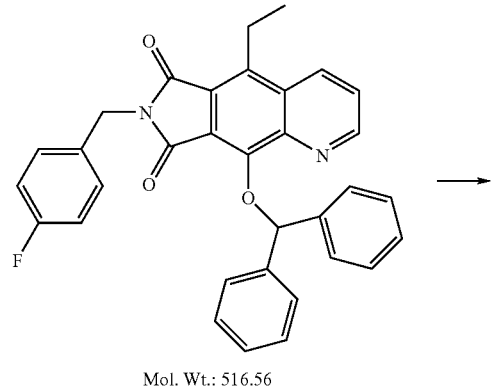

Mol. Wt.: 516.56
61

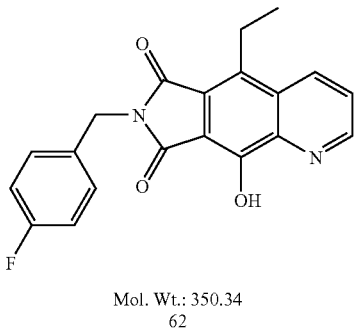

Mol. Wt.: 350.34
62

Example 61

The compound 59 (157 g, 0.11 mmol) was dissolved in anhydrous THF (5 mL) and MeOH (0.5 mL) at room temperature. To this was added sodium borohydride (13 mg, 0.33 mmol) slowly. The mixture was stirred at room temperature for 1 hour under nitrogen. It was diluted with EtOAc (50 mL), and washed with 1N HCl, saturated NaHCO$_3$ and brine. The organic phase was dried (MgSO$_4$) and concentrated. The residue was purified by silica gel prep-TLC, eluting with EtOAc/Hexane (3/7) to afford the product 61 (12.5 mg, 22%).

Example 62

The compound 61 (11 mg, 0.01 mmol) was dissolved in dichloromethane (1 mL) at room temperature under nitrogen. Triethylsilane (200 µL) was added followed by TFA (100 µL) slowly. The mixture became smoky and dark and was stirred at room temperature for 30 min. The solvent was removed under reduced pressure. The crude product was triturated in diethylether/hexane to afford a yellow solid TFA salt of 62, 8 mg, 75%. $^1$H NMR (CDCl$_3$): δ 9.0 (d, 1H), 8.5 (d, 1H), 7.7 (dd, 1H), 7.5 (dd, 2H), 7.0 (m, 2H), 4.8 (s, 2H), 3.5 (q, 2H), 1.3 (t, 3H). MS: 451 (M+1).

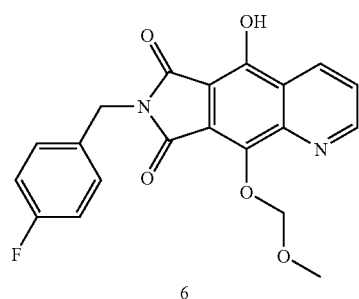

6

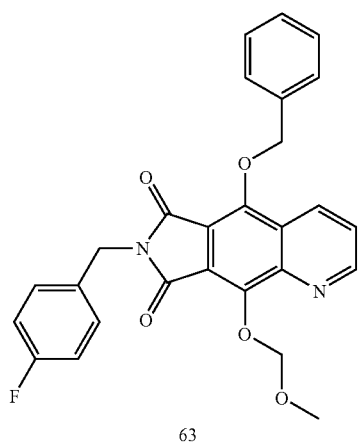

63

Example 63

Mono-phenol 6 (0.02 g, 0.052 mmol) was added to 1.5 mL dry dimethylformamide. To this was added benzyl bromide (0.0124 ml, 0.104 mmol) and $K_2CO_3$ (0.0215 g, 0.156 mmol) and stirred at 50° C. After 1.5 hrs reaction completed by TLC. Diluted with 100 mL ethylacetate, washed with saturated $NH_4Cl$ solution and brine. The organic phase was dried ($MgSO_4$), concentrated, and chromatographed (25% ethylacetate/hexanes) to give product 63 (0.013 g, 0.0275 mmol, 53%.). $^1$H NMR ($CDCl_3$) δ 9.03 (dd, 1H), 8.6 (d, 1H), 7.54 (m, 6H), 7.4 (m, 2H), 7.05 (dd, 2H), 5.8 (s, 2H), 5.6 (s, 2H), 4.9 (s, 2H), 3.7 (s, 3H). MSW: 473 (M+1)

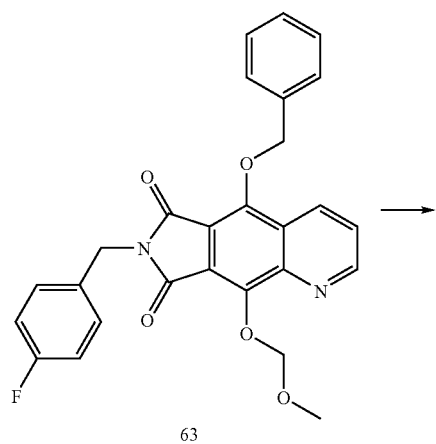

63

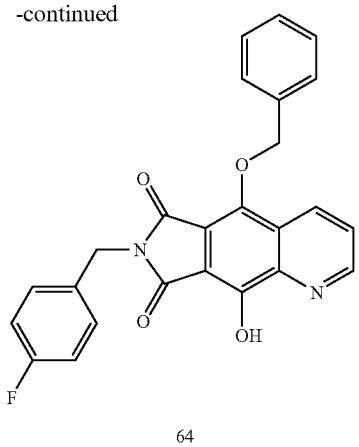

64

Example 64

Benzyl ether (0.013 g, 0.0275 mmol) was dissolved in 1 mL dry dichloromethane. To this was added trifluoroacetic acid (0.0213 mL, 0.275 mmol) and stirred 2.5 hrs. Concentrated off volatiles, azeotroped with toluene (2×), concentrated to give crude product. Triturated with 1:1 diethylether/hexanes to give product 64 (0.0078 g, 0.0182 mmol, 66%). $^1$H NMR ($CDCl_3$) δ 8.96 (dd, 1H), 8.6 (d, 1H), 7.6 (dd, 1H), 7.5 (m, 5H), 7.37 (m, 2H), 7.05 (dd, 2H), 5.6 (s, 2H), 4.88 (s, 2H). MS: 429 (M+1), 427 (M−1)

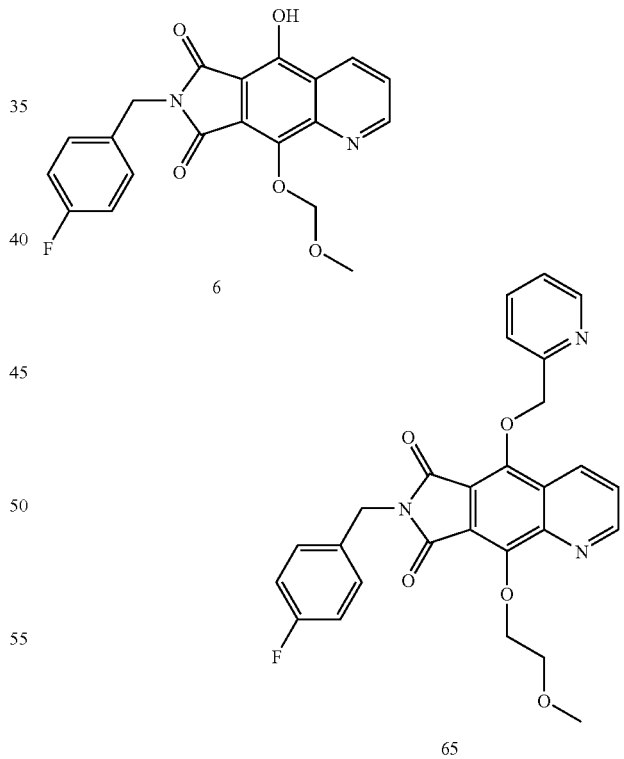

6

65

Example 65

Monophenol 6 (0.04 g, 0.1047 mmol) was dissolved in 2 mL of dry dimethylformamide. To this was added 2-bromomethyl pyridine HBr salt (0.0529 g, 0.209 mmol) and $K_2CO_3$ (0.144 g, 1.047 mmol.) Stirred at 50° C. for twelve hours. Diluted with ethylacetate, washed with brine (saturated NaCl) and 1M HCl, dried (MgSO$_4$,), and concentrated. The crude product was chromatographed (20 to 50% ethylacetate/hexanes) to give product 65: (0.0032 g, 0.0067 mmol, 6.5%.) $^1$H NMR (CDCl$_3$) δ 9.03 (d, 1H), 8.72 (d, 1H), 8.6 (d, 1H), 7.8 (dd, 1H), 7.7 (dd, 1H), 7.57 (dd, 1H), 7.48 (dd, 2H),7.0 (dd, 2H), 5.8 (s, 2H), 5.65 (s, 2H), 4.86 (s, 2H), 3.72 (s, 3H.) MS: 488 (M+1)

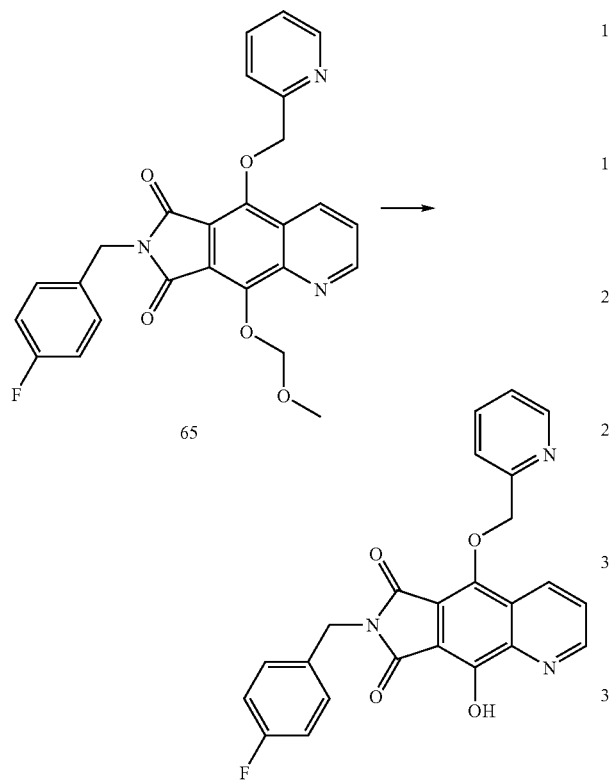

Example 66

Pyridyl ether 65 (0.0032 g, 0.0067 mmol) was dissolved in 1 mL dry dichloromethane. To this was added trifluoroacetic acid (0.0052 mL, 0.0676 mmol) and stirred 12 hrs. Concentrated off volatiles, azeotroped with toluene (2×), concentrated to give crude product. Triturated with 1:1 diethylether/hexanes to give product 66 (0.0012 g, 0.0028 mmol, 42%.) $^1$H NMR (CDCl$_3$) δ 8.96 (d, 1H), 8.73 (d, 1H), 8.6 (d, 1H),7.8 (dd, 1H), 7.7 (d, 1H), 7.63 (dd, 1H), 7.5 (dd, 2H), 7.3 (m, 1H), 7.04 (dd, 2H), 5.67 (s, 2H), 4.87 (s, 2H.) MS: 430 (M+1), 428 (M−1)

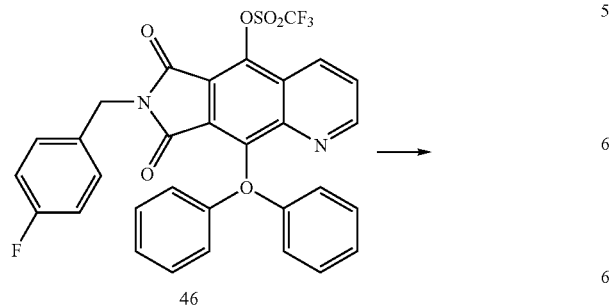

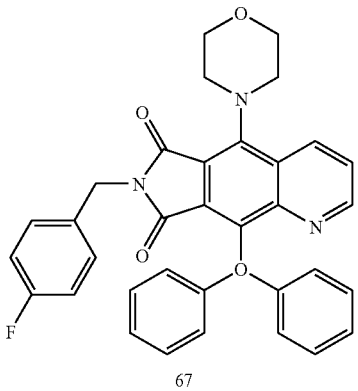

Example 67

Triflate 46 in benzene was concentrated to give (0.0225 g, 0.0353 mmol) and dissolved in 3 mL of dichloroethane. To this was added triethylamine (0.0073 mL, 0.0529 mmol) and morpholine (0.0092 ml, 0.118 mmol) and reaction stirred at 65° C. After 15 hrs, reaction still incomplete by TLC, added another 0.118 mL of morpholine. After 21 hrs reaction time concentrated off volatiles and chromatographed (10 to 25% ethylacetate/hexanes) to give product 67 (0.0061 g, 0.01, 30%). $^1$H NMR (CDCl$_3$) δ 9.09 (dd, 1H), 8.89 (d, 1H), 8.03 (s, 1H), 7.65 (m, 5H), 7.49 (dd, 1H), 7.27 (m, 7H), 7.06 (dd, 2H), 4.85 (s, 2H), 3.92 (dd, 4H), 3.92 (br m, 4H). MS: 574 (M+1)

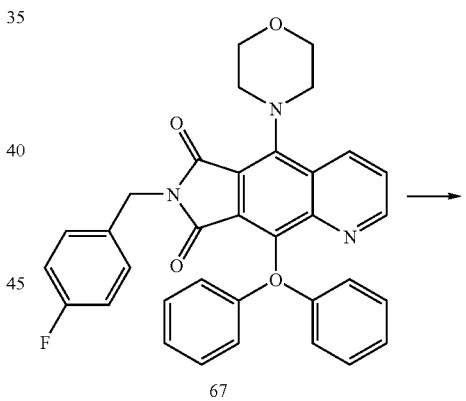

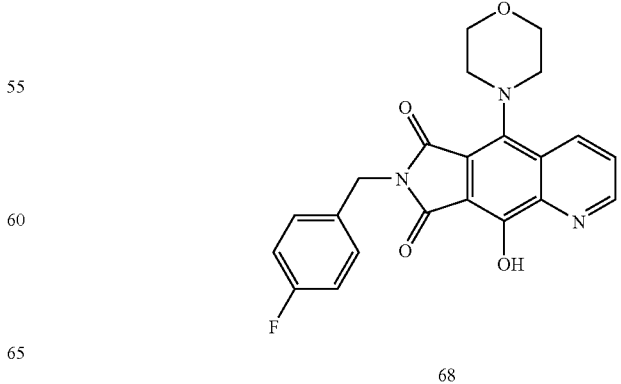

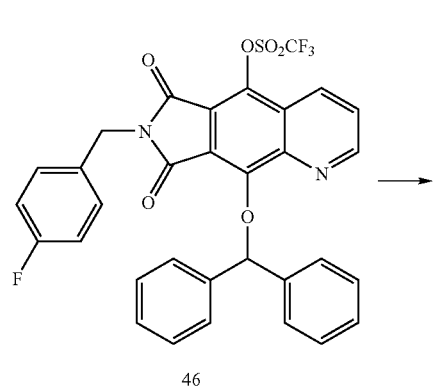

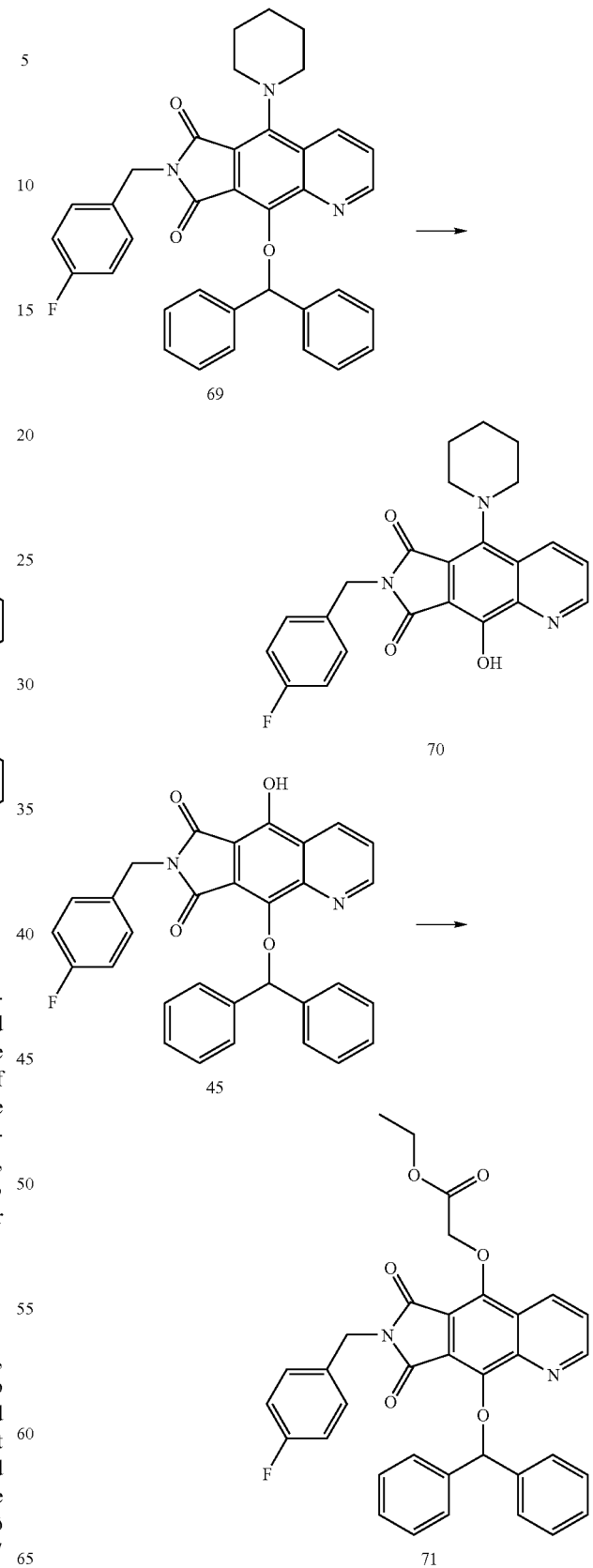

Example 68

Tertiary amine 67 was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene, solidified with hexane and concentrated to give crude. Triturated with 1:1 diethylether/hexanes to give product 68 (0.002 g, 0.0049 mmol, 49%). $^1$H NMR (CDCl$_3$) δ 8.98 (m, 2H), 7.7 (dd, 1H), 7.53 (dd, 2H), 7.05 (dd, 2H), 4.86 (s, 2H), 3.96 (dd, 4H), 3.35 (br m, 4H). MS: 408 (M+1), 406 (M−1)

Example 69

Triflate 46 in benzene was concentrated to give (0.045 g, 0.0706 mmol) and dissolved in 3 mL of dichloroethane. To this was added triethylamine (0.0147 mL, 0.1059 mmol) and morpholine (0.0209 ml, 0.2118 mmol) and reaction stirred at 70° C. After 15 hrs of stirring, concentrated off volatiles and chromatographed (8 to 10% ethylacetate/hexanes) to give product 69 (0.0085 g, 0.01488,44%.) $^1$H NMR (CDCl$_3$) δ 9.068 (dd, 1H), 8.79 (d, 1H), 7.8 (s, 1H), 7.6 (d, 4H), 7.57 (dd, 1H), 7.46 (dd, 2H), 7.27 (m, 6H), 7.06 (dd, 2H), 4.84 (s, 2H), 3.24 (br s, 4H), 1.73 (br s, 6H.) MS: 572 (M+1)

Example 70

Tertiary amine 69 was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene, solidified with hexane and concentrated to give crude. Triturated with 1:1 diethylether/hexanes to give product 70 (0.0043 g, 0.0106 mmol, 72%.) $^1$H NMR (CDCl$_3$) δ 8.96 (dd, 1H), 8.85 (d, 1H), 7.66 (dd, 1H), 7.5 (m, 2H), 7.04 (dd, 2H), 4.85 (s, 2H), 3.29 (br s, 4H), 1.77 (br s, 6H.) MS: 406 (M+1), 404 (M−1)

Example 71

Monophenol 45 (0.03 g, 0.0595 mmol) was dissolved in 2 mL dry dimethylformamide. To this was added ethyl bromoacetate (0.0131 mL, 0.119 mmol) and freshly ground K$_2$CO$_3$ (0.025 g, 0.178 mmol.) Stirred at 50° C., for two hours until starting material consumed. Concentrated off some solvent, diluted with ethylacetate, washed with saturated NH$_4$Cl solution, concentrated organics to give crude product. Chromatographed (10 to 25% ethylacetate/hexanes) to give product 71 (0.0321 g, 0.054 mmol, 91%.) $^1$H NMR (CDCl$_3$) δ 9.1 (dd, 1H), 8.96 (d, 1H), 7.9 (s,1H), 7.62 (d, 4H), 7.445 (m, 2H), 7.27 (m, 7 H), 7.059 (dd, 2H), 5.21 (s, 2H), 4.83 (s, 2H), 4.22 (q, 2H), 1.23 (t, 3H). MS: 591 (M+1).

Example 72

Ethyl ester 71 was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated with 1:1 diethylether/hexanes to give product 72 (0.0209 g, 0.049 mmol, 91%.) $^1$H NMR (CDCl$_3$) δ 9.0 (m, 2H), 7.7 (dd, 1H), 7.5 (dd, 2H), 7.04 (dd, 2H), 5.33 (s, 2H), 4.84 (s, 2H), 4.24 (q, 2H), 1.28 (t, 3H.) MS: 425 (M+1), 423

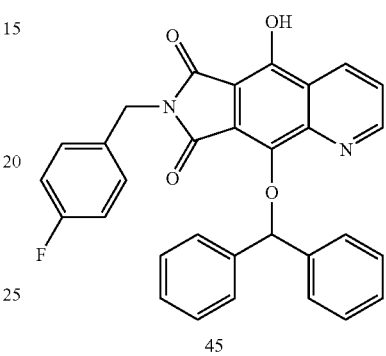

45

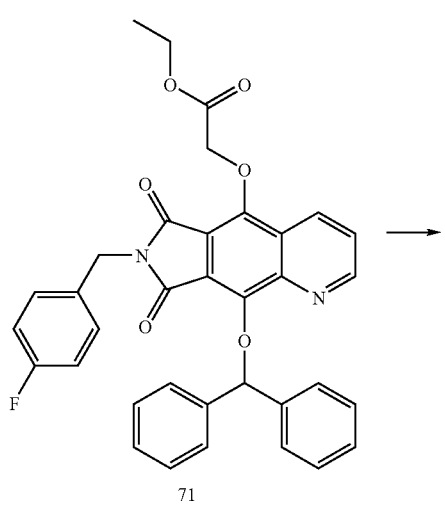

71

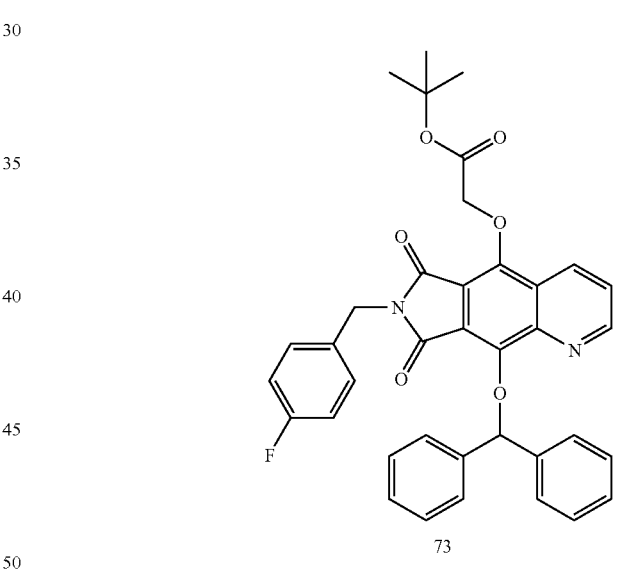

73

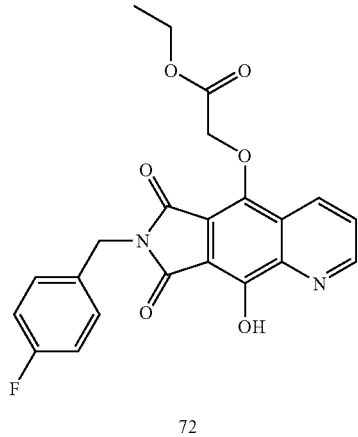

72

Example 73

Monophenol 45 (0.03 g, 0.0595 mmol) was dissolved in 2 mL dry dimethylformamide. To this was added t-butyl bromoacetate (0.0175 mL, 0.119 mmol) and freshly ground K$_2$CO$_3$ (0.025 g, 0.178 mmol.) Stirred at 50° C., for one hour until starting material consumed. Concentrated off some solvent, diluted with ethylacetate, washed with saturated NH$_4$Cl solution, concentrated organics to give crude product. Chromatographed (10 to 15% ethylacetate/hexanes) to give product 73 (0.0309 g, 0.05 mmol, 84%.) $^1$H NMR (CDCl$_3$) δ 9.09 (dd, 1H), 8.97 (d, 1H), 7.92 (s,1H), 7.62 (d, 4H), 7.44 (m, 2H), 7.27 (m,7H), 7.05 (dd, 2H), 5.12 (s, 2H), 4.83 (s, 2H), 1.38 (s, 9H.) MS: 619 (M+1)

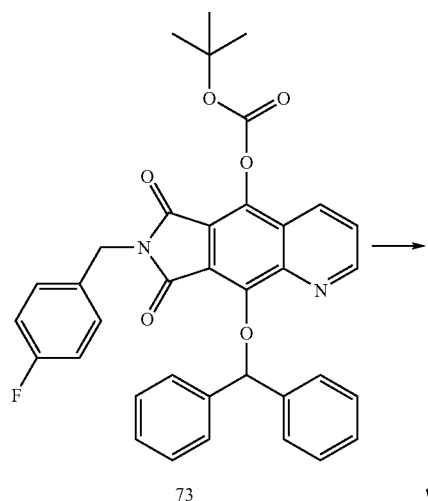

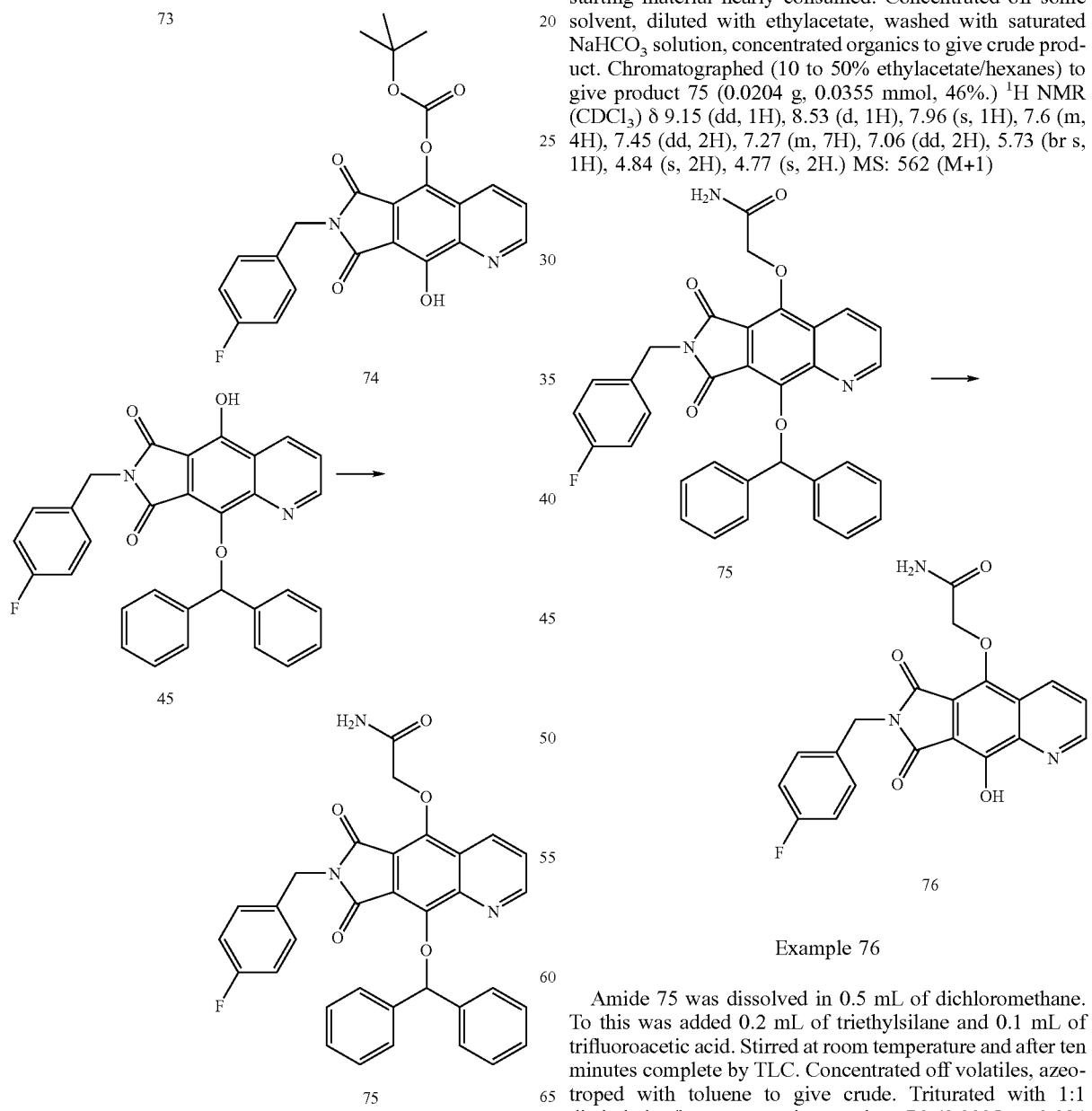

Example 74

Tertiary Butyl ester 73 was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated with 1:1 diethylether/hexanes to give product 74 (0.0189 g, 0.042 mmol, 84%.) $^1$H NMR (CDCl$_3$) δ 9.05 (m, 2H), 7.72 (dd, 1H), 7.5 (dd, 2H), 7.04 (dd, 2H), 5.22 (s, 2H), 4.84 (s, 2H), 1.44 (s, 9H.) MS: 453 (M+1), 451 (M−1)

Example 75

Monophenol 45 (0.04 g, 0.079 mmol) was dissolved in 1 mL dry dimethylformamide. To this was added 2-bromoacetamide (0.022 g, 0.158 mmol) and freshly ground K$_2$CO$_3$ (0.0345 g, 0.25 mmol.) Stirred at 60° C., for three hours until starting material nearly consumed. Concentrated off some solvent, diluted with ethylacetate, washed with saturated NaHCO$_3$ solution, concentrated organics to give crude product. Chromatographed (10 to 50% ethylacetate/hexanes) to give product 75 (0.0204 g, 0.0355 mmol, 46%.) $^1$H NMR (CDCl$_3$) δ 9.15 (dd, 1H), 8.53 (d, 1H), 7.96 (s, 1H), 7.6 (m, 4H), 7.45 (dd, 2H), 7.27 (m, 7H), 7.06 (dd, 2H), 5.73 (br s, 1H), 4.84 (s, 2H), 4.77 (s, 2H.) MS: 562 (M+1)

Example 76

Amide 75 was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated with 1:1 diethylether/hexanes to give product 76 (0.0095 g, 0.024 mmol, 67%.) $^1$H NMR (CD$_3$SOCD$_3$) δ 9.08 (dd, 1H), 8.93

(d, 1H), 7.87 (dd, 1H), 7.73 (br s, 1H), 7.41 (dd, 2H), 7.19 (dd, 2H), 4.86 (s, 2H), 4.75 (s, 2H.) MS: 396 (M+1), 394 (M−1)

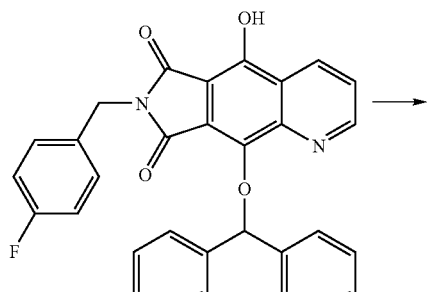

45

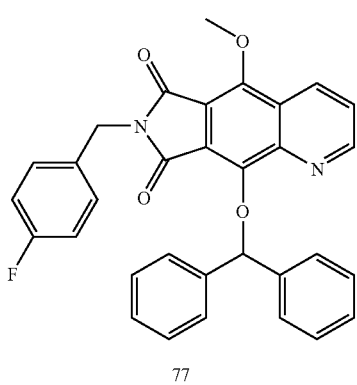

77

Example 77

Monophenol 45 (2.9 g, 5.75 mmol) was dissolved in 20 mL dry dimethylformamide. To this was added methyl iodide (3.58 mL, 57.5 mmol) and freshly ground $K_2CO_3$ (3.17 g, 23 mmol.) Stirred at 40° C. for one hour, until starting material consumed. Diluted with dichloromethane, washed with saturated $NH_4Cl$ solution, 2.5% LiCl solution, concentrated organics to give crude product. Chromatographed (15 to 55% ethylacetate/hexanes to give product 77 (2.54 g, 4.9 mmol, 85%.) $^1$H NMR (CDCl$_3$) δ 9.1 (dd, 1H), 8.64 (dd, 1H), 7.91 (s, 1H), 7.62 (m, 5H), 7.46 (dd, 2H), 7.27 (m, 7H), 7.05 (dd, 2H), 4.84 (s, 2H), 4.28 (s, 3H.) MS: 519 (M+1)

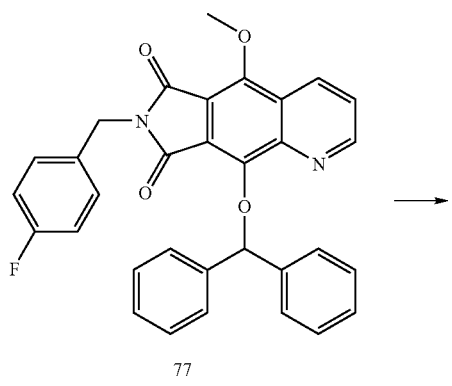

77

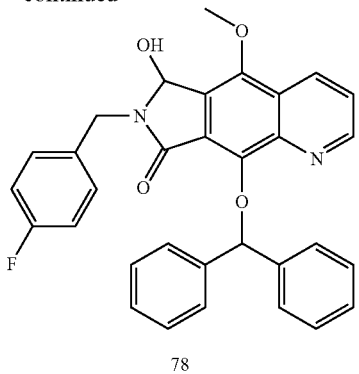

78

Example 78

Methyl ether 77 was dissolved in 115 mL of dry tetrahydrofuran and 25 mL of dry methanol. To this was added three equivalents of a 0.5 M solution of $NaBH_4$ (29.4 mL, 14.7 mmol) in 2-methoxyethyl ether. After 15 hrs at room temperature, concentrated off some solvent, diluted with dichloromethane, washed with 1M HCl solution with NaCl added, concentrated, chromatographed (15-66% ethylacetate/hexanes) to give oil. Triturated with hexane to give product 78 (1.3 g, 2.5 mmol, 68%.) $^1$H NMR (CD$_3$SOCD$_3$) δ 9.08 (dd, 1H), 8.5 (d, 1H), 7.89 (s, 1H), 7.75 (d, 2H), 7.69 (dd, 1H), 7.63 (d, 2H), 7.42 (dd, 2H), 7.27(m, 7H), 6.9(d, 1H), 5.92 (dd, 1H), 4.97 (d J=15 Hz, 1H), 4.45 (d J=15Hz, 1H), 4.04 (s, 3H.) MS: 521 (M+1)

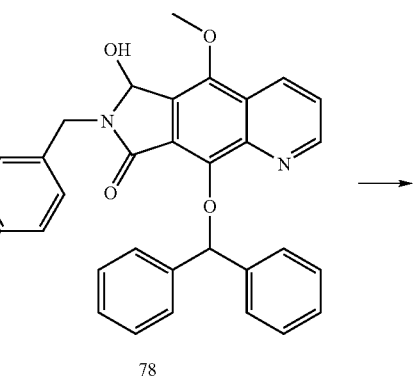

78

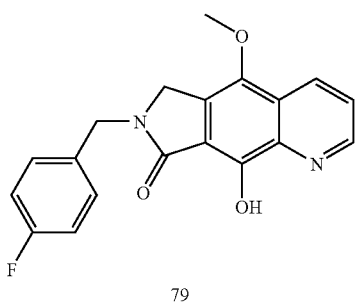

79

Example 79

Aminal 78 was dissolved in 15 mL of dichloromethane. To this was added 2 mL of triethylsilane and 1 mL of trifluoroacetic acid. Stirred at room temperature and after ten minutes complete by TLC. Concentrated off volatiles, azeotroped with toluene to give crude. Triturated with 1:1 diethylether/hexanes to give reduced product. Dissolved in 30 mL of dichloromethane and cooled to 0° C. To this was added 4 mL of triethylsilane and trimethylsilyltriflate (1.36 mL, 7.5 mmol.) Stirred vigorously for three minutes, then concentrated off volatiles, diluted with dichloromethane, washed quickly with saturated NaHCO$_3$ solution, concentrated organics to give crude product 79. Triturated with 1:1 diethylether/hexanes to give product (0.806 g, 2.38 mmol, 95% for two steps.) $^1$H NMR (CDCl$_3$) δ 8.96 (dd, 1H), 8.50 (d, 1H), 7.56 (dd, 1H), 7.37 (dd, 2H), 7.09 (dd, 2H), 4.78 (s, 2H), 4.51 (s, 2H), 3.98 (s, 3H). MS: 339 (M+1), 337 (M−1).

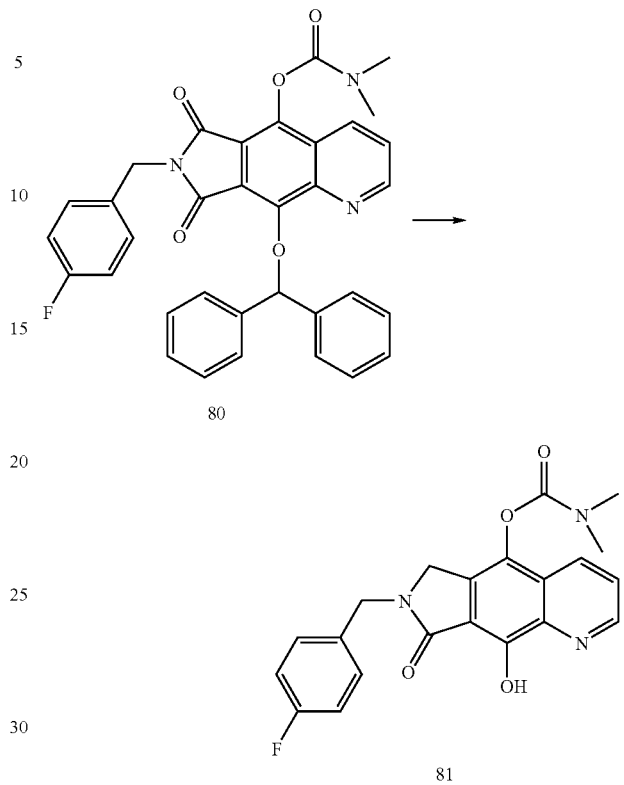

Example 80

Monophenol 45 (0.02 g, 0.0396 mmol) was dissolved in 1 mL dry dichloromethane. To this was added at 0° C. triethylamine (0.0165 mL, 0.1188 mmol) and dimethylcarbamoyl chloride (0.0054 mL, 0.0594 mmol). Catalytic amount of DMAP was also added. Stirred at room temperature overnight. Dilute with dichloromethane, washed with saturated NaHCO$_3$ solution and saturated NH$_4$Cl solution, concentrated to give crude. Triturated with 1:1 diethylether/hexanes and chromatographed (10% methanol/45% ethylacetate/45% hexanes) to give product 80 (0.012 g, 0.0198 mmol, 50%.) $^1$H NMR (CDCl$_3$) δ 9.12 (s, 1H), 8.4 (d, 1H), 7.97 (s, 1H), 7.62 (d, 4H), 7.43 (dd, 2H), 7.27 (m, 7H), 7.05 (dd, 2H), 4.81 (s, 2H), 3.26 (s, 3H), 3.09 (s, 3H.) MS: 576 (M+1)

Example 81

Carbamate 80 (0.012 g, 0.0198 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated with 1:1 diethylether/hexanes to give product 81 (0.0054 g, 0.013 mmol, 67%.) $^1$H NMR (CDCl$_3$) δ 8.98 (s, 1H), 8.49 (d, 1H), 7.7 (dd, 1H), 7.46 (dd, 2H), 7.03 (dd, 2H), 4.83 (s, 2H), 3.31 (s, 3H), 3.12 (s, 3H). MS: 410 (M+1), 408 (M−1).

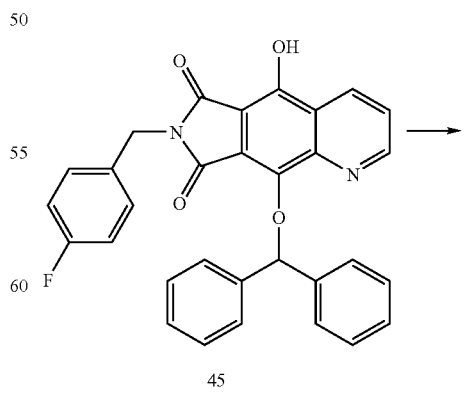

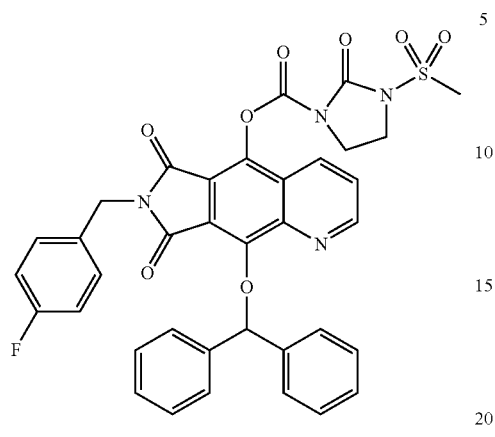

82

Example 82

Monophenol 45 (0.035 g, 0.0694 mmol) was dissolved in 1 mL dry dichloroethane. To this was added triethylamine (0.038 mL, 0.277 mmol) and 3-chlorocarbonyl-1-methanesulfonyl-2-imidazolidinone (0.0314 g, 0.1388 mmol Stirred at room temperature for five minutes. Dilute with dichloromethane, washed with saturated $NaHCO_3$ solution and saturated $NH_4Cl$ solution, dried ($MgSO_4$), concentrated to give crude. Chromatographed (10% methanol/45% ethylacetate/45% hexanes) to give product 82 (0.036 g, 0.0518 mmol, 75%.) $^1$H NMR ($CDCl_3$) 9.16 (dd, 1H), 8.49 (dd, 1H), 8.00 (s, 1H), 7.66 (dd, 1H), 7.61 (d, 4H), 7.40 (dd, 2H), 7.27 (m, 6H), 7.05 (dd, 2H), 4.81 (s, 2H), 4.2 (dd, 2H), 4.08 (dd, 2H), 3.92 (s, 3H). MS: 695 (M+1).

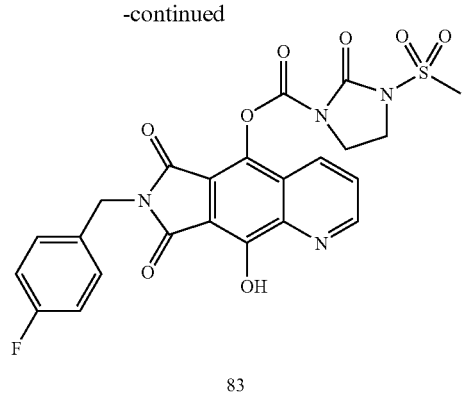

83

Example 83

Carbamate 82 (0.036 g, 0.0518 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated with 1:1 diethylether/hexanes to give product 83 (0.025 g, 0.047 mmol, 91%.) $^1$H NMR ($CDCl_3$) δ 9.04 (d, 1H), 8.58 (d, 1H), 7.75 (dd, 1H), 7.43 (dd, 2H), 7.04 (dd, 2H), 4.82 (s, 2H), 4.22 (dd, 2H), 4.10 (dd, 2H). MS: 529 (M+1), 527 (M−1).

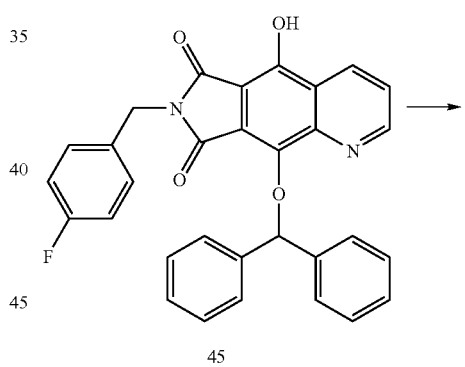

45

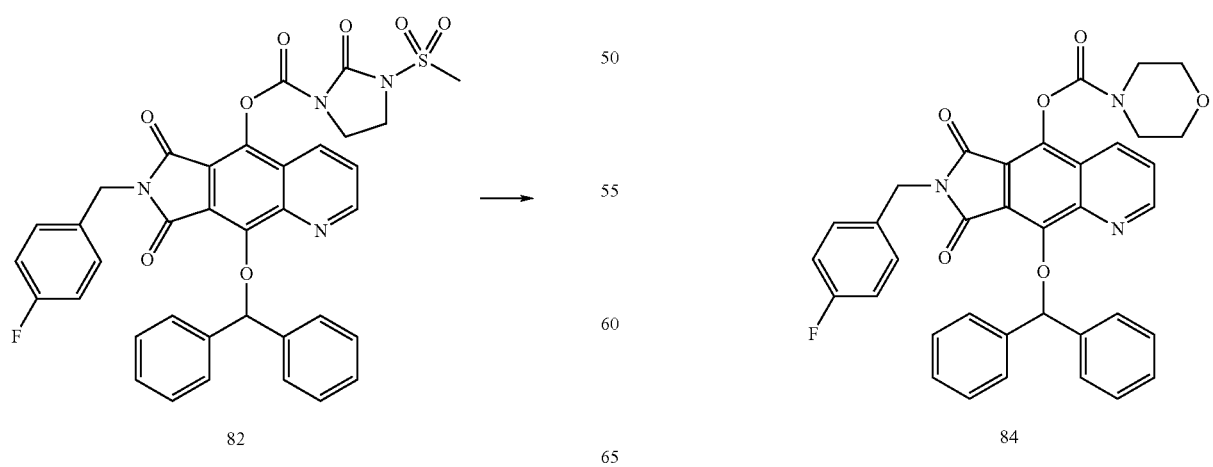

82 → 84

Example 84

Monophenol 45 (0.045 g, 0.089 mmol) was dissolved in 1 mL dry dichloroethane. To this was added triethylamine (0.049 mL, 0.356 mmol) and 4-morpholine carbonyl chloride (0.0207 mL, 0.178 mmol.) Stirred at room temperature for 1.5 hours. Dilute with dichloromethane, washed with saturated NaHCO$_3$, concentrated to give crude. Chromatographed (15% to 60% ethylacetate/hexanes) to give product 84 (0.039 g, 0.063 mmol, 71%.) $^1$H NMR (CDCl$_3$) 9.13 (dd, 1H), 8.40 (d, 1H), 7.98 (s, 1H), 7.62 (dd, 4H), 7.4 (dd, 2H), 7.27 (m, 7H), 7.05 (dd, 2H), 4.81 (s, 2H), 3.84 (br s, 6H), 3.62 (br s, 2H.) MS: 618 (M+1)

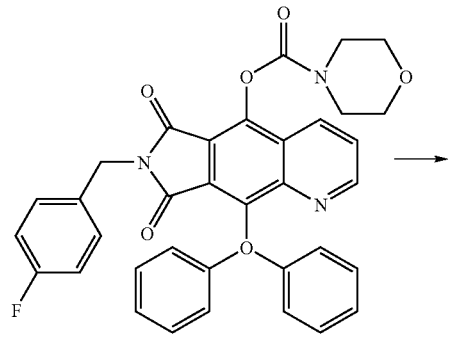

Example 85

Carbamate 84 (0.039 g, 0.063 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated with 1:1 diethylether/hexanes to give product 85 (0.014 g, 0.032 mmol, 51%.) $^1$H NMR (CDCl$_3$) δ 9.0 (d, 1H), 8.48 (d, 1H), 7.72 (dd, 1H), 7.49 (dd, 2H), 7.04 (dd, 2H), 4.83 (s, 2H), 3.88 (br s, 6H), 3.66 (br s, 2H.) MS: 452 (M+1), 450 (M−1)

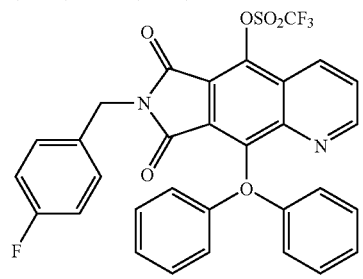

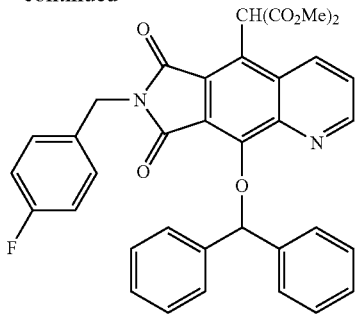

Example 86

Triflate 46 in benzene concentrated to give (0.048 g, 0.075 mmol) and dissolved in 1 mL dry tetrahydrofuran. To this was added freshly ground K$_2$CO$_3$ (0.069, 0.5 mmol) and dimethylmalonate (0.017 mL, 0.15 mmol) and stirred at 50° C. After 15 hours, starting material consumed, concentrated to give oil. Chromatographed (5% to 30% ethylacetate/hexanes) to give product 86 (0.012 g, 0.0195 mmol, 26%.) $^1$H NMR (CDCl$_3$) δ 9.09 (d, 1H), 8.51 (d, 1H), 8.12 (s, 1H), 7.65 (d, 4H), 7.57 (dd, 1H), 7.48 (dd, 2H), 7.27 (m, 6H), 7.07 (dd, 2H), 4.85 (s, 2H), 3.72 (6H.) MS: 619 (M+1)

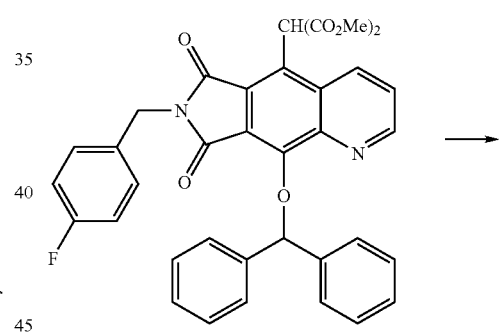

Example 87

Di-ester 86 (0.008 g, 0.0129 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated twice with 1:1 diethylether/hexanes to give product 87 (0.0022 g, 0.0049 mmol, 38%.) $^1$H NMR (CDCl$_3$) δ 8.95 (d, 1H), 8.60 (d, 1H), 7.70 (dd, 1H), 7.55 (dd, 2H), 7.05 (dd, 2H), 4.87 (s, 2H), 3.76 (s, 6H.) MS: 453 (M+1), 451 (M−1)

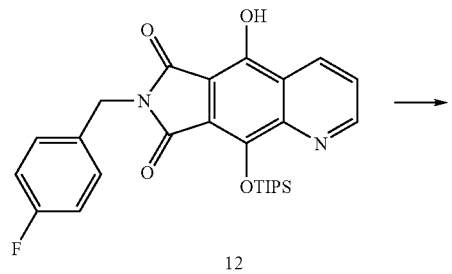

12

Example 88

Mono-phenol 12 (0.03 g, 0.06 mmol) was dissolved in 1 mL of dichloroethane. To this was added triethylamine (0.033 mL, 0.24 mmol) and 2-oxo-1-imidazolidinecarbonyl chloride (0.0178 g, 0.12 mmol.) Catalytic amount of DMAP added, and stirred at room temperature for three hours. Diluted with dichloromethane, washed with saturated NH$_4$Cl solution, concentrated to give crude. Chromatographed (10% ethylacetate/hexane to 10% methanol/45% ethylacetate/45% hexanes) to give product 88 (0.0247 g, 0.0395 mmol, 68%.) $^1$H NMR (CDCl$_3$) δ 8.96 (s, 1H), 8.53 (d, 1H), 7.63 (dd, 1H), 7.43 (dd, 2H), 7.03 (dd, 2H), 4.81 (s, 2H), 4.25 (dd, 2H), 3.69 (dd, 2H), 1.55 (m, 3H), 1.14 (d, 18H.) MS: 607 (M+1)

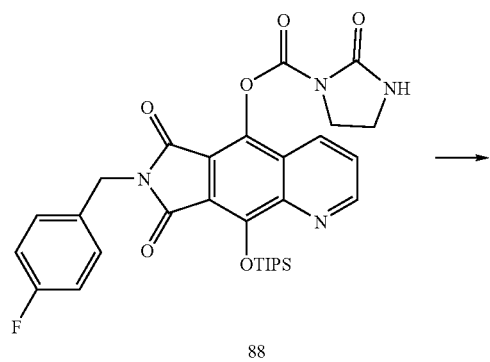

88

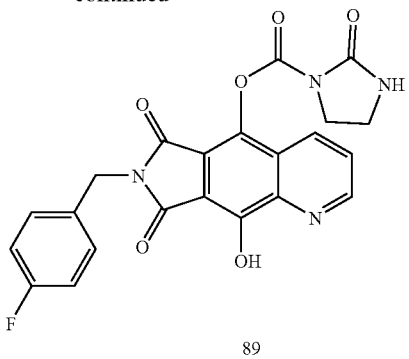

89

Example 89

Urea 88 (0.024 g, 0.0395 mmol) was dissolved in 1 mL of dry dichloromethane. To this was added ten equivalents (0.03 mL, 0.395 mmol) of trifluoroacetic acid. Stirred at room temperature, for fifteen hours. Concentrated off volatiles, azeotroped with toluene (2×), concentrated to give crude. Crude product triturated with 1:1 diethylether/hexanes to give product 89 (0.0119 g, 0.026 mmol, 67%.) $^1$H NMR (CDCl$_3$) δ 9.00 (d, 1H), 8.58 (d, 1H), 7.73 (dd, 1H), 7.47 (dd, 2H), 7.03 (dd, 2H), 4.83 (s, 2H), 4.28 (dd, 2H), 3.70 (dd, 2H.) MS: 451 (M+1), 449 (M−1)

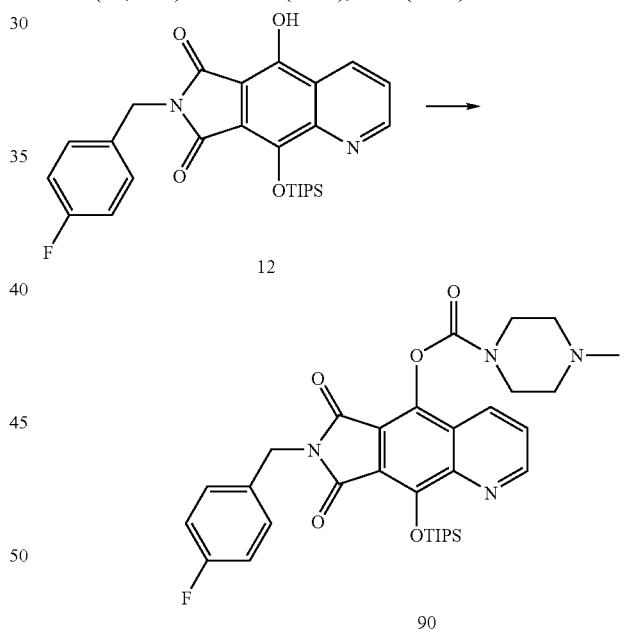

Example 90

Mono-phenol 12 (0.04 g, 0.08 mmol) was dissolved in 1.5 mL dry tetrahydrofuran. To this was added triethylamine (0.0445 mL, 0.32 mmol) and bispentafluorophenyl carbonate (0.063 g, 0.16 mmol) and catalytic dimethylaminopyridine. Stirred at room temperature. After three hours, added methyl piperazine (0.04 mL, 0.36 mmol.) After two hours TLC indicated product formed however TIPSCl was removed. Diluted with dichloromethane, washed with saturated NH$_4$Cl solution, concentrated organics to give crude. Dissolved in 1.5 mL dichloroethane, added triethylamine (0.11 mL, 0.8 mmol) and TTPSCl (0.085 mL, 0.4 mmol) and stirred at 50° C. Stirred for four hours until starting material was consumed. Diluted with dichloromethane, washed with saturated brine, concentrated organics to give crude. Chromatographed (50% ethylacetate/hexanes to 20% methanol/60% ethylacetate/20%hexanes) to give product 90 (0.027 g, 0.0435 mmol, 54% for two steps.) $^1$H NMR (CDCl$_3$) δ 9.05 (d, 1H), 8.60 (d, 1H), 7.61 (dd, 1H), 7.41 (dd, 2H), 7.03 (dd, 2H), 4.81 (s, 2H), 3.71 (br m, 8H), 2.43 (s, 3H), 1.60 (m, 3H), 1.15 (d, 18H.) MS: 621 (M+1)

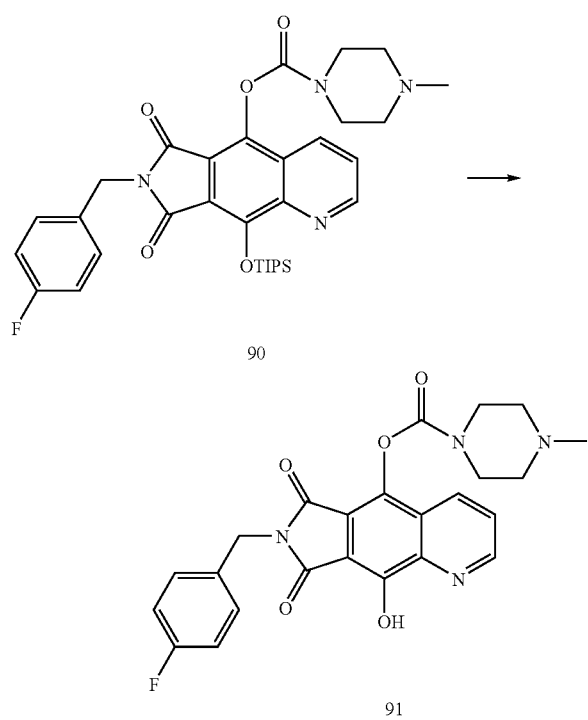

Example 91

Mono-carbamate 90 (0.027 g, 0.0435 mmol) was dissolved in 1 mL of dichloromethane. To this was added trifluoroacetic acid (0.067 mL, 0.87 mmol) and stirred at room temperature. After twenty hours, concentrated off volatiles, azeotroped with toluene (2×), concentrated to give crude. Triturate with 1:1 diethylether/hexanes to give product 91 (0.0177 g, 0.038 mmol, 87%.) $^1$H NMR (CD$_3$SOCD$_3$) δ 9.09 (s, 1H), 8.71 (d, 1H), 7.67 (dd, 1H), 7.42 (dd, 2H), 7.07 (dd, 2H), 4.81 (s, 2H), 3.45 (br m, 8H), 2.90 (s, 3H.) MS: 465 (M+1), 463 (M–1)

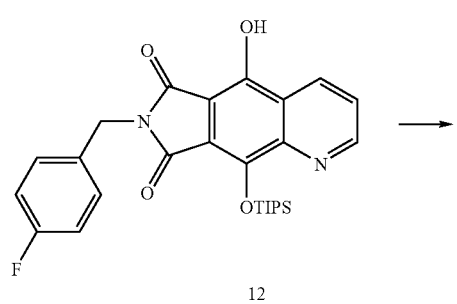

12

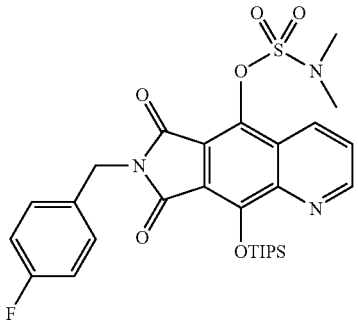

92

Example 92

Mono-phenol 12 (0.04 g, 0.08 mmol) was dissolved in 1.5 mL dichloromethane. To this was added triethylamine (0.044 mL, 0.32 mmol), dimethylsulfamoyl chloride (0.017 mL, 0.16 mmol) and catalytic dimethylaminopyridine. Stirred at room temperature for 30 minutes. Diluted with dichloromethane, washed with saturated NH4Cl solution, concentrated organics to give crude. Chromatographed (25% ethylacetate/hexanes) to give product 92 (0.017 g, 0.02828 mmol, 35%.) $^1$H NMR (CDCl$_3$) δ 8.95 (d, 1H), 8.79 (d, 1H), 7.66 (dd, 1H), 7.45 (dd, 2H), 7.03 (dd, 2H), 4.84 (s, 2H), 3.24 (s, 6H), 1.55 (M, 3 h), 1.14 (d, 18H.) MS: 602 (M+1)

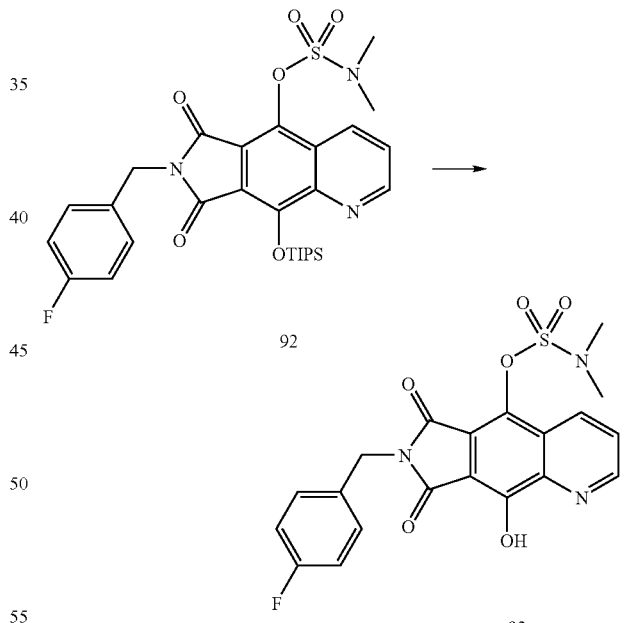

Example 93

Mono-carbamate 92 (0.017 g, 0.02828 mmol) was dissolved in 1 mL of dichloromethane. To this was added trifluoroacetic acid (0.044 mL, 0.5657 mmol) and stirred at room temperature. After twenty hours, concentrated off volatiles, azeotroped with toluene (2×), concentrated to give crude. Triturate with 1:1 diethylether/hexanes to give product 93 (0.0081 g, 0.018 mmol, 64%.) $^1$H NMR (CDCl$_3$) δ

9.00 (d, 1H), (8.84 (d, 1H), 7.76 (dd, 1H), 7.49 (dd, 2H), 7.03 (dd, 2H), 4.86 (s, 2H), 3.24 (s, 6H.) MS: 446 (M+1), 444 (M−1)

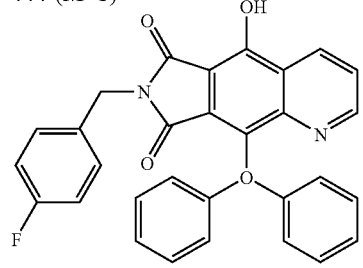

45

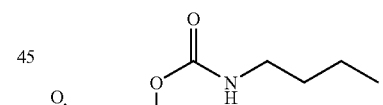

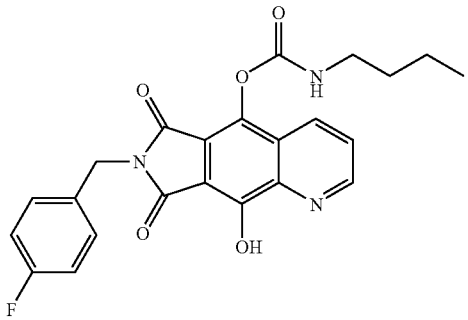

-continued

95

Example 95

Carbamate 94 (0.006 g, 0.0099 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude which was triturated twice with 1:1 diethylether/hexanes to give product 95 (0.0014 g, 0.003 mmol, 32%.) $^1$H NMR (CDCl$_3$) δ 8.98 (s, 1H), 8.49 (d, 1H), 7.68 (dd, 1H), 7.47 (dd, 2H), 7.03 (dd, 2H), 5.40 (m, 1H), 4.83 (s, 2H), 3.38 (q, 2H), 3.15 (m, 2H), 1.49 (m, 2H), 1.03 (t, 3H.) MS: 438 (M+1), 436 (M−1)

94

Example 94

Mono-phenol 45 (0.04 g, 0.08 mmol) was dissolved in 1.5 mL tetrahydrofuran. To this was added diisopropylethylamine (0.052 mL, 0.3 mmol), bis-pentafluorophenyl carbonate (0.047 g, 0.119 mmol) and catalytic dimethylaminopyridine. Stirred at room temperature. After 75 minutes, cooled to 0° C., n-butylamine (0.079 mL, 0.08 mmol) added. Stirred for 1.5 hours, then diluted with dichloromethane, washed with saturated brine, 1 M HCl, concentrated organics to give crude. Chromatographed (25% ethylacetate/hexanes to give product 94 (0.0028 g, 0.0048 mmol, 6%.) $^1$H NMR (CDCl$_3$) δ 9.12 (d, 1H), 8.41 (d, 1H), 7.98 (s, 1H), 7.61 (d, 4H), 7.43 (dd, 2H), 7.27 (m, 7H), 7.043 (dd, 2H), 5.37 (m, 1H), 4.82 (s, 2H), 3.35 (q, 2H), 1.67 (m, 2H), 1.49 (m, 2H), 1.01 (t, 3H.) MS: 604 (m+1)

Example 96

Monophenol 45 (0.05 g, 0.099 mmol) was dissolved in 0.5 mL of dichloromethane. To this was added triethylamine (0.03 mL, 0.2 mmol) and pyrrolidine carbonyl chloride (0.0214 mL, 0.2 mmol.) Stirred at 30° C. for fifteen hours. Diluted with dichloromethane, washed with 1 M HCl solution, concentrated organics to give crude. Chromatographed (20% to 50% ethylacetate/hexanes) to give product 96 (0.033 g, 0.0555 mmol, 57%.) $^1$H NMR (CDCl$_3$) δ 9.11 (dd, 1H), 8.45 (d, 1H), 7.97 (s, 1H), 7.62 (d, 5H), 7.40 (dd, 2H), 7.27 (m, 6H), 7.05 (dd, 2H), 4.81 (s, 2H), 3.75 (dd, 2H), 3.54 (dd, 2H), 2.05 (m, 4H.) MS: 602 (M+1)

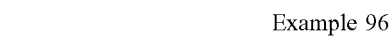

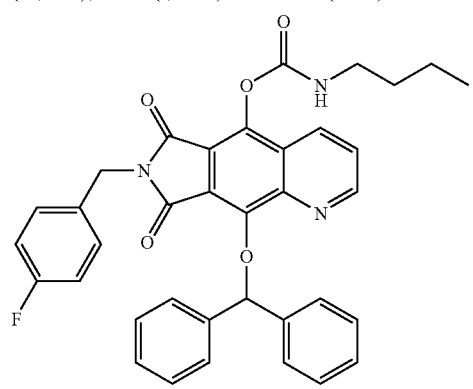

94

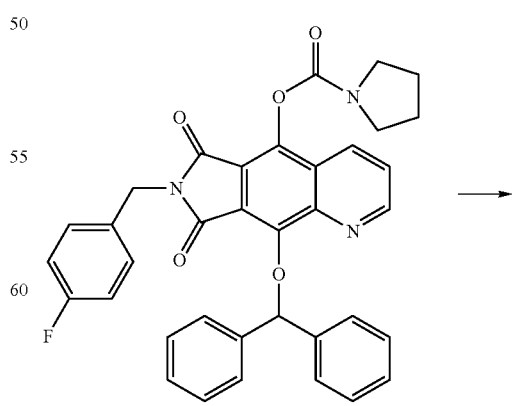

96

-continued

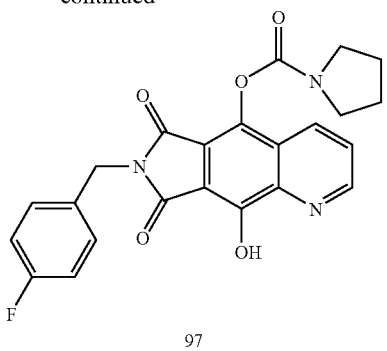

97

Example 97

Carbamate 96 (0.033 g, 0.055 mmol) was dissolved in 0.5 mL of dichloromethane. Triethylsilane (0.2 mL) and of trifluoroacetic acid (0.1 mL) were added. The mixture was stirred at room temperature and was complete after ten minutes by TLC. The mixture was concentrated in vacuo and azeotroped with toluene to give a crude residue which was triturated twice with 1:1 diethylether/hexanes to give product 97 (0.0123 g, 0.028 mmol, 51%). $^1$H NMR (CDCl$_3$) δ 8.98 (d, 1H), 8.51 (d, 1H), 7.70 (dd, 1H), 7.46 (dd, 2H), 7.03 (dd, 2H), 4.82 (s, 2H), 3.81 (dd, 2H), 3.57 (dd, 2H), 2.09 (m, 4H.) MS: 436 (M+1), 434 (M−1)

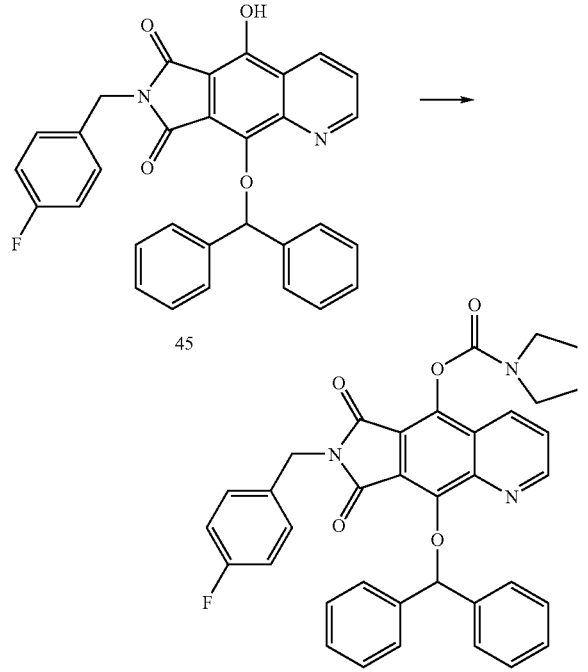

Example 98

Monophenol 45 (0.03 g, 0.06 mmol) was dissolved in 1.5 mL of dichloromethane. Triethylamine (0.033 mL, 0.238 mmol) and diethylcarbamoyl chloride (0.015 mL, 0.119 mmol) were added. The mixture was stirred at 60° C. for five hours. The mixture was diluted with dichloromethane, washed with 1 M HCl solution, and concentrated to give crude product. The crude product was chromatographed (20% to 50% ethylacetate/hexanes) to give product 98 (0.0237 g, 0.040 mmol, 66%.) $^1$H NMR (CDCl$_3$) δ 9.12 (s, 1H), 8.34 (d, 1H), 7.97 (s, 1H), 7.63 (d, 4H), 7.40 (dd, 2H), 7.27 (m, 7H), 7.01 (dd, 2H), 4.81 (s, 2H), 3.61 (dd, 2H), 3.50 (q, 2H), 1.41 (t, 3H), 1.37 (t, 3H.) MS: 604 (M+1)

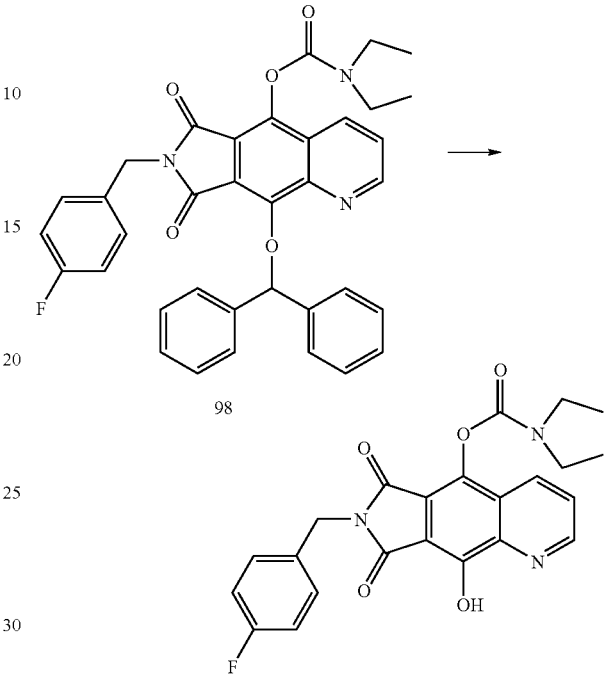

Example 99

Carbamate 98 (0.023 g, 0.04 mmol) was dissolved in 0.5 mL of dichloromethane. Triethylsilane (0.2 mL) and trifluoroacetic acid (0.1 mL) were added. The mixture was stirred at room temperature and after ten minutes was complete by TLC. Concentrated off volatiles, azeotroped with toluene to give crude. Triturated twice with 1:1 diethylether/hexanes to give product 99 (0.01 g, 0.024 mmol, 60%.) $^1$H NMR (CDCl$_3$) δ 8.98 (d, 1H), 8.45 (d, 1H), 7.70 (dd, 1H), 7.48 (dd, 2H), 7.03 (dd, 2H), 4.82 (s, 2H), 3.67 (M−1) 2H), 3.48 (q, 2H), 1.46 (t, 3H), 1.32 (t, 3H.) MS: 438 (M+1), 436 (M−1)

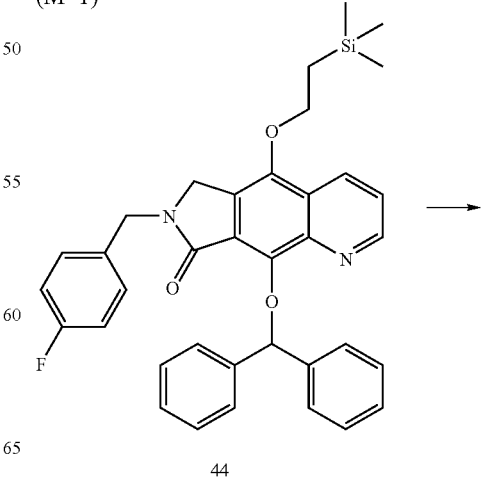

44

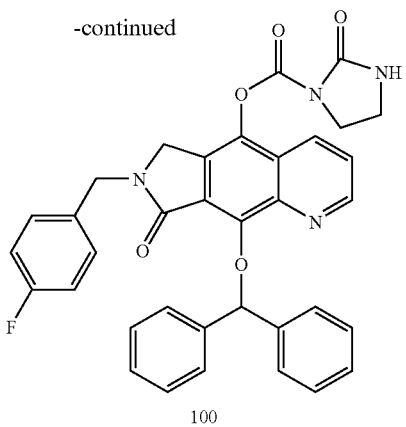

100

Example 100

Trimethylsilyl ether 44 (0.022 g, 0.0373 mmol) was dissolved in 0.5 mL dry tetrahydrofuran. To this was added triethylamine (0.031 mL, 0.2238 mmol) and 1 M tetrabutylammonium fluoride solution in tetrahydrofuran (0.0559 mL, 0.0559 mmol.) Stirred at room temperature 10 minutes until starting material consumed. Then added catalytic amount of dimethylaminopyridine and 2-oxo-1-imidazolidinecarbonyl chloride (0.022 g, 0.1492 mmol.) Stirred at room temperature for three hours, then diluted with dichloromethane, washed with 1M HCl solution, saturated NaHCO$_3$, saturated brine, concentrated to give crude. Chromatographed (50% ethylacetate/hexanes to 1:1:1 methanol, ethylacetate, hexanes) to give product 100 (0.0197 g, 0.031 mmol, 88%.) $^1$H NMR (CDCl$_3$) δ 9.04 (dd, 1H), 8.31 (d, 1H), 8.02 (s, 1H), 7.73 (d, 4H), 7.53 (dd, 1H), 7.27 (m, 6H), 7.04 (dd, 2H), 5.00 (s, 1H) 4.80 (s, 2H), 4.10 (dd, 2H), 3.64 (dd, 2H.) MS: 603 (M+1)

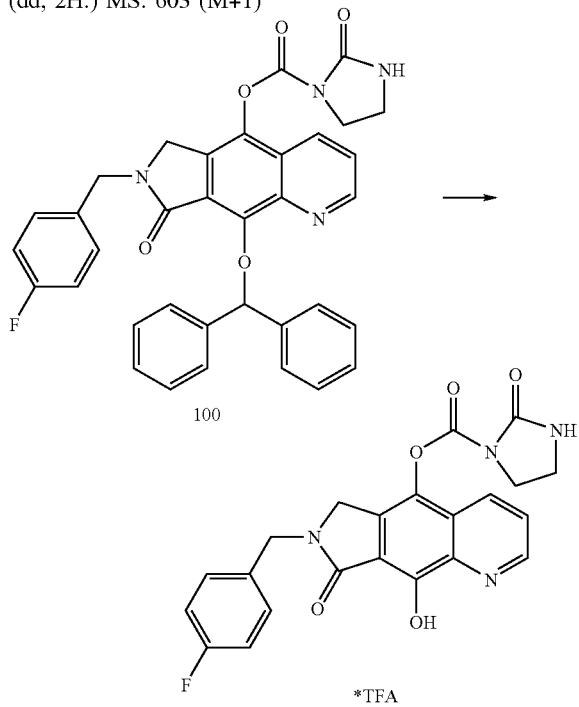

Example 101

Carbamate 100 (0.019 g, 0.031 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated twice with 1:1 diethylether/hexanes to give product 101 (0.006 g, 0.011 mmol, 35%.) $^1$H NMR (CD$_3$SOCD$_3$) δ 8.98 (s, 1H), 8.48 (d, 1H), 7.77 (dd, 1H), 7.72 (s, 1H), 7.36 (dd, 2H), 7.22 (dd, 2H), 4.70 (s, 2H), 4.37 (s, 2H), 4.03 (dd, 2H), 3.41 (dd, 2H.) $^{19}$F NMR: −74.6 MS: 437 (M+1), 435 (M−1)

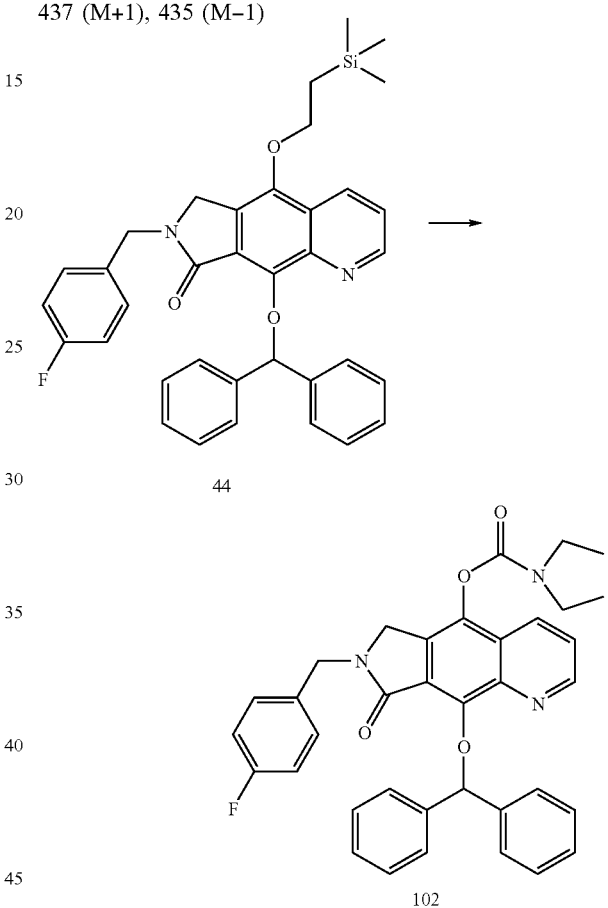

Example 102

Trimethylsilylethyl ether 44 (0.03 g, 0.0508 mmol) was dissolved in 0.5 mL dry tetrahydrofuran. Triethylamine (0.042 mL, 0.3048 mmol) and 1 M tetrabutylammonium fluoride solution in tetrahydrofuran (0.1016 mL, 0.1016 mmol) were added and stirred at room temperature for 10 minutes until starting material was consumed. A catalytic amount of dimethylaminopyridine was added, followed by diethylcarbamoyl chloride (0.026 mL, 0.2032 mmol). The mixture was stirred at room temperature for four hours, then diluted with dichloromethane, washed with 1M HCl solution, saturated NaHCO$_3$, saturated brine, and concentrated to the crude product. Chromatographed (25% to 50% ethylacetate/hexanes) to give product 102 (0.014 g, 0.024 mmol, 47%.) $^1$H NMR (CDCl$_3$) δ 9.04 (s, 1H), 8.11 (d, 1H), 8.03 (s, 1H), 7.76 (d, 4H), 7.51 (dd, 1H), 7.27 (m, 8H), 7.08 (dd, 2H), 4.80 (s, 2H), 4.21 (s, 2H), 3.53 (q, 2H), 3.40 (q, 2H), 1.33 (t, 3H), 1.23 (t, 3H.) MS: 590 (M+1)

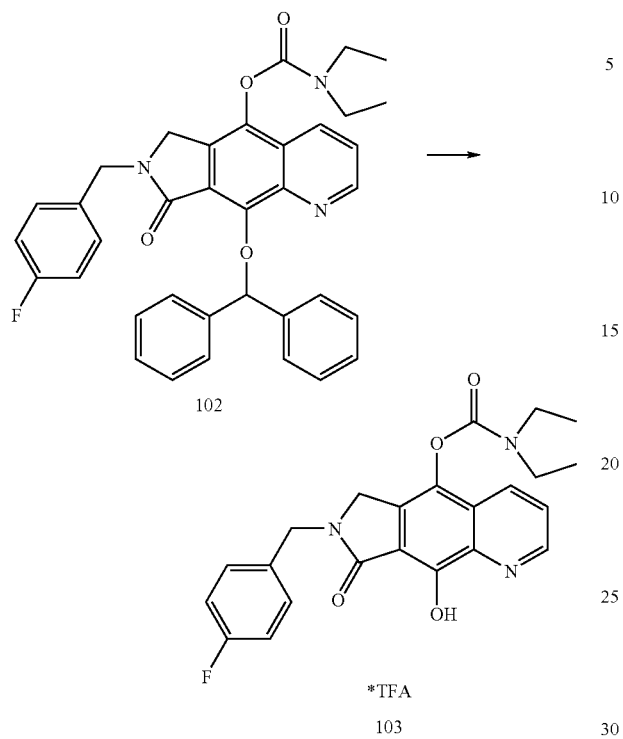

102

103 *TFA

Example 103

Carbamate 102 (0.01 g, 0.0169 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated twice with 1:1 diethylether/hexanes to give product 103 (0.0073 g, 0.014 mmol, 80%.) $^1$H NMR (CDCl$_3$) δ 9.01 (s, 1H), 8.23 (d, (1H), 7.60 (dd, 1H), 7.33 (dd, 2H), 7.09 (dd, 2H), 4.77 (s, 2H), 4.37 (s, 2H), 3.56 (q, 2H), 3.43 (q, 2H), 1.37 (t, 3H), 1.26 (t, 3H.) $^{19}$F NMR: −76.2 MS: 424 (M+1), 422 (m−1)

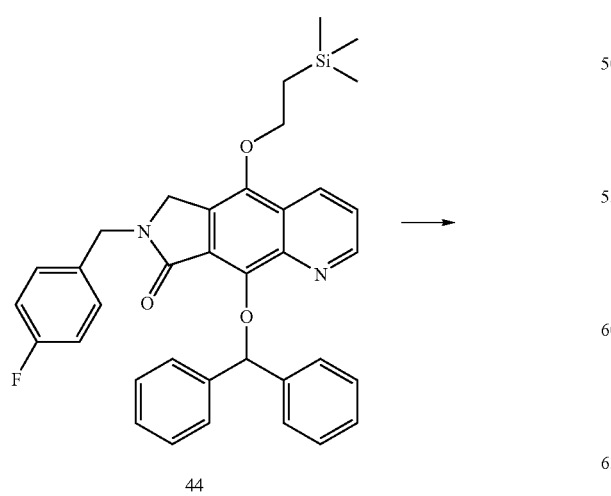

44

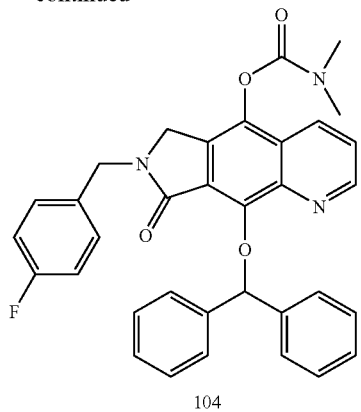

104

Example 104

Trimethylsilylethyl ether 44 (0.03 g, 0.0508 mmol) was dissolved in 0.5 mL dry tetrahydrofuran. To this was added triethylamine (0.042 mL, 0.3048 mmol) and 1 M tetrabutylammonium fluoride solution in tetrahydrofuran (0.1016 mL, 0.1016 mmol.) Stirred at room temperature 10 minutes until starting material consumed. Then added catalytic amount of dimethylaminopyridine and dimethylcarbamoyl chloride (0.0187 mL, 0.2032 mmol.) Stirred at room temperature for six hours, then diluted with dichloromethane, washed with 1M HCl solution, saturated NaHCO$_3$, saturated brine, concentrated to give crude. Chromatographed (20% to 50% ethylacetate/hexanes) to give product 104 (0.014 g, 0.024 mmol, 48%.) $^1$H NMR (CDCl$_3$) δ 9.04 (d, 1H), 8.14 (d, 1H), 8.03 (s, 1H), 7.75 (d, 4H), 7.51 (dd, 1H), 7.27 (m, 8H), 7.16 (dd, 2H), 4.80 (s, 2H0, 4.23 (s, 2H), 3.19 (s, 3H), 3.02 (s, 3H.) MS: 562 (M+1)

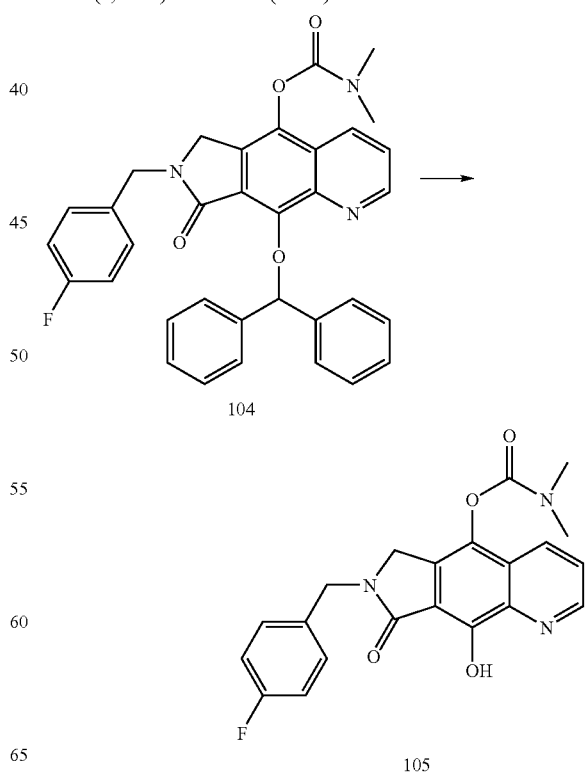

104

105

Example 105

Carbamate 104 (0.012 g, 0.021 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated twice with 1:1 diethylether/hexanes to give product 105 (0.0068 g, 0.017 mmol, 82%.) $^1$H NMR (CDCl$_3$) δ 8.96 (s, 1H), 8.25 (d, 1H), 7.59 (dd, 1H), 7.36 (dd, 2H), 7.09 (dd, 2H), 4.77 (s, 2H), 4.38 (s, 2H), 3.24 (s, 3H), 3.06 (s, 3H.) MS: 396 (M+1), 394 (M−1)

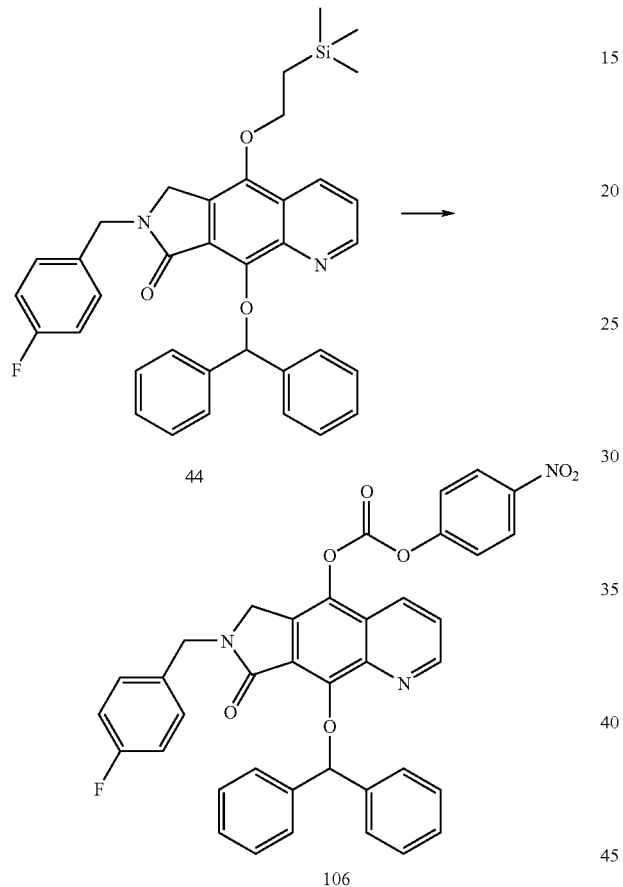

Example 106

Trimethylsilylethyl ether 44 (0.03 g, 0.0508 mmol) was dissolved in 0.5 mL dry tetrahydrofuran. To this was added triethylamine (0.0282 mL, 0.2032 mmol) and 1 M tetrabutylammonium fluoride solution in tetrahydrofuran (0.076 mL, 0.076 mmol.) Stirred at room temperature 10 minutes until starting material consumed. After fifteen minutes, diluted with dichloromethane, washed with washed with 1M HCl solution, saturated NaHCO$_3$, saturated brine, concentrated to give crude. Diluted in 1 mL dichloromethane. To this was added triethylamine (0.028 mL, 0.2032 mmol), para-nitrochloroformate (0.02 g, 0.1016 mmol) and catalytic dimethylaminopyridine. Stirred at room temperature for 30 minutes, then diluted with dichloromethane, washed with saturated NH$_4$Cl solution, concentrated organics to give crude. Chromatographed (50% ethylacetate/hexanes) to give product 106 (0.009 g, 0.0137 mmol, 27%) $^1$H NMR (CDCl$_3$) δ 9.10 (s, 1H), 8.16 (d, 2H), 8.10 (s, 1H), 7.71 (d, 4H), 7.53 (dd, 1H), 7.27 (m, 9H), 7.09 (dd, 2H), 6.93 (d, 2H), 4.79 (s, 2H), 4.23 (s, 2H.) MS: 656 (M+1)

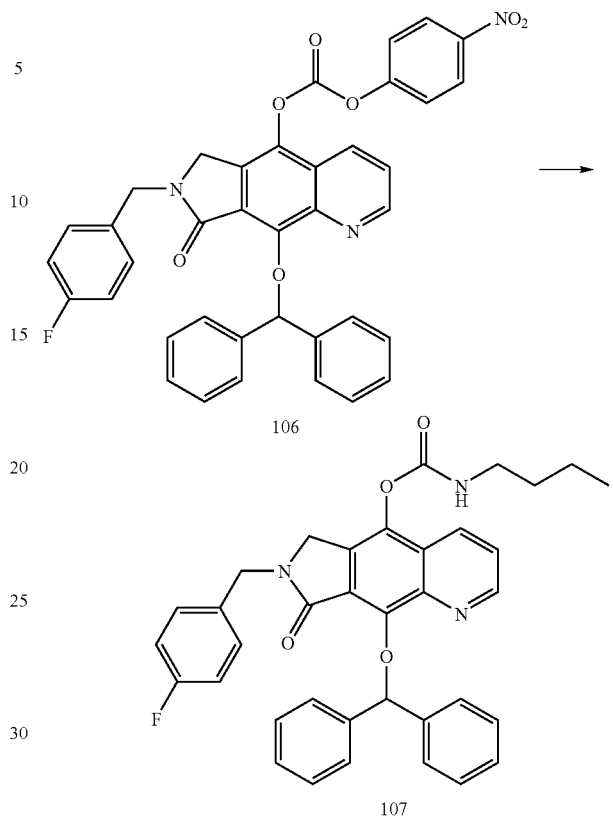

Example 107

Carbonate 106 (0.009 g, 0.0137 mmol) was dissolved in 0.5 mL dichloromethane. To this was added triethylamine (0.0282 mL, 0.2032 mmol) and n-butylamine (0.01 mL, 0.1016 mmol) and stirred at room temperature. After 15 minutes, starting material consumed. Diluted with dichloromethane, washed with 1M HCl solution, saturated brine, concentrated to give crude. Chromatographed (30% ethylacetate/hexanes) to give product 107 (0.0075 g, 0.012 mmol, 88%.) $^1$H NMR (CDCl$_3$) δ 9.02 (s, 1H), 8.15 (d, 1H), 8.04 (s,1H), 7.75 (d, 4H), 7.50 (dd, 1H), 7.27 (m, 6H), 7.08 (dd, 2H), 5.18 (s, 1H), 4.80 (s, 2H), 4.21 (s, 2H), 3.31 (q, 2H), 1.59 (m, 2H), 1.41 (m, 2H), 0.99 (t, 3H.) MS: 590 (M+1)

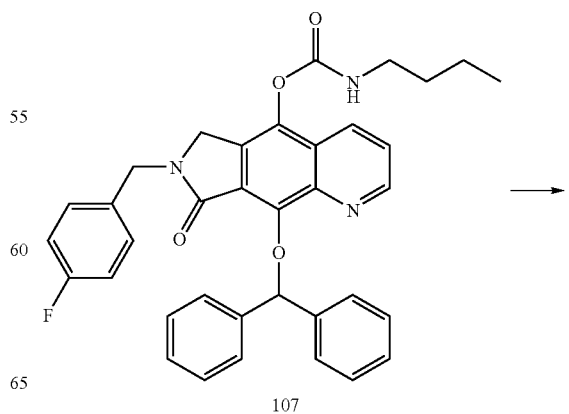

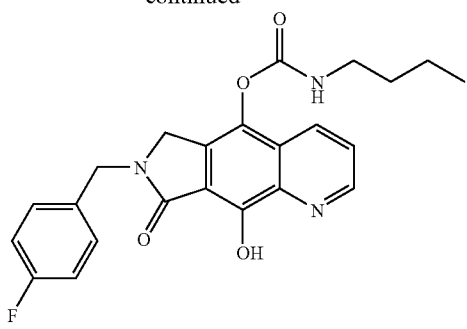

108

Example 108

Carbamate 107 (0.007 g, 0.012 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated twice with 1:1 diethylether/hexanes to give product 108 (0.0028 g, 0.0066 mmol, 56%.) $^1$H NMR (CDCl$_3$) δ 8.98 (s, 1H), 8.27 (d, 1H), 7.59 (dd, 1H), 7.31 (dd, 2H), 7.06 (dd, 2H), 5.19 (s, 1H), 4.77 (s, 2H), 4.37 (s, 2H), 3.32 (q, 2H), 1.65 (m, 2H), 1.44 (m, 2H), 1.01 (t, 3H) MS: 424 (M+1), 422 (M-1)

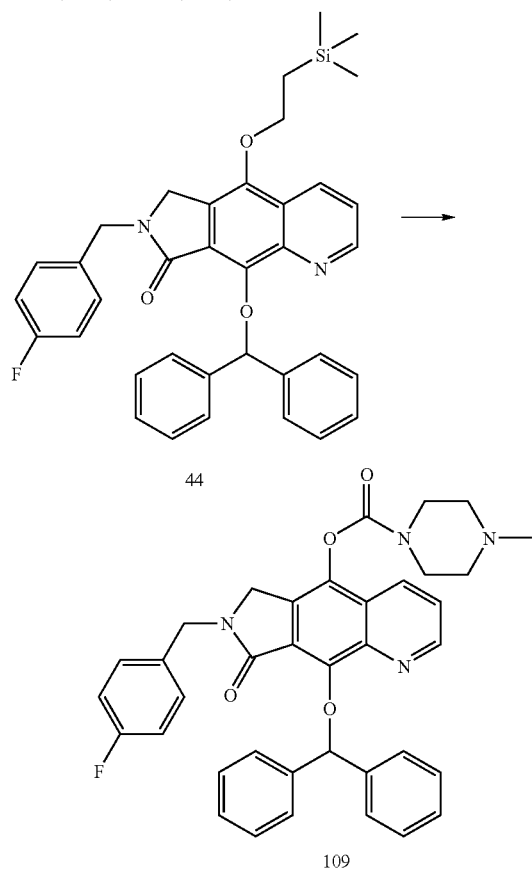

44

109

Example 109

Trimethylsilylethyl ether 44 (0.01 g, 0.0169 mmol) was dissolved in 0.5 mL dry tetrahydrofuran. To this was added triethylamine (0.014 mL, 0.0339 mmol) and 1 M tetrabutylammonium fluoride solution in tetrahydrofuran (0.0339 mL, 0.0339 mmol.) Stirred at room temperature 10 minutes until starting material consumed. Diluted with dichloromethane, washed with washed with 1M HCl solution, saturated NaHCO$_3$, saturated brine, concentrated to give crude. Dissolved in 0.5 mL dichloromethane, added catalytic dimethylaminopyridine, triethylamine (0.042 mL, 0.1017 mmol) and cooled to 0° C. To this was added a 1M solution of triphosgene in dichloromethane (0.1017 mL, 0.1017 mmol) and stirred 30 minutes. Methyl piperazine (0.0168 mL, 0.1521 mmol) was then added and stirred at room temperature for fifteen minutes. Diluted with dichloromethane, washed with brine, concentrated volatiles to give crude. Chromatographed (50% ethylacetate/hexanes to 10% methanol/ethylacetate) to give product 109 (0.0055 g, 0.009 mmol, 53%.) $^1$H NMR (CDCl$_3$) δ 9.04 (d, 1H), 8.10 (d, 1H), 8.03 (s, 1H), 7.75 (d, 4H), 7.52 (dd, 1H), 7.27 (m, 8H), 7.05 (dd, 2H), 4.80 (s, 2H), 4.22 (s, 2H), 3.77 (br s, 2H), 3.58 (br s, 2H), 2.48 (br s, 4H), 2.37 (s, 3H.) MS: 617 (M+1)

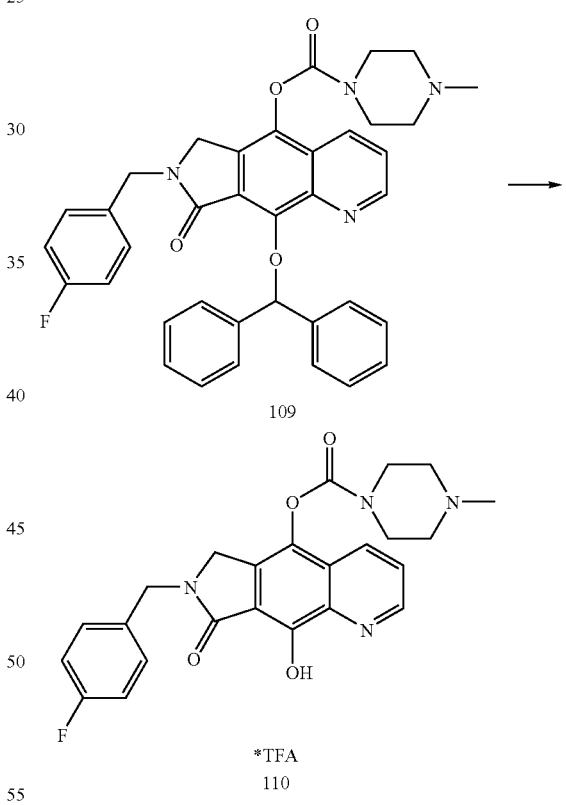

109

*TFA
110

Example 110

Carbamate 109 (0.007 g, 0.01136 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated twice with 1:1 diethylether/hexanes to give product 110 (0.004 g, 0.007 mmol, 63%.) $^1$H NMR (CDCl$_3$) δ 9.00 (s, 1H), 8.11 (d, 1H), 7.59 (dd, 1H), 7.35 (dd, 2H), 7.08 (dd, 2H), 4.78 (s, 2H), 4.35 (s, 2H), 3.50 (br m, 8H), 2.93 (s, 3H.), $^{19}$F NMR: −76.2 MS: 451 (M+1), 449 (M−1)

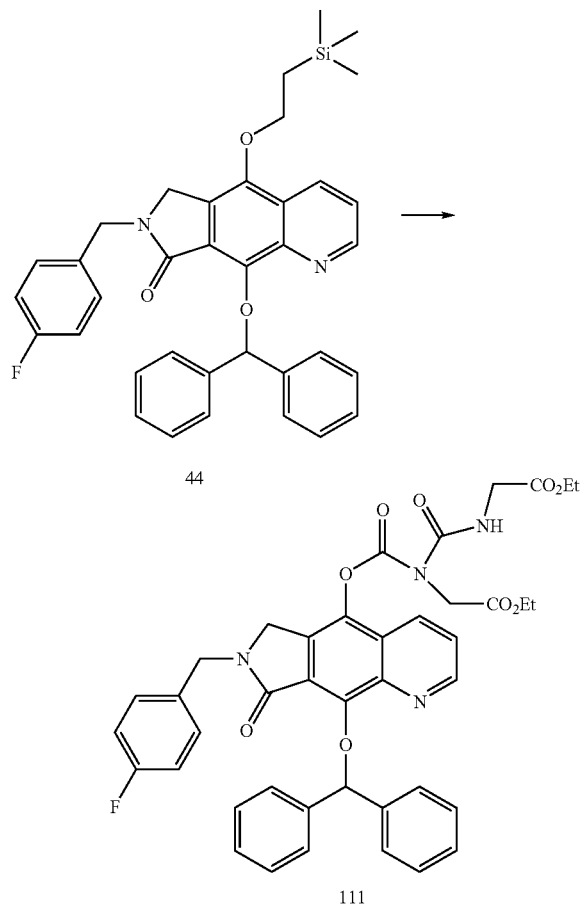

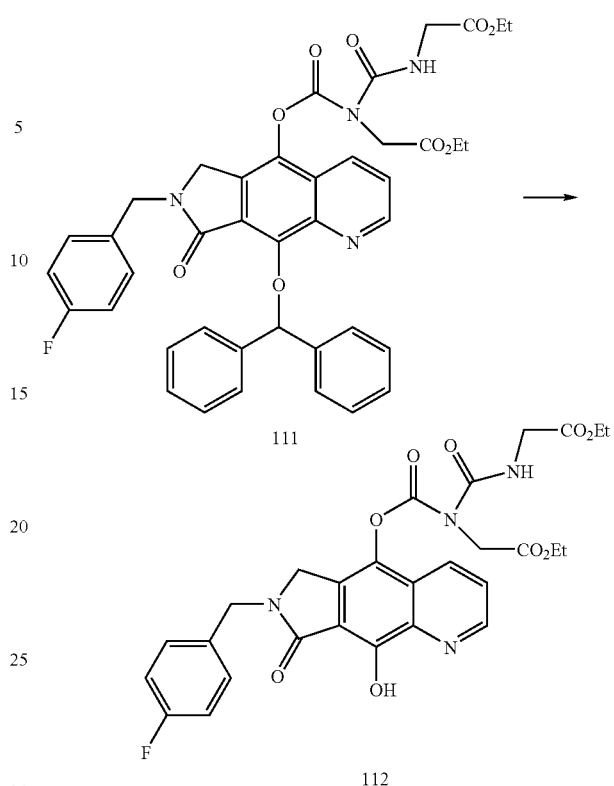

Example 112

Carbamate 111 (0.011 g, 0.0177 mmol) was dissolved in 0.5 mL of dichloromethane. To this was added 0.2 mL of triethylsilane and 0.1 mL of trifluoroacetic 5 acid. Stirred at room temperature and after ten minutes complete by TLC. Concentrated off volatiles, azeotroped with toluene to give crude. Triturated twice with 1:1 diethylether/hexanes to give product 112 (0.0056 g, 0.0095 mmol, 54%.) $^1$H NMR (CDCl$_3$) δ 8.99 (s, 1H), 8.76 (s, 1H), 8.27 (d, 1H), 7.63 (dd, 1H), 7.35 (dd, 2H), 7.09 (dd, 2H), 4.79 (d, 4H), 4.33 (d, 2H), 4.23 (m, 4H), 4.09 (d, 2H), 1.30 (m, 6H.) MS: 583 (M+1), 581 (M−1)

Example 111

Trimethylsilylethyl ether 44 (0.02 g, 0.0339 mmol) was dissolved in 0.5 mL dry tetrahydrofuran. Triethylamine (0.0188 mL, 0.135 mmol) and 1 M tetrabutylammonium fluoride solution in tetrahydrofuran (0.0678 mL, 0.0678 mmol) were added. The mixture was stirred at room temperature for 10 minutes until starting material consumed. The mixture was diluted with dichloromethane, washed with 1M HCl solution, saturated NaHCO$_3$, saturated brine, and concentrated to give crude. The crude residue was dissolved in 0.5 mL dichloromethane, and catalytic dimethylaminopyridine, triethylamine (0.0188 mL, 0.135 mmol) and ethyl isocyanatoacetate (Aldrich, St. Louis, Mo., 0.011 mL, 0.1017 mmol) were added and stirred at room temperature (Satchell and Satchell, Chem. Soc. Rev. (1975) 4:231-250; R. G. Arnold etal., Chem. Soc. (1957) 57:47-76). After four hours, starting material was consumed. The mixture was diluted with dichloromethane, washed with 1M HCl, brine, and concentrated in vacuo to give crude product. The crude product was chromatographed on silica gel (10% to 50% ethylacetate/hexanes) to give product 111 (0.0118 g, 0.156 mmol, 46%) $^1$H NMR (CDCl$_3$) δ 9.07 (d, 1H), 8.73 (s, 1H), 8.17 (d, 1H), 8.08 (s, 1H), 7.76 (d, 4H), 7.57 (dd, 1H), 7.27 (m, 8H), 7.08 (dd, 2H), 4.81 (s, 2H), 4.74 (s, 2H), 4.20 (m, 4H), 4.07 (d, 4H), 1.27 (m, 6H). MS: 749 (M+1), 747 (M−1).

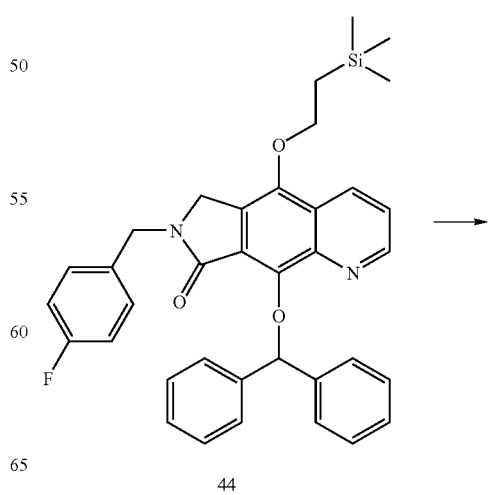

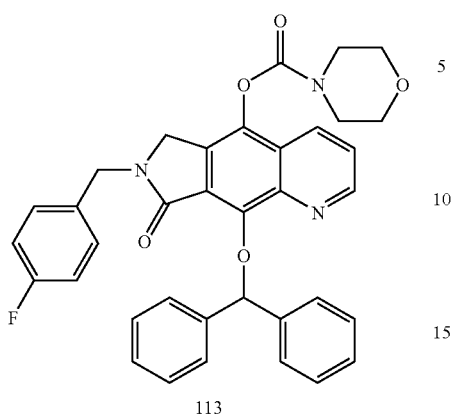

113

Example 113

Trimethylsilylethyl ether 44 (0.02 g, 0.0339 mmol) was dissolved in 0.5 mL dry tetrahydrofuran. To this was added triethylamine (0.019 mL, 0.14 mmol) and 1 M tetrabutylammonium fluoride solution in tetrahydrofuran (0.0678 mL, 0.0678 mmol.) Stirred at room temperature 10 minutes until starting material consumed. Diluted with dichloromethane, washed with washed with 1M HCl solution, saturated NaHCO$_3$, saturated brine, concentrated to give crude. Dissolved in 0.5 mL dichloromethane, added catalytic dimethylaminopyridine, triethylamine (0.019 mL, 0.14 mmol) and cooled to 0° C. To this was added a 1M solution of triphosgene in dichloromethane (0.0678 mL, 0.0678 mmol) and stirred 60 minutes. Morpholine (0.009 mL, 0.1016 mmol) was then added and stirred at room temperature for 30 minutes. Diluted with dichloromethane, washed with 1M HCl, brine, concentrated volatiles to give crude. Chromatographed (40% ethylacetate/hexanes to 60% ethylacetate/hexanes) to give product 113 (0.0176 g, 0.028 mmol, 86%.) $^1$H NMR (CDCl$_3$) δ 9.05 (d, 1H), 8.09 (d, 1H), 8.04 (s, 1H), 7.75 (d, 4H), 7.53 (dd, 1H), 7.27 (m, 8H), 7.06 (dd, 2H), 4.81 (s, 1H), 4.23 (s, 2H), 3.78 (br s, 6H), 3.56 (br s, 2H.) MS: 604 (M+1), 602 (M−1)

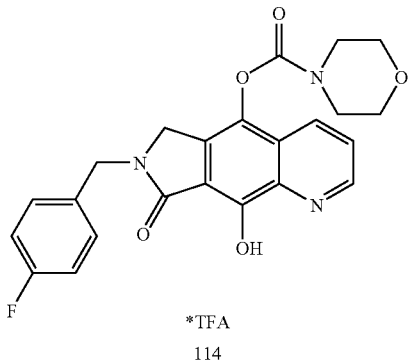

*TFA

114

Example 114

Carbamate 113 (0.017 g, 0.028 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated twice with 1:1 diethylether/hexanes to give product 114 (0.0085 g, 0.015 mmol, 55%.) $^1$H NMR (CDCl$_3$) δ 9.02 (s, 1H), 8.24 (d, 1H), 7.62 (dd, 1H), 7.33 (dd, 2H), 7.07 (dd, 2H), 4.78 (s, 2H), 4.39 (s, 2H), 3.82 (br s, 6H), 3.60 (br s, 2H.) $^{19}$F NMR: −76.2 MS: 438 (M+1), 436 (M−1)

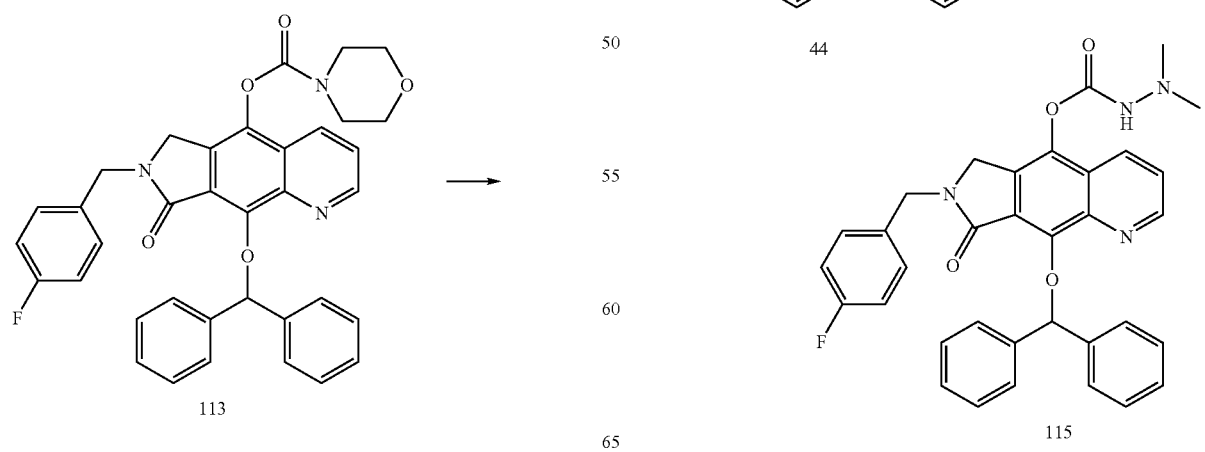

Example 115

Trimethylsilylethyl ether 44 (0.02 g, 0.0339 mmol) was dissolved in 0.5 mL dry tetrahydrofuran. To this was added diisopropylethylamine (0.024 mL, 0.135 mmol) and 1 M tetrabutylammonium fluoride solution in tetrahydrofuran (0.0678 mL, 0.0678 mmol.) Stirred at room temperature 10 minutes until starting material consumed. Diluted with dichloromethane, washed with washed with 1M HCl solution, saturated NaHCO$_3$, saturated brine, concentrated to give crude. Dissolved in 0.5 mL dichloromethane, added catalytic dimethylaminopyridine, diisopropylethylamine (0.024 mL, 0.135 mmol) and cooled to 0° C. To this was added a 1M solution of triphosgene (bis[trichloromethyl] carbonate) in dichloromethane (0.0678 mL, 0.0678 mmol) and stirred 45 minutes. Dimethylhydrazine (0.01 mL, 0.135 mmol) was then added and stirred at room temperature for 20 minutes. Diluted with dichloromethane, washed with saturated NH$_4$Cl solution, concentrated volatiles to give crude. Chromatographed (10% ethylacetate/hexanes to 60% ethylacetate/hexanes) and purified by preparatory TLC plate (60% ethylacetate/hexanes) to give product 115 (0.004 g, 0.0069 mmol, 20%.) $^1$H NMR (CDCl$_3$) δ 9.05 (d, 1H), 8.11 (d, 1H), 8.04 (s, 1H), 7.75 (d, 4H), 7.5 (dd, 1H), 7.27 (m, 8H), 7.07 (dd, 2H), 614 (s, 1H), 4.80 (s, 2H), 4.23 (s, 2H), 2.70 (6H.) MS: 577 (M+1)

crude. Triturated twice with 1:1 diethylether/hexanes to give product 116 (0.003 g, 0.0057 mmol, 37%.) $^1$H NMR (CDCl$_3$) δ 8.96 (s, 1H), 8.24 (d, 1H), 7.56 (dd, 1H), 7.33 (dd, 2H), 7.06 (dd, 2H), 4.76 (s, 2H), 4.39 (s, 2H), 2.74 (s, 3H.) $^{19}$F NMR: −76.1 MS: 411 (M+1), 409 (M−1)

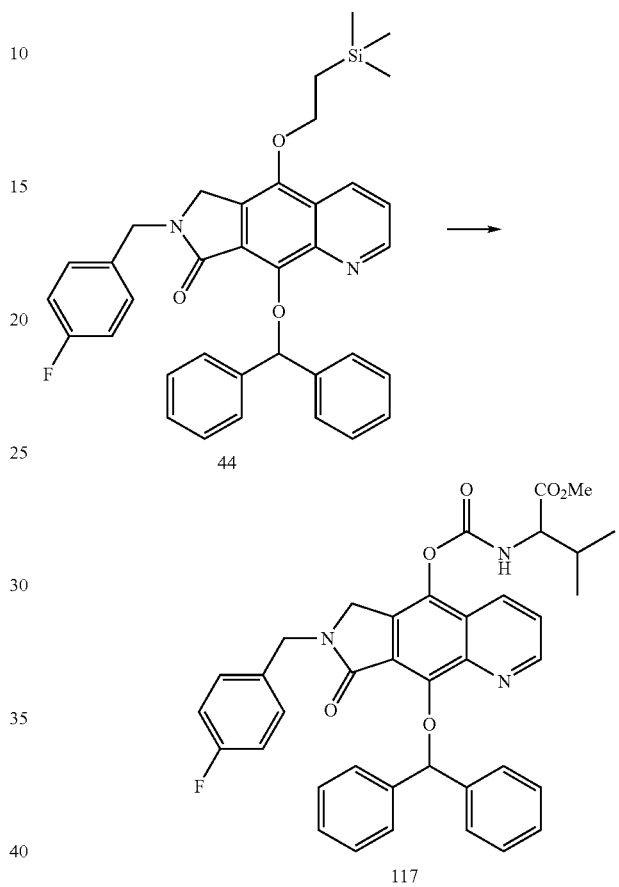

44

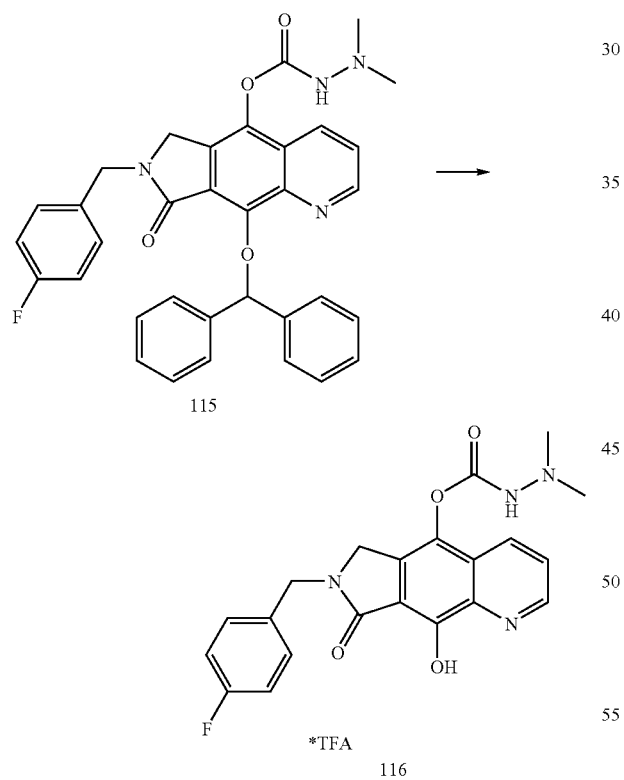

115

116 *TFA

Example 116

Carbamate 115 (0.009 g, 0.0156 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give

117

Example 117

Trimethylsilylethyl ether 44 (0.02 g, 0.0339 mmol) was dissolved in 0.5 mL dry tetrahydrofuran. To this was added triethylamine (0.0188 mL, 0.135 mmol) and 1 M tetrabutylammonium fluoride solution in tetrahydrofuran (0.0678 mL, 0.0678 mmol.) Stirred at room temperature 10 minutes until starting material consumed. Diluted with dichloromethane, washed with washed with 1M HCl solution, saturated, saturated brine, concentrated to give crude. Dissolved in 0.5 mL dichloromethane, added catalytic dimethylaminopyridine, triethylamine (0.0188 mL, 0.135 mmol) and methyl (s)-(−)-2-isocyanato-3-methyl butyrate (0.0048 mL, 0.0339 mmol) and stirred at room temperature. After 4.5 hours, starting material consumed. Diluted with dichloromethane, washed with saturated NH$_4$Cl solution, concentrated organics to give crude. Chromatographed (10% to 50% ethylacetate/hexanes) to give product 117 (0.0085 g, 0.013 mmol, 39%.) $^1$H NMR (CDCl$_3$) δ 9.03 (s, 1H), 8.17 (d, 1H), 8.05 (s, 1H), 7.75 (4H), 7.52 (dd, 1H), 7.27 (m,8H), 7.07 (dd, 2H), 5.70 (d, 1H), 4.80 (s, 2H), 4.21 (s, 2H), 3.79 (s, 3H), 2.28 (dsp, 1H), 1.03 (d, 3H), 0.98 (d, 3H.) MS: 649 (M+1)

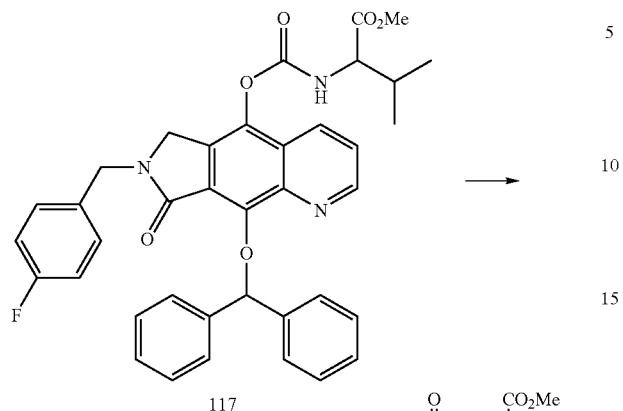

117

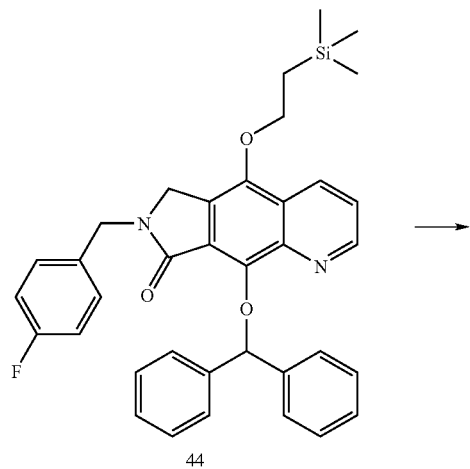

118

Example 118

Carbamate 117 (0.004 g, 0.006 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated twice with 1:1 diethylether/hexanes to give product 118 (0.0027 g, 0.0046 mmol, 76%.) $^1$H NMR (CDCl$_3$) δ 9.00 (s, 1H), 8.31 (d, 1H), 7.60 (dd, 1H), 7.33 (dd, 2H), 7.09 (dd, 2H), 5.76 (d, 1H), 4.77 (s, 2H), 4.36 (s, 2H), 3.81 (s, 3H), 2.28 (dsp, 1H), 1.06 (d, 3H), 1.00 (d, 3H.) $^{19}$F NMR: −76.2 MS: 482 (M+1), 480 (M−1)

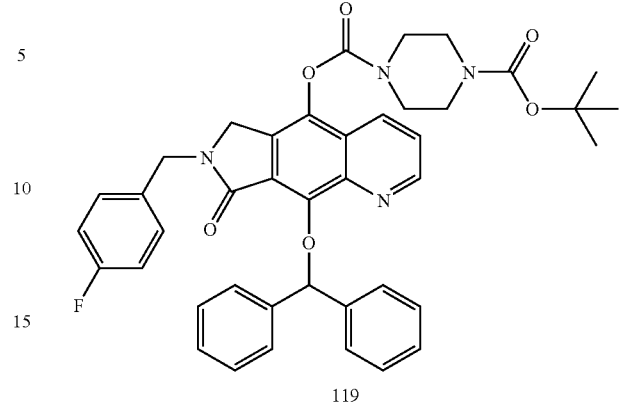

119

Example 119

Trimethylsilylethyl ether 44 (0.2 g, 0.339 mmol) was dissolved in 3 mL dry tetrahydrofuran. To this was added triethylamine (0.139 mL, 1 mmol) and 1 M tetrabutylammonium fluoride solution in tetrahydrofuran (0.0678 mL, 0.0678 mmol.) Stirred at room temperature 10 minutes until starting material consumed. Diluted with dichloromethane, washed with washed with 1M HCl solution, saturated brine, concentrated to give crude. Dissolved in 3 mL dichloromethane, added catalytic dimethylaminopyridine, triethylamine (0.754 mL, 5.4 mmol) and cooled to 0° C. To this was added a 1M solution of triphosgene in dichloromethane (0.1356 mL, 0.1356 mmol) and stirred 50 minutes. BOC-piperazine (0.37 g, 2 mmol) was then added and stirred at room temperature for 30 minutes. Diluted with dichloromethane, washed with 1M HCl, brine, concentrated volatiles to give crude. Chromatographed (10% to 30% acetone/toluene) to give product 119 (0.1158 g, 0.166 mmol, 49%.) $^1$H NMR (CDCl$_3$) δ 9.04 (d, 1H), 8.09 (d, 1H), 8.04 (s, 1H0, 7.75 (d, 4H), 7.50 (dd, 1H), 7.27 (m, 8H), 7.05 (dd, 2H), 4.80 (s, 2H), 4.22 (s, 2H), 3.73 (br s, 2H), 3.53 (br s, 4H), 1.51 (s, 9H.) MS: 688 (M+1)

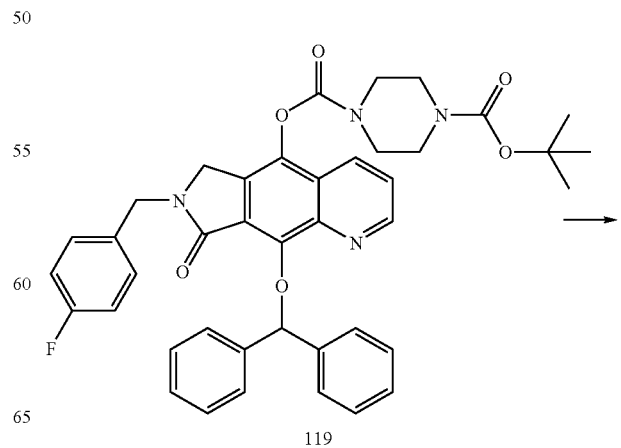

119

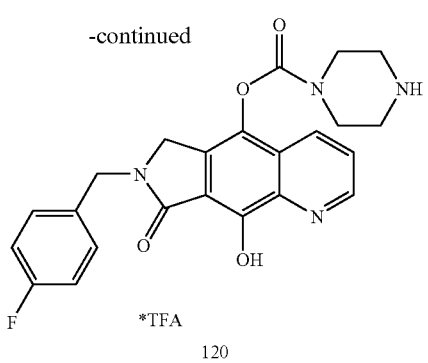

120

Example 120

Carbamate 119 (0.057 g, 0.082 mmol) was dissolved in 1 mL of dichloromethane. To this was added 0.4 mL of triethylsilane and 0.2 mL of trifluoroacetic acid. Stirred at room temperature and after ten minutes complete by TLC. Concentrated off volatiles, azeotroped with toluene to give crude. Then dissolved in 1 mL dichloromethane, 1 ml trifluoroacetic acid. Stirred at room temperature for one hour. Concentrated off volatiles, azeotroped with toluene to give crude. Triturated twice with 1:1 diethylether/hexanes to give product 120 (0.0317 g, 0.059 mmol, 72%.) $^1$H NMR (CD$_3$SOCD$_3$) δ 8.97 (br m, 2H), 8.40 (d, 1H), 7.75 (dd, 1H), 7.35 (dd, 2H), 7.23 (dd, 2H), 4.71 (s, 2H), 4.38 (s, 2H), 3.91 (br s, 2H), 3.24 (br s, 4H.) $^{19}$F NMR: −74.5 MS: 437 (M+1), 435 (M−1)

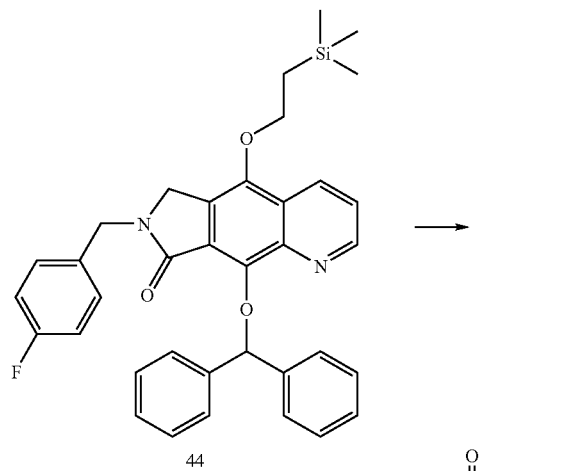

44

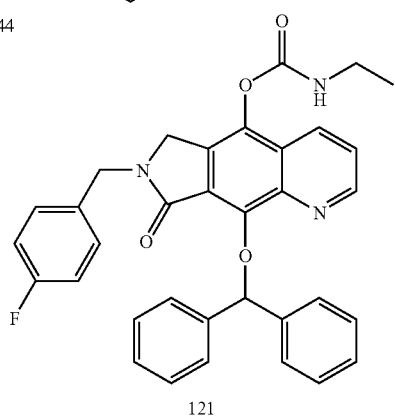

121

Example 121

Trimethylsilylethyl ether 44 (0.035 g, 0.0596 mmol) was dissolved in 0.8 mL dry tetrahydrofuran. To this was added triethylamine (0.05 mL, 0.358 mmol) and 1 M tetrabutylammonium fluoride solution in tetrahydrofuran (0.119 mL, 0.119 mmol.) Stirred at room temperature 10 minutes until starting material consumed. Diluted with dichloromethane, washed with washed with 1M HCl solution, saturated brine, concentrated to give crude. Dissolved in 0.8 mL dichloromethane, added triethylamine (0.05 mL, 0.358 mmol) and ethyl isocyanate (0.0046 mL, 0.0595 mmol) and stirred at room temperature. After 6 hours, starting material consumed. Diluted with dichloromethane, washed with saturated brine, concentrated organics to give crude. Chromatographed (10% to 50% ethylacetate/hexanes) to give product 121 (0.0112 g, 0.023 mmol, 39%.) $^1$H NMR (CDCl$_3$) δ 9.05 (s, 1H), 8.17 (d, 1H), 8.04 (s, 1H), 7.76 (d, 4H), 7.50 (dd, 1H), 7.27 (m, 8H), 7.05 (dd, 2H), 4.80 (s, 2H), 4.23 (s, 2H), 3.33 (q, 2H), 1.27 (t, 3H.) MS: 562 (M+1)

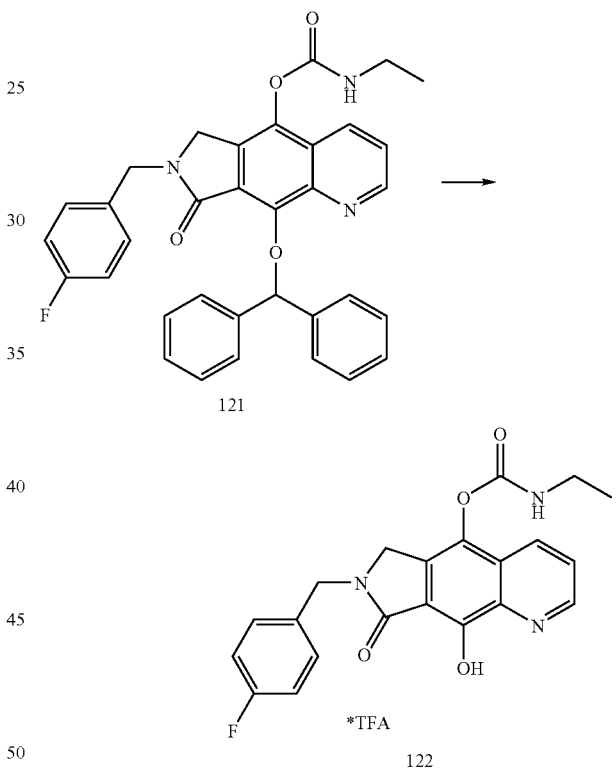

Example 122

Carbamate 121 (0.0112 g, 0.023 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated twice with 1:1 diethylether/hexanes to give product 122 (0.0033 g, 0.0076 mmol, 33%.) $^1$H NMR (CDCl$_3$) δ 9.06 (s, 1H), 8.37 (d, 1H), 7.64 (dd, 1H), 7.33 (dd, 2H), 7.06 (dd, 2H), 5.24 (s, 1H), 4.77 (s, 2H), 4.39 (s, 2H), 3.38 (q, 2H), 1.30 (t, 3H.) $^{19}$F NMR: −76.2 MS: 397 (M+1), 395 (M+1)

Example 123

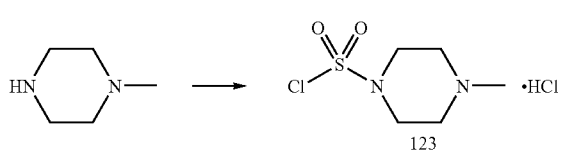

N-Methyl piperazine (0.33 mL, 3 mmol) was added slowly and with caution to a mixture of sulfuryl chloride (0.72 mL, 9 mmol) in 6 mL of acetonitrile. The solution was heated to reflux for 15 hours. After starting material consumed, solution concentrated to oil, azeotroped with toluene (2×), concentrated to give crude product which was triturated with diethylether to give the product 123 as a pale brown solid (0.5 g, 71%.) $^1$H NMR (CD$_3$SOCD$_3$) δ 3.90 (br s, 2H), 3.59 (br s, 2H.), 3.38 (br. S, 4H), 2.67 (s, 3H); MS: 200 (M+1).

Example 124

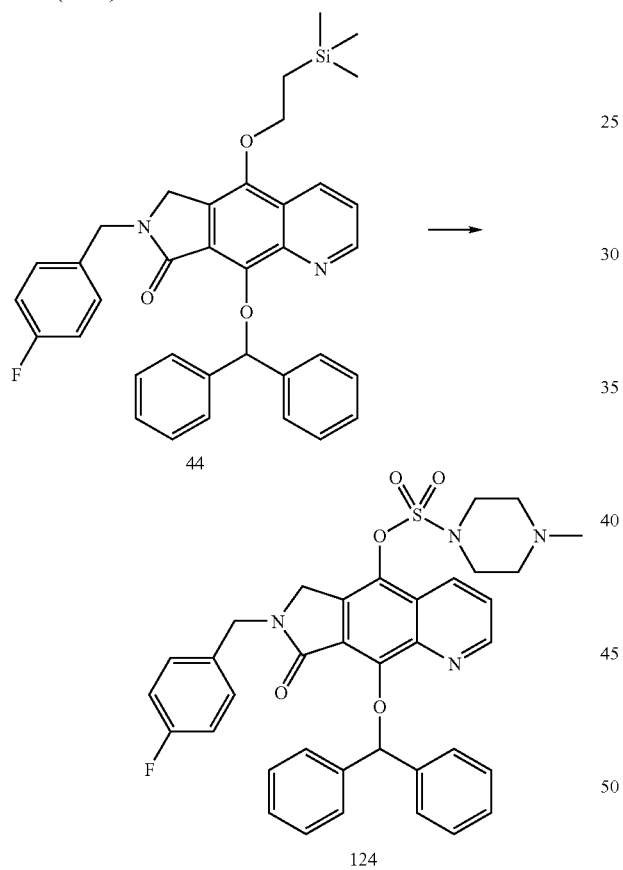

Trimethylsilylethyl ether 44 (0.03 g, 0.0508 mmol) was dissolved in 0.5 mL dry tetrahydrofuran. Triethylamine (0.021 mL, 0.1525 mmol) and 1 M tetrabutylammonium fluoride solution in tetrahydrofuran (0.1016 mL, 0.1016 mmol.) were added. The mixture was stirred at room temperature 10 minutes until starting material was consumed, then diluted with dichloromethane, washed with washed with 1M HCl solution, saturated brine, and concentrated. The crude product was dissolved in 0.5 mL dichloromethane. Catalytic dimethylaminopyridine, triethylamine (0.035 mL, 0.254 mmol) and methyl piperazine sulfamoyl chloride HCl salt 123 (0.024 g, 0.1016 mmol) were added and stirred at room temperature. After 15 hours, starting material was consumed. The mixture was diluted with dichloromethane, washed with saturated brine, and concentrated organics to give crude product which was chromatographed (1% to 10% methanol/dichloromethane) to give product 124 (0.016 g, 0.0246 mmol, 48%.) $^1$H NMR (CDCl$_3$) δ 9.07 (s, 1H), 8.38 (d, 1H), 8.08 (s, 1H), 7.75 (d, 4H), 7.55 (dd, 1H), 7.27 (m, 8H), 7.08 (dd, 2H), 4.81 (s, 2H), 4.46 (s, 2H), 3.51 (br s, 4H), 2.54 (br s, 4H), 3.35 (s, 3H.) MS: 653 (M+1)

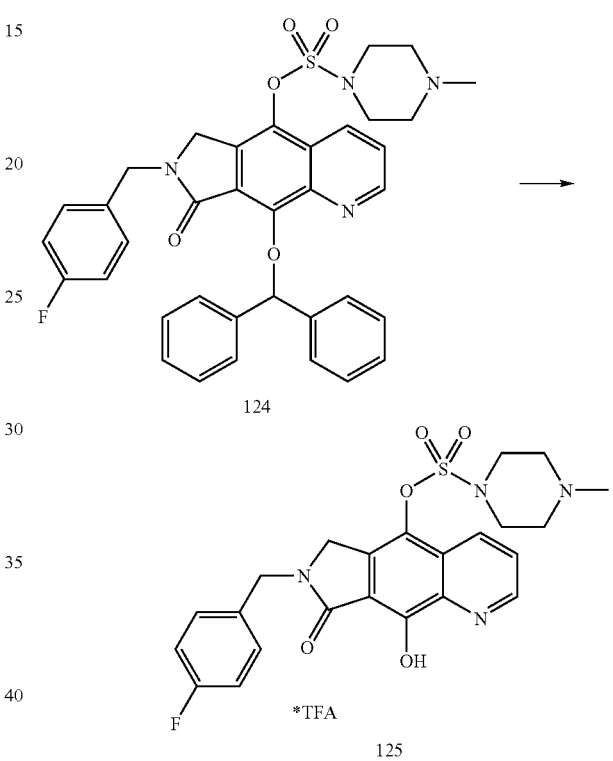

Example 125

Sulfamate 124 (0.016 g, 0.0246 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated twice with 1:1 diethylether/hexanes to give product 125 (0.008 g, 0.0133 mmol, 54%.) $^1$H NMR (CDCl$_3$) δ 9.02 (s, 1H), 8.37 (d, 1H), 7.67 (dd, 1H), 7.33 (dd, 2H), 7.06 (dd, 2H), 4.80 (s, 2H), 4.57 (s, 2H), 3.95 (br s, 4H), 3.29 (br s, 4H), 2.89 (s, 3H.) $^{19}$F NMR: −76.2 MS: 487 (M+1), 485 (M−1)

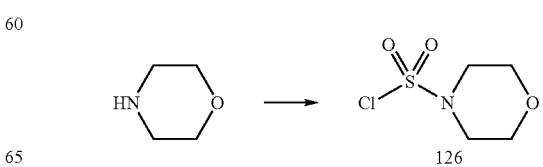

Example 126

Morpholine (0.436 mL, 5 mmol) was added slowly and with caution to a mixture of sulfuryl chloride (1.205 mL, 15 mmol) in 5 mL acetonitrile. Heated to reflux and stirred for 24 hours. After starting material consumed, solution concentrated to oil, azeotroped with toluene (2×), concentrated to give crude product 126 stored as a 2M solution in dichloromethane (0.999 g, 5 mmol, 100%.) $^1$H NMR (CD$_3$SOCD$_3$) δ 3.80 (br s, 4H), 3.28 (br s, 4H.) MS: 186 (M+1)

dine, triethylamine (0.025 mL, 0.1828 mmol) and 2 M morpholine sulfamoyl chloride solution 126 in dichloromethane (0.05 g, 0.10 mmol) and stirred at room temperature. After 1.5 hours, starting material consumed. Diluted with dichloromethane, washed with saturated brine, concentrated organics to give crude. Chromatographed (10% to 40% ethylacetate/hexanes) to give product 127 (0.0199 g, 0.031 mmol, 68%.) $^1$H NMR (CDCl$_3$) δ 9.07 (s, 1H), 8.35 (d, 1H), 8.09 (s, 1H), 7.75 (d, 4H), 7.56 (dd, 1H), 7.27 (m, 8H), 7.05 (dd, 2H), 4.82 (s, 2H), 4.46 (s, 2H), 3.81 (m, 4H), 3.75 (m, 4H), 3.48 (m, 4H), 3.37 (m, 4H.) MS: 790 (M+1)

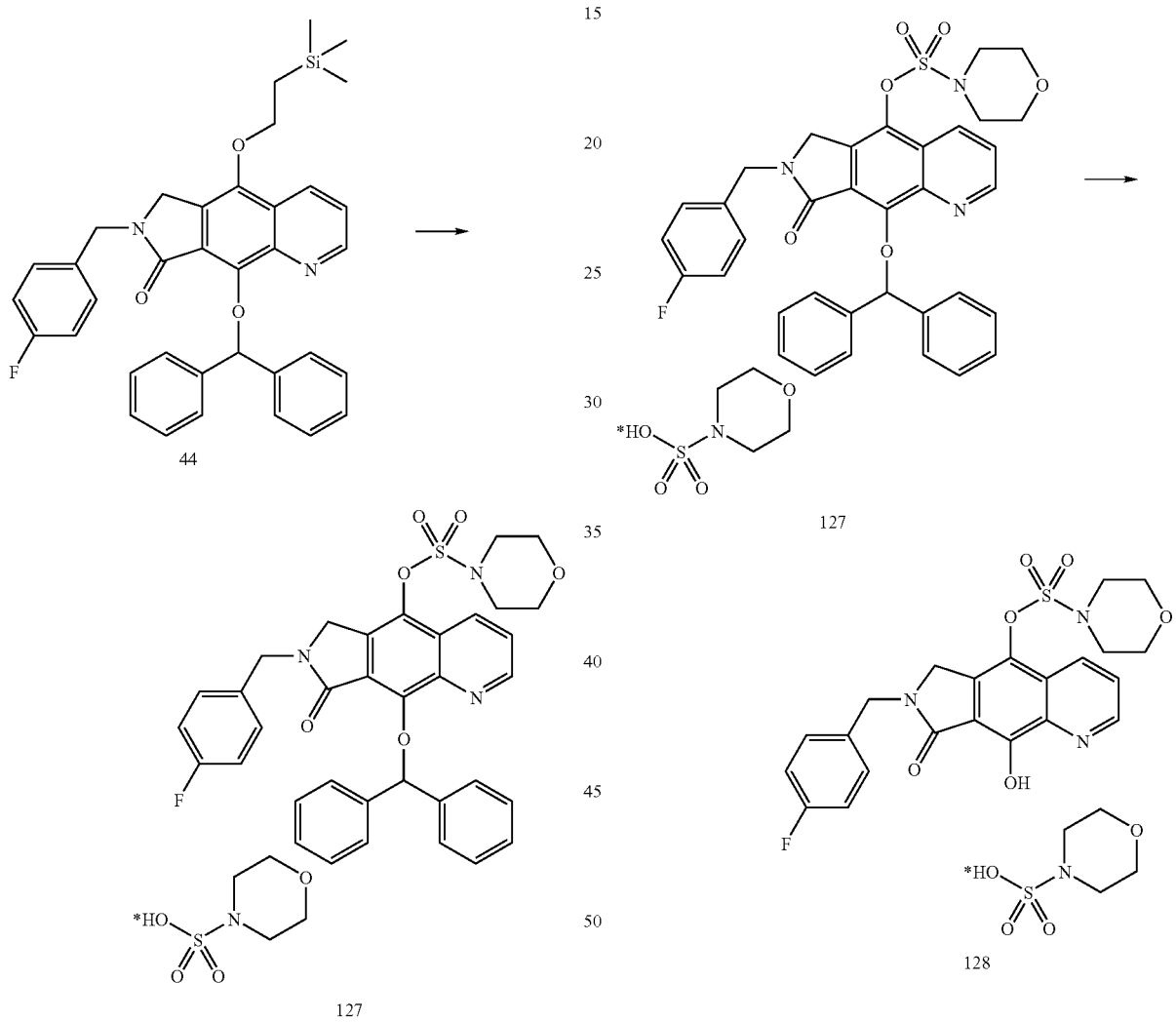

Example 127

Trimethylsilylethyl ether 44 (0.027 g, 0.0457 mmol) was dissolved in 0.5 mL dry tetrahydrofuran. To this was added triethylamine (0.025 mL, 0.1828 mmol) and 1 M tetrabutylammonium fluoride solution in tetrahydrofuran (0.0915 mL, 0.0915 mmol.) Stirred at room temperature 10 minutes until starting material consumed. Diluted with dichloromethane, washed with washed with 1M HCl solution, saturated brine, concentrated to give crude. Dissolved in 0.5 mL dichloromethane, added catalytic dimethylaminopyri-

Example 128

Sulfamate 127 (0.095 g, 0.012 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated twice with 1:1 diethylether/hexanes to give product 128 (0.0054 g, 0.0086 mmol, 71%.) $^1$H NMR (CDCl$_3$) δ 9.00 (s, 1H), 8.45 (d, 1H), 7.65 (dd, 1H), 7.33 (dd, 2H), 7.10 (dd, 2H), 4.79 (s, 2H), 4.59 (s, 2H), 3.86 (m, 4H), 3.76 (m, 4H), 3.59 (m, 4H), 3.28 (m, 4H.) MS: 624 (M+1), 622 (M−1)

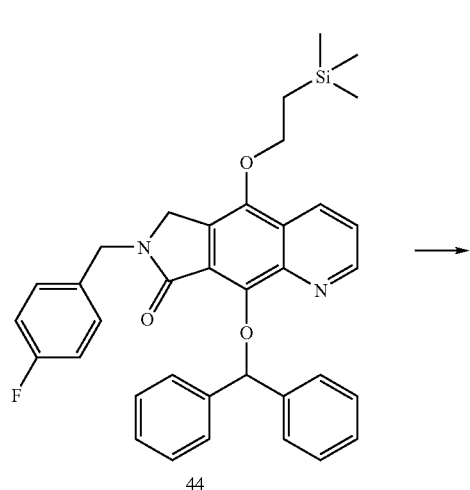

Example 129

Trimethylsilylethyl ether 44 (0.1 g, 0.169 mmol) was dissolved in 2 mL dry tetrahydrofuran. To this was added triethylamine (0.094 mL, 0.676 mmol) and 1 M tetrabutylammonium fluoride solution in tetrahydrofuran (0.339 mL, 0.339 mmol.) Stirred at room temperature 10 minutes until starting material consumed. Diluted with dichloromethane, washed with washed with 1M HCl solution, saturated brine, concentrated to give crude. Dissolved in 1.5 mL dichloromethane, added catalytic dimethylaminopyridine, triethylamine (0.139 mL, 1 mmol) and cooled to 0° C. To this was added triphosgene (0.1 g, 0.339 mmol) and stirred 40 minutes. BOC-aminopiperidine (0.135 g, 0.678 mmol) was then added and stirred at room temperature for 10 minutes. Diluted with dichloromethane, washed with 1M HCl, brine, concentrated volatiles to give crude. Chromatographed (10% to 50% ethylacetate/hexanes) to give product 129 (0.072 g, 0.097 mmol, 59%.) $^1$H NMR (CDCl$_3$) δ 9.04 (dd, 1H), 8.07 (d, 1H), 8.04 (s, 1H), 7.74 (d, 4H), 7.50 (dd, 1H), 7.27 (m, 8H), 7.06 (dd, 2H), 4.80 (s, 2H), 4.48 (br s, 1H), 4.28 (m, 1H), 4.21 (s, 3H), 3.71 (br s, 2H), 3.21 (dd, 2H), 3.03 (dd, 2H), 1.48 (s, 9H.) MS: 717 M+1)

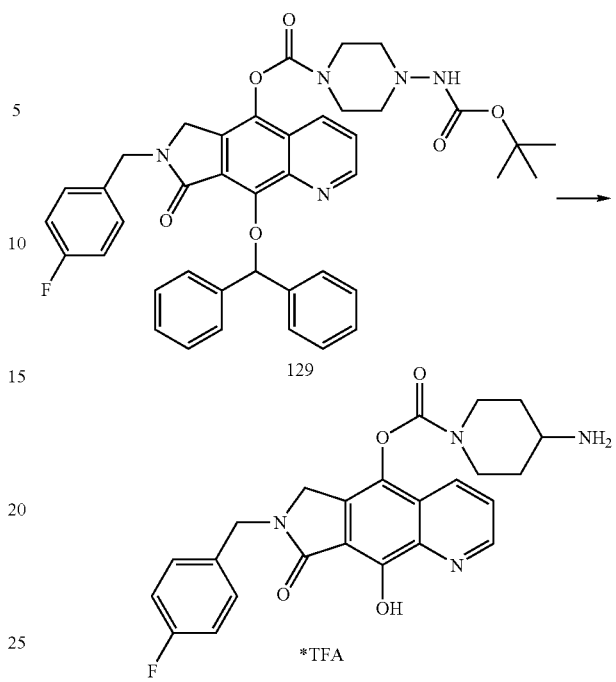

Example 130

Carbamate 129 (0.07 g, 0.097 mmol) was dissolved in 2 mL of dichloromethane. To this was added 0.5 mL of triethylsilane and 0.2 mL of trifluoroacetic acid. Stirred at room temperature and after ten minutes complete by TLC. Concentrated off volatiles, azeotroped with toluene to give crude. Then dissolved in 1.5 mL dichloromethane, 1.5 ml trifluoroacetic acid. Stirred at room temperature for one hour. Concentrated off volatiles, azeotroped with toluene to give crude. Triturated twice with 1:1 diethylether/hexanes to give product 130 (0.0329 g, 0.058 mmol, 60%.) $^1$H NMR (CD$_3$SOCD$_3$) δ 8.98 (s, 1H), 8.22 (d, 1H), 7.95 (s, 2H), 7.74 (dd, 1H), 7.35 (dd, 2H), 7.19 (dd, 2H), 4.70 (s, 2H), 4.35 (s, 3H), 4.00 (br s, 1H), 3.44 (br s, 7H.) $^{19}$F NMR: −74.1 MS: 451 (M+1), 449 (M−1)

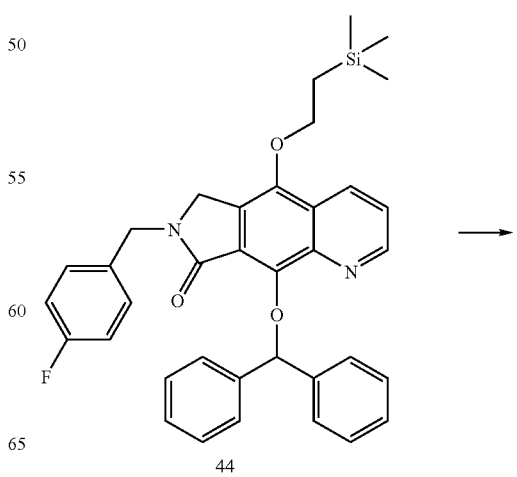

-continued

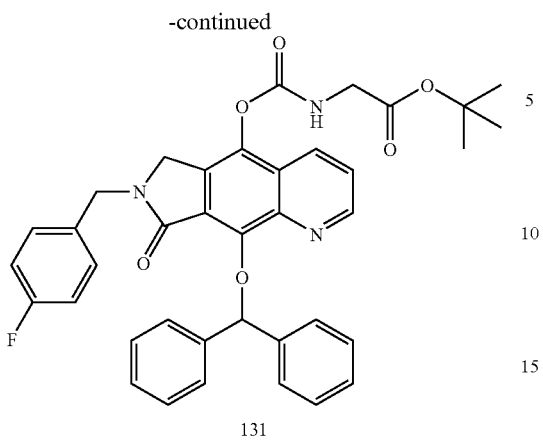

131

Example 131

Triphosgene (0.06 g, 0.2032 mmol) was added to 0.5 mL dichloromethane and cooled to 0° C. To this was slowly added glycine tertiary-butyl ester HCl salt (0.034 g, 0.2032 mmol) and triethylamine (0.14 mL, 1 mmol) and stirred at 0° C. Stirred thirty minutes until starting material consumed. Simultaneously, in a separate flask trimethylsilylethyl ether compound 44 was dissolved in 0.5 mL tetrahydrofuran. To this was added triethylamine (0.028 mL, 0.2032 mmol) and 1M tetrabutylammonium fluoride in tetrahydrofuran (0.1016 mL, 0.1016 mmol) and stirred at room temperature. After 20 minutes, diluted with dichloromethane, washed with 1M HCl solution and brine, concentrated to give crude. At 0° C., crude dissolved in 0.5 mL dichloromethane and added to the glycine isocyanate prepared in situ above. Stirred at 0° C. for 5minutes, then stirred for one hour at room temperature. Diluted with dichloromethane, washed with 1M HCl solution, brine, concentrated to give crude. Chromatographed (10% to 40% ethylacetate/hexanes) to give product 131 (0.017 g, 0.026 mmol, 52%.) $^1$H NMR (CDCl$_3$) δ 9.03 (d, 1H), 8.20 (dd, 1H), 8.05 (s, 1H), 7.75 (d, 4H), 7.51 (dd, 1H), 7.27 (m, 8H), 7.04 (dd, 2H), 5.66 (s, 1H), 4.79 (s, 2H), 4.23 (s, 2H), 3.93 (d, 2H), 1.5 (s, 9H.) MS: 648 (M+1)

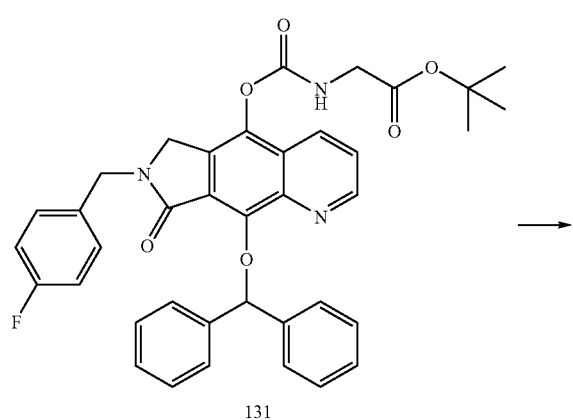

131

-continued

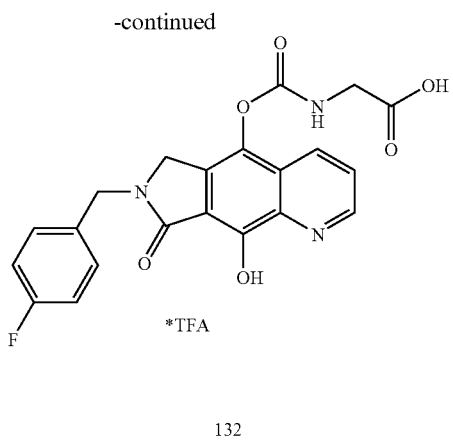

132

Example 132

Carbamate 131 (0.017 g, 0.026 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Then dissolved in 0.5 mL dichloromethane, 0.2 mL triethylsilane, 0.2 ml trifluoroacetic acid. Stirred at room temperature for three hours. Concentrated off volatiles, azeotroped with toluene to give crude. Triturated with 1:1 diethylether/hexanes to give product 132 (0.0088 gm, 0.021 mmol, 80%.) $^1$H NMR (CD$_3$SOCD$_3$) δ 8.97 (s, 1H), 8.40 (s, 1H), 8.30 (d, 1H), 7.74 (dd, 1H), 7.37 (m, 2H), 7.23 (m, 2H), 4.69 (s, 2H0, 4.32 (s, 2H), 3.76 (d, 2H.) $^{19}$F NMR: −74.3 MS: 426 (M+1), 424 (M−1)

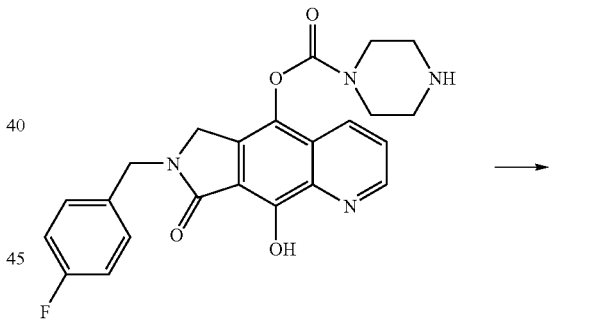

120

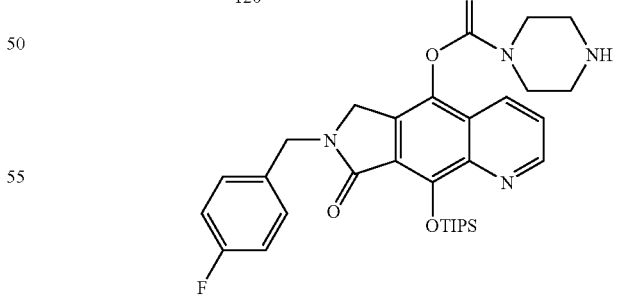

133

Example 133

Carbamate 120 (0.019 g, 0.0435 mmol) was dissolved in 0.5 mL of dichloroethane. To this was added triethylamine (0.072 mL, 0.52 mmol) and triisopropylsilyl chloride (0.058 mL, 0.26 mmol) and stirred at 50° C. After 19 hours, starting material consumed, diluted with dichloromethane, washed with 1M HCl solution, brine and concentrated to give crude. Chromatographed to give product 133 (0.012 g, 0.0203 mmol, 47%.) $^1$H NMR (CDCl$_3$) δ 8.86 (s, 1H), 8.06 (d, 1H), 7.54 (dd, 1H), 7.33 (dd, 2H), 7.08 (dd, 2H), 4.78 (s, 2H), 4.21 (s, 4H), 4.01 (br s, 2H), 3.35 (br s,4H), 11.58 (m, 1H), 1.16 (d, 18H.) MS: 593 (M+1)

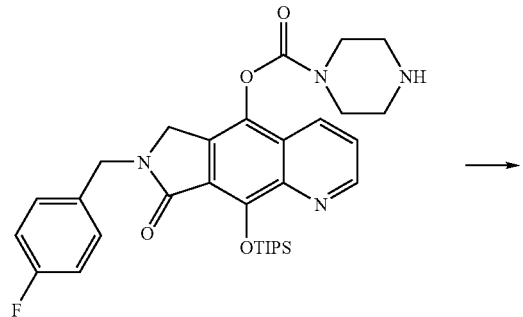

133

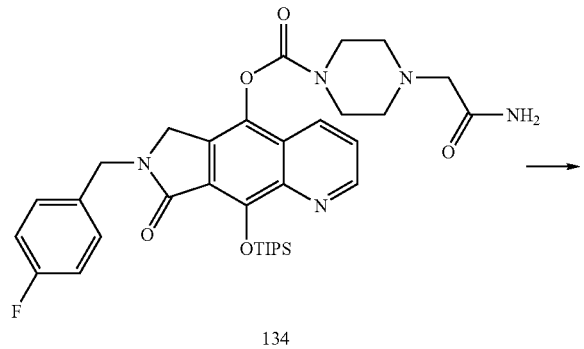

134

Example 134

Piperazine carbamate 133 (0.012 g, 0.0203 mmol) was dissolved 0.5 mL of acetonitrile and 0.2 mL dichloromethane. To this was added Cs$_2$CO$_3$ (0.0325 g, 0.1 mmol) and 2-bromoacetamide (0.009 g, 0.0608 mmol.) Stirred at room temperature for 3.5 days, until starting material was consumed. Diluted with dichloromethane, washed with saturated NH$_4$Cl solution, concentrated to give product 134 (0.0037 g, 0.0057, 28%.) $^1$H NMR (CDCl$_3$) δ 8.87 (dd, 1H), 8.11 (d, 1H), 7.73 (s, 1H), 7.53 (dd, 1H), 7.34 (dd, 2H), 7.07 (dd, 2H), 4.78 (s, 2H), 4.23 (s, 2H), 3.84 (br s, 2H), 3.64 (br s, 2H), 3.14 (s, 2H), 2.62 (br s, 4H), 1.58 (m, 3H), 1.17 (d, 18H.) MS: 650 (M+1)

-continued

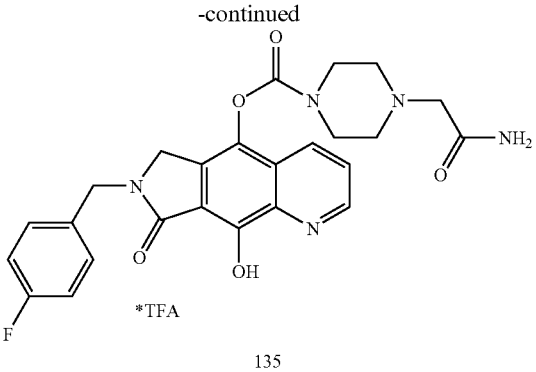

135

Example 135

Mono-carbamate 134 (0.0037 g, 0.0057 mmol) was dissolved in 0.2 mL of dichloromethane. To this was added trifluoroacetic acid (0.009 mL, 0.114 mmol) and stirred at room temperature. After twenty hours, concentrated off volatiles, azeotroped with toluene (2×), concentrated to give crude. Triturate with 1:1 diethylether/hexanes to give product 135 (0.0015 g, 0.0024 mmol, 43%.) $^1$H NMR (CD$_3$OD) δ 8.96 (s, 1H), 8.38 (s, 1H), 7.75 (m, 2H), 7.39 (dd, 2H), 7.11 (dd, 2H), 4.87 (s, 2H), 4.42 (s, 2H), 4.0 (br m, 8H), 3.3 (s, 2H.) $^{19}$F: −77.73 MS: 494 (M+1), 492 (M−1)

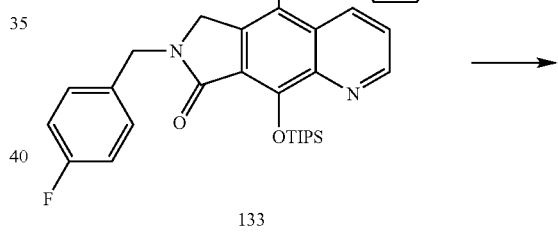

133

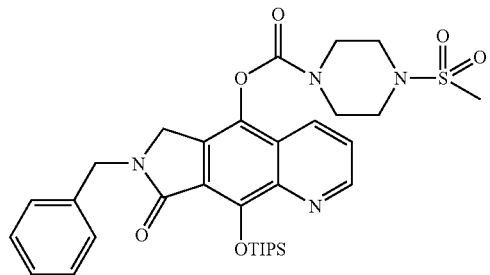

136

Example 136

Piperazine carbamate 133 (0.033 g, 0.056 mmol) was dissolved in 0.5 mL dichloromethane. To this was added catalytic dimethylaminopyridine, triethylamine (0.031 mL, 0.225 mmol) and methanesulfonyl chloride (0.0087 mL, 0.112 mmol) at 0° C. After five minutes, continued stirring at room temperature. After one hour starting material consumed. Diluted with dichloromethane, washed with saturated NH₄Cl solution, dried (Na₂SO₄) concentrated to give crude. Chromatographed (10% to 60% ethylacetate/hexanes) to give product 136 (0.013 g, 0.019 mmol, 35%.) ¹H NMR (CDCl₃) δ 8.88 (dd, 1H), 8.08 (d, 1H), 7.53 (dd, 1H), 7.33 (dd, 2H), 7.05 (dd, 2H), 4.79 (s, 2H), 4.23 (s, 2H), 3.93 (br s, 2H), 3.72 (br s, 2H), 3.37 (br s, 4H), 2.88 (s, 3H), 1.58 (m, 3H), 1.17 (d, 18H.) MS: 671 (M+1)

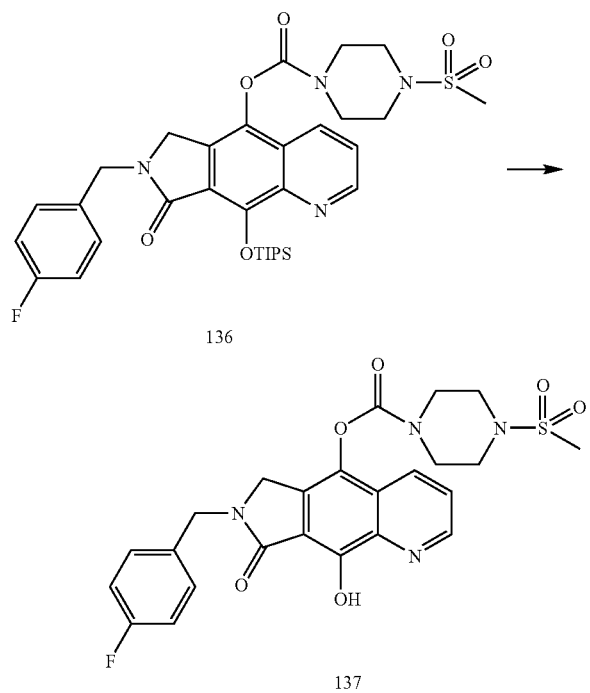

Example 137

Mono-carbamate 136 (0.013 g, 0.019 mmol) was dissolved in 0.5 mL of dichloromethane. To this was added trifluoroacetic acid (0.056 mL, 0.72 mmol) and stirred at room temperature. After twenty hours, concentrated off volatiles, azeotroped with toluene (2×), concentrated to give crude. Triturate with 1:1 diethylether/hexanes to give product 137 (0.0066 g, 0.013 mmol, 68%.) ¹H NMR (CDCl₃) δ 9.01 (s, 1H), 8.17 (s, 1H), 7.61 (s, 1H), 7.27 (dd, 2H), 7.07 (dd, 2H), 4.79 (s, 2H), 4.37 (s, 2H), 3.93 (br s, 2H), 3.72 (br s, 2H), 3.39 (br s, 4H), 2.89 (s, 3H.) MS: 515 (M+1), 513 (M−1)

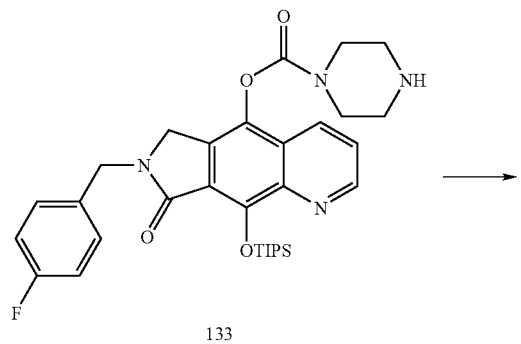

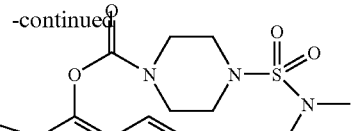
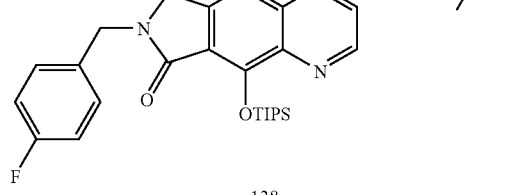

Example 138

Piperazine carbamate 133 (0.033 g, 0.056 mmol) was dissolved in 0.5 mL dichloromethane. To this was added catalytic dimethylaminopyridine, triethylamine (0.031 mL, 0.225 mmol) and methanesulfonyl chloride (0.0087 mL, 0.112 mmol) at 0° C. After five minutes, continued stirring at room temperature. After one hour starting material consumed. Diluted with dichloromethane, washed with saturated NH₄Cl solution, dried (Na₂SO₄) concentrated to give crude. Chromatographed (10% to 50% ethylacetate/hexanes) to give product 138 (0.012 g, 0.017 mmol, 31%.) ¹H NMR (CDCl₃) δ 8.87 (dd, 1H), 8.09 (d, 1H), 7.53 (dd, 1H), 7.31 (dd, 2H), 7.07 (dd, 2H), 4.79 (s, 2H), 4.23 (s, 2H), 3.87 (br s, 2H), 3.66 (br s, 2H), 3.35 (br s, 4H), 2.89 (s, 6H), 1.56 (m, 3H), 1.17 (d, 18H.) MS: 700 (M+1)

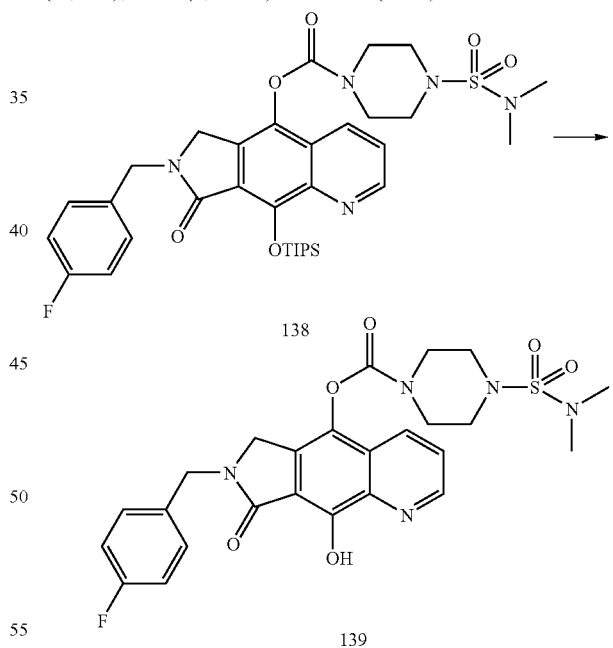

Example 139

Mono-carbamate 138 (0.012 g, 0.017 mmol) was dissolved in 0.5 mL of dichloromethane. To this was added trifluoroacetic acid (0.056 mL, 0.72 mmol) and stirred at room temperature. After twenty hours, concentrated off volatiles, azeotroped with toluene (2×), concentrated to give crude. Triturate with 1:1 diethylether/hexanes to give product 139 (0.0039 g, 0.007 mmol, 42%.) ¹H NMR (CDCl₃) δ 9.00 (s, 1H), 8.18 (d, 1H), 7.60 (s, 1H), 7.27 (dd, 2H), 7.07

(dd, 2H), 4.78 (s, 2H), 4.36 (s, 2H), 3.88 br s, 2H), 3.67 (br s, 2H), 3.35 (br s, 4H), 2.89 (s, 6H.) MS: 544 (M+1), 542 (M−1)

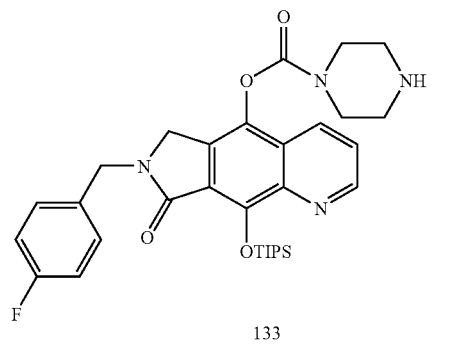

133

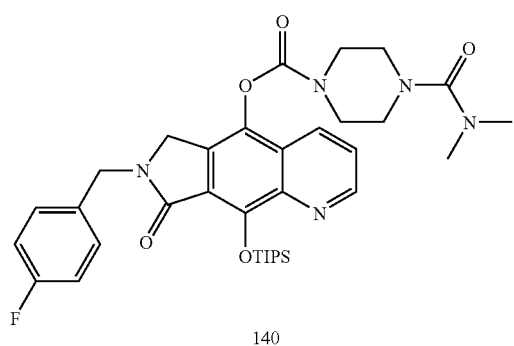

140

Example 140

Piperazine carbamate 133 (0.033 g, 0.056 mmol) was dissolved in 0.5 mL dichloromethane. To this was added catalytic dimethylaminopyridine, triethylamine (0.031 mL, 0.225 mmol) and methanesulfonyl chloride (0.0087 mL, 0.112 mmol) at 0° C. After five minutes, continued stirring at room temperature. After one hour starting material consumed. Diluted with dichloromethane, washed with saturated NH$_4$Cl solution, dried (Na$_2$SO$_4$) concentrated to give crude. Chromatographed (50% to 100% ethylacetate/hexanes) to give product 140 (0.012 g, 0.018 mmol, 32%.) $^1$H NMR (CDCl$_3$) δ 8.85 (dd, 1H), 8.11 (d, 1H), 7.52 (dd, 1H), 7.31 (dd, 2H), 7.07 (dd, 2H), 4.79 (s, 2H), 4.23 (s, 2H), 3.82 (br s, 2H), 3.60 (br s, 2H), 3.34 (br s,4H), 2.91 (s, 6H), 1.56 (m, 3H), 1.17 (d, 18H.) MS: 664 (M+1)

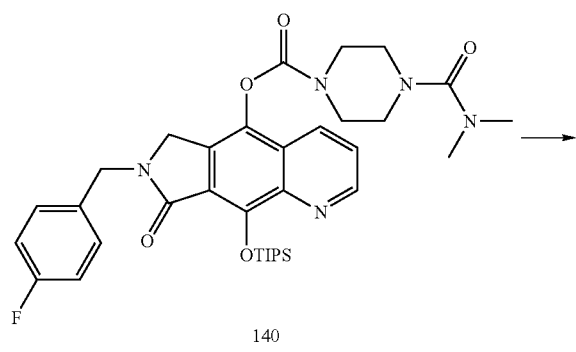

140

-continued

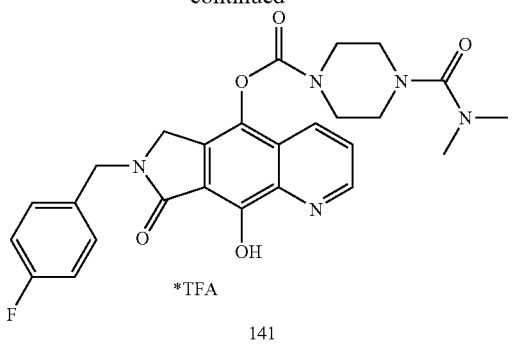

141

Example 141

Mono-carbamate 140 (0.012 gm, 0.018 mmol) was dissolved in 0.5 mL of dichloromethane. To this was added trifluoroacetic acid (0.056 mL, 0.72 mmol) and stirred at room temperature. After twenty hours, concentrated off volatiles, azeotroped with toluene (2×), concentrated to give crude. Triturate with 1:1 diethylether/hexanes to give product 141 (0.0051 g, 0.0083 mmol, 46%.) $^1$H NMR (CDCl$_3$) δ 9.00 (s, 1H), 8.21 (s, 1H), 7.60 (s, 1H), 7.27 (dd, 2H), 7.07 (dd, 2H), 4.76 (s, 2H), 4.37 (s, 2H), 3.83 (br s, 2H), 3.61 (br s, 2H), 3.35 (br s, 4H), 2.92 (s, 6H.) $^{19}$F: −76.3 MS: 508 (M+1), 506 (M−1)

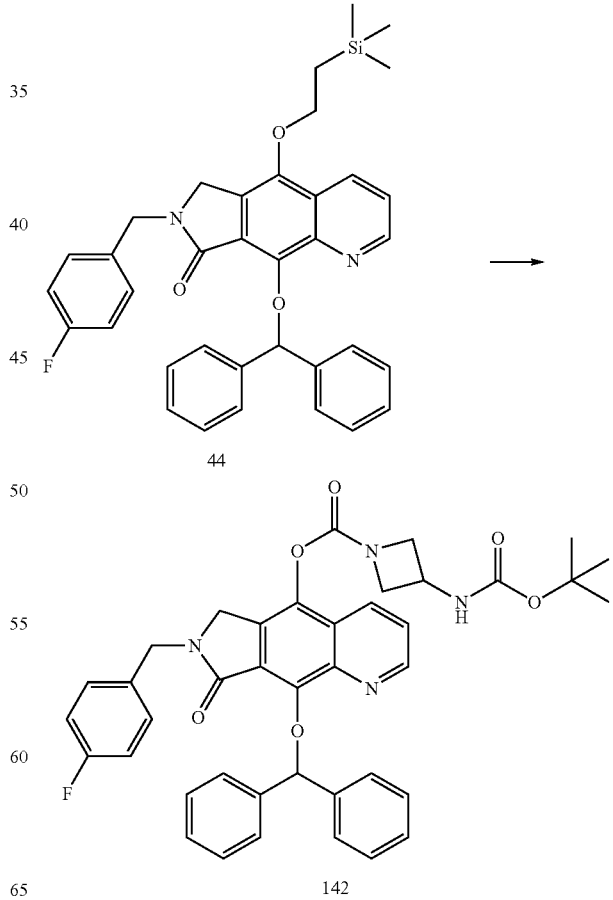

44

142

Example 142

Trimethylsilylethyl ether 44 (0.03 g, 0.0508 mmol) was dissolved in 0.5 mL dry tetrahydrofuran. To this was added triethylamine (0.028 mL, 0.2032 mmol) and 1 M tetrabutylammonium fluoride solution in tetrahydrofuran (0.1016 mL, 0.1016 mmol.) Stirred at room temperature 10 minutes until starting material consumed. Diluted with dichloromethane, washed with washed with 1M HCl solution, saturated brine, dried (Na$_2$SO$_4$,) concentrated to give crude. Dissolved in 0.5 mL dichloromethane, added catalytic dimethylaminopyridine, triethylamine (0.08 mL, 0.6 mmol) and cooled to 0° C. To this was added triphosgene (0.03 g, 0.1016 mmol) and stirred 30 minutes. Azetid-3-yl carbamic acid t-butyl ester (0.035 g, 0.2032 mmol) and triethylamine (0.08 mL, 0.6 mmol) was then added and stirred at room temperature for 50 minutes. Diluted with dichloromethane, washed with 1M HCl, brine, dried (Na$_2$SO$_4$,) concentrated volatiles to give crude. Chromatographed (10% to 50% ethylacetate/hexanes) to give product 142 (0.024 g, 0.035 mmol, 69%.) $^1$H NMR (CDCl$_3$) δ 9.04 (dd, 1H), 8.17 (d, 1H), 8.03 (s, 1H), 7.74 (d, 4H), 7.51 (dd, 1H), 7.27 (m, 8H), 7.08 (dd, 2H), 5.00 (m, 1H), 4.80 (, 2H), 4.52 (m, 2H), 4.23 (s, 2H), 3.91 (m, 2H), 1.48 (s, 9H.) MS: 689 (M+1)

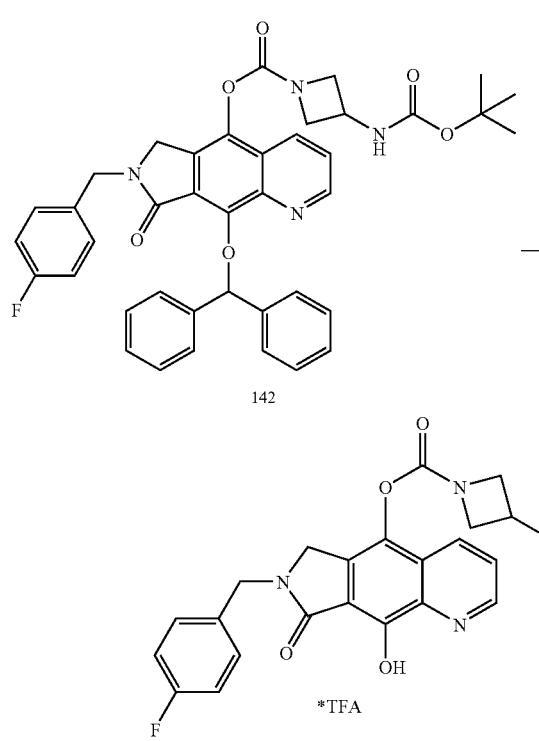

Example 143

Carbamate 142 (0.024 g, 0.035 mmol) was dissolved in 0.5 mL of dichloromethane. To this was added 0.4 mL of triethylsilane and 0.2 mL of trifluoroacetic acid. Stirred at room temperature and after ten minutes complete by TLC. Concentrated off volatiles, azeotroped with toluene to give crude. Then dissolved in 0.75 mL dichloromethane, 0.75 ml trifluoroacetic acid. Stirred at room temperature for one hour. Concentrated off volatiles, azeotroped with toluene to give crude. Triturated twice with 1:1 diethylether/hexanes to give product 143 (0.0128 g, 0.024 mmol, 68%.) $^1$H NMR (CD$_3$SOCD$_3$) δ 9.00 (s, 1H), 8.38 (br s, 3H), 7.75 (s, 1H), 7.36 (br s, 2H), 7.22 (br s, 2H), 4.72 (s, 2H), 4.32 (br m, 5H), 3.14 (br s, 2H.) $^{19}$F NMR: −74.0 MS: 423 (M+1), 421 (M+1)

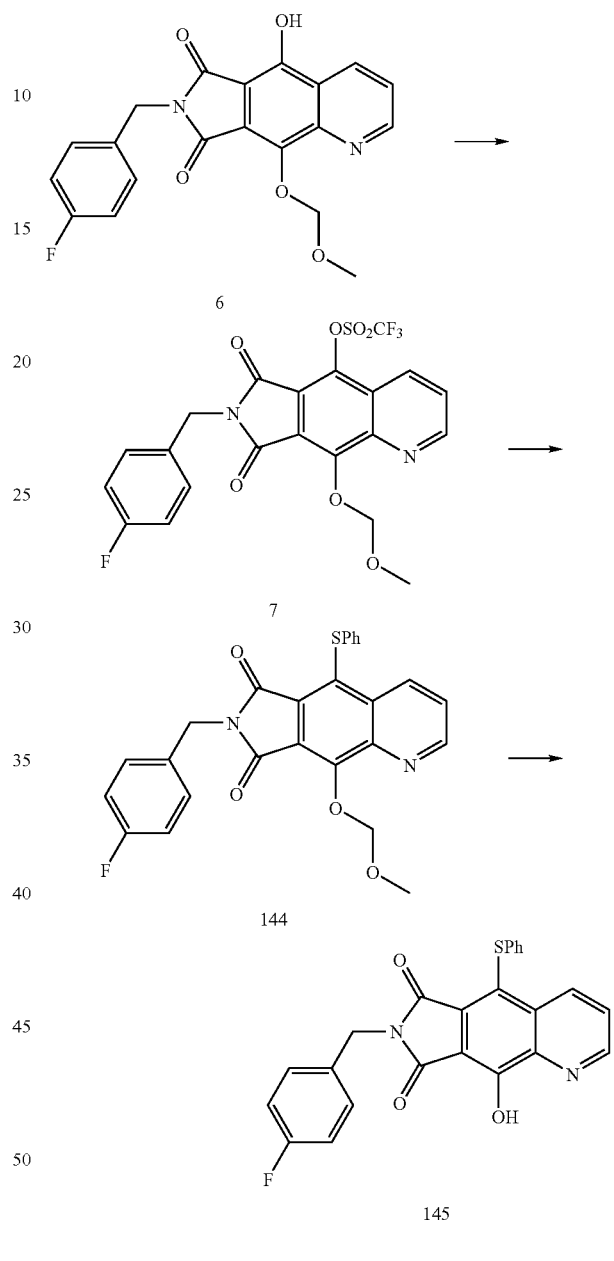

Example 144

To crude triflate 7 (0.025 g, 0.048 mmol) in 1 mL of dichloroethane was added triethylamine (0.014 mL, 0.096 mmol) and benzenethiol (0.008 ml, 0.072 mmol) and the solution stirred at room temperature. After 15 hrs, the mixture was concentrated and chromatographed on silica gel eluting with EtOAc/hexanes to give compound 144 (0.01 g, 44%) as a yellow oil. $^1$H NMR (CDCl$_3$) δ 9.2 (m, 2H), 7.6 (dd, 1H), 7.06 (m, 5H), 7.0 (t, 2H), 5.97 (s, 2H), 4.85 (s, 2H), 3.72 (s, 3H); MS: 474 (M+1)

Example 145

MOM ether 144 (0.009 g, 0.019 mmol) in 1 mL of dichloromethane was treated with TFA (0.015 mL, 0.19 mmol) at room temperature for 15 hrs. The volatiles were removed in vacuo and the residue was triturated with diethylether to afford 7-(4-fluoro-benzyl)-9-hydroxy-5-phenylsulfanyl-pyrrolo[3,4-g]quinoline-6,8-dione 145 as a yellow solid. $^1$H NMR (CDCl$_3$) δ 9.31 (d, 2H), 7.81 (m, 1H), 7.46 (dd, 2H),7.17 (m, 5H), 7.04 (t, 2H), 5.97 (s, 2H), 4.88 (s, 2H); MS: 430 (M+1).

Example 146

To the triflate 5 (0.045 g, 0.07 mmol) in toluene (0.7 mL)/ethanol (0.3 mL)/water (0.2 mL) were added potassium carbonate (0.037 g, 0.175 mmol), trans-phenylvinylbronic acid (0.016 g, 0.105 mmol) and tetrakis (triphenylphosphine)-palladium (0) (0.012 g, 0.011 mmol). The mixture in the flask was flushed with argon three times. It was heated to 120° C. under argon for 3 hours. Cooling to room temperature, it was diluted with EtOAc and washed with 1N HCl, saturated NaHCO$_3$ and brine. The organic phase was dried (MgSO$_4$) and concentrated. The residue was chromatographed on a silica gel column, eluting with EtOAc/Hexane to afford the product 146 (0.031 g, 75%). MS: 613 (M+Na).

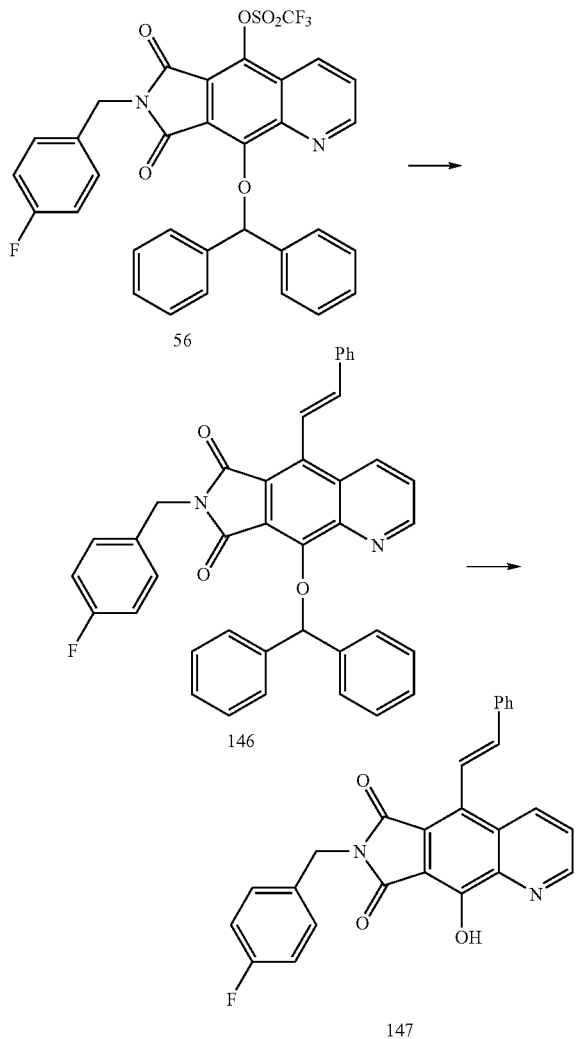

Example 147

Compound 146 (8 mg, 0.013 mmol) was dissolved in dichloromethane (1 mL) at room temperature under nitrogen. Triethylsilane (0.034 mL) was added followed by TFA (0.02 mL) slowly. The mixture was stirred at room temperature for 30 min. The solvent was removed at reduced pressure. The crude product was triturated in diethylether/hexane to afford a yellow solid 7-(4-fluoro-benzyl)-9-hydroxy-5-styryl-pyrrolo[3,4-g]quinoline-6,8-dione 147 (0.005 g, 88%. $^1$H NMR (CDCl$_3$): δ 8.99 (d, 1H), 8.88 (d, 1H), 8.05 (d, 1H), 7.67 (m, 3H), 7.36-7.52 (m, 5H), 7.01 (m, 3H), 4.87 (s, 2H); MS: 425 (M+1).

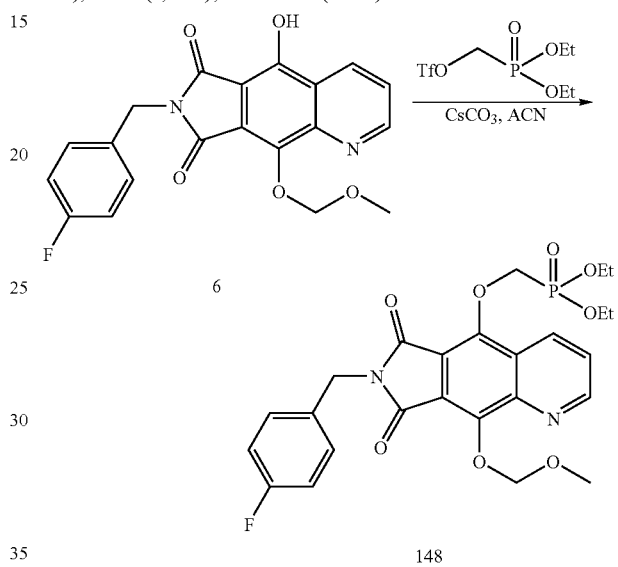

Example 148

To a solution of trifluoromethanesulfonic acid diethoxyphosphorylmethyl ester (D. P. Phillion, etal, *Tetra. Lett.*, 27 (1986) 1477-1480, 0.040 g, 0.104 mmol) dissolved in acetonitrile (0.75 mL) was added the phenol 6 (0.044 g, 0.146 mmol) and CsCO$_3$ (0.102 g, 0.314 mmol). The reaction mixture was stirred at room temperature for 3 hours under an inert atmosphere then filtered and concentrated in vacuo. The residue was purified by silica gel chromatography (3/1—ethylacetate/hexane) to afford the product 148 (0.014 g, 25%) as a solid: $^1$H NMR (CDCl$_3$) δ 9.1 (d, 1H), 8.9 (d, 1H), 7.6 (dd, 1H), 7.5 (dd, 2H), 7.0 (t, 2H), 5.8 (s, 2H), 5.0 (d, 2H), 4.8 (s, 2H), 4.2 (m, 4H), 3.7 (s, 3H), 1.3 (t, 6H); $^{31}$P NMR (CDCl$_3$) δ 19.0; MS: 533 (M+1).

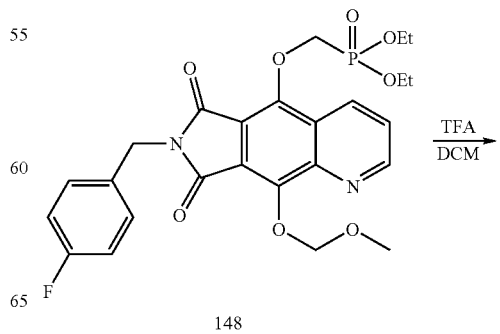

-continued

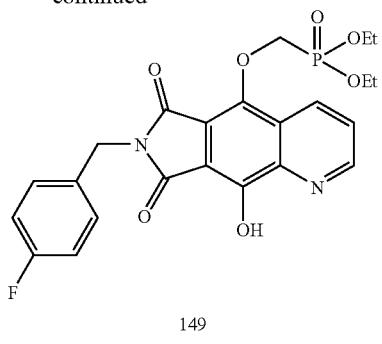

149

Example 149

A solution of the phosphonate 148 (0.014 g, 0.026 mmol) in dichloromethane (0.96 mL) was treated with trifluoroacetic acid (0.020 mL, 0.260 mmol). The reaction mixture was stirred at room temperature under an inert atmosphere for 3 hours. The volatiles were removed in vacuo with toluene. The solid was triturated in diethylether/hexane to afford the product 149 (0.011 g, 86%) as a TFA salt: $^1$H NMR (CDCl$_3$) δ 9.0 (d, 1H), 8.9 (d, 1H), 7.7 (dd, 1H), 7.5 (dd, 2H), 7.0 (t, 2H), 5.0 (d, 2H), 4.9 (s, 2H), 4.2 (m, 4H), 1.3 (s, 6H); $^{31}$P NMR (CDCl$_3$) δ 19.2; MS: 489 (M+1), 487 (M−1).

6

150

Example 150

Dibenzyl hydroxymethyl phosphonate triflate was prepared from dibenzyl hydroxymethyl phosphonate (M. Krecmerova, et al, *Czech. Chem. Commun.*, 55, 1990, 2521-2536) by the method of: Y. Xu, etal, *J. Org. Chem.*, 61 (1996) 7697-7701. To a solution of dibenzyl hydroxymethyl phosphonate triflate (, 0.050 g, 0.131 mmol) dissolved in acetonitrile (1.87 mL) was added the phenol 6 (0.078 g, 0.183 mmol) and CsCO$_3$ (0.102 g, 0.314 mmol). The reaction mixture was stirred at room temperature for 3 hours under an inert atmosphere then filtered and concentrated in vacuo. The residue was purified by silica gel chromatography (1/1—ethylacetate/hexane) to afford the product 150 (0.030 g, 35%) as a solid: $^1$H NMR (CDCl$_3$) δ 9.0 (d, 1H), 8.65 (d, 1H), 7.5 (dd, 2H), 7.4 (dd, 1H), 7.3 (m, 10H), 7.0 (t, 2H), 5.8 (s, 2H), 5.1 (m, 4H), 4.9 (d, 2H), 4.8 (s, 2H), 3.7 (s, 3H); $^{31}$P NMR (CDCl$_3$) δ 20.1; MS: 657 (M+1).

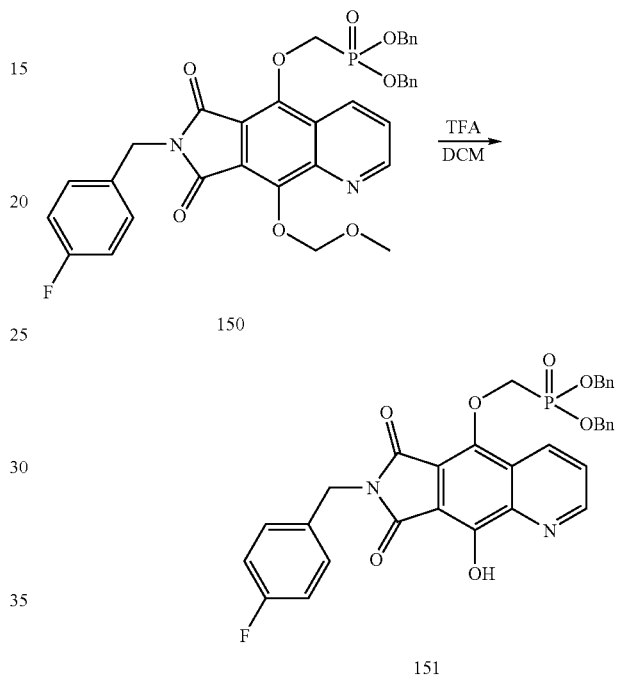

150

151

Example 151

A solution of the phosphonate 150 (0.029 g, 0.044 mmol) in dichloromethane (1.6 mL) was treated with trifluoroacetic acid (0.034 mL, 0.44 mmol). The reaction mixture was stirred at room temperature under an inert atmosphere for 3 hours. The volatiles were removed in vacuo with toluene. The solid was triturated in diethylether/hexane to afford the product 151 (0.024 g, 89%) as a TFA salt: $^1$H NMR (CDCl$_3$) δ 8.9 (d, 1H), 8.6 (d, 1H), 7.5 (dd, 2H), 7.45 (dd, 1H), 7.3-7.2 (m, 10H), 7.0 (t, 2H), 5.1-5.0 (m, 4H), 5.0 (d, 2H), 4.8 (s, 2H); $^{31}$P NMR (CDCl$_3$) δ 20.3; MS: 613 (M+1), 611 (M−1).

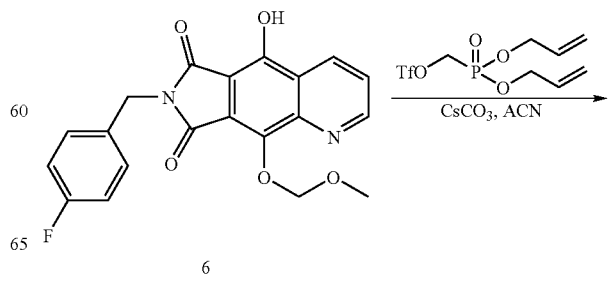

6

-continued

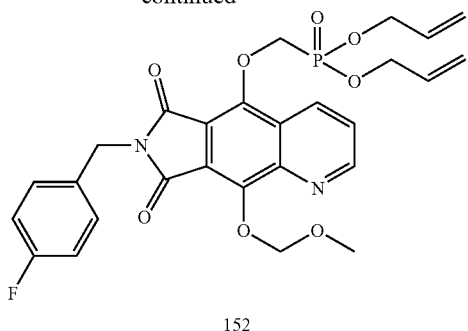

152

Example 152

To a solution of diallyl hydroxymethyl phosphonate triflate (prepared by a method similar to: D. P. Phillion, etal, *Tetra. Lett.*, 27 (1986) 1477-1480 and Y. Xu, etal, *J. Org. Chem.*, 61 (1996) 7697-7701, 0.153 g, 0.471 mmol) dissolved in acetonitrile (6.7 mL) was added 7-(4-fluorobenzyl)-5-hydroxy-9-methoxymethoxy-pyrrolo [3,4-g] quinoline-6,8-dione 6 (0.060 g, 0.157 mmol) and $CsCO_3$ (0.154 g, 0.471 mmol). The reaction mixture was stirred at room temperature for 2 hours under an inert atmosphere then filtered and concentrated in vacuo. The residue was purified by silica gel chromatography (3/1—ethylacetate/hexane) to afford [7-(4-fluoro-benzyl)-9-methoxymethoxy-6,8-dioxo-7,8-dihydro-6H-pyrrolo[3,4-g]quinolin-5-yloxymethyl]-phosphonic acid diallyl ester 152 (0.051 g, 59%) as a solid: $^1$H NMR (CDCl$_3$) δ 9.05 (d, 1H), 8.85 (d, 1H), 7.6 (dd, 1H), 7.45 (dd, 2H), 7.0 (t, 2H), 5.9 (m, 2H), 5.8 (s, 2H), 5.3 (d, 2H), 5.2 (d, 2H), 5.0 (d, 2H), 4.8 (s, 2H), 4.6 (m, 4H), 3.7 (s, 3H); $^{31}$P NMR (CDCl$_3$) δ 19.9; MS: 557 (M+1).

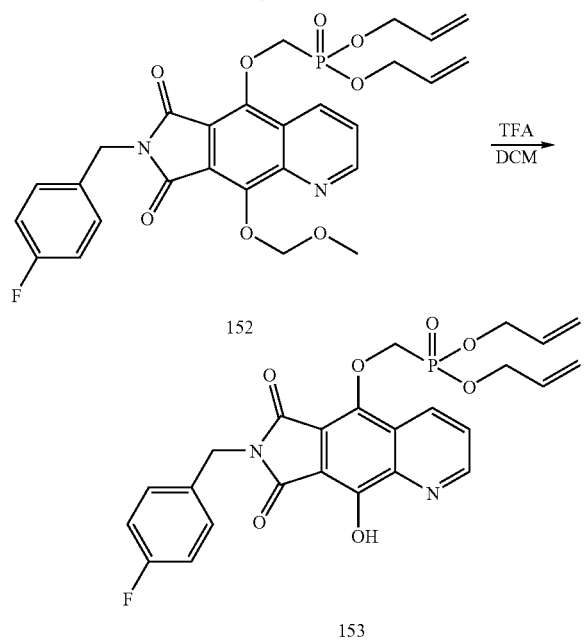

152

TFA / DCM →

153

Example 153

A solution of the phosphonate 152 (0.0065 g, 0.0117 mmol) in dichloromethane (0.425 mL) was treated with trifluoroacetic acid (0.009 mL, 0.117 mmol). The reaction mixture was stirred at room temperature under an inert atmosphere for 1 hour. The volatiles were removed in vacuo with toluene. The solid was triturated in diethylether/hexane to afford the product 153 (0.006 g, 100%) as a TFA salt: $^1$H NMR (CDCl$_3$) δ 9.0 (d, 1H), 8.9 (d, 1H), 7.7 (dd, 2H), 7.5 (dd, 1H), 7.0 (t, 2H), 5.9 (m, 2H), 5.3 (d, 2H), 5.2 (d, 2H), 5.0 (d, 2H), 4.85 (s, 2H), 4.6 (m, 4H); $^{31}$P NMR (CDCl$_3$) δ 20.0; MS: 513 (M+1), 511 (M+1).

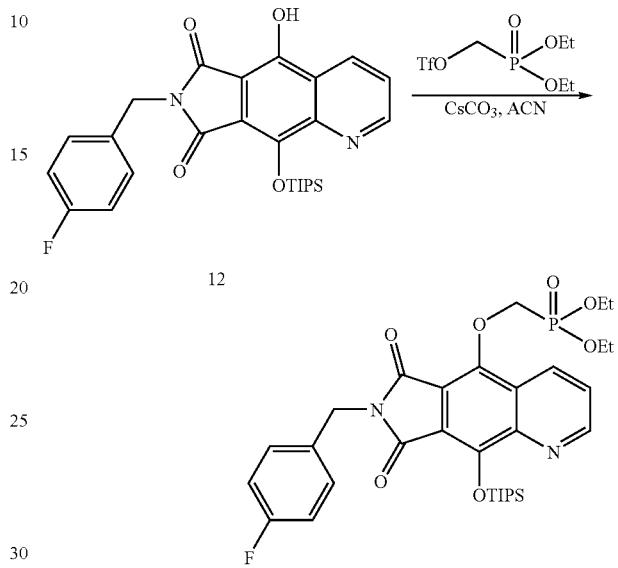

12

→ CsCO$_3$, ACN

154

Example 154

Diethyl hydroxymethyl phosphonate triflate was prepared from diethyl hydroxymethyl phosphonate (Aldrich, St. Louis, Mo.,) by the method of: D. P. Phillion, et al, *Tetra. Lett.*, 27, 1986, 1477-1480. To a solution of diethyl hydroxymethyl phosphonate triflate (0.61 g, 0.202 mmol) dissolved in acetonitrile (2.9 mL) was added the phenol 12 (0.100 g, 0.202 mmol) and $CsCO_3$ (0.198 g, 0.607 mmol). The reaction mixture was stirred at room temperature for 3 hours under an inert atmosphere then filtered and concentrated in vacuo. The residue was purified by silica gel chromatography (1/1—ethylacetate/hexane) to afford the product 154 (0.130 g, 100%) as a solid: $^1$H NMR (CDCl$_3$) δ 8.95 (d, 1H), 8.9 (d, 1H), 7.6 (dd, 1H), 7.5 (dd, 2H), 7.0 (t, 2H), 4.9 (d, 2H), 4.8 (s, 2H), 4.2 (m, 4H), 1.5 (m, 3H), 1.3 (t, 6H), 1.2 (d, 18H); $^{31}$P NMR (CDCl$_3$) δ 19.5; MS: 645 (M+1).

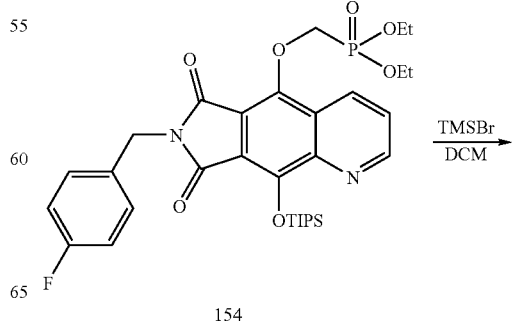

154

TMSBr / DCM →

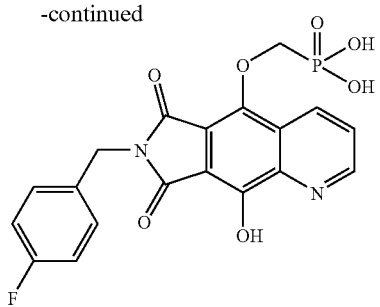

155

Example 155

A solution of the phosphonate 154 (0.020 g, 0.031 mmol) in dichloromethane (0.311 mL) was treated with trimethylsilane bromide (0.0246 mL, 0.186 mmol). The reaction mixture was stirred at room temperature overnight under an inert atmosphere. The volatiles were removed in vacuo with methanol. The solid was washed with dichloromethane to afford the diacid 155 (0.010 g, 77%): $^1$H NMR (CD$_3$OD) δ 9.5 (d, 1H), 9.2 (d, 1H), 8.2 (dd, 1H), 7.5 (dd, 2H), 7.1 (t, 2H), 5.0 (d, 2H), 4.9 (s, 2H); $^{31}$P NMR (CD$_3$OD) δ 16.2; MS: 433 (M+1), 431 (M−1).

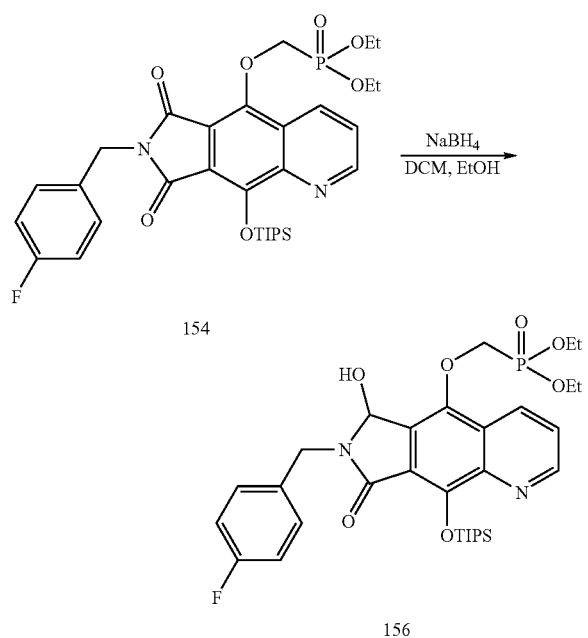

Example 156

To a solution of the phosphonate 154 (0.038 g, 0.059 mmol) dissolved in dichloromethane (0.297 mL) and ethanol (0.297 mL) was added sodium borohydride (0.475 mL, 0.237 mmol). The reaction mixture stirred at room temperature overnight under an inert atmosphere and then was concentrated in vacuo. The residue was dissolved in ethylacetate and washed with saturated NH$_4$Cl and brine. The organic phase was dried (MgSO$_4$) then concentrated in vacuo. The residue was purified by silica gel chromatography (1/99—methanol/dichloromethane) to afford the product 156 (0.022 g, 59%): $^1$H NMR (CDCl$_3$) δ 8.9 (d, 1H), 8.4 (d, 1H), 7.5 (dd, 1H), 7.4 (dd, 2H), 7.0 (t, 2H), 6.0 (s, 1H), 5.8 (bs, 1H), 5.2 (d, 1H), 4.6-4.4 (m, 2H), 4.4 (d, 1H), 4.3-4.2 (m, 4H), 1.6 (m, 3H), 1.4 (m, 6H), 1.15 (d, 18H); $^{31}$P NMR (CDCl$_3$) δ 20.95; MS: 647 (M+1).

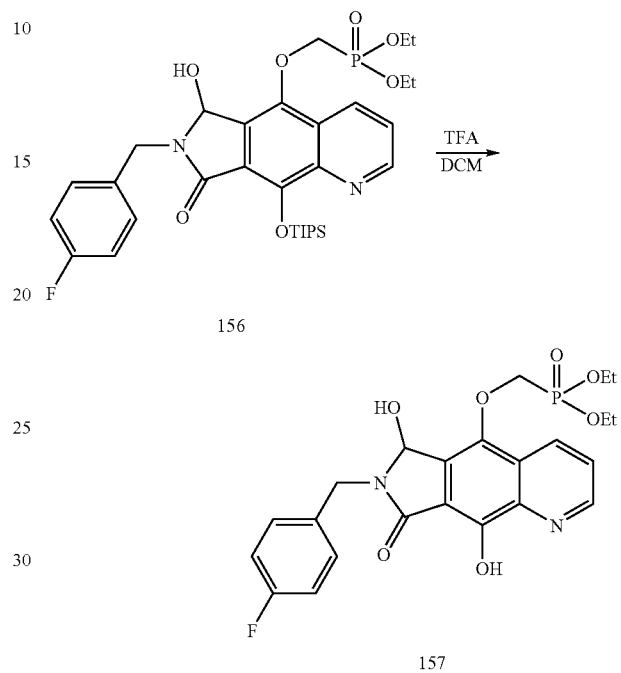

Example 157

A solution of the phosphonate 156 (0.025 g, 0.039 mmol) in dichloromethane (1.41 mL) was treated with trifluoroacetic acid (0.030 mL, 0.390 mmol). The reaction mixture was stirred at room temperature under an inert atmosphere overnight. The volatiles were removed in vacuo, azeotroping to dryness with toluene. The solid was triturated in diethylether/hexane to afford the product 157 (0.021 g, 100%) as a TFA salt: $^1$H NMR (CDCl$_3$) δ 9.0 (d, 1H), 8.6 (d, 1H), 7.6 (dd, 1H), 7.4 (dd, 2H), 7.0 (t, 2H), 6.2 (bs, 1H), 6.0 (s, 1H), 5.1 (d, 1H), 4.7-4.5 (m, 2H), 4.5 (d, 1H), 4.25 (m, 4H), 1.4 (m, 6H); $^{31}$P NMR (CDCl$_3$) δ 20.1; MS: 491 (M+1), 489 (M−1).

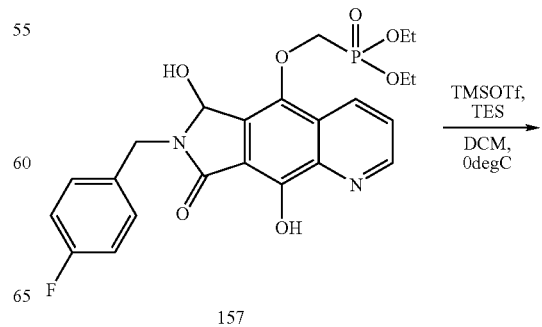

157

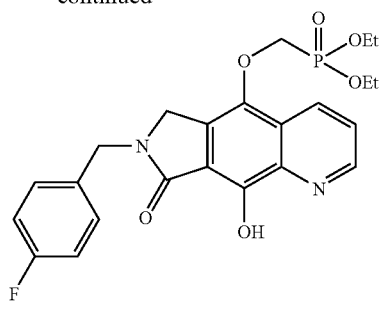

158

Example 158

A solution of phosphonate 157 (0.0185 g, 0.0378 mmol) in dichloromethane (0.455 mL) was cooled to 0° C. Triethylsilane (0.0603 mL, 0.378 mmol) and then trimethylsilane triflate (0.0205 mL, 0.113 mmol) were added. The reaction stirred for 15 minutes under an inert atmosphere. The mixture was partitioned between dichloromethane and water. The organic phase was washed with saturated NaHCO$_3$ then dried (MgSO$_4$) and concentrated in vacuo. The solid was triturated in diethylether/hexane to afford the product 158 (0.015 g, 84%): $^1$H NMR (CDCl$_3$) δ 9.0 (dd, 1H), 8.6 (dd, 1H), 7.6 (dd, 1H), 7.35 (dd, 2H), 7.15 (t, 2H), 4.8 (s, 2H), 4.5 (s, 2H), 4.3 (d, 2H), 4.2 (m, 4H), 1.3 (t, 6H); $^{31}$P NMR (CDCl$_3$) δ 18.7; MS: 475 (M+1).

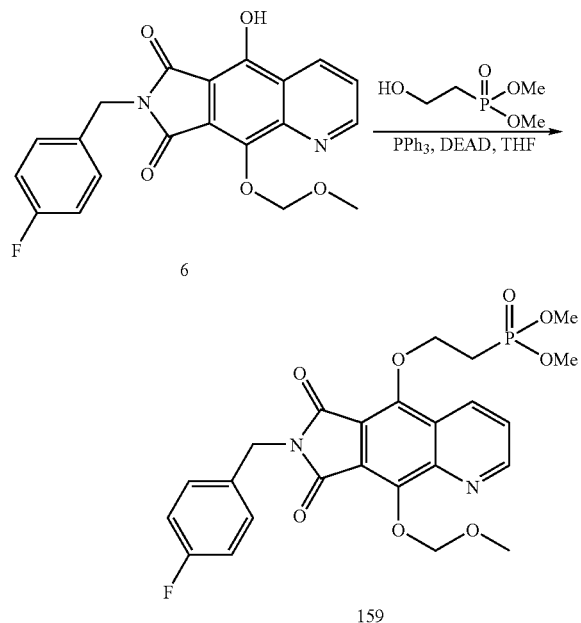

Example 159

To a solution of phenol 6 (0.063 g, 0.165 mmol) dissolved in THF (0.86 mL) was added dimethyl hydroxyethyl phosphonate (0.076 g, 0.495 mmol), triphenylphosphine (0.108 g, 0.412 mmol), and diethyl azodicarboxylate (0.039 mL, 0.247 mmol). The reaction mixture stirred at room temperature under an inert atmosphere overnight. The residue was purified directly by silica gel chromatography (5/95—methanol/ethylacetate) to afford the product 159 (0.022 g, 26%): $^1$H NMR (CDCl$_3$) δ 9.05 (d, 1H), 8.9 (d, 1H), 7.6 (dd, 1H), 7.5 (dd, 2H), 7.0 (t, 2H), 5.8 (s, 2H), 4.8 (d, 2H), 4.75 (m, 2H), 3.8 (d, 6H), 3.7 (s, 3H), 2.5 (m, 2H); $^{31}$P NMR (CDCl$_3$) δ 30.2; MS: 519 (M+1).

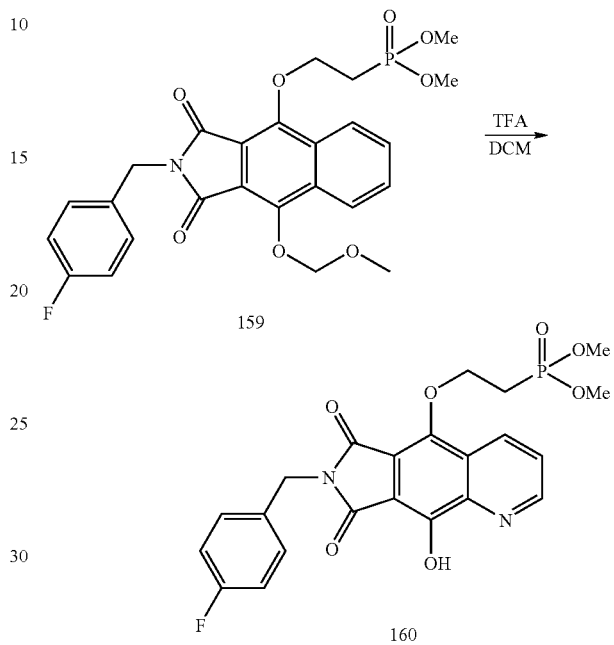

Example 160

A solution of the phosphonate 159 (0.012 g, 0.024 mmol) in dichloromethane (0.863 mL) was treated with trifluoroacetic acid (0.018 mL, 0.240 mmol). The reaction mixture was stirred at room temperature under an inert atmosphere overnight. The volatiles were removed in vacuo with toluene. The solid was triturated in diethylether/hexane to afford the product 160 (0.0095 g, 84%) as a TFA salt: $^1$H NMR (CDCl$_3$) δ 9.0 (d, 1H), 8.9 (d, 1H), 7.7 (dd, 1H), 7.5 (dd, 2H), 7.0 (t, 2H), 4.85 (d, 2H), 4.8 (m, 2H), 3.8 (d, 6H), 2.5 (m, 2H); $^{31}$P NMR (CDCl$_3$) δ 30.3; MS: 475 (M+1), 473 (M−1).

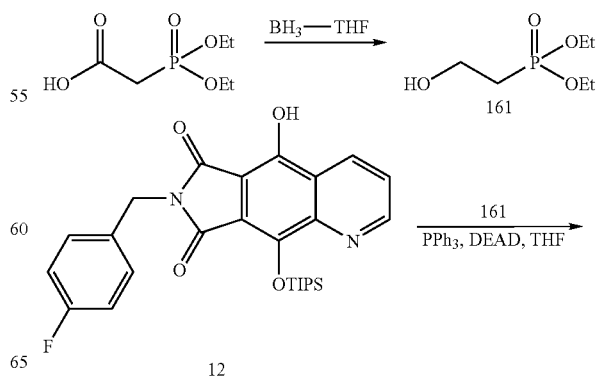

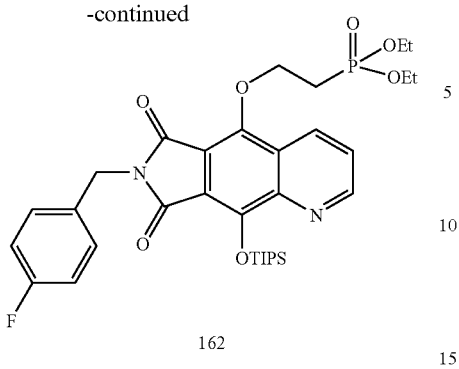

162

Example 161

A solution of diethyl phosphonacetic acid (0.700 g, 3.57 mmol) dissolved in THF was cooled to 0° C. Borane-THF complex (7.14 mL) in 1M THF was added dropwise. The reaction mixture was stirred for 3 hours under an inert atmosphere then concentrated in vacuo. The residue was directly purified by silica gel chromatography (5/95—methanol/ethylacetate) to afford the product, diethyl hydroxyethyl phosphonate, 161 (0.583 g, 90%) as an oil: $^1$H NMR (CDCl$_3$) δ 4.1 (m, 4H), 3.9 (m, 2H), 2.1 (m, 2H), 1.3 (t, 6H); $^{31}$P NMR (CDCl$_3$) δ 30.4; MS: 183 (M+1).

Example 162

To a solution of phenol 12 (0.023 g, 0.046 mmol) dissolved in THF (0.24 mL) was added diethyl hydroxyethyl phosphonate 161 (0.025 g, 0.137 mmol), triphenylphosphine (0.030 g, 0.114 mmol), and diethyl azodicarboxylate (0.011 mL, 0.069 mmol). The reaction mixture stirred at room temperature under an inert atmosphere overnight. The residue was purified directly by silica gel chromatography (75/25—ethylacetate/hexane). The residue was purified again by silica gel chromatography (80/20 toluene/acetone) to afford the product 162 (0.032 g, 48%): $^1$H NMR (CDCl$_3$) δ 8.9 (d, 1H), 8.8 (d, 1H), 7.6 (dd, 1H), 7.45 (dd, 2H), 7.0 (t, 2H), 4.8 (s, 2H), 4.7 (m, 2H), 4.15 (m, 4H), 2.5 (m, 2H), 1.5 (m, 3H), 1.3 (t, 6H), 1.2 (d, 18H); $^{31}$P NMR (CDCl$_3$) δ 27.6; MS: 659 (M+1).

Example 163

A solution of the phosphonate 162 (0.012 g, 0.018 mmol) in dichloromethane (0.663 mL) was treated with trifluoroacetic acid (0.014 mL, 0.180 mmol). The reaction mixture was stirred at room temperature under an inert atmosphere overnight. The volatiles were removed in vacuo with toluene. The solid was triturated in diethylether/hexane to afford the product 163 (0.008 g, 89%) as a TFA salt: $^1$H NMR (CDCl$_3$) δ 9.0 (dd, 1H), 8.9 (dd, 1H), 7.7 (dd, 1H), 7.5 (dd, 2H), 7.0 (t, 2H), 4.8 (s, 2H), 4.75 (m, 2H), 4.15 (m, 4H), 2.45 (m, 2H), 1.3 (t, 6H); $^{31}$P NMR (CDCl$_3$) δ 27.5; MS: 503 (M+1), 501 (M−1).

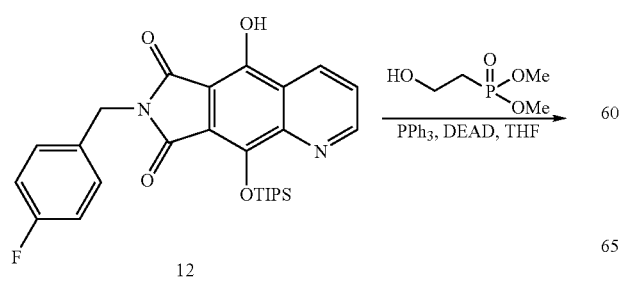

12

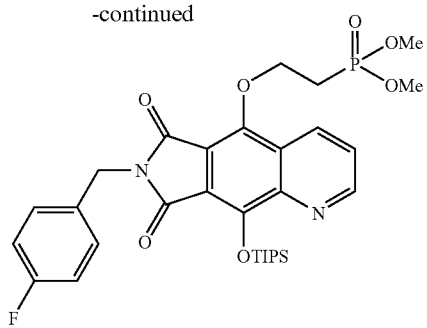

164

Example 164

To a solution of phenol 12 (0.097 g, 0.196 mmol) dissolved in THF (1.02 mL) was added (2-hydroxyethyl)-phosphonic acid dimethyl ester (0.091 g, 0.589 mmol), triphenylphosphine (0.129 g, 0.491 mmol), and diethyl azodicarboxylate (0.046 mL, 0.295 mmol). The reaction mixture stirred at room temperature under an inert atmosphere overnight. The residue was purified directly by silica gel chromatography (85/15—ethylacetate/hexane) to afford a mixture of product 164 and triphenylphosphine oxide (0.160 g): $^1$H NMR (CDCl$_3$) δ 8.95 (d, 1H), 8.75 (d, 1H), 7.7-7.4 (m, 12H), 7.0 (t, 2H), 4.8 (s, 2H), 4.7 (m, 2H), 3.8 (d, 6H), 2.5 (m, 2H), 1.5 (m, 3H), 1.2 (d, 18H); $^{31}$P NMR (CDCl$_3$) δ 30.5 (triphenylphosphine oxide), 29.3; MS: 631 (M+1).

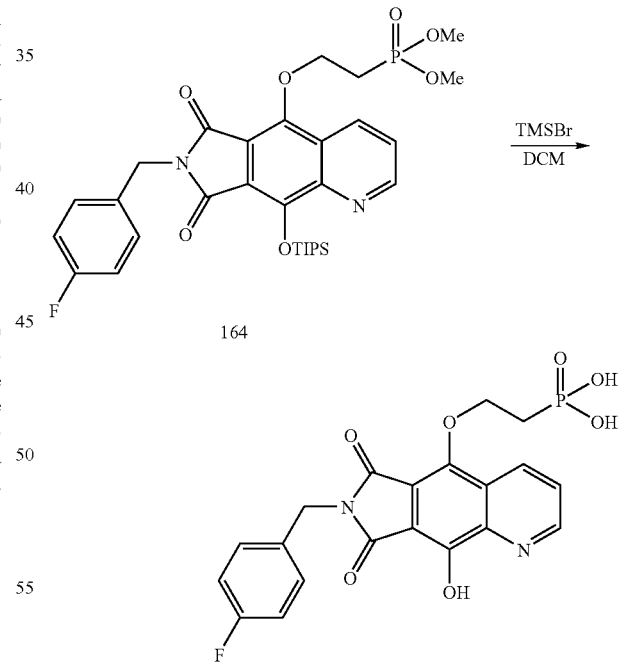

Example 165

A solution of the phosphonate 164 (0.025 g, 0.040 miol) in dichloromethane (0.397 mL) was treated with trimethylsilane bromide (0.0314 mL, 0.24 mmol). The reaction mixture was stirred at room temperature under an inert atmosphere overnight. The volatiles were removed in vacuo with methanol. The solid was washed with dichloromethane to afford the diacid 165 (0.0094 g, 53%): $^1$H NMR (CD$_3$OD) δ 9.4 (dd, 1H), 9.1 (dd, 1H), 8.05 (dd, 1H), 7.5 (dd, 2H), 7.1 (t, 2H), 4.9 (s, 2H), 4.8 (m, 2H), 2.45 (m, 2H); $^{31}$P NMR (CD$_3$OD) δ 24.7; MS: 447 (M+1), 445 (M−1).

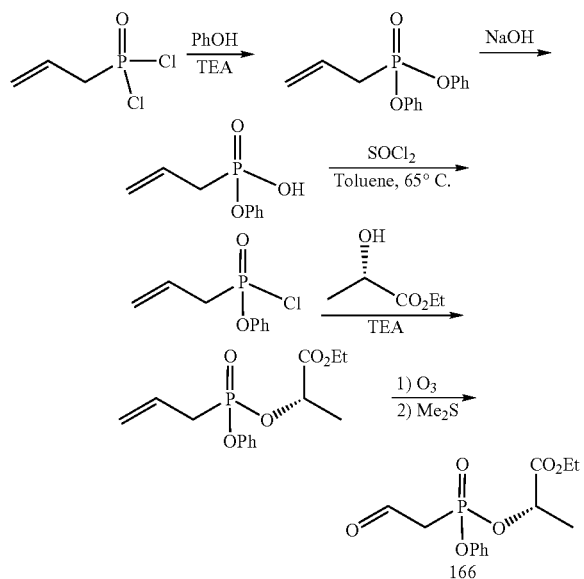

Example 166

To a solution of allylphosphonic dichloride (4 g, 25.4 mmol) and phenol (5.2 g, 55.3 mmol) in CH$_2$Cl$_2$ (40 mL) at 0° C. was added triethylamine (TEA, 8.4 mL, 60 mmol). After stirring at room temperature for 1.5 h, the mixture was diluted with hexane-ethylacetate and washed with HCl (0.3 N) and water. The organic phase was dried over MgSO$_4$, filtered and concentrated under reduced pressure. The residue was filtered through a pad of silica gel (eluted with 2:1 hexane-ethyl acetate) to afford crude product diphenol allylphosphonate (7.8 g, containing the excessive phenol) as an oil which was used directly without any further purification. The crude material was dissolved in CH$_3$CN (60 mL), and NaOH (4.4N, 15 mL) was added at 0° C. The resulting mixture was stirred at room temperature for 3 h, then neutralized with acetic acid to pH=8 and concentrated under reduced pressure to remove most of the acetonitrile. The residue was dissolved in water (50 mL) and washed with CH$_2$Cl$_2$ (three 25 mL portions). The aqueous phase was acidified with concentrated HCl at 0° C. and extracted with ethyl acetate. The organic phase was dried over MgSO$_4$, filtered, evaporated and co-evaporated with toluene under reduced pressure to yield desired monophenol allylphosphonate (4.75 g. 95%) as an oil.

To a solution of monophenol allylphosphonate (4.75 g, 24 mmol) in toluene (30 mL) was added SOCl$_2$ (5 mL, 68 mmol) and DMF (0.05 mL). After stirring at 65° C. for 4 h, the reaction was complete as shown by $^{31}$P NMR. The reaction mixture was evaporated and co-evaporated with toluene under reduced pressure to give the mono chloride (5.5 g) as an oil. To a solution of the mono chloride in CH$_2$Cl$_2$ (25 mL) at 0° C. was added ethyl (S)-lactate (3.3 mL, 28.8 mmol), followed by TEA. The mixture was stirred at 0° C. for 5 min, then at room temperature for 1 h, and concentrated under reduced pressure. The residue was partitioned between ethylacetate and HCl (0.2N), the organic phase was washed with water, dried over MgSO$_4$, filtered and concentrated under reduced pressure. The residue was purified by chromatography on silica gel to afford the allyl monolactate (5.75 g, 80%) as an oil (2:1 mixture of two isomers): $^1$H NMR (CDCl$_3$) δ 7.1-7.4 (m, 5H), 5.9 (m, 1H), 5.3 (m, 2H), 5.0 (m, 1H), 4.2 (m, 2H), 2.9 (m, 2H), 1.6; 1.4 (d, 3H), 1.25 (m, 3H); $^{31}$P NMR (CDCl$_3$) δ 25.4, 23.9.

A solution of the allyl monolactate (2.5 g, 8.38 mmol) in CH$_2$Cl$_2$ (30 mL) was bubbled with ozone air at −78° C. until the solution became blue, then bubbled with nitrogen until the blue color disappeared. Methyl sulfide (3 mL) was added at −78° C. The mixture was warmed up to room temperature, stirred for 16 h and concentrated under reduced pressure to give desired aldehyde 166 (3.2 g, as a 1:1 mixture of DMSO): $^1$H NMR (CDCl$_3$) δ 9.8 (m, 1H), 7.1-7.4 (m, 5H), 5.0 (m, 1H), 4.2 (m, 2H), 3.4 (m, 2H), 1.6; 1.4 (d, 3H), 1.25 (m, 3H). $^{31}$P NMR (CDCl$_3$) δ 17.7, 15.4.

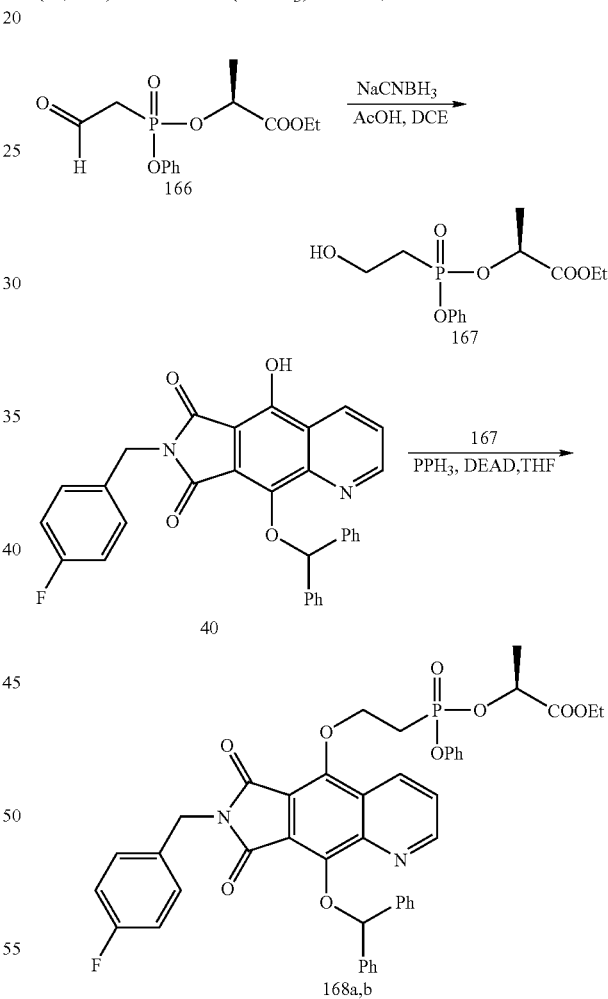

Example 167

To a solution of 2-[(2-oxo-ethyl)-phenoxy-phosphinoyloxy]-propionic acid ethyl ester; aldehyde 166 (0.082 g, 0.218 mmol) in a 1:1 mixture of DMSO and 1,2-dichloroethane was added acetic acid (0.050 mL, 0.870 mmol) then sodium cyanoborohydride (0.027 g, 0.435 mmol). The reaction mixture stirred at room temperature for three hours under an inert atmosphere. Saturated NaHCO$_3$ was added to the reaction mixture and was stirred for five more minutes. The mixture was concentrated in vacuo to remove most of the dichloroethane. Brine was added and then the crude product was extracted into ethylacetate. The organic phase was dried (MgSO$_4$) and concentrated. The residue was purified by silica gel chromatography (5/95—methanol/dichloromethane) to afford the product 167 (0.047 g, 73%), an oil as a mixture of two diastereomers: $^1$H NMR (CDCl$_3$) δ 7.1-7.4 (m, 5H), 5.1 (m, 1H), 4.25 (m, 2H), 4.1 (m, 2H), 2.3 (m, 4H), 1.6 & 1.4 (d, 3H), 1.25 (m, 3H); $^{31}$P NMR (CDCl$_3$) δ 29.0, 26.8.

Example 168

To a solution of phenol 40 (0.033 g, 0.065 mmol) dissolved in THF (0.34 mL) was added ethyl-lactate phosphonate alcohol 167 (0.029 g, 0.097 mmol), triphenylphosphine (0.043 g, 0.162 mmol), and diethyl azodicarboxylate (0.015 mL, 0.097 mmol). The reaction mixture stirred at room temperature under an inert atmosphere overnight. The residue was purified directly by silica gel chromatography (50/50—ethylacetate/hexane) to afford the product 168 (0.027 g, 53%). Separation of the diastereomers by chromatography allowed for characterization of 168a (0.016 g): $^1$H NMR (CDCl$_3$) δ 9.1 (dd, 1H), 8.8 (dd, 1H), 7.9 (s, 1H), 7.6 (m, 4H), 7.55 (m, 1H), 7.4 (dd, 2H), 7.1-7.4 (m, 11H), 7.0 (t, 2H), 5.0 (m, 1H), 4.9 (s, 2H), 4.8 (m, 2H), 4.1 (q, 3H), 2.75 (m, 2H), 1.4 (d, 3H), 1.2 (t, 3H); $^{31}$P NMR (CDCl$_3$) δ 26.05; MS: 790 (M+1)—and 168b (0.011 g): $^1$H NMR (CDCl$_3$) δ 9.1 (dd, 1H), 8.8 (dd, 1H), 7.95 (s, 1H), 7.6 (m, 4H), 7.55 (m, 1H), 7.40 (dd, 2H), 7.1-7.4 (m, 11H), 7.05 (t, 2H), 5.05 (m, 1H), 4.85 (s, 2H), 4.8 (m, 2H), 4.15 (q, 3H), 2.7 (m, 2H), 1.55 (d, 3H), 1.2 (t, 3H); $^{31}$P NMR (CDCl$_3$) δ 24.37; MS: 790 (M+1)

Example 169a

A solution of the phosphonate 168a (0.013 g, 0.0165 mmol) in dichloromethane (0.5 mL) was treated with trifluoroacetic acid (0.1 mL) and triethylsilane (0.2 mL). The reaction mixture was stirred at room temperature under an inert atmosphere for 20 minutes. The volatiles were removed in vacuo with toluene. The solid was triturated in diethylether/hexane to afford the product 169a (0.008 g, 80%) as a TFA salt: $^1$H NMR (CDCl$_3$) δ 8.95 (dd, 1H), 8.9 (dd, 1H), 7.6 (m, 1H), 7.5 (dd, 2H), 7.1-7.4 (m, 5H), 7.0 (,t 2H), 5.0 (m, 1H), 5.0 (m, 2H), 4.85 (s, 2H), 4.15 (q, 3H), 2.8 (m, 2H), 1.4 (d, 3H), 1.25 (t, 3H); $^{31}$P NMR (CDCl$_3$) δ 26.13; MS: 623 (M+1), 621 (M−1).

Example 169b

A solution of the phosphonate 168b (0.011 g, 0.014 mmol) in dichloromethane (0.5 mL) was treated with trifluoroacetic acid (0.1 mL) and triethylsilane (0.2 mL). The reaction mixture was stirred at room temperature under an inert atmosphere for 20 minutes. The volatiles were removed in vacuo with toluene. The solid was triturated in diethylether/hexane to afford the product 169b (0.005 g, 60%) as a TFA salt: $^1$H NMR (CDCl$_3$) δ 8.95 (dd, 1H), 8.9 (dd, 1H), 7.65 (m, 1H), 7.5 (dd, 2H), 7.1-7.4 (m, 5H), 7.0 (t, 2H), 5.1 (m, 2H), 4.9 (m, 1H), 4.85 (s, 2H), 4.15(q, 3H), 2.7 (m, 2H), 1.55 (d, 3H), 1.2 (t, 3H); $^{31}$P NMR (CDCl$_3$) δ 24.44; MS: 623 (M+1), 621 (M−1).

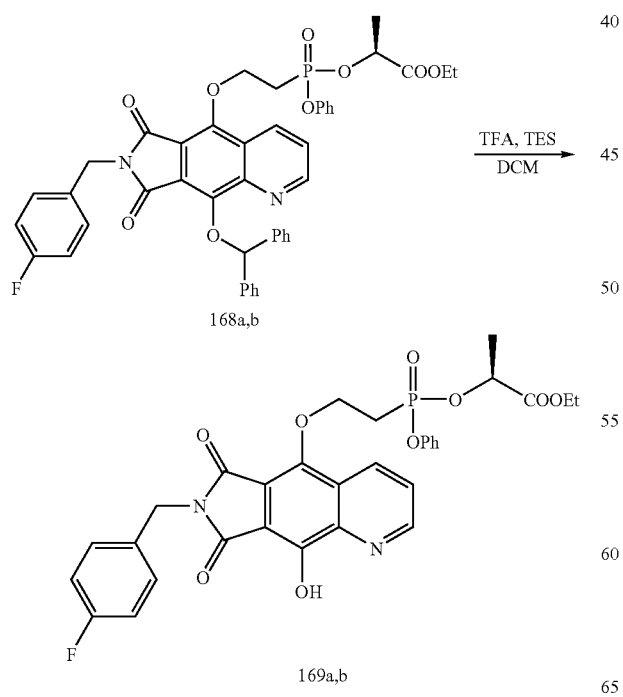

Example 170

A solution of ethyl-lactate phosphonate 169 (0.021 g, 0.034 mmol) in DMSO (0.675 mL) and phosphate buffer saline (3.38 ml) was heated to 40° C. The reaction mixture was treated with esterase-from porcine liver (0.200 mL) and stirred overnight. Another equivalent of esterase was added the following day and the mixture stirred another day. The mixture was concentrated and purified by reversed phase HPLC to afford the product 170 (0.008 g, 46%) as a solid: $^1$H NMR (CD$_3$OD) δ 8.95 (dd, 1H), 8.9 (dd, 1H), 7.75 (m, 1H), 7.45 (dd, 2H), 7.05 (t, 2H), 4.9 (s, 2H), 4.85 (m, 3H), 2.5 (m, 2H), 1.5 (d, 3H); $^{31}$P NMR (CD$_3$OD) δ 26.26; MS: 519 (M+1), 517 (M−1).

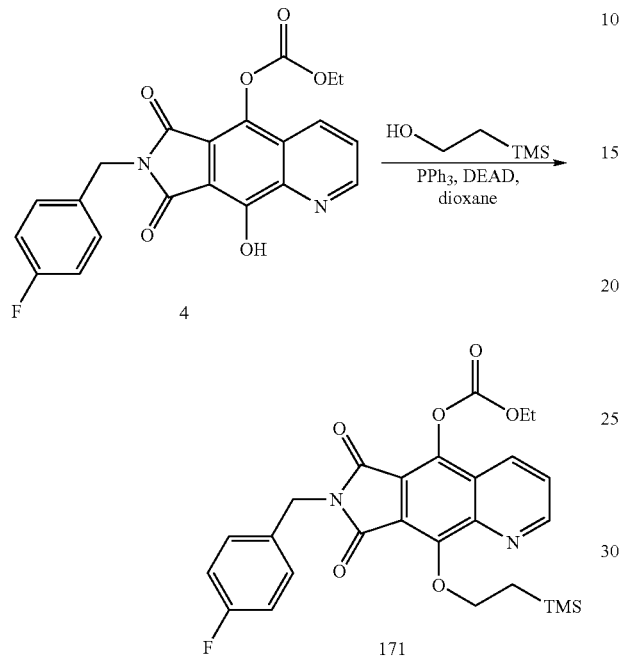

Example 171

To a solution of phenol 4 (1.14 g, 2.79 mmol) dissolved in dioxane (27.9 mL) was added 2-(trimethylsilyl)-ethanol (0.600 mL, 4.18 mmol), triphenylphosphine (1.46 g, 5.57 mmol), and diethyl azodicarboxylate (0.88 mL, 5.57 mmol). The reaction mixture stirred at room temperature under an inert atmosphere overnight. The residue was purified directly by silica gel chromatography (30/70—ethylacetate/hexane) to afford the product 171 (0.240 g, 67%): $^1$H NMR (CDCl$_3$) δ 9.1 (dd, 1H), 8.5 (dd, 1H), 7.65 (dd, 1H), 7.45 (dd, 2H), 7.0 (t, 2H), 4.9 (m, 2H), 4.8 (s, 2H), 4.45 (q, 2H), 1.5 (t, 3H), 1.4 (m, 2H), 0.1 (s, 9H): MS: 510 (M+1).

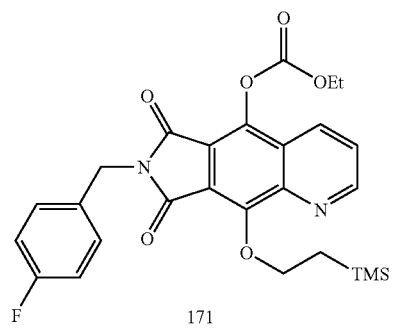

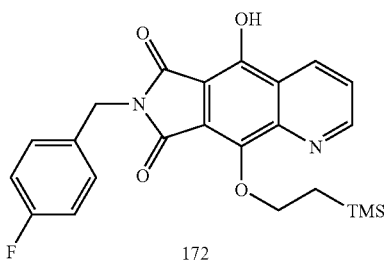

Example 172

To the ethyl carbonate 171 (0.716 g, 1.4 mmol) in THF (70.2 mL) was added a solution (45 mL) of K$_2$CO$_3$ (1.94 g, 14 mmol) in water and 4-dimethylaminopyridine (0.035 g, 0.281 mmol). The yellow solution was stirred at room temperature under an inert atmosphere overnight. Most of THF was removed in vacuo and the remaining solution was diluted with dichloromethane, washed with 1N HCl and brine, then dried (MgSO$_4$) and concentrated. The crude product was triturated in diethylether/hexane to afford the yellow solid product 172 (0.428 g, 70%): $^1$H NMR (CDCl$_3$) δ 9.1 (dd, 1H), 8.65 (dd, 1H), 7.6 (dd, 1H), 7.5 (dd, 2H), 7.0 (t, 2H), 4.85 (s, 2H), 4.85 (m, 2H), 1.35 (m, 2H), 0.1 (s, 9H); MS: 438 (M+1).

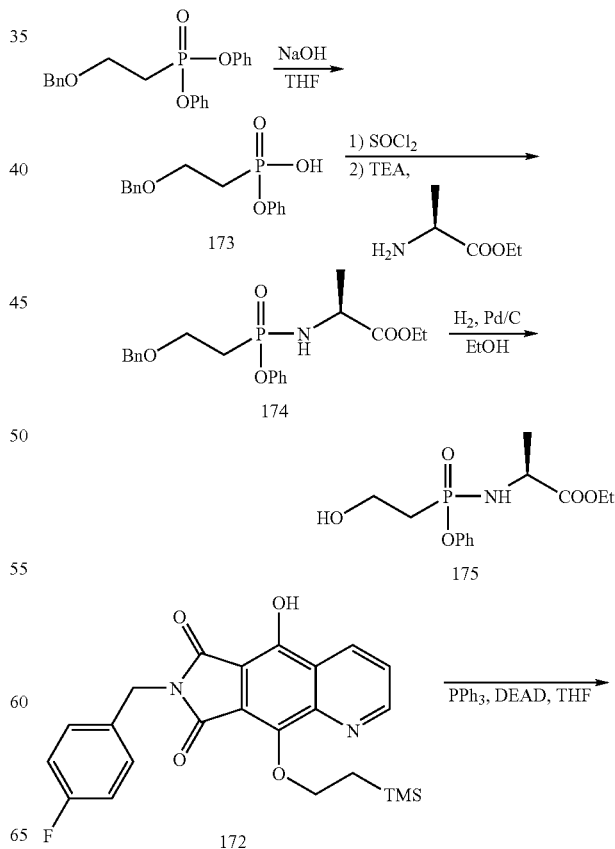

-continued

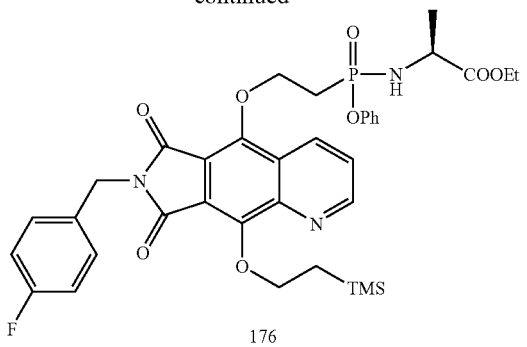

176

Example 173

To a solution of (2-benzyloxy-ethyl)-phosphonic acid dibenzyl ester (0.200 g, 0.543 mmol) in THF was added a solution of NaOH (1.36 mL, 1M) in water. The reaction mixture was stirred at room temperature for 3 hours. Most of THF was removed in vacuo and the residue was dissolved in water. The aqueous solution was washed with ethylacetate three times then acidified with 1N HCl (to pH=1) then extracted with ethylacetate. The organic phase was dried (MgSO$_4$), concentrated and co-evaporated with toluene in vacuo to afford the mono-acid, (2-benzyloxy-ethyl)-phosphonic acid monobenzyl ester, 173 (0.160 g. 100%) as an oil with no further purification: $^1$H NMR (CDCl$_3$) δ 9.25 (bs, 1H), 7.4-7.1 (m, 10H), 4.5 (s, 2H), 3.8 (m, 2H), 2.25 (m, 2H); $^{31}$P NMR (CDCl$_3$) δ 28.63.

Example 174

To a solution of the mono-acid 173 (0.160 g, 0.576 mmol) dissolved in acetonitrile (3.84 mL) was added thionyl chloride (0.42 mL, 5.76 mmol). The reaction mixture was heated to 70° C. and stirred for 3 hours at which point the reaction was completed as shown by $^{31}$P NMR (CDCl$_3$) δ 36.7. The reaction mixture was concentrated as such to afford the intermediate mono-chloridate as an oil which was immediately dissolved in dichloromethane (2.88 mL) and treated with triethylamine (0.321 mL, 2.30 mmol). The reaction mixture was cooled to 0° C. and L-alanine ethyl ester (0.265 g, 1.73 mmol) was added. The mixture was stirred overnight at room temperature under an inert atmosphere and then was concentrated in vacuo. The residue was partitioned between ethylacetate and saturated NH$_4$Cl, and the organic phase was washed with brine, dried (MgSO$_4$) then concentrated in vacuo. The residue was purified by chromatography on silica gel washed with methanol prior to use (1/1—ethylacetate/hexane) to afford the amidate 174 (0.095 g, 45%) as an oil with a 1:1.2 mixture of diastereomers: $^1$H NMR (CDCl$_3$) δ 7.1-7.4 (m, 10H), 4.6 (s, 2H), 4.1 (q, 2H), 3.8 (m, 2H), 3.65 (m, 1H), 2.3 (m, 2H), 1.3 & 1.2 (d, 3H), 1.25 (t, 3H); $^{31}$P NMR (CDCl$_3$) δ 29.51, 28.70.

Example 175

To a solution of the amidate 174 (0.095 g, 0.243 mmol) dissolved in ethanol (4.9 mL) was added palladium (on carbon). The reaction was purged under a vacuum then submitted to hydrogen gas (via balloon attached to the reaction vessel). After several purges between gas and vacuum the reaction mixture was stirred at room temperature for 4 hours. The mixture was filtered with Celite and concentrated in vacuo to afford the alcohol 175 (0.74 g, 100%) as an oil with a 1:1.2 mixture of diastereomers without further purification: $^1$H NMR (CDCl$_3$) δ 7.4-7.1 (m, 5H), 4.15 (m, 2H), 3.7 (q, 2H), 3.5 (m, 1H), 2.2 (m, 2H), 1.35 & 1.25 (d, 3H), 1.25 (m, 3H); $^{31}$P NMR (CDCl$_3$) δ 30.82, 30.54.

Example 176

To a solution of phenol 172 (0.073 g, 0.167 mmol) dissolved in THF (1.67 mL) was added the alcohol 175 (0.075 g, 0.25 mmol), triphenylphosphine (0.087 g, 0.33 mmol), and diethyl azodicarboxylate (0.042 mL, 0.33 mmol). The reaction mixture stirred at room temperature under an inert atmosphere overnight. The residue was purified directly by chromatography on silica gel washed with methanol prior to use (80/20—toluene/acetone) to afford the product 176 (0.065 g, 54%) with a 1:1.2 mixture of diastereomers: $^1$H NMR (CDCl$_3$) δ 9.1 (dd, 1H), 8.8 (dd, 1H), 7.6 (dd, 1H), 7.5 (dd, 2H), 7.4-7.1 (m, 5H), 2.65 (m, 2H), 4.85 (s, 2H), 4.85-4.7 (m, 4H), 4.2 (q, 1H), 4.15 (m, 2H), 4.0-3.8 (m, 1H), 2.65 (m, 2H), 1.4 & 1.25 (d, 3H), 1.3 (m, 2H), 1.2 (m, 3H), 0.10 (s, 9H); $^{31}$P NMR (CDCl$_3$) δ 27.84, 26.96; MS: 722 (M+1).

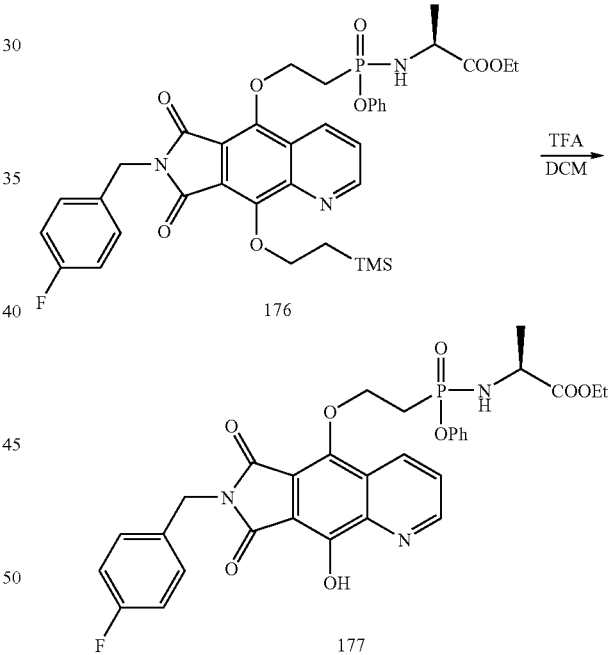

Example 177

A solution of the phosphonate 176 (0.030 g, 0.042 mmol) in dichloromethane (0.832 mL) was treated with trifluoroacetic acid (0.064 mL, 0.84 mmol). The reaction mixture was stirred at room temperature under an inert atmosphere for 45 minutes. The volatiles were removed in vacuo with toluene. The solid was triturated in diethylether/hexane to afford the product 177 (0.022 g, 85%) as a TFA salt with a 1:1.2 mixture of diastereomers: $^1$H NMR (CDCl$_3$) δ 9.0 (dd, 1H), 8.85 (dd, 1H), 7.65 (dd, 1H), 7.5 (dd, 2H), 7.4-7.1 (m, 5H), 7.0 (t, 2H), 4.85 (s, 2H), 4.85 (m, 2H), 4.15 (m, 1H), 4.15 (m, 1H), 4.1 (m, 2H), 3.8 (m, 1H), 2.65 (m, 2H), 1.35 & 1.30 (d, 3H), 1.2 (m, 3H); $^{31}$P NMR (CDCl$_3$) δ 27.86, 27.05; MS: 622 (M+1), 620 (M−1).

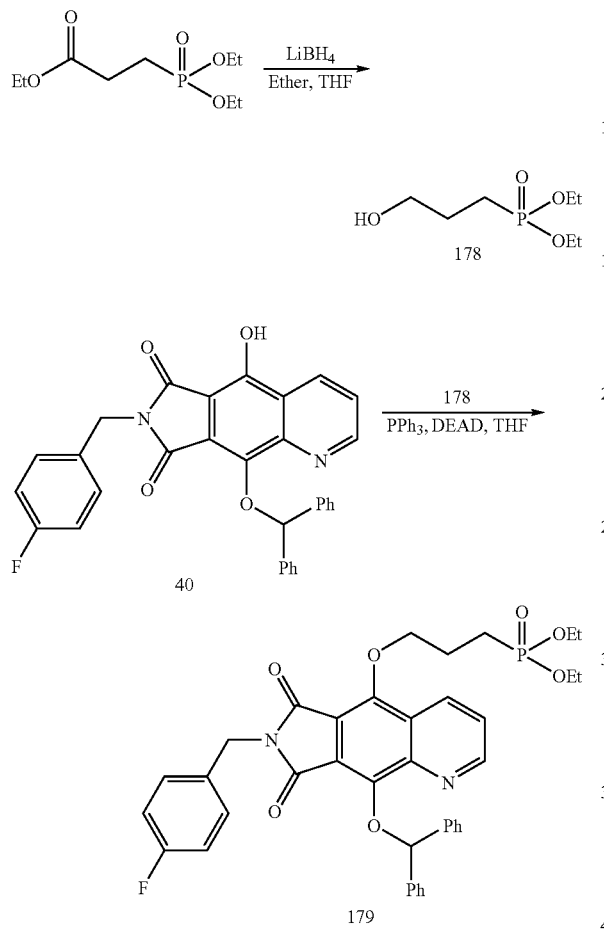

Example 178

A solution of (2-ethoxy-ethyl)-phosphonic acid diethyl ester (0.500 g, 2.1 mmol) in ether (8.5 mL) and THF (1.5 mL) was treated with lithium borohydride. The reaction mixture stirred at room temperature for 1 hour and was then concentrated in vacuo. The crude mixture was partitioned between dichloromethane and water. The organic phase was washed with saturated NaHCO$_3$ and brine, dried (MgSO$_4$), then concentrated in vacuo. The residue was purified by silica gel chromatography (5/95—methanol/dichloromethane) to afford (3-hydroxy-propyl)-phosphonic acid diethyl ester 178 (0.100 g, 24%) as an oil: $^1$H NMR (CDCl$_3$) δ 4.1 (m, 4H), 3.7 (m, 2H), 2.95 (bs, 1H), 1.85 (m, 4H), 1.30 (t, 3H); $^{31}$P NMR (CDCl$_3$) δ 33.26; MS: 197 (M+1).

Example 179

To a solution of phenol 40 (0.023 g, 0.046 mmol) dissolved in THF (0.45 mL) was added the alcohol 178 (0.013 g, 0.068 mmol), triphenylphosphine (0.024 g, 0.091 mmol), and diethyl azodicarboxylate (0.014 mL, 0.091 mmol). The reaction mixture stirred at room temperature under an inert atmosphere overnight. The residue was purified directly by silica gel chromatography (90/10—ethylacetate/hexane) to afford the product 179 (0.024 g, 76%): $^1$H NMR (CDCl$_3$) δ 9.1 (dd, 1H), 8.6 (dd, 1H), 7.9 (dd, 1H), 7.6 (m, 6H), 7.4 (dd, 2H), 7.2 (m, 6H), 7.0 (t, 2H), 4.8 (s, 2H), 4.5 (t, 2H), 4.15 (m, 2H), 2.2 (m, 2H), 2.0 (m, 2H), 1.35 (t, 3H); $^{31}$P NMR (CDCl$_3$) δ 31.48; MS: 684 (M+1).

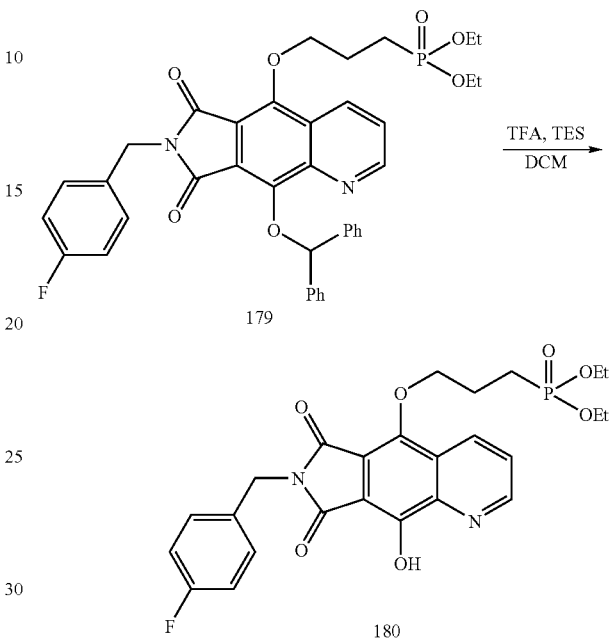

Example 180

A solution of the phosphonate 179 (0.028 g, 0.041 mmol) in dichloromethane (0.5 mL) was treated with trifluoroacetic acid (0.1 mL) and triethylsilane (0.2 mL). The reaction mixture was stirred at room temperature under an inert atmosphere for 20 minutes. The volatiles were removed in vacuo with toluene. The solid was triturated in diethylether/hexane to afford the product 180 (0.020 g, 95%) as a TFA salt: $^1$H NMR (CDCl$_3$) δ 9.0 (dd, 1H), 8.7 (dd, 1H), 7.65 (dd, 1H), 7.5 (dd, 2H), 7.0 (t, 2H), 4.85 (s, 2H), 4.6 (t, 2H), 4.15 (m, 2H), 2.25 (m, 2H), 2.05 (m, 2H), 1.35 (t, 3H); $^{31}$P NMR (CDCl$_3$) δ 31.45; MS: 517 (M+1), 516 (M−1).

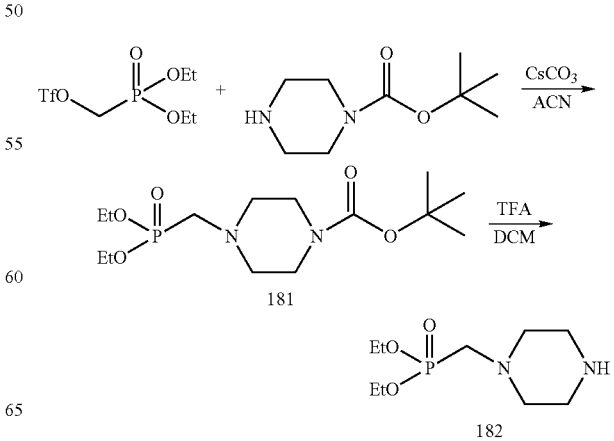

salt: ¹H NMR (CDCl₃) δ 11.0 (bs, 1H), 4.2 (m, 4H), 3.45 (t, 4H), 3.35 (m, 4H), 3.2 (d, 2H), 1.4 (t, 6H); ³¹P NMR (CDCl₃) δ 19.16; MS: 237 (M+1).

Example 183

A solution of the phenol intermediate 45 (0.044 mmol) in dichloromethane (0.441 mL) was treated with triethylamine (0.025 mL, 0.176 mmol) and cat. 4-dimethylaminopyridine. The reaction mixture was cooled to 0° C. then triphosgene (0.026 g, 0.088 mmol) in a 1M solution of dichloromethane was added. The mixture stirred at room temperature under an inert atmosphere for 2 hours, then the free piperazine linker phosphonate 182 (0.046 g, 0.132 mmol) in a 1M solution of dichloromethane treated with triethylamine (0.025 mL, 0.176 mmol) was added, and the mixture was stirred overnight. The mixture was partitioned between dichloromethane and water. The organic phase was washed with saturated NH₄Cl and brine, dried (MgSO₄), and concentrated in vacuo. The residue was purified by silica gel chromatography (3/97—methanol/dichloromethane) to afford the product 183 (0.016 g, 64%): ¹H NMR (CDCl₃) δ 9.05 (dd, 1H), 8.1 (dd, 1H), 8.0 (s, 1H), 7.75 (d, 4H), 7.5 (dd, 1H), 7.4-7.m, 8H), 7.05 (t, 2H), 4.8 (s, 2H), 4.2 (s, 2H), 4.15 (m, 4H), 3.75 (m, 2H), 3.6 (m, 2H), 2.85 (d, 2H), 2.8 (m, 2H), 2.75 (m, 2H), 1.35 (t, 6H); ³¹P NMR (CDCl₃) δ 23.57; MS: 753 (M+1).

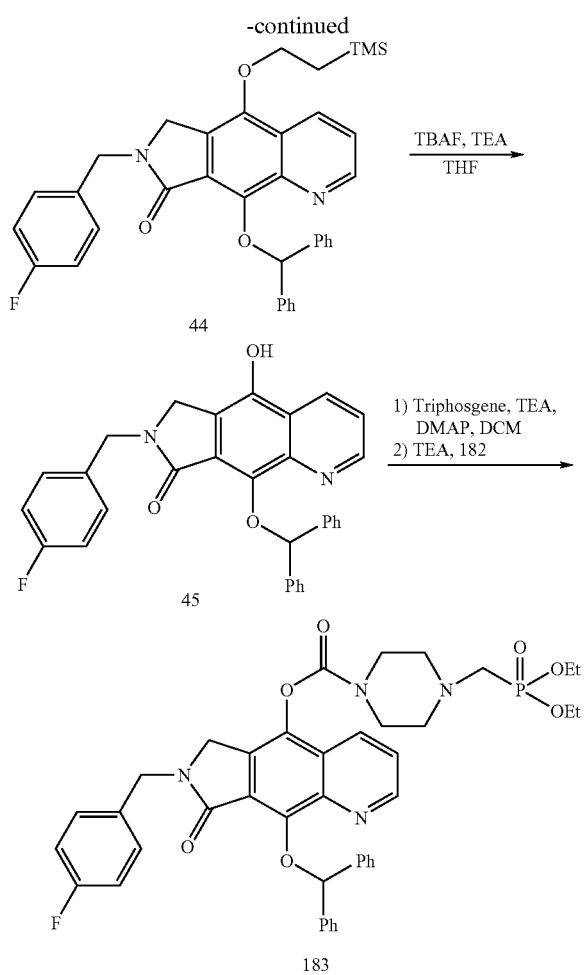

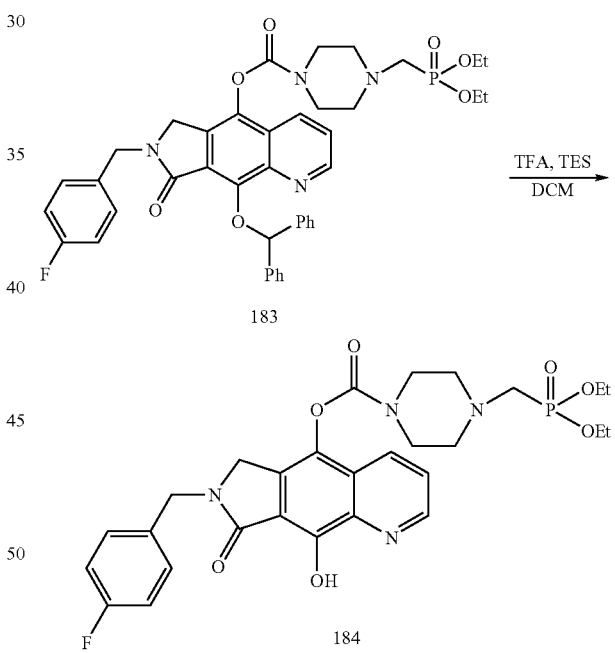

Example 181

To a solution of I-BOC-piperazine (0.200 g, 1.08 mmol) in acetonitrile (10.4 mL) was added CsCO₃ (1.05 g, 3.23 mmol) and then cooled to 0° C. Trifluoromethanesulfonic acid diethoxyphosphorylmethyl ester (0.387 g, 1.29 mmol) dissolved in acetonitrile (5 mL) was added in a dropwise manner. The reaction mixture was stirred at room temperature for 1 hour upon which it was concentrated in vacuo. The reaction mixture was taken into ethylacetate then washed with saturated NH₄Cl and brine, dried (MgSO₄), then concentrated in vacuo. The residue was purified using silica gel chromatography (3/97—methanol/dichloromethane) to afford the product 181 (0.310 g, 86%) as an oil: ¹H NMR (CDCl₃) δ 4.15 (m, 4H), 3.45 (t, 4H), 2.8 (d, 2H), 2.6 (m, 4H), 1.45 (s, 9H), 1.35 (t, 6H); ³¹P NMR (CDCl₃) δ 24.03; MS: 337 (M+1).

Example 182

A solution of the BOC protected piperazine linker phosphonate 181 (0.310 g, 0.923 mmol) in dichloromethane (6.15 mL) was treated with trifluoroacetic acid (0.711 mL, 9.23 mmol). The reaction mixture was stirred at room temperature under an inert atmosphere overnight. The volatiles were removed in vacuo with toluene to afford the free piperazine linker phosphonate 182 (0.323 g, 100%) as a TFA Example 184

A solution of the phosphonate 183 (0.016 g, 0.021 mmol) in dichloromethane (0.5 mL) was treated with trifluoroacetic acid (0.1 mL) and triethylsilane (0.2 mL). The reaction mixture was stirred at room temperature under an inert atmosphere for 20 minutes. The volatiles were removed in vacuo with toluene. The solid was triturated in diethylether/hexane to afford the product 184 (0.0125 g, 100%) as a TFA salt: ¹H NMR (CDCl₃) δ 9.0 (dd, 1H), 8.2 (dd, 1H), 7.6 (dd, 1H), 7.3 (m, 2H), 7.05 (t, 2H), 4.75 (s, 2H), 4.35 (s, 2H), 4.2

(m, 4H), 3.95 (m, 2H), 3.75 (m, 2H), 3.2 (d, 2H), 3.2 (m, 2H), 3.1 (m, 2H), 1.4 (t, 6H); $^{31}$P NMR (CDCl$_3$) δ 19.93; MS: 587 (M+1), 585 (M−1).

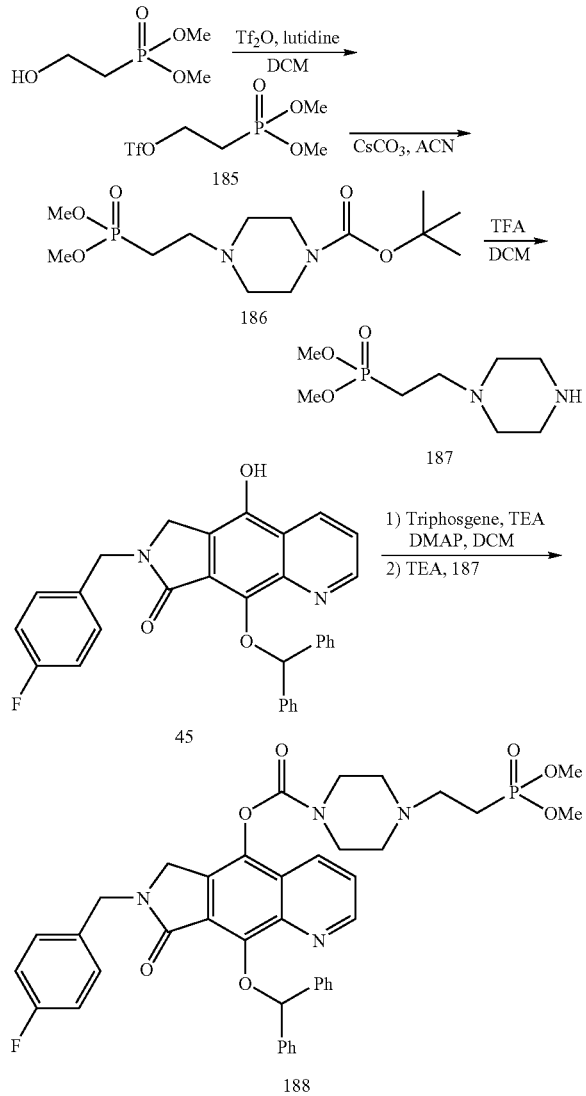

Example 185

To a solution of (2-hydroxy-ethyl)-phosphonic acid dimethyl ester (0.250 g, 1.62 mmol) in dichloromethane (4 mL) was added 2,6-lutidine (0.284 mL, 2.44 mmol). The reaction mixture was cooled to −40° C. and trifluoromethanesulfonic anhydride (0.355 mL, 2.11 mmol) was added. The mixture stirred in the cold bath under an inert atmosphere for 2 hours at which point the reaction was completed as shown by $^{31}$P NMR (CDCl$_3$) δ 25.7. The mixture was partitioned between dichloromethane and water both cooled by an ice-water bath. The organic phase was washed with brine, dried (MgSO$_4$), and concentrated in vacuo to afford trifluoromethanesulfonic acid dimethoxy-phosphoryl-2-ethyl ester 185 as an oil which was immediately carried forward with no further purification or characterization.

Example 186

To a solution of 1-BOC-piperazine (0.252 g, 1.35 mmol) in acetonitrile (14.3 mL) was added CsCO$_3$ (1.32 g, 4.06 mmol) and then cooled to 0° C. Trifluoromethanesulfonic acid dimethoxy-phosphoryl-2-ethyl ester 185 (0.464 g, 1.62 mmol) dissolved in acetonitrile (5 mL) was added in a dropwise manner. The reaction mixture was stirred at room temperature overnight upon which it was concentrated in vacuo. The reaction mixture was taken into ethylacetate then washed with saturated NH$_4$Cl and brine, dried (MgSO$_4$), then concentrated in vacuo. The residue was purified using silica gel chromatography (5/95—methanol/dichloromethane) to afford the BOC protected piperazine linker phosphonate 186 (0.162 g, 31% over 2 steps) as an oil: $^1$H NMR (CDCl$_3$) δ 3.75 (d, 6H), 3.4 (m, 4H), 2.65 (m, 2H), 2.4 (m, 4H), 1.95 (m, 2H), 1.45 (s, 9H); $^{31}$P NMR (CDCl$_3$) δ 33.06; MS: 323 (M+1).

Example 187

A solution of the BOC protected piperazine linker phosphonate 186 (0.162 g, 0.503 nimol) in dichloromethane (3.35 mL) was treated with trifluoroacetic acid (0.388 mL, 5.03 mmol). The reaction mixture was stirred at room temperature under an inert atmosphere overnight. The volatiles were removed in vacuo with toluene to afford the free piperazine linker phosphonate 187 (0.169 g, 100%) as a TFA salt: $^1$H NMR (CD$_3$OD) δ 3.8 (d, 6H), 3.45 (m, 4H), 3.2 (m, 4H), 3.15 (m, 2H), 2.3 (m, 2H); $^{31}$P NMR (CDCl$_3$) δ 3.8 (d, 6H), (M+1).

Example 188

A solution of the phenol intermediate 45 (0.046 mmol) in dichloromethane (0.458 mL) was treated with triethylamine (0.026 mL, 0.183 mmol) and a catalytic amount of 4-dimethylaminopyridine. The reaction mixture was cooled to 0° C. then triphosgene (0.027 g, 0.092 mmol) in a 1M solution of dichloromethane was added. The mixture was stirred at room temperature under an inert atmosphere for 2 hours, then the free piperazine linker phosphonate 187 (0.046 g, 0.137 mmol) in a 1M solution of dichloromethane treated with triethylamine (0.026 mL, 0.183 mmol) was added dropwise. The mixture was stirred overnight and then partitioned between dichloromethane and water. The organic phase was washed with saturated NH$_4$Cl and brine, dried (MgSO$_4$), and concentrated in vacuo. The residue was purified by silica gel chromatography (8/92—methanol/ethylacetate) to afford the product 188 (0.019 g, 56%): $^1$H NMR (CDCl$_3$) δ 9.05 (dd, 1H), 8.1 (dd, 1H), 8.05 (s, 1H), 7.75 (m, 4H), 7.5 (dd, 1H), 7.4-7.1 (m, 8H), 7.1 (t, 2H), 4.8 (s, 2H), 4.2 (s, 2H), 3.8 (d, 6H), 3.6 (m, 4H), 2.75 (m, 2H), 2.55 (m, 4H), 2.1 (m, 2H); $^{31}$P NMR (CDCl$_3$) δ 32.65; MS: 739 (M+1).

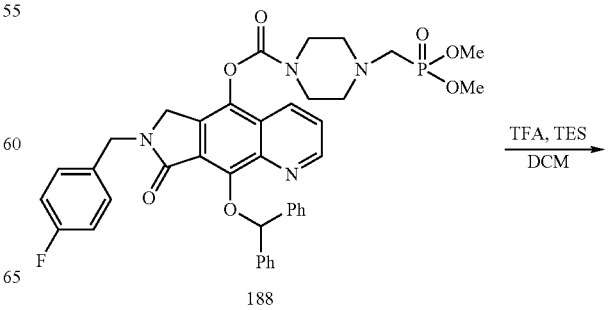

188

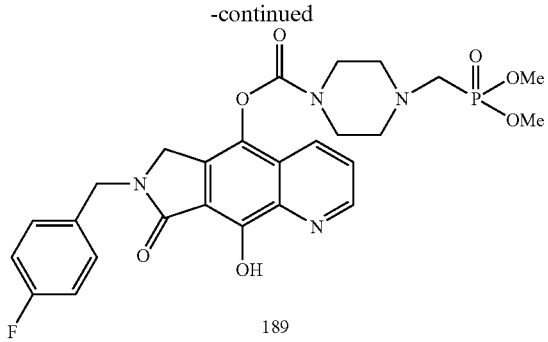

Example 189

A solution of the phosphonate 188 (0.019 g, 0.026 mmol) in dichloromethane (0.5 mL) was treated with trifluoroacetic acid (0.1 mL) and triethylsilane (0.2 mL). The reaction mixture was stirred at room temperature under an inert atmosphere for 20 minutes. The volatiles were removed in vacuo with toluene. The solid was triturated in diethylether/hexane to afford the product 189 (0.013 g, 74%) as a TFA salt: $^{1}$H NMR (CDCl$_3$) δ 8.9 (dd, 1H), 8.15 (dd, 1H), 7.55 (dd, 1H), 7.35 (m, 2H), 7.05 (t, 2H), 4.75 (s, 2H), 4.35 (s, 2H), 4.2 (m, 2H), 3.95 (m, 2H), 3.8 (d, 6H), 3.4 (m, 4H), 3.35 (m, 2H), 2.4 (m, 2H); $^{31}$P NMR (CDCl$_3$) δ 27.31; MS: 573 (M+1).

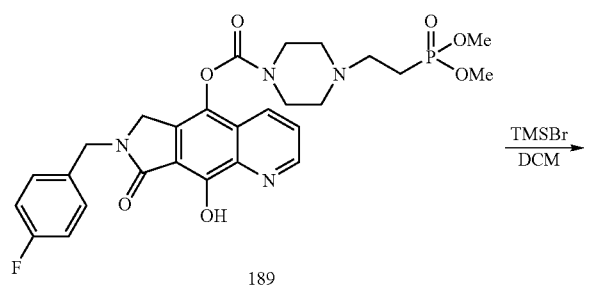

Example 190

A solution of the phosphonate 189 (0.006 g, 0.009 mmol) in dichloromethane (0.088 mL) was treated with trimethylsilane bromide (0.007 mL, 0.053 mmol). The reaction mixture was stirred at room temperature overnight under an inert atmosphere. The volatiles were removed in vacuo with methanol. The solid was washed with dichloromethane to afford the diacid 190 (0.006 g, 100%): $^{1}$H NMR (CD$_3$OD) δ 9.3 (dd, 1H), 9.2 (dd, 1H), 8.2 (dd, 1H), 7.4 (m, 2H), 7.1 (t, 2H), 4.8 (s, 2H), 4.6 (s, 2H), 3.6-3.2 (m, 10H), 2.35 (m, 2H); $^{31}$P NMR (CD$_3$OD) δ 21.43; MS: 545 (M+1), 543 (M−1).

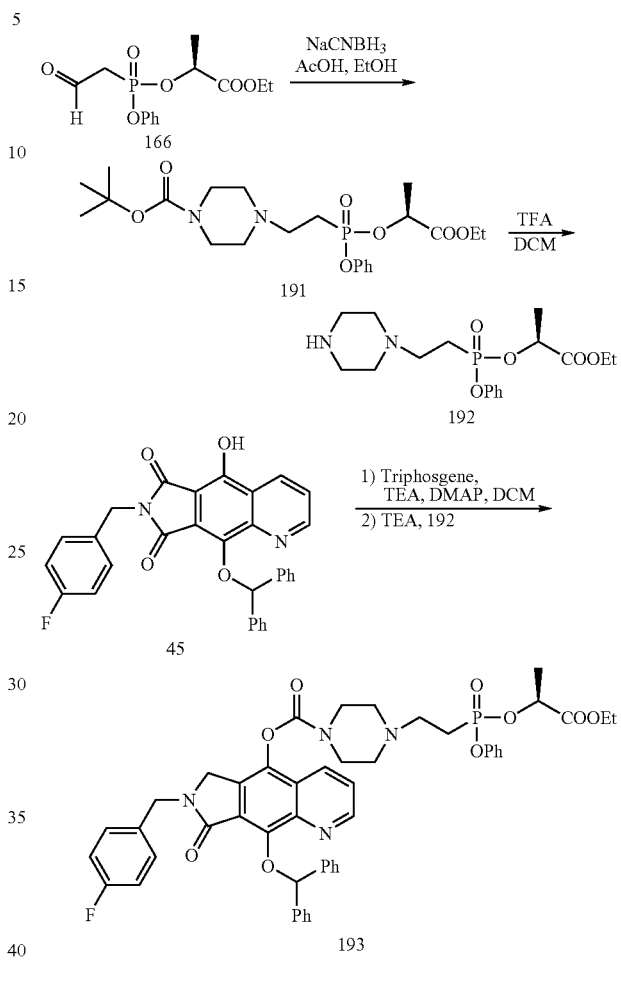

Example 191

To a solution of 2-[(2-oxo-ethyl)-phenoxy-phosphinoyloxy]-propionic acid ethyl ester, aldehyde 166, as a 1:1 mixture of DMSO (0.050 g, 0.167 mmol) and 1-BOC-piperazine (0.034 g, 0.183 mmol) dissolved in ethanol (1.67 mL) was added acetic acid (0.038 mL, 0.667 mmol). The reaction mixture was stirred at room temperature for 2.5 hours then sodium cyanoborohydride (0.021 g, 0.333 mmol) was added. The reaction mixture stirred at room temperature overnight. Saturated NaHCO$_3$ was added to the reaction mixture and was stirred for five more minutes. The mixture was concentrated in vacuo to remove most of the ethanol. Brine was added and then the crude product was extracted into ethylacetate. The organic phase was dried (MgSO$_4$) and concentrated. The residue was purified by silica gel chromatography (5/95—methanol/dichloromethane) to afford the product 191 (0.050 g, 64%), an oil as a mixture of diastereomers: $^{1}$H NMR (CDCl$_3$) δ 7.4-7.1 (m, 5H), 5.0 (m, 1H), 4.2 (m, 2H), 3.4 (m, 4H), 2.8 (m, 2H), 2.4 (m, 4H), 2.2 (m, 2H), 1.6 & 1.35 (d, 3H), 1.4 (s, 9H), 1.2 (t, 3H); $^{31}$P NMR (CDCl$_3$) δ 28.83, 27.18; MS: 471 (M+1).

Alternatively, a solution of 2-[(2-oxo-ethyl)-phenoxy-phosphinoyloxy]-propionic acid ethyl ester 166, as a 1:1 mixture with DMSO (0.500 g, 1.67 mmol), and piperazine- 1-carboxylic acid tert-butyl ester (1-BOC-piperazine, 0.340 g, 1.83 mmol) dissolved in ethanol (1.67 mL) was added 4 Å molecular sieves (0.300 g) and acetic acid (0.400 mL, 6.8 mmol). The reaction mixture was stirred at room temperature for 1.5 hours then sodium cyanoborohydride (0.212 g, 3.33 mmol) was added. The reaction mixture stirred at room temperature for 3 hours and was concentrated in vacuo then redissolved in chloroform. The mixture was washed with saturated $NaHCO_3$ and brine, dried ($NaSO_4$), filtered and concentrated. The residue was treated with diethyl ether. Solid precipitate was filtered off, and the filtrate was concentrated to afford 4-{2-[(1-Ethoxycarbonyl-ethoxy)-phenoxy-phosphoryl]-ethyl}-piperazine-1-carboxylic acid tert-butyl ester 191 (0.600 g, 77%) as an oil (mixture of two diastereomers).

Example 192

A solution of 4-{2-[(1-ethoxycarbonyl-ethoxy)-phenoxy-phosphoryl]-ethyl}-piperazine-1-carboxylic acid tert-butyl ester 191 (0.050 g, 0.106 mmol) in dichloromethane (0.709 mL) was treated with trifluoroacetic acid (0.082 mL, 1.06 mmol). The reaction mixture was stirred at room temperature under an inert atmosphere for 4 hours. The volatiles were removed in vacuo with toluene to afford the free piperazine linker phosphonate 192 (0.051 g, 100%) as a TFA salt (mixture of two diastereomers): $^1$H NMR ($CDCl_3$) δ 10.8 (bs, 1H), 7.5-7.1 (m, 5H), 5.0 (m, 1H), 4.2 (m, 4H), 3.7 (m, 8H), 2.65 (m, 2H), 1.6 & 1.4 (d, 3H), 1.25 (t, 3H); $^{31}$P NMR ($CDCl_3$) δ 25.58, 20.86; MS: 371 (M+1).

Alternatively a solution of 4-{2-[(1-ethoxycarbonyl-ethoxy)-phenoxy-phosphoryl]-ethyl}-piperazine-1-carboxylic acid tert-butyl ester 191 (0.100 g, 0.212 mmol) in methylene chloride (2 mL) was treated with trifluoroacetic acid (0.340 mL, 4.41 mmol). The reaction mixture was stirred at room temperature under an inert atmosphere for 6 hours. The volatiles were removed in vacuo with ethyl acetate to afford the trifluoroacetate salt of 2-[phenoxy-(2-piperazin-1-yl-ethyl)-phosphinoyloxy]-propionic acid ethyl ester 192 (0.103 g, 100%) (mixture of two diastereomers).

Example 193

A solution of the phenol intermediate 45 (0.039 mmol) in dichloromethane (0.386 mL) was treated with triethylamine (0.022 mL, 0.155 mmol) and cat. 4-dimethylaminopyridine. The reaction mixture was cooled to 0° C. then triphosgene (0.023 g, 0.077 mmol) in a 1M solution of dichloromethane was added. The mixture stirred at room temperature under an inert atmosphere for 2 hours, then the free piperazine linker phosphonate 192 (0.056 g, 0.115 mmol) in a 1M solution of dichloromethane treated with triethylamine (0.022 mL, 0.155 mmol) was added, and the mixture was stirred overnight. The mixture was partitioned between dichloromethane and water. The organic phase was washed with saturated $NH_4Cl$ and brine, dried ($MgSO_4$), and concentrated in vacuo. The residue was purified by silica gel chromatography (5/95—methanol/dichloromethane) to afford the product 193 (0.013 g, 50%) as a mixture of diastereomers: $^1$H NMR ($CDCl_3$) δ 9.05 (dd, 1H), 8.1 (dd, 1H), 8.05 (s, 1H), 7.75 (d, 4H), 7.5 (dd, 1H), 7.4-7.1 (m, 11H), 7.05 (t, 2H), 5.1 (m, 1H), 4.8 (s, 2H), 4.2 (s, 2H), 4.15 (m, 2H), 3.8-3.4 (m, 4H), 3.0-2.2 (m, 8H), 1.6 & 1.4 (d, 3H), 1.2 (t, 3H); $^{31}$P NMR ($CDCl_3$) δ 28.30, 26.59; MS: 887 (M+1).

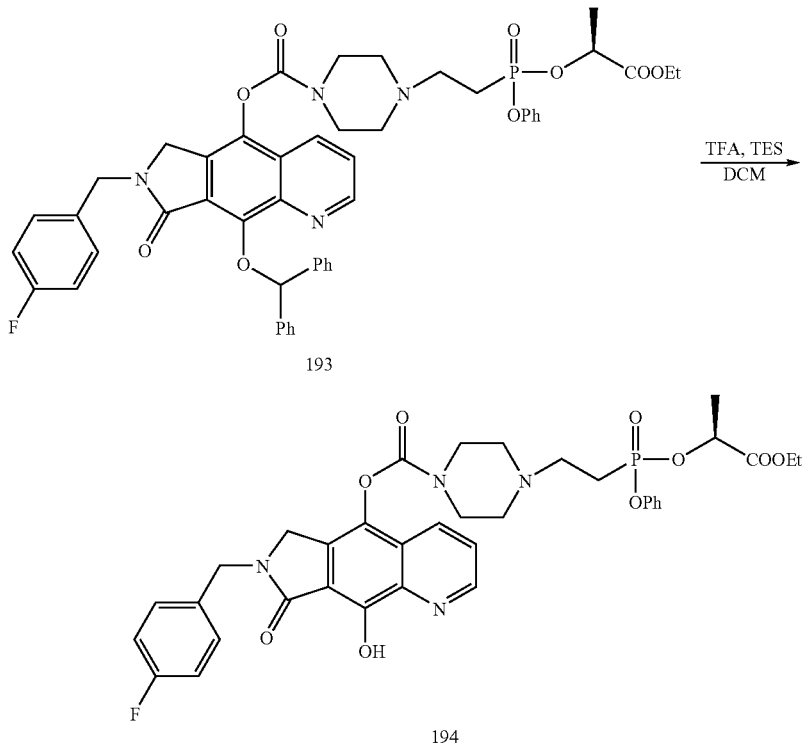

Example 194

A solution of the phosphonate 193 (0.013 g, 0.015 mmol) in dichloromethane (0.5 mL) was treated with trifluoroacetic acid (0.1 mL) and triethylsilane (0.2 mL). The reaction mixture was stirred at room temperature under an inert atmosphere for 20 minutes. The volatiles were removed in vacuo with toluene. The solid was triturated in diethylether/hexane to afford the product 194 (0.010 g, 80%) as a TFA salt: $^1$H NMR (CDCl$_3$) δ 8.95 (dd, 1H), 8.15 (dd, 1H), 7.55 (dd, 1H), 7.35 (m, 2H), 7.3-7.1 (m, 5H), 7.05 (t, 2H), 5.0 (m, 1H), 4.75 (s, 2H), 4.35 (s, 2H), 4.2 (m, 2H), 3.8-3.6 (m, 4H), 3.4-3.0 (m, 6H), 2.5-2.7 (m, 2H), 1.6 & 1.4 (d, 3H), 1.25 (t, 3H); $^{31}$P NMR (CDCl$_3$) δ 23.39, 21.67; MS: 721 (M+1).

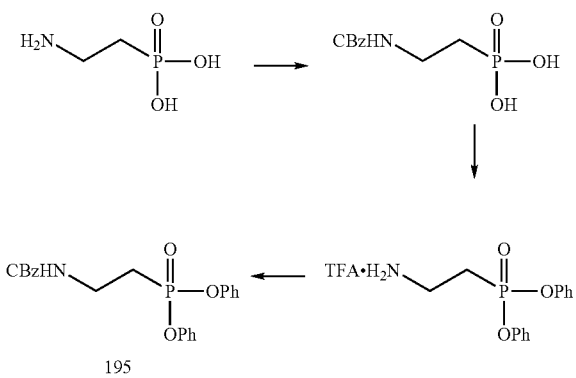

Example 195

To a solution of 2-aminoethylphosphonic acid (1.26 g, 10.1 mmol) in 2N NaOH (10.1 mL, 20.2 mmol) was added benzyl chloroformate (1.7 mL, 12.1 mmol). After the reaction mixture was stirred for 2 d at room temperature, the mixture was partitioned between Et$_2$O and water. The aqueous phase was acidified with 6N HCl until pH=2. The resulting colorless solid was dissolved in MeOH (75 mL) and treated with Dowex 50WX8-200 (7 g). After the mixture was stirred for 30 minutes, it was filtered and evaporated under reduced pressure to give carbobenzoxyaminoethyl phosphonic acid (2.37 g, 91%) as a colorless solid.

To a solution of carbobenzoxyaminoethyl phosphonic acid (2.35 g, 9.1 mmol) in pyridine (40 mL) was added phenol (8.53 g, 90.6 mmol) and 1,3-dicyclohexylcarbodi-imide (7.47 g, 36.2 mmol). After the reaction mixture was warmed to 70° C. and stirred for 5 h, the mixture was diluted with CH$_3$CN and filtered. The filtrate was concentrated under reduced pressure and diluted with EtOAc. The organic phase was washed with sat. NH$_4$Cl, sat. NaHCO$_3$, and brine, then dried over Na$_2$SO$_4$, filtered, and evaporated under reduced pressure. The crude product was chromatographed on silica gel twice (eluting 40-60% EtOAc/hexane) to give diphenyl 2-aminoethyl phosphonic acid (2.13 g, 57%) as a colorless solid.

To a solution of diphenyl 2-aminoethyl phosphonic acid (262 mg, 0.637 mmol) in iPrOH (5 mL) was added TFA (0.05 mL, 0.637 mmol) and 10% Pd/C (26 mg). After the reaction mixture was stirred under H$_2$ atmosphere (balloon) for 1 h, the mixture was filtered through Celite. The filtrate was evaporated under reduced pressure to give diphenyl carbobenzoxyaminoethyl phosphonate 195 (249 mg, 100%) as a colorless oil.

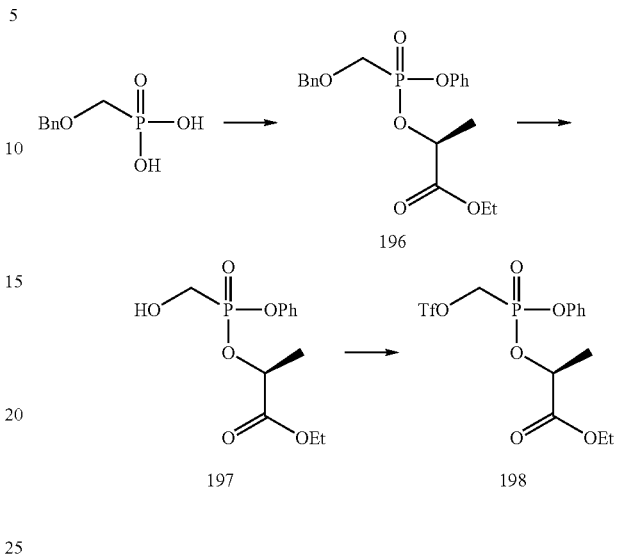

Example 196

To a solution of benzyloxymethyl phosphonic acid (520 mg, 2.57 mmol) in CH$_3$CN (5 mL) was added thionyl chloride (0.75 mL, 10.3 mmol) and heated to 70° C. in an oil bath. After the reaction mixture was stirred for 2 h at 70° C., the mixture was concentrated and azeotroped with toluene. To a solution of the crude chloridate in toluene (5 mL) was added tetrazole (18 mg, 0.26 mmol) at 0° C. To this mixture was added phenol (121 mg, 1.28 mmol) and triethylamine (0.18 mL, 1.28 mmol) in toluene (3 mL) at 0° C. After the reaction mixture was warmed to room temperature and stirred for 2 h, ethyl lactate (0.29 mL, 2.57 mmol) and triethylamine (0.36 mL, 2.57 mmol) in toluene (2.5 mL) were added. The reaction mixture was stirred for 16 hours at room temperature, at which time the mixture was partitioned between EtOAc and sat. NH$_4$Cl. The organic phase was washed with sat. NH$_4$Cl, 1M NaHCO$_3$, and brine, then dried over Na$_2$SO$_4$, filtered, and evaporated under reduced pressure. The crude product was chromatographed on silica gel (eluting 20-40% EtOAc/hexane) to give two diastereomers (isomer A and isomer B) of 2-(benzyloxymethyl-phenoxy-phosphinoyloxy)-propionic acid ethyl ester 196 (66 mg, 109 mg, 18% total) as colorless oils.

Example 197a

To a solution of benzyl phosphonate 196 isomer A (66 mg, 0.174 mmol) in EtOH (2 mL) was added 10% Pd/C (13 mg). After the reaction mixture was stirred under H$_2$ atmosphere (balloon) for 6 h, the mixture was filtered through Celite. The filtrate was evaporated under reduced pressure to give alcohol 197a isomer A (49 mg, 98%) as a colorless oil.

Example 197b

To a solution of benzyl phosphonate 196 isomer B (110 mg, 0.291 mmol) in EtOH (3 mL) was added 10% Pd/C (22 mg). After the reaction mixture was stirred under H$_2$ atmosphere (balloon) for 6 h, it was filtered through Celite. The filtrate was evaporated under reduced pressure to give alcohol 197b isomer B (80 mg, 95%) as a colorless oil.

Example 198a

To a solution of alcohol 197a isomer A (48 mg, 0.167 mmol) in $CH_2Cl_2$ (2 mL) was added 2,6-lutidine (0.03 mL, 0.250 mmol) and trifluoromethanesulfonic anhydride (0.04 mL, 0.217 mmol) at –40° C. (dry ice-$CH_3CN$ bath). After the reaction mixture was stirred for 15 min at –40° C., the mixture was warmed to 0° C. and partitioned between $Et_2O$ and 1M $H_3PO_4$. The organic phase was washed with 1M $H_3PO_4$ (3 times), dried over $Na_2SO_4$, filtered, and evaporated under reduced pressure to give triflate 198a isomer A (70 mg, 100%) as a pale yellow oil.

Example 198b

To a solution of alcohol 197b isomer B (80 mg, 0.278 mmol) in $CH_2Cl_2$ (3 mL) was added 2,6-lutidine (0.05 mL, 0.417 mmol) and trifluoromethanesulfonic anhydride (0.06 mL, 0.361 mmol) at –40° C. (dry ice-$CH_3CN$ bath). After the reaction mixture was stirred for 15 min at –40° C., the mixture was warmed to 0° C. and partitioned between $Et_2O$ and 1M $H_3PO_4$. The organic phase was washed with 1M $H_3PO_4$ (3 times), dried over $Na_2SO_4$, filtered, and evaporated under reduced pressure to give triflate 198b isomer B (115 mg, 98%) as a pale yellow oil.

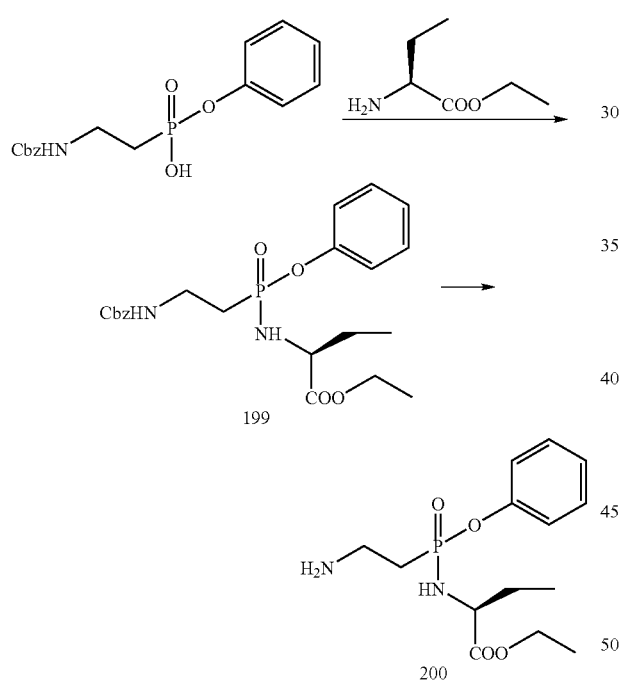

Example 199

To a stirred solution of phenyl 2-carbobenzoxyaminoethyl phosphonate (1 g, 3 mmol) in 30 mL of acetonitrile at room temperature under $N_2$ was added thionyl chloride (0.67 mL, 9 mmol). The resulted mixture was stirred at 60-70° C. for 0.5 h. After cooled to room temperature, the solvent was removed under reduced pressure, and the residue was added 30 mL of DCM, followed by DIEA (1.7 mL, 10 mmol), L-alanine butyric acid ethyl ester hydrochloride (1.7 g, 10 mmol) and TEA (1.7 mL, 12 mmol). After 4 h at room temperature, the solvent was removed under reduced pressure, and the residue was diluted with DCM and washed with brine and water, dried over $Na_2SO_4$, filtered and concentrated. The residue was purified by chromatography on silica gel (Hexane/EtOAc 1:1) to give 199 (670 mg, 50%) as a yellow oil. $^1H$ NMR ($CDCl_3$) δ 7.33-7.11 (m, 10H), 5.70 (m, 1H), 5.10 (s, 2H), 4.13-3.53 (m, 5H), 2.20-2.10 (m, 2H), 1.76-1.55 (m, 2H), 1.25-1.19 (m, 3H), 0.85-0.71 (m, 3H); $^{31}P$ NMR ($CDCl_3$) δ 30.2 and 29.9; MS (ESI) 471 (M+Na).

Example 200

A solution of compound 199 (450 mg) was dissolved in 9 mL of EtOH, then 0.15 mL of acetic acid and 10% Pd/C (90 mg) was added. The resulted mixture was stirred under H2 atmosphere (balloon) for 4 h. After filtration through Celite, the filtered was evaporated under reduced pressure to afford the compound 200 (300 mg, 95%) as a colorless oil. $^1H$ NMR ($CDCl_3$) δ 7.29-7.12 (m, 5H), 4.13-3.53 (m, 5H), 2.20-2.10 (m, 2H), 1.70-1.55 (m, 2H), 1.24-1.19 (m, 3H), 0.84-0.73(m, 3H); $^{31}P$ NMR ($CDCl_3$) δ 29.1 and 28.5; MS (ESI) 315 (M+1).

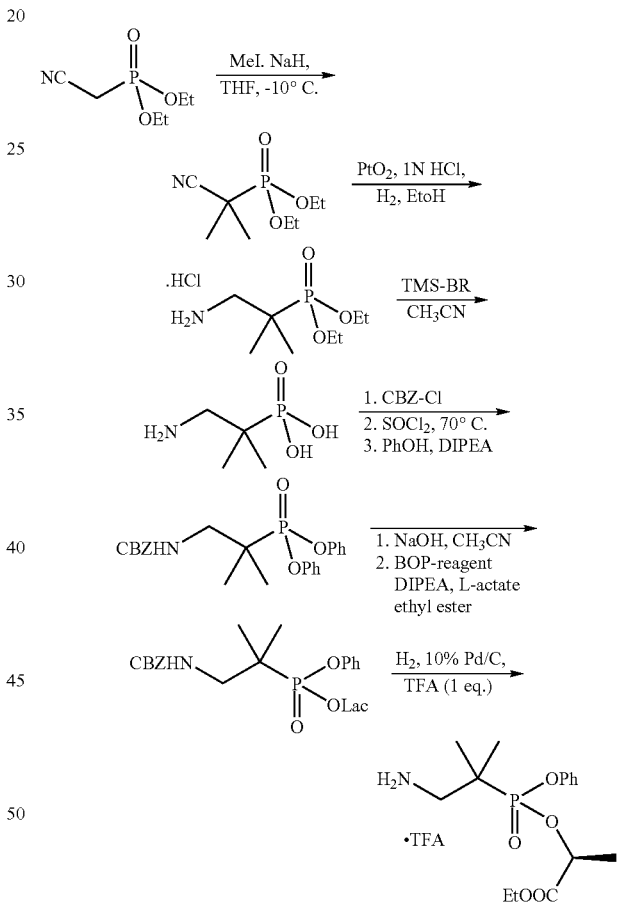

Example 201

A ThF solution (30 mL) of NaH (3.4 g of 60% oil dispersion, 85 mmol) was cooled to –10° C., followed by the addition of diethyl (cyanomethyl)phosphonate (5 g, 28.2 mmol) and iodomethane (17 g, 112 mmol). The resulting solution was stirred at –10° C. for 2 hr, then 0° C. for 1 hr, was worked up, and purified to give diethyl (cyano(dimethyl)methyl) phosphonate (5 g, 86%).

Diethyl (cyano(dimethyl)methyl) phosphonate was reduced to the amine derivative by the described procedure (J. Med. Chem. 1999, 42, 5010-5019) whereby a solution of ethanol (150 mL) and 1N HCl aqueous solution (22 mL) of diethyl (cyano(dimethyl)methyl) phosphonate (2.2 g, 10.7 mmol) was hydrogenated at 1 atmosphere in the presence of $PtO_2$ (1.25 g) at room temperature overnight. The catalyst was filtered through a Celite pad. The filtrate was concentrated to dryness, to give crude diethyl 2-amino-1,1-dimethyl-ethyl phosphonate (2.5 g, as HCl salt).

Crude diethyl 2-amino-1,1-dimethyl-ethyl phosphonate (2.5 g) in 30 mL $CH_3CN$ was cooled to 0° C., and treated with TMSBr (8 g, 52 mmol) for 5 hr. The reaction mixture was stirred with methanol for 1.5 hr at room temperature, concentrated, recharged with methanol, concentrated to dryness to give crude 2-Amino-1,1-dimethyl-ethyl phosphonic acid which was used for next reaction without further purification.

2-Amino-1,1-dimethyl-ethyl phosphonic acid was protected with CBZ, followed by the reaction with thionyl chloride at 70° C. The CBZ protected dichloridate was reacted with phenol in the presence of DIPEA. Removal of one phenol, follow by coupling with ethyl L-lactate gave N-CBZ-2-amino-1,1-dimethyl-ethyl phosphonate derivative. Hydrogenation of N-CBZ derivative at 1 atmosphere in the presence of 10% Pd/C and 1 eq. of TFA gave lactate phenyl (2-amino-1,1-dimethyl-ethyl)phosphonate 201 as the TFA salt.

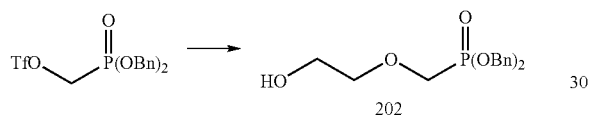

202

Example 202

Powdered magnesium tert-butoxide (2.05 g, 12.02 mmol) was added to a solution of dibenzyl trifluoromethane sulfonic hydroxymethyl phosphonate (4.10 g, 9.66 mmol) and anhydrous ethylene glycol (5.39 mL, 96.6 mmol) in anhydrous DMF (30 mL) at 0° C. The reaction mixture was stirred at 0° C. for 1.5 h, then concentrated. The residue was partitioned between EtOAc and $H_2O$ and washed with 1 N HCl, saturated $NaHCO_3$ solution, and brine. Organic layer dried ($MgSO_4$), concentrated and purified (silica gel, 4% MeOH/$CH_2Cl_2$) to give (2-hydroxy-ethoxymethyl)-phosphonic acid dibenzyl ester 202 as a colorless oil (1.55 g, 48%). $^1$H NMR (300 MHz, $CDCl_3$): δ 7.37 (s, 10 H, Ar), 5.40-5.05 (m, 4 H, $CH_2$Ph), 3.84 (d, J=8.1 Hz, 2 H, $PCH_2$O), 3.70-3.60 (m, 4 H, $OCH_2CH_2$O, $OCH_2CH_2$O); $^{31}$P NMR (121 MHz, $CDCl_3$): δ 22.7.

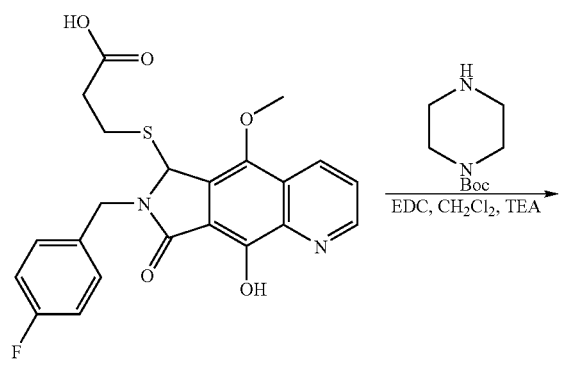

24

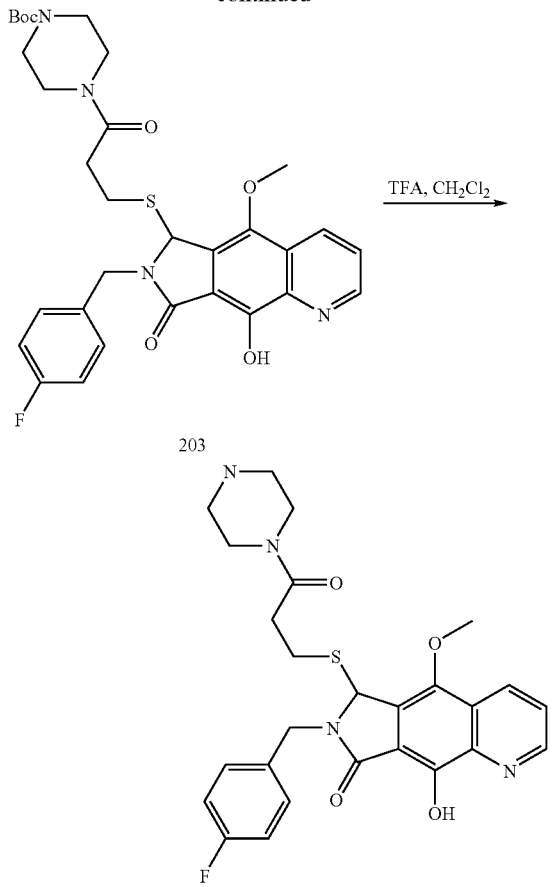

203

204

Example 203

A solution of 24 (Example 24) (38 mg, 0.086 mmol) in $CH_2Cl_2$ (0.86 mL) was stirred with EDC (33 mg, 0.172 mmol), TEA (12 μL, 0.086 mmol), and 1-Boc-piperazine (19 mg, 0.103 mmol) at ambient temperature for 15 h when LCMS analysis demonstrated completion of the reaction. The reaction mixture was worked up by dilution of the mixture with $CH_2Cl_2$ and washing the organic layer with $H_2O$. The organic layer was dried in vacuo and the residue, 4-{3-[7-(4-fluoro-benzyl)-9-hydroxy-5-methoxy-8-oxo-7,8-dihydro-6H-pyrrolo [3,4-g]quinolin-6-ylsulfanyl]-propionyl}-piperazine-1-carboxylic acid tert-butyl ester 203 was carried forward for deprotection.

Example 204

A solution of 203 (52 mg, 0.085 mmol) in 0.8 mL of trifluoroacetic acid and 0.8 mL of $CH_2Cl_2$ was stirred at room temperature for 1 h when the starting material was completely consumed as detected by LCMS. The solution was dried in vacuo and re-dissolved in 1:1 mixture of MeOH-$H_2O$. The product 204 was purified by RP-HPLC using a 5-95% A. Buffer A contained $CH_3CN$-1% TFA and buffer B was $H_2O$-1% TFA. $^1$H NMR (300 MHz, $CD_3OD$) δ 2.19-2.40 (m, 4H), 3.06-3.20 (m, 4H), 3.43-3.56 (m, 2H), 3.63-3.74 (m, 2H), 4.08 (s, 3H), 4.62 (d, 1H, J=15 Hz), 5.16 (d, 1H, J=15 Hz), 5.76 (s, 1H), 7.10 (t, 2H, J=9 Hz), 7.46 (t, 2H, J=8 Hz), 7.74 (dd, 1H, J=4, 8 Hz), 8.69 (d, 1H, J=8 Hz), 8.96 (d, 1H, J=4 Hz); $^{19}$F NMR (282.6 MHz, CD$_3$OD) δ −77.7, 60.0; EI MS (m/z) 511.0 [M+H]$^+$.

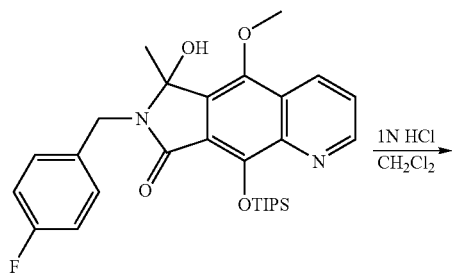

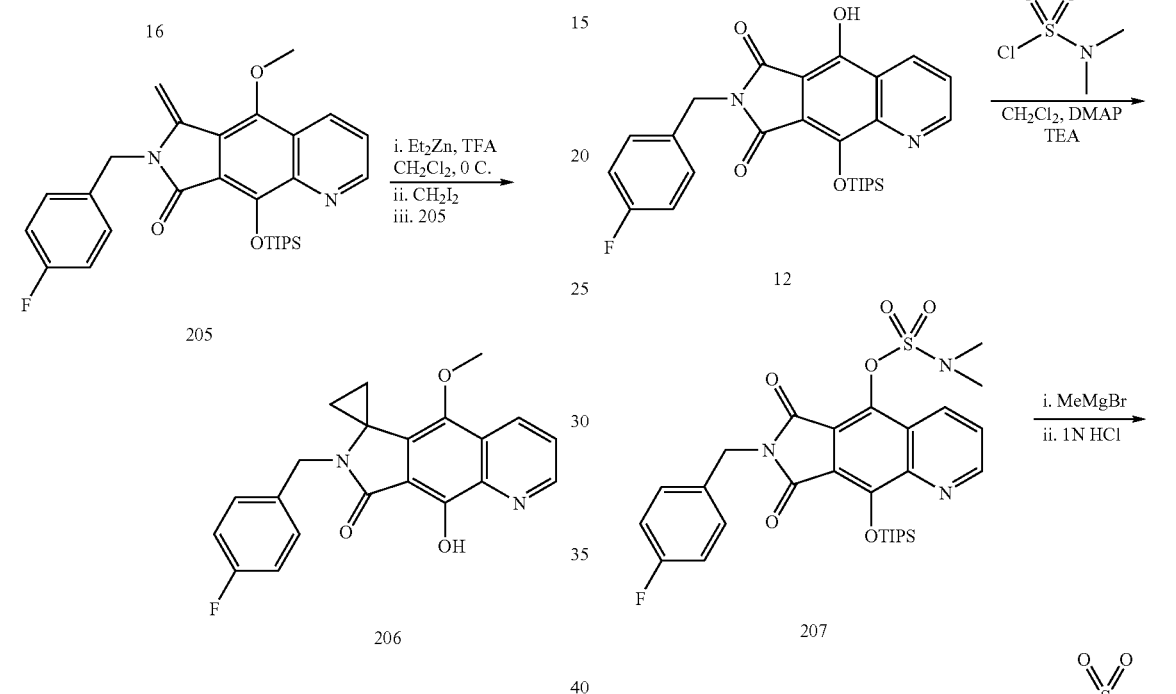

Example 205

Grignard product 16 (Example 16) was worked up by addition of ethyl acetate and stirring of the organic layer with aqueous 1N HCl for 30 minutes. The layers were separated and the organic layer was washed with the 1N HCl solution 2 more times. The organic layer was checked with LCMS to assure complete elimination of the alcohol resulted from the Grignard reaction to the eliminated product 205. The organic layer was dried in vacuo and the residue was purified by column chromatography using CH$_2$Cl$_2$ to give 205. $^1$H NMR (300 MHz, CDCl$_3$) δ 1.15 (d, 18H, J=8 Hz), 1.56 (septet, 3H, J=8 Hz), 3.95 (s, 3H), 4.82 (s, 1H), 4.99 (s, 2H), 5.53 (s, 1H), 7.01 (t, 2H, J=8 Hz), 7.28 (dd, 2H, J=5, 9 Hz), 7.54 (dd, 1H, J=4, 8 Hz), 8.46 (d, 1H, J=8 Hz), 8.87 (d, 1H, J=3 Hz); $^{19}$F NMR (282.6 MHz, CDCl$_3$) δ 61.06; EI MS (m/z) 507.4 [M+H]$^+$.

Example 206

A solution of diethylzinc (0.134 mmol, 134 μL of a 1M mixture) and 134 μL of CH$_2$Cl$_2$ was added to TFA (0.134 mmol, 10.4 μL) under a N$_2$ atmosphere at 0° C. The mixture was stirred at cooled temperature for 15 minutes, then a solution of CH$_2$I$_2$ (0.134 mmol, 11 μL) in 100 μL of CH$_2$Cl$_2$ was added. After 10 minutes, a solution of 205 in 100 μL of CH$_2$Cl$_2$ was added and the ice bath removed. The reaction mixture was stirred at ambient temperature for 1 hour when LCMS analysis demonstrated complete consumption of the starting materials. The product 206 was purified by RP-HPLC using a 20-80% A. Buffer A contained CH$_3$CN-1% TFA and buffer B was H$_2$O-1% TFA. $^1$H NMR (300 MHz, CD$_3$OD) δ 1.58 (t, 2H, J=5 Hz), 1.79 (t, 2H, J=5 Hz), 3.95 (s, 3H), 4.61 (s, 2H), 7.07 (t, 2H, J=9 Hz), 7.32 (dd, 2H, J=5, 8 Hz), 7.84 (dd, 1H, J=4, 8 Hz), 8.77 (d, 1H, J=8Hz), 8.98 (d, 1H, J=4 Hz); $^{19}$F NMR (282.6 MHz, CD$_3$OD) δ −78.0, 59.3; EI MS (m/z) 365.3 [M+H]$^+$, 387.3 [M+Na]$^+$.

Example 207

A solution of 12 (Example 12, 65 mg, 0.131 mmol) in 1.3 mL of CH$_2$Cl$_2$ was stirred with dimethyl sulfamoyl chloride (38 mg, 0.262 mmol), TEA (73 μL, 0.63 mmol), and DMAP (2 mg, 0.013 mmol) for 2 hours at room temperature when LCMS analysis demonstrated complete consumption of the starting materials. The reaction was worked up by dilution with CH$_2$Cl$_2$ and washing the organic layer with H$_2$O. The solvent was removed under reduced pressure and the product was purified by column chromatography to yield 59 mg of 207 (75%) as a white solid. $^1$H NMR (300 MHz, CDCl$_3$) δ 1.12 (d, 18H, J=8 Hz), 1.53 (septet, 3H, J=8 Hz), 3.23 (s, 6H), 4.84 (s, 2H), 7.00 (t, 2H, J=8 Hz), 7.45 (dd, 2H, J=6,9 Hz), 7.65 (dd, 1H, J=4, 8 Hz), 8.77 (dd, 1H, J=2, 8 Hz), 8.94 (dd, 1H, J=2, 4 Hz); $^{19}$F NMR (282.6 MHz, CDCl$_3$) δ 62.0; EI MS (m/z) 624.2 [M+Na]$^+$.

Example 208

A solution of 207 (30 mg, 0.050 mmol) in 0.25 mL of THF was stirred with 33 µL (0.10 mmol) of methylmagnesium bromide for 1 hour at room temperature. The solution was diluted with CH$_2$Cl$_2$ and stirred with aqueous 1N HCl for 30 minutes. Removal of the solvent in vacuo yielded 26 mg (87%) of the product 208 as a green oil. $^1$H NMR (300 MHz, CDCl$_3$) δ 1.14 (d, 18H, J=8 Hz), 1.56 (septet, 3H, J=8 Hz), 2.97 (s, 6H), 4.94 (s, 1H), 5.00 (s, 2H), 5.59 (s, 1H), 7.00 (t, 2H, J=8 Hz), 7.21-7.32 (m, 2H), 7.55-7.62 (m, 1H), 8.50 (d, 1H, J=8 Hz), 8.88 (br s, 1H); $^{19}$F NMR (282.6 MHz, CDCl$_3$) δ 61.3; EI MS (m/z) 600.2 [M+H]$^+$, 622.2 [M+Na]$^+$.

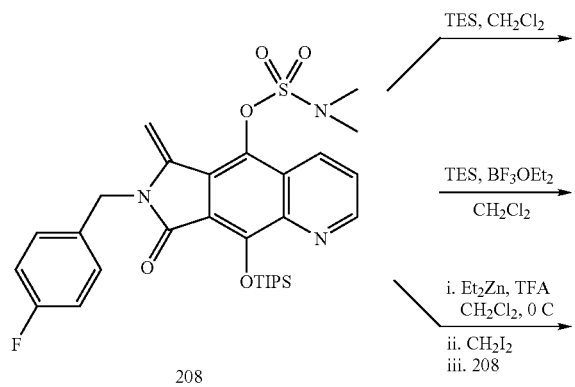

208

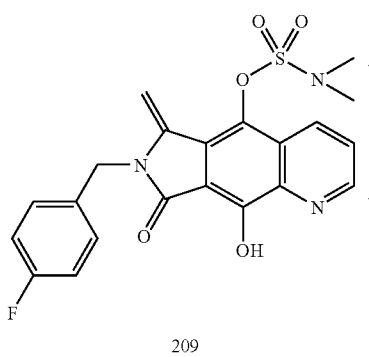

209

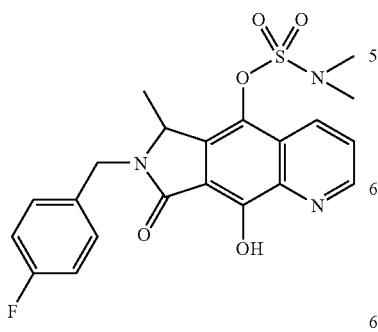

210

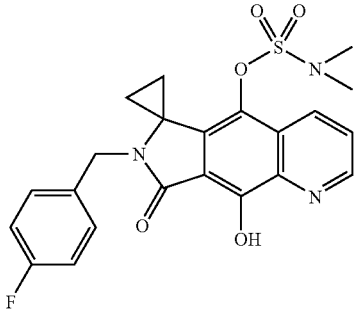

211

Example 209

A solution of 208 (13 mg, 0.022 mmol) and TFA (0.11 mL) and CH$_2$Cl$_2$ (0.11 mL) was allowed to stir at room temperature overnight. The solvent was removed in vacuo and the residue was purified by RP-HPLC using a 20-80% A to give product 209. Buffer A contained CH$_3$CN-1% TFA and buffer B was H$_2$O-1% TFA. $^1$H NMR (300 MHz, CDCl$_3$) δ 3.06 (s, 3H), 3.07 (s, 3H), 5.00 (s, 2H), 5.12 (s, 1H), 5.71 (s, 1H), 6.96-7.07 (m, 2H), 7.22-7.33 (m, 2H), 7.71 (dd, 1H, J=4, 9 Hz), 8.67 (d, 1H, J=8 Hz), 9.05 (br s, 1H); $^{19}$F NMR (282.6 MHz, CDCl$_3$) δ −76.2, 62. 1; EI MS (m/z) 444.2 [M+H]$^+$, 466.1 [M+Na]$^+$.

Example 210

Under a N$_2$ atmosphere, a solution of 208 (14 mg, 0.023 mmol) in CH$_2$Cl$_2$ (0.23 mL) was stirred with triethylsilane (15 µL, 0.093 mmol) and boron trifluoride diethyletherate (BF$_3$OEt$_2$, 20 µL, 0.164 mmol) at ambient temperature overnight. The reaction mixture was worked up by removing the solvent under reduced pressure and precipitation from EtOAc-Hex to provide 7.5 mg of the product 210 as a yellow solid. $^1$H NMR (300 MHz, CDCl$_3$) δ 1.56 (d, 3H, J=7 Hz), 3.16 (s, 6H), 4.42 (d, 1H, J=15 Hz), 5.02 (q, 1H, J=6 Hz), 5.09 (d, 1H, J=15 Hz), 7.06 (t, 2H, J=8 Hz), 7.33(dd, 2H, J=5, 9 Hz), 7.72-7.79 (m, 1H), 8.62 (d, 1H, J=9 Hz), 9.15 (br s, 1H); $^{19}$F NMR (282.6 MHz, CDCl$_3$) δ −76.2, 62.5; EI MS (m/z) 446.2 [M+H]$^+$, 468.2 [M+Na]$^+$.

Example 211

Under a N$_2$ atmosphere, to a solution of diethylzinc (0.074 mmol, 74 µL of a 1M mixture) and 74 µL of CH$_2$Cl$_2$ was added TFA (0.074 mmol, 5.7 µL) at 0° C. This mixture was stirred at cooled temperature for 15 minutes when a solution of CH$_2$I$_2$ (0.074 mmol, 6 µL) in 50 µL of CH$_2$Cl$_2$ was added. After 10 minutes, a solution of 208 in 50 µL of CH$_2$Cl$_2$ was added and the ice bath removed. The reaction mixture was stirred at ambient temperature for 1 hour when LCMS analysis demonstrated complete consumption of the starting materials. The product 211 was purified by RP-HPLC using a 20-80% A. Buffer A contained CH$_3$CN-1% TFA and buffer B was H$_2$O-1% TFA. $^1$H NMR (300 MHz, CD$_3$OD) δ 1.46 (br t, 2H), 2.10 (br t, 2H), 3.14 (s, 6H), 4.55 (s, 2H), 7.02 (t, 2H, J=9 Hz), 7.21-7.31 (m, 2H), 7.60-7.68 (m, 1H), 8.58-8.65 (m, 1H), 9.05-9.08 (m, 1H); EI MS (m/z) 458.2 [M+H]$^+$, 480.1 [M+Na]$^+$.

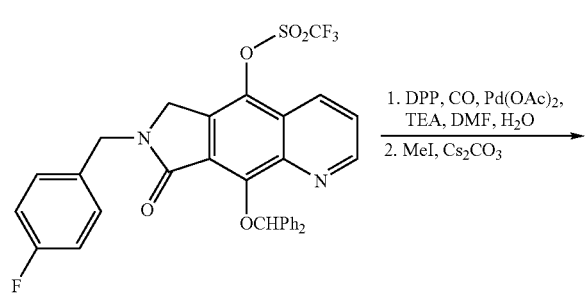

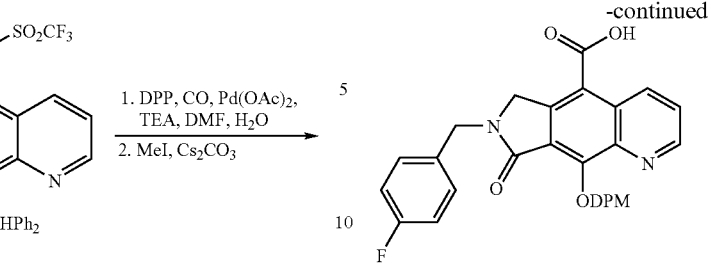

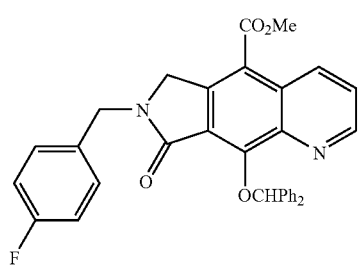

Example 212

To trifluoro-methanesulfonic acid 9-benzhydryloxy-7-(4-fluoro-benzyl)-8-oxo-7,8-dihydro-6H-pyrrolo[3,4-g]quinolin-5-yl ester 46 (1.48 g, 2.39 mmol) and 1,3-bis(diphenylphosphino)propane (DPPP) (295 mg, 0.7 mmol) in DMF (20 mL) and water (1 mL) in a two-necked round bottom flask were added Pd(OAc)$_2$ (107 mg, 0.48 mmol). The solution was degassed under high vacuum and flushed with carbon monoxide from a balloon. The flushing was repeated five times. TEA (0.733 mL, 3.26 mmol) was introduced. The mixture was heated under CO atmosphere for 2.5 hours and cooled down to the room temperature. MeI (0.74 mL, 12 mmol) and Cs$_2$CO$_3$ were added and stirring was continued under a nitrogen atmosphere for 45 minutes. The mixture was diluted with EtOAc (300 mL), washed with water, 1N aqueous HCl and brine, dried over MgSO$_4$ and concentrated. The crude product was purified by chromatography on a silica gel column eluting with 15% to 35% of EtOAc in hexane to afford 9-benzhydryloxy-7-(4-fluoro-benzyl)-8-oxo-7,8-dihydro-6H-pyrrolo[3,4-g]quinoline-5-carboxylic acid methyl ester 212, (0.9 g, 1.69 mmol, 70%) as a yellow solid. $^1$H NMR (CDCl$_3$): 89.25 (d, 1H), 9.05 (m, 1H), 7.80 (d, 4H), 7.56 (dd, 1H), 7.0-7.4 (m, 11H), 4.85 (s, 2H), 4.55 (s, 2H), 3.95 (s, 3H); MS: 555 (M+Na).

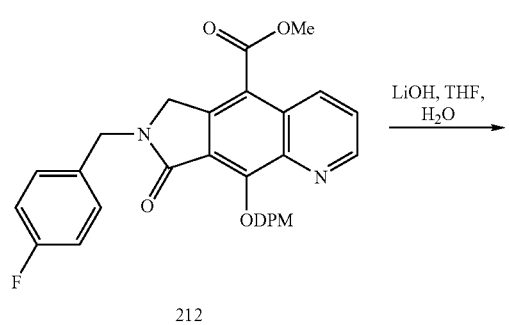

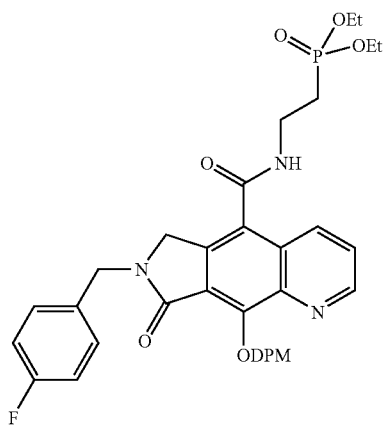

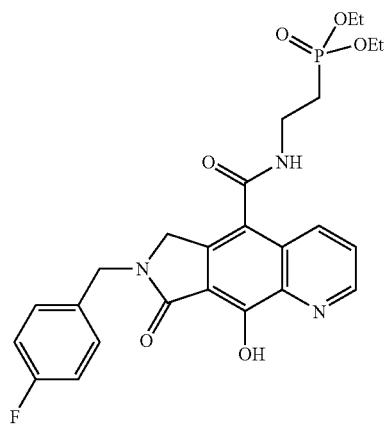

Example 213

A solution of 9-benzhydryloxy-7-(4-fluoro-benzyl)-8-oxo-7,8-dihydro-6H-pyrrolo[3,4-g]quinoline-5-carboxylic acid methyl ester 212 (54 mg, 0.10 mmol) in 1.0 mL of a 1:1:1 mixture of THF:MeOH: H$_2$O was stirred with LiOH (9.7 mg, 0.41 mmol) overnight when the starting materials were completely consumed as judged by TLC (DPM=benzhydryl, Ph$_2$CH—). The reaction mixture was dried under reduced pressure and the residue was dissolved in EtOAc. The organic layer was stirred with saturated aqueous NH$_4$Cl for 30 minutes. The aqueous layer was checked by TLC to assure complete transfer of the products to the organic layer. The organic layer was dried in vacuo to yield 45.5 mg (87%) of 9-benzhydryloxy-7-(4-fluoro-benzyl)-8-oxo-7,8-dihydro-6H-pyrrolo[3,4-g]quinoline-5-carboxylic acid 213 as a white solid. The product was carried on without purification. MS (m/z) 519.2 [M+H]+, 541.2 [M+Na]+.

Alternatively, methyl ester 212 (0.071 g, 0.1334 mmol) was dissolved in 2.4 mL of tetrahydrofuran and 0.6 mL of DI H$_2$O. To this was added LiOH (0.013 g, 0.5338 mmol) and mixture stirred at room temperature. After 15 hours, starting material consumed. Diluted with dichloromethane, washed with 1M HCl solution, dried (Na$_2$SO$_4$), concentrated to give 213 (0.068 g, 0.1313 mmol, 98%.) $^1$H NMR (CD$_3$SOCD$_3$) δ 9.25 (d, 1H), 9.12 (dd, 1H), 8.17 (s, 1H), 7.75 (d, 5H), 7.37 (dd, 2H), 7.24 (m, 6H), 4.82 (s, 2H), 4.59 (s, 2H.) MS: 517 (M−1.)

Example 214

A solution of the oxalate salt (HO$_2$CCO$_2^-$) of diethyl (aminoethyl)phosphonate (12 mg, 0.042 mmol) in 0.21 mL of DMF was mixed with DIEA (15 μL, 0.084 mmol) until the reaction became clear. To this solution was added 213 (11 mg, 0.021 mmol) and O-(7-azabenzotriazol-1-yl)-N,N,N',N'-tetramethyluronium hexafluorophosphate (HATU) (16 mg, 0.042 mmol). This mixture was stirred at room temperature for 2 hours when it was warmed to 60° C. with a heat gun for 1 minute. LCMS analysis demonstrated complete consumption of the starting materials. The reaction mixture was directly loaded onto a silica gel column and the product was quickly eluted with a gradient of EtOAc-10% MeOH/EtOAc to provide 12.7 mg (88%) of the product 214. $^1$H NMR (300 MHz, CD$_3$OD) δ 1.29 (t, 6, J=7 Hz), 2.18 (dt, 2H, J=7, 18 Hz), 3.53-3.65 (m, 2H), 4.08 (septet, 4H, J=7 Hz), 4.46 (s, 2H), 4.83 (s, 2H), 7.06-7.25 (m, 8H), 7.40 (dd, 2H, J=5, 9 Hz), 7.61-7.68 (m, 6H), 8.04 (s, 1H), 8.44 (d, 1H, J=7 Hz), 9.04-9.09 (m, 1H); $^{31}$P (121.4 MHz, CD$_3$OD) δ 29.5; MS (m/z) 682.1 [M+H]+, 704.2 [M+Na]+.

Example 215

A solution of 214 (12.7 mg, 0.019 mmol) in 0.19 mL of CH$_2$Cl$_2$ was stirred with TFA (144 μL, 1.9 mmol) and TES (304 μL, 1.9 mmol) for 45 minutes under a N$_2$ atmosphere. TLC and LCMS analysis indicated complete reaction at that time. The reaction was worked up by removing the solvent under reduced pressure. The residue was purified by crystallization from EtOAc-Hex to yield 8.6 mg (71%) of (2-{[7-(4-fluoro-benzyl)-9-hydroxy-8-oxo-7,8-dihydro-6H-pyrrolo[3,4-g]quinoline-5-carbonyl]-amino}-ethyl)-phosphonic acid diethyl ester 215 as a yellow solid. $^1$H NMR (500 MHz, CD$_3$OD) δ 1.33 (t, 6H, J=7 Hz), 2.24 (dt, 2H, J=19, 7 Hz), 3.70 (septet, 2H, J=8 Hz), 4.09-4.17 (m, 4H), 4.61 (s, 2H), 4.78 (s, 2H), 7.10 (t, 2H, J=9 Hz), 7.41 (dd, 2H, J=6, 8 Hz), 7.76 (br d, 1H, J=5 Hz), 8.71 (d, 1H, J=9 Hz), 8.95 (br s, 1H); $^{31}$P (121.4 MHz, CD$_3$OD) δ 29.5; MS (m/z) 516.3 [M+H]+, 1030.9 [2M]+, 1053.0 [2M+Na]+.

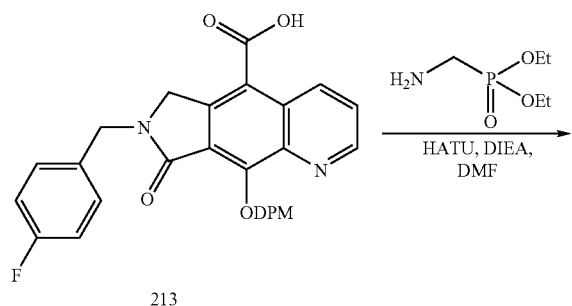

213

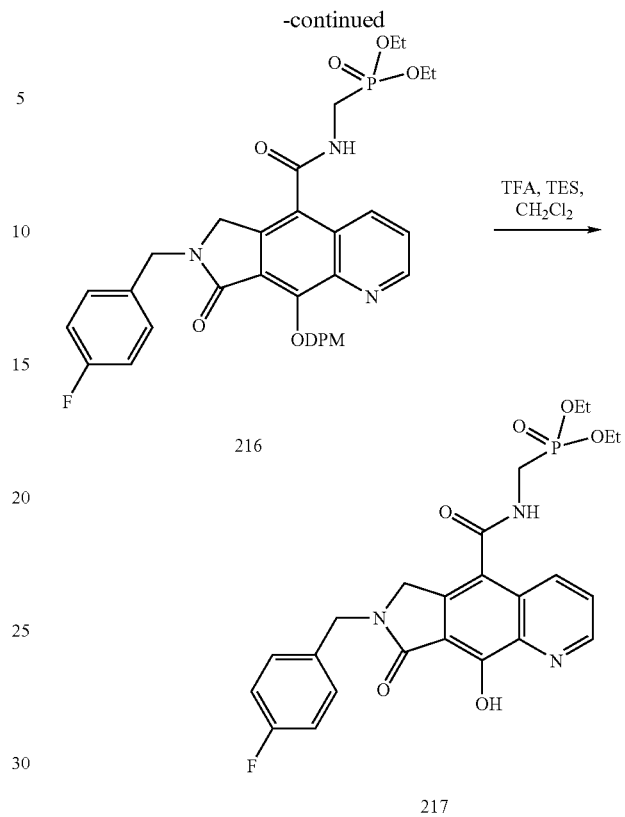

216

217

Example 216

A solution of oxalate salt of diethyl(aminomethyl)phosphonate (8 mg, 0.031 mmol) in 0.31 mL of DMF and DIEA (22 μL, 0.124 mmol) was added to 213 (16 mg, 0.031 mmol) and HATU (24 mg, 0.062 mmol). The solution was stirred at ambient temperature for 2 hours when another batch of the amine and the coupling reagent equivalent to the above amounts were added. The reaction was heated with a heat gun to 60° C. for 1 minute and the reaction was analyzed by LCMS. The reaction mixture was loaded onto a flash column and ({[9-benzhydryloxy-7-(4-fluoro-benzyl)-8-oxo-7,8-dihydro-6H-pyrrolo[3,4-g]quinoline-5-carbonyl]-amino}-methyl)-phosphonic acid diethyl ester 216 was eluted with EtOAc-10% MeOH to provide 20 mg (97%) of a clear oil. MS (m/z) 668.1 [M+H]+, 690.3 [M+Na]+.

Example 217

A solution of 216 (20 mg, 0.030 mmol) in 0.30 mL of CH$_2$Cl$_2$ was stirred with TFA (231 μL, 3.00 mmol) and TES (479 μL, 3.00 mmol) for 30 minutes when the starting materials were completely consumed as judged by TLC and LCMS. The reaction was worked up by removal of the solvent in vacuo and crystallizing the product from EtOAc-Hex to provide 10 mg (66%) of ({[7-(4-Fluoro-benzyl)-9-hydroxy-8-oxo-7,8-dihydro-6H-pyrrolo[3,4-g]quinoline-5-carbonyl]-amino}-methyl)-phosphonic acid diethyl ester 217 as a yellow solid. $^1$H NMR (300 MHz, CD$_3$OD) δ 1.32 (t, 6H, J=7 Hz), 3.96 (d, 2H, J=12 Hz), 4.16 (septet, 4H, J=7 Hz), 4.56 (s, 2H), 4.79 (s, 2H), 7.10 (t, 2H, J=9 Hz), 7.39 (dd, 2H, J=9 Hz), 7.76 (br s, 1H), 8.66 (d, 1H, J=8 Hz), 8.95 (br s, 1H); $^{31}$P (121.4 MHz, CD$_3$OD) δ 23.2; $^{19}$F NMR (282.6 MHz, CD$_3$OD) δ −76.2, 59.9; MS (m/z) 502.5 [M+H]+, 1003.0 [2M]+, 1025.1 [2M+Na]+.

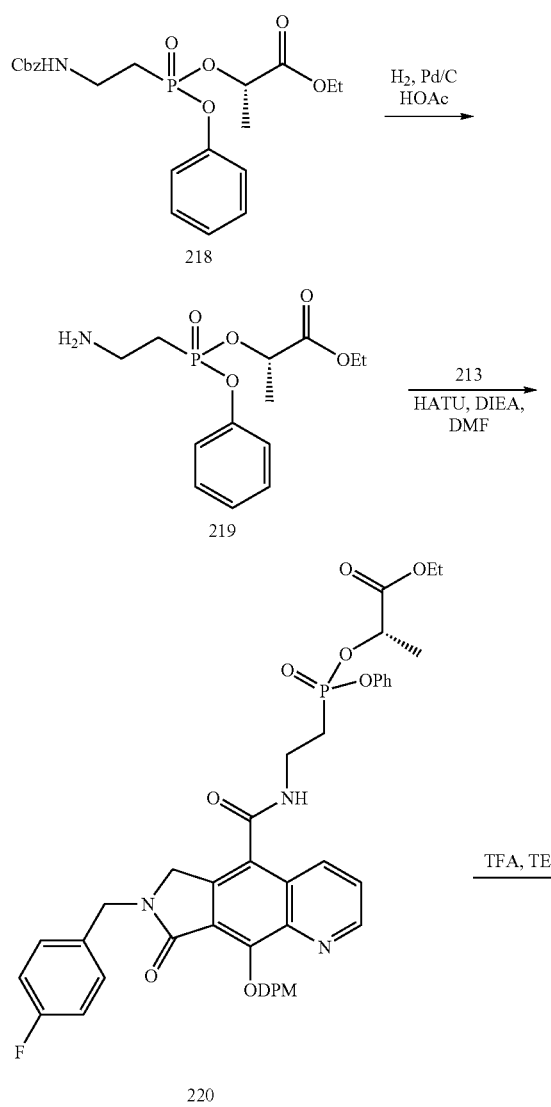

Example 218

S-lactate ester 218

Example 219

A solution of 2-[(2-benzyloxycarbonylamino-ethyl)-phenoxy-phosphinoyloxy]-propionic acid ethyl ester 218 (240 mg, 0.551 mmol) with approximately 50% purity and a ratio of 2:1 of diastereomers was dissolved in 5.5 mL of ethanol with acetic acid (63 μL, 1.10 mmol). To this solution was added 36 mg of 10% Pd/C and the solution was degassed under a hydrogen atmosphere three times. The solution was vigorously stirred at room temperature for 3 hours when TLC showed complete consumption of the starting materials. The mixture was filtered through a pad of Celite and dried to provide 174 mg (87%) of 2-[(2-amino-ethyl)-phenoxy-phosphinoyloxy]-propionic acid ethyl ester; compound with acetic acid 219 as a clear oil.

Example 220

A solution of 13.5 mg of 213 in 0.13 mL of DMF was stirred with HATU (20 mg, 0.052 mmol) at room temperature for 10 minutes. To this solution was added a premixed solution of 219 (28 mg, 0.078 mmol) of approximately 50% purity in 0.130 mL of DMF and DIEA (13.4 mg, 0.104 mmol). The reaction mixture was gently heated with a heat gun for 30 seconds and then the reaction was allowed to proceed at room temperature for 2 hours when LCMS demonstrated complete consumption of the carboxylic acid. The reaction mixture was loaded onto a silica gel column and purified with EtOAc-10% MeOH to provide 9.5 mg of 3-[(2-{[9-Benzhydryloxy-7-(4-fluoro-benzyl)-8-oxo-7,8-dihydro-6H-pyrrolo[3,4-g]quinoline-5-carbonyl]-amino}-ethyl)-phenoxy-phosphinoyl]-2-methyl-propionic acid ethyl ester 220 which was carried on to the next step.

Example 221

A solution of 220 (9.5 mg, 11.8 μmol) was stirred with 0.12 mL of dry dichloromethane with trifluoroacetic acid (93 μL, 1.18 mmol) and triethylsilane (189 μL, 1.18 mmol) for 1 hour at room temperature when TLC showed complete consumption of the starting materials. The reaction mixture was dried in vacuo and azeotroped from dichloromethane three times. The solid product was triturated with EtOAc-Hex to get 6 mg of 2-[(2-{[7-(4-Fluoro-benzyl)-9-hydroxy-8-oxo-7,8-dihydro-6H-pyrrolo [3,4-g]quinoline-5-carbonyl]-amino}-ethyl)-phenoxy-phosphinoyloxy]-propionic acid ethyl ester 221 as a pale yellow solid. The NMR of the two diastereomers in CDCl$_3$ is broad and indicates presence of rotamers. VT NMR in DMSO at 85° C. resulted in drastic sharpening of the peaks. $^1$H NMR (300 MHz, DMSO-d6, 85° C.) δ 1.15-1.26 (m, 3H), 1.35 and 1.47 (d, 3H, J=7 Hz), 2.23-2.45 (m, 2H), 3.58-3.57 (m, 2H), 4.08-4.19 (m, 2H), 4.56 (s, 2H), 4.69 (s, 2H), 4.93-5.04 (m, 1H), 7.14 (t, 2H, J=9 Hz), 7.18-7.23 (m, 3H), 7.35-7.42 (m, 4H), 7.65 (dd, 1H, J=4, 8 Hz), 8.42 (br s, 1H), 8.55 (d, 1H, J=9 Hz), 8.92 (d, 1H, J=4H); $^{31}$P (121.4 MHz, DMSO-d6, 85° C.) δ 26.1, 28.3; MS (m/z) 636.5 [M+H]$^+$.

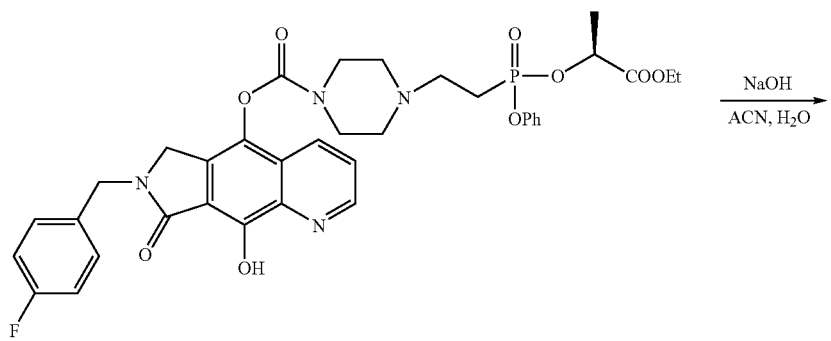

194

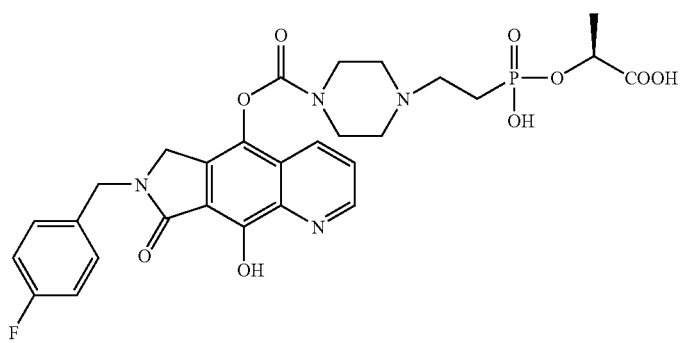

222

Example 222

A solution of the trifluoroacetate salt of 4-{2-[(1-ethoxy-carbonyl-ethoxy)-phenoxy-phosphoryl]-ethyl}-piperazine-1-carboxylic acid 7-(4-fluoro-benzyl)-9-hydroxy-8-oxo-7,8-dihydro-6H-pyrrolo[3,4-g]quinolin-5-yl ester 194 (0.045 g, 0.054 mmol) in acetonitrile (ACN, 0.68 mL) and water (0.68 mL) was treated with an aqueous solution of NaOH (0.162 mL, 1M). The reaction mixture was stirred at room temperature for 3 hours. The mixture was cooled to 0° C., then acidified with a 2N aqueous solution of HCl to pH=1. Acetonitrile was removed in vacuo then purified by reversed phase HPLC to afford the trifluoroacetate salt of 4-{2-[(1-carboxy-ethoxy)-hydroxy-phosphoryl]-ethyl}-piperazine-1-carboxylic acid 7-(4-fluoro-benzyl)-9-hydroxy-8-oxo-7,8-dihydro-6H-pyrrolo[3,4-g]quinolin-5-yl ester; compound with trifluoro-acetic acid 222 (0.032 g, 80%): $^1$H NMR (CD$_3$OD) δ 9.0 (d, 1H), 8.5 (d, 1H), 7.75 (dd, 1H), 7.4 (dd, 2H), 7.1 (t, 2H), 4.8 (s, 2H), 4.45 (s, 2H), 4.3-3.7 (m, 4H), 3.7-3.35 (m, 6H), 2.2 (m, 2H), 1.55 (d, 3H); $^{31}$P NMR (CDCl$_3$) δ 19.8; MS: 617 (M+1).

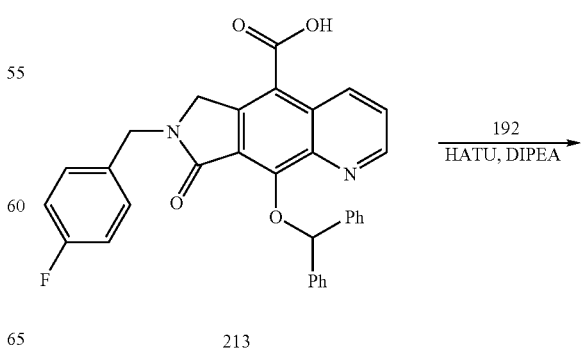

213

-continued

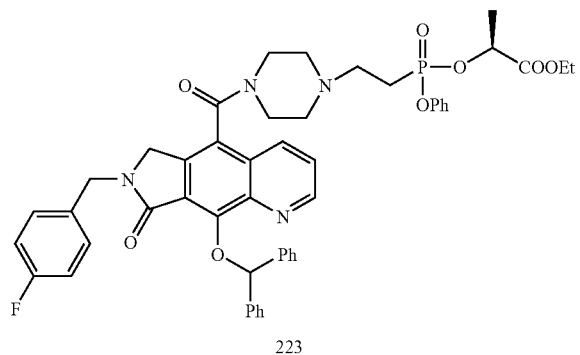

223

Example 223

A solution of the 9-benzhydryloxy-7-(4-fluoro-benzyl)-8-oxo-7,8-dihydro-6H-pyrrolo[3,4-g]quinoline-5-carboxylic acid 213 (0.415 g, 0.80 mmol) and HATU (0.608 g, 1.60 mmol) in N,N-dimethylformamide (DMF) (2.5 mL) was stirred under an inert atmosphere at room temperature for 5 minutes. To the solution was added a premixed solution of 2-[phenoxy-(2-piperazin-1-yl-ethyl)-phosphinoyloxy]-(S)-propionic acid ethyl ester: compound with trifluoroacetic acid 192 (0.580 g, 1.20 mmol), N,N-Diisopropylethylamine (DIPEA) (0.700 mL, 4.0 mmol) in DMF (3.5 mL). The reaction mixture was stirred at room temperature for 5 hours. The mixture was diluted with ethyl acetate, washed with saturated NaHCO$_3$ (twice), water (twice) and brine (twice), dried (NaSO$_4$), and concentrated. The residue was purified by silica gel chromatography (5/95—methanol/methylene chloride) to afford 2-[(2-{4-[9-benzyhydryloxy-7-(4-fluoro-benzyl-8-oxo-7,8-dihydro-6H-pyrrolo [3,4-g]quinoline-5-carbonyl]-piperazin-1-yl}-ethyl)-phenoxy-phosphinoyloxy]-(S)-propionic acid ethyl ester 223 (0.625 g, 90%) as mixture of diastereomers: $^1$H NMR (CDCl$_3$) δ 9.07 (dd, 1H), 8.15 (s, 1H), 8.05 (dd, 1H), 7.75 (d, 4H), 7.52 (dd, 1H), 7.4-7.1 (m, 13H), 7.05 (t, 2H), 5.02 (m, 1H), 5.0-4.6 (dd, 2H), 4.4-4.0 (dd, 2H), 4.17 (m, 2H), 4.0-3.5 (m, 3H), 3.0 (m, 2H), 2.7-2.5 (m, 3H), 2.4-2.1 (m, 4H), 1.6 & 1.4 (d, 3H), 1.25 (t, 3H); $^{31}$P NMR (CDCl$_3$) δ 28.3, 26.5; MS: 871 (M+1).

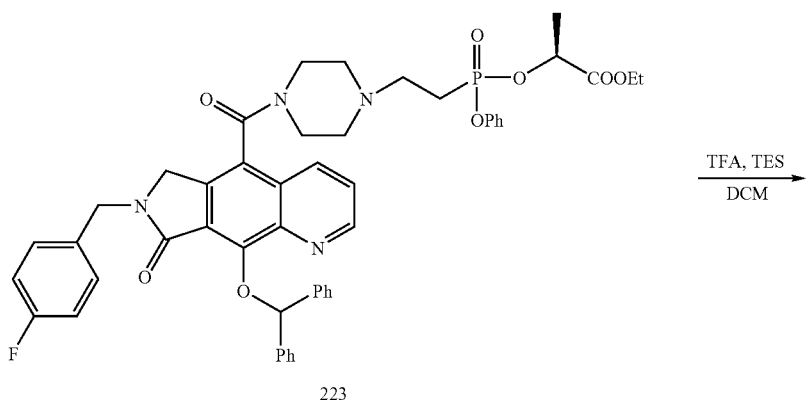

223

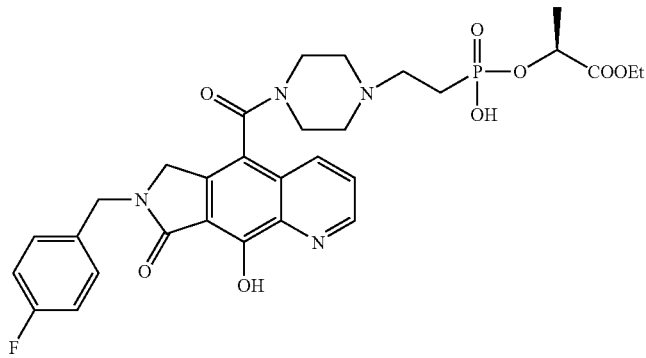

224

Example 224

A solution of 2-[(2-{4-[9-benzyhydryloxy-7-(4-fluoro-benzyl-8-oxo-7,8-dihydro-6H-pyrrolo[3,4-g]quinoline-5-carbonyl]-piperazin-1-yl}-ethyl)-phenoxy-phosphinoyloxy]-propionic acid ethyl ester 223 (0.420 g, 0.483 mmol) in methylene chloride (2 mL) was treated with trifluoroacetic acid (0.4 mL) and triethylsilane (0.8 mL). The reaction mixture was stirred at room temperature under an inert atmosphere for 40 minutes. The volatiles were removed in vacuo with toluene. The product was triturated in diethyl ether/hexane with sonicaton to afford the trifluoroacetate salt of 2-{[2-4-2-[7-(4-fluoro-benzyl)-9-hydroxy-8-oxo-7,8-dihydro-6H-pyrrolo[3,4-g]quinolin-5-yl]-acetyl}-piperazin-1-yl)-ethyl]-phenoxy-phosphinoyloxy}-propionic acid ethyl ester 224 (0.370 g, 94%): $^1$H NMR (CDCl$_3$) δ 9.0 (d, 1H), 8.15 (dd, 1H), 7.67 (dd, 1H), 7.35-7.1 (m, 7H), 7.05 (t, 2H), 5.0 (m, 1H), 5.0-4.6 (m, 2H), 4.6-4.25 (m, 2H), 4.25-3.95 (m, 5H), 3.7-2.8 (m, 8H), 2.7-2.5 (m, 2H), 1.6 & 1.4 (d, 3H), 1.25 (t, 3H); $^{31}$P NMR (CDCl$_3$) δ 23.0, 21.0; MS: 705 (M+1).

mL, 0.1016 mmol.) Stirred at room temperature 10 minutes until starting material consumed. Diluted with dichloromethane, washed with washed with 1M HCl solution, saturated brine, concentrated to give crude. Dissolved in 1.5 mL dichloromethane, added catalytic dimethylaminopyridine, triethylamine (0.16 mL, 0.6 mmol) and cooled to 0° C. To this was added triphosgene (0.03 g, 0.1016 mmol) and stirred 40 minutes. BOC-aminopyrrolidine (0.038 g, 0.2032 mmol) was then added and stirred at room temperature for 10 minutes. The mixture was diluted with dichloromethane, washed with 1M HCl, brine, concentrated volatiles to give crude product. Chromatographed (10% to 30% acetone/toluene) to give 225 (0.0108 g, 0.0153 mmol, 30%.) $^1$H NMR (CDCl$_3$) δ 9.03 (dd, 1H), 8.11 (d, 1H), 8.03 (s, 1H), 7.74 (d, 4H), 7.50 (dd, 1H), 7.27 (m, 8H), 7.07 (dd, 2H), 4.80 (s, 2H), 4.65 (br s, 1H), 4.30 (br s, 1H), 4.24 (s, 2H), 3.95 (br s, 1H), 3.74 (m, 2H), 3.58 (m, 2H), 1.48 (s, 9H) MS: 703 M+1)

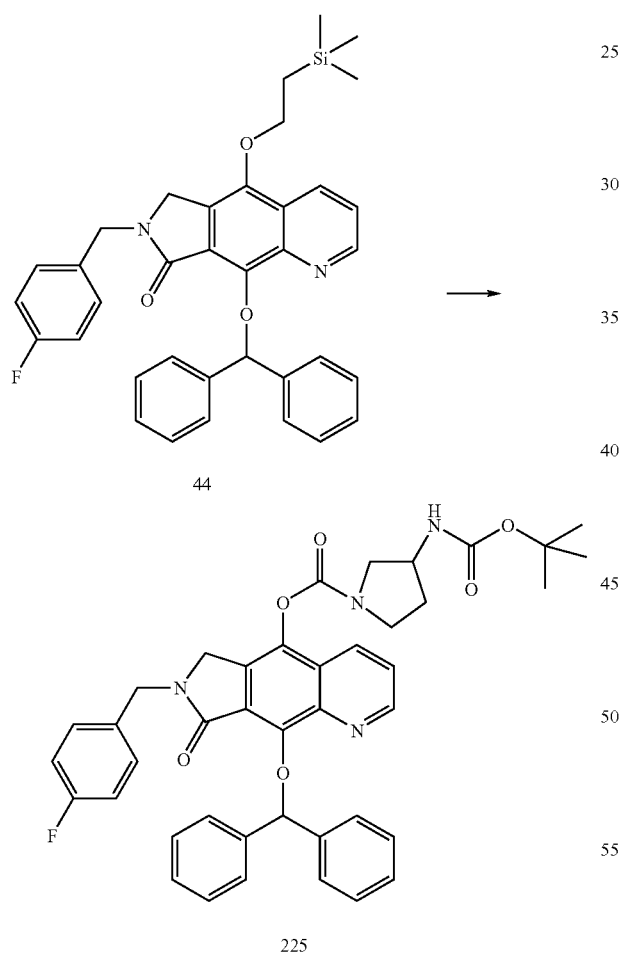

44

225

Example 225

Trimethylsilylethyl ether 44 (0.03 g, 0.0508 mmol) was dissolved in 2 mL dry tetrahydrofuran. To this was added triethylamine (0.028 mL, 0.2032 mmol) and 1 M tetrabutylammonium fluoride solution in tetrahydrofuran (0.1016

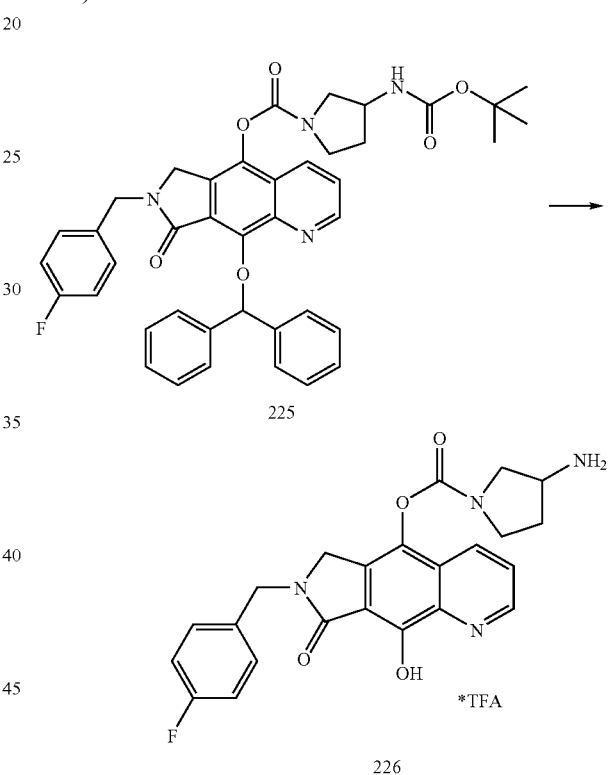

225

226

Example 226

Carbamate 225 (0.0108 g, 0.0153 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Then dissolved in 0.3 mL dichloromethane, 0.3 ml trifluoroacetic acid. Stirred at room temperature for one hour. Concentrated off volatiles, azeotroped with toluene to give crude. Triturated twice with 1:1 diethyl ether/hexanes to give the trifluoroacetate salt of 3-amino-pyrrolidine-1-carboxylic acid 7-(4-fluoro-benzyl)-9-hydroxy-8-oxo-7,8-dihydro-6H-pyrrolo[3,4-g]quinolin-5-yl ester 226 (0.0057 g, 0.0104 mmol, 68%.) $^1$H NMR (CD$_3$SOCD$_3$) δ 9.00 (s, 1H), 8.41 (s, 1H), 8.21 (s, 1H), 7.76 (dd, 1H), 7.36 (dd, 2H), 7.22

(dd, 2H), 4.72 (s, 2H), 4.36 (s, 2H), 3.93-3.35 (m, 7H) $^{19}$F NMR: −73.9 MS: 437 (M+1), 435 (M−1)

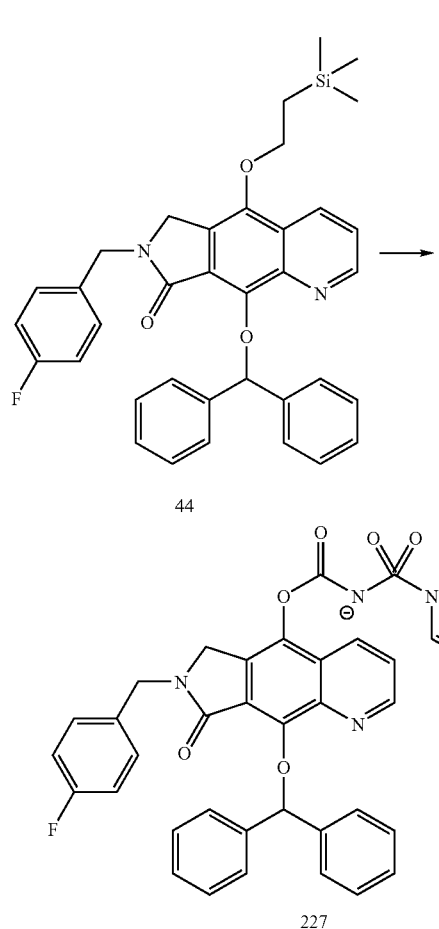

44

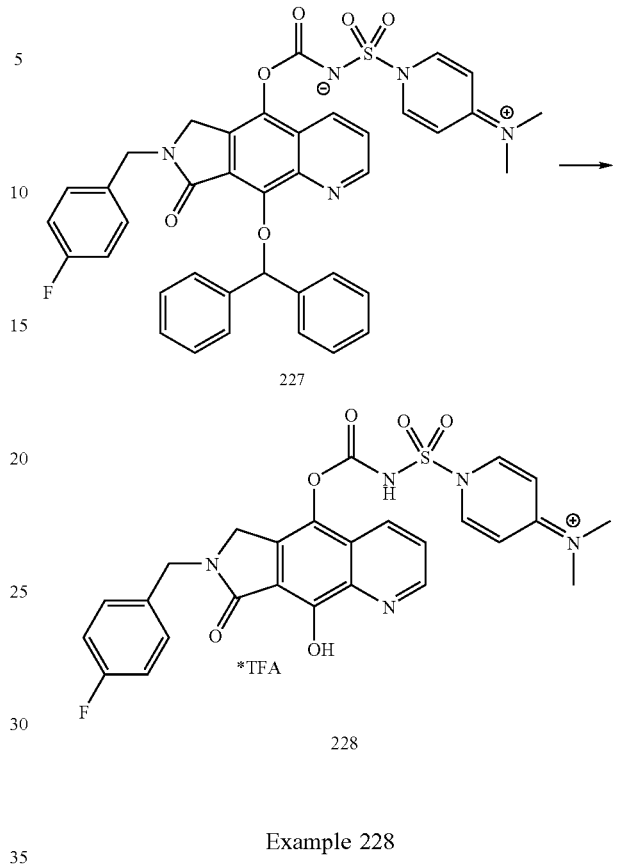

227

Example 227

2-Amino-1,2,4 thiadiazole (0.006 g, 0.06 mmol) and triethylamine (0.0376 mL, 0.27 mmol) were added to 1 mL dichloromethane and cooled to 0° C. To this was slowly added chlorosulfonylisocyanate (0.007 mL, 0.08 mmol) at 0° C. Stirred thirty minutes until starting material consumed. Simultaneously, in a separate flask trimethylsilylethyl ether 44 was dissolved in 0.5 mL tetrahydrofuran. To this was added triethylamine (0.0376 mL, 0.27 mmol) and 1M tetrabutylammonium fluoride in tetrahydrofuran (0.135, 0.135 mmol) and stirred at room temperature. After 20 minutes, diluted with dichloromethane, washed with 1M HCl solution and brine, concentrated to give crude. At 0° C., dissolved in 0.5 mL dichloromethane and added to the solution prepared in situ above. Stirred at 0° C. for 5minutes, catalytic DMAP added, then stirred for one hour at room temperature. Diluted with dichloromethane, washed with 1M HCl solution, brine, concentrated to give crude. Chromatographed (5 to 30% methanol/dichloromethane) to give dimethylaminopyridine adduct 227 (0.033 g, 0.046 mmol, 68%.) $^1$H NMR (CDCl$_3$) δ 8.97 (dd, 1H), 8.54 (d, 2H), 8.19 (d, 1H), 8.00 (s, 1H), 7.72 (d, 4H), 7.42 (dd, 1H), 7.26-7.14 (m, 7H), 7.02 (dd, 2H), 6.52 (d, 2H), 4.74 (s, 2H), 4.17 (s, 2H), 3.22 (s, 6H.) MS: 718 (M+1).

Example 228

Carbamate 227 (0.007 gm, 0.0097 mmol) was dissolved in 0.25 mL of dichloromethane. To this was added 0.1 mL of triethylsilane and 0.05 mL of trifluoroacetic acid. Stirred at room temperature and after ten minutes complete by TLC. Concentrated off volatiles, azeotroped with toluene to give crude. Triturated twice with 1:1 diethyl ether/hexanes to give 228 (0.004 g, 0.0073 mmol, 75%.) $^1$H NMR (CD$_3$SOCD$_3$) δ 9.22 (d, 1H), 9.09 (s, 1H), 8.47 (s, 1H), 8.19 (s, 1H), 8.01 (s, 1H), 7.37 (s, 2H), 7.19 (s, 1H), 6.96 (s, 2H), 4.76 (s, 2H), 4.45 (s, 2H), 3.21 (d, 6H.) $^{19}$F NMR: −75.95 MS: 552 (M+1), 550 (M−1)

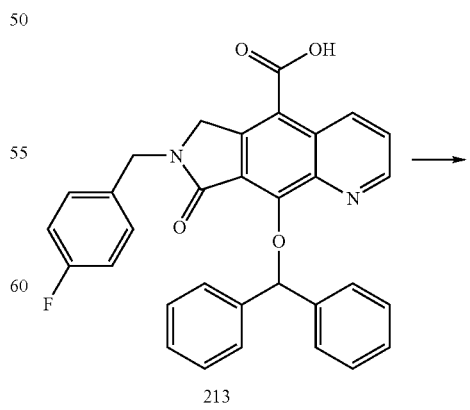

213

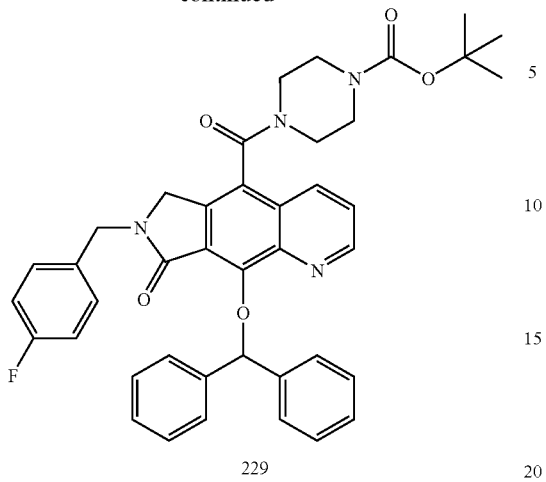

229

Example 229

Carboxylic acid 213 (0.015 g, 0.029 mmol) was dissolved in 0.8 mL of dimethylformamide. To this was added BOC-piperazine (0.0116 g, 0.058 mmol), triethylamine (0.012 mL, 0.087 mmol), 1-(3-Dimethylaminopropyl)-3-ethylcarbodiimide hydrochloride (0.011 g, 0.058 mmol), 1-Hydroxybenzotriazole hydrate (0.0059 g, 0.0435 mmol) and stirred at room temperature. After 15 hours, starting material was consumed. Dilute with dichloromethane, washed with 1M HCl solution, saturated brine solution, dried (Na$_2$SO$_4$), concentrated to give crude product. Chromatographed (10 to 50% ethyl acetate/hexanes) to give 4-[9-benzhydryloxy-7-(4-fluoro-benzyl)-8-oxo-7,8-dihydro-6H-pyrrolo[3,4-g]quinoline-5-carbonyl]-piperazine-1-carboxylic acid tert-butyl ester 229 (0.009 g, 0.013 mmol, 45%.) $^1$H NMR (CDCl$_3$) 9.075 (s, 1H), 8.15 (s, 1H), 8.03 (d, 1H), 7.74 (dd, 4H), 7.53 (dd, 1H), 7.27 (m, 8H), 7.04 (dd, 2H), 4.91 (d, J=17 Hz, 1H), 4.69 (d, J=17 Hz, 1H), 4.41 (d, J=17 Hz, 1H), 4.055 (d, J=17 Hz, 1H), 3.55-2.96 (br m, 8H), 1.44 (s, 9H.) MS: 687 (M+1).

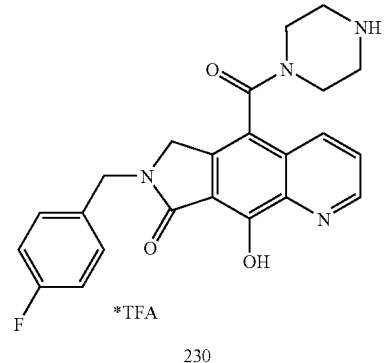

230

Example 230

Carboxamide 229 (0.0108 g, 0.0153 mmol) was dissolved in 1 mL of dichloromethane. To this was added 0.4 mL of triethylsilane and 0.2 mL of trifluoroacetic acid. Stirred at room temperature and after ten minutes complete by TLC. Concentrated off volatiles, azeotroped with toluene to give crude. Then dissolved in 0.6 mL dichloromethane, 0.6 ml trifluoroacetic acid. Stirred at room temperature for one hour. Concentrated off volatiles, azeotroped with toluene to give crude. Triturated twice with 1:1 diethyl ether/hexanes to give 7-(4-fluoro-benzyl)-9-hydroxy-5-(piperazine-1-carbonyl)-6,7-dihydro-pyrrolo[3,4-g]quinolin-8-one 230 (0.039 g, 0.0682 mmol, 100%.) $^1$H NMR (CD$_3$SOCD$_3$) δ 98.97 (s, 2H), 8.32 (d, 1H), 7.74 (s, 1H), 7.36 (dd, 2H), 7.19 (dd, 2H), 4.86 (d, 1H), 4.58 (d, 1H), 4.42 (d, 1H), 4.34 (d, 1H), 3.9-2.90 (m, 8H.) $^{19}$F NMR: -74.202 MS: 421 (M+1), 419 (M-1)

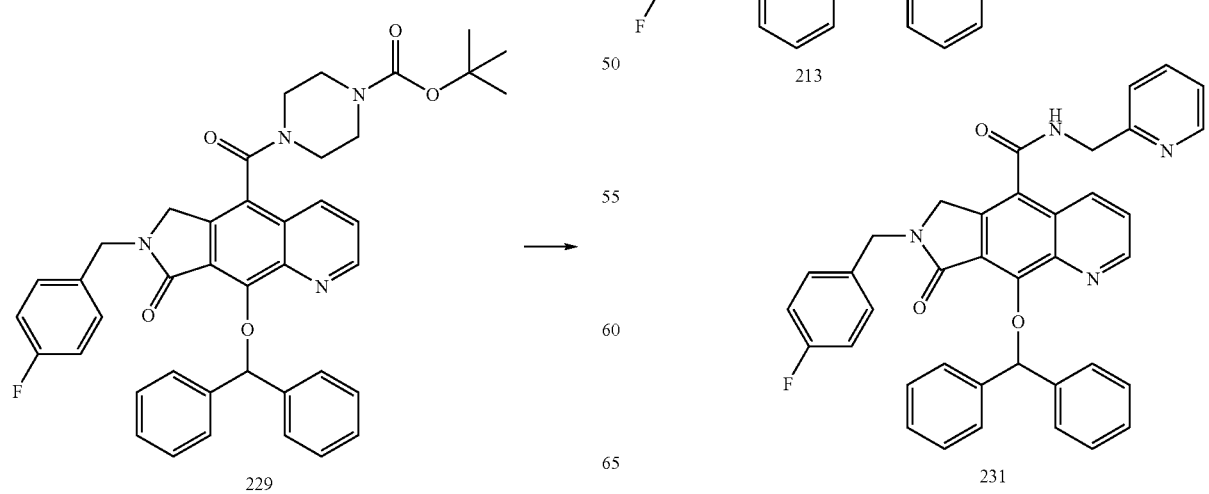

Example 231

Carboxylic acid 213 (0.010 g, 0.0193 mmol) was dissolved in 0.3 mL of dimethylformamide. To this was added 2-aminomethylpyridine (0.004 g, 0.0386 mmol), triethylamine (0.008 mL, 0.058 mmol), 1-(3-Dimethylaminopropyl)-3-ethylcarbodiimide hydrochloride (0.074 g, 0.0386 mmol), 1-Hydroxybenzotriazole hydrate (0.0039 g, 0.029 mmol) and stirred at room temperature. After 15 hours, starting material was consumed. Dilute with dichloromethane, washed with 1M HCl solution, saturated brine solution, dried ($Na_2SO_4$), concentrated to give crude product. Chromatographed (0 to 8% methanol/dichloromethane) to give 9-benzhydryloxy-7-(4-fluoro-benzyl)-8-oxo-7,8-dihydro-6H-pyrrolo[3,4-g]quinoline-5-carboxylic acid (pyridin-2-ylmethyl)-amide 231 (0.007 g, 0.011 mmol, 59%.) $^1$H NMR (CDCl$_3$) 8.94 (s, 1H), 8.45 (d, 2H), 8.05 (s, 1H), 7.70 (d, 4H), 7.57-7.17 (m, 12H), 7.05 (d, 2H), 4.78 (s, 1H), 4.69 (d, J=5 Hz, 1H), 4.38 (s, 1H). MS: 609 (M+1).

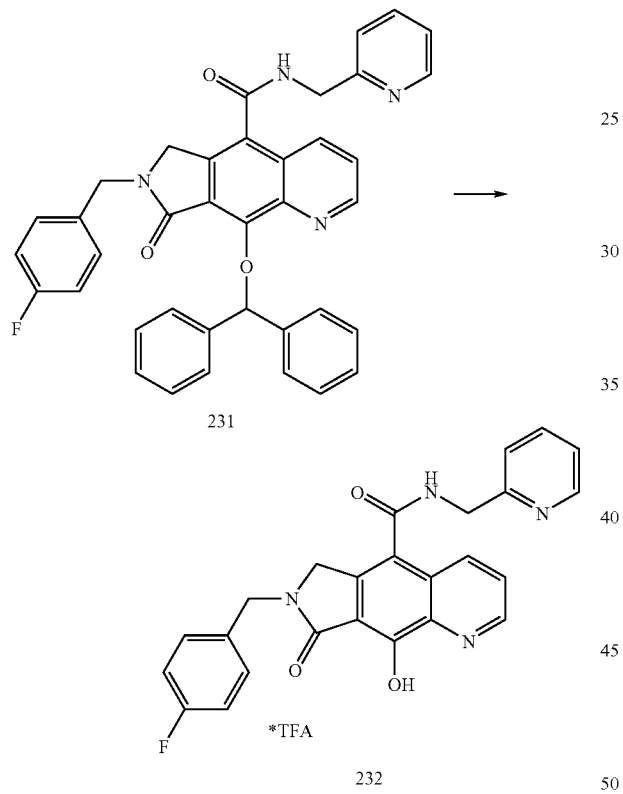

Example 232

Carboxamide 231 (0.225 g, 0.355 mmol) was dissolved in 1 mL of dichloromethane. To this was added 0.5 mL of triethylsilane and 0.25 mL of trifluoroacetic acid. Stirred at room temperature and after ten minutes complete by TLC. Concentrated off volatiles, azeotroped with toluene to give crude. Triturated twice with 1:1 diethyl ether/hexanes to give 7-(4-fluoro-benzyl)-9-hydroxy-8-oxo-7,8-dihydro-6H-pyrrolo[3,4-g]quinoline-5-carboxylic acid (pyridin-2-ylmethyl)-amide 232 (0.11 g, 0.20 mmol, 56%.) $^1$H NMR (CD$_3$SOCD$_3$) δ 9.18 (s, 1H), 8.96 (d, 1H), 8.65 (dd, 2H), 8.09 (dd, 1H), 7.76 (dd, 1H), 7.64 (dd, 1H), 7.36 (dd, 2H), 7.22 (dd, 2H), 4.70 (s, 4H), 4.54 (s, 2H). $^{19}$F NMR: −75.37 MS: 443 (M+1), 441 (M−1)

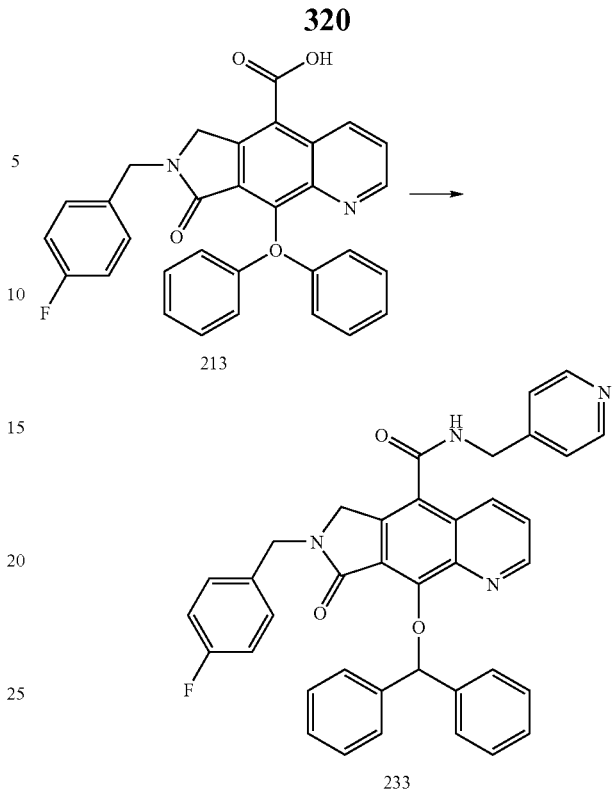

Example 233

Carboxylic acid 213 (0.010 g, 0.0193 mmol) was dissolved in 0.3 mL of dimethylformamide. To this was added 4-aminomethylpyridine (0.004 mL, 0.0386 mmol), triethylamine (0.008 mL, 0.058 mmol), 1-(3-Dimethylaminopropyl)-3-ethylcarbodiimide hydrochloride (0.074 g, 0.0386 mmol), 1-Hydroxybenzotriazole hydrate (0.0039 g, 0.029 mmol) and stirred at room temperature. After 15 hours, starting material was consumed. Dilute with dichloromethane, washed with 1M HCl solution, saturated brine solution, dried ($Na_2SO_4$), concentrated to give crude product. Chromatographed (0 to 8% methanol/dichloromethane) to give 233 (0.0048 g, 0.008 mmol, 41%.) $^1$H NMR (CDCl$_3$) δ 8.71 (s, 1H), 8.66 (d, 2H), 7.99 (dd, 2H), 7.65 (s, 1H), 7.51 (s, 4H), 7.34 (m, 9H), 7.05 (dd, 2H), 4.69 (s, 2H), 4.25 (d, 2H), 4.00 (s, 2H). MS: 609 (M+1).

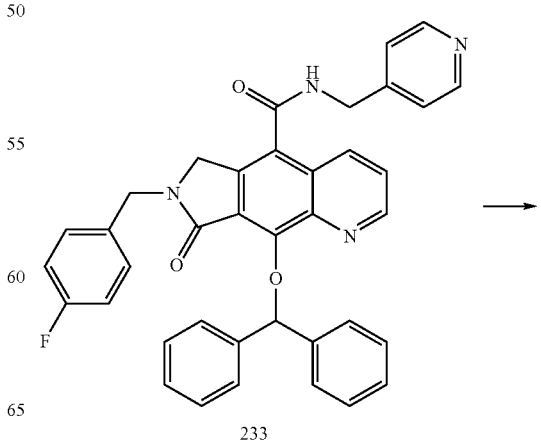

-continued

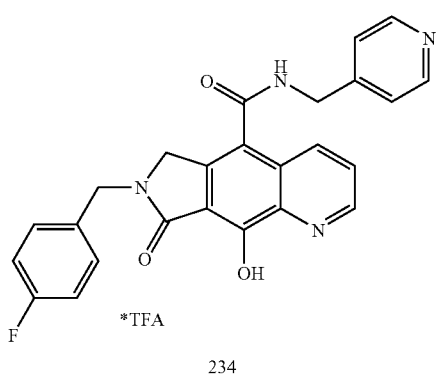

234

Example 234

Carboxamide 233 (0.137 g, 0.225 mmol) was dissolved in 1 mL of dichloromethane. To this was added 0.5 mL of triethylsilane and 0.25 mL of trifluoroacetic acid. Stirred at room temperature and after ten minutes complete by TLC. Concentrated off volatiles, azeotroped with toluene to give crude. Triturated twice with 1:1 diethyl ether/hexanes to give 7-(4-fluoro-benzyl)-9-hydroxy-8-oxo-7,8-dihydro-6H-pyrrolo[3,4-g]quinoline-5-carboxylic acid (pyridin-4-ylmethyl)-amide 234 (0.114 g, 0.20 mmol, 91%.) $^1$H NMR (CD$_3$SOCD$_3$) δ 9.24 (dd, 1H), 8.98 (d, 1H), 8.77 (dd, 2H), 8.53 (d, 1H), 7.79 (dd, 3H), 7.40 (dd, 2H), 7.23 (dd, 2H), 4.71 (s, 4H), 4.56 (s, 2H). $^{19}$F NMR: −74.906 MS: 443 (M+1), 441 (M−1)

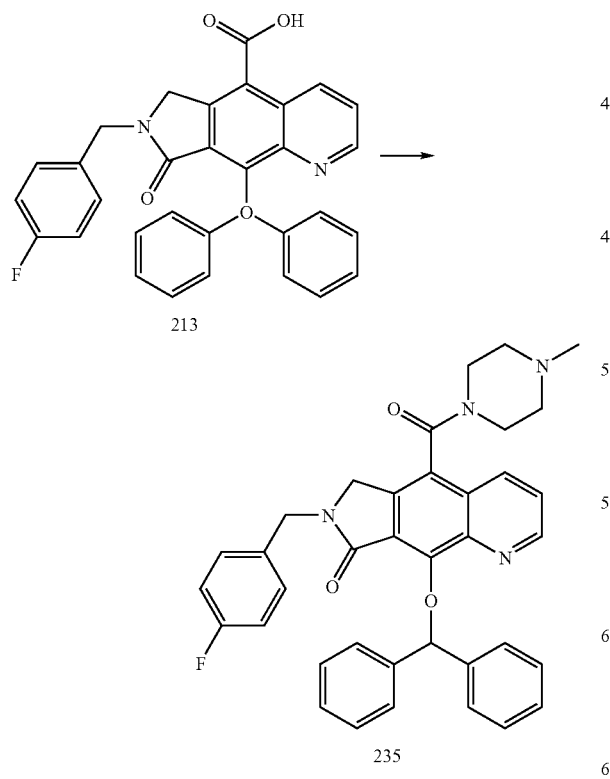

Example 235

Carboxylic acid 213 (0.020 g, 0.0386 mmol) was dissolved in 0.4 mL of dimethylformamide. To this was added methyl piperazine (0.0085 mL, 0.077 mmol), diisopropylethylamine (0.027 mL, 0.154 mmol), O-(7-Azabenzotriazol-1-yl)-N,N,N',N'-tetramethyluronium hexafluorophosphate (0.029 g, 0.0777 mmol) and stirred at room temperature. After 15 hours, starting material was consumed. Dilute with dichloromethane, washed with saturated brine solution, dried (Na$_2$SO$_4$), concentrated to give crude product. Chromatographed (0 to 8% methanol/dichloromethane) to give 235 (0.017 g, 0.028 mmol, 73%.) $^1$H NMR (CDCl$_3$) δ 9.06 (dd, 1H), 8.13 (s, 1H), 8.05 (dd, 1H), 7.76 (dd, 4H), 7.53 (dd, 1H), 7.27 (m, 8H), 7.06 (dd, 2H), 4.93 (d, J=15 Hz, 1H), 4.72 (d, J=15 Hz, 1H), 4.36 (d, J=15 Hz, 1H), 4.066 (d, J=15 Hz, 1H), 3.88-2.97 (m, 8H), 2.28 (s, 3H.) MS: 601 (M+1).

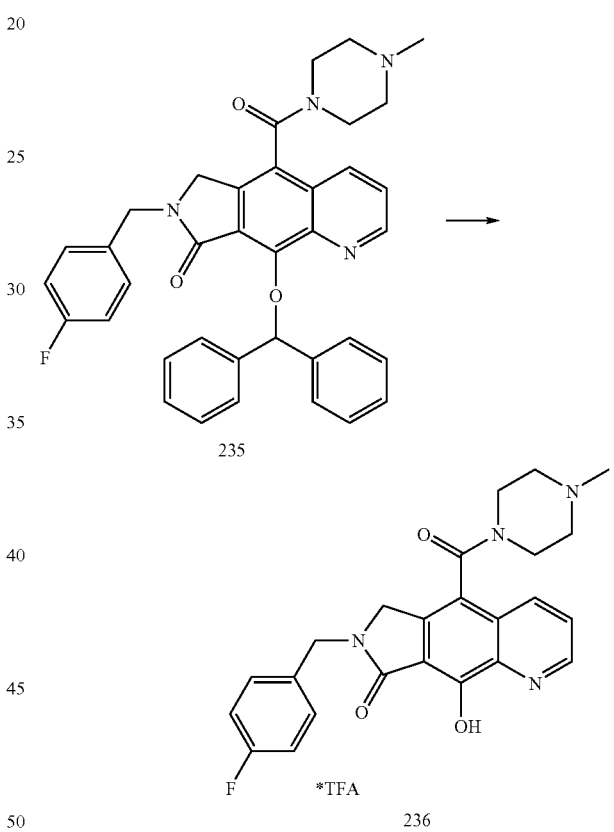

Example 236

Carboxamide 235 (0.015 g, 0.025 mmol) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated twice with 1:1 diethyl ether/hexanes to give 7-(4-fluoro-benzyl)-9-hydroxy-5-(4-methyl-piperazine-1-carbonyl)-6,7-dihydro-pyrrolo[3,4-g]quinolin-8-one 236 (0.0135 g, 0.227 mmol, 91%.) $^1$H NMR 90° C(CD$_3$SOCD$_3$) δ 8.98 (dd, 1H), 8.28 (d, 1H), 7.74 (dd, 1H), 7.40 (dd, 2H), 4.72 (s, 4H), 4.40 (s, 4H), 3.5 (br s, 4H), 2.81 (s, 3H.) $^{19}$F NMR: −74.688 MS: 436 (M+1), 434 (M−1)

323

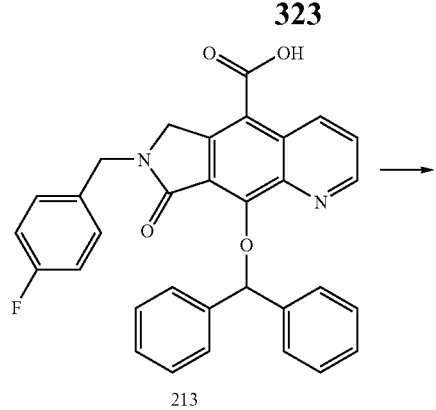

213

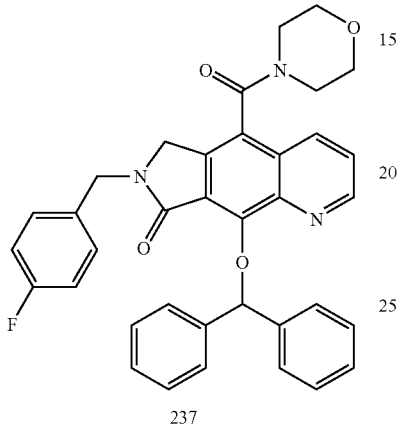

237

Example 237

Carboxylic acid 213 (0.10 g, 0.193 mmol) was dissolved in 2 mL of dimethylformamide. To this was added morpholine (0.0337 mL, 0.386 mmol), diisopropylethylamine (0.135 mL, 0.772 mmol), O-(7-azabenzotriazol-1-yl)-N,N,N',N'-tetramethyluronium hexafluorophosphate (HATU, 0.146 g, 0.386 mmol) and stirred at room temperature. After 15 hours, starting material was consumed. Dilute with dichloromethane, washed with 1M HCl solution, saturated brine solution, dried (Na₂SO₄), concentrated to give crude product. Chromatographed (0 to 5% methanol/dichloromethane) to give pure product (0.06 g, 0.102 mmol, 53%.) ¹H NMR (CDCl₃) δ 9.08 (dd, 1H), 8.15 (s, 1H), 8.06 (dd, 1H), 7.76 (dd, 4H), 7.55 (dd, 1H), 7.30 (m, 8H), 7.07 (dd, 2H), 4.95 (d, J=15 Hz, 1H), 4.70 (d, J=15 Hz, 1H), 4.42 (d, J=15 Hz, 1H), 4.14 (d, J=15 Hz, 1H), 3.94-3.79 (m, 4H), 3.41 (m, 2H), 2.99 (m, 2H.) MS: 588 (M+1).

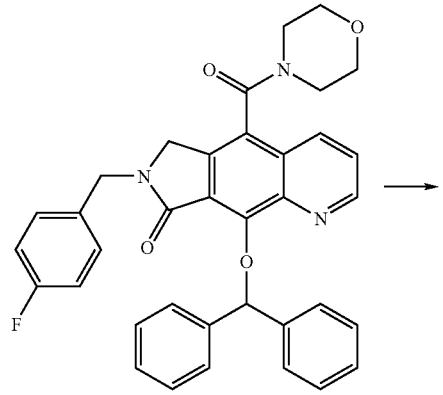

237

324

-continued

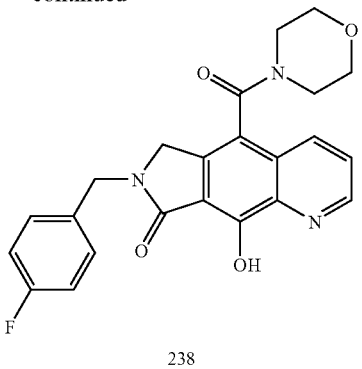

238

Example 238

Carboxamide 237 (0.06 g, 0.102 mmol) was dissolved in 1 mL of dichloromethane. To this was added 0.4 mL of triethylsilane and 0.2 mL of trifluoroacetic acid. Stirred at room temperature and after ten minutes complete by TLC. Concentrated off volatiles, azeotroped with toluene to give crude. Triturated twice with 1:1 diethyl ether/hexanes to give 7-(4-fluoro-benzyl)-9-hydroxy-5-(morpholine-4-carbonyl)-6,7-dihydro-pyrrolo[3,4-g]quinolin-8-one 238 (0.0459 g, 0.109 mmol, 100%.) ¹H NMR (CDCl₃) δ 9.05 (dd, 1H), 8.20 (d, 1H), 7.64 (dd, 1H), 7.35 (m, 2H), 7.08 (dd, 2H), 4.91 (d, J=15 Hz, 1H), 4.68 (d, J=15 Hz, 1H), 4.59 (d, J=15 Hz, 1 Hz), 4.24 (d, J=15 Hz, 1H), 3.99 (m, 3H), 3.5 (s, 2H), 3.18 (s, 2H.) MS: 436 (M+1), 434 (M−1)

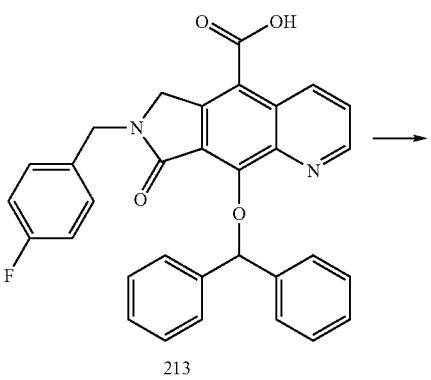

213

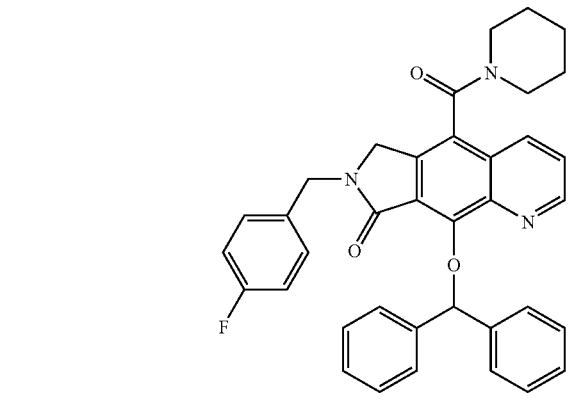

239

Example 239

Carboxylic acid 213 (0.018 g, 0.0347 mmol) was dissolved in 0.5 mL of dimethylformamide. To this was added piperidine (0.0068 mL, 0.0695 mmol), diisopropylethylamine (0.024 mL, 0.139 mmol), HATU (0.027 g, 0.0695 mmol) and stirred at room temperature. After 2.5 hours, starting material was consumed. Dilute with ethyl acetate, washed with 2.5% LiCl solution, saturated brine solution, dried (Na$_2$SO$_4$), concentrated to give crude 239. $^1$H NMR (CDCl$_3$) δ 9.04 (dd, 1H), 8.12 (s, 1H), 8.06 (d, 1H), 7.75 (dd, 4H), 7.52 (dd, 1H), 7.30 (m, 8H), 7.06 (dd, 2H), 4.94 (d, J=15 Hz, 1H), 4.69 (d, J=15 Hz, 1H), 4.40 (d, J=15 Hz, 1H), 4.07 (d, J=15 Hz, 1H), 3.91 (s, 1H), 3.71 (s, 1H), 3.28 (s, 1H), 3.18 (s, 1H), 2.0-1.28 (m, 6H.) MS: 586 (M+1).

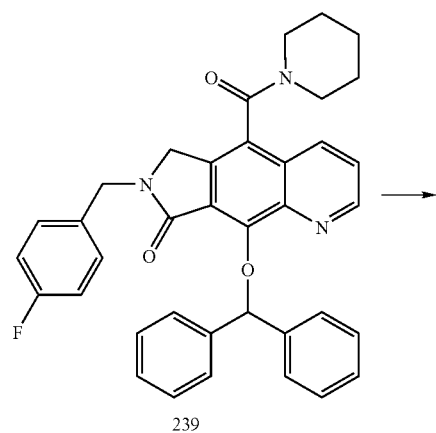

239

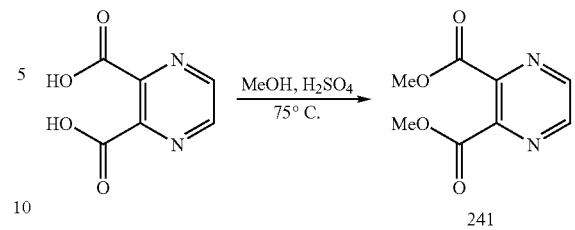

240

Example 240

Carboxamide 239 (crude) was dissolved in 0.5 mL of dichloromethane. To this was added 0.2 mL of triethylsilane and 0.1 mL of trifluoroacetic acid. Stirred at room temperature and after ten minutes complete by TLC. Concentrated off volatiles, azeotroped with toluene to give crude. Triturated twice with 1:1 diethyl ether/hexanes to give 7-(4-fluoro-benzyl)-9-hydroxy-5-(piperidine-1-carbonyl)-6,7-dihydro-pyrrolo[3,4-g]quinolin-8-one 240 (0.0084 g, 0.02 mmol, 58% for 2 steps.) $^1$H NMR (CDCl$_3$) δ 8.97 (dd, 1H), 8.17 (d, 1H), 7.60 (dd, 1H), 7.34 (dd, 2H), 7.07 (dd, 2H), 4.91 (d, J=15 Hz, 1H), 4.66 (d, J=15 Hz, 1H), 4.56 (d, J=15 Hz, 1 Hz), 4.22 (d, J=15 Hz, 1H), 3.91 (s, 1H), 3.75 (s, 1H), 3.11 (s, 2H), 1.7-1.3 (m, 6H.) MS: 420 (M+1), 418 (M−1)

Example 241

To a mixture of pyrazine-2,3-dicarboxylic acid (20 g, 119 mmol, 1 equiv.) was added MeOH (80 mL) followed by dropwise addition of concentrated H$_2$SO$_4$ (36 mL, 680 mmol, 5.7 equiv.) over 45 minutes. This method is similar to that that cited for a different substrate (*J. Am. Chem. Soc.*, 73, 1951, 5614-5616). The reaction was heated at 75° C. for 16 hours and then cooled and quenched with water (200 mL). It was extracted with EtOAc (4×60 mL) and the organic layer washed several times with water (3×50 ml), saturated NaHCO$_3$ (50 ml), brine solution (50 mL). It was dried over Na$_2$SO$_4$, filtered and concentrated in vacuo to yield pyrazine-2,3-dicarboxylic acid methyl ester 241 as a brown solid (47%, 10.97 g, 55.9 mmol). $^1$H NMR (300 MHz) CDCl$_3$ δ 8.79 (d, J=2.7 Hz, 2 H), 4.05 (s, 3 H), 4.04 (s, 3 H). TLC Rf: 0.7 ethyl acetate/methanol (9/1)

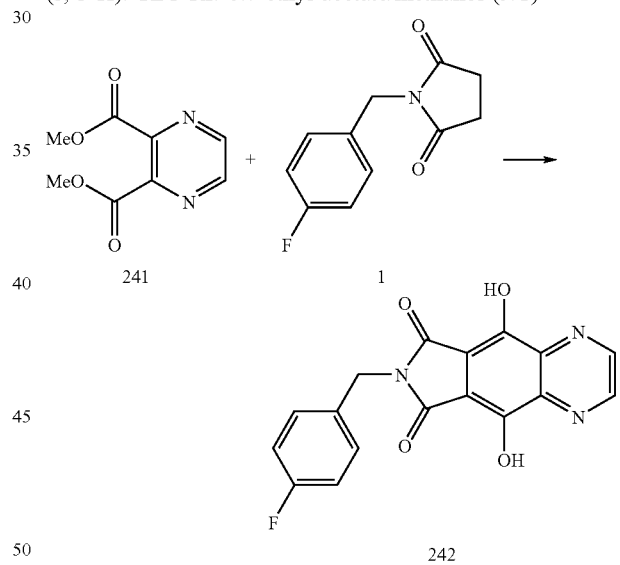

Example 242

Into a flask containing pyrazine-2,3-dicarboxylic acid methyl ester 241 (10.70 g, 54.6 mmol, 1 equiv.) was added THF (150 mL) under a nitrogen atmosphere followed by 1-(4-Fluoro-benzyl)-pyrrolidine-2,5-dione 1 (11.30 g, 54.6 mmol, 1 equiv.). MeOH (1.8 mL) was then added and at 0° C. was added NaH (4.8 g, 120.1 mmol, 2.2 equiv.) carefully in four portions. Refluxing was carried out for 20 hours after which the reaction was cooled and placed in a 0° C. icebath. HCl (6 N, 30 mL, H$_2$O) was slowly added while vigorously stirring. The resulting solid was filtered, and washed thoroughly with water followed by ether. It was then dried in a vacuum oven (60° C.,12 hours) to realize 8.7 gm (47%, 25.66 mmol) of 7-(4-fluoro-benzyl)-5,9-dihydroxy-pyrrolo

[3,4-g]quinoxaline-6,8-dione 242. $^1$H NMR (300 MHz) CDCl$_3$ δ 7.15-7.33 (m, 5 H), 5.91 (s, 2 H), 3.96 (s, 3 H), 3.88 (s, 3 H). MS: 340.3 (M+1).

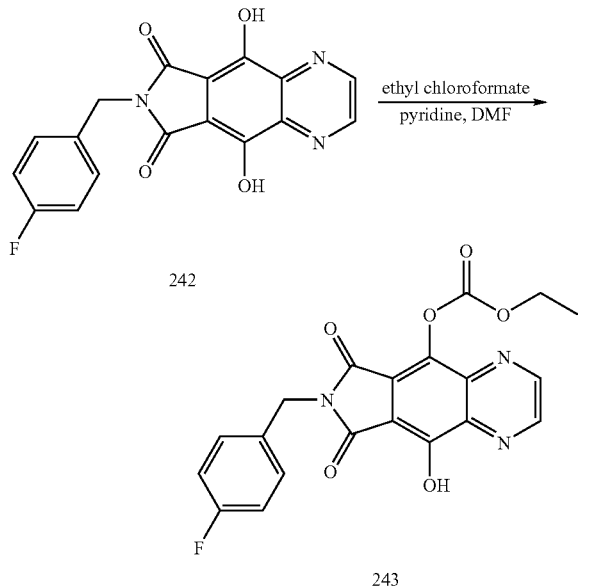

Example 243

7-(4-Fluoro-benzyl)-5,9-dihydroxy-pyrrolo [3,4-g]quinoxaline-6,8-dione 242 (1 g, 2.95 mmol, 1 equiv.) was dissolved in DMF (30 ml, 0.1 M) and pyridine (477 μL, 5.89 mmol, 2 equiv.) before ethyl chloroformate was added (237 μL, 2.95 mmol, 1 equiv.). The reaction was stirred for 16 hours before being quenched with HCl (30 ml, 1 N) and extracted with ethyl acetate (2×30 mL). The organic layer washed several times with water (4×30 mL), saturated NaHCO$_3$ (50 mL), brine solution (50 mL). It was dried over Na$_2$SO$_4$, filtered and concentrated in vacuo. Recrystallization was carried out in ethyl acetate and Hexanes to yield carbonic acid ethyl ester 7-(4-fluoro-benzyl)-9-hydroxy-6,8-dioxo-7,8-dihydro-6H-pyrrolo[3,4-g]quinoxalin-5-yl ester 243 as a light brown solid (98%, 1.20 g, 2.89 mmol). $^1$H NMR (300 MHz) CDCl$_3$ δ 9.09 (d, J=6 Hz, 1 H), 8.97 (d, J=6 Hz, 1 H), 8.65 (bs, 1 H), 7.46 (d, J=4.8 Hz, 2 H), 7.03 (d, J=4.8 Hz, 2 H), 4.85 (s, 2 H), 4.04 (q, J=2.8 Hz, 2 H), 1.43 (q, J=2.8 Hz, 3 H). MS: 412.6 (M+1).

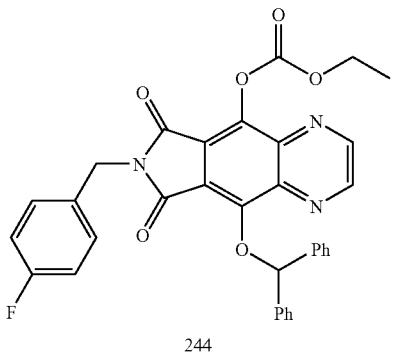

Example 244

Carbonic acid mono-[1-(1-benzyl-4-methylene-2,5-dioxo-pyrrolidin-3-ylidene)-ethyl]ester 243 (1.1 g, 2.68 mmol, 1 equiv.) was dissolved in 1,2 dichloroethane (50 mL, 0.055 M) and to this was added diphenyldiazomethane (1.05 g, 5.35 mmol, 2 equiv.) and heated at 70° C. under a nitrogen atmosphere for 24 hours. The reaction was concentrated in vacuo and purified by silica gel chromatography using 4/1 Hexanes/Ethyl acetate to obtain carbonic acid 9-benzhydryloxy-7-(4-fluoro-benzyl)-6,8-dioxo-7,8-dihydro-6H-pyrrolo [3,4-g]quinoxalin-5-yl ethyl ester 244 (70%, 1085 mg, 1.87 mmol). $^1$H NMR (300 MHz) CDCl$_3$ δ 9.09 (d, J=6 Hz, 1 H), 8.97 (d, J=6 Hz, 1 H), 8.65 (bs, 1 H), 7.46 (d, J=4.8 Hz, 2 H), 7.03 (d, J=4.8 Hz, 2 H), 4.85 (s, 2 H), 4.04 (q, J=2.8 Hz, 2 H), 1.43 (q, J=2.8 Hz, 3 H). MS: 600.2 (M+23). TLC R$_f$: 0.3 Hexanes/Ethyl acetate (7/3)

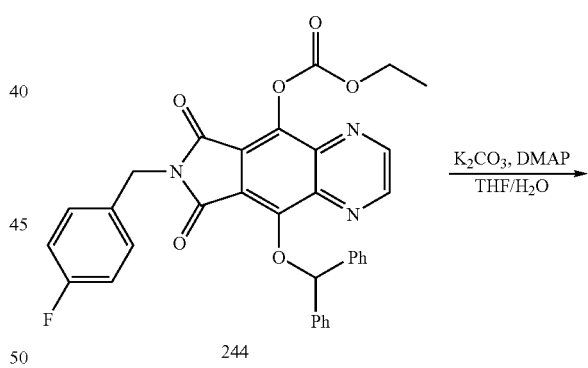

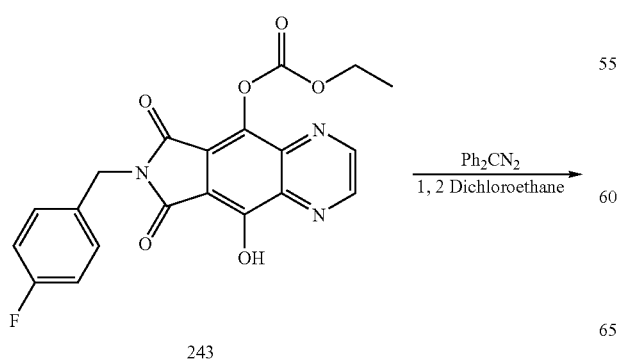

Example 245

Carbonic acid 9-benzhydryloxy-7-(4-fluoro-benzyl)-6,8-dioxo-7,8-dihydro-6H-pyrrolo[3,4-g]quinoxalin-5-yl ester ethyl ester 244 (500 mg, 0.87 mmol) was dissolved in THF (9 mL, 0.1 M) along with DMAP (211 mg, 1.73 mmol, 2 equiv.). A solution of $K_2CO_3$ (1.20 g, 8.66 mmol, and 10 equiv.) was dissolved separately in $H_2O$ (6 mL) before being transferred to the reaction mixture. The reaction was allowed to stir for 18 hours and quenched with HCl (20 mL, 1 N) and extracted with ethyl acetate (2×30 mL). The organic layer was washed with saturated $NH_4Cl$ solution (25 mL), brine solution (25 mL) and dried over $Na_2SO_4$ and concentrated in vacuo to yield 5-benzhydryloxy-7-(4-fluoro-benzyl)-9-hydroxy-pyrrolo[3,4-g]quinoxaline-6,8-dione 245 (94%, 413 mg, 0.82 mmol). $^1$H NMR (300 MHz) $CDCl_3$ δ 9.08 (d, J=1.5 Hz, 1 H), 8.92 (d, J=1.5 Hz, 1H), 7.67 (s, 1 H), 7.67-7.42 (dd, $J_1$=1.5 Hz, $J_2$=8.4 Hz, 4 H), 7.43-7.48 (m, 2 H), 7.19-7.27 (m, 7 H), 7.03-7.20 (m, 1 H), 4.86 (s, 2 H). MS: 528.0 (M+23). TLC $R_f$: 0.2 Hexanes/Ethyl acetate (8/2)

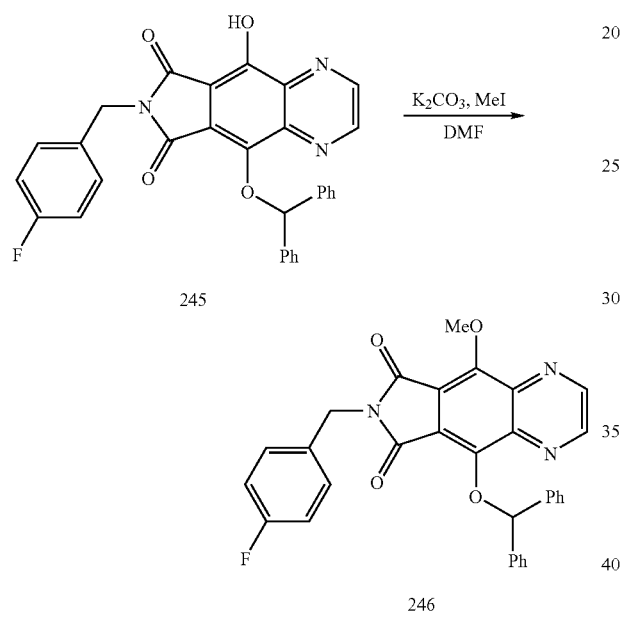

245

246

Example 246

Into a flask containing 5-benzhydryloxy-7-(4-fluoro-benzyl)-9-hydroxy-pyrrolo[3,4-g]quinoxaline-6,8-dione 245 (350 mg, 0.69 mmol, 1 equiv.) was added DMF (20 mL) followed by $K_2CO_3$ (478 mg, 3.46 mmol, 5 equiv.). To this was added MeI (983 μL, 6.93 mmol, 10 equiv.) under a nitrogen atmosphere and stirred for 16 hours. To the reaction was then added water (50 mL) and extracted with ethyl acetate (2×40 mL). The organic layer was washed several times with water (3×30 mL), saturated $NaHCO_3$ (40 mL), brine solution (30 mL). It was dried over $Na_2SO_4$, filtered and concentrated in vacuo before being purified by silica gel chromatography using 3/2 Hexanes/ethyl acetate to obtain 5-benzhydryloxy-7-(4-fluoro-benzyl)-9-methoxy-pyrrolo[3,4-g]quinoxaline-6,8-dione 246 (78%, 280 mg, 0.54 mmol) as a yellow solid. $^1$H NMR (300 MHz) $CDCl_3$ δ 9.03 (d, J=1.5 Hz, 1 H), 8.97 (d, J=1.5 Hz, 1 H), 7.75 (s, 1 H), 7.60 (dd, $J_1$=1.5 Hz, $J_2$=8.4 Hz, 4 H), 7.43-7.48 (m, 2 H), 7.19-7.27 (m, 7 H), 7.03-7.20 (m, 1H), 4.86 (s, 2 H), 4.37 (s, 3 H). MS: 542.0 (M+23). TLC $R_f$: 0.5 Hexanes/Ethyl acetate (1/1)

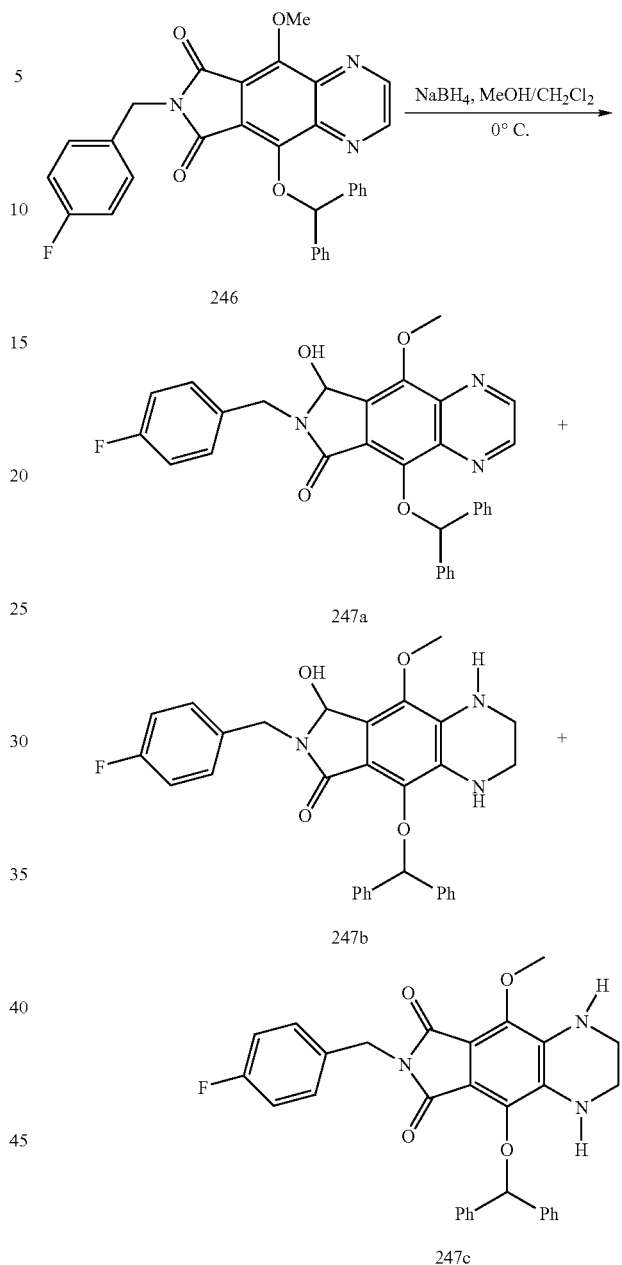

246

247a

247b

247c

Example 247

5-Benzhydryloxy-7-(4-fluoro-benzyl)-9-methoxy-pyrrolo[3,4-g]quinoxaline-6,8-dione 246 (10 mg, 0.019 mmol, 1 equiv.) was dissolved in $CH_2Cl_2$ (0.2 mL) and MeOH (0.5 mL) under a nitrogen atmosphere at 0° C. Sodium borohydride ($NaBH_4$) was added (115 μL, 0.057 mmol, 3 equiv., 0.5 M). The reaction was allowed to stir for 1 hour and then quenched with water (5 mL) and extracted with ethyl acetate (2×5 mL). The organic layer was washed several times with water (2×10 mL), brine solution (10 mL). It was dried over $Na_2SO_4$, filtered and concentrated in vacuo and purified by preparatory thin-layer chromatography (PTLC) using 3/2 Hexanes/Ethyl acetate to obtain 5-benzhydryloxy-7-(4-fluoro-benzyl)-8-hydroxy-9-methoxy-7,8-dihydro-pyrrolo

[3,4-g]quinoxalin-6-one 247a (34%, 3 mg) and reduced species: 5-benzhydryloxy-7-(4-fluoro-benzyl)-8-hydroxy-9-methoxy-1,2,3,4,7,8-hexahydro-pyrrolo[3,4-g]quinoxalin-6-one 247b (21%, 2 mg) and 5-benzhydryloxy-7-(4-fluoro-benzyl)-9-methoxy-1,2,3,4-tetrahydro-pyrrolo[3,4-g]quinoxaline-6,8-dione 247c (34%, 3.4 mg).

247a: $^1$H NMR (300 MHz) CDCl$_3$ δ 8.86 (d, J=1.8 Hz, 1 H), 8.82 (d, J=1.8 Hz, 1 H), 7.69 (s, 1 H), 7.69-7.56 (m, 1 H), 7.54-7.56 (m, 1H), 7.16-7.32 (m, 10 H), 7.01-7.17 (s, 2 H), 5.78 (bs, 1 H), 5.18 (d, J=14.7 Hz, 1 H), 4.38 (d, J=13.5 Hz,1 H), 4.18 (s, 3 H), 3.83 (s, 2 H). MS: 544.0(M+23). TLC R$_f$: 0.3 Hexanes/Ethyl acetate (3/2)

247b: $^1$H NMR (300 MHz) CDCl$_3$ δ 7.27-7.7.40 (m, 12 H), 6.95-7.01 (m, 2 H), 4.70 (s, 2 H), 4.01 (s, 3 H), 3.32 (t, J=3.9 Hz, 2 H), 3.13 (t, J=5.1 Hz, 2 H), 2.75 (s, 2 H). MS: 545.9 (M+23). TLC R$_f$: 0.25 Hexanes/Ethyl acetate (1/1)

247c: $^1$H NMR (300 MHz) CDCl$_3$ δ 7.27-7.7.40 (m, 12 H), 5.58 (bs, 1 H), 5.01 (d, J=14.1 Hz, 1 H), 4.21 (d, J=9.6 Hz, 1 H), 3.85 (s, 3 H), 3.32-3.45 (m, 2 H), 3.02-3.05 (t, J=5.1 Hz, 2 H), 1.63 (bs, 2 H). R$_f$: 0.2 Hexanes/Ethyl acetate (1/1)

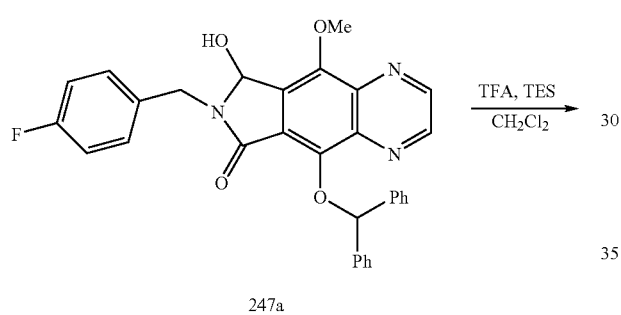

247a

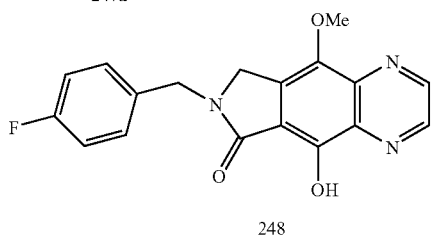

248

Example 248

Into a flask containing 5-benzhydryloxy-7-(4-fluoro-benzyl)-8-hydroxy-9-methoxy-7,8-dihydro-pyrrolo[3,4-g]quinoxalin-6-one 247a (20 mg, 0.038 mmol, 1 equiv.) was added CH$_2$Cl$_2$ (1 mL) under a nitrogen atmosphere. Triethylsilane (200 µL) was added followed by trifluoroacetic acid (200 µL). The reaction was allowed to stir for 1 hour and then concentrated in vacuo until thoroughly dried. To the oil was Hexanes/Ethyl ether (15 mL, 1/1 ratio) and sonicated. The resulting solid was then filtered, washed in hexanes, and air dried to give 7-(4-fluoro-benzyl)-5-hydroxy-9-methoxy-7,8-dihydro-pyrrolo[3,4-g]quinoxalin-6-one 248 (38%, 7.2 mg, 0.0.14 mmol). $^1$H NMR (300 MHz) CDCl$_3$ δ 8.95 (d, J=13.8 Hz, 2 H), 7.23-7.27 (m, 2 H), 6.96-7.05 (s, 2 H), 4.79 (2 H), 4.55 (s, 2 H), 4.14 (s, 3 H). $^{19}$F NMR (300 MHz) CDCl$_3$ δ 62.80. MS: 340.1 (M+1)

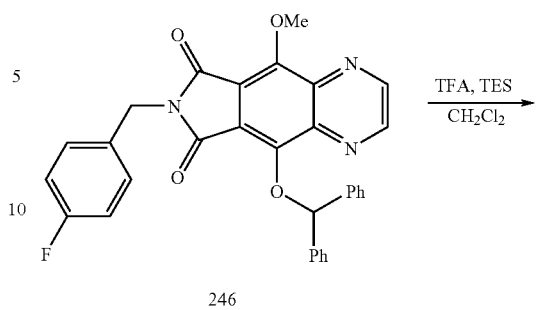

246

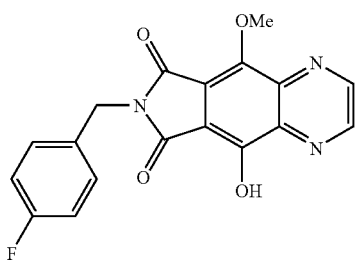

249

Example 249

Into a flask containing 5-benzhydryloxy-7-(4-fluoro-benzyl)-9-methoxy-pyrrolo[3,4-g]quinoxaline-6,8-dione 246 (10 mg, 0.019 mmol, 1 equiv.) was added CH$_2$Cl$_2$ (1 mL) and under a nitrogen atmosphere was added triethylsilane (200 µL) followed by trifluoroacetic acid (200 µL). The reaction was allowed to stir for 1.5 hours and concentrated in vacuo until thoroughly dried. To the oil was added Hexanes/Ethyl ether (20 mL, 1/1 ratio) and sonicated. The resulting solid was filtered, washed in hexanes and air dried to give 7-(4-fluoro-benzyl)-5-hydroxy-9-methoxy-pyrrolo[3,4-g]quinoxaline-6,8-dione 249 (67%, 4.6 mg, 0.015 mmol). $^1$H NMR (300 MHz) CDCl$_3$ δ 9.07 (d, J=1.8 Hz, 1 H), 8.97 (d, J=1.8 Hz, 1 H), 7.23-7.27 (m, 2 H), 6.96-7.05 (s, 2 H), 4.87 (s, 2 H), 4.46 (s, 3 H). $^{19}$F NMR (300 MHz) CDCl$_3$ δ 62.77 MS: 354.0 (M+1)

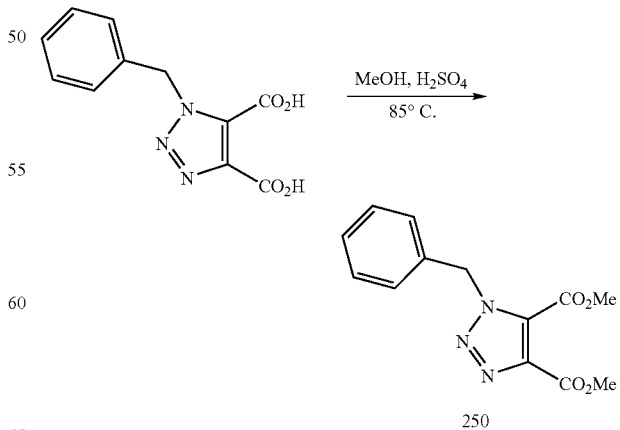

250

Example 250

To commercially available, 1-benzyl-1H-[1,2,3]triazole-4,5-dicarboxylic acid (4.5 g, 18.2 mmol, 1 equiv.) was added MeOH (30 mL) followed by dropwise addition of $H_2SO_4$ (5.5 mL, 103.75 mmol, 5.7 equiv.) over 20 minutes by a method similar to *J. Am. Chem. Soc.*, 73, 1951, 5614-5616. The reaction was heated at 85° C. for 2 h. The reaction was cooled and quenched with water (100 mL). It was extracted with ethyl acetate (4×40 mL) and the organic layer washed several times with water (3×50 mL), saturated $NaHCO_3$ (50 mL), brine solution (50 mL). It was dried over $Na_2SO_4$, filtered and concentrated in vacuo to yield 1-Benzyl-1H-[1,2,3]triazole-4,5-dicarboxylic acid dimethyl ester 250 as a brown solid (76%, 3.85 g, 55.9 mmol). $^1$H NMR (300 MHz) $CDCl_3$ δ 7.15-7.33 (m, 5 H), 5.41 (s, 2 H), 3.92 (s, 3 H), 3.84 (s, 3 H).

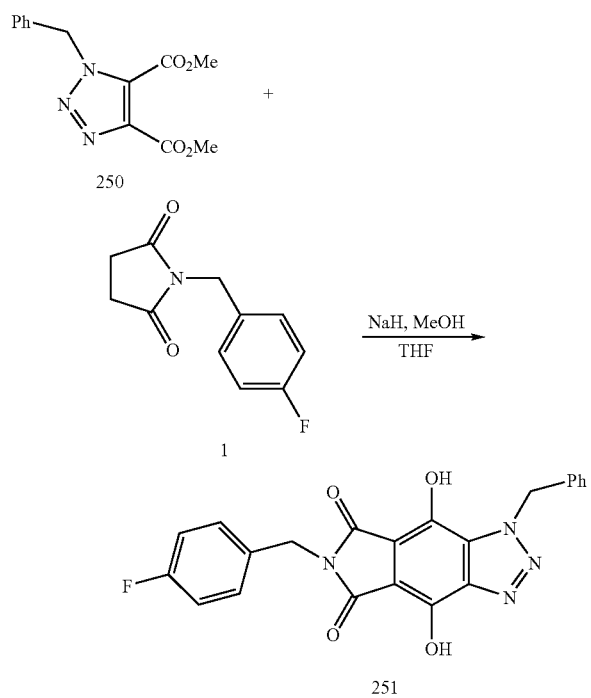

Example 251

Into a flask containing 1-benzyl-1H-[1,2,3]triazole-4,5-dicarboxylic acid dimethyl ester 250 (3.75 g, 13.64 mmol, 1 equiv.) was added THF (150 mL) under a nitrogen followed by 1-(4-fluoro-benzyl)-pyrrolidine-2,5-dione 1 (2.82 g, 13.64 mmol, 1 equiv.). Methanol (MeOH, 1.1 mL) was added and at 0° C. was added NaH (1.20 g, 29.99 mmol, 2.2 equiv., 60% dispersion) carefully in four portions. Refluxing was carried out for 20 hours after which the reaction was cooled and placed in a 0° C. icebath. HCl (6 N, 20 mL, $H_2O$) was slowly added while vigorously stirring. The resulting solid was filtered, and washed thoroughly with water followed by ether. It was then dried in a vacuum oven (60° C., overnight) to realize 3.34 gm (60%, 8.18 mmol) of 1-benzyl-6-(4-fluoro-benzyl)-4,8-dihydroxy-1H-pyrrolo[3',4':4,5]benzo[1,2-d][1,2,3]triazole-5,7-dione 251. $^1$H NMR (300 MHz) $CD_3OD$ δ 9.51 (b, 1 H), 7.45-7.35 (m, 8 H), 7.15-7.33 (m, 2 H), 5.92 (s, 2 H), 4.78 (s, 2 H).

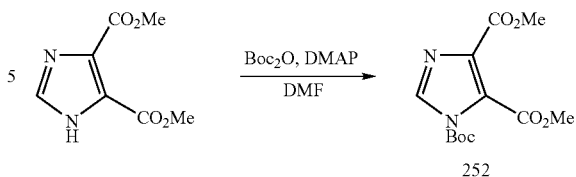

Example 252

1H-Imidazole-4,5-dicarboxylic acid dimethyl ester (2 g, 10.87 mmol, 1 equiv.) was dissolved in THF (55 mL, 0.2 M) and DMAP (1.46 g, 11.95 mmol, 1.1 equiv.) before Di-tert-butyl dicarbonate (3.50 g, 16.29 mmol, 1.4 equiv.) was added. The reaction was stirred for 16 hours before being quenched with saturated $NH_4Cl$ (30 mL) and extracted with ethyl acetate (2×30 mL) and the organic layer washed several times with water (4×30 mL), brine solution (50 mL). It was dried over $Na_2SO_4$, filtered and concentrated in vacuo. Imidazole-1,4,5-tricarboxylic acid 1-tert-butyl ester 4,5-dimethyl ester 252 (3.85 g, 100%, 10.87 mmol). $^1$H NMR (300 MHz) $CDCl_3$ δ 8.02 (s, 1 H), 3.99 (s, 3 H), 3.92 (s, 3 H). MS: 306.8 (M+23). TLC $R_f$: 0.6 Hexanes/Ethyl acetate (1/1)

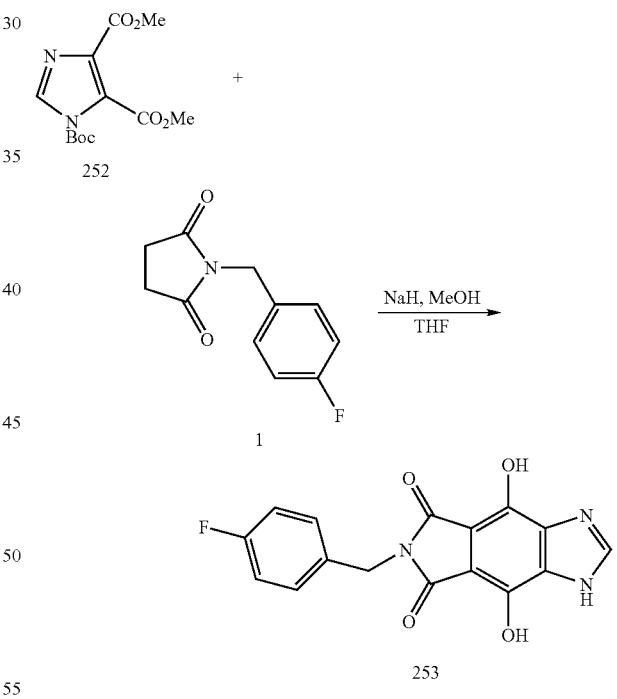

Example 253

Into a flask containing imidazole-1,4,5-tricarboxylic acid 1-tert-butyl ester 4,5-dimethyl ester 252 (3.85 g, 13.55 mmol, 1 equiv.) was added THF (55 mL) under a nitrogen atmosphere followed by 1-(4-fluoro-benzyl)-pyrrolidine-2,5-dione 1 (2.80 g, 13.55 mmol, 1 equiv.). MeOH (0.4 mL) was added and at 0° C. was added NaH (1.20 g, 29.81 mmol, 2.2 equiv., 60% dispersion) carefully in four portions. Refluxing was carried out for 20 hours after which the reaction was cooled and placed in a 0° C. icebath. HCl (6 N, 30 mL, H₂O) was slowly added while vigorously stirring. The resulting solid was filtered, and washed thoroughly with water followed by ether. It was then dried in a vacuum oven (60° C., overnight) to realize 2.70 gm of a crude solid which was recrystallized with dioxane (650 mL). 6-(4-fluoro-benzyl)-4,8-dihydroxy-1H-1,3,6-triaza-s-indacene-5,7-dione 253 1.65 g, 5.01 mmol). ¹H NMR (300 MHz) DMSO d₆ δ 8.64 (s, 1 H), 7.25-7.35 (m, 2 H), 7.10-7.29 (m, 2 H), 4.66 (s, 2 H). ¹⁹F NMR (300 MHz) CDCl₃ δ 61.34. MS: 328.1 (M+1)

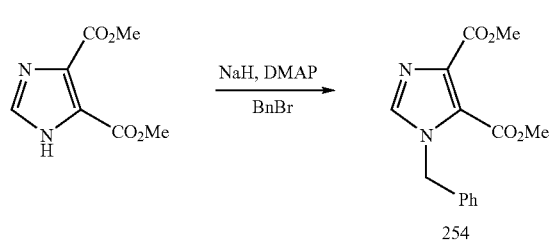

Example 254

1H-Imidazole-4,5-dicarboxylic acid dimethyl ester (1.5 g, 8.15 mmol, 1 equiv.) was dissolved in MeOH (10 mL) and benzyl bromide (1.16 mL, 9.77 rmmol, 1.1 equiv.) before sodium hydride (360 mg, 1.1 equiv., 60% dispersion) and sodium iodide (200 mg) was added. The reaction was stirred for 16 hours before being quenched with saturated NH₄Cl (30 mL) and extracted with ethyl acetate (2×30 mL) and the organic layer washed several times with water (4×30 mL), brine solution (50 mL). It was dried over Na₂SO₄, filtered and concentrated in vacuo. 1-Benzyl-1H-imidazole-4,5-dicarboxylic acid dimethyl ester 254 (2.01 g, 90%, 7.33 mmol). ¹H NMR (300 MHz) CDCl₃ δ 7.58 (s, 1 H), 7.33-7.42 (m, 3 H), 7.14-7.18 (m, 2 H), 5.41 (s, 2 H), 3.92 (s, 3 H), 3.84 (s, 3 H). MS: 275.1 (M+1)

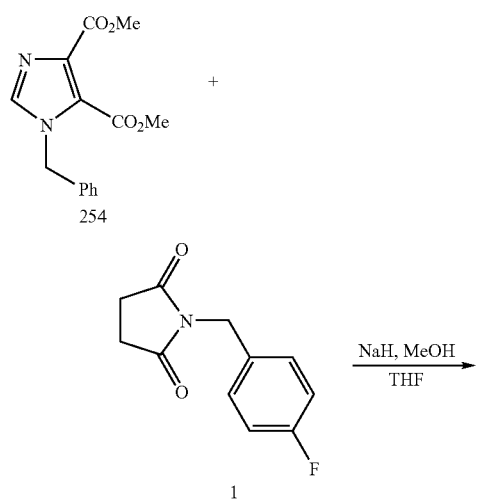

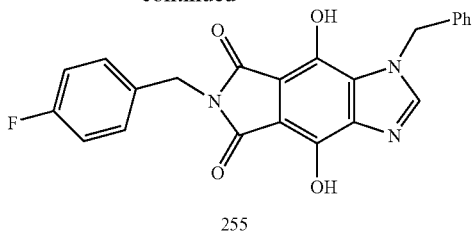

Example 255

Into a flask containing1-benzyl-1H-imidazole-4,5-dicarboxylic acid dimethyl ester 254 (2.80 g, 10.22 mmol, 1 equiv.) was added THF (35 mL) under a nitrogen atmosphere followed by 1-(4-Fluoro-benzyl)-pyrrolidine-2,5-dione 1 (2.2 g, 10.22 mmol, 1 equiv.). MeOH (0.5 mL) was then added and at 0° C. was added NaH (940 mg, 23.49 mmol, 2.2 equiv.) carefully in four portions. Refluxing was carried out for 20 hours after which the reaction was cooled and placed in a 0° C. icebath. HCl (6 N, 30 mL, H₂O) was slowly added while vigorously stirring. The resulting solid was filtered, and washed thoroughly with water followed by ether. It was then dried in a vacuum oven (60° C., 12 hours) to realize 4.20 gm of a crude solid. It was recrystallized with dioxane (700 ml) to realize 1-benzyl-6-(4-fluoro-benzyl)-4,8-dihydroxy-1H-1,3,6-triaza-s-indacene-5,7-dione 255 (1.74 g, 41%, 4.19 mmol). ¹H NMR (300 MHz) DMSO d₆ δ 10.40 (bs, 1 H), 8.73 (s, 1 H), 7.22-7.7.43 (m, 3 H), 7.05-7.18 (m, 2 H), 5.65 (s, 2 H), 4.60 (s, 2 H). MS: 418.1 (M+1).

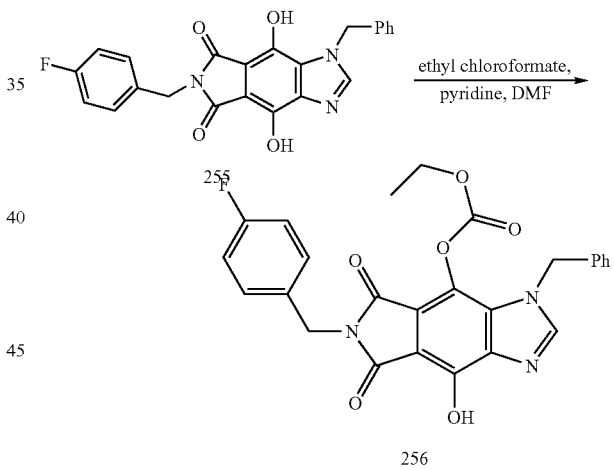

Example 256

1-Benzyl-6-(4-fluoro-benzyl)-4,8-dihydroxy-1H-1,3,6-triaza-s-indacene-5,7-dione 255 (1 g, 2.39 mmol, 1 equiv.) was dissolved in a flask containing DMF (24 mL, 0.1 M) and pyridine (290 µL, 2.88 mmol, 1.5 equiv.). Ethyl chloroformate was added (231 µL, 2.88 mmol, 1.2 equiv.) under a nitrogen atmosphere. The reaction was stirred for 16 hours before being quenched with saturated NH₄Cl (30 mL) and extracted with ethyl acetate (2×30 mL) and the organic layer washed several times with water (4×30 mL), saturated NaHCO₃ (50 mL), brine solution (50 mL). It was dried over Na₂SO₄, filtered and concentrated in vacuo. Trituration was carried out with Hexanes/Ethyl acetate (1/4, 100 mL) to remove the corresponding biscarbonate to give carbonic acid 3-benzyl-6-(4-fluoro-benzyl)-8-hydroxy-5,7-dioxo-3,5,6,7-tetrahydro-1,3,6-triaza-s-indacen-4-yl ester ethyl ester 256 (13%, 145 mg, 0.296 mmol). ¹H NMR (300 MHz) DMSO d$_6$ δ 8.63 (s, 1 H), 7.45-7.35 (m, 6 H), 7.15-7.33 (m, 4 H), 5.59 (s, 2 H), 4.63 (s, 2 H), 3.98 (q, J=6.9 Hz, 2 H), 1.17 (t, J=6.9 Hz, 3 H). MS: 490.2 (M+1). TLC R$_f$: 0.6 Ethyl acetate.

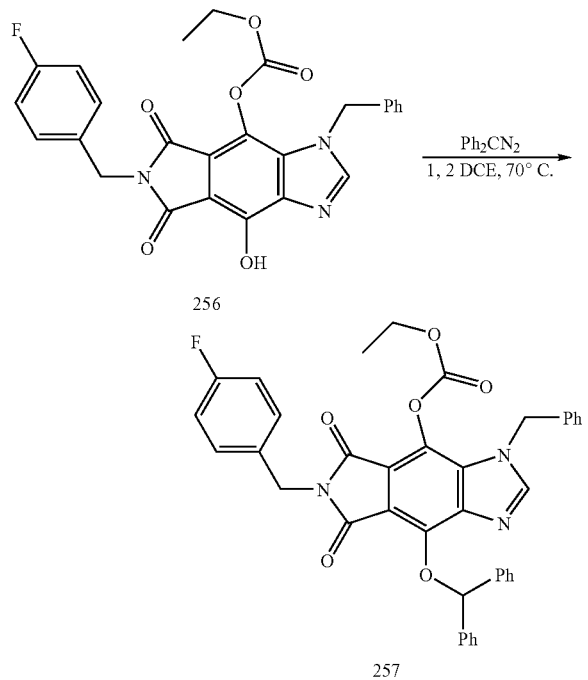

256

Example 257

Carbonic acid 3-benzyl-6-(4-fluoro-benzyl)-8-hydroxy-5,7-dioxo-3,5,6,7-tetrahydro-1,3,6-triaza-s-indacen-4-yl ester ethyl ester 256 (140 mg, 0.28 mmol, 1 equiv.) was dissolved in 1,2 dichloroethane (20 mL) and to this was added diphenyldiazomethane (72 mg, 0.37 mmol, 1.3 equiv.) and heated at 70° C. under a nitrogen atmosphere for 24 hours. The reaction was then concentrated in vacuo and purified by silica gel chromatography using 7/3 Hexanes/Ethyl acetate to obtain carbonic acid 8-benzhydryloxy-3-benzyl-6-(4-fluoro-benzyl)-5,7-dioxo-3,5,6,7-tetrahydro-1,3,6-triaza-s-indacen-4-yl ester ethyl ester 257 (78%, 135 mg, 0.22 mmol). $^1$H NMR (300 MHz) CDCl$_3$ δ 8.17 (s, 1 H), 7.91 (s, 1 H), 7.68 (d, J=7.2 Hz, 4 H), 7.21-7.42 (m, 12 H), 6.95-7.06 (s, 4 H), 5.49 (s, 2 H), 4.76 (s, 2 H), 4.11 (q, J=6.9 Hz, 2 H), 1.17 (t, J=6.9 Hz, 3 H). MS: 678.1 (M+23). TLC R$_f$: 0.3 Hexanes/Ethyl acetate (7/3)

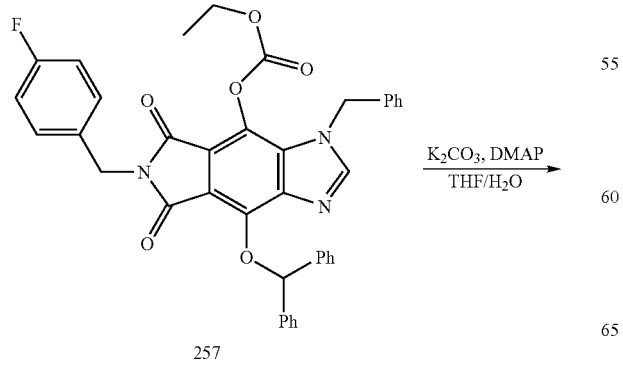

257

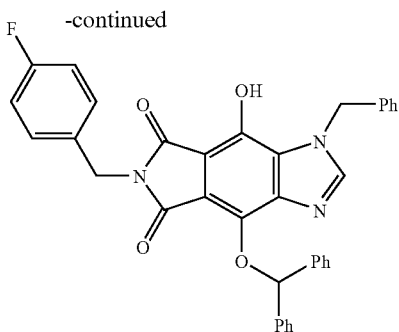

258

Example 258

Carbonic acid 8-benzhydryloxy-3-benzyl-6-(4-fluoro-benzyl)-5,7-dioxo-3,5,6,7-tetrahydro-1,3,6-triaza-s-indacen-4-yl ester ethyl ester 257 (130 mg, 0.20 mmol) was dissolved in THF (5 mL, 0.1 M) along with DMAP (24 mg, 0.40 mmol, 2 equiv.). A solution of K$_2$CO$_3$ (276 mg, 1.99 mmol, 10 equiv.) was dissolved separately in H$_2$O (6 mL) before transferring to the reaction mixture. The reaction was allowed to stir for 18 hr and quenched with HCl (20 mL, 1 N) and extracted with ethyl acetate (2×30 ml). The organic layer was washed with saturated NH$_4$Cl solution (25 mL), brine solution (25 mL) and dried over Na$_2$SO$_4$ and concentrated in vacuo to yield 4-Benzhydryloxy-1-benzyl-6-(4-fluoro-benzyl)-8-hydroxy-1H-1,3,6-triaza-s-indacene-5,7-dione 258 (94%, 103 mg, 0.188 mmol) as an off white oil. $^1$H NMR (300 MHz) CDCl$_3$ δ 8.28 (bs, 1 H), 7.94 (s, 1 H), 7.89 (s, 1 H), 7.64-7.43 (m, 4 H), 7.17-7.43 (m, 12 H), 6.98-7.04 (s, 2 H), 5.57 (s, 2 H), 4.77 (s, 2 H). MS: 584.1 (M+1).

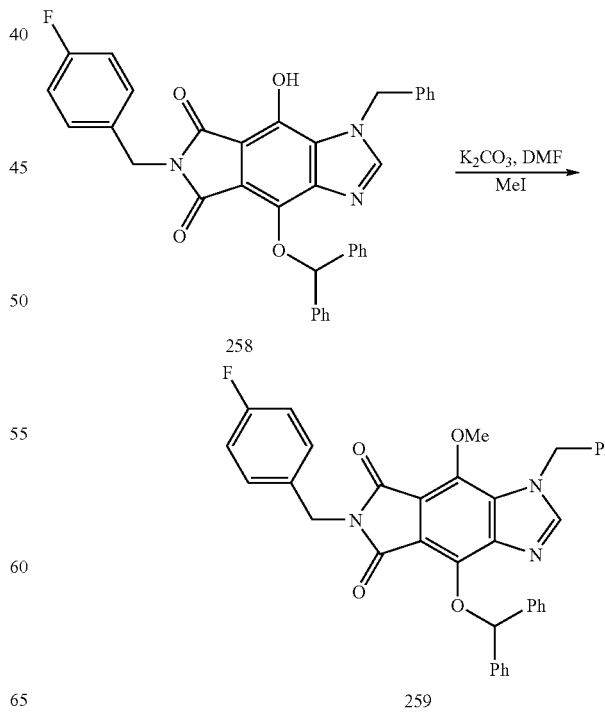

258

259

Example 259

Benzhydryloxy-1-benzyl-6-(4-fluoro-benzyl)-8-hydroxy-1H-1,3,6-triaza-s-indacene-5,7-dione 258 (103 mg, 0.177 mmol, 1 equiv.) was added to a flask containing DMF (4 mL) followed by K$_2$CO$_3$ (122 mg, 0.88 mmol, 5 equiv.). To this was added methyl iodide (MeI, 109 μL, 1.76 mmol, 10 equiv.) under a nitrogen atmosphere and stirred for 16 hours. To the reaction was added water (50 mL) and extracted with ethyl acetate (2×40 mL). The organic layer was washed several times with water (3×30 mL), saturated NaHCO$_3$ (40 mL), brine solution (30 mL). It was dried over Na$_2$SO$_4$, filtered and concentrated in vacuo and purified by silica gel chromatography using 7/3 Hexanes/Ethyl acetate to obtain 4-benzhydryloxy-1-benzyl-6-(4-fluoro-benzyl)-8-methoxy-1H-1,3,6-triaza-s-indacene-5,7-dione 259 (73%, 75 mg, 0.125 mmol). $^1$H NMR (300 MHz) CDCl$_3$ δ 8.09 (s, 1 H), 7.94 (s, 1 H), 7.88 (s, 1 H), 7.64-7.43 (m, 4 H), 7.41-7.46 (m, 2 H), 7.17-7.43 (m, 10 H), 6.98-7.04 (m, 3 H), 5.56 (s, 2 H), 4.80 (s, 2 H), 3.84 (s, 3 H). MS: 620.1 (M+23). TLC R$_f$: 0.6 Hexanes/Ethyl acetate (1/1).

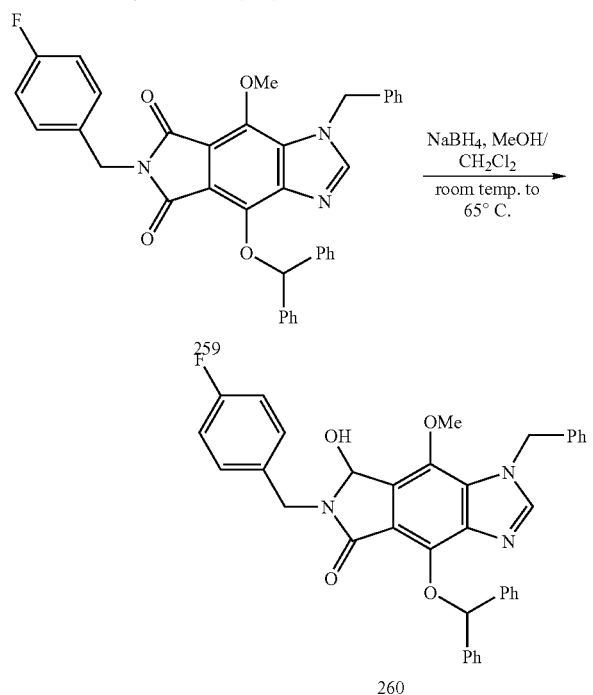

Example 260

4-Benzhydryloxy-1-benzyl-6-(4-fluoro-benzyl)-8-methoxy-1H-1,3,6-triaza-s-indacene-5,7-dione 259 (54 mg, 0.092 mmol, 1 equiv.) was dissolved in CH$_2$Cl$_2$ (2 mL) and MeOH (0.5 mL) and under a nitrogen atmosphere. Sodium borohydride (NaBH$_4$, 736 μL, 0.37 mmol, 4 equiv., 0.5 M) was added. The reaction was allowed to stir for 1 hour at room temperature and heated to 65° C. for 2 hours before being quenched with water (5 mL) and extracted with ethyl acetate (2×5 mL). The organic layer was washed several times with water (2×10 mL), brine solution (10 mL). It was dried over Na$_2$SO$_4$, filtered and concentrated in vacuo and purified by preparatory thin-layer chromatography (PTLC) using 3/2 Hexanes/Ethyl acetate to obtain 260 (51%, 28 mg, 0.047 mmol). $^1$H NMR (300 MHz) CDCl$_3$ δ 7.86 (d, J=7.2 Hz, 2 H), 7.59 (d, J=7.2 Hz, 2 H), 7.46-7.32 (m, 4 H), 7.32-7.21 (m, 4 H), 7.03-7.18 (m, 6 H), 6.91-7.01 (m, 2 H), 5.95 (bs, 1 H), 5.56 (s, 2 H), 5.62-5.52 (m, 1 H), 5.28 (d, J=15.9 Hz, 1 H), 5.14 (d, J=15.9 Hz, 1 H), 4.49 (d, J=15.9 Hz, 1 H), 3.37 (s, 3 H). MS: 622.0 (M+23). TLC R$_f$: 0.25 Hexanes/Ethyl acetate (3/2)

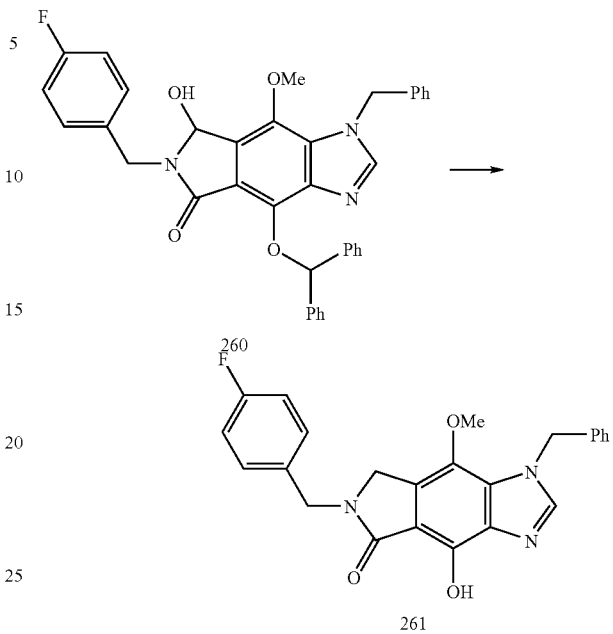

Example 261

4-Benzhydryloxy-1-benzyl-6-(4-fluoro-benzyl)-7-hydroxy-8-methoxy-6,7-dihydro-1H-1,3,6-triaza-s-indacen-5-one 260 (28 mg, 0.047 mmol, 1 equiv.) was added to CH$_2$Cl$_2$ (1 mL) under a nitrogen atmosphere. Triethylsilane (200 μL) was added, followed by trifluoroacetic acid (200 μL). The reaction was allowed 1 hour and concentrated in vacuo until thoroughly dried. Hexanes/Ethyl ether (15 mL, 1/1 ratio) was added to the oil and sonicated. The resulting solid was then filtered and washed in Hexanes and air dried to give 7-(4-fluoro-benzyl)-5-hydroxy-9-methoxy-7,8-dihydro-pyrrolo[3,4-g]quinoxalin-6-one 261 (100%, 20 mg, 0.047 mmol) as a light gray powder. $^1$H NMR (300 MHz) CDCl$_3$ δ 9.11 (bs 1 H), 7.86 (s, 1 H), 7.33-7.23 (m, 5 H), 7.01 7.07 (s, 4 H), 5.57 (s, 2 H), 4.71 (s, 2 H), 4.37 (s, 2 H), 3.57 (s, 3 H). $^{19}$F NMR (300 MHz) CDCl$_3$ δ 62.25. MS: 418.2 (M+1)

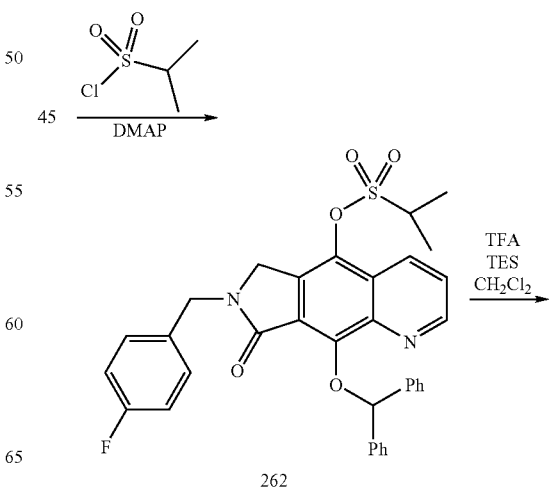

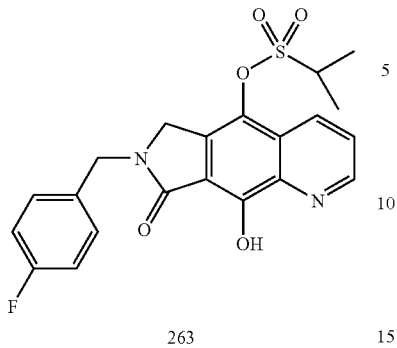

263

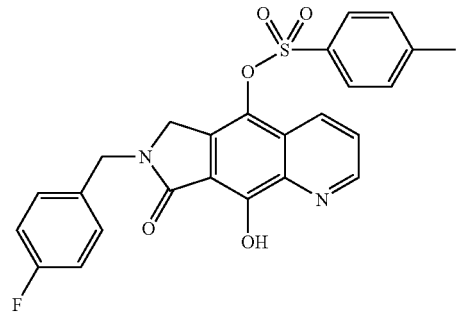

265

Example 262

To 0.051 mmol crude 45 was added triethylamine (100 μl), DMAP (catalytic amount) and isopropylsulfonyl chloride (18 μl, 0.154 mmol). The reaction mixture was stirred at room temperature for 24 hours under an inert atmosphere. The reaction was monitored by TLC (EtOAc/hexane 3/7) ($R_f$44=0.5, $R_f$45=0, $R_f$262=0.2) and LC/MS. After completion of the reaction, the mixture was diluted with EtOAc (20 mL) and washed with 1N HCl, saturated NaHCO$_3$ and brine. The organic phase was dried (MgSO$_4$), filtered and concentrated in vacuo. The residue was purified by silica gel chromatography (ethylacetate/hexane—3/7) to afford propane-2-sulfonic acid 9-benzhydryloxy-7-(4-fluoro-benzyl)-8-oxo-7,8-dihydro-6H-pyrrolo[3,4-g]quinolin-5-yl ester 262 (8.7 mg, 29%).

Example 263

To a solution of 262 (8.7 mg, 0.015 mmol) dissolved in dichloromethane (1 mL) was added trifluoroacetic acid (100 μl) and triethylsilane (200 μl). The reaction mixture was stirred at room temperature for 30 min under an inert atmosphere then concentrated in vacuo. The residue was triturated with diethyl ether/hexane (1/1) to afford the trifluoroacetate salt of propane-2-sulfonic acid 7-(4-fluoro-benzyl)-9-hydroxy-8-oxo-7,8-dihydro-6H-pyrrolo[3,4-g]quinolin-5-yl ester 263 (5.3 mg, 0.010 mmol, 68%) as a yellow solid: $^1$H NMR (CDCl$_3$) δ 9.0 (d, 1H), 8.4 (d, 1H), 7.6 (m, 1H), 7.3 (m, 2H), 7.0 (t, 2H), 4.8 (s, 2H), 4.6 (s, 2H), 3.7 (m, 1H), 1.7 (m, 6H); MS: 431 (M+1).

Example 264

Triethylamine (100 μl), DMAP (catalytic amount) and p-tosyl-chloride (30 mg, 0.154 mmol) were added to 0.051 mmol 45. The reaction mixture was stirred at room temperature for 24 hours under an inert atmosphere. The reaction was monitored by TLC (EtOAc/hexane 3/7) ($R_f$44=0.5, $R_f$45=0, $R_f$264=0.3) and LC/MS. After completion of the reaction, the mixture was diluted with EtOAc (20 mL) and washed with 1N HCl, saturated NaHCO$_3$ and brine. The organic phase was dried (MgSO$_4$), filtered and concentrated in vacuo. The residue was purified by silica gel chromatography (ethylacetate/hexane—3/7) to afford toluene-4-sulfonic acid 9-benzhydryloxy-7-(4-fluoro-benzyl)-8-oxo-7,8-dihydro-6H-pyrrolo[3,4-g]quinolin-5-yl ester 264 (15.3 mg, 47%).

Example 265

To a solution of 264 (15.3 mg, 0.015 mmol) dissolved in dichloromethane (1 mL) was added trifluoroacetic acid (100 μl) and triethylsilane (200 μl). The reaction mixture was stirred at room temperature for ½ hours under an inert atmosphere then concentrated in vacuo. The residue was triturated with diethyl ether/hexane (1/1) to afford the trifluoroacetate salt of toluene-4-sulfonic acid 7-(4-fluoro-benzyl)-9-hydroxy-8-oxo-7,8-dihydro-6H-pyrrolo[3,4-g]quinolin-5-yl ester 265 (11.6 mg, 0.020 mmol, 83%) as a yellow solid: $^1$H NMR (CDCl$_3$) δ 8.9 (d, 1H), 8.0 (d, 1H), 7.8 (m, 1H), 7.3 (m, 6H), 7.0 (t, 2H), 5.3 (s, 1H, OH), 4.7 (s, 2H), 4.4 (s, 2H), 2.4 (s, 3H); MS: 479 (M+1).

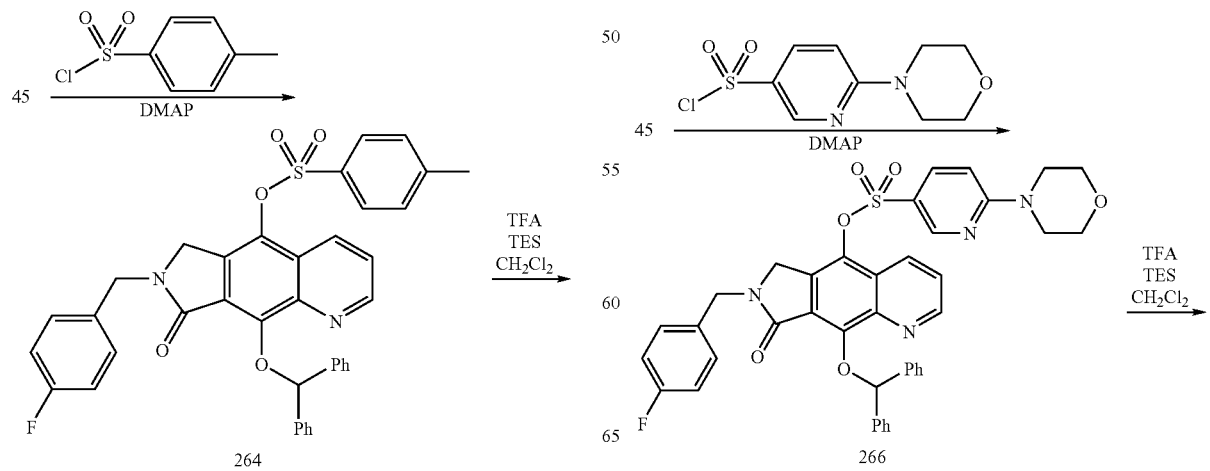

-continued

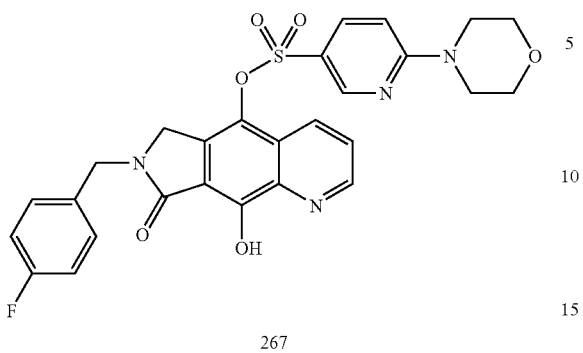

267

Example 266

Triethylamine (50 μl), DMAP (catalytic amount) and 6-Morpholin-4-yl-pyridine-3-sulfonyl chloride (26.3 mg, 0.10 mmol) were added to 0.034 mmol 45. The reaction mixture was stirred at room temperature for 18 hours under an inert atmosphere. The reaction was monitored by TLC (EtOAc/hexane 3/7) ($R_f$ 44=0.5, $R_f$ 45=0, $R_f$ 266=0.3) and LC/MS. After completion of the reaction, the mixture was diluted with EtOAc (20 mL) and washed with 1N HCl, saturated NaHCO$_3$ and brine. The organic phase was dried (MgSO$_4$), filtered and concentrated in vacuo. The residue was purified by silica gel chromatography (ethylacetate/hexane—3/7) to afford 6-morpholin-4-yl-pyridine-3-sulfonic acid 9-benzhydryloxy-7-(4-fluoro-benzyl)-8-oxo-7,8-dihydro-6H-pyrrolo[3,4-g]quinolin-5-yl ester 266 (14.6 mg, 59%).

Example 267

To a solution of 266 (14.6 mg, 0.020 mmol) dissolved in dichloromethane (1 mL) was added trifluoroacetic acid (100 μl) and triethylsilane (200 μl). The reaction mixture was stirred at room temperature for ½ hours under an inert atmosphere then concentrated in vacuo. The residue was triturated with diethyl ether/hexane (1/1) to afford the TFA salt of 6-morpholin-4-yl-pyridine-3-sulfonic acid 7-(4-fluoro-benzyl)-9-hydroxy-8-oxo-7,8-dihydro-6H-pyrrolo[3,4-g]quinolin-5-yl ester 267 (9.0 mg, 68%) as a yellow solid: $^1$H NMR (CDCl$_3$) δ 8.9 (d, 1H), 8.6 (s, 1H), 8.0 (dd, 1H), 7.7 (dd, 1H), 7.5 (m, 1H), 7.3 (m, 2H), 7.0 (t, 2H), 6.5 (d, 2H), 4.8 (s, 2H), 4.6 (s, 2H), 3.7 (d, 4H), 3.6 (d, 4H); MS: 551 (M+1).

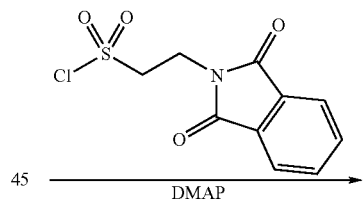

-continued

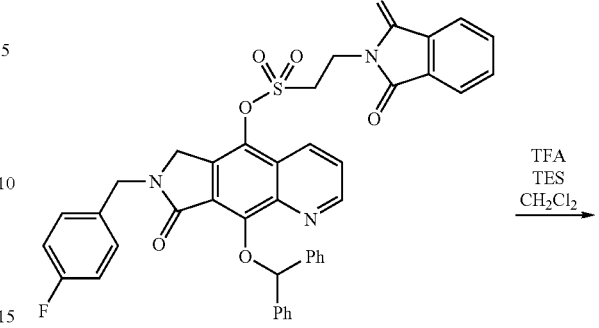

268

TFA
TES
CH$_2$Cl$_2$

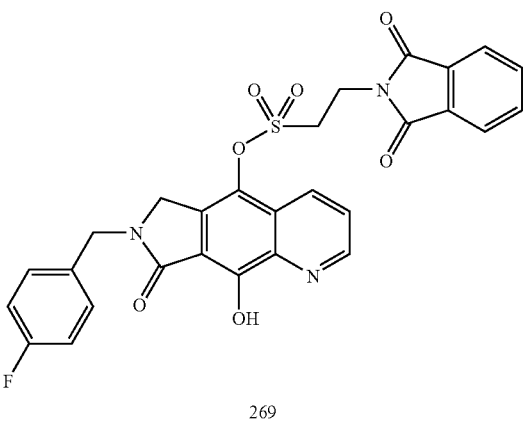

269

Example 268

Triethylamine (50 μl), DMAP (catalytic amount) and 2-(1,3-dioxo-1,3-dihydro-isoindol-2-yl)-ethanesulfonyl chloride (27.4 mg, 0.10 mmol) were added to 0.034 mmol 45. The reaction mixture was stirred at room temperature for 18 hours under an inert atmosphere. The reaction was monitored by TLC (EtOAc/hexane 3/7) ($R_f$ 44=0.5, $R_f$ 45=0, $R_f$ 268=0.4) and LC/MS. After completion of the reaction, the mixture was diluted with EtOAc (20 mL) and washed with 1N HCl, saturated NaHCO$_3$ and brine. The organic phase was dried (MgSO$_4$), filtered and concentrated in vacuo. The residue was purified by silica gel chromatography (ethylacetate/hexane—3/7) to afford 2-(1,3-dioxo-1,3-dihydro-isoindol-2-yl)-ethanesulfonic acid 9-benzhydryloxy-7-(4-fluoro-benzyl)-8-oxo-7,8-dihydro-6H-pyrrolo[3,4-g]quinolin-5-yl ester 268 (12.2 mg, 50%).

Example 269

To a solution of 268 (12.2 mg, 0.017 mmol) dissolved in dichloromethane (1 mL) was added trifluoroacetic acid (100 μl) and triethylsilane (200 μl). The reaction mixture was stirred at room temperature for ½ hours under an inert atmosphere then concentrated in vacuo. The residue was triturated with diethyl ether/hexane (1/1) to afford 2-(1,3-dioxo-1,3-dihydro-isoindol-2-yl)-ethanesulfonic acid 7-(4-fluoro-benzyl)-9-hydroxy-8-oxo-7,8-dihydro-6H-pyrrolo[3,4-g]quinolin-5-yl ester 269, TFA salt, (9.0 mg, 76%) as a yellow solid: $^1$H NMR (CDCl$_3$) δ 9.0 (d, 1H), 8.5 (dd, 1H), 7.9 (m, 2H), 7.8 (m, 2H), 7.7 (m, 1H), 7.3 (m, 2H), 7.0 (t, 2H), 4.8 (s, 2H), 4.6 (s, 2H), 4.4 (q, 2H), 3.9 (q, 2H); MS: 562 (M+1).

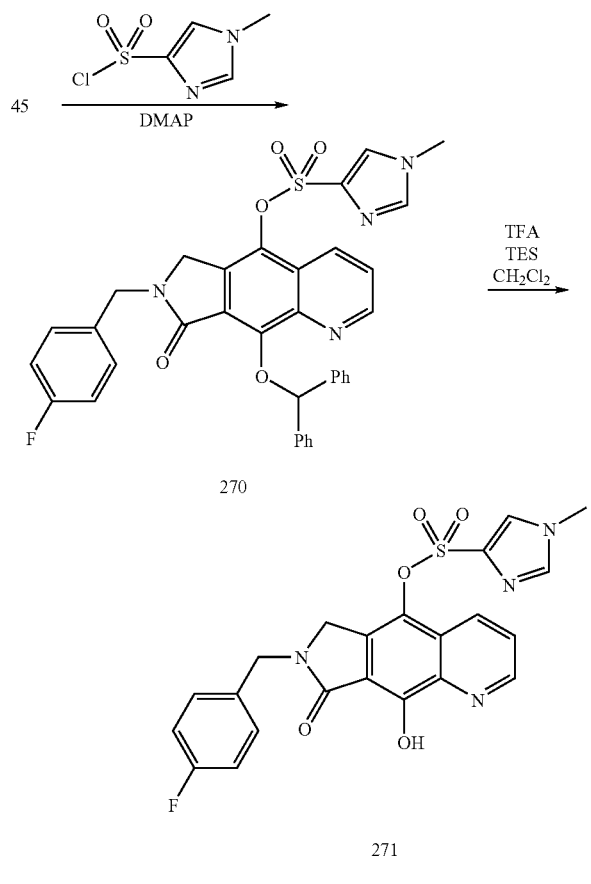

270

271

Example 270

Triethylamine (50 μl), DMAP (catalytic amount) and 1-methyl-1H-imidazole-4-sulfonyl chloride (18.1 mg, 0.10 mmol) were added to 0.034 mmol crude 45. The reaction mixture was stirred at room temperature for 18 hours under an inert atmosphere. The reaction was monitored by TLC (EtOAc/hexane 3/7) ($R_f$ 44=0.5, $R_f$ 45=0, $R_f$ 270=0.05) and LC/MS. After completion of the reaction, the mixture was diluted with EtOAc (20 mL) and washed with 1N HCl, saturated NaHCO$_3$ and brine. The organic phase was dried (MgSO$_4$), filtered and concentrated in vacuo to give the crude mixture of 1-methyl-1H-imidazole-4-sulfonic acid 9-benzhydryloxy-7-(4-fluoro-benzyl)-8-oxo-7,8-dihydro-6H-pyrrolo[3,4-g]quinolin-5-yl ester 270.

Example 271

To a solution of crude 270 dissolved in dichloromethane (1 mL) was added trifluoroacetic acid (100 μl) and triethylsilane (200 μl). The reaction mixture was stirred at room temperature for ½ hours under an inert atmosphere then concentrated in vacuo. The residue was purified by HPLC to afford 1-methyl-1H-imidazole-4-sulfonic acid 7-(4-fluoro-benzyl)-9-hydroxy-8-oxo-7,8-dihydro-6H-pyrrolo[3,4-g]quinolin-5-yl ester 271, TFA salt, (2.5 mg) as a yellow solid: $^1$H NMR (CD$_3$OD) δ 8.9 (d, 1H), 8.4 (d, 1H), 7.85 (s, 1H), 7.78 (s, 1H), 7.6 (m, 1H), 7.4 (m, 2H), 7.1 (t, 2H), 4.8 (s, 2H), 4.5(s, 2H), 3.8 (s, 3H); MS: 469 (M+1). HPLC conditions: mobile phase A was 0.1% TFA in water, mobile phase b was 0.1% TFA in CH$_3$CN; gradient from 5% to 60% B in 20 min; flow rate was 20 mL/min; column was Phenomenex, luna 5μ, C18(2), 150 mm×21.1 mm.

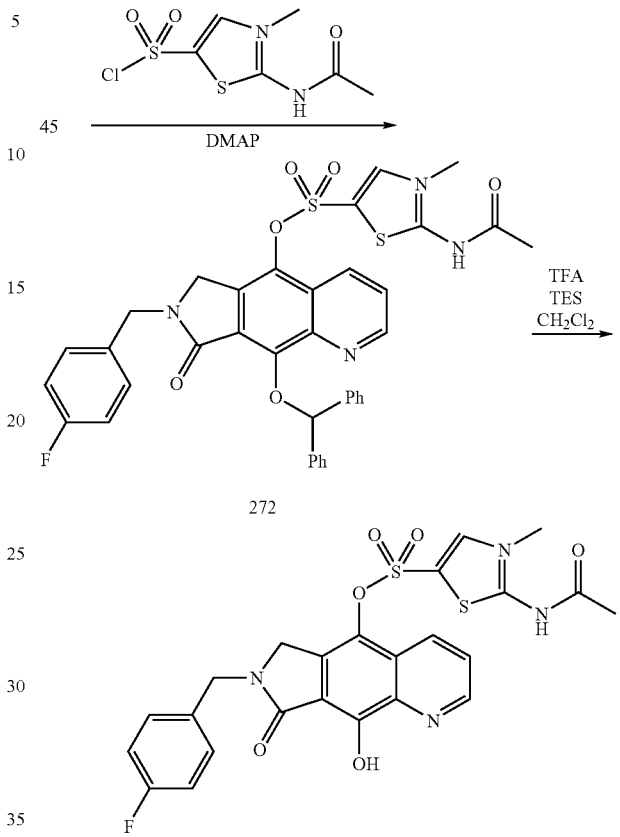

272

273

Example 272

Triethylamine (50 g), DMAP (catalytic amount) and 2-acetylamino-4-methyl-thiazole-5-sulfonyl chloride (25.5 mg, 0.10 mmol) were added to 0.034 mmol 45. The reaction mixture was stirred at room temperature for 18 hours under an inert atmosphere. The reaction was monitored by TLC (EtOAc/hexane 3/7) ($R_f$ 44=0.5, $R_f$ 45=0, $R_f$ 272=0.2) and LC/MS. After completion of the reaction, the mixture was diluted with EtOAc (20 mL) and washed with 1N HCl, saturated NaHCO$_3$ and brine. The organic phase was dried (MgSO$_4$), filtered and concentrated in vacuo. The residue was purified by silica gel chromatography (ethylacetate/hexane—3/7) to afford 2-acetylamino-4-methyl-thiazole-5-sulfonic acid 9-benzhydryloxy-7-(4-fluoro-benzyl)-8-oxo-7,8-dihydro-6H-pyrrolo[3,4-g]quinolin-5-yl ester 272 (18.9 mg, 79%).

Example 273

To a solution of 272 (18.9 mg, 0.027 mmol) dissolved in dichloromethane (1 mL) was added trifluoroacetic acid (100 μl) and triethylsilane (200 μl). The reaction mixture was stirred at room temperature for ½ hours under an inert atmosphere then concentrated in vacuo. The residue was triturated with diethyl ether/hexane (1/1) to afford 2-acetylamino-4-methyl-thiazole-5-sulfonic acid 7-(4-fluoro-benzyl)-9-hydroxy-8-oxo-7,8-dihydro-6H-pyrrolo[3,4-g]quinolin-5-yl ester 273, TFA salt, (13.2 mg, 74%) as a yellow solid: ¹H NMR (CD₃OD) δ 8.9 (d, 1H), 8.2 (d, 1H), 7.6 (m, 1H), 7.4 (m, 2H), 7.1 (t, 2H), 4.7 (s, 2H), 4.4 (s, 2H), 2.23 (s, 3H), 2.21 (s, 3H); MS: 543 (M+1).

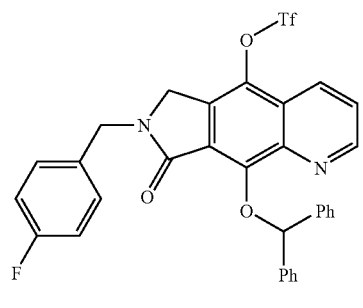

46

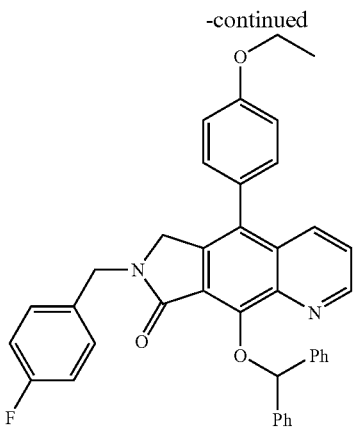

275

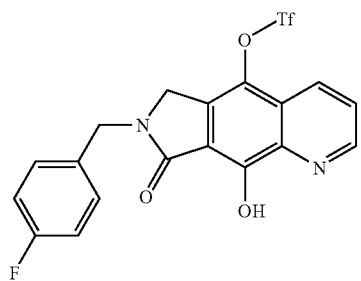

274

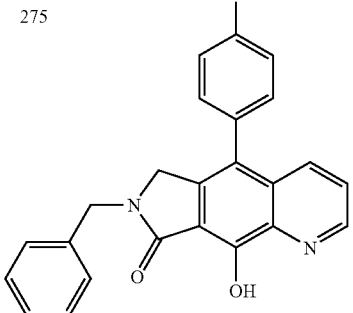

276

Example 274

To a solution of trifluoro-methanesulfonic acid 9-benzhydryloxy-7-(4-fluoro-benzyl)-8-oxo-7,8-dihydro-6H-pyrrolo[3,4-g]quinolin-5-yl ester 46 (28 mg, 0.045 mmol) dissolved in dichloromethane (2 mL) was added trifluoroacetic acid (100 µl) and triethylsilane (200 µl). The reaction mixture was stirred at room temperature for ½ hours under an inert atmosphere then concentrated in vacuo. The residue was triturated with diethyl ether/hexane (1/1) to afford trifluoro-methanesulfonic acid 7-(4-fluoro-benzyl)-9-hydroxy-8-oxo-7,8-dihydro-6H-pyrrolo[3,4-g]quinolin-5-yl ester 274, (13.7 mg, 0.03 mmol, 67%) as a yellow solid: ¹H NMR (CDCl₃) δ 9.0 (d, 1H), 8.4 (d, 1H), 7.7 (dd, 1H), 7.3 (dd, 2H), 7.1 (t, 2H), 4.8 (s, 2H), 4.6 (s, 2H); MS: 457 (M+1).

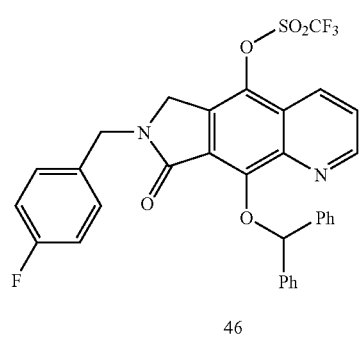

46

Example 275

To a solution of trifluoro-methanesulfonic acid 9-benzhydryloxy-7-(4-fluoro-benzyl)-8-oxo-7,8-dihydro-6H-pyrrolo[3,4-g]quinolin-5-yl ester 46 (40 mg, 0.064 mmol) dissolved in toluene (3 mL)/ethanol (0.6 mL)/water (0.4 mL) was added K₂CO₃ (27 mg, 0.192 mmol), 4-ethoxyphenolboronic acid (22 mg, 0.128 mmol) and tetrakis-(triphenylphosphine)-palladium(0) (15 mg, 0.013 mmol). The reaction mixture in the flask was flashed with argon three times. It was then heated to 120° C. under argon 3 hours. The reaction was monitored by TLC (EtOAc/hexane 3/7) (R_f 46=0.6, R_f 275=0.4) and LC/MS. After cooling to room temperature, the mixture was diluted with EtOAc (20 mL) and washed with 1N HCl, saturated NaHCO₃ and brine. The organic phase was dried (MgSO₄), filtered and concentrated in vacuo. The residue was purified by silica gel chromatography (ethylacetate/hexane—1/3) to afford 9-benzhydryloxy-5-(4-ethoxy-phenyl)-7-(4-fluoro-benzyl)-6,7-dihydro-pyrrolo[3,4-g]quinolin-8-one 275 (8.0 mg, 21%) as a solid: ¹H NMR (CDCl₃) δ 9.0 (d, 1H), 8.1 (s, 1H), 7.9 (d, 1H), 7.8-7.5 (dd, 4H), 7.5 (s, 1H), 7.4 (dd, 2H), 7.3-7.1 (m, 10H), 7.0 (t, 2H), 4.8 (s, 2H), 4.1 (m, 2H), 4.0 (s, 1H), 1.4 (t, 3H); MS: 595 (M+1).

Example 276

To a solution of 9-benzhydryloxy-5-(4-ethoxy-phenyl)-7-(4-fluoro-benzyl)-6,7-dihydro-pyrrolo[3,4-g]quinolin-8-one 275 (8 mg, 0.013 mmol) dissolved in dichloromethane (1 mL) was added trifluoroacetic acid (100 µl) and triethylsilane (200 µl). The reaction mixture was stirred at room temperature for ½ hours under an inert atmosphere then concentrated in vacuo. The residue was triturated with diethyl ether/hexane (1/1) to afford 5-(4-ethoxy-phenyl)-7-(4-fluoro-benzyl)-9-hydroxy-6,7-dihydro-pyrrolo[3,4-g]quinolin-8-one 276, TFA salt, (1.8 mg, 0.003 mmol, 25%) as a yellow solid: $^1$H NMR (CDCl$_3$) δ 9.0 (d, 1H), 8.1 (d, 1H), 7.7 (m, 2H), 7.6 (dd, 1H), 7.5 (dd, 2H), 7.2 (dd, 2H), 7.1 (t, 2H), 4.7 (s, 2H), 4.2(s, 2H), 4.1 (m, 2H), 1.5 (t, 3H); MS: 429 (M+1).

organic phase was dried (MgSO$_4$), filtered and concentrated in vacuo to afford crude 3-[9-benzhydryloxy-7-(4-fluoro-benzyl)-8-oxo-7,8-dihydro-6H-pyrrolo[3,4-g]quinolin-5-yl]-benzoic acid ethyl ester 277.

Example 278

To a solution of 277 dissolved in dichloromethane (2 mL) was added trifluoroacetic acid (200 µl) and triethylsilane (400 µl). The reaction mixture was stirred at room temperature for ½ hours under an inert atmosphere then concentrated in vacuo. The residue was redissolved in DMSO (1 mL) and purified by prep-HPLC to afford 3-[7-(4-fluoro-benzyl)-9-hydroxy-8-oxo-7,8-dihydro-6H-pyrrolo[3,4-g]quinolin-5-yl]-benzoic acid ethyl ester 278, TFA salt, (25 mg, 0.003 mmol, 44% in two steps) as a yellow solid: $^1$H NMR (CDCl$_3$) δ 9.0 (d, 1H), 8.2 (d, 1H), 8.0 (s, 1H), 7.7 (m, 1H), 7.6 (dd, 1H), 7.5 (dd, 2H), 7.0 (m, 2H), 7.1 (t, 2H), 4.7 (dd, 2H), 4.4(q, 2H), 4.3 (dd, 2H), 1.4 (t, 3H); MS: 457 (M+1). HPLC conditions: mobile phase A was 0.1% TFA in water, mobile phase b was 0.1% TFA in CH$_3$CN; gradient from 5% to 60% B in 20 min; flow rate was 20 mL/min; column was Phenomenex, luna 5µ, C18 (2), 150 mm×21.1 mm.

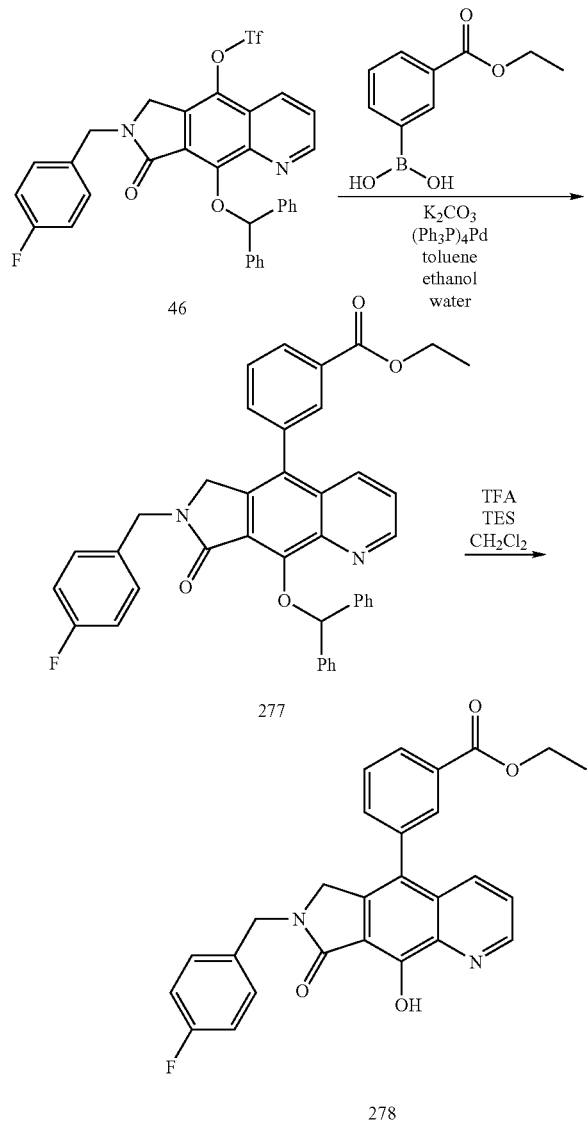

277

278

Example 277

To a solution of trifluoro-methanesulfonic acid 9-benzhydryloxy-7-(4-fluoro-benzyl)-8-oxo-7,8-dihydro-6H-pyrrolo[3,4-g]quinolin-5-yl ester 46 (43 mg, 0.07 mmol) dissolved in toluene (3 mL)/ethanol (0.6 mL)/water (0.4 mL) was added K$_2$CO$_3$ (29 mg, 0.21 mmol), (3-ethoxycarbonylphenyl)boronic acid (28 mg, 0.14 mmol) and tetrakis-(triphenylphosphine)-palladium(0) (16 mg, 0.014 mmol). The reaction mixture in the flask was flashed with argon three times. It was then heated to 120° C. under argon 3 hours. The reaction was monitored by TLC (EtOAc/hexane 3/7) (R$_f$ 46=0.6, R$_f$ 277=0.3) and LC/MS. After cooling to room temperature, the mixture was diluted with EtOAc (20 mL) and washed with 1N HCl, saturated NaHCO$_3$ and brine. The

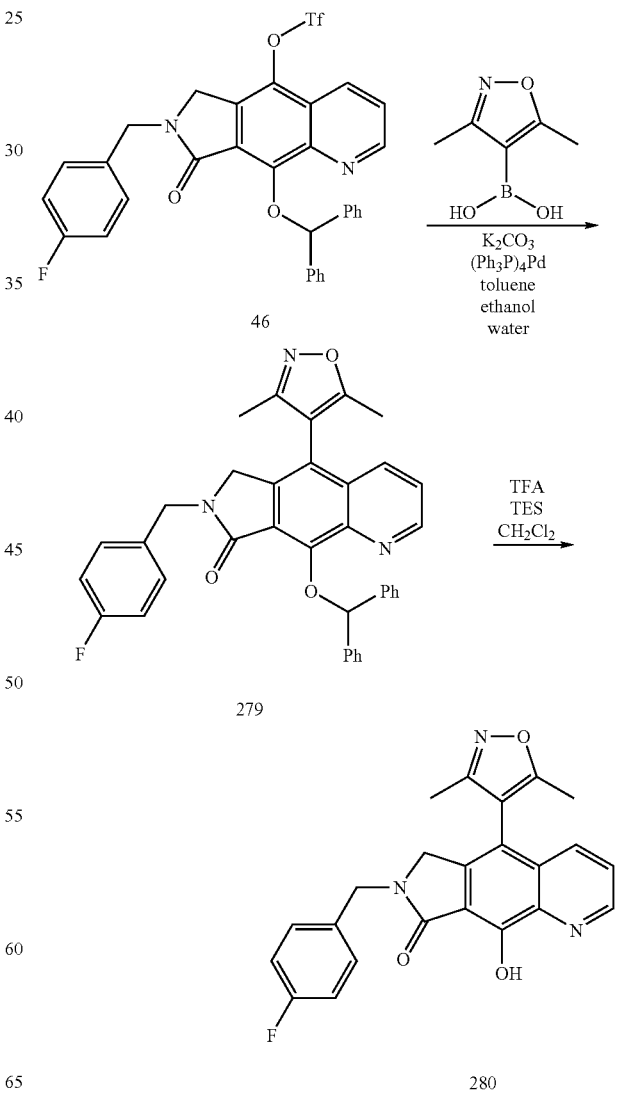

279

280

Example 279

To a solution of trifluoro-methanesulfonic acid 9-benzhydryloxy-7-(4-fluoro-benzyl)-8-oxo-7,8-dihydro-6H-pyrrolo[3,4-g]quinolin-5-yl ester 46 (23.6 mg, 0.038 mmol) dissolved in toluene (3 mL)/ethanol (0.6 mL)/water (0.4 mL) was added $K_2CO_3$ (16 mg, 0.11 mmol), 3,5-dimethylisoxazole-4-boronic acid (11 mg, 0.076 mmol) and tetrakis-(triphenylphosphine)-palladium(0) (9 mg, 0.007 mmol). The reaction mixture in the flask was flashed with argon three times. It was then heated to 120° C. under argon 3 hours. The reaction was monitored by LC/MS. After cooling to room temperature, the mixture was diluted with EtOAc (20 mL) and washed with 1N HCl, saturated $NaHCO_3$ and brine. The organic phase was dried ($MgSO_4$), filtered and concentrated in vacuo to afford crude 9-benzhydryloxy-5-(3,5-dimethyl-isoxazol-4-yl)-7-(4-fluoro-benzyl)-6,7-dihydro-pyrrolo[3,4-g]quinolin-8-one 279.

Example 280

To a solution of 279 dissolved in dichloromethane (1 mL) was added trifluoroacetic acid (100 µl) and triethylsilane (200 µl). The reaction mixture was stirred at room temperature for ½ hours under an inert atmosphere then concentrated in vacuo. The residue was dissolved in DMSO (1 mL) and purified by prep-HPLC to remove $Ph_3PO$. The crude mixture was diluted with EtOAC and extracted with 1N HCl. The aqueous phase containing product 280 was re-purified by HPLC to afford 5-(3,5-dimethyl-isoxazol4-yl)-7-(4-fluoro-benzyl)-9-hydroxy-6,7-dihydro-pyrrolo[3,4-g]quinolin-8-one 280, (0.4 mg) as a TFA salt solid: $^1$H NMR ($CD_3OD$) δ 9.0 (d, 1H), 8.1 (d, 1H), 8.0 (s, 1H), 7.7 (m, 1H), 7.4 (dd, 1H), 7.1 (t, 2H), 4.8 (s, 2H), 4.2(s, 2H), 2.0 (s, s, 2×3H); MS: 404 (M+1). HPLC conditions: mobile phase A was 0.1% TFA in water, mobile phase b was 0.1% TFA in $CH_3CN$; gradient from 5% to 60% B in 20 min; flow rate was 20 mL/min; column was Phenomenex, luna 5µ, C18 (2), 150 mm×21.1 mm.

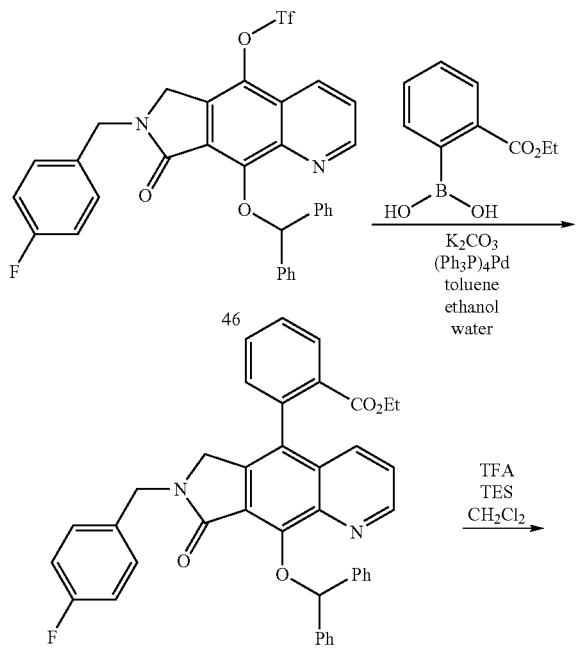

Example 281

To a solution of trifluoro-methanesulfonic acid 9-benzhydryloxy-7-(4-fluoro-benzyl)-8-oxo-7,8-dihydro-6H-pyrrolo[3,4-g]quinolin-5-yl ester 46 (33.5 mg, 0.05 mmol) dissolved in toluene (3 mL)/ethanol (0.6 mL)/water (0.4 mL) was added $K_2CO_3$ (22 mg, 0.15 mmol), (2-ethoxycarbonylphenyl)boronic acid (22 mg, 0.10 mmol) and tetrakis-(triphenylphosphine)-palladium(0)(12.5 mg, 0.01 mmol). The reaction mixture in the flask was flashed with argon three times. It was then heated to 120° C. under argon 3 hours. The reaction was monitored by TLC (EtOAc/hexane 3/7) ($R_f$ 46=0.6, $R_f$ 281=0.5) and LC/MS. After cooling to room temperature, the mixture was diluted with EtOAc (20 mL) and washed with 1N HCl, saturated $NaHCO_3$ and brine. The organic phase was dried ($MgSO_4$), filtered and concentrated in vacuo. The residue was purified by flash chromatography on silica gel with EtOAc/Hexane (3/7) to afford pure 2-[9-benzhydryloxy-7-(4-fluoro-benzyl)-8-oxo-7,8-dihydro-6H-pyrrolo[3,4-g]quinolin-5-yl]-benzoic acid ethyl ester 281, 9 mg, 26.8%.

Example 282

To a solution of 281 dissolved in dichloromethane (2 mL) was added trifluoroacetic acid (200 µl) and triethylsilane (400 µl). The reaction mixture was stirred at room temperature for ½ hours under an inert atmosphere then concentrated in vacuo. The residue was triturated with diethyl ether/hexane (1/1) to afford 2-[7-(4-fluoro-benzyl)-9-hydroxy-8-oxo-7,8-dihydro-6H-pyrrolo[3,4-g]quinolin-5-yl]-benzoic acid ethyl ester 282, TFA salt, (2.5 mg) as a yellow solid: $^1$H NMR ($CD_3OD$) δ 8.9 (d, 1H), 8.0 (d, 1H), 8.0 (s, 1H), 7.8-7.6 (m, 3H), 7.5 (dd, 1H), 7.3 (m, 2H+1H), 7.0 (t, 2H), 4.7 (dd, 2H), 4.1 (dd, 2H), 3.7 (m, 2H), 0.6 (t, 3H); MS: 457 (M+1).

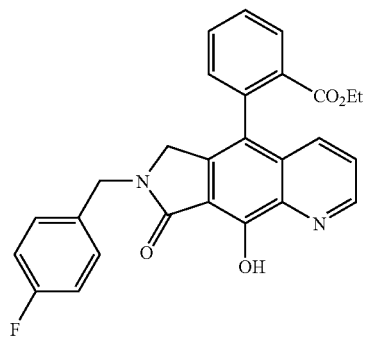

282

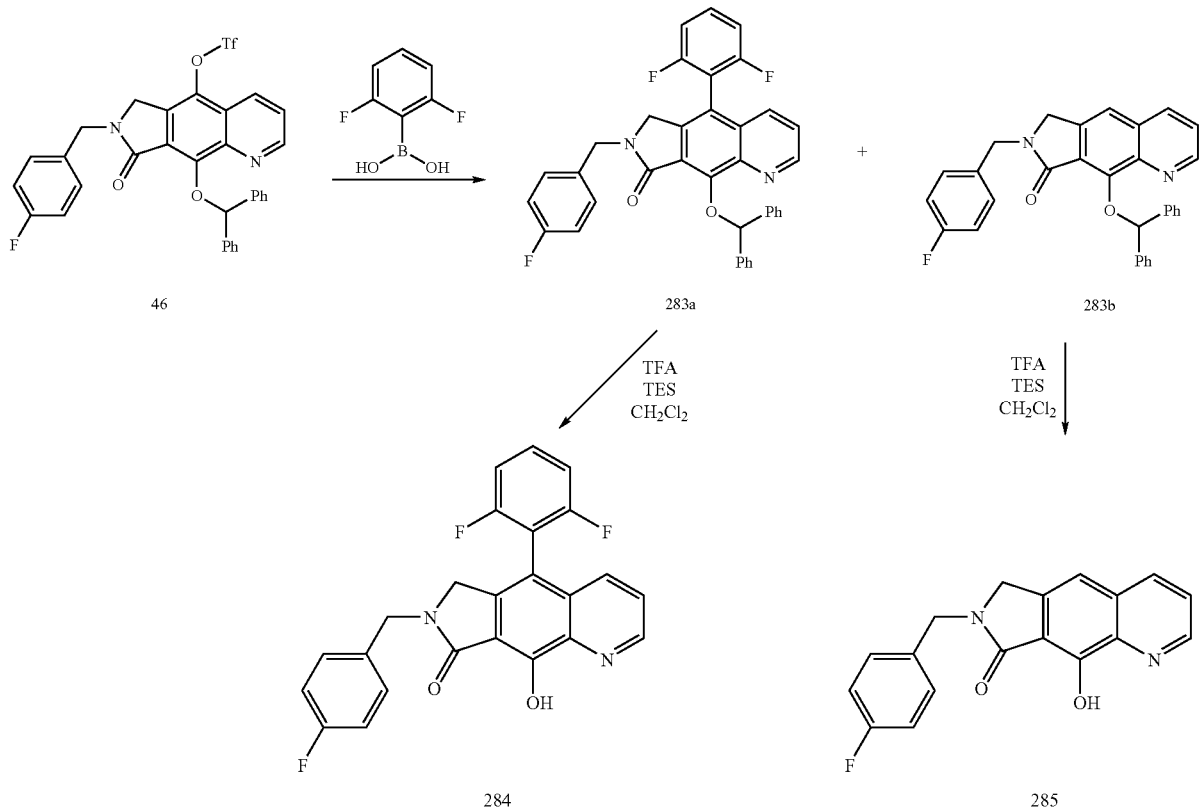

Example 283

To a solution of trifluoro-methanesulfonic acid 9-benzhydryloxy-7-(4-fluoro-benzyl)-8-oxo-7,8-dihydro-6H-pyrrolo[3,4-g]quinolin-5-yl ester 46 (40 mg, 0.064 mmol) dissolved in toluene (3 mL)/ethanol (0.6 mL)/water (0.4 mL) was added $K_2CO_3$ (29 mg, 0.16 mmol), (2,6-difluorophenyl)boronic acid (20 mg, 0.128 mmol) and tetrakis-(triphenylphosphine)-palladium(0) (15 mg, 0.01 mmol). The reaction mixture in the flask was flashed with argon three times. It was then heated to 120° C. under argon for 3 hours. The reaction was monitored by TLC (EtOAc/hexane 3/7) ($R_f$ 46=0.6, $R_f$ 283a=0.4, $R_f$ 283b=0.3) and LC/MS. After cooling to room temperature, the mixture was diluted with EtOAc (20 mL) and washed with 1N HCl, saturated $NaHCO_3$ and brine. The organic phase was dried ($MgSO_4$), filtered and concentrated in vacuo. The residue was purified by flash chromatography on silica gel with EtOAc:hexane (3/7) to separate pure 9-benzhydryloxy-5-(2,6-difluoro-phenyl)-7-(4-fluoro-benzyl)-6,7-dihydro-pyrrolo [3,4-g]quinolin-8-one 283a, 6 mg, 17%; and pure 9-benzhydryloxy-7-(4-fluoro-benzyl)-6,7-dihydro-pyrrolo[3,4-g]quinolin-8-one 283b, 11.0 mg, 36%.

Example 284

To a solution of 283a (9 mg) dissolved in dichloromethane (1 mL) was added trifluoroacetic acid (100 µl) and triethylsilane (200 µl). The reaction mixture was stirred at room temperature for ½ hours under an inert atmosphere then concentrated in vacuo. The residue was triturated with diethyl ether/hexane (1/1) to afford 5-(2,6-difluoro-phenyl)-7-(4-fluoro-benzyl)-9-hydroxy-6,7-dihydro-pyrrolo[3,4-g]quinolin-8-one 284, TFA salt, (3.2 mg) as a yellow solid: $^1$H NMR ($CDCl_3$) δ 9.0 (d, 1H), 8.0 (d, 1H), 7.6 (m, 1H), 7.5 (dd, 1H), 7.2 (m, 2H), 7.1 (m, 4H), 4.7 (s, 2H), 4.2(s, 2H); MS: 421 (M+1).

Example 285

To a solution of 283b (11 mg) dissolved in dichloromethane (1 mL) was added trifluoroacetic acid (100 µl) and triethylsilane (200 µl). The reaction mixture was stirred at room temperature for ½ hours under an inert atmosphere then concentrated in vacuo. The residue was triturated with diethyl ether/hexane (1/1) to afford 7-(4-fluoro-benzyl)-9-hydroxy-6,7-dihydro-pyrrolo[3,4-g]quinolin-8-one 285, TFA salt, (3.9 mg) as a yellow solid: $^1$H NMR ($CDCl_3$) δ 9.1 (d, 1H), 8.3 (d, 1H), 7.6 (m, 1H), 7.35 (s, 1H), 7.33 (m, 2H), 7.0 (t, 2H), 4.8 (s, 2H), 4.4(s, 2H); MS: 309 (M+1).

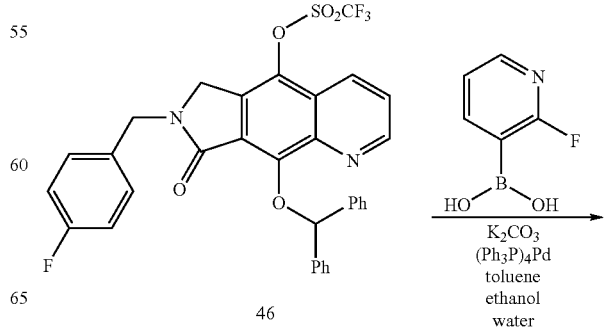

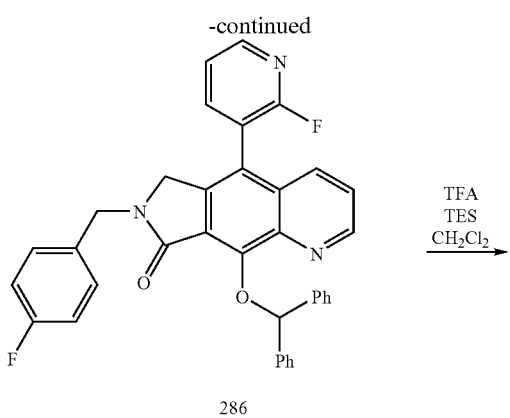

286

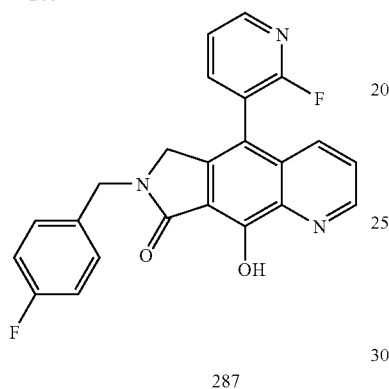

287

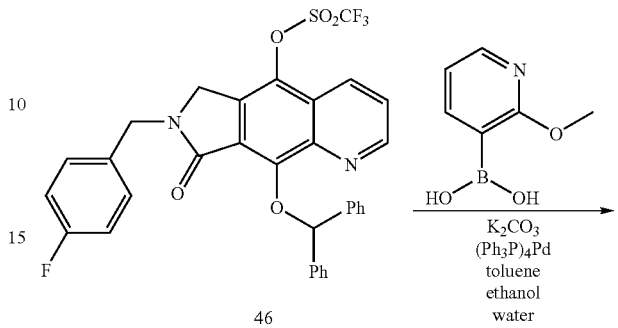

46

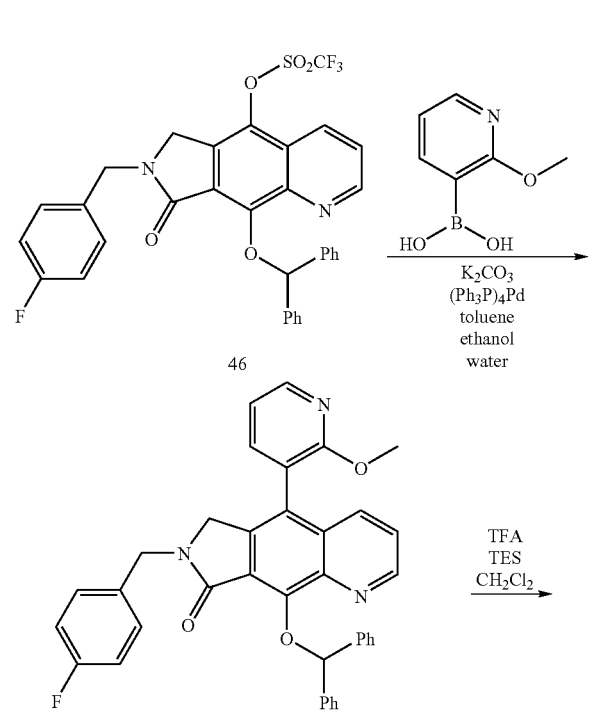

288

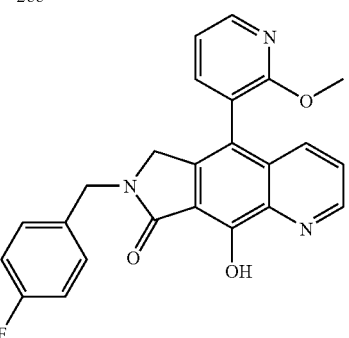

289

Example 286

To a solution of trifluoro-methanesulfonic acid 9-benzhydryloxy-7-(4-fluoro-benzyl)-8-oxo-7,8-dihydro-6H-pyrrolo[3,4-g]quinolin-5-yl ester 46 (40 mg, 0.064 mmol) dissolved in toluene (3 mL)/ethanol (0.6 mL)/water (0.4 mL) was added $K_2CO_3$ (29 mg, 0.16 mmol), 2-fluoropyridine-3-boronic acid (18 mg, 0.128 mmol) and tetrakis-(triphenylphosphine)-palladium(0)(15 mg, 0.01 mmol). The reaction mixture in the flask was flashed with argon three times. It was then heated to 120° C. under argon 3 hours. The reaction was monitored by TLC (EtOAc/hexane 3/7) ($R_f$ 46=0.6, $R_f$ 286=0.1) and LC/MS. After cooling to room temperature, the mixture was diluted with EtOAc (20 mL) and washed with 1N HCl, saturated $NaHCO_3$ and brine. The organic phase was dried ($MgSO_4$), filtered and concentrated in vacuo. The residue was purified by flash chromatography on silica gel with EtOAc/Hexane (1/1) to afford pure 9-benzhydryloxy-7-(4-fluoro-benzyl)-5-(2-fluoro-pyridin-3-yl)-6,7-dihydro-pyrrolo[3,4-g]quinolin-8-one (15), 10.6 mg, 29%.

Example 287

To a solution of 286 (10.6 mg) dissolved in dichloromethane (1 mL) was added trifluoroacetic acid (100 μl) and triethylsilane (200 μl). The reaction mixture was stirred at room temperature for ½ hours under an inert atmosphere then concentrated in vacuo. The residue was purified by HPLC to afford 7-(4-fluoro-benzyl)-5-(2-fluoro-pyridin-3-yl)-9-hydroxy-6,7-dihydro-pyrrolo[3,4-g]quinolin-8-one 287, TFA salt, (3.2 mg) as a yellow solid: $^1$H NMR (CDCl$_3$) δ 9.0 (d, 1H), 8.4 (d, 1H), 7.9 (d, 1H), 7.8 (dd, 1H), 7.5 (m, 1H), 7.4 (m, 1H), 7.3 (m, 2H), 7.0 (t, 2H), 4.7 (dd, 2H), 4.2(dd, 2H); MS: 404 (M+1). HPLC conditions: mobile phase A was 0.1% TFA in water, mobile phase b was 0.1% TFA in CH$_3$CN; gradient from 5% to 60% B in 20 min; flow rate was 20 mL/min; column was Phenomenex, luna 5μ, C18(2), 150 mm×21.1 mm.

Example 288

To a solution of trifluoro-methanesulfonic acid 9-benzhydryloxy-7-(4-fluoro-benzyl)-8-oxo-7,8-dihydro-6H-pyrrolo[3,4-g]quinolin-5-yl ester 46 (40 mg, 0.064 mmol) dissolved in toluene (3 μL)/ethanol (0.6 mL)/water (0.4 mL) was added $K_2CO_3$ (29 mg, 0.16 mmol), 2-methoxypyridine-3-boronic acid (20 mg, 0.128 mmol) and tetrakis-(triphenylphosphine)-palladium(0)(15 mg, 0.01 mmol). The reaction mixture in the flask was flashed with argon three times. It was then heated to 120° C. under argon 3 hours. The reaction was monitored by TLC (EtOAc/hexane 3/7) ($R_f$ 46=0.6, $R_f$ 288=0.1) and LC/MS. After cooling to room temperature, the mixture was diluted with EtOAc (20 mL) and washed with 1N HCl, saturated $NaHCO_3$ and brine. The organic phase was dried ($MgSO_4$), filtered and concentrated in vacuo. The residue was purified by flash chromatography on silica gel with EtOAc/Hexane (1/1) to afford pure 9-benzhydryloxy-7-(4-fluoro-benzyl)-5-(2-methoxy-pyridin-3-yl)-6,7-dihydro-pyrrolo[3,4-g]quinolin-8-one (17), 18.0 mg, 48%.

Alternatively, according to a modified Suzuki coupling method of C. H. Chen; Tetrahedron Letter; EN; 44; 5747-5750; 2003, to a solution of trifluoro-methanesulfonic acid 9-benzhydryloxy-7-(4-fluoro-benzyl)-8-oxo-7,8-dihydro-6H-pyrrolo[3,4-g]quinolin-5-yl ester 46 (266.2 mg, 0.428 mmol) dissolved in toluene (5 mL) was added $Na_2CO_3$ (2M in water, 500 µl), 2-methoxypyridine-3-boronic acid (164 mg, 1.07 mmol) and tetrakis-(triphenylphosphine)-palladium(0)(100 mg, 0.086 mmol). The reaction mixture in the flask was flashed with argon three times. It was then heated to 120° C. under argon 4 hours. The reaction was monitored by TLC (EtOAc/hexane 3/7) ($R_f1$=0.6, $R_f17$=0.1) and LC/MS. After cooling to room temperature, the mixture was diluted with EtOAc (20 mL) and washed with 1N HCl, saturated $NaHCO_3$ and brine. The organic phase was dried ($MgSO_4$), filtered and concentrated in vacuo. The residue was purified by flash chromatography on silica gel with EtOAc/Hexane (1/1) to afford pure 9-benzhydryloxy-7-(4-fluoro-benzyl)-5-(2-methoxy-pyridin-3-yl)-6,7-dihydro-pyrrolo[3,4-g]quinolin-8-one 288, 125 mg, 50%. $^1$H NMR ($CDCl_3$) δ 9.0 (dd, 1H), 8.3 (dd, 1H), 8.2 (s, 1H), 7.8 (dd, 4H), 7.7 (dd, 1H), 7.4 (dd, 1H), 7.3-7.1 (m, 8H), 7.0 (m, 2H+1H), 4.7 (dd, 2H), 4.1(dd, 2H), 3.8 (s, 1H); MS: 582 (M+1).

Example 289

To a solution of 288 (18 mg) dissolved in dichloromethane (1 mL) was added trifluoroacetic acid (100 µl) and triethylsilane (200 µl). The reaction mixture was stirred at room temperature for ½ hours under an inert atmosphere then concentrated in vacuo. The residue was purified by HPLC to afford 7-(4-fluoro-benzyl)-5-(2-methoxy-pyridin-3-yl)-9-hydroxy-6,7-dihydro-pyrrolo[3,4-g]quinolin-8-one 289, TFA salt, (11.6 mg, 68%) as a yellow solid: $^1$H NMR ($CDCl_3$) δ 9.0 (d, 1H), 8.3 (d, 1H), 7.9 (d, 1H), 7.5 (m, 2H), 7.2 (m, 1H+1H), 7.0 (m, 2H+1H), 4.7 (dd, 2H), 4.1(dd, 2H), 3.8 (s, 1H); MS: 416 (M+1). HPLC conditions: mobile phase A was 0.1% TFA in water, mobile phase b was 0.1% TFA in $CH_3CN$; gradient from 5% to 60% B in 20 min; flow rate was 20 mL/min; column was Phenomenex, luna 5µ, C18(2), 150 mm×21.1 mm.

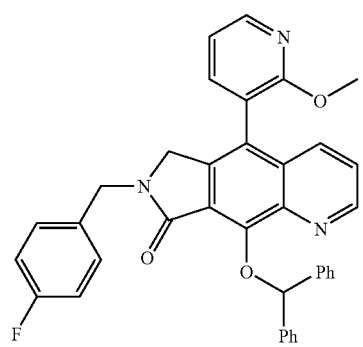

288

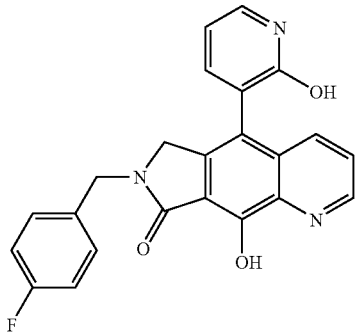

290

Example 290

To a solution of 9-benzhydryloxy-7-(4-fluoro-benzyl)-5-(2-methoxy-pyridin-3-yl)-6,7-dihydro-pyrrolo[3,4-g]quinolin-8-one 288 (99 mg, 0.17 mmol) dissolved in methanol (20 mL) was added p-toluenesulfonic acid monohydrate (390 mg, 2.05 mmol) and lithium iodide (1.37 g, 10.26 mmol). The reaction mixture was heated to 120° C. under nitrogen for 10 hours. The reaction was monitored by LC/MS. After cooling to room temperature, the solvent was removed under reduced pressure. The residue was dissolved in 2 mL DMSO and 100 µl of TFA. It was purified by HPLC to afford 7-(4-fluoro-benzyl)-9-hydroxy-5-(2-hydroxy-pyridin-3-yl)-6,7-dihydro-pyrrolo[3,4-g]quinolin-8-one 290, TFA salt, (44.4 mg, 51%) as a yellow solid: $^1$H NMR ($CD_3OD$) δ 8.9 (dd, 1H), 8.2(dd, 1H), 7.7 (m, 1H+1H), 7.6 (d, 2H), 7.4 (m, 2H), 7.1 (m, 2H), 6.6 (t, 1H), 4.8 (dd, 2H), 4.3(d, 2H); MS: 402 (M+1). HPLC conditions: mobile phase A was 0.1% TFA in water, mobile phase b was 0.1% TFA in $CH_3CN$; gradient from 5% to 60% B in 20 min; flow rate was 20 mL/min; column was Phenomenex, luna 5µ, C18(2), 150 mm×21.1 mm.

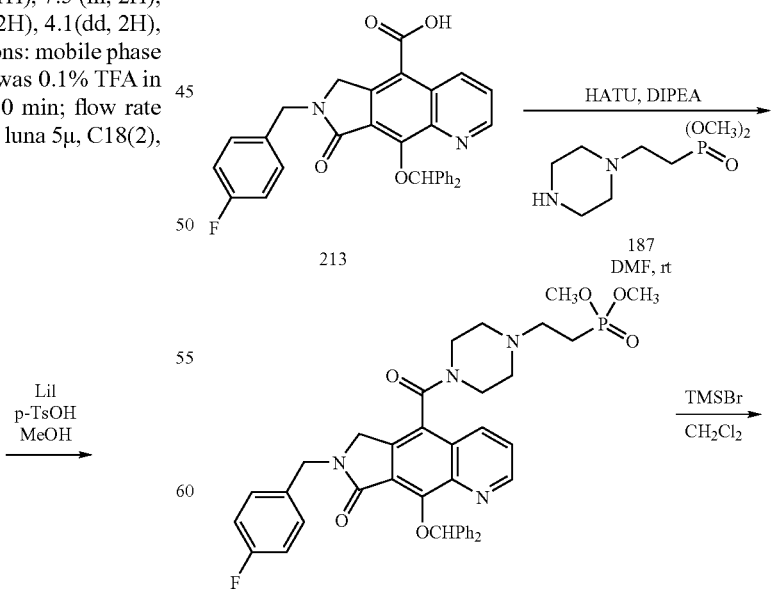

-continued

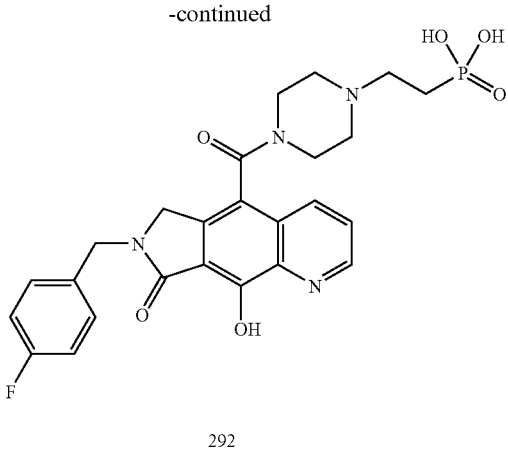

292

Example 291

To a solution of the trifluoroacetate salt of (2-piperazin-1-yl-ethyl)-phosphonic acid dimethyl ester 187 (0.023 g, 0.077 mmol) in 1 ml DMF was added diisopropylethylamine (33 µL, 0.192 mmol). This mixture was added to a solution of 9-benzhydryloxy-7-(4-fluoro-benzyl)-8-oxo-7,8-dihydro-6H-pyrrolo[3,4-g]quinoline-5-carboxylic acid 213 (0.020 g, 0.038 mmol) that had been mixed with HATU (0.0293 g, 0.077 mmol) in 1 ml of DMF. The reaction was stirred at rt under inert atmosphere for 3 h, at which time TLC in 100% EtOAc showed complete consumption of starting material. The reaction mixture was introduced directly onto silica gel (99/1 EtOH/Et₃N) to give 20 mg of (2-{4-[9-benzhydryloxy-7-(4-fluoro-benzyl)-8-oxo-7,8-dihydro-6H-pyrrolo[3,4-g]quinoline-5-carbonyl]-piperazin-1-yl}-ethyl)-phosphonic acid dimethyl ester 291 after flash chromatography.

Example 292

An excess of trimethylsilyl bromide (TMSBr, 0.015 g, 0.1 mmol) was added to (2-{4-[9-benzhydryloxy-7-(4-fluoro-benzyl)-8-oxo-7,8-dihydro-6H-pyrrolo[3,4-g]quinoline-5-carbonyl]-piperazin-1-yl}-ethyl)-phosphonic acid dimethyl ester 291 in 1 mL of CH₂Cl₂. After stirring at room temperature (rt) for 16 h, volatiles were removed under vacuum and the residue was triturated with Et₂O to provide pure the HBr salt of (2-{4-[7-(4-Fluoro-benzyl)-9-hydroxy-8-oxo-7,8-dihydro-6H-pyrrolo[3,4-g]quinoline-5-carbonyl]-piperazin 1-yl}-ethyl)-phosphonic acid 292 (12 mg, 95%) as a yellow solid. $^1$H NMR (DMSO) δ: 8.95 (d, 1H), 8.75 (d, 1H), 8.54 (1H, d), 8.35 (bm, 1H), 7.78 (m, 2H), 7.52 (m, 2H), 7.4-7.32 (bm, 2H), 7.15 (t, 2H), 4.85 (bm, 1H) 4.45 (bm, 2H) 2.04 (bm, 2H); $^{31}$P NMR (DMSO) δ 19.9; MS: 529 (M+H).

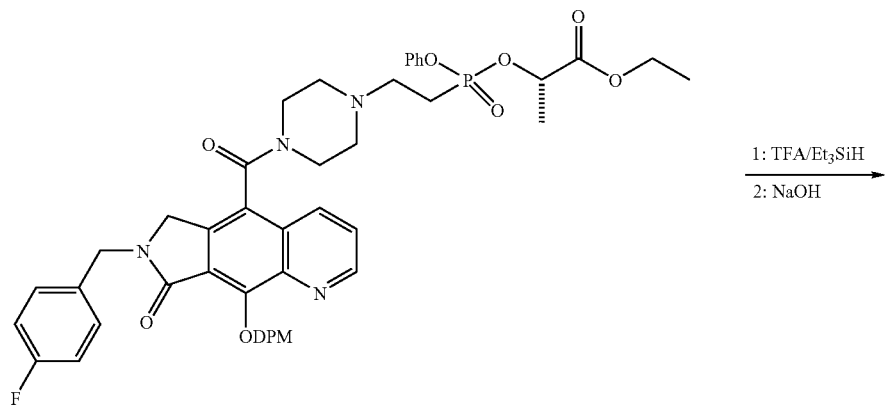

223

1: TFA/Et₃SiH
2: NaOH

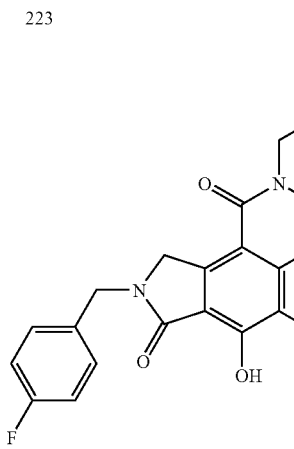

293

Example 293

To a solution of 2-[(2-{4-[9-benzhydryloxy-7-(4-fluoro-benzyl)-8-oxo-7,8-dihydro-6H-pyrrolo[3,4-g]quinoline-5-carbonyl]-piperazin-1-yl}-ethyl)-phenoxy-phosphinoyloxy]-propionic acid ethyl ester 223 (15 mg, 0.017 mmol) in 1ml $CH_2Cl_2$ at rt was added an excess of TFA (10 μL, 0.085 mmol) and triethylsilane (30 μL, 0.17 mmol). The reaction was stirred under $N_2$ with monitoring via LC/MS. After 8 h, the volatiles were removed by vacuum and the residue dissolved in 1 mL of a 1/1 mixture of acetonitrile/water. 50 μL of 1M NaOH was added and the reaction was stirred at rt overnight. At this time, the product was introduced directly onto reverse phase HPLC to afford, after lyophilization, 2-[(2-{4-[7-(4-fluoro-benzyl)-9-hydroxy-8-oxo-7,8-dihydro-6H-pyrrolo [3,4-g]quinoline-5-carbonyl]-piperazin-1-yl}-ethyl)-hydroxy-phosphinoyloxy]-propionic acid as the trifluoroacetate salt, 293 (5 mg, 39%). $^1$H NMR ($D_2O$) δ: 9.10 (d, 1H), 8.95-8.72 (bm, 1H), 8.14 (bs, 1H), 7.20-7.3 (bm, 2H), 6.92-7.08 (bs, 2H), 4.65-4.25 (m, 4H), 3.78-3.65 (bs, 1H), 3.62-3.10 (bm, 9H), 2.75 (d, 2H), 1.95 (m, 2H), 1.35 (d, 3H); $^{31}$P NMR ($D_2O$) δ 19.5; MS: 629 (M+H).

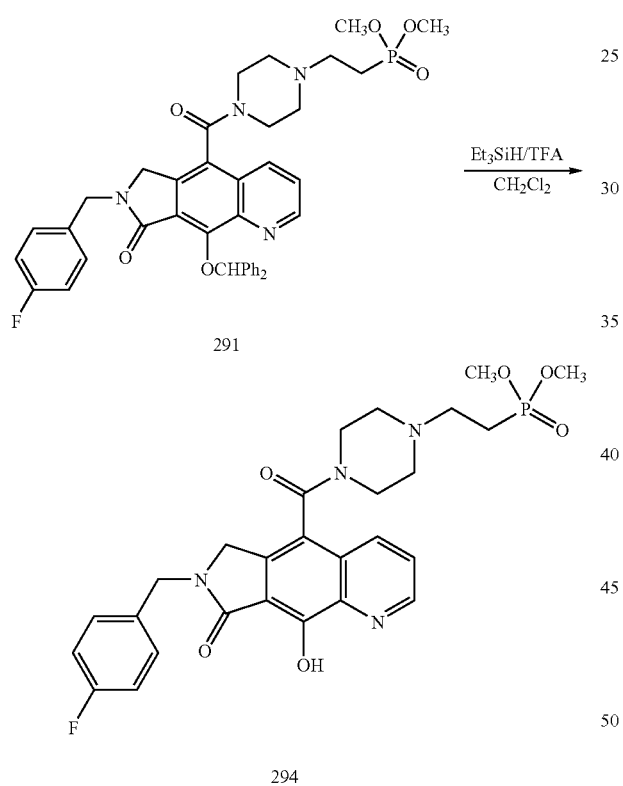

Example 294

To (2-{4-[9-benzhydryloxy-7-(4-fluoro-benzyl)-8-oxo-7,8-dihydro-6H-pyrrolo[3,4-g]quinoline-5-carbonyl]-piperazin-1-yl}-ethyl)-phosphonic acid dimethyl ester 291 (5 mg, 0.0069 mmol) in 1 mL $CH_2Cl_2$ is added $CF_3CO_2H$ (6 μL, 0.035 mmol) and triethylsilane (12 μL, 0.07 mmol). After 2 h, the volatile reaction components were removed by vacuum and the residue was washed with diethyl ether to give (2-{4-[7-(4-fluoro-benzyl)-9-hydroxy-8-oxo-7,8-dihydro-6H-pyrrolo[3,4-g]quinoline-5-carbonyl]-piperazin-1-yl}-ethyl)-phosphonic acid 294 as the trifluoroacetate salt (4.5 mg, 97%): $^1$H NMR ($CD_3OD$) δ: 8.90 (d, 0.7H) 8.74 (d, 0.3H), 8.45 (d, 0.3H), 8.31 (d, 0.7H), 7.75 (dd, 0.7H), 7.55 (dd, 0.3H), 7.40 (m, 2H), 7.12 (m, 2H), 4.54 (s, 2H), 4.15 (bs, 1H), 3.85 (s, 3H), 3.75 (s, 3H), 3.62-3.40 (bs, 2H), 3.12 (bs, 2H), 2.45-2.30(m, 2H); $^{19}$F NMR ($CD_3OD$) δ $^-$78, $^-$127; $^{31}$P NMR ($CD_3OD$) δ 29; MS: 556 (M+H).

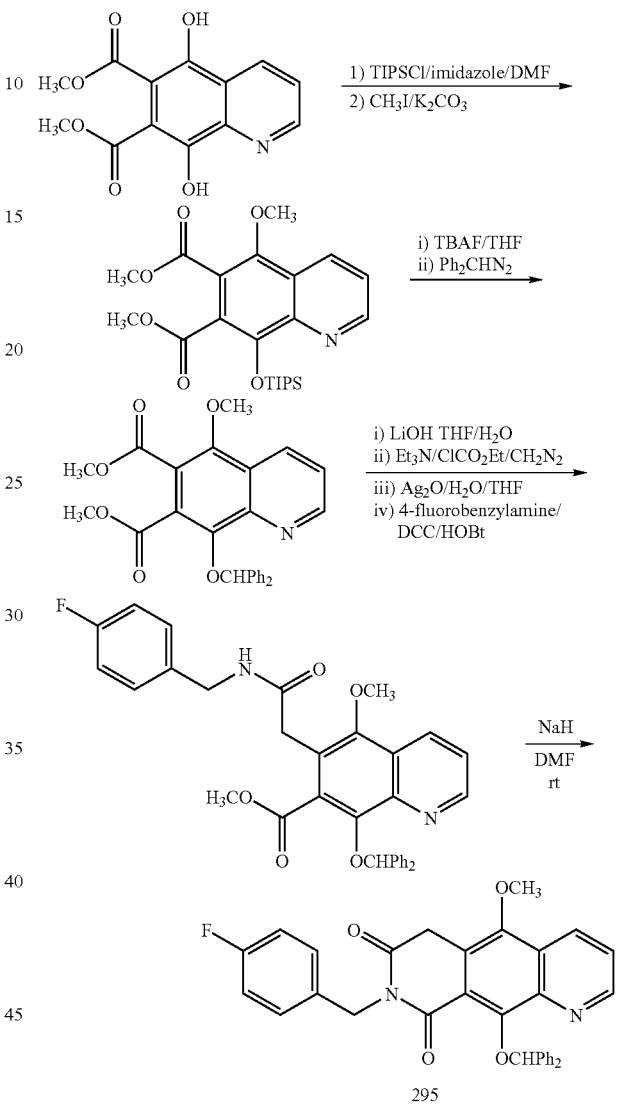

Example 295

Imidazole (0.74 g, 10.8 mmol) and chlorotriisopropylsilane (TIPSCl, 1.15 g, 6.0 mmol) were added to 5,8-dihydroxy-quinoline-6,7-dicarboxylic acid dimethyl ester (prepared by the method in Oguchi, S. *Bulletin of the Chemical Society of Japan* 1974, 47, 1291, 1.5 g, 5.4 mmol) in 20 mL DMF. The reaction was stirred for 48 h at rt and then the reaction was partitioned between 0.5 L methyl t-butyl ether and 150 mL saturated aq. LiCl. The organic layer was dried over $Na_2SO_4$ and the solvent removed by rotary evaporation. The residue (1.4 g, 3.2 mmol) was redissolved in 25 mL DMF and treated with $K_2CO_3$ (0.66 g, 4.8 mmol) followed by methyl iodide (MeI, 0.6 g, 4.8 μL) at rt. After 2 h, the reaction mixture was concentrated and purified by introduction of the reaction mixture onto silica gel for flash chromatography (4/1 hexanes/ethyl acetate) to give 5-methoxy- 8-triisopropylsilanyloxy-quinoline-6,7-dicarboxylic acid dimethyl ester (1.4 g, 59% overall yield): $^1$H NMR (CDCl$_3$) δ 8.85 (d, 1H), 8.45 (d, 1H), 7.50 (dd, 1H), 4.05 (s, 3H), 3.95 (s, 3H), 3.90 (s, 3H), 1.45 (septet, 3H), 1.05 (d, 9H); MS: 448 (M+H).

A 1M solution of TBAF in THF (4 ml) was added to 5-methoxy-8-triisopropylsilanyloxy-quinoline-6,7-dicarboxylic acid dimethyl ester (0.85 g, 1.9 mmol) in 20 ml dry THF. The reaction was stirred at rt for 1 h, at which time the reaction mixture was concentrated and the residue dissolved in 100 mL diethyl ether and washed with 25 mL 1N HCl, followed by 25 mL of saturated aq. NaCl. The organic layer was concentrated and the residue was dissolved in 40 mL dichloroethane. Diphenyldiazomethane (0.7 g, 3.8 mmol) was added and the reaction temperature was raised to 70° C. for 24 h. The reaction mixture was concentrated and the residue chromatographed on silica gel (1/1 hexanes/EtOAc) to give 8-benzhydryloxy-5-methoxy-quinoline-6,7-dicarboxylic acid dimethyl ester (0.8 g, 61% yield overall). $^1$H NMR (CDCl$_3$) δ 8.85 (d, 1H), 8.45 (d, 1H), 7.45 (dd, 1H), 3.98 (s, 3H), 3.85 (s, 3H), 3.74 (s, 3H); MS: 480 (M+Na).

Lithium hydroxide (LiOH, 0.07 g, 2.95 mmol) was added to 8-benzhydryloxy-5-methoxy-quinoline-6,7-dicarboxylic acid dimethyl ester (0.27 g, 0.59 mmol) in 1 mL 3/1 THF/H$_2$O. The reaction was heated at 45° C. and after 24 h, the reaction was diluted with 50 mL dichloromethane and acidified with 1 mL 0.1 M HCl. The organic layer was dried over Na$_2$SO$_4$ and concentrated to give 180 mg of an oil which was dissolved in 5 mL THF, triethylamine (0.168 g, 1.2 mmol) and ethyl chloroformate (0.064 g, 0.6 mmol). After 2 h, the reaction was diluted with diethyl ether and washed with brine. The organic layer was dried over Na$_2$SO$_4$ and the organic layer decanted from drying agent. The ether layer was cooled to 0° C. and a solution of ca. 0.3 M diazomethane in diethyl ether (4 mL, ca. 1.2 mmol) was added dropwise. After stirring for 24 h to effect diazotization, the ether layer was removed along with excess diazomethane via rotary evaporation. The resulting residue was dissolved in 4 mL of 1/1 THF/water, and silver(I) oxide (0.035 g, 0.15 mmol) was added. The reaction was heated to 60° C. for a period of 4 h, then the reaction mixture was diluted with 50 mL EtOAc and acidified with 10 ml 1N HCl. The organic layer was dried over Na$_2$SO$_4$ and concentrated. The resulting residue was then taken up in 2 mL THF, and treated with hydroxybenzotriazole (HOBt, 0.08 g, 0.6 mmol), dicyclohexylcarbodiimide (DCC, 0.12 g, 0.6 mmol) and 4-fluorobenzylamine (0.07 g, 0.6 mmol). After a period of 16h, the reaction was introduced directly to chromatography on silica gel (100% diethyl ether) to give 8-benzhydryloxy-6-[(4-fluoro-benzylcarbamoyl)-methyl]-5-methoxy-quinoline-7-carboxylic acid methyl ester (0.12 g, 38% overall yield): $^1$H NMR (CDCl$_3$) δ 8.85 (d, 1H), 8.35 (d, 1H), 7.60-6.8 (cm, 12H), 6.15 (s, 1H), 4.30 (m, 2H), 3.95 (s, 3H), 3.75 (s, 3H), 3.65 (s, 2H), 3.54 (t, 1H); MS: 587 (M+Na).

A 60% sodium hydride (NaH) mineral oil dispersion (0.002 g, 0.06 mmol was added to a solution of 8-benzhydryloxy-6-[(4-fluoro-benzylcarbamoyl)-methyl]-5-methoxy-quinoline-7-carboxylic acid methyl ester (0.020 g, 0.04 mmol) in 1 mL of anhydrous DMF. The resulting indigo-tinted solution was stirred at rt for a period of 30 min, and then diluted with diethyl ether (50 ml) and washed with sat. aq. NH$_4$Cl (25 mL). The organic layer was dried over Na$_2$SO$_4$ and solvent was removed by rotary evaporation. The residue was purified by silica gel chromatography (1/1 hexanes/diethyl ether and then 100% MeOH to elute product fractions) to give 9-benzhydryloxy-7-(4-fluoro-benzyl)-10-methoxy-5H-1,7-diaza-anthracene-6,8-dione 295 (9 mg, 48%).

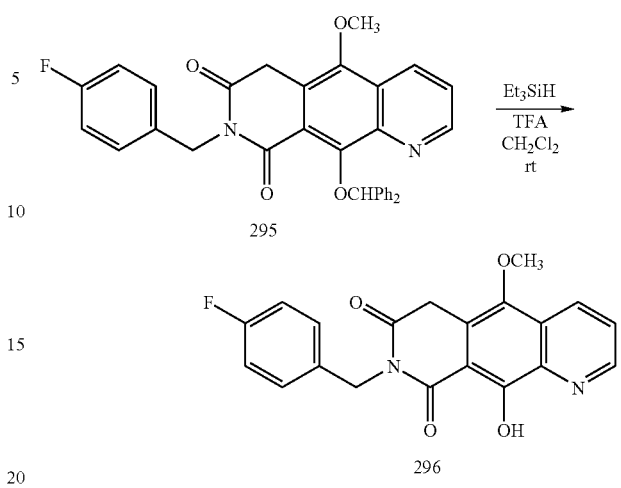

Example 296

9-Benzhydryloxy-7-(4-fluoro-benzyl)-10-methoxy-5H-1,7-diaza-anthracene-6,8-dione 295 (6 mg, 0.01 mmol) in 1 mL CH$_2$Cl$_2$ was treated with 0.1 mL trifluoroacetic acid and 0.05 mL triethylsilane. After 1 h, volatiles were removed and the product was purified via trituration with diethyl ether to give the trifluoroacetate salt of 7-(4-Fluoro-benzyl)-9-hydroxy-10-methoxy-5H-1,7-diaza-anthracene-6,8-dione 296 (5 mg, 62%): $^1$H NMR (CDCl3) δ 12.98 (s, 1H), 9.10 (d, 1H), 8.35 (d, 1H), 7.65 (m, 1H), 7.55 (m, 2H), 7.04 (t, 2H), 5.2 (s, 2H), 4.75 (s, 1H), 4.20 (s, 1H), 3.95 (s, 3H); MS: 367 (M+Na).

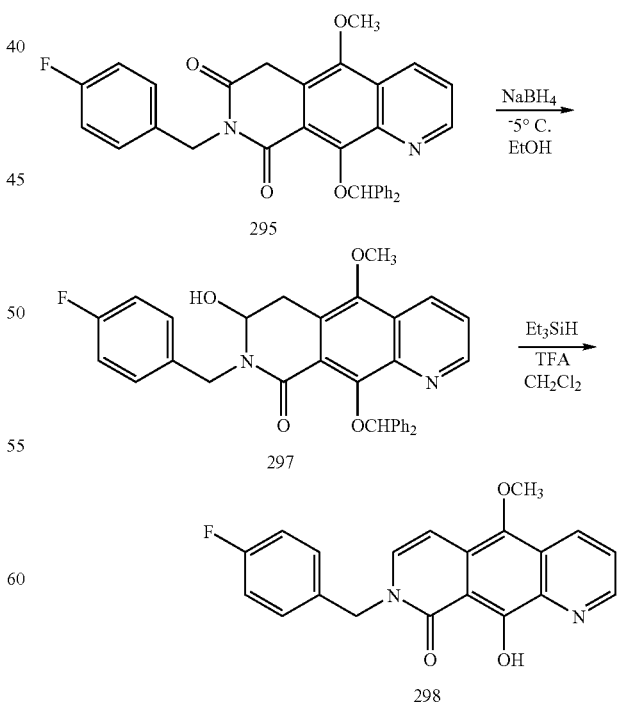

Example 297

Sodium borohydride (NaBH$_4$, 0.021 g, 0.56 mmol) was added to 9-benzhydryloxy-7-(4-fluoro-benzyl)-10-methoxy-5H-1,7-diaza-anthracene-6,8-dione 295 (30 mg, 0.056 mmol) in 1 mL EtOH at −5° C. The reaction was stirred at low temperature for a period of 2 h, then the reaction was diluted with CH$_2$Cl$_2$ (25 mL) and washed with 10 mL sat. aq. sodium bicarbonate solution. The aqueous layer was then washed twice with 25 ml portions of CH$_2$Cl$_2$ and the combined organic layers washed with brine and dried over Na$_2$SO$_4$. The reduction product was purified on silica gel (100% Et$_2$O) to give 6 mg of 9-benzhydryloxy-7-(4-fluoro-benzyl)-10-methoxy-5H-1,7-diaza-anthracene-6-hydroxy, 8-one 297.

Example 298

9-Benzhydryloxy-7-(4-fluoro-benzyl)-10-methoxy-5H-1,7-diaza-anthracene-6-hydroxy, 8-one 297 (6 mg, 0.01 mmol) was dissolved in 1 mL CH$_2$Cl$_2$ and treated with 0.1 mL trifluoroacetic acid and 0.1 mL triethylsilane. After 1 hr, volatiles were removed and the product was purified via trituration with diethyl ether to give the trifluoroacetate salt of 7-(4-Fluoro-benzyl)-9-hydroxy-10-methoxy-7H-1,7-diaza-anthracen-8-one 298 (2 mg, 38%). $^1$H NMR (CD$_3$OD) δ 9.35 (d, 1H), 8.75 (d, 1H), 7.80 (dd, 1H), 7.33 (m, 2H), 7.08 (m, 3H), 6.85 (d, 1H), 5.15 (s, 2H), 3.95 (s, 3H).; MS: 351 (M+H).

Example 299

To 2,4-dimethoxybenzyl-alcohol (4.3 g, 25.6 mmol) and pyrrolidine-2,5-dione (succinimide, 1.2 g, 12.2 mmol) dissolved in tetrahydrofuran (25 ml) and dichloromethane (25 ml) was added triphenyphosphine (6.4 g, 24.4 mmol). After cooling to 0° C., diethylazidodicarboxylate (DEAD, 4.25 g, 24.4 mmol) was added dropwise to the reaction mixture. The reaction mixture was then allowed to warm to room temperature and kept at room temperature with stirring overnight. Following concentration in vacuo, 100 ml of a (1:1) hexane/ether solution was added and this mixture was stored at 0° C. overnight. The resulting solid precipitate was filtered off and the filtrate was concentrated in vacuo. The resulting residue was purified by silica gel chromatography (3/1—ethyl acetate/hexane) to afford 1-(2,4-dimethoxy-benzyl)-pyrrolidine-2,5-dione 299 (1.4 g, 5.6 mmol, 46%). $^1$H NMR (CDCl$_3$) δ 7.07 (d, 1H), 6.38 (m, 2H), 4.60 (s, 2H), 3.76 (s, 3H), 2.62 (s, 4H).

Example 300

To 1-(2,4-dimethoxy-benzyl)-pyrrolidine-2,5-dione 299 (1.4 g, 5.6 mmol) and pyridine-2,3-dicarboxylic acid dimethyl ester (1.13 g, 5.8 mmol) dissolved in tetrahydrofuran (60 ml) and methanol (7.0 ml) was added a 60% dispersion of sodium hydride in mineral oil (NaH, 492 mg, 12.3 mmol). The reaction mixture was warmed to 80° C. and kept at 80° C. with stirring overnight. The reaction mixture was placed in an ice bath and titrated to a pH of 4 with 1 M HCl. 200 ml of ether was added and the resulting yellow solid was collected by filtration. The solid was washed twice with ether, twice with water, and dried under high vacuum with heating to provide 7-(2,4-dimethoxy-benzyl)-5,9-dihydroxy-pyrrolo[3,4-g]quinoline-6,8-dione 300 (1.1 g, 52%). $^1$H NMR (d-DMSO) δ 10.8 (broad, 2H), 9.0 (d, 1H), 8.67 (d, 1H), 7.72 (m, 1H), 6.90 (d, 1H), 6.5 (d, 1H), 6.38 (dd, 1H), 4.58 (s, 2H), 3.76 (s, 3H), 3.66 (s, 3H). MS: 382.1 (M+1)

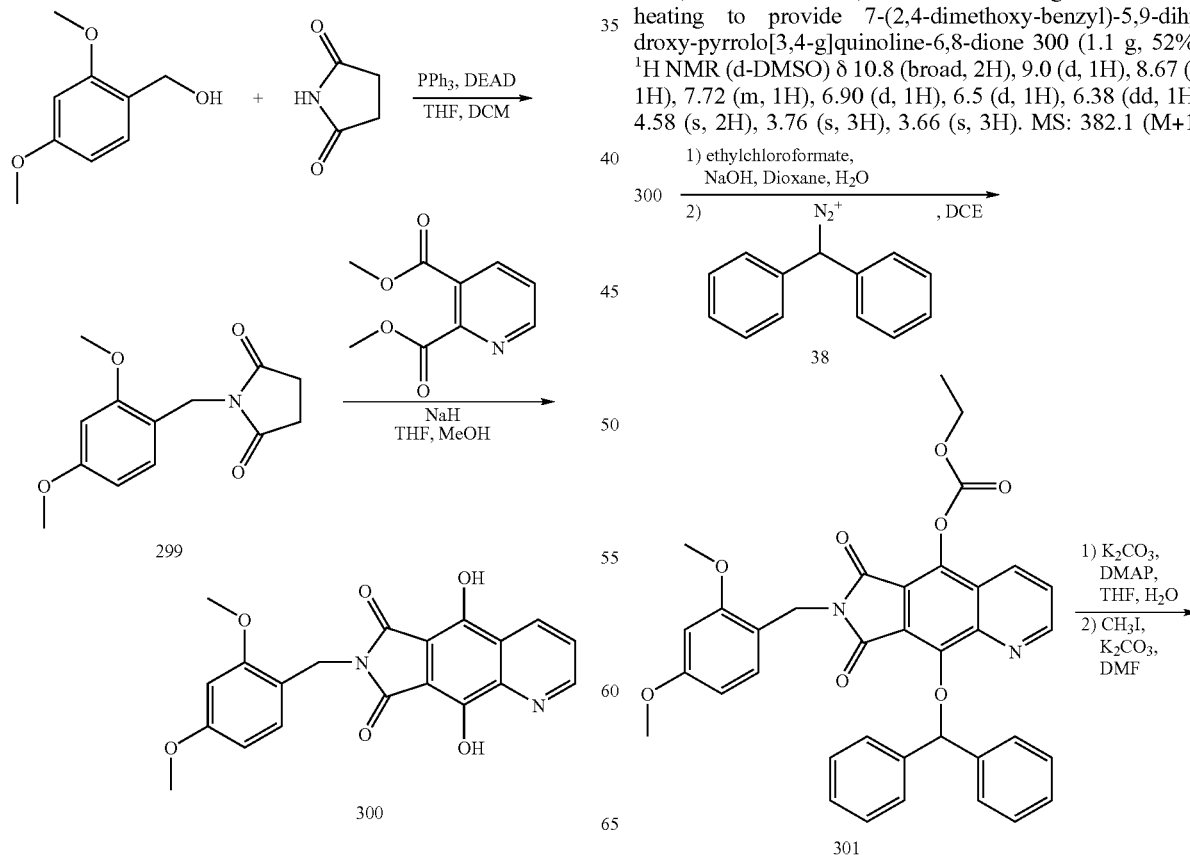

299

300

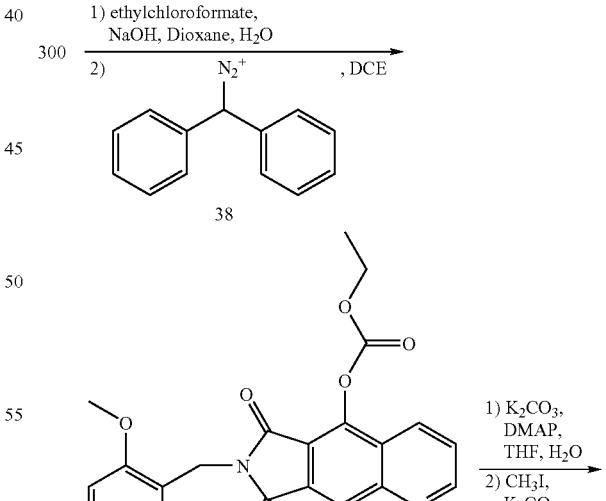

301

-continued

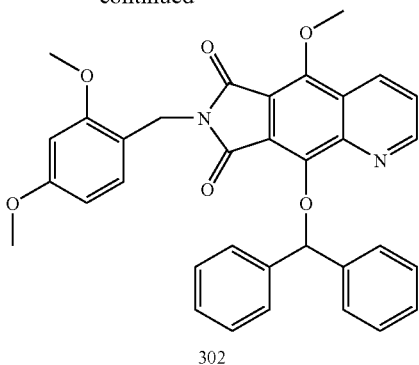

302

Example 301

7-(2,4-Dimethoxy-benzyl)-5,9-dihydroxy-pyrrolo[3,4-g]quinoline-6,8-dione 300 (1.1 g, 2.9 mmol) was dissolved in dioxane (14.5 ml) and H$_2$O (9.7 ml) and cooled to 0° C. To this reaction mixture was added 1.0 M NaOH (5.8 ml, 5.8 mmol), followed by ethylchloroformate (347.3 mg, 3.2 mmol). After stirring at 0° C. for 30 minutes, dioxane (10 ml) and ethylchloroformate (51 mg, 0.5 mmol) were added and the reaction stirred for another 30 minutes at 0° C. The reaction mixture was quenched with the addition of acetic acid (0.6 ml) and concentrated in vacuo. The crude mixture was diluted with ethyl acetate and washed once with 5% citric Acid (aqueous), twice with water, once with brine, and dried over magnesium sulfate. The resulting residue was dissolved in 1,2-dichloroethane (30 ml) and diphenyl-methanediazonium 38 (diphenyldiazomethane, 1.1 g, 5.6 mmol) was added. The reaction mixture was then stirred overnight at room temperature. Following dilution with dichloromethane, the reaction mixture was washed with once with water, once with brine, dried over magnesium sulfate, and concentrated in vacuo. The residue was purified by silica gel chromatography (1/1-Hexanes/Ethyl Acetate) to afford carbonic acid 9-benzhydryloxy-7-(2,4-dimethoxy-benzyl)-6,8-dioxo-7,8-dihydro-6H-pyrrolo [3,4-g]quinolin-5-yl ester ethyl ester 301 (1.2 g, 1.9 mmol, 66%). $^1$H NMR (CDCl$_3$) δ 9.10 (dd, 1H), 8.40 (dd, 1H), 7.95 (s, 1H), 7.68 (m, 1H), 7.60 (d, 4H), 7.15 (m, 6H), 7.0 (d, 1H), 6.40 (d, 1H), 6.36 (d, 1H), 4.80 (s, 2H), 4.35 (q, 2H), 3.75 (s, 3H), 3.73 (s, 3H), 1.31 (t, 3H). MS: 641.2 (M+23).

Example 302

Potassium carbonate (2.6 g, 19.0 mmol) and N,N-dimethyl-aminopyridine (DMAP, 0.464 g, 3.8 mmol) were added to carbonic acid 9-benzhydryloxy-7-(2,4-dimethoxy-benzyl)-6,8-dioxo-7,8-dihydro-6H-pyrrolo[3,4-g]quinolin-5-yl ester ethyl ester 301 (1.2 g, 1.9 mmol) dissolved in tetrahydrofuran (40 ml) and water (20 ml) was added. After stirring overnight at room temperature, the reaction mixture was concentrated in vacuo and diluted with ethyl acetate. It was washed twice with 5% citric Acid (aqueous), twice with water, once with brine, dried over magnesium sulfate, and concentrated in vacuo. The resulting residue was dissolved in dimethylformamide (10 ml). To this reaction mixture was added potassium carbonate (1.24 g, 9.0 mmol) and iodomethane (methyl iodide, MeI, 2.55 g, 18.0 mmol). After stirring overnight at room temperature, the reaction mixture was diluted with ethyl acetate, washed twice with 5% citric acid, twice with water, once with brine, and concentrated in vacuo to afford 9-benzhydryloxy-7-(2,4-dimethoxy-benzyl)-5-methoxy-pyrrolo[3,4-g]quinoline-6,8-dione 302 (1.1 g, 1.9 mmol, 100%). $^1$H NMR (d-DMSO) δ 9.16 (dd, 1H), 8.60 (dd, 1H), 7.82 (s, 1H), 7.75 (m, 1H), 7.54 (d, 4H), 7.16 (m, 6H), 6.82 (d, 1H), 6.56 (d, 1H), 6.44 (dd, 1H), 4.66 (s, 2H), 4.10 (s, 3H), 3.76 (s, 3H), 3.70 (s, 3H). MS: 583.2 (M+23).

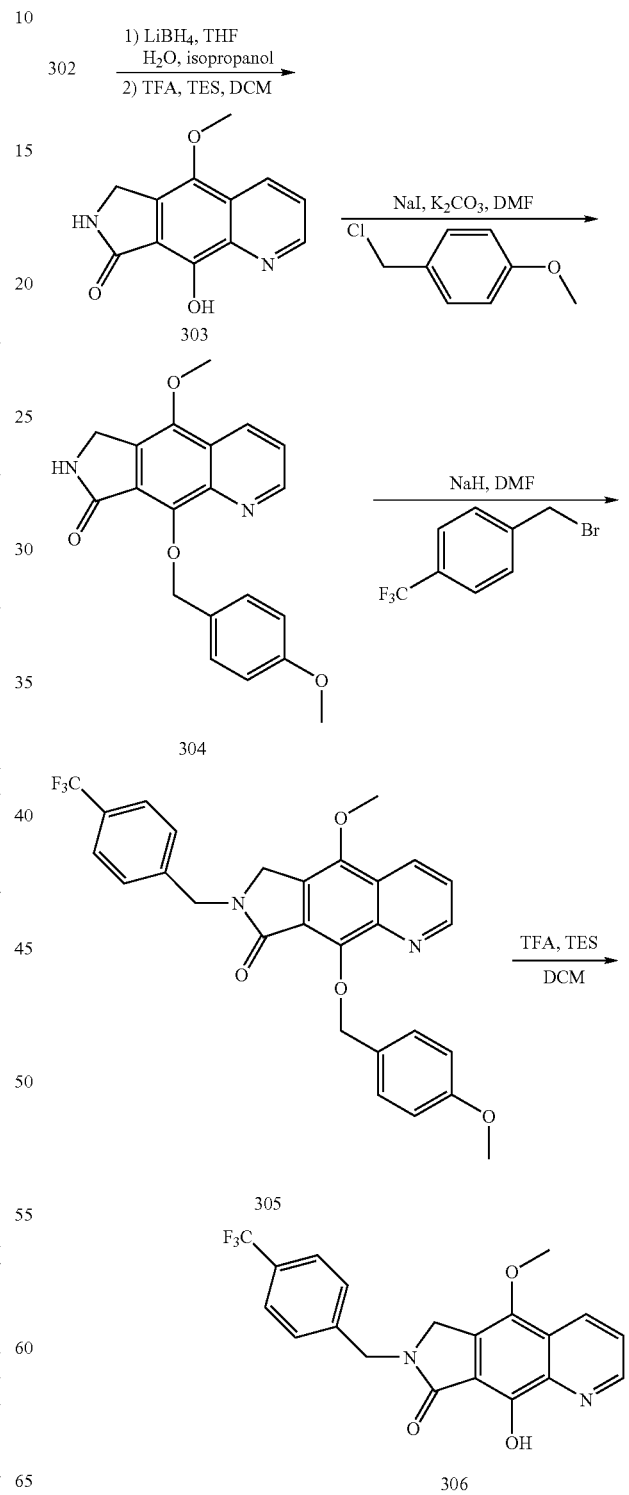

Example 303

9-Benzhydryloxy-7-(2,4-dimethoxy-benzyl)-5-methoxy-pyrrolo [3,4-g]quinoline-6,8-dione 302 (500 mg, 0.89 mmol) was dissolved in tetrahydrofuran (6.0 ml), water (1.2 ml), and isopropanol (2.4 ml) and cooled to 0° C. Lithium borohydride (LiBH$_4$, 96.9 mg, 4.45 mmol) was then added and the reaction mixture was removed from the ice bath and stirred at room temperature for 2 hours. After quenching with acetic acid (0.5 ml), the reaction mixture was diluted with ethyl acetate, washed with twice with water, once with brine, and concentrated in vacuo. The resulting residue was dissolved in dichloromethane (9.2 ml) and triethylsilane (1.8 ml), and cooled to 0° C. After adding trifluoroacetic acid (3.6 ml), the reaction mixture was warmed to room temperature and stirred at room temperature for 1 hour. The mixture was concentrated in vacuo and the resulting residue was redissolved in trifluoroacetic acid (10 ml) and triethylsilane (2 ml). It was then warmed to 75° C. and stirred at 75° C. for 2 hours. The reaction mixture was concentrated in vacuo and azeotroped three times with a (1:1) toluene/tetrahydrofuran solution. The resulting residue was triturated three times with a (3:1) hexane/ether mixture. The remaining solid in the filter funnel and reaction flask was dissolved in methanol, combined, and concentrated in vacuo to afford 9-hydroxy-5-methoxy-6,7-dihydro-pyrrolo[3,4-g]quinolin-8-one 303 (240 mg, 113%). $^1$H NMR (d-DMSO) δ 8.84 (dd, 1H), 8.58 (broad, 1H), 8.50 (dd, 1H), 7.60 (m, 1H), 4.60 (s, 2H), 3.94 (s, 3H). MS: 231.1 (M+1).

Example 304

Potassium carbonate (60.1 mg, 0.435 mmol), 4-methoxy-benzylchloride (41 mg, 0.26 mmol), and sodium iodide (6.3 mg, 0.043 mmol) were added to 9-hydroxy-5-methoxy-6,7-dihydro-pyrrolo[3,4-g]quinolin-8-one 303 (20 mg, 0.087 mmol) dissolved in dimethylformamide 8 (0.4 ml). The reaction mixture was warmed to 60° C. and stirred at 60° C. for one hour. After cooling the reaction mixture to 0° C., acetic acid (0.06 ml) was added and the mixture was concentrated in vacuo. The residue was diluted with ethyl acetate and washed once with 5% Citric Acid, twice with water, once with brine, and concentrated in vacuo. The residue was purified by silica gel chromatography (9/1-dichloromethane/methanol) to afford 5-methoxy-9-(4-methoxy-benzyloxy)-6,7-dihydro-pyrrolo[3,4-g]quinolin-8-one 304 (16 mg, 0.046 mmol, 53%). $^1$H NMR (CDCl$_3$) δ 9.0 (dd, 1H), 8.64 (dd, 1H), 7.51 (d, 2H), 7.46 (m, 1H), 6.80 (d, 2H), 6.50 (broad, 1H), 5.60 (s, 2H), 3.98 (s, 3H), 3.72 (s, 3H). MS: 351.1 (M+1).

Example 305

5-Methoxy-9-(4-methoxy-benzyloxy)-6,7-dihydro-pyrrolo[3,4-g]quinolin-8-one 304 (25.4 mg, 0.073 mmol,) was dissolved in dimethylformamide (0.4 ml) and cooled to 0° C. Sodium hydride (3.6 mg, 0.095 mmol) was added, followed by stirring at 0° C. for 5 minutes. 4-trifluoromethyl-benzyl-bromide (21.0 mg, 0.088 mmol) was added and the reaction mixture was allowed to warm to room temperature and kept at room temperature with stirring for 5 minutes. It was cooled to 0° C., quenched with acetic acid (0.030 ml), and concentrated in vacuo. The mixture was diluted with ethyl acetate, washed twice with water, once with brine, dried over magnesium sulfate, and concentrate in vacuo. The residue was purified by silica gel chromatography (99/1—ethyl acetate/acetic acid) to afford 5-Methoxy-9-(4-methoxy-benzyloxy)-7-(4-trifluoromethyl-benzyl)-6,7-dihydro-pyrrolo[3,4-g]quinolin-8-one 305 (13 mg, 0.026 mmol, 35%). $^1$H NMR δ 9.15 (dd, 1H), 8.60 (dd, 1H), 7.60 (m, 4H), 7.40 (d, 2H), 6.80 (d, 2H), 5.85 (s, 2H), 4.80 (s, 2H), 4.42 (s, 2H), 3.98 (s, 3H), 3.86 (s, 3H). MS: 509.2 (M+1).

Example 306

To 5-methoxy-9-(4-methoxy-benzyloxy)-7-(4-trifluoromethyl-benzyl)-6,7-dihydro-pyrrolo[3,4-g]quinolin-8-one 305 (13 mg, 0.026 mmol) dissolved in dichloromethane (0.200 ml) was added triethylsilane (TES, 0.05 ml) and trifluoroacetic acid (TFA, 0.100 ml). After stirring at room temperature for 15 minutes, the reaction mixture was concentrated in vacuo and azeotroped three times with a (1:1) tetrahydrofuran to toluene mixture. The resulting residue was then triturated three times with a (3:1) hexane to ether mixture to afford 9-hydroxy-5-methoxy-7-(4-trifluoromethyl-benzyl)-6,7-dihydro-pyrrolo[3,4-g]quinolin-8-one 306 (7 mg, 0.014 mmol, 54%). $^1$H NMR (CD$_3$OD) δ 9.0 (dd, 1H), 8.58 (dd, 1H), 7.60 (d, 2H), 7.40 (d, 2H), 4.80 (s, 2H), 4.50 (s, 2H), 3.95 (s, 3H). $^{19}$F NMR δ −63, −76.2. MS: 389.1 (M+1).

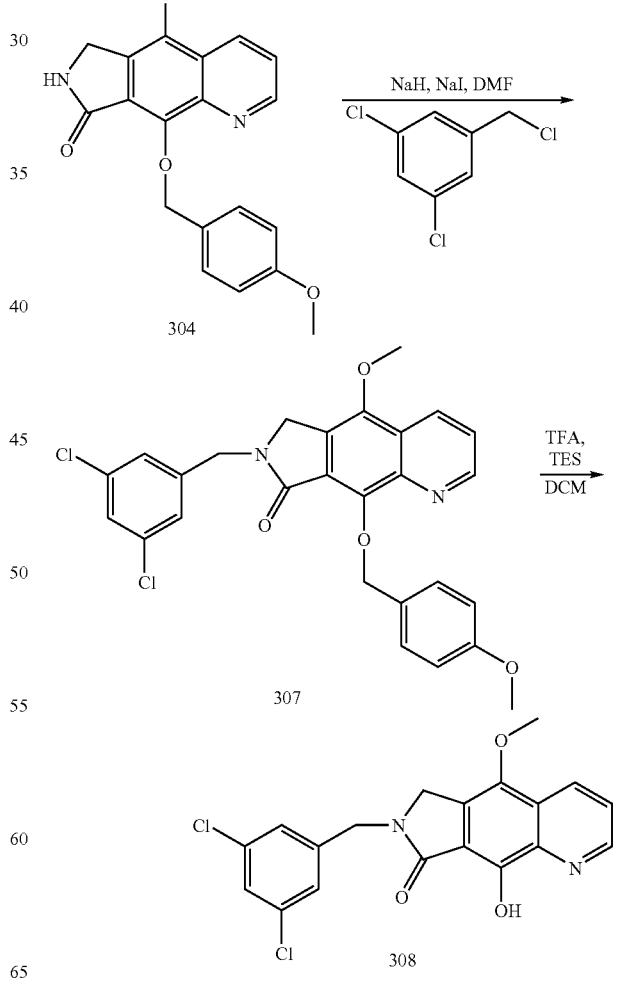

Example 307

5-Methoxy-9-(4-methoxy-benzyloxy)-6,7-dihydro-pyrrolo[3,4-g]quinolin-8-one 304 (17 mg, 0.049 mmol) was dissolved in dimethylformamide (0.3 ml) and cooled to 0° C. After adding sodium hydride (2.5 mg, 0.064 mmol), the reaction was stirred for 5 minutes at 0° C. 3,5-Dichlorobenzylchloride (11.5 mg, 0.059 mmol) and a catalytic amount of sodium iodide were then added. The reaction mixture was warmed to room temperature and stirred at room temperature for 30 minutes. It was then cooled to 0° C., acidified with acetic acid (0.030 ml), and concentrated in vacuo. The resulting residue was diluted with ethyl acetate, washed twice with water, once with brine, and concentrated in vacuo. The residue was purified by silica gel chromatography (99/1-ethyl acetate/acetic acid) to afford 7-(3,5-dichloro-benzyl)-5-methoxy-9-(4-methoxy-benzyloxy)-6,7-dihydro-pyrrolo[3,4-g]quinolin-8-one 307 (7 mg, 40%). $^1$H NMR (CDCl$_3$) δ 9.0 (dd, 1H), 8.40 (dd, 1H), 7.60 (d, 2H), 7.55 (m, 1H), 7.20 (m, 3H), 6.80 (d, 2H), 5.60 (s, 2H), 4.75(s, 2H), 4.40 (s, 2H), 3.95 (s, 3H), 3.75 (s, 3H). MS: 509.1 (M+1).

Example 308

In a manner similar to the protocol described in Example 306, 7-(3,5-dichloro-benzyl)-5-methoxy-9-(4-methoxy-benzyloxy)-6,7-dihydro-pyrrolo[3,4-g]quinolin-8-one 307 (17 mg, 0.049 mmol) was deprotected to provide 7-(3,5-dichloro-benzyl)-9-hydroxy-5-methoxy-6,7-dihydro-pyrrolo[3,4-g]quinolin-8-one 308 (10 mg, 0.020 mmol, 41%). $^1$H NMR (CD$_3$OD) δ 9.0 (dd, 1H), 8.60 (d, 1H), 7.60 (m, 1H), 7.20 (m, 3H) 4.75 (s, 2H), 4.45 (s, 2H), 4.0 (s, 3H). $^{19}$F δ −76. MS: 390.1 (M+1).

Example 309

To a solution of 1-(2-bromo-ethyl)-4-fluoro-benzene (587 mg, 3.7 mmol) and pyrrolidine-2,5-dione (succinimide, 733.3 mg, 7.4 mmol) in dimethylformamide (15 ml) was added potassium carbonate (2.0 g, 14.8 mmol) and sodium iodide (277 mg, 1.9 mmol). The reaction mixture was warmed to 60° C. and kept at 60° C. overnight with stirring. The reaction mixture was cooled to room temperature and concentrated in vacuo. The concentrate was diluted with ethyl acetate and washed twice with a saturated sodium bicarbonate aqueous solution, twice with water, once with brine, and concentrated in vacuo. The residue was purified by silica gel chromatography (100% ethylacetate) to afford 1-[2-(4-fluoro-phenyl)-ethyl]-pyrrolidine-2,5-dione 309 (570 mg, 2.6 mmol, 70%) as a solid. $^1$H NMR (CDCl$_3$) δ 7.14 (m, 2H), 6.94 (t, 2H), 3.68 (t, 2H), 2.84 (t, 2H), 2.63 (s, 4H).

Example 310

To 1-[2-(4-Fluoro-phenyl)-ethyl]-pyrrolidine-2,5-dione 309 (270 mg, 1.22 mmol and pyridine-2,3-dicarboxylic acid dimethyl ester (261.6 mg, 1.34 mmol) dissolved in tetrahydrofuran (12.0 ml) and methanol (1.4 ml) was added a 60% dispersion of sodium hydride in mineral oil (108 mg, 2.7 mmol). The reaction mixture was warmed to 80° C. and kept at 80° C. with stirring overnight. The reaction mixture was then placed in an ice bath and titrated to a pH of 4 with 1 M HCl. Two hundred (200) ml of diethylether was then added and the resulting yellow solid was collected by filtration. The solid was washed twice with ether, twice with water, and dried under high vacuum with heating to provide 7-[2-(4-fluoro-phenyl)-ethyl]-5,9-dihydroxy-pyrrolo[3,4-g] quinoline-6,8-dione 310 (250 mg, 0.71 mmol, 58%). $^1$H NMR (d-DMSO) δ 10.7 (broad, 1H), 8.98 (dd, 1H), 8.66 (dd, 1H), 7.73 (m, 1H), 7.18 (m, 2H), 7.04 (t, 2H), 3.72 (t, 2H), 2.86 (t, 2H). MS: 353.1 (M+1).

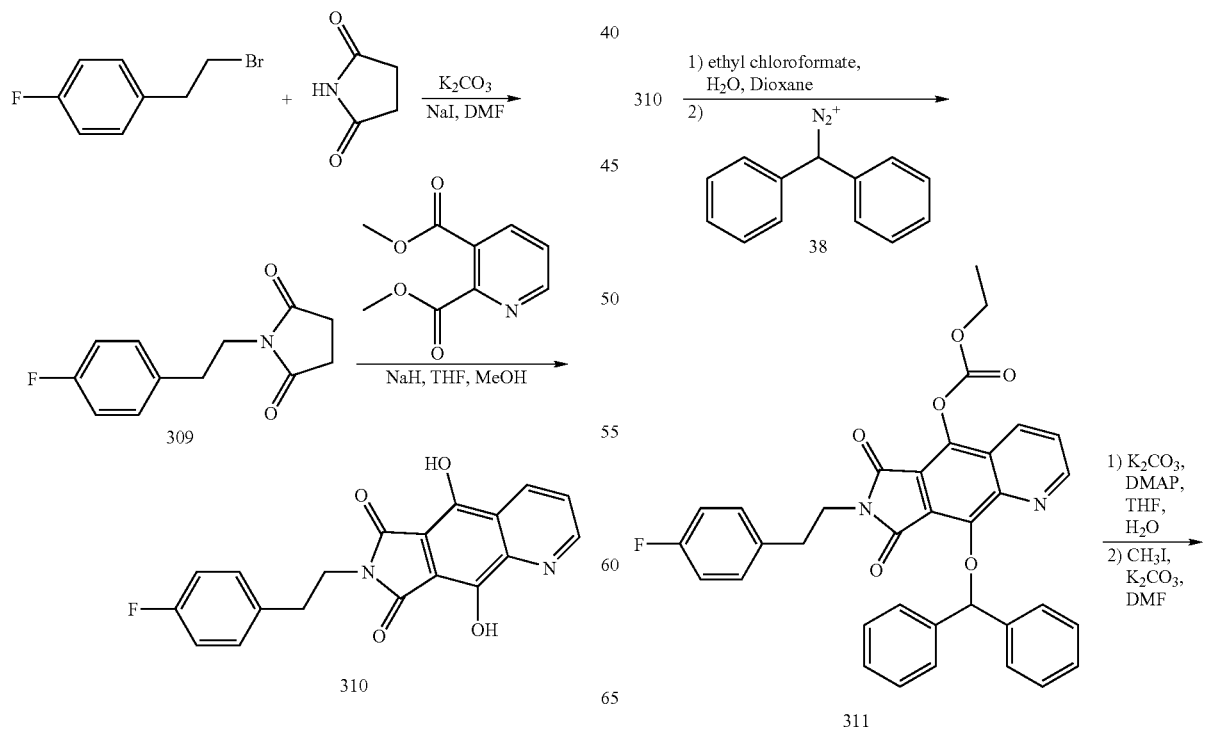

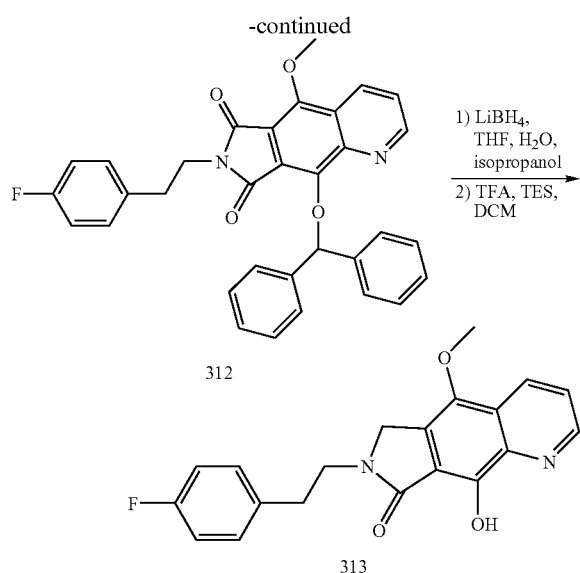

Example 311

7-[2-(4-Fluoro-phenyl)-ethyl]-5,9-dihydroxy-pyrrolo[3,4-g]quinoline-6,8-dione 310 (250 mg, 0.71 mmol).was dissolved in dioxane (3.6 ml) and H$_2$O (2.4 ml) and cooled to 0° C. After 1.0 M NaOH (1.42 ml, 1.42 mmol) and ethylchloroformate (84.6 mg, 0.78 mmol) were added, the reaction was stirred at 0° C. for one hour. The reaction mixture was quenched with the addition of acetic acid (0.6 ml) and concentrated in vacuo. The crude mixture was diluted with ethyl acetate and washed once with 5% Citric Acid (aqueous), twice with water, once with brine, dried over magnesium sulfate, and concentrated in vacuo. The resulting residue was dissolved in 1,2-dichloroethane (4.0 ml) and to this was added diphenyl-methanediazonium 38 (252 mg, 1.3 mmol). The reaction mixture was then stirred overnight at room temperature. Following dilution with dichloromethane, the reaction mixture was washed with once with water, once with brine, dried over magnesium sulfate, and concentrated in vacuo. The residue was then purified by silica gel chromatography (1/1—hexane/ethyl acetate) to afford carbonic acid 9-benzhydryloxy-7-[2-(4-fluoro-phenyl)-ethyl]-6,8-dioxo-7,8-dihydro-6H-pyrrolo[3,4-g]quinolin-5-yl ester ethyl ester 311 (251 mg, 0.425 mmol, 65%). $^1$H NMR (d-DMSO) δ 9.19 (dd, 1H), 8.52 (dd, 1H), 7.90 (s, 1H), 7.80 (m, 1H), 7.54 (m, 4H), 7.20 (m, 8H), 7.02 (t, 2H), 4.24 (q, 2H), 3.79 (t, 2H), 2.90 (t, 2H), 1.25 (t, 3H). MS: 599.2 (M+23).

Example 312

To carbonic acid 9-benzhydryloxy-7-[2-(4-fluoro-phenyl)-ethyl]-6,8-dioxo-7,8-dihydro-6H-pyrrolo[3,4-g]quinolin-5-yl ester ethyl ester 311 (140 mg, 0.24 mmol) dissolved in tetrahydrofuran (0.50 ml) and water (0.25 ml) was added potassium carbonate (345.4 mg, 2.5 mmol) and N,N-dimethyl-aminopyridine (DMAP, 29.3 mg, 3.8 mmol). After stirring overnight at room temperature, the reaction mixture was concentrated in vacuo and diluted with ethyl acetate. It was then washed twice with 5% citric Acid (aqueous), twice with water, once with brine, dried over magnesium sulfate, and concentrated in vacuo. The resulting residue was dissolved in dimethylformamide (3.0 ml). To this solution was added potassium carbonate (179 mg, 1.3 mmol) and iodomethane (319 mg, 2.6 mmol). After stirring overnight at room temperature, the reaction mixture was diluted with ethyl acetate. It was then washed twice with 5% citric Acid, twice with water, once with brine, and concentrated in vacuo to afford 9-benzhydryloxy-7-[2-(4-fluoro-phenyl)-ethyl]-5-methoxy-pyrrolo[3,4-g]quinoline-6,8-dione 312 (130 mg, 0.24 mmol, 100%). $^1$H NMR (CDCl$_3$) δ 9.16 (dd, 1H), 8.58 (dd, 1H), 7.82 (s, 1H), 7.74 (m, 1H), 7.55 (m, 4H), 7.20 (m, 8H), 7.0 (t, 2H), 4.04 (s, 3H), 3.87 (t, 2H), 2.91 (t, 2H). MS: 555.2 (M+23).

Example 313

9-Benzhydryloxy-7-(2,4-dimethoxy-benzyl)-5-methoxy-pyrrolo[3,4-g]quinoline-6,8-dione 312 (130 mg, 0.24 mmol) was dissolved in tetrahydrofuran (1.6 ml), water (0.64 ml), and isopropanol (0.32 ml) and cooled to 0° C. Lithium borohydride (26.6 mg, 1.22 mmol) was then added and the reaction mixture was removed from the ice bath and stirred at room temperature for 2 hours. After quenching with acetic acid (0.12 ml), the reaction mixture was diluted with ethyl acetate. It was then washed with twice with water, once with brine, and concentrated in vacuo. The resulting residue was dissolved in dichloromethane (1.2 ml) and triethylsilane (0.6 ml) and trifluoroacetic acid (3.6 ml). The reaction mixture was then stirred at room temperature for 1 hour. The mixture was then concentrated in vacuo and azeotroped three times with a (1:1) toluene/tetrahydrofuran solution. The resulting residue was triturated three times with a (3:1) hexane/ether mixture and the remaining solid in the filter funnel and reaction flask was dissolved in methanol, combined, and concentrated in vacuo to afford 7-[2-(4-Fluoro-phenyl)-ethyl]-9-hydroxy-5-methoxy-6,7-dihydro-pyrrolo[3,4-g]quinolin-8-one 313 (40 mg, 0.086 mmol, 36%). $^1$H NMR (d-DMSO) δ 8.85 (dd, 1H), 8.648 (dd, 1H), 7.65 (m, 1H), 7,28 (t, 2H), 7.06 (t, 2H), 4.60 (s, 2H), 3.95 (s, 3H), 3.68 (t, 2H), 2.95 (t, 2H). $^{19}$F NMR δ 60.0, −75.6. MS: 353.1 (M+1).

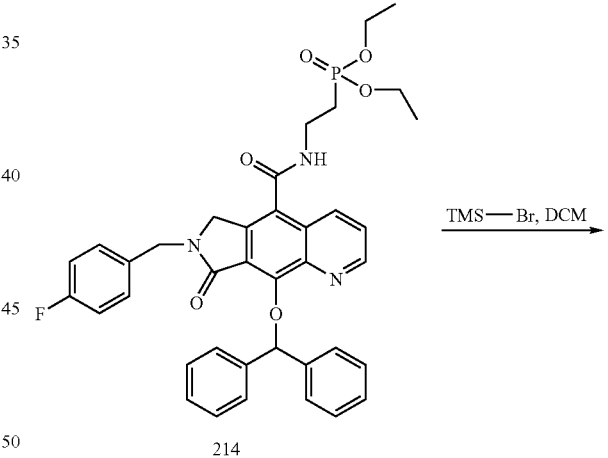

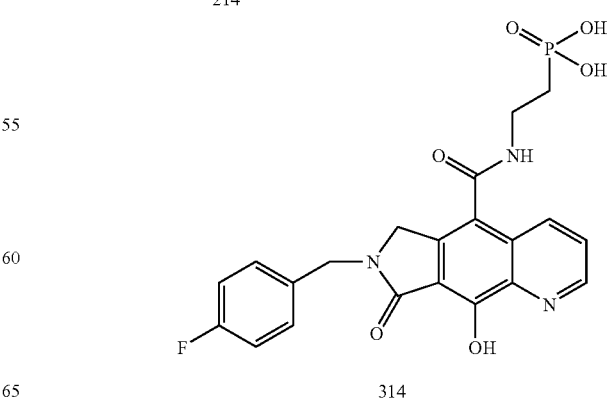

Example 314

To (2-{[9-benzhydryloxy-7-(4-fluoro-benzyl)-8-oxo-7,8-dihydro-6H-pyrrolo [3,4-g]quinoline-5-carbonyl]-amino}-ethyl)-phosphonic acid diethyl ester 214 (16 mg, 0.023 mmol) dissolved in dichloromethane (0.30 ml) was added trimethylsilylbromide (TMS-Br, 39 mg, 0.25 mmol). After 4 hours of stirring at room temperature, more trimethylsilyl-bromide (24 mg, 0.16 mmol) was added and the reaction mixture stirred for another 2 hours. The reaction mixture was cooled to 0° C., quenched with methanol (1.0 ml), and concentrated in vacuo. It was then triturated three times (3/1—hexane/ether) and the remaining residue in the flask and filter was dissolved in methanol, combined, and concentrated in vacuo. The residue was dissolved in dimethylsulfoxide (0.40 ml), filtered through a glass plug, and purified by reverse-phase preparatory HPLC to provide (2-{[7-(4-fluoro-benzyl)-9-hydroxy-8-oxo-7,8-dihydro-6H-pyrrolo[3,4-g]quinoline-5-carbonyl]-amino}-ethyl)-phosphonic acid 314 (7 mg, 0.012 mmol, 52%). $^1$H NMR (CD$_3$OD) δ 8.96 (d, 1H), 8.77 (d, 1H), 7.78 (m, 1H), 7.42 (m, 2H), 7.10 (t, 2H), 4.80 (s, 2H), 4.63 (s, 2H), 3.72 (m, 2H), 2.16 (m, 2H). $^{31}$P δ 25.0. $^{19}$F δ −78.0, −116.0. MS: 460.1 (M+1).

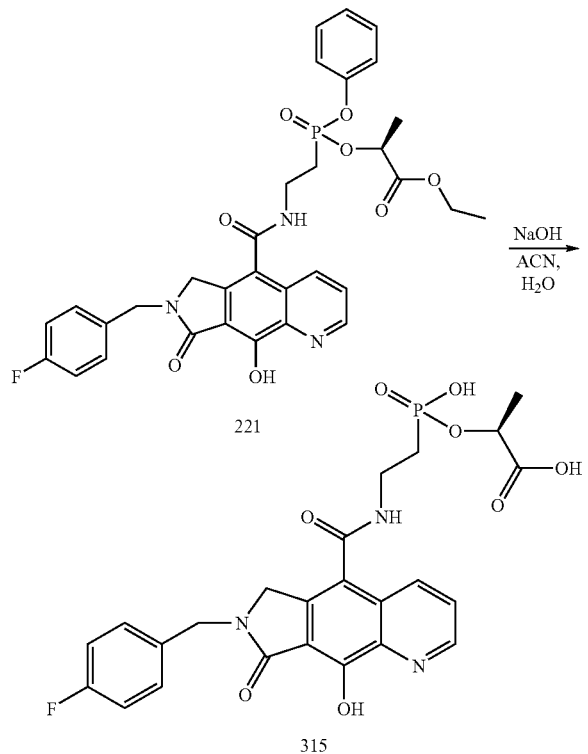

221

Example 315

To 2-[(2-{[7-(4-fluoro-benzyl)-9-hydroxy-8-oxo-7,8-dihydro-6H-pyrrolo[3,4-g]quinoline-5-carbonyl]-amino}-ethyl)-phenoxy-phosphinoyloxy]-propionic acid ethyl ester 221 (15 mg, 0.024 mmol) dissolved in acetonitrile (0.10 ml) and water (0.05 ml) was added 1.0 M NaOH (0.072 ml). The reaction mixture was stirred at room temperature for 3 hours, cooled to 0° C., and quenched with 1.0 M HCl (0.1 ml). The mixture was concentrated in vacuo and the resulting residue was redissolved in dimethylsulfoxide, filtered through a glass plug, and purified by reverse phase preparatory HPLC to afford 2-[(2-{[7-(4-fluoro-benzyl)-9-hydroxy-8-oxo-7,8-dihydro-6H-pyrrolo[3,4-g]quinoline-5-carbonyl]-amino}-ethyl)-hydroxy-phosphinoyloxy]-propionic acid 315 (9 mg, 0.014 mmol, 60%). $^1$H NMR (CD$_3$OD) δ 9.0 (d, 1H), 8.80 (d, 1H), 7.80 (m, 1H), 7.42 (M, 2H), 7.10 (t, 2H), 4.80 (d, 2H), 4.62 (s, 2H), 3.75 (m, 2H), 2.20 (m, 2H), 1.46 (d, 3H). $^3$P δ 27.8. $^{19}$F δ −78.0, −118.0. MS: 532.1 (M+1).

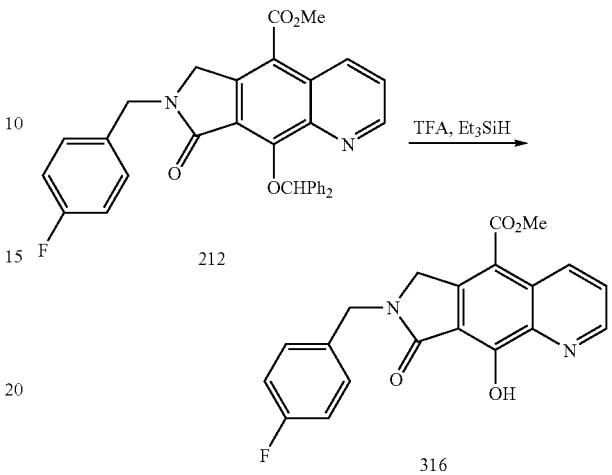

Example 316

To a solution of 9-benzhydryloxy-7-(4-fluoro-benzyl)-8-oxo-7,8-dihydro-6H-pyrrolo[3,4-g]quinoline-5-carboxylic acid methyl ester 212 (3 mg, 0056 mmol) in dichloromethane (1 mL) were added TFA (0.1 mL) and triethylsilane (0.2 mL). Stirring was continued at the room temperature for 1 hour and the volatiles were evaporated in vacuo. The residue was triturated in Et$_2$O/hexane to afford 7-(4-fluoro-benzyl)-9-hydroxy-8-oxo-7,8-dihydro-6H-pyrrolo[3,4-g]quinoline-5-carboxylic acid methyl ester 316 (2.0 mg, 100%) as a yellow solid: $^1$H NMR (CDCl$_3$) δ 9.5 (d, 1H), 9.0 (m, 1H), 7.66 (dd, 1H), 7.35 (dd, 2H), 7.0 (t, 2H), 4.8 (s, 2H), 4.7 (s, 2H), 4.0 (s, 3H); MS: 365 (M−1).

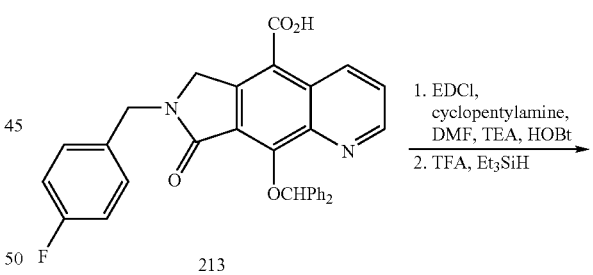

213

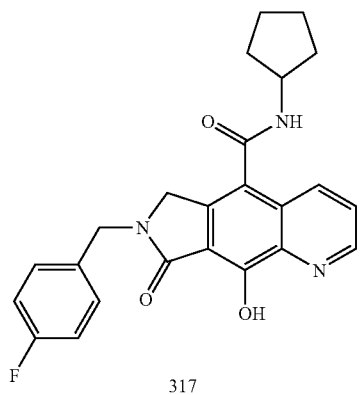

317

Example 317

To a solution of 9-benzhydryloxy-7-(4-fluoro-benzyl)-8-oxo-7,8-dihydro-6H-pyrrolo[3,4-g]quinoline-5-carboxylic acid 213 (6 mg, 0.0116 mmol) in DMF (0.5 mL) at the room temperature were added triethylamine (TEA, 5 μL, 0.034 mmol), cyclohexylamine (2.3 μL, 0.022 mmol), 1-(3-dimethylaminopropyl)-3-ethylcarbodiimide hydrochloride (EDCI, 4.4 mg, 0.022 mmol) and 1-hydroxybenzotriazole (HOBt, 2.3 mg, 0.0174 mmol). The solution was stirred under a nitrogen atmosphere for 5 hours and diluted with EtOAc. The organic layer was washed with water, 1N aqueous HCl, saturated aqueous NaHCO$_3$ and brine, dried over MgSO$_4$ and concentrated in vacuo. The crude product was chromatographed on a silica gel column eluting with EtOAc/hexane to afford the protected final product, which was treated in dichloromethane (1 mL) with TFA (0.1 mL) and triethylsilane (0.2 mL) at the room temperature for 1 hour. The volatiles were evaporated in vacuo and the residue was triturated in Et$_2$O/hexane to afford 7-(4-fluoro-benzyl)-9-hydroxy-8-oxo-7,8-dihydro-6H-pyrrolo[3,4-g]quinoline-5-carboxylic acid cyclopentylamide 317 (2.6 mg, 54%) as yellow solid. $^1$H NMR (CDCl$_3$) δ 8.96 (dd, 1H), 8.53 (d, 1H), 7.62 (dd, 1H), 7.27 (m, 2H), 7.04 (t, 2H), 6.34 (m, 1H), 4.63 (s, 2H), 4.48 (m, 3H), 2.2 (m, 2H), 1.50-1.90 (m, 6H); MS: 418 (M−1).

g, 0.0386 mmol) was dissolved in 0.3 mL of dimethylformamide. To this was added 2-methylaminopyridine (0.0079 mL, 0.0772 mmol), diisopropylethylamine (0.027 mL, 0.1544 mmol), O-(7-Azabenzotriazol-1-yl)-N,N,N',N'-tetramethyluronium hexafluorophosphate (0.03 g, 0.0772 mmol) and stirred at room temperature. After 15 hours, starting material was consumed. Purified by reverse phase HPLC (0.1% TFA, H$_2$O/ACN) to give 7-(4-fluoro-benzyl)-9-hydroxy-8-oxo-7,8-dihydro-6H-pyrrolo[3,4-g]quinoline-5-carboxylic acid methyl-pyridin-2-yl-amide 318 (0.0017 g, 0.003 mmol, 8%.) $^1$H NMR (CDCl$_3$) δ 9.02 (dd, 1H), 8.50 (d, 1H), 8.18 (d, 1H), 7.65 (dd, 1H), 7.38 (m, 5H), 7.08 (dd, 2H), 4.94 (dd, J=15 Hz, 11Hz, 2H), 4.49 (d, J=17 Hz, 1H), 4.19 (d, J=17 Hz, 1H), 3.61 (s, 3H.) MS: 443 (M+1).

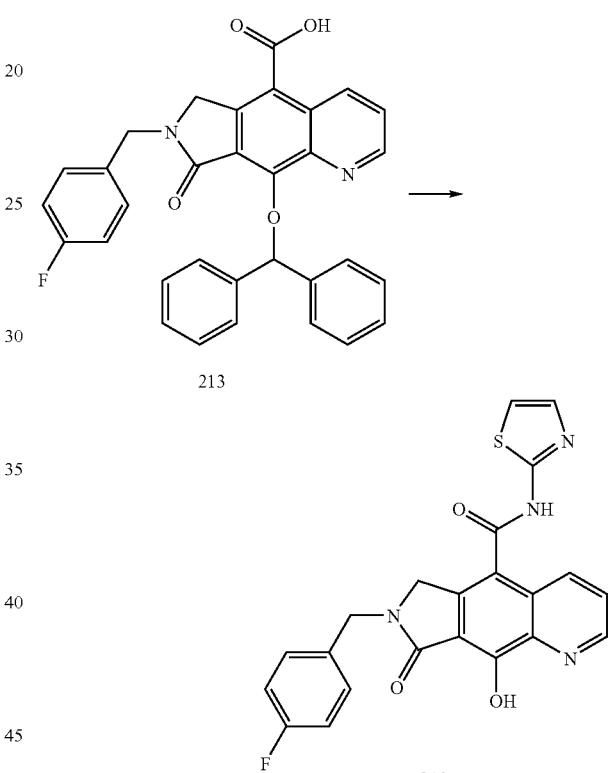

213

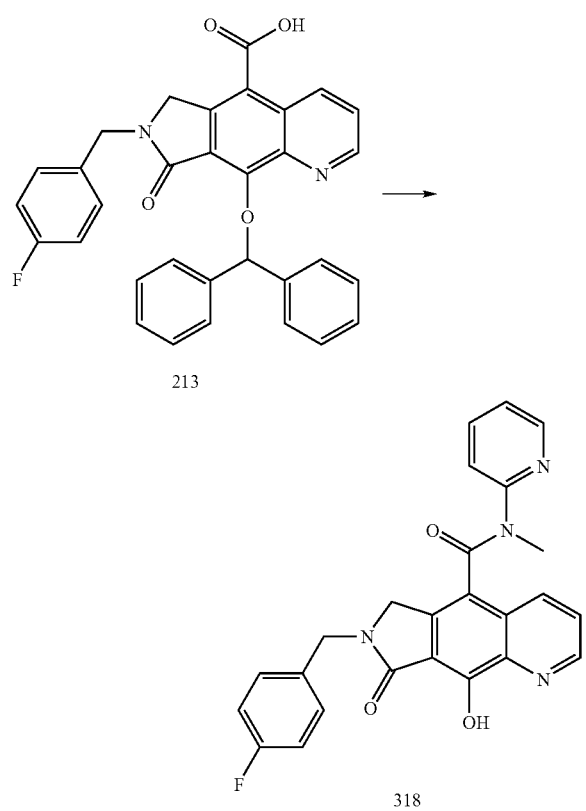

213

318

Example 318

9-Benzhydryloxy-7-(4-fluoro-benzyl)-8-oxo-7,8-dihydro-6H-pyrrolo[3,4-g]quinoline-5-carboxylic acid 213 (0.02

319

Example 319

9-Benzhydryloxy-7-(4-fluoro-benzyl)-8-oxo-7,8-dihydro-6H-pyrrolo[3,4-g]quinoline-5-carboxylic acid 213 (0.02 g, 0.0386 mmol) was dissolved in 0.3 mL of dimethylformamide. To this was added 2-aminothiazole (0.0077 mL, 0.0772 mmol), diisopropylethylamine (0.027 mL, 0.1544 mmol), O-(7-Azabenzotriazol-1-yl)-N,N,N',N'-tetramethyluronium hexafluorophosphate (0.03 g, 0.0772 mmol) and stirred at room temperature. After 15 hours, starting material was consumed. Purified by reverse phase HPLC (0.1% TFA, H$_2$O/ACN) to give 7-(4-fluoro-benzyl)-9-hydroxy-8-oxo-7,8-dihydro-6H-pyrrolo[3,4-g]quinoline-5-carboxylic acid thiazol-2-ylamide 319 (0.01 g, 0.023 mmol, 60%.) $^1$H NMR (CDCl$_3$) δ 9.02 (dd, 1H), 8.61 (d, 1H), 7.65 (dd, 1H), 7.55 (d, 1H), 7.38 (dd, 2H), 7.21 (d, 1H), 7.07 (dd, 2H), 4.78 (s, 2H), 4.67 (s, 2H.) MS: 435 (M+1).

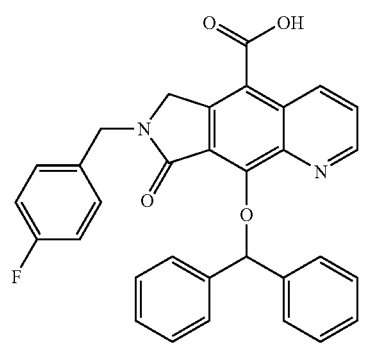

213

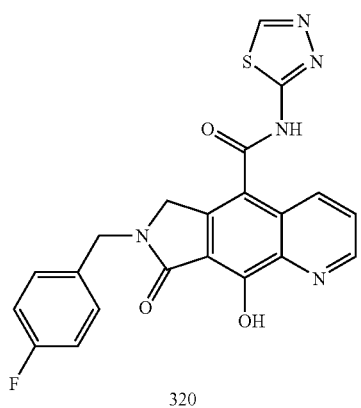

Example 320

9-Benzhydryloxy-7-(4-fluoro-benzyl)-8-oxo-7,8-dihydro-6H-pyrrolo[3,4-g]quinoline-5-carboxylic acid 213 (0.02 g, 0.0386 mmol) was dissolved in 0.3 mL of dimethylformamide. To this was added 2-amino-1,3,4-thiadiazole (0.0078 mL, 0.0772 mmol), diisopropylethylamine (0.027 mL, 0.1544 mmol), O-(7-Azabenzotriazol-1-yl)-N,N,N',N'-tetramethyluronium hexafluorophosphate (0.03 g, 0.0772 mmol) and stirred at room temperature. After 15 hours, starting material was consumed. Purified by reverse phase HPLC (0.1% TFA, H$_2$O/ACN) to give 7-(4-fluoro-benzyl)-9-hydroxy-8-oxo-7,8-dihydro-6H-pyrrolo[3,4-g]quinoline-5-carboxylic acid [1,3,4]thiadiazol-2-ylamide 320 (0.0066 g, 0.015 mmol, 40%.) $^1$H NMR (CDCl$_3$) δ 9.02 (dd, 1H), 8.81 (s, 1H), 8.65 (d, 1H), 7.65 (dd, 1H), 7.38 (dd, 2H), 7.05 (dd, 2H), 4.74 (s, 2H), 4.64 (s, 2H.) MS: 436 (M+1).

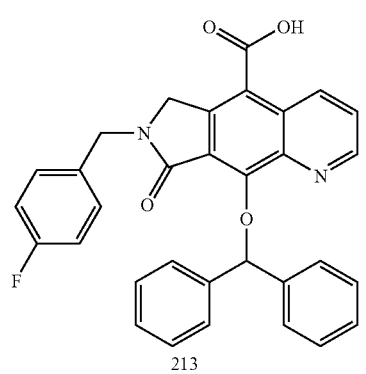

213

-continued

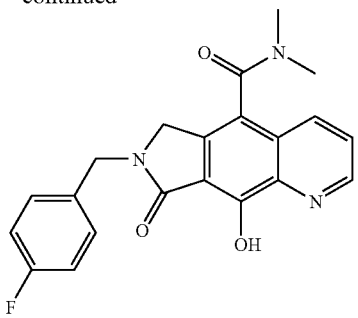

Example 321

9-Benzhydryloxy-7-(4-fluoro-benzyl)-8-oxo-7,8-dihydro-6H-pyrrolo[3,4-g]quinoline-5-carboxylic acid 213 (0.02 g, 0.0386 mmol) was dissolved in 0.3 mL of dimethylformamide. To this was added dimethylamine (2M in THF) (0.0386 mL, 0.0772 mmol), diisopropylethylamine (0.027 mL, 0.1544 mmol), O-(7-Azabenzotriazol-1-yl)-N,N,N',N'-tetramethyluronium hexafluorophosphate (0.03 g, 0.0772 mmol) and stirred at room temperature. After 15 hours, starting material was consumed. Purified by reverse phase HPLC (0.1% TFA, H$_2$O/ACN) to give 7-(4-fluoro-benzyl)-9-hydroxy-8-oxo-7,8-dihydro-6H-pyrrolo[3,4-g]quinoline-5-carboxylic acid dimethylamide 321 (0.014 g, 0.037 mmol, 97%.) $^1$H NMR (CDCl$_3$) o9.07 (dd, 1H), 8.18 (d, 1H), 7.65 (dd, 3H), 7.03(dd, 2H), 4.79 (dd, 2H), 4.53 (d, J=17 Hz, 1H), 4.25 (d, J=17 Hz, 1H), 3.24 (s, 3H), 3.21 (s, 3H.) MS: 380 (M+1).

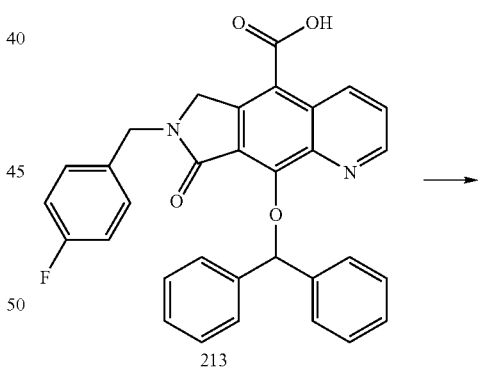

213

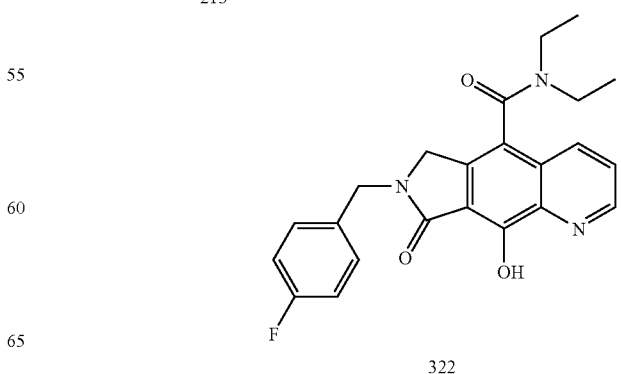

322

Example 322

9-Benzhydryloxy-7-(4-fluoro-benzyl)-8-oxo-7,8-dihydro-6H-pyrrolo[3,4-g]quinoline-5-carboxylic acid 213 (0.02 g, 0.0386 mmol) was dissolved in 0.3 mL of dimethylformamide. To this was added diethylamine (0.0056 mL, 0.0772 mmol), diisopropylethylamine (0.027 mL, 0.1544 mmol), O-(7-Azabenzotriazol-1-yl)-N,N,N',N'-tetramethyluronium hexafluorophosphate (0.03 g, 0.0772 mmol) and stirred at room temperature. After 15 hours, starting material was consumed. Purified by reverse phase HPLC (0.1% TFA, $H_2O$/ACN) to give 7-(4-fluoro-benzyl)-9-hydroxy-8-oxo-7,8-dihydro-6H-pyrrolo[3,4-g]quinoline-5-carboxylic acid diethylamide 322 (0.0134 g, 0.033 mmol, 86%.) $^1$H NMR ($CDCl_3$) δ 9.07 (dd, 1H), 8.18 (d, 1H), 7.65 (m, 3H), 7.07(dd, 2H), 4.72 (dd, 2H), 4.56 (d, J=17 Hz, 1H), 4.23 (d, J=17 Hz, 1H), 3.66 (q, 2H), 3.11 (q, 2H), 1.35 (t, 3H), 0.965 (t, 3H.) MS: 408 (M+1).

Example 323

HIV Integrase Assay ($IC_{50}$ Determination)

IC50 is the inhibitory concentration that reduces the strand transfer activity of recombinant integrase by 50%.

HIV Integrase assay was carried out in Reacti-Bind High Binding Capacity Streptavidin coated plates (Pierce #15502) in 100 μl reactions following the method of Hazuda etal *Nucleic Acids Res*. (1994) 22:1121-22. The wells of the plate are rinsed once with PBS. Each well is then coated at room temperature for 1 h with 100 μl of 0.14 μM double-stranded donor DNA of Hazuda etal.

After coating, the plate was washed twice with PBS. 3'processing of the donor DNA is started by adding 80 μl of Integrase/buffer mixture (25 mM HEPES, pH 7.3, 12.5 mM DTT, 93.75 mM NaCl, 12.5 mM $MgCl_2$, 1.25% Glycerol, 0.3125 μM integrase) to each well. 3'-Processing was allowed to proceed for 30 min at 37° C., after which, 10 μl of test compound and 10 μl of 2.5 μM digoxigenin (DIG)-labeled, double-stranded Target DNA, according to Hazuda etal, were added to each well to allow strand transfer to proceed for 30 min at 37° C. The plate was then washed three times with 2×SSC for 5 min and rinsed once with PBS. For detection of integrated product, 100 μl of a 1/2000 dilution of HRP-conjugated anti-DIG antibody (Pierce #31468) were added to each well and incubated for 1 hour. The plate was then washed three times for 5 min each, with 0.05% Tween-20 in PBS. For signal development and amplification, 100 μL of SuperSignal ELISA Femto Substrate (Pierce #37075) were added to each well. Chemiluminescence (in relative light units) was read immediately at 425 nm in the SPECTRAmax GEMINI Microplate Spectrophotometer using the end point mode at 5 sec per well. For $IC_{50}$ determinations, eight concentrations of test compounds in a 1/2.2 dilution series were used. Certain compounds of the invention, including those in Tables 1-5, had a strand transfer $IC_{50}$ less than about 10 μM.

Example 324

Anti-HIV Assay ($EC_{50}$ Determination)

EC50 (also commonly referred to as ED50 or IC50) is the effective concentration that inhibits 50% of viral production, 50% of viral infectivity, or 50% of the virus-induced cytopathic effect.

Anti-HIV assay was carried out in 96-well Clear Bottom Black Assay Plate (Costar #3603) in 100 μl of culture medium, using the CellTiter-Glo™ Reagent (Promega # G7570) for signal detection. MT-2 cells (1.54×10⁴ cells) were infected with wild-type virus at an m.o.i. of about 0.025, and grown in the presence of various drug concentrations (serial 5-fold dilutions) in 100 μl of RPMI medium containing 10% FBS, 2% glutamine, 1% HEPES and 1% penicillin/streptomycin for 5 days. At the end of the incubation period, 100 μl of CellTiter-Glo™ Reagent was added to each well in the Assay Plate and the chemiluminescence (in relative light units) was measured after 10 mins of incubation with the Wallac Victor² 1420 MultiLabel Counter. Certain compounds of the invention, including those in Tables 1-5, had an anti-HIV MT2 $EC_{50}$ less than about 10 μM.

Example 325

Cytotoxicity Assay ($CC_{50}$ Determination)

For the determination of compound cytotoxicity, the plate and reagents are the same as those of anti-HIV assay. Uninfected MT-2 cells (1.54×10⁴ cells)were grown in the presence of various drug concentrations (serial 3-fold dilutions) in 100 μl of RPMI medium containing 10% FBS, 2% glutamine, 1% HEPES and 1% penicillin/streptomycin for 5 days. At the end of the incubation period, 100 μl of CellTiter-Glo™ Reagent was added to each well in the assay plate and the chemilurninescence (in relative light units) was measured after 10 mins of incubation with the Wallac Victor² 1420 MultiLabel Counter. Certain compounds of the invention, including those in Tables 1-5, had cytotoxicity MT2 $CC_{50}$ less than about 10 μM.

The foregoing specification teaches the principles of the present invention, with Examples provided for the purpose of illustration, and fully discloses how to make and use the present invention. The invention is not limited to the particular embodiments described herein but includes all modifications within the scope of the appended claims and their equivalents. Those skilled in the art will recognize through routine experimentation that various changes and modifications can be made without departing from the scope of this invention.

All publications, including, but not limited to, patents and patent applications cited in this specification, are herein incorporated by reference as if each individual publication were specifically and fully set forth.

We claim:
1. A compound having the structure:

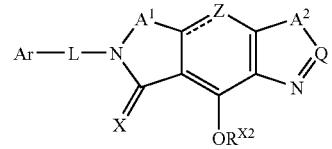

wherein:
$A^1$ is independently selected from $C(R^2)_2$, $CR^2OR$, $CR^2OC(=O)R$, $C(=O)$, $C(=S)$, $CR^2SR$, and $C(=NR)$,
$A^2$ is independently selected from $C(R^2)_2$—$C(R^3)_2$, $C(R^2)=C(R^3)$ and $C(=O)C(R^3)_2$;
Q is $CR^4$;

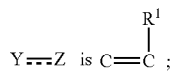

L is selected from a bond, O, S, S—S, S(=O), S(=O)$_2$, S(=O)$_2$NR, NR, N—OR, C$_1$-C$_{12}$ alkylene, C$_1$-C$_{12}$ substituted alkylene, C$_2$-C$_{12}$ alkenylene, C$_2$-C$_{12}$ substituted alkenylene, C$_2$-C$_{12}$ alkynylene, C$_2$-C$_{12}$ substituted alkynylene, C(=O)NH, OC(=O)NH, NHC(=O)NH, C(=O), C(=O)NH(CH$_2$)$_n$, or (CH$_2$CH$_2$O)$_n$, where n is optionally 1, 2, 3, 4, 5, or 6;

X is selected from O, S, NH, NR, N—OR, N—NR$_2$, N—CR$_2$OR and N—CR$_2$NR$_2$;

Ar is selected from (a) a C$_3$-C$_{12}$ carbocycle, C$_3$-C$_{12}$ substituted carbocycle, C$_6$-C$_{20}$ aryl, C$_6$-C$_{20}$ substituted aryl, C$_2$-C$_{20}$ heteroaryl, and C$_2$-C$_{20}$ substituted heteroaryl;

or (b) a saturated, unsaturated or aromatic ring or ring system having a mono- or bicyclic carbocycle or heterocycle containing 3 to 12 ring atoms;

R$^2$, R$^3$ and R$^4$ are each independently selected from H, F, Cl, Br, I, OH, —NH$_2$, —NH$_3^+$, —NHR, —NR$_2$, —NR$_3^+$, C$_1$-C$_8$ alkylhalide, carboxylate, sulfate, sulfamate, sulfonate, 5-7 membered ring sultam, C$_1$-C$_8$ alkylsulfonate, C$_1$-C$_8$ alkylamino, 4-dialkylaminopyridinium, C$_1$-C$_8$ alkylhydroxyl, C$_1$-C$_8$ alkylthiol, —SO$_2$R, —SO$_2$Ar, —SOAr, —SAr, —SO$_2$NR$_2$, —SOR, —CO$_2$R, —C(=O)NR$^2$, 5-7 membered ring lactam, 5-7 membered ring lactone, —CN, —N$_3$, —NO$_2$, C$_1$-C$_8$ alkoxy, C$_1$-C$_8$ trifluoroalkyl, C$_1$-C$_8$ alkyl, C$_1$-C$_8$ substituted alkyl, C$_3$-C$_{12}$ carbocycle, C$_3$-C$_{12}$ substituted carbocycle, C$_6$-C$_{20}$ aryl, C$_6$-C$_{20}$ substituted aryl, C$_2$-C$_{20}$ heteroaryl, and C$_2$-C$_{20}$ substituted heteroaryl, polyethyleneoxy, phosphonate, phosphate, and a prodrug moiety;

when taken together on a single carbon, two R$^2$ or two R$^3$ may form a spiro ring;

R$^1$ is independently selected from CR$_3$, NRSO$_2$R, OC(=O)NR, OC(=O)R, SR, H, F, Cl, Br, I, OH, —NH$_2$, —NH$_3^+$, —NHR, —NR$_2$, —NR$_3^+$, C$_1$-C$_8$ alkylhalide, carboxylate, sulfate, sulfamate, sulfonate, 5-7 membered ring sultam, C$_1$-C$_8$ alkylsulfonate, C$_1$-C$_8$ alkylamino, 4-dialkylaminopyridinium, C$_1$-C$_8$ alkylhydroxyl, C$_1$-C$_8$ alkylthiol, —SO$_2$R, —SO$_2$Ar, —SOAr, —SAr, —SO$_2$NR$_2$, —SOR, —CO$_2$R, —C(=O)NR$_2$, 5-7 membered ring lactam, 5-7 membered ring lactone, —CN, —N$_3$, —NO$_2$, C$_1$-C$_8$ alkoxy, C$_1$-C$_8$ trifluoroalkyl, C$_1$-C$_8$ alkyl, C$_1$-C$_8$ substituted alkyl, C$_3$-C$_{12}$ carbocycle, C$_3$-C$_{12}$ substituted carbocycle, C$_6$-C$_{20}$ aryl, C$_6$-C$_{20}$ substituted aryl, C$_2$-C$_{20}$ heteroaryl, and C$_2$-C$_{20}$ substituted heteroaryl, polyethyleneoxy, phosphonate, phosphate, and a prodrug moiety;

R is independently selected from H, C$_1$-C$_8$ alkyl, C$_1$-C$_8$ substituted alkyl, C$_6$-C$_{20}$ aryl, C$_6$-C$_{20}$ substituted aryl, C$_2$-C$_{20}$ heteroaryl, and C$_2$-C$_{20}$ substituted heteroaryl, polyethyleneoxy, phosphonate, phosphate, and a prodrug moiety;

R$^{X2}$ is independently selected from H, C$_1$-C$_8$ alkyl, C$_1$-C$_5$ substituted alkyl, C$_6$-C$_{20}$ aryl, C$_6$-C$_{20}$ substituted aryl, C$_2$-C$_{20}$ heteroaryl, and C$_2$-C$_{20}$ substituted heteroaryl, polyethyleneoxy, phosphonate, phosphate, a prodrug moiety, and a protecting group selected from benzyhydryl (CHPh$_2$), trialkylsilyl (R$_3$Si), 2-trimethylsiloxyethyl, alkoxymethyl (CH$_2$OR), and ester (C(=O)R);

and the tautomers, salts, solvates, resolved enantiomers and purified diastereomers thereof;

with the proviso that when Y=Z is C=C(OH), X is O, A$^1$ is C(=O), A$^2$ is C(R$^2$)=C(R$^3$), and Q is CH, then L is not a bond.

2. A compound of claim 1 selected from the structures:

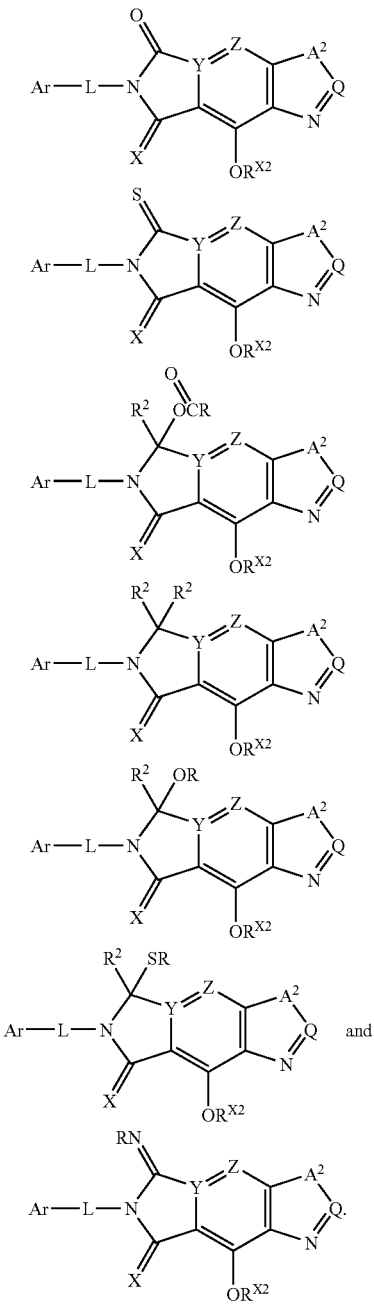

3. A compound of claim 1 wherein A$^1$ is CH$_2$.

4. A compound of claim 1 wherein Ar is a saturated, unsaturated or aromatic ring or ring system having a mono- or bicyclic carbocycle or heterocycle containing 3 to 12 ring atoms.

5. A compound of claim 1 wherein R$^1$ is selected from R, OR, NR$_2$, NHR, NHSO$_2$R and NRSO$_2$R.

6. A compound of claim 1 selected from the structures:

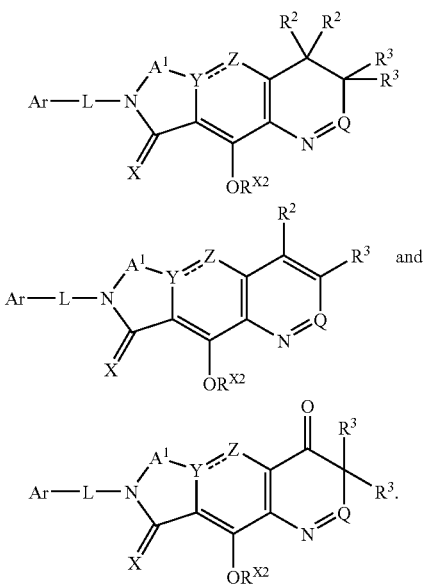

7. A compound of claim 1 wherein $R^{X2}$ is a protecting group selected from the group consisting of benzyhydryl (CHPh$_2$), trialkylsilyl (R$_3$Si), 2-trimethylsiloxyethyl, alkoxymethyl (CH$_2$OR), and ester (C(=O)R).

8. A compound of claim 1 having the structure:

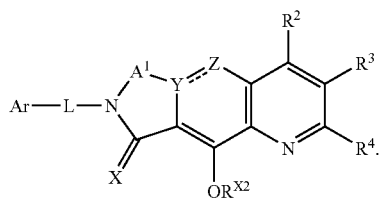

9. A compound of claim 1 having Formula I:

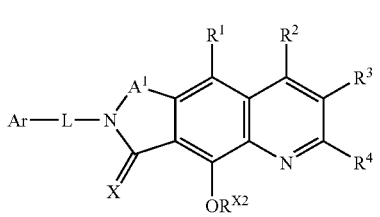

wherein $R^{X2}$ is H and X is O.

10. A compound of claim 1 wherein L is not a bond.

11. A compound of claim 1 wherein $R^4$ is H.

12. A compound of claim 1 wherein Ar is $C_6$-$C_{20}$ substituted aryl.

13. A compound of claim 1 having at least one phosphonate group.

14. A compound of claim 1 wherein substituted alkyl, substituted alkylene, substituted alkyenylene, substituted alkynylene, substituted carbocycle, substituted aryl, and substituted heteroaryl are independently substituted with one or more substituents selected from F, Cl, Br, I, OH, —NH$_2$, —NH$_3^+$, —NHR, —NR$_2$, —NR$_3^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylammopyridinium, $C_1$-$C_8$ alkylhydroxyl, $C_1$-$C_8$ alkylthiol, —SO$_2$R, —SO$_2$Ar, —SOAr, —SAr, —SO$_2$NR$_2$, —SOR, —CO$_2$R, —C(=O)NR$_2$, 5-7 membered ring lactam, 5-7 membered ring lactone, —CN, —N$_3$, —NO$_2$, $C_1$-$C_8$ alkoxy, $C_1$-$C_8$ trifluoroalkyl, $C_1$-$C_8$ alkyl, $C_3$-$C_{12}$ carbocycle, $C_6$-$C_{20}$ aryl, $C_2$-$C_{20}$ heteroaryl, polyethyleneoxy, phosphonate, phosphate, and a prodrug moiety.

15. The compound of claim 1 wherein $A^1$ is CH$_2$, C(CH$_3$)$_2$,

16. The compound of claim 9 wherein X is O; L is CH$_2$; and Ar is substituted phenyl.

17. The compound of claim 16 wherein Ar is 4-fluorophenyl.

18. The compound of claim 9 wherein X is O; and $R^2$, $R^3$ and $R^4$ are each H.

19. The compound of claim 9 wherein X is O; $A^1$ is CH$_2$; and $R^2$, $R^3$ and $R^4$ are each H.

20. The compound of claim 1 wherein Ar—L is selected from the structures:

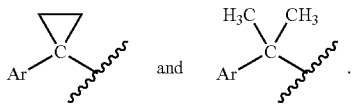

21. A compound of claim 9 having Formula Ia:

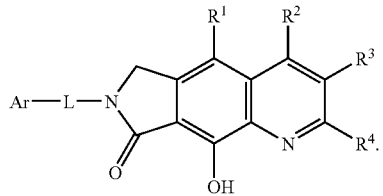

22. A compound of claim 9 having the structure:

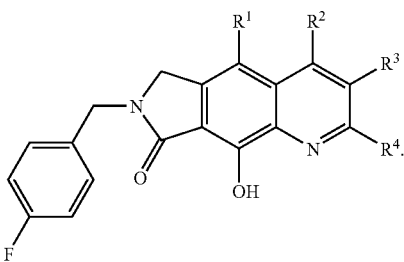

23. A compound of claim 22 selected from the structures:

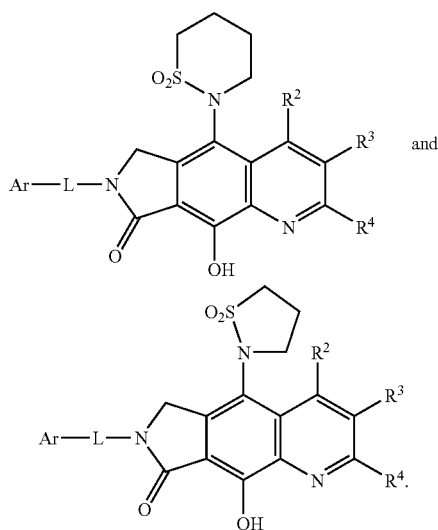

24. A compound of claim 9 wherein Ar—L is para-fluorobenzyl.

25. A compound of claim 9 having the structure:

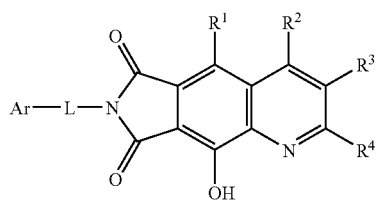

with the proviso that when $R^1$ is OH, and $R^2$, $R^3$, and $R^4$ are H, then L is not a bond.

26. A compound of claim 1 wherein $R_1$ is selected from $CR_3$, $C(=O)NR_2$, $OC(=O)OR$, $OC(=O)NR_2$, $OC(=O)R$, $OSO_2NR_2$ (sulfamate), $NR_2$, $NRSO_2R$, $SR$, $S(O)R$, $SO_2R$ and $SO_2NR_2$ (sulfonamide).

27. The compound of claim 26 wherein at least one R is a prodrug moiety.

28. A compound of claim 1 wherein at least one of $R^1$, $R^2$, $R^3$, and $R_4$ selected from the structures:

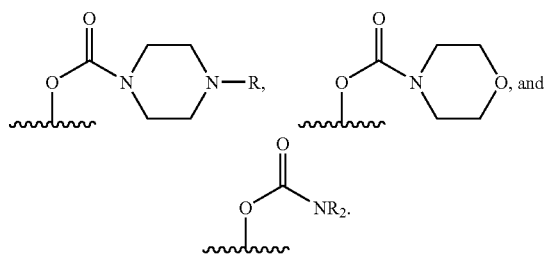

29. A compound of claim 1 wherein at least one of $R^1$, $R^2$, $R^3$, and $R_4$ is selected from the structures:

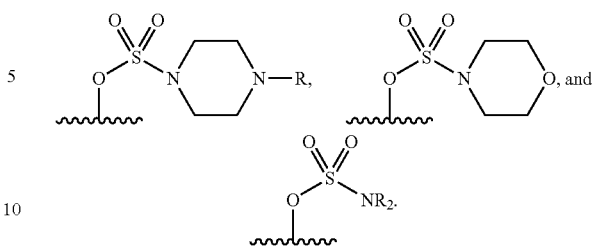

30. A compound of claim 1 wherein at least one of $R^1$, $R^2$, $R^3$, and $R_4$ selected from the structures:

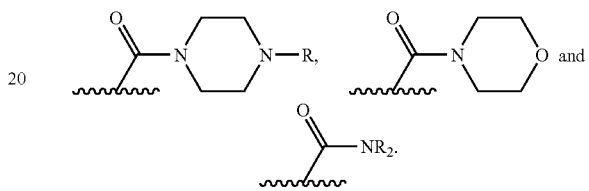

31. A compound of claim 1 wherein at least one of $R^1$, $R^2$, $R^3$, and $R_4$ is a lactam having the structures:

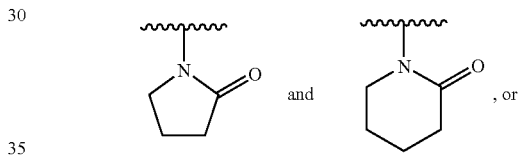

a sultam having the structures:

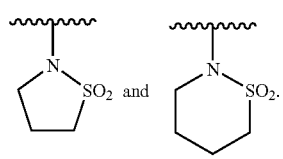

32. A compound of claim 1 wherein Ar is selected from the structures:

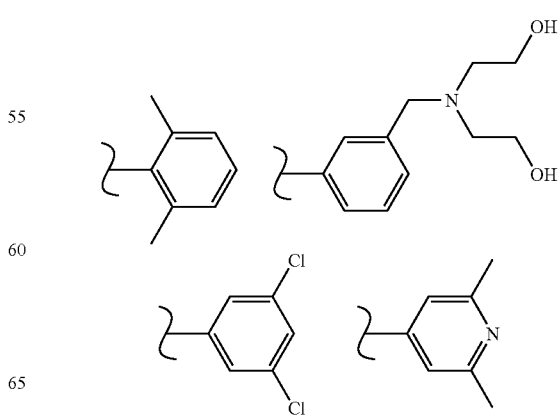

-continued

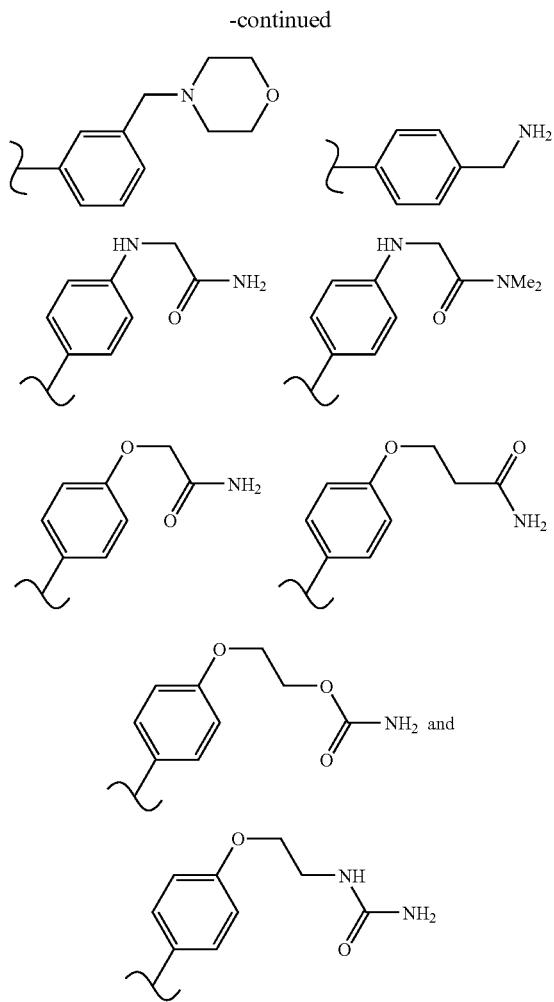

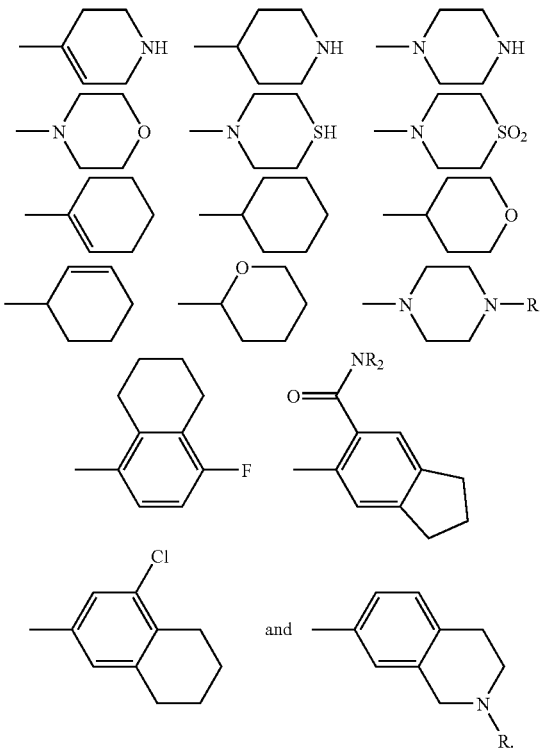

where the wavy line ⌒ indicates the covalent attachment site to L.

33. A compound of claim 1 wherein Ar is selected from the structures:

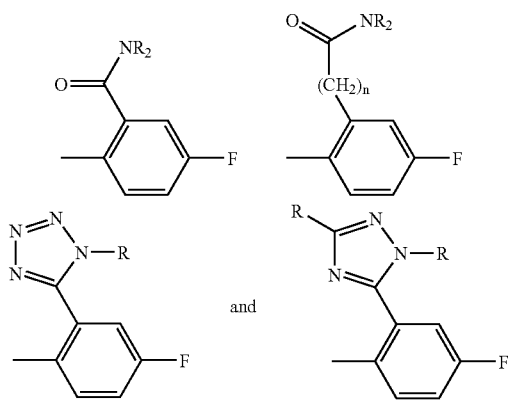

where n is 1 to 6.

34. A compound of claim 1 wherein Ar is selected from the structures:

35. A compound of claim 1 comprising a prodrug moiety selected from the structures:

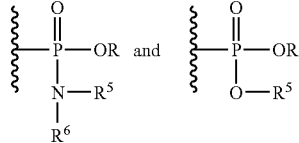

wherein $R^5$ is —$CR_2CO_2R^7$ where $R^6$ and $R^7$ are independently H or $C_1$-$C_8$ alkyl.

36. The compound of claim 1 comprising a phosphonate or prodrug moiety having the structure:

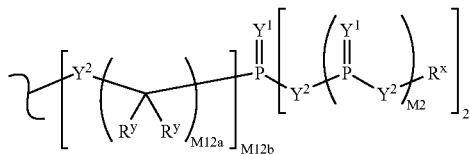

wherein:
$Y^1$ is independently O, S, $N(R^x)$, $N(O)(R^X)$, $N(OR^X)$, $N(O)(OR^X)$, or $N(N(R^X)_2)$;
$Y^2$ is independently a bond, O, $N(R^X)$, $N(O)(R^X)$, $N(OR^X)$, $N(O)(OR^X)$, $N(N(R^X)_2)$, —S(O)— (sulfoxide), —$S(O)_2$— (sulfone), —S— (sulfide), or —S—S— (disulfide);
M2 is 0, 1 or 2;
M12a is 1, 2, 3, 4, 5, 6, 7, 8, 9, 10, 11, or 12;
M12b is 0, 1, 2, 3, 4, 5, 6, 7, 8, 9, 10, 11, or 12;

$R^y$ is independently H, $C_1$-$C_6$ alkyl, $C_1$-$C_6$ substituted alkyl, $C_6$-$C_{20}$ aryl, $C_6$-$C_{20}$ substituted aryl, or a protecting group, or where taken together at a carbon atom, two vicinal $R^y$ groups form a carbocycle or a heterocycle; and $R^x$ is independently H, $C_1$-$C_6$ alkyl, $C_1$-$C_6$ substituted alkyl, $C_6$-$C_{20}$ aryl, $C_6$-$C_{20}$ substituted aryl, or a protecting group, or the formula:

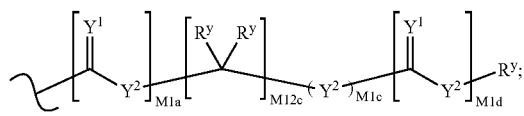

where M1a, M1c, and M1d are independently 0 or 1, and M12c is 0, 1, 2, 3, 4, 5, 6, 7, 8, 9, 10, 11 or 12.

37. The compound of claim 36 wherein the phosphonate or prodrug moiety has the structure:

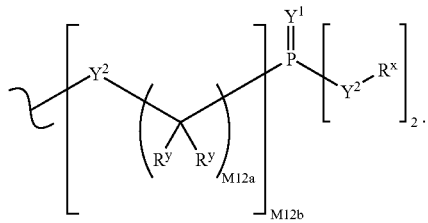

38. The compound of claim 37 wherein the phosphonate or prodrug moiety has the structure:

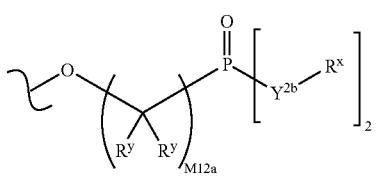

where $Y^{2b}$ is O or N($R^X$).

39. The compound of claim 37 wherein the phosphonate or prodrug moiety has the structure:

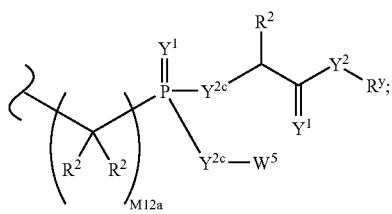

where $W^5$ is a carbocycle, and $Y^{2c}$ is O, N($R^y$) or S.

40. The compound of claim 39 wherein $W^5$ is selected from the structures:

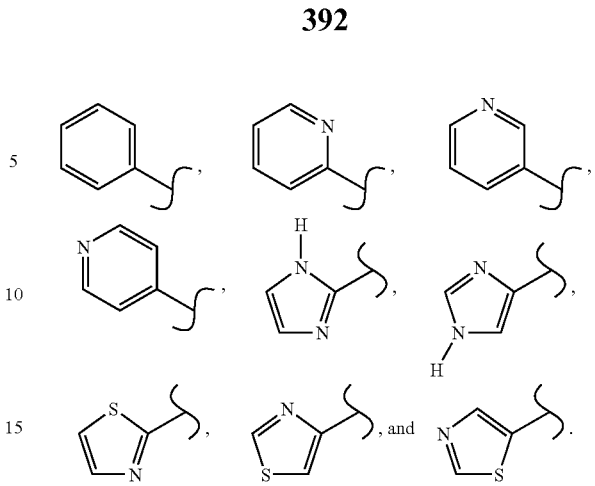

41. The compound of claim 37 wherein the phosphonate or prodrug moiety has the structure:

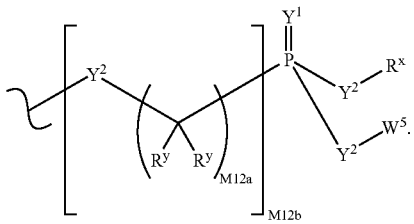

42. The compound of claim 1 wherein the phosphonate or prodrug moiety has the structure:

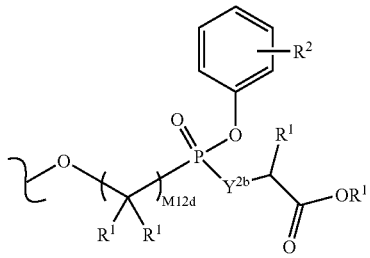

wherein $Y^{2b}$ is O or N($R^X$); M12d is 1, 2, 3, 4, 5, 6, 7 or 8; $R^1$ is H or $C_1$-$C_6$ alkyl; and the phenyl carbocycle is substituted with 0 to 3 $R^2$ groups where $R^2$ is $C_1$-$C_6$ alkyl or substituted alkyl.

43. The compound of claim 1 wherein the phosphonate or prodrug moiety has the structure:

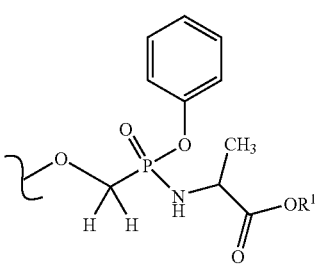

or

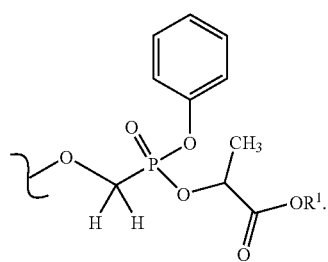
44. The compound of claim 36 wherein $R^X$ is selected from the structures:
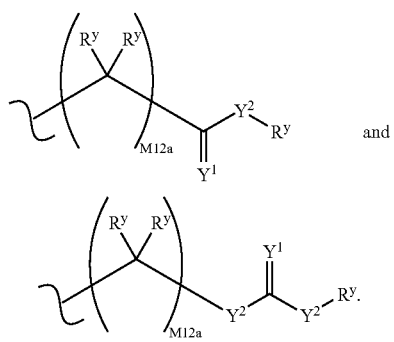
45. A compound selected from the structures:
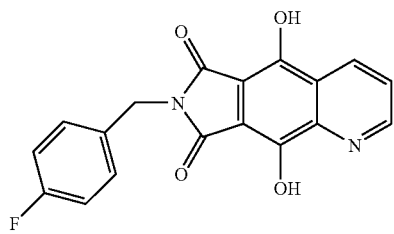
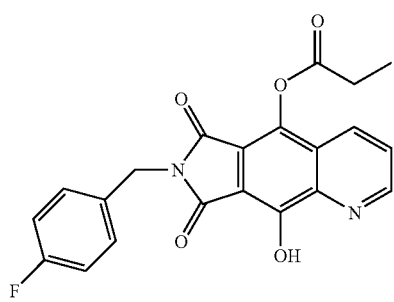
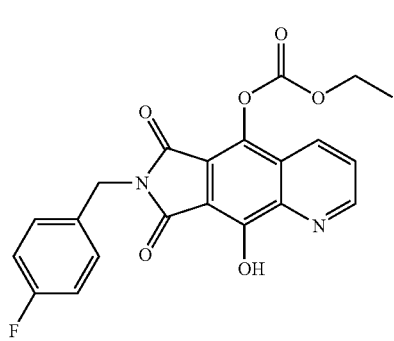
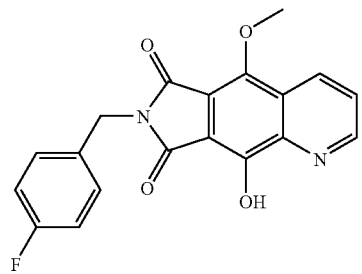
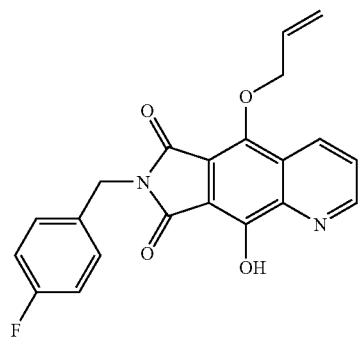
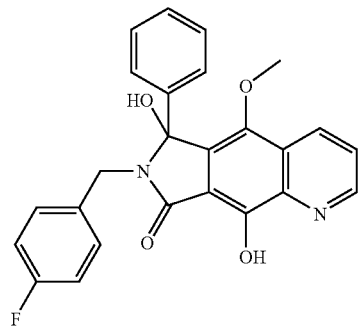
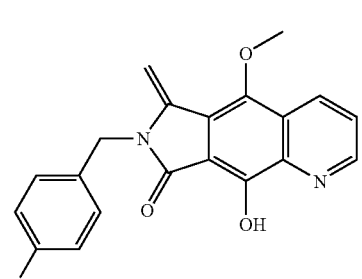
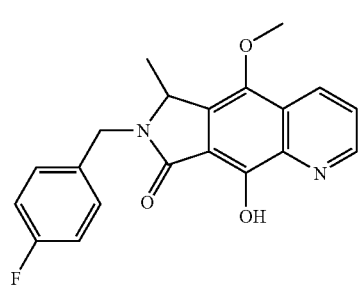

46. A compound of claim 1 wherein none of $R^2$, $R^3$, $R_4$, R, or $R^{x2}$ is a prodrug moiety.

47. A compound selected from the structures:

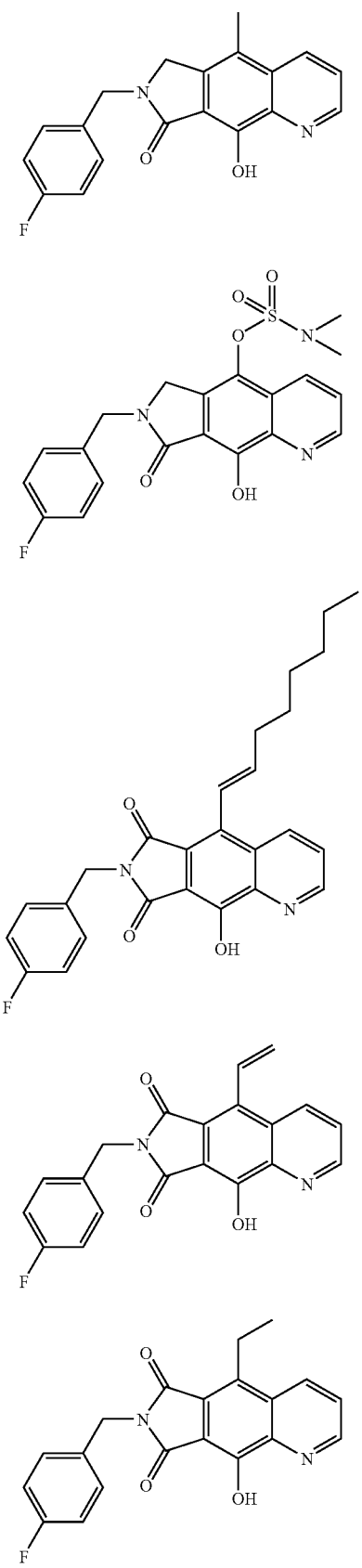
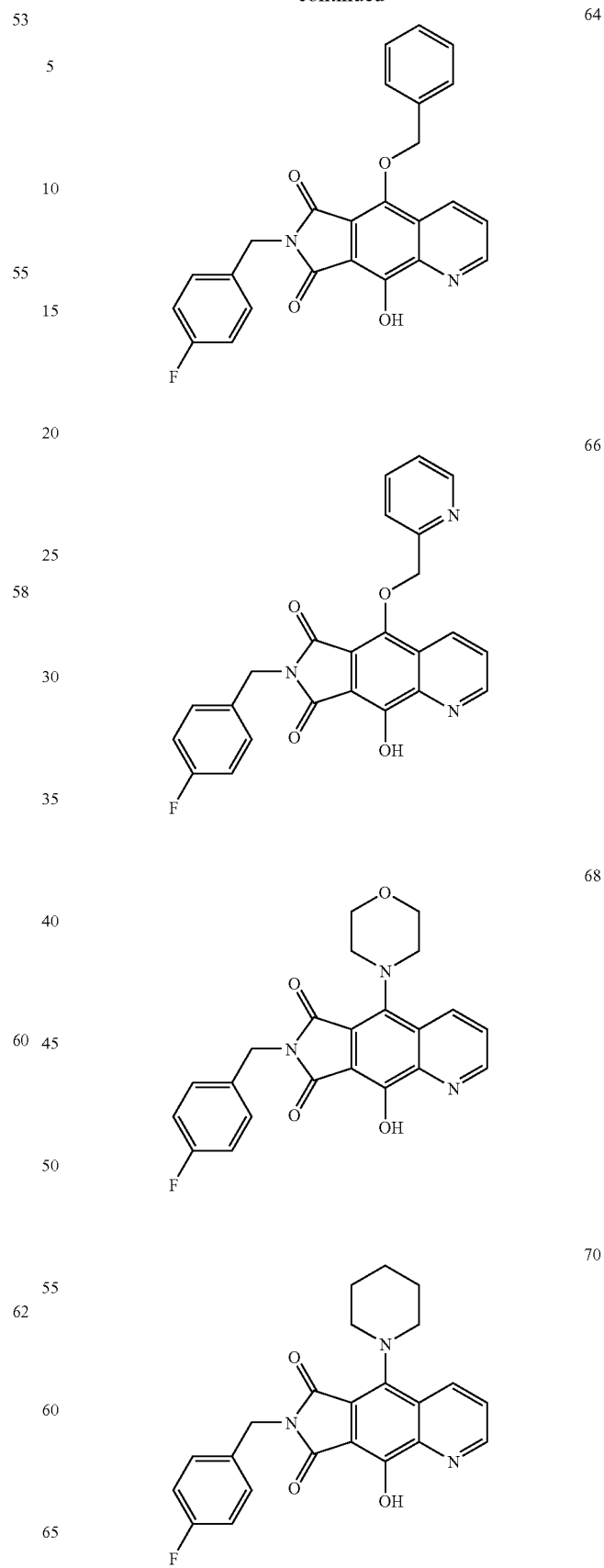

-continued
72
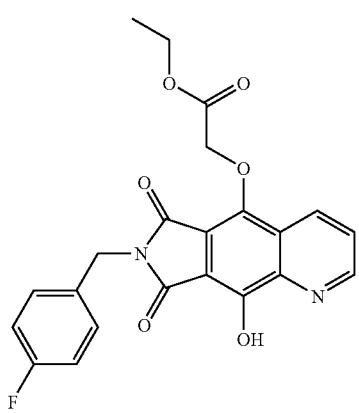
74
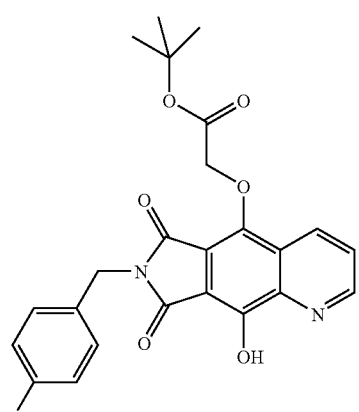
76
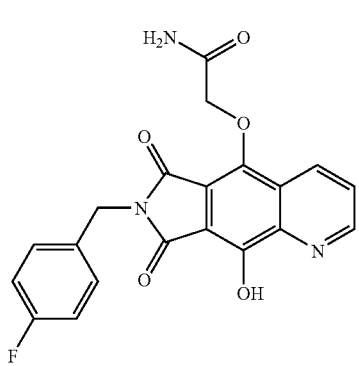
79
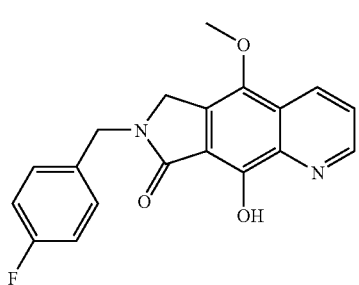
-continued
81
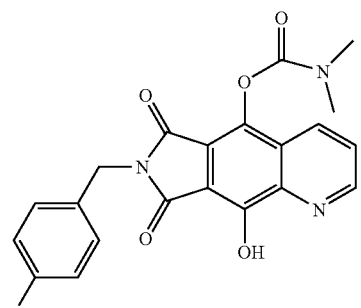
83
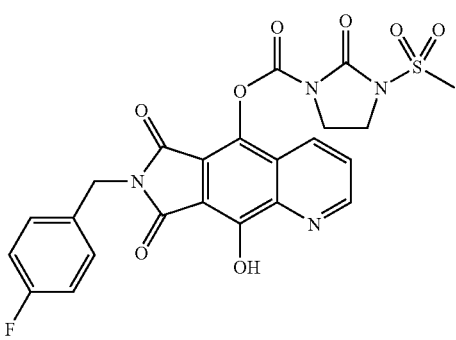
85
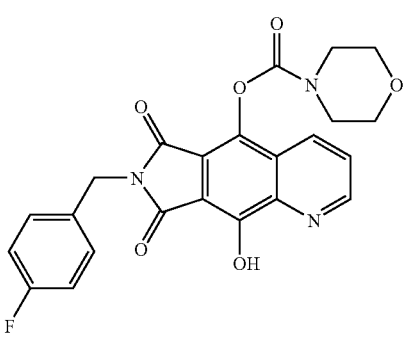
87
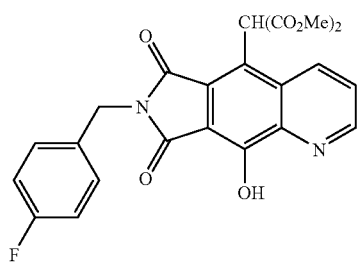
89
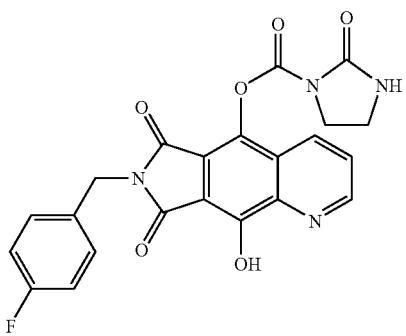

-continued
91
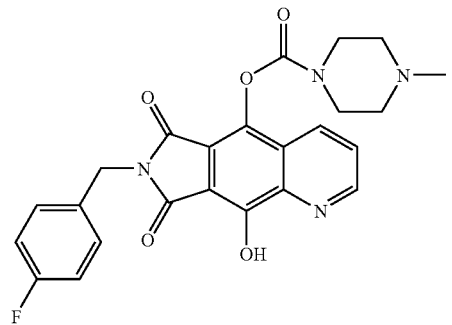
93
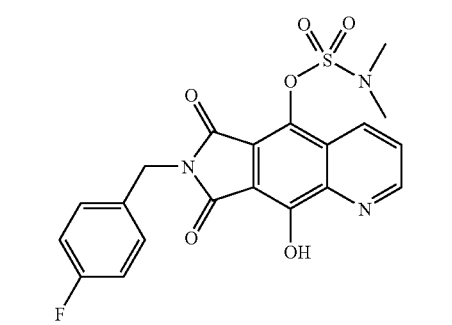
95
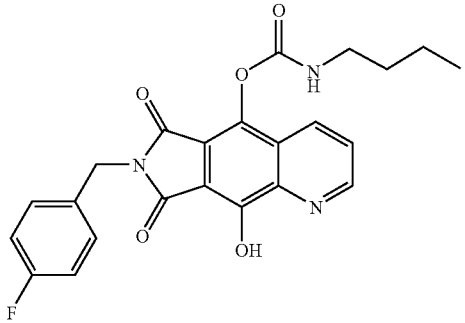
97
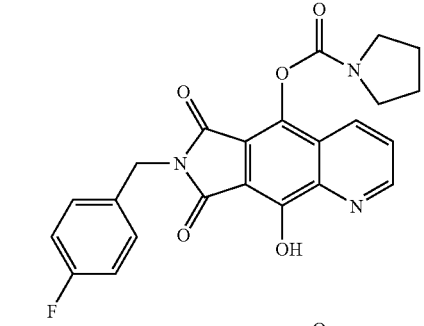
99
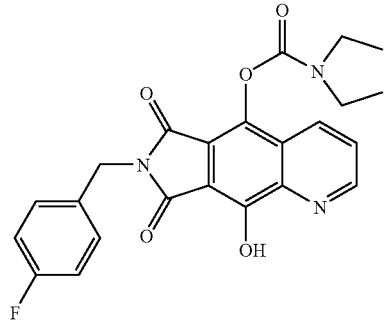
-continued
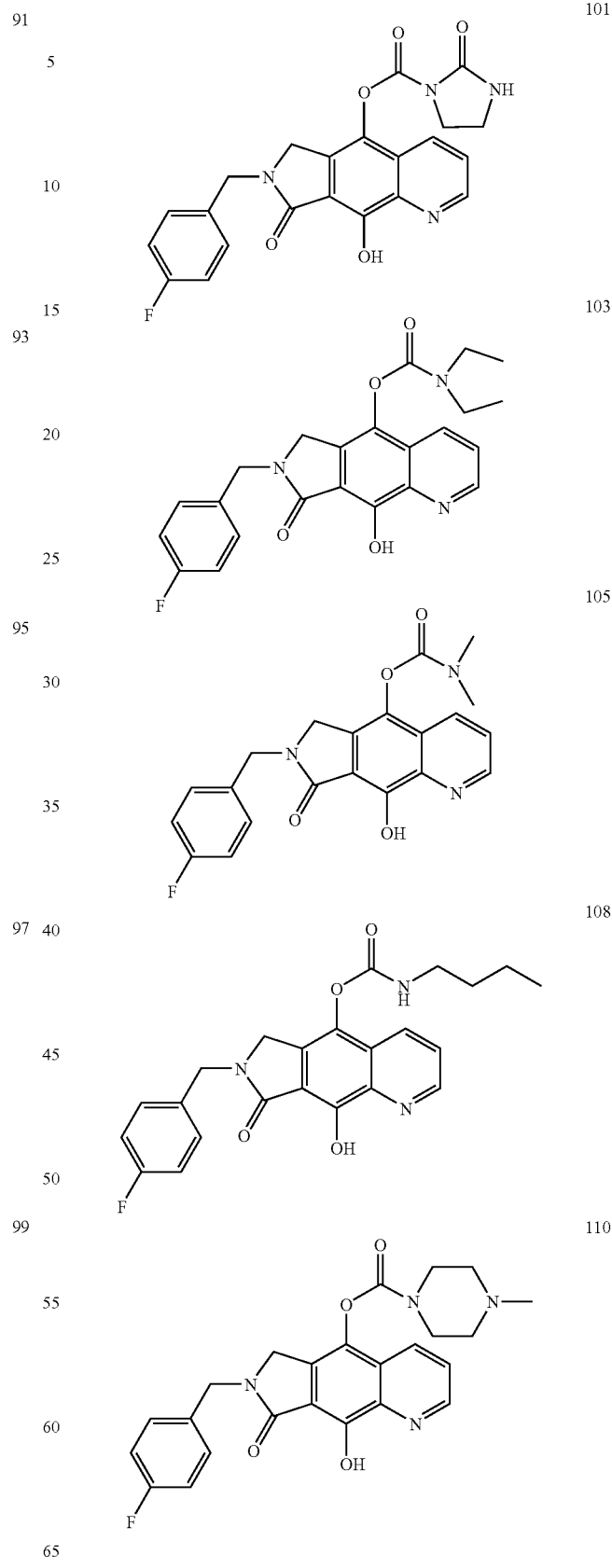

-continued
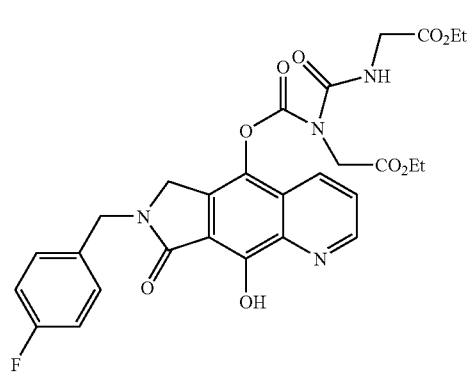
112
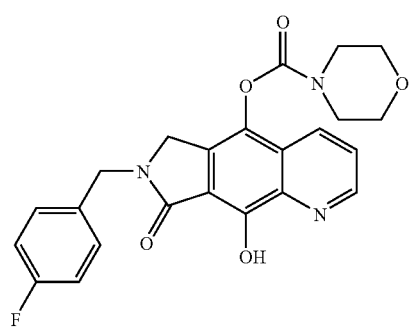
114
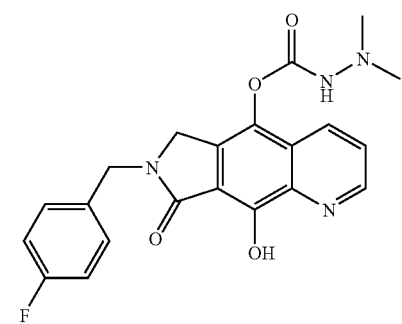
116
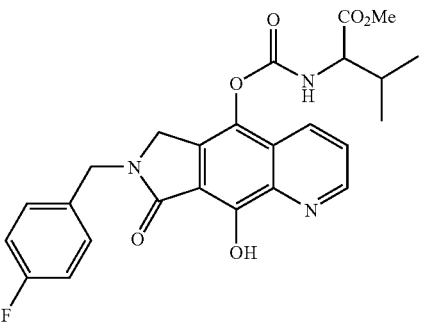
118
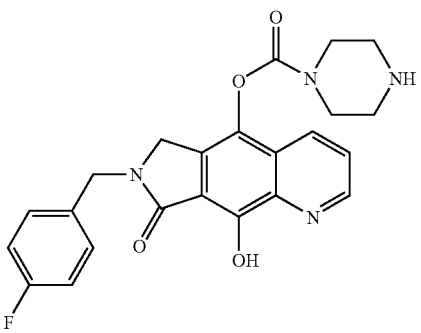
120
-continued
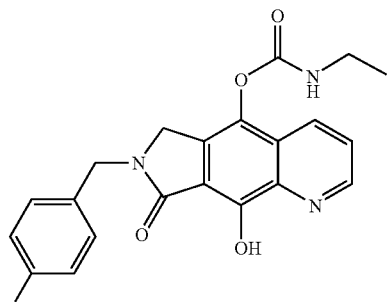
122
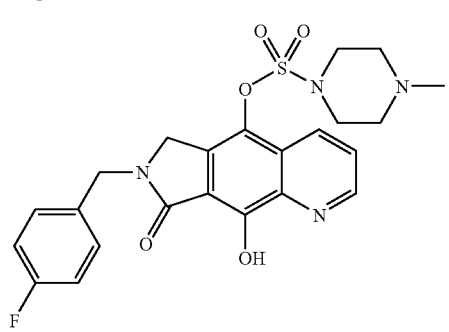
125
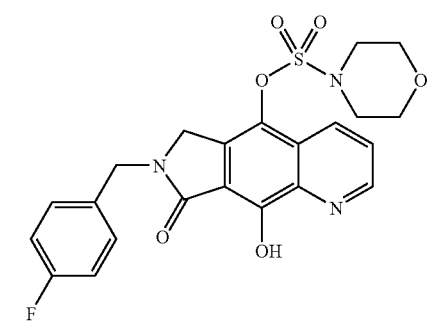
128
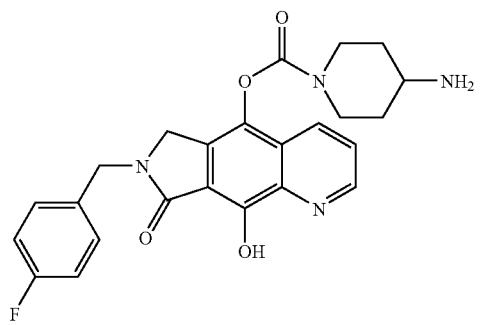
130
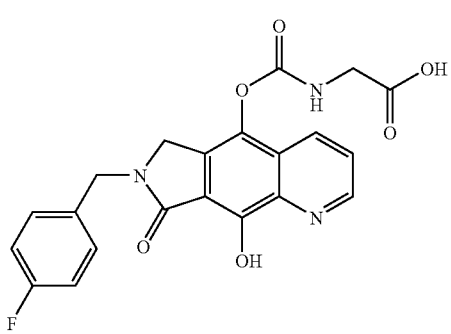
132

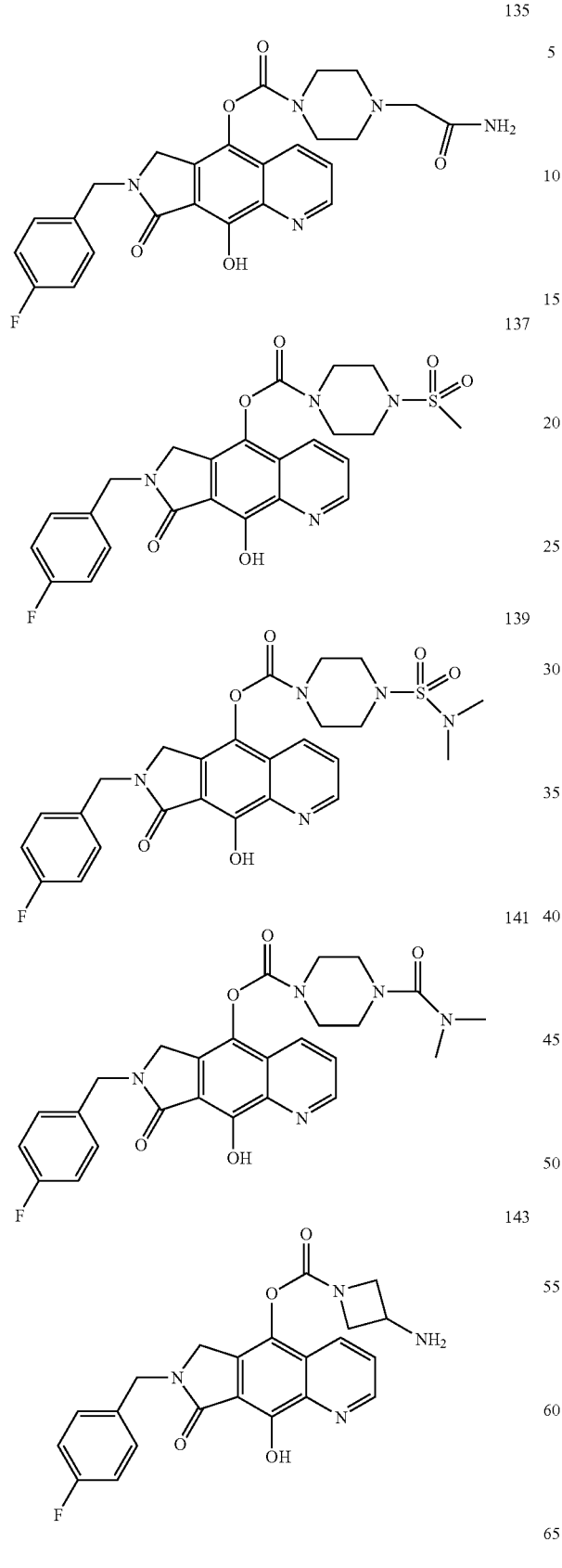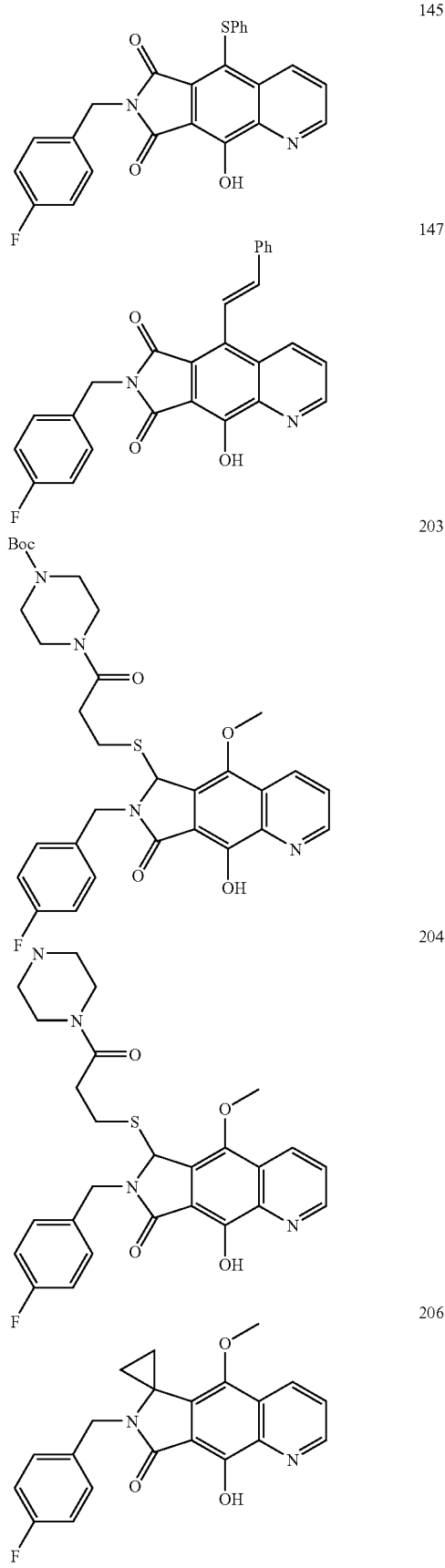

-continued
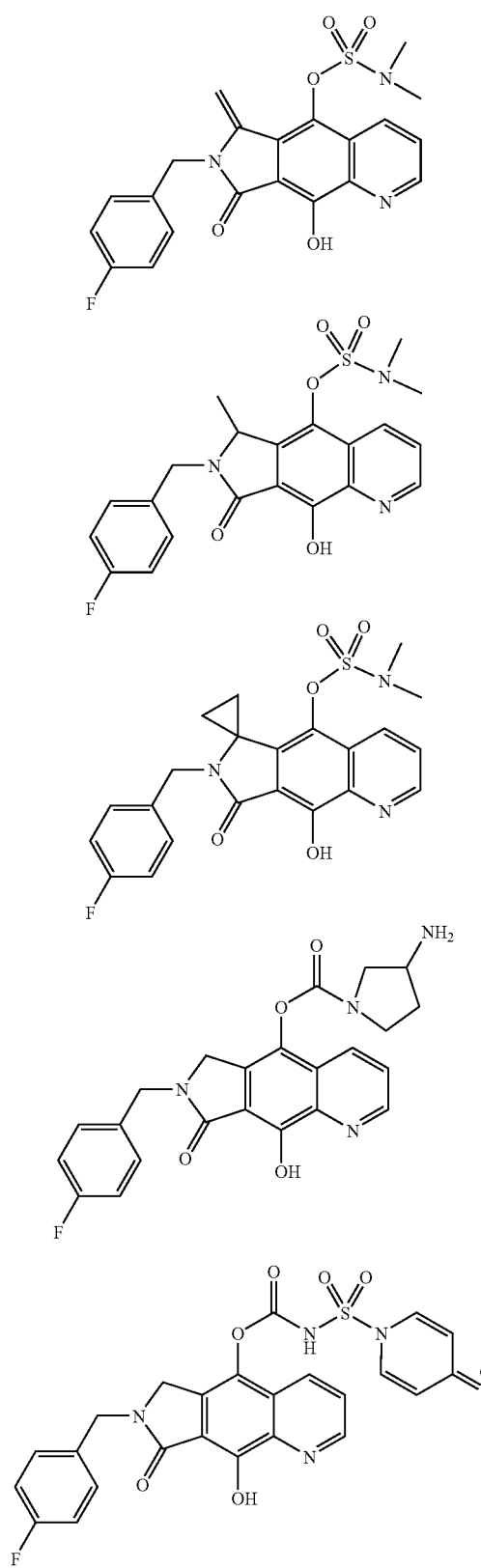
-continued
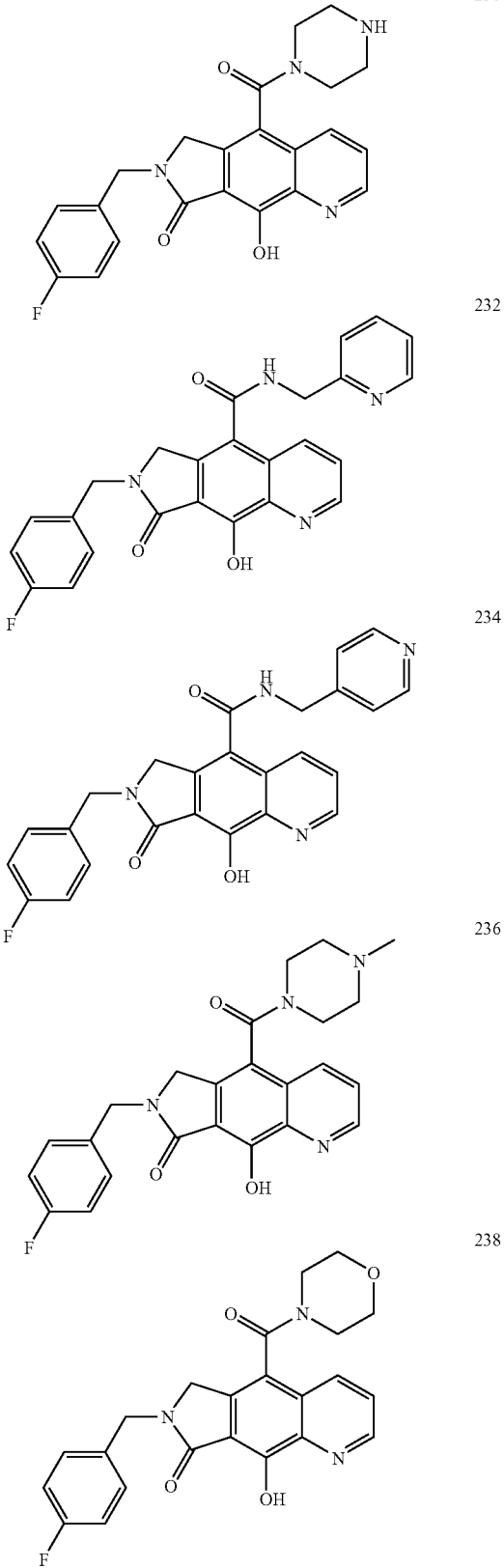

-continued
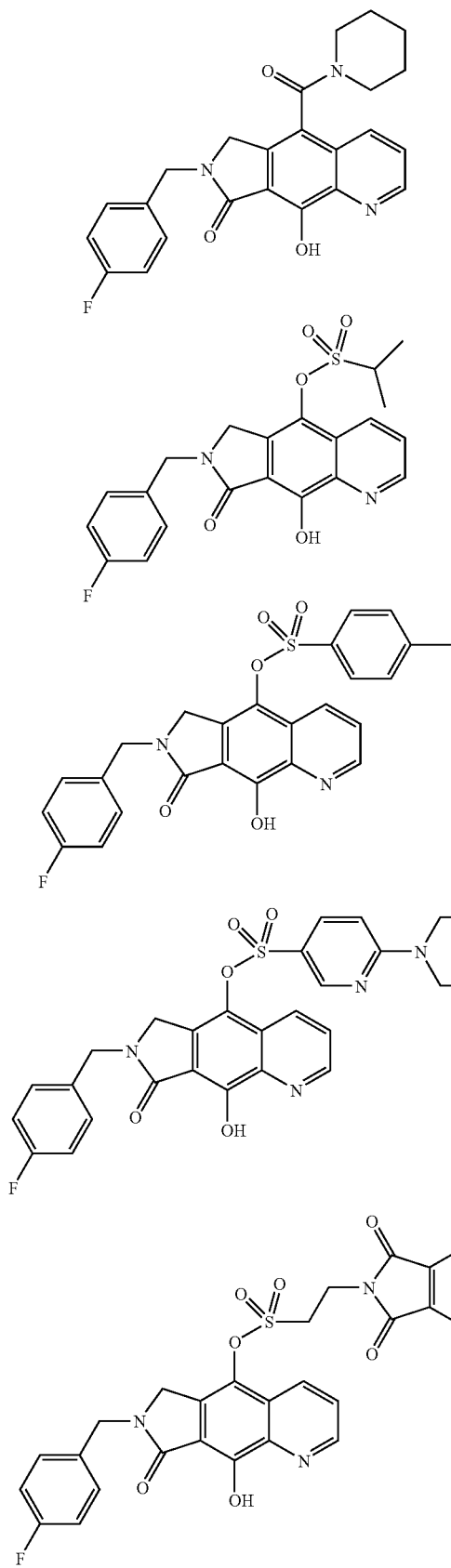
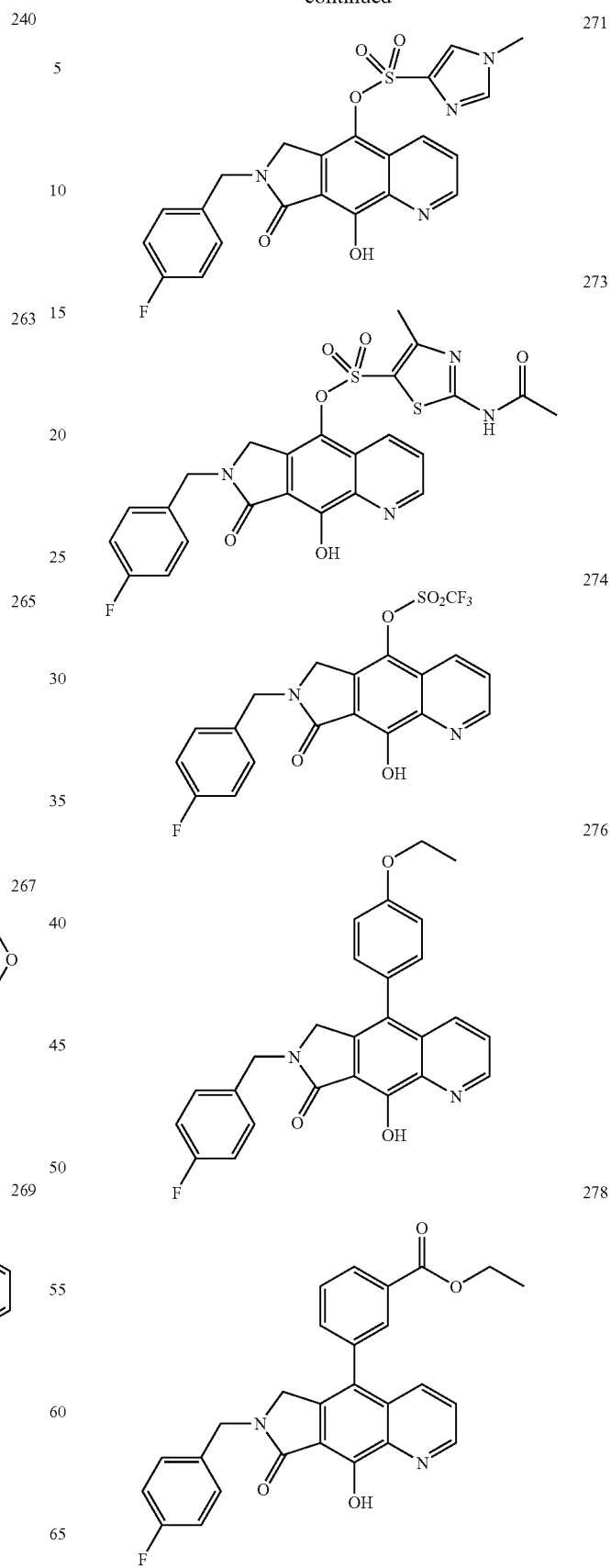

411
-continued
280
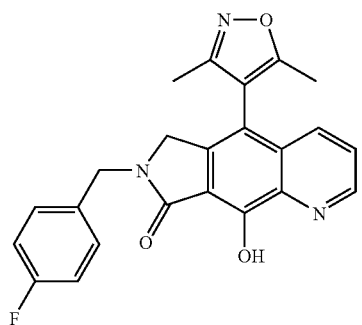
282
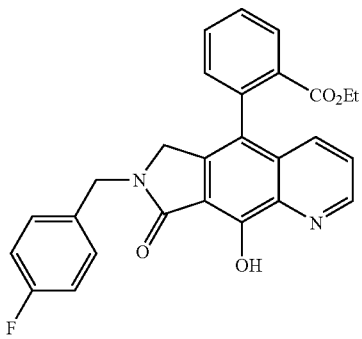
284
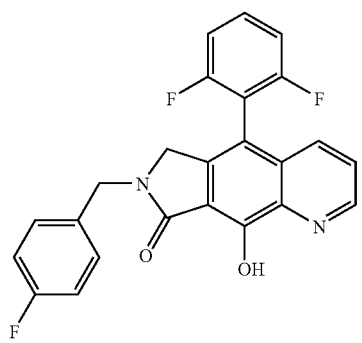
285
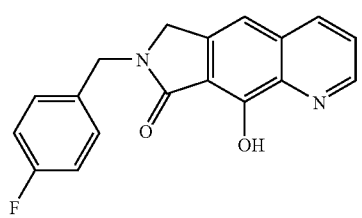
287
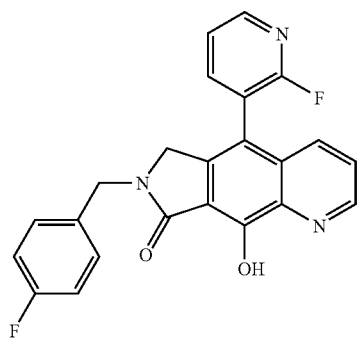
412
-continued
289
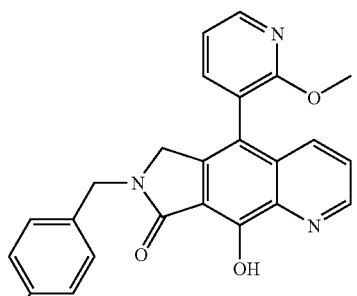
290
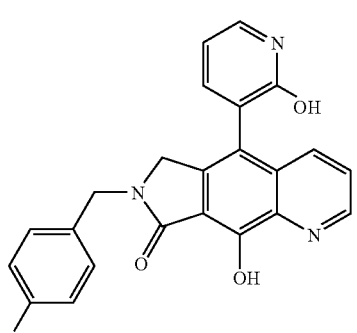
296
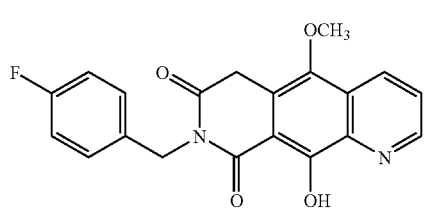
298
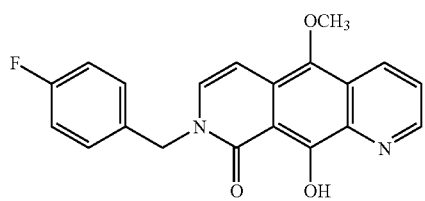
300
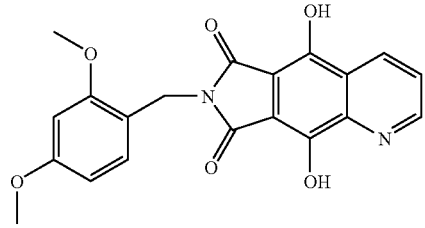
306
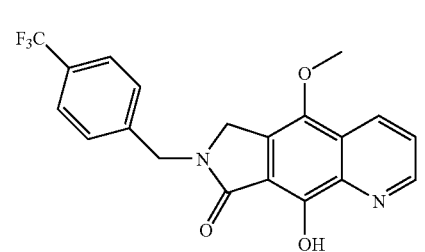

413
-continued
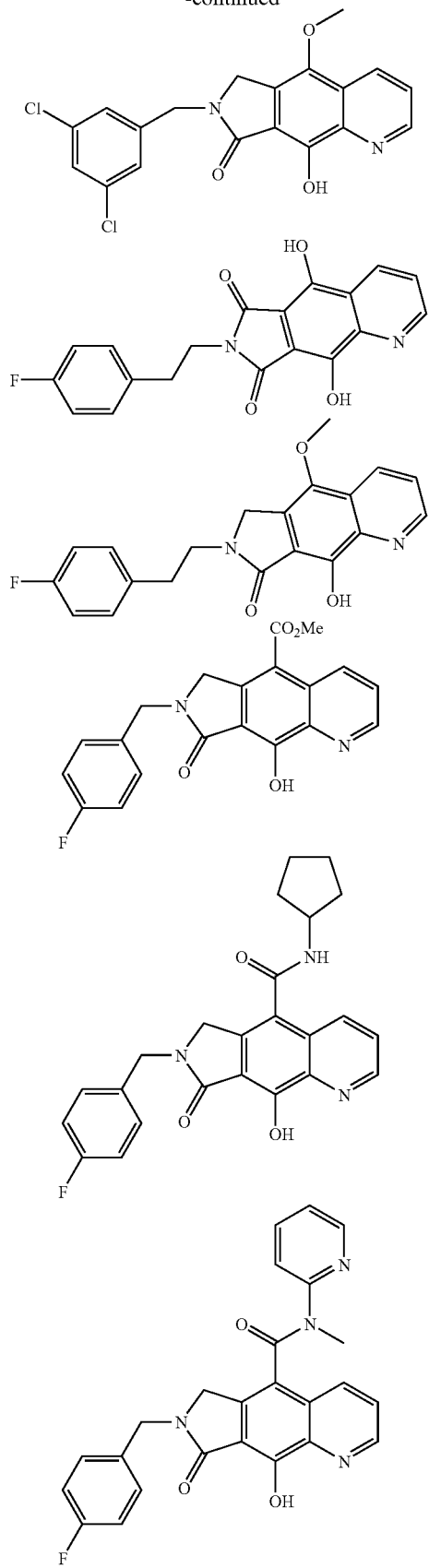
414
-continued
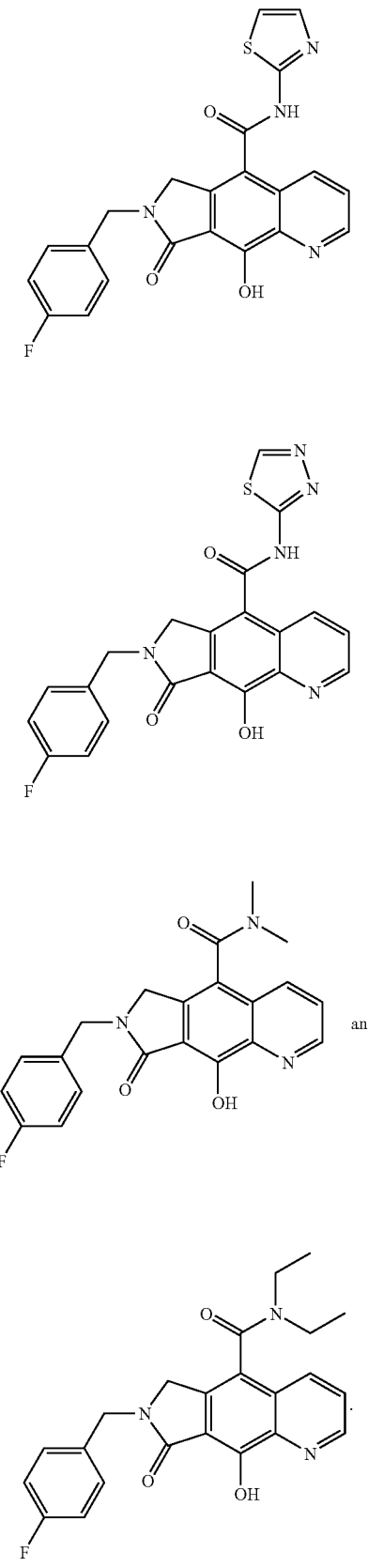
and

48. A compound selected from the structures:
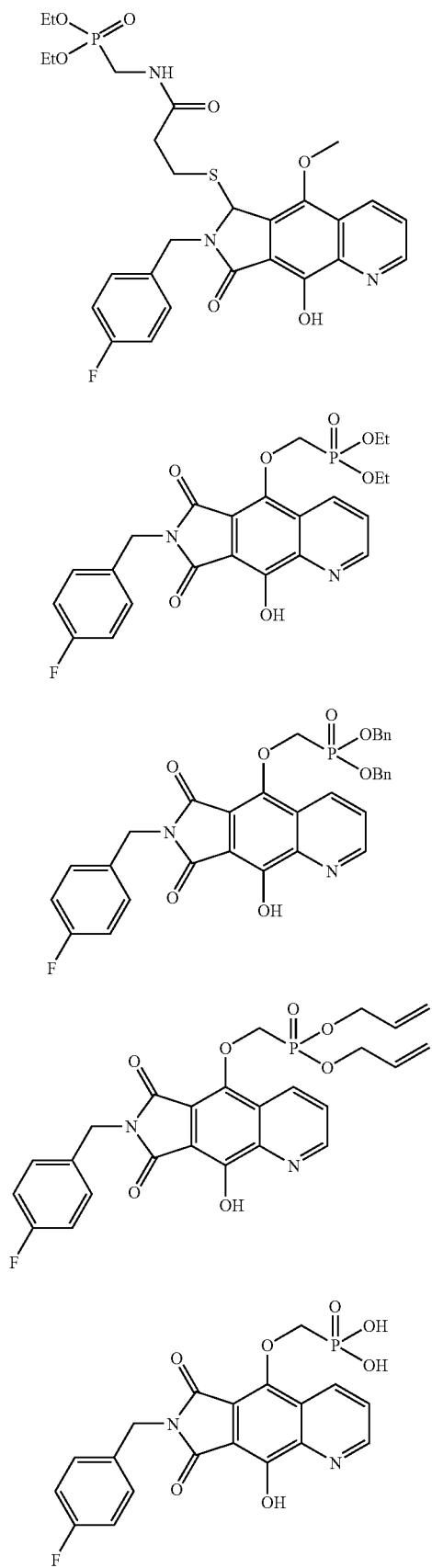
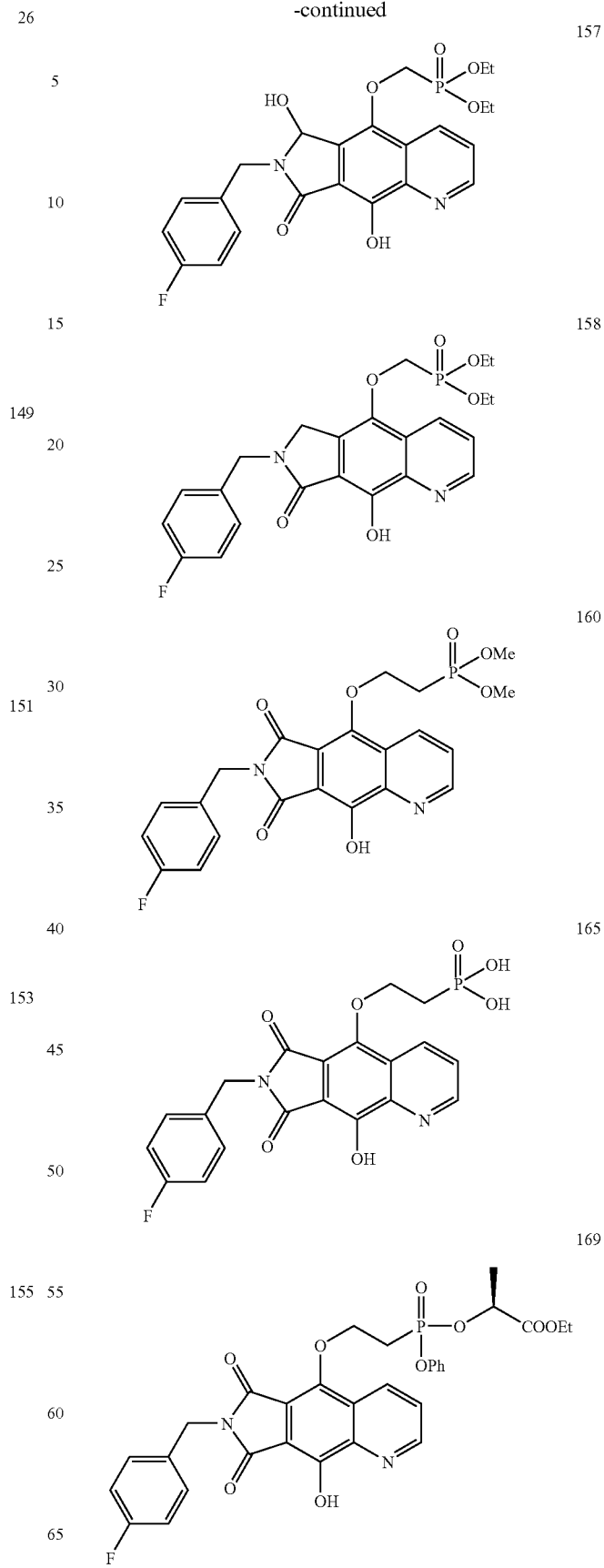

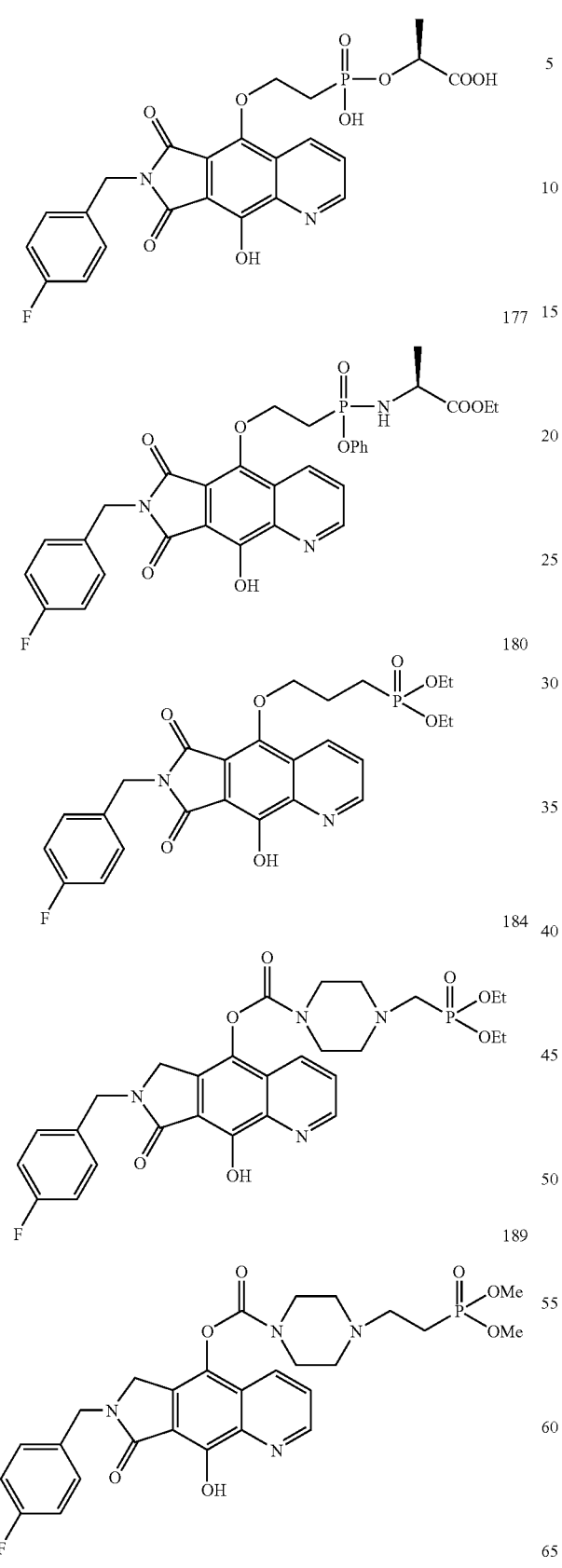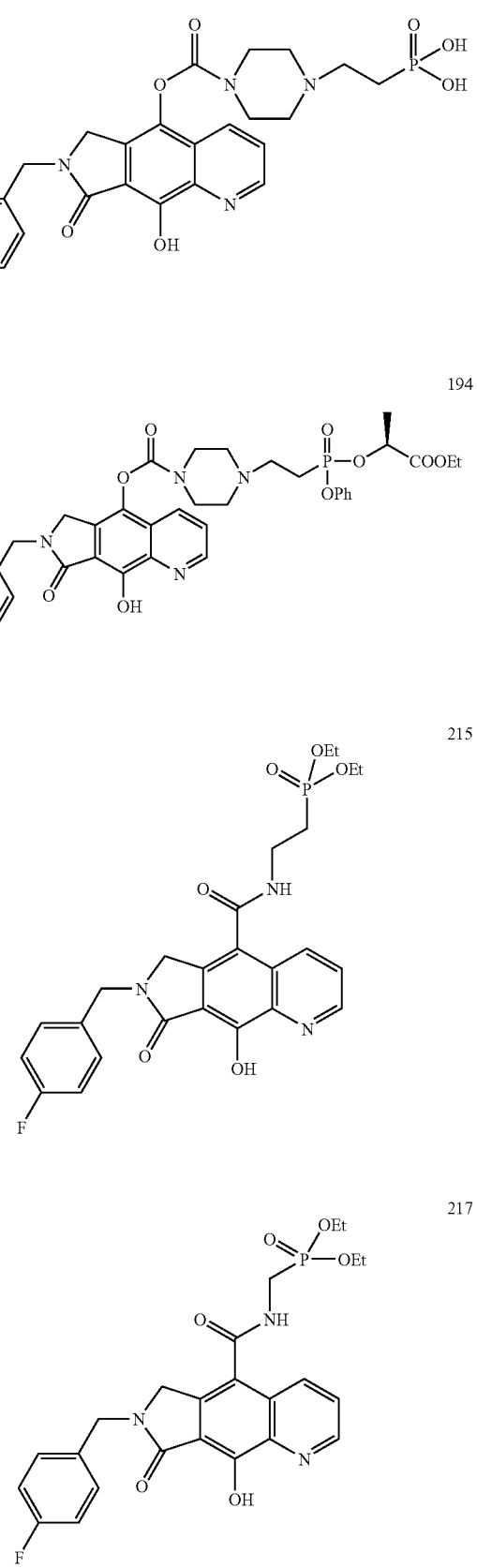

-continued
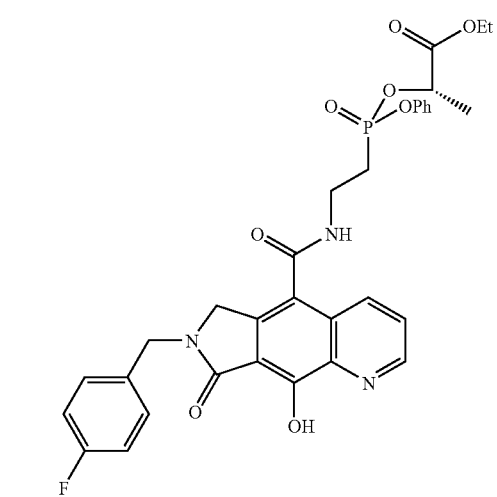
221
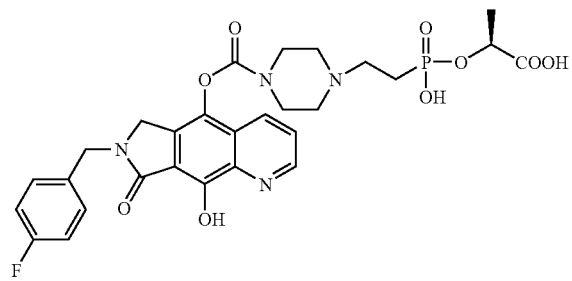
222
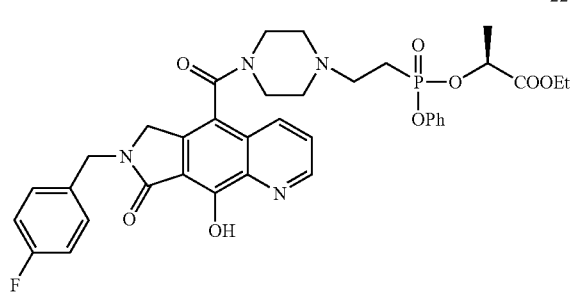
224
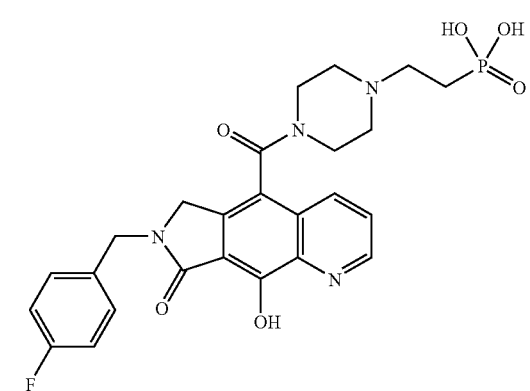
292
-continued
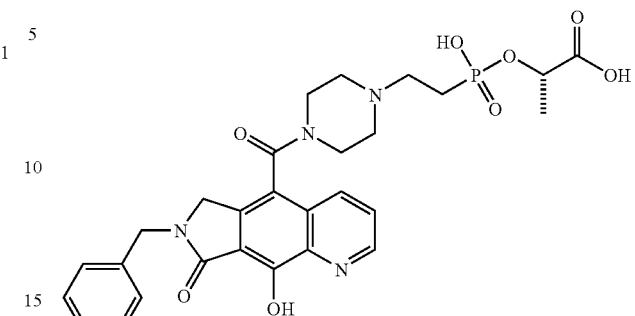
293
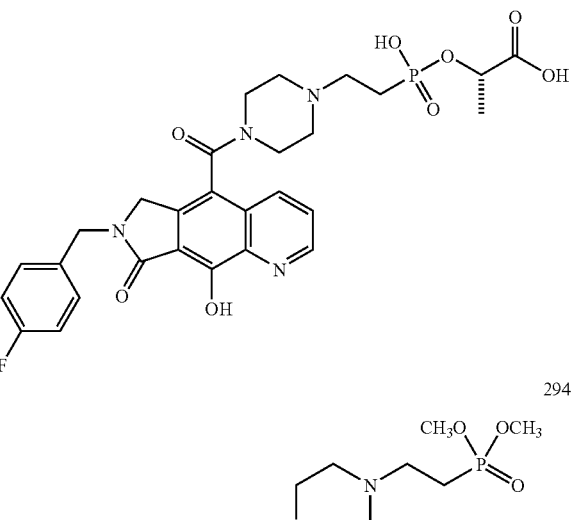
294
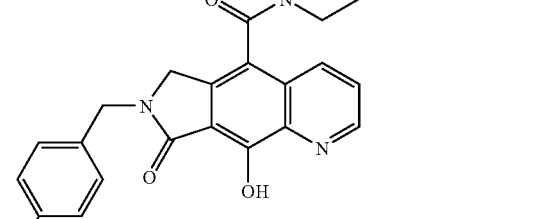
314
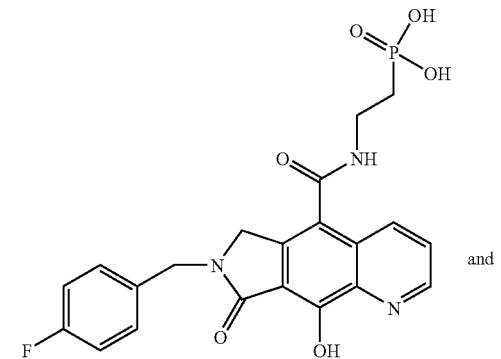
and
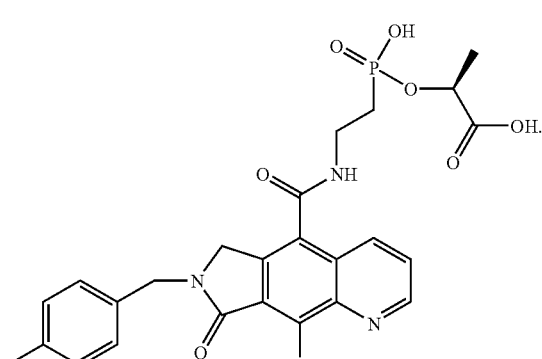
315

49. A compound having the structure:

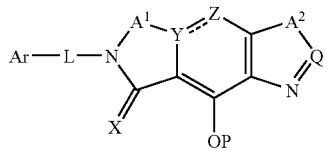

wherein:

$A^1$ is independently selected from $C(R^2)_2$, $CR^2OR$, $CR^2OC(=O)R$, $C(=O)$, $C(=S)$, $CR^2SR$, and $C(=NR)$, $A^2$ is independently selected from $C(R^2)_2-C(R^3)_2$, $C(R^2)=C(R^3)$, and $C(=O)C(R^3)_2$;

Q is $CR^4$;

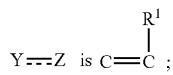

L is selected from a bond, O, S, S—S, S(=O), S(=O)$_2$, S(=O)$_2$NR, NR, N—OR, $C_1$-$C_{12}$ alkylene, $C_1$-$C_{12}$ substituted alkylene, $C_2$-$C_{12}$ alkenylene, $C_2$-$C_{12}$ substituted alkenylene, $C_2$-$C_{12}$ alkynylene, $C_2$-$C_{12}$ substituted alkynylene, C(=O)NH, OC(=O)NH, NHC(=O)NH, C(=O), C(=O)NH(CH$_2$)$_2$, or (CH$_2$CH$_2$O)$_2$, where n is optionally 1, 2, 3, 4, 5, or 6;

X is selected from O, S, NH, NR, N—OR, N—NR$_2$, N—CR$_2$OR and N—CR$_2$NR$_2$;

Ar is selected from (a) a $C_3$-$C_{12}$ carbocycle, $C_3$-$C_{12}$ substituted carbocycle, $C_6$-$C_{20}$ aryl, $C_6$-$C_{20}$ substituted aryl, $C_2$-$C_{20}$ heteroaryl, and $C_2$-$C_{20}$ substituted heteroaryl;

or (b) a saturated, unsaturated or aromatic ring or ring system having a mono- or bicyclic carbocycle or heterocycle containing 3 to 12 ring atoms;

$R^2$, $R^3$ and $R^4$ are each independently selected from H, F, Cl, Br, I, OH, —NH$_2$, —NH$_3^+$, —NHR, —NR$_2$, —NR$_3^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —SO$_2$R, —SO$_2$Ar, —SOAr, —SAr, —SO$_2$NR$_2$, —SOR, —CO$_2$R, —C(=O)NR$_2$, 5-7 membered ring lactam, 5-7 membered ring lactone, —CN, —N$_3$, —NO$_2$, $C_1$-$C_8$ alkoxy, $C_1$-$C_8$ trifluoroalkyl, $C_1$-$C_8$ alkyl, $C_1$-$C_8$ substituted alkyl, $C_3$-$C_{12}$ carbocycle, $C_3$-$C_{12}$ substituted carbocycle, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, and phosphate;

when taken together on a single carbon, two $R^2$ or two $R^3$ may form a spiro ring;

$R^1$ is independently selected from CR$_3$, NRSO$_2$R, OC(=O)NR, OC(=O)R, SR, H, F, Cl, Br, I, OH, —NH$_2$, —NH$_3^+$, —NHR, —NR$_2$, —NR$_3^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —SO$_2$R, —SO$_2$Ar, —SOAr, —SAr, —SO$_2$NR$_2$, —SOR, —CO$_2$R, —C(=O)NR$_2$, 5-7 membered ring lactam, 5-7 membered ring lactone, —CN, —N$_3$, —NO$_2$, $C_1$-$C_8$ alkoxy, $C_1$-$C_8$ trifluoroalkyl, $C_1$-$C_8$ alkyl, $C_1$-$C_8$ substituted alkyl, $C_3$-$C_{12}$ carbocycle, $C_3$-$C_{12}$ substituted carbocycle, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, and phosphate;

$R^1$ is independently selected from CR$_3$, NRSO$_2$R, OC(=O)OR, OC(=O)NR$_2$ OC(+O)R, SR, H, F, Cl, Br, I, OH, —NH$_2$, —NH$_3^+$, —NHR, —NR$_2$, —NR$_3^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —SO$_2$R, —SO$_2$Ar, —SOAr, —SAr, —SO$_2$NR$_2$, —SOR, —CO$_2$R, —C(=O)NR$_2$, 5-7 membered ring lactam, 5-7 membered ring lactone, —CN, —N$_3$, —NO$_2$, $C_1$-$C_8$ alkoxy, $C_1$-$C_8$ trifluoroalkyl, $C_1$-$C_8$ alkyl, $C_1$-$C_8$ substituted alkyl, $C_3$-$C_{12}$ carbocycle, $C_3$-$C_{12}$ substituted carbocycle, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, and phosphate;

R is independently selected from H, $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, and phosphate;

$R^{x2}$ is independently selected from H, $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, and phosphate;

and the tautomers, salts, solvates, resolved enantiomers and purified diastereomers thereof;

with the proviso that when Y=Z is C=C(OH), X is O, $A^1$ is C(=O), $A^2$ is $C(R^2)=C(R^3)$, and Q is CH, then L is not a bond; and P is a protecting group selected from benzyhydryl (CHPh$_2$), trialkylsilyl (R$_3$Si), 2-trimethylsiloxyethyl, alkoxymethyl (CH$_2$OR), and ester (C(=O)R).

50. A process for preparation of a compound having the structure:

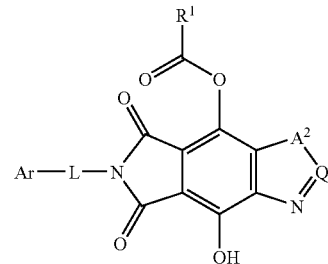

comprising reacting a succinimide compound having the structure:

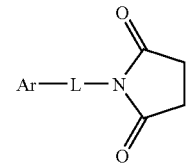

with a heterocyclic compound having the structure:

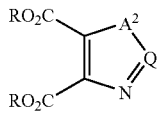

and reacting with an acylation reagent having a formula selected from:

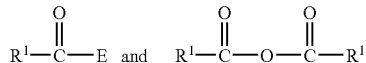

wherein:
$A^2$ is selected from $C(R^2)_2$—$C(R^3)_2$, $C(R^2)$=$C(R^3)$, and $C(=O)C(R^3)_2$;
Q is $CR^4$;
L is selected from a bond, O, S, NR, N—OR, $C_1$-$C_{12}$ alkyldiyl, $C_1$-$C_{12}$ substituted alkyldiyl, C(=O)NH, C(=O), S(=O), S(=O)$_2$, C(=O)NH(CH$_2$)$_n$, and (CH$_2$CH$_2$O)$_n$, where n ranges from 1 to 6;
Ar is selected from (a) a $C_6$-$C_{20}$ aryl, $C_6$-$C_{20}$ substituted aryl, $C_2$-$C_{20}$ heteroaryl, and $C_2$-$C_{20}$ substituted heteroaryl or (b) a saturated, unsaturated or aromatic ring or ring system having a mono- or bicyclic carbocycle or heterocycle containing 3 to 12 ring atoms;
$R^1$ selected from R, OR, NR$_2$, NHR, NHSO$_2$R, and NRSO$_2$R;
E is selected from Cl, imidazole, and hydroxybenzotriazole;
$R^2$, $R^3$ and $R^4$ are each independently selected from H, F, Cl, Br, I, OH, —NH$_2$, —NH$_3^+$, —NHR, —NR$_2$, —NR$_3^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —SO$_2$R, —SO$_2$Ar, —SOAr, —SAr, —SO$_2$NR$_2$, —SOR, —CO$_2$R, —C(=O)NR$_2$, 5-7 membered ring lactam, 5-7 membered ring lactone, —CN, —N$_3$, —NO$_2$, $C_1$-$C_8$ alkoxy, $C_1$-$C_8$ trifluoroalkyl, $C_1$-$C_8$ alkyl, $C_1$-$C_8$ substituted alkyl, $C_3$-$C_{12}$ carbocycle, $C_3$-$C_{12}$ substituted carbocycle, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, phosphate, and a prodrug moiety; and
R is selected from $C_1$-$C_6$ alkyl, $C_1$-$C_6$ substituted alkyl, $C_6$-$C_{20}$ aryl, $C_6$-$C_{20}$ substituted aryl, $C_2$-$C_{20}$ heteroaryl, $C_2$-$C_{20}$ substituted heteroaryl, polyethyleneoxy, phosphonate, phosphate, and a prodrug moiety.

51. The process of claim 50 for preparation of a compound having the structure:

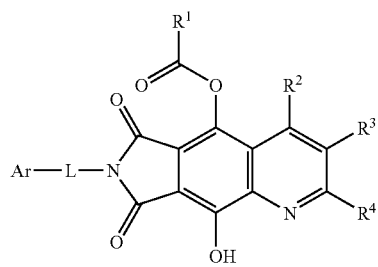

wherein the heterocyclic compound has the structure:

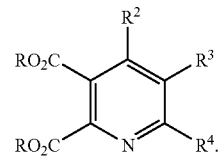

52. A process for preparation of a compound having the structure:

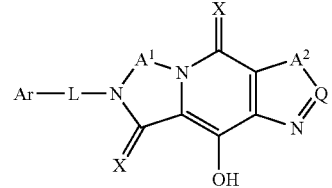

comprising reacting a compound having the structure:

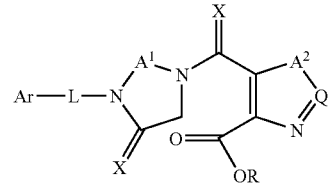

with a basic reagent comprising hydroxide, an alkoxide or an amine;
wherein:
$A^1$ is independently selected from $C(R^2)_2$, $CR^2OR$, $CR^2OC(=O)R$, C(=O), C(=S), $CR^2SR$, and C(=NR),
$A^2$ is independently selected from $C(R^2)_2$—$C(R^3)_2$, $C(R^2)$=$C(R^3)$, and $C(=O)C(R^3)_2$;
Q is $CR^4$;
X is selected from O, S, NH, NR, N—OR, N—NR$_2$, N—CR$_2$OR and N—CR$_2$NR$_2$;
L is selected from a bond, O, S, NR, N—OR, $C_1$-$C_{12}$ alkyldiyl, $C_1$-$C_{12}$ substituted alkyldiyl, C(=O)NH, C(=O), S(=O), S(=O)$_2$, C(=O)NH(CH$_2$)$_n$, and (CH$_2$CH$_2$O)$_n$, where n ranges from 1 to 6;
Ar is selected from (a) a $C_6$-$C_{20}$ aryl, $C_6$-$C_{20}$ substituted aryl, $C_2$-$C_{20}$ heteroaryl, and $C_2$-$C_{20}$ substituted heteroaryl;
or (b) a saturated, unsaturated or aromatic ring or ring system having a mono- or bicyclic carbocycle or heterocycle containing 3 to 12 ring atoms;
$R^2$, $R^3$ and $R^4$ are each independently selected from H, F, Cl, Br, I, OH, —NH$_2$, —NH$_3^+$, —NHR, —NR$_2$, —NR$_3^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —SO$_2$R, —SOAr, —SOAr, —SAr, —SO$_2$NR$_2$, —SOR, —CO$_2$R, —C(=O)NR$_2$, 5-7 membered ring lactam, 5-7 membered ring lactone, —CN, —N$_3$, —NO$_2$, $C_1$-$C_8$ alkoxy, $C_1$-$C_8$ trifluoroalkyl, $C_1$-$C_8$ alkyl, $C_1$-$C_8$ substituted alkyl, $C_3$-$C_{12}$ carbocycle, $C_3$-$C_{12}$ substituted carbocycle, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, phosphate, and a prodrug moiety; and R is selected from $C_1$-$C_6$ alkyl, $C_1$-$C_6$ substituted alkyl, $C_6$-$C_{20}$ aryl, $C_6$-$C_{20}$ substituted aryl, $C_2$-$C_{20}$ heteroaryl, $C_2$-$C_{20}$ substituted heteroaryl, polyethyleneoxy, phosphonate, phosphate, and a prodrug moiety.

53. A process for preparation of a compound having structure 115:

115

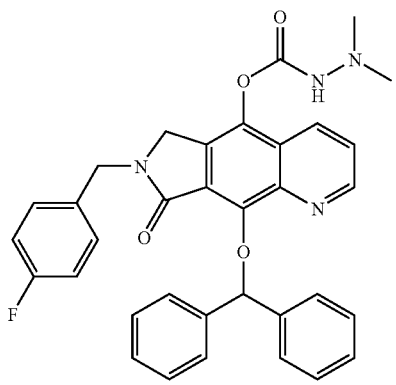

comprising reacting a compound having the structure 44:

44

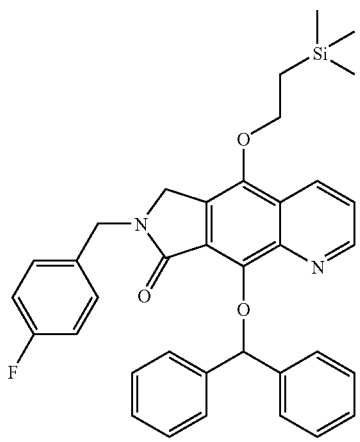

with tetrabutylammonium fluoride to form a desilylated intermediate; and reacting the desilylated intermediate with triphosgene (bis(trichloromethyl)carbonate), followed by dimethylhydrazine to form structure 115.

54. A compound of claim 1 substituted with phosphonate and capable of accumulating in human PBMC.

55. The compound of claim 54 wherein the intracellular half-life of the compound or an intracellular metabolite of the compound in human PBMC is increased by at least about 50% when compared to the analog of the compound not having the phosphonate.

56. The compound of claim 55 wherein the half-life is improved by at least about 100%.

57. A pharmaceutical composition comprising a therapeutically effective amount of a compound of claim 1 and a pharmaceutically acceptable carrier.

58. A compound having the structure:

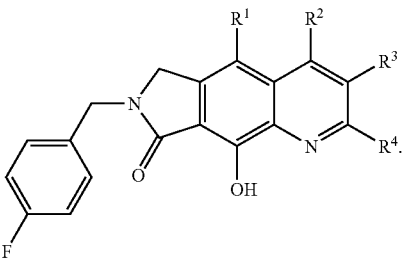

wherein $R^1$ is selected from R, OR, $NR_2$, NHR, $NHSO_2R$ and $NRSO_2R$;

$R^2$, $R^3$ and $R^4$ are each independently selected from H, F, Cl, Br, I, OH, $-NH_2$, $-NH_3^+$, $-NHR$, $-NR_2$, $-NR_3^+$, $C_1$-$C_8$ alkylhalide, carboxylate, sulfate, sulfamate, sulfonate, 5-7 membered ring sultam, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, $-SO_2R$, $-SO_2Ar$, $-SOAr$, $-SAr$, $-SO_2NR_2$, $-SOR$, $-CO_2R$, $-C(=O)NR_2$, 5-7 membered ring lactam, 5-7 membered ring lactone, $-CN$, $-N_3$, $-NO_2$, $C_1$-$C_8$ alkoxy, $C_1$-$C_8$ trifluoroalkyl, $C_1$-$C_8$ alkyl, $C_1$-$C_8$ substituted alkyl, $C_3$-$C_{12}$ carbocycle, $C_3$-$C_{12}$ substituted carbocycle, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, phosphate, and a prodrug moiety; and R is independently selected from H, $C_1$-$C_8$ alkyl, $C_1$-$C_8$ substituted alkyl, $C_6$-$C_{20}$ aryl, $C_6$-$C_{20}$ substituted aryl, $C_2$-$C_{20}$ heteroaryl, and $C_2$-$C_{20}$ substituted heteroaryl, polyethyleneoxy, phosphonate, phosphate, and a prodrug moiety;

and the tautomers, salts, solvates, resolved enantiomers and purified diastereomers thereof.

59. A compound having the structure:

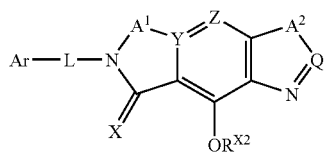

wherein:
$A^1$ is independently selected from $C(R^2)_2$, $CR^2OR$, $CR^2OC(=O)R$, $C(=O)$, $C(=S)$, $CR^2SR$, and $C(=NR)$,
$A^2$ is independently selected from $C(R^2)_2-C(R^3)_2$, $C(R^2)=C(R^3)$ and $C(=O)C(R^3)_2$;
Q is $CR^4$;

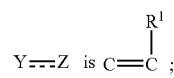

L is selected from a bond, O, S, S—S, $S(=O)$, $S(=O)_2$, $S(=O)_2NR$, NR, N—OR, $C_1$-$C_{12}$ alkylene, $C_1$-$C_{12}$ substituted alkylene, $C_2$-$C_{12}$ alkenylene, $C_2$-$C_{12}$ substituted alkenylene, $C_2$-$C_{12}$ alkynylene, $C_2$-$C_{12}$ substituted alkynylene, $C(=O)NH$, $OC(=O)NH$, $NHC(=O)NH$, $C(=O)$, $C(=O)NH(CH_2)_n$, or $(CH_2CH_2O)_n$, where n is optionally 1, 2, 3, 4, 5, or 6;

X is selected from O, S, NH, NR, N—OR, N—NR$_2$, N—CR$_2$OR and N—CR$_2$NR$_2$;

Ar is selected from (a) a C$_3$-C$_{12}$ carbocycle, C$_3$-C$_{12}$ substituted carbocycle, C$_6$-C$_{20}$ aryl, C$_6$-C$_{20}$ substituted aryl, C$_2$-C$_{20}$ heteroaryl, and C$_2$-C$_{20}$ substituted heteroaryl;

or (b) a saturated, unsaturated or aromatic ring or ring system having a mono- or bicyclic carbocycle or heterocycle containing 3 to 12 ring atoms;

R$^2$, R$^3$ and R$^4$ are each independently selected from H, F, Cl, Br, I, OH, —NH$_2$, —NH$_3^+$, —NHR, —NR$_2$, —NR$_3^+$, C$_1$-C$_8$ alkylhalide, carboxylate, sulfate, sulfamate, sulfonate, 5-7 membered ring sultam, C$_1$-C$_8$ alkylsulfonate, C$_1$-C$_8$ alkylamino, 4-dialkylaminopyridinium, C$_1$-C$_8$ alkylhydroxyl, C$_1$-C$_8$ alkylthiol, —SO$_2$R, —SO$_2$Ar, —SOAr, —SAr, —SO$_2$NR$_2$, —SOR, —CO$_2$R, —C(=O)NR$_2$, 5-7 membered ring lactam, 5-7 membered ring lactone, —CN, —N$_3$, —NO$_2$, C$_1$-C$_8$ alkoxy, C$_1$-C$_8$ trifluoroalkyl, C$_1$-C$_8$ alkyl, C$_1$-C$_8$ substituted alkyl, C$_3$-C$_{12}$ carbocycle, C$_3$-C$_{12}$ substituted carbocycle, C$_6$-C$_{20}$ aryl, C$_6$-C$_{20}$ substituted aryl, C$_2$-C$_{20}$ heteroaryl, and C$_2$-C$_{20}$ substituted heteroaryl, polyethyleneoxy, phosphonate, and phosphate;

when taken together on a single carbon, two R$^2$ or two R$^3$ may form a spiro ring;

R$^1$ is independently selected from CR$_3$, NRSO$_2$R, OC(=O)NR, OC(=O)R, SR, H, F, Cl, Br, I, OH, —NH$_2$, —NH$_3^+$, —NHR, —NR$_2$, —NR$_3^+$, C$_1$-C$_8$ alkylhalide, carboxylate, sulfate, sulfamate, sulfonate, 5-7 membered ring sultam, C$_1$-C$_8$ alkylsulfonate, C$_1$-C$_8$ alkylamino, 4-dialkylaminopyridinium, C$_1$-C$_8$ alkylhydroxyl, C$_1$-C$_8$ alkylthiol, —SO$_2$R, —SO$_2$Ar, —SOAr, —SAr, —SO$_2$NR$_2$, —SOR, —CO$_2$R, —C(=O)NR$_2$, 5-7 membered ring lactam, 5-7 membered ring lactone, —CN, —N$_3$, —NO$_2$, C$_1$-C$_8$ alkoxy, C$_1$-C$_8$ trifluoroalkyl, C$_1$-C$_8$ alkyl, C$_1$-C$_8$ substituted alkyl, C$_3$-C$_{12}$ carbocycle, C$_3$-C$_{12}$ substituted carbocycle, C$_6$-C$_{20}$ aryl, C$_6$-C$_{20}$ substituted aryl, C$_2$-C$_{20}$ heteroaryl, and C$_2$-C$_{20}$ substituted heteroaryl, polyethyleneoxy, phosphonate, and phosphate;

R is independently selected from H, C$_1$-C$_8$ alkyl, C$_1$-C$_8$ substituted alkyl, C$_6$-C$_{20}$ aryl, C$_6$-C$_{20}$ substituted aryl, C$_2$-C$_{20}$ heteroaryl, and C$_2$-C$_{20}$ substituted heteroaryl, polyethyleneoxy, phosphonate, and phosphate;

R$^{x2}$ is independently selected from H, C$_1$-C$_8$ alkyl, C$_1$-C$_8$ substituted alkyl, C$_6$-C$_{20}$ aryl, C$_6$-C$_{20}$ substituted aryl, C$_2$-C$_{20}$ heteroaryl, and C$_2$-C$_{20}$ substituted heteroaryl, polyethyleneoxy, phosphonate, phosphate, and a protecting group selected from benzyhydryl (CHPh$_2$), trialkylsilyl (R$_3$Si), 2-trimethylsiloxyethyl, alkoxymethyl (CH$_2$OR), and ester (C(=O)R);

and the tautomers, salts, solvates, resolved enantiomers and purified diastereomers thereof;

with the proviso that when Y=Z is C=C(OH), X is O, A$^1$ is C(=O), A$^2$ is C(R$^2$)=C(R$^3$), and Q is CH, then L is not a bond.

60. The compound of claim 59 wherein A$^1$ is CH$_2$, or

61. The compound of claim 59 having Formula I:

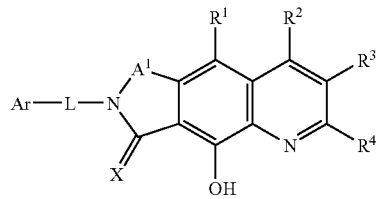

wherein X is O.

62. The compound of claim 61 wherein L is CH$_2$ and Ar is substituted phenyl.

63. The compound of claim 61 wherein A$^1$ is CH$_2$ and R$^2$, R$^3$ and R$^4$ are each H.

64. The compound of claim 59 having the Formula:

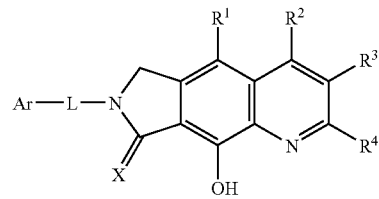

wherein X is O.

65. The compound of claim 64 wherein L is CH$_2$ and Ar is substituted phenyl.

66. The compound of claim 65 wherein R$^2$, R$^3$, and R$^4$ are each H.

* * * * *